(12) United States Patent
Keller et al.

(10) Patent No.: US 10,514,383 B2
(45) Date of Patent: Dec. 24, 2019

(54) DIAGNOSIS AND TREATMENT OF NEONATAL ENCEPHALOPATHY

(71) Applicant: InfanDx AG, Cologne (DE)

(72) Inventors: Matthias Keller, Essen (DE); David Enot, Creully (FR)

(73) Assignee: InfanDx AG, Köln (DE)

(*) Notice: Subject to any disclaimer, the term of this patent is extended or adjusted under 35 U.S.C. 154(b) by 0 days.

(21) Appl. No.: 14/353,969

(22) PCT Filed: Oct. 25, 2012

(86) PCT No.: PCT/EP2012/071174
§ 371 (c)(1),
(2) Date: Apr. 24, 2014

(87) PCT Pub. No.: WO2013/060788
PCT Pub. Date: May 2, 2013

(65) Prior Publication Data
US 2014/0308687 A1 Oct. 16, 2014

(30) Foreign Application Priority Data
Oct. 25, 2011 (EP) .................................. 11008563

(51) Int. Cl.
*G01N 33/68* (2006.01)
*G01N 27/447* (2006.01)
*G16B 20/00* (2019.01)
*G16C 20/70* (2019.01)

(52) U.S. Cl.
CPC ........ *G01N 33/6896* (2013.01); *G01N 27/447* (2013.01); *G01N 2800/28* (2013.01); *G01N 2800/38* (2013.01); *G01N 2800/60* (2013.01); *G16B 20/00* (2019.02); *G16C 20/70* (2019.02)

(58) Field of Classification Search
None
See application file for complete search history.

(56) References Cited

U.S. PATENT DOCUMENTS

| 2007/0003965 A1 | 1/2007 | Ramsay et al. |
| 2007/0004044 A1 | 1/2007 | Ramsay et al. |
| 2014/0308687 A1 | 10/2014 | Keller et al. |

FOREIGN PATENT DOCUMENTS

| WO | 2010/128054 A | 11/2010 |
| WO | 2011012553 A1 | 2/2011 |

OTHER PUBLICATIONS

Kurinczuk et al., Early Human Development 86, 2010; 329-338.*
Guillet et al., Pediatric Research, 2012; 71: 205-209.*
Eicher et al., Pediatr Neurol 2005; 32: 11-17.*
Diller and Zhu, Annu. Rev. Biomed. Eng. 2009; 11: 135-162.*
The website: blog.minitab.com/blog/adventures-in-statistics-2/understanding-hypothesis-tests:-significance-levels-alpha-and-p-values-in-statistics; downloaded Jan. 7, 2016; 6 pages total.*
Author manuscript of Fatemi et al., published in final edited form as: Clin Perinatol. Dec. 2009; 36(4): 835-vii. doi:10.1016/j.clp.2009.07.011 (Year: 2009).*
Solberg, R., et al., "Metabolomic Analyses of Plasma Reveals New Insights into Asphyxia and Resuscitation in Pigs", PLoS ONE, Mar. 9, 2010, pp. 1-12, vol. 5.
Chu, C.Y., et al., "Metabolomic and Bioinformatic Analyses in Asphyxiated Neonates", Clin. Biochem., Mar. 2006, pp. 203-209, vol. 39, No. 3.
Mueller, P., et al., "Mass Spectrometric Quantifications of Organic Acids and Acylcarnitines in Early Random Urine Specimens of Newborns with Perinatal Complications: Feasibility Study for the Prediction of the Neuro Developmental Outcome", The Internet Journal of Pediatrics and Neonatology, Jan. 1, 2007, pp. 1-16, vol. 7, No. 2.
Spitzer, A.R., et al., "Proteomics-and Metabolomics-Based Neonatal Diagnostics in Assessing and Managing the Critically Ill Neonate", Clin. Perinatol, 2008, pp. 695-716, vol. 35, No. 4.
Lingwood, B.E., et al., "MAP2 Provides Reliable Early Assessment of Neural Injury in the Newborn Piglet Model of Birth Asphyxia", J. Neurosc. Meth., Jun. 2008, pp. 140-146, vol. 171, No. 1.
Vasquez-Vivar J., et al., "Tetrahydrobiopterin in the Prevention of Hypertonia in Hypoxic Fetal Brain", Ann. Neurol., Sep. 2009, pp. 323-331, vol. 66, No. 3.
International application No. PCT/EP2012/071174, Written Opinion of the International Searching Authority, dated Apr. 25, 2014.
International application No. PCT/EP2012/071174, Notification Concerning Transmittal of International Preliminary Report on Patentability, dated May 8, 2014.
Liu, Jia, et al., "Outcome-Related Metabolomic Patterns from 1H/31P NMR After Mild Hypothermia Treatments of Oxygen-Glucose Deprivation in a Neonatal Brain Slice Model of Asphyxia", Journal of Cerebral Blood Flow & Metabolism, 2011, pp. 547-559, vol. 31.
Luetjohann, D., et al., "Cholesterol Dynamics in the Foetal and Neonatal Brain as Reflected by Circulatory Levels of 24S-Hydroxycholesterol", Acta Paediatr, 2001, pp. 652-657, vol. 90.
Shankaran, Seetha, et al., "Whole-Body Hypothermia for Neonates with Hypoxic-Ischemic Encephalopathy", The New England Journal of Medicine, Oct. 13, 2005.

(Continued)

*Primary Examiner* — Christina M Borgeest
(74) *Attorney, Agent, or Firm* — Cahn & Samuels, LLP

(57) ABSTRACT

Metabolites and signatures (panels) of metabolites are applicable as biomarkers in clinical diagnosis, in particular for neonatal encephalopathy. They are useful tools in differential clinical diagnosis for early detection of brain injury, determination of brain areas affected by the insults and prediction of adverse neurological outcome and may also be applied in diagnosing disease progression and treatment effect. An in vitro method for predicting the likelihood of neonatal encephalopathy of distinct brain areas, identification of affected brain area(s) of neonatal encephalopathy and risk of brain damage and prognosis and neurological outcome due to identification of the type and extent of damage of distinct brain tissues, in particular of hippocampus and/or basal ganglia, is provided.

23 Claims, 9 Drawing Sheets

(56) References Cited

OTHER PUBLICATIONS

Jonsson, M., et al., "Neonatal encephalopathy and the association to asphyxia in labor", American Journal of Obstetrics & Gynecology, Dec. 2014, 211:667.e1-8.

D'Alton, et. al, "Neonatal Encephalopathy and Neurologic Outcome, Second Edition, Report of the American College of Obstetricians and Gynecologists' Task Force on Neonatal Encephalopathy", Pediatrics, vol. 133, No. 5, 2014.

Hagberg et al., "Perinatal brain damage: The term infant", Neurobiology of Disease 92 (2016), 102-112.

Lawn et al., "Setting Research Priorities to Reduce Almost One Million Deaths from Birth Asphyxia by 2015", PLoS Medicine | www.plosmedicine.org, Jan. 2011, vol. 8, Issue 1, 1-11.

Walsh et al., "The Metabolomic Profile of Umbilical Cord Blood in Neonatal Hypoxic Ischaemic Encephalopathy", PLOS ONE | www.plosone.org, Dec. 2012, vol. 7, Issue 12, 1-12.

Martinello et al., "Management and investigation of nenatal encephalopathy:2017 update", Arch Dis Child Fetal Neonatal Ed, F1-F13 (2017).

Van Bel, et al., "Drugs for neuroprotection after birth asphyxia: Pharmacologic adjuncts to hypothermia", Seminars in Perinatology, 40 (2016), 152-159.

Odd et al., "Resuscitation at birth and cognition at 8 years of age: a cohort study", The Lancet vol. 373, May 2009, 1615-1622.

Groenendaal et al., "Selection of babies for intervention after birth asphyxia", Semin Neonatol, 2000, vol. 5, 17-32.

Beckstrom et al, "Application of comprehensive two-dimensional gas chromatography with time-of-flight mass spectrometry method to identify potential biomarkers of perinatal asphyxia in a non-human primate model", Journal of Chromatography A, 1218 (2011), 1899-1906.

\* cited by examiner

DIAGNOSIS AND TREATMENT OF NEONATAL ENCEPHALOPATHY

This U.S. patent application is a national stage application of PCT/EP2012/071174 filed on 25 Oct. 2012 and claims priority of European patent document EP 11008563.6 filed on 25 Oct. 2011, the entireties of which are incorporated herein by reference.

The invention generally relates to the identification of metabolites and signatures (panels) of metabolites, which are applicable as biomarkers in clinical diagnosis, in particular for neonatal encephalopathy. They are useful tools in differential clinical diagnosis for early detection of brain tissues affected by brain damage and may also be applied in diagnosing disease progression and determination of affected brain areas and determination of associated adverse neurological outcome. The present invention more particularly relates to an in vitro method for predicting the likelihood of neonatal encephalopathy of distinct brain areas, identification of affected brain area(s) of neonatal encephalopathy and risk of brain damage and prognosis and neurological outcome due to identification of the type and extent of damage of distinct brain tissues, in particular of hippocampus and/or basal ganglia.

BACKGROUND OF THE INVENTION

Neonatal encephalopathy (NE) is a serious condition with life long consequences. NE is the most important cause of morbidity and mortality in the term born baby. About 10% of those affected die and 25% are severely handicapped due to long-term complications such as cerebral palsy, mental retardation with learning difficulties, cerebral visual impairments and/or epilepsy. Its long-term consequences impose a large burden on the child and family and on worldwide healthcare budgets. The estimated costs of the treatment of sequelae of NE in the US is around 750 000 US $ per patient. One major reason for NE is pre-, peri- and postnatal asphyxia, a condition in which the fetus or newborn lacks oxygen. In the Western world about 0.9% of newborns, about 130.000 in the developed world and 30.000 in European Union suffer from a moderate to severe form of perinatal asphyxia. However NE could not always be explained by moderate to severe asphyxia and the cause of NE often could not be identified. It has been shown that foetuses/newborns with rather mild asphyxia, who initially seem to recover without complications, will have behavioural problems in childhood, which can be traced back to the perinatal insult.

A study published in Lancet suggests that the definition of NE does not include all patients with long-term neurological outcome after resuscitation (Odd D E, Lewis G, Whitelaw A, Gunnell D. Lancet. 2009 May 9; 373(9675):1615-22). Resuscitated infants asymptomatic for the "classically defined" encephalopathy, however, undergoing actual brain damage (or prone to actual brain damage) might result in a larger proportion of adults with low IQs than do those who develop neurological symptoms consistent with encephalopathy. Based on this publication 40% of cases with long-term adverse neurological outcome are missed by current, state of the art, diagnostic means. Thus, in summary neonatal encephalopathy and its long-lasting consequences is a huge burden to the child, to its family. Consequently, there is a lack of early markers identifying newborns at risk for NE.

Till date, therapy was limited to supportive care including adequate oxygenation and restoring of circulation by appropriate, rapid and effective resuscitation. It is vital to maintain adequate ventilation, systemic blood pressure, tissue perfusion, and normoglycaemia, to control seizures, and to correct electrolyte and acid-base disorders. However, in the past few years hypothermia (whole body hypothermia or selective head cooling), has been introduced to reduce morbidity and mortality following perinatal asphyxia in term born neonates. In a recent meta-analysis combining the results of 1320 neonates the effect of moderate hypothermia was found to be associated with a moderate reduction in death and neurological impairment at 18 months. It is of outmost importance that the therapeutic benefit of hypothermia is strongly dependent on the time point of its initiation. The earlier the diagnosis is made and the early therapy can be started the more neuroprotection can be achieved. Accordingly, early detection of neonatal encephalopathy and severity assessment is vital to therapeutic success.

Current diagnostic tests to evaluate whether a newborn is at risk to develop neurological sequelae have major limitations with low sensitivity and specificity. The diagnostic criteria for neonatal encephalopathy in term newborn infants require i) signs of perinatal and postnatal asphyxia, abnormal blood gas values (increase in base deficit, blood lactate values, low cord pH in the umbilical artery (UApH) and need for resuscitation, and ii) signs of brain involvement and abnormal neurology characterized by neurological scores (Sarnat or Thompson score) and any presence of seizure activity and iii) demonstrating electroencephalographic evidence of abnormal cerebral function by means of the amplitude-integrated or ten-lead standard EEG. These established tests, however, have major limitations. We have recently shown that that so called "abnormal blood gas values" do not correlate with the extent of hypoxia. This is reflected by low sensitivity and specificity for NE [Groenendaal, de Vroes Semin Neonatol 2000, Vol 5 17-32]. The most precise test currently established is the use of amplitude integrated EEG (aEEG) with a sensitivity and specificity of 80% in the first 6 hours of life. The use of aEEG is challenged by its availability, required expertise and timing. It is not available in all children's hospitals and in none of the delivery units. Thus the diagnosis by aEEG can only be made after transfer into a children's clinic in which the tool and the medical expertise is available. In addition the process of implementation of the aEEG and the evaluation of the signal takes at least 30 to 45 minutes. This is of particular importance since it is known that treatment is more effective the earlier it is initiated. Imaging technologies such as MRT (Magnetic Resonance Tomography), however, are applicable from day three after birth only and therefore, are not useful for early diagnosis and timely therapy.

Currently used diagnostic methods thus require time and appropriate equipment with high costs, do not recognize affected parts of the brain along with individual prognosis, afford results too late for appropriate therapy and with frequently unsatisfying sensitivities. These available diagnostic means, therefore, have major limitations such as reduced area under the curve (AUC) and/or delay of diagnosis or increased costs due to equipment required. Accordingly, these procedures also do not allow a timely assessment of an acute and rapidly evolving disease nor a differentiation of brain areas affected by hypoxia. Overall the situation is far from satisfying and from providing a rapid, reliable and precise diagnosis of brain damage in neonates, let alone a differentiation of affected brain areas or tissues, a prerequisite, however, for selection and initiation of appropriate therapy; there is still an urgent need for differentiation of brain injury from any other state of health to enable timely and adequate treatment.

Due to these limitations academic research groups have been looking for potential alternative biomarkers of NE like interleukin-1b, 6, 8, 9, 12, NSE, S100, CK-BB, Phosphorylated axonal neurofilament heavy chain (pNF-H protein2) Ubiquitin C-terminal hydrolase 1 (UCHL1 protein) (Ramaswamy et al. (2009) Pediatr Neurol, Vol 40, 215-226). However, although these markers have been published, none of these were finally developed to a diagnostic product because of major limitations. The studies are not uniform and show a significant amount of heterogeneity with a tremendous variation in the assessment of outcomes and variation in inclusion criteria. Most frequently the inclusion of patients was based on "established" tests. Thus most of the studies confirm the diagnosis of the established tests and were most precise for infants with severe injury who are already easily identified and do not provide any additional information. Most of the studies had small sample size, so it is not possible to calculate true predictive value for all of the mentioned biomarkers and no attempt has been made to correlate concentrations of these marker candidates with brain areas affected by NE. In addition, correlation is strongest at times well after the latent phase, which is way too late for early and therefore, effective treatment.

In summary there is no single precise biomarker available to diagnose or predict neonatal encephalopathy in newborns at an early stage e.g. immediately after birth or any biomarker which provides information on brain areas affected by damaging conditions. Lesions detectable on a biochemical level only such as by using endogenous metabolites as biomarkers and not monitorable by alternate means, however, can be used to assess neurological outcome which is of outstanding value for clinical diagnosis.

In classical patient screening and diagnosis, the medical practitioner uses a number of diagnostic tools for diagnosing a patient suffering from a certain disease. Among these tools, measurement of a series of single routine parameters, e.g. in a blood sample, is a common diagnostic laboratory approach. These single parameters comprise for example enzyme activities and enzyme concentration and/or enzyme detection As far as such diseases are concerned, which easily and unambiguously can be correlated with one single parameter or a few number of parameters achieved by clinical chemistry, these parameters have proved to be indispensable tools in modern laboratory medicine and diagnosis. However, in complex pathophysiological conditions, for which an unambiguously assignable single parameter or marker is not available, differential diagnosis from blood or tissue samples is currently difficult to impossible.

Only recently metabolomic analyses for specific diagnostic approaches were described in the prior art:

According to WO 2011/012553 A1 a method for predicting the likelihood of an onset of an inflammation associated organ failure is provided, which is based on quantitative metabolomics analysis of a biological sample of a mammalian subject in vitro. In particular, the concentration of acylcarnitines, sphingomyelins, hexoses and glycerophospholipids in plasma by means of FIA-MS/MS is determined. Furthermore, amino acids and biogenic amines were analyzed by reversed phase LC-MS/MS in plasma. Prostanoids—a term summarizing prostaglandins (PG), thromboxanes (TX) and prostacylines—and oxidised fatty acid metabolites in plasma extracts were analysed by LC-ESI-MS/MS and in brain homogenate extracts by online solid phase extraction (SPE)-LC-MS/MS. Furthermore, energy metabolism (organic acids) was analyzed by LC-MS/MS. For the quantitative analysis of energy metabolism intermediates (glycolysis, citrate cycle, pentose phosphate pathway, urea cycle) hydrophilic interaction liquid chromatography (HILIC)-ESI-MS/MS method was applied.

WO 2010/128054 A1, corresponding to EP 2 249 161 A1, describes a method of diagnosing asphyxia. In particular, said document refers to a method for in vitro diagnosing e.g. perinatal asphyxia and disorders related to hypoxia, characterized by quantitatively detecting in at least one biological sample of at least one tissue of a mammalian subject a plurality of asphyxia specific compounds having a molecular weight of less than 1500 Dalton, except lactate, comprising the steps of:
a) selecting said compounds;
b) measuring at least one of the parameters selected from the group consisting of: concentration, level or amount of each individual metabolite of said plurality of metabolites in said sample, qualitative and/or quantitative molecular pattern and/or molecular signature; and using and storing the obtained set of values in a database;
c) calibrating said values by comparing asphyxia-positive and/or asphyxia-negative reference parameters;
d) comparing said measured values in the sample with the calibrated values, in order to assess whether the patient is asphyxia-positive or asphyxia-negative.

The method according to WO 2010/128054 A1 uses asphyxia specific compounds as biomarkers which are endogenous compounds being selected from the group consisting of: biogenic amines; carnitine-derived compounds; amino acids; bile acids; carboxylic acids; eicosanoids; lipids; precursors of cholesterol, cholesterol metabolites, prostanoids; and sugars. Furthermore, WO 2010/128054 A1 relates to a method of in vitro estimating duration of hypoxia in a patient, a method for in vitro monitoring of normoxic, hypoxic and hyperoxic conditions and/or normobaric and hyperbaric oxygen therapy and a kit for carrying out the methods thereof.

However, neither assignment of metabolite concentrations to total brain damage or NE nor to distinct brain regions nor neurological outcome in neonates is addressed with the metabolomic studies disclosed in WO 2011/012553 A1 and WO 2010/128054 A1.

Solberg R and colleagues ("Metabolomic Analyses of Plasma Reveals New Insights into Asphyxia and Resuscitation in Pigs", PLoS ONE, 2010, 5(3)) disclose detection of a number of metabolites in plasma taken before and after hypoxia as well as after resuscitation, in asphyxiated piglets, in order to evaluate pathophysiological mechanisms of hypoxemia in newborns. Hypoxemia of different durations was induced in newborn piglets before randomization for resuscitation with 21% or 100% oxygen for 15 min in order to detect markers of the duration/severity of hypoxia and to detect markers of therapy response due to different resuscitation protocols. The metabolites of the study of Solberg et al. includes amino acids, particularly branched chained amino acids, metabolites of the Krebs cycle, including alpha-ketoglutarate, succinate and fumarate, biogenic amines, bile acids, prostaglandins, sphingolipids, glycerophospholipids, oxysterols and acylcarnitines. Assessment of brain injuries per se, or biomarkers to detect brain injuries per se are not comprised by the Solberg et al. paper (cf. page 9, left column, lines 2-3), and identification or differentiation of brain areas or tissues or assessment of neurological outcome is not addressed.

Beckstrom et al. (J ChromatogrA, 2011 Vol 1218, 1899-1906) evaluated whether metabolomic profiling can reveal metabolite changes in plasma after asphyxia in a *Macaca nemestrina* model of perinatal asphyxia. The metabolic profile of post-asphyxia samples showed marked variability compared to the pre-asphyxia samples. This metabolomic analysis confirmed lactate and creatinine as markers of asphyxia and discovered new metabolites including succinic acid and malate (intermediates in the Krebs cycle) and arachidonic acid (a brain fatty acid and inflammatory marker). Although these metabolite changes reflect the changes of asphyxia (similarly to the publication of Solberg et. al.), the metabolite changes were not related to brain injury, to identification or differentiation of brain areas or tissues or assessment of neurological outcome.

Chu, C. Y et al. (Clinical Biochemistry, 2006, Vol 39, 203-209) describe metabolomic and bioinformatic analyses in asphyxiated neonates. In particular they analyzed urine of such neonates and defined eight urinary organic acids which were significantly associated with the prognosis of neurodevelopmental handicap with high sensitivity and specificity. They further divided said acids into two classes of acids, one consisting of acids which were associated with good neonatal outcome (ethylmalonate, 3-hydroxy-3-methylglutarate, 2-hydroxyglutarate, 2-oxogluturate) and the other with poor outcome (glutarate, methylmalonate, 3-hydroxybutyrate, orotate). No blood samples were analyzed; nor were said urinary metabolites or combinations thereof correlated to brain injury, injured areas of the brain or any neurological behaviour scoring. However all of these metabolites we determined only in urine samples, and, moreover, not within the first hours of life.

Finally, Mueller et. al. ("Mass Spectrometric Quantifications of Organic Acids and Acylcarnitines in Early Random Urine Specimens of Newborns with Perinatal Complications: Feasability Study for the Prediction of the Neuro-Developmental Outcome", The Internet Journal of Pediatrics and Neonatology, 20077(2)) describe the use of mass spectrometric quantifications of organic acids and acylcarnitines for the prediction of the neuro-developmental outcome in newborns with perinatal complications. This group investigated a number of 65 quantitatively determined metabolites (42 organic acids, 22 acylcarnitines, free carnitine and 15 ratios) in urine of infants within the first 72 hours of life of infants. Reliable prediction for development of NE caused by severe asphyxia was demonstrated with metabolite monitoring of the lactic acid/creatinine ratio in urine of asphyxiated newborns. However, an unexpected result of the Mueller et al. study was the finding that the total amount of urinary acylcarnitines did not significantly differ between the comparison group and the patient group with severe neurological defects. Blood metabolite concentration changes related to brain injury, to identification or differentiation of brain areas or tissues, or assessment of neurological outcome were not described. Müller et al. observed a limited number of metabolic carboxylic acid combinations for predicting the neurological outcome of preterm and term newborns at the end of the first year of life. Said metabolite combinations comprise lactic acid in combination with one or more of 3-hydroxybutyric acid, 3-hydroxyisovaleric acid, methylmalonic acid, 4-hydroxyphenyllactic acid, and 5-oxoproline. Again, all of these metabolites we determined only in urine samples, and, moreover, not within the first hours of life.

In summary so far no metabolic markers or marker signatures have been identified for indicating and diagnosing NE at a time point as early as possible (defined as within the first 6 hours after the insult) in infants. No teaching is found in the prior art suggesting that there might exist markers applicable to the identification of neonatal encephalopathy and/or differentiation of brain tissues altered by hypoxic conditions. Solely a couple of intermediates, possibly involved in pathobiochemistry, have been discussed in the wider context of brain damage and chemical mediators that may contribute to gray matter injury.

Thus, the problem underlying the present invention is to provide an early diagnostic approach for assessing NE in infants with high sensitivities and specificities, capable of determining brain tissues involved and/or brain tissues damaged and/or prone to subsequent future damage and/or predict neurological outcome.

SUMMARY OF THE INVENTION

Given the remarkable and rapid potential of NE in infants to progress into an irreversible and/or life-threatening condition, the current situation is highly problematic and unsatisfying. An early and reliable multi-parameter diagnosis in small sample sizes for identification of patients with potential NE, identification of respective brain tissues affected and/or adverse neurological outcome is highly valuable since treatment (induced therapeutic hypothermia) is available and its efficiency increases the earlier the therapy is initiated. Early diagnosis as defined here includes diagnosis within the first 6 hours after birth and the therapeutic time window to start hypothermia is 6 hours.

The above mentioned problems are solved by the embodiments as defined in the attached claims.

As will be explained in more detail below, the present invention relates to markers of NE, in particular of brain injury and neurological behavioural outcome in infants, its severity and distribution (affected brain areas). In particular embodiments, the present invention provides metabolites that are differentially present in infants affected by NE. The present invention also identifies a series of metabolites (or signatures of metabolites) as being differentially present in subjects depending on the severity of brain injury in basal ganglia, hippocampus or other distinct brain tissues and neurological outcome.

The present invention thus provides a solution to the aforementioned diagnostic problems based on the application of a new technology in this context and on previously unknown lists of endogenous metabolites as diagnostic marker for the identification NE and of affected brain tissues. Since metabolite concentration differences in biological fluids and tissues provide links to the various phenotypical responses, metabolites are suitable biomarker candidates.

The present invention allows for an early accurate, rapid, and sensitive prediction and diagnosis of NE in infants with an assignment of damage to distinct brain tissues and assessment of neurological outcome, in particular but not limited to hippocampus and basal ganglia through a measurement of a plurality (2 or more) of endogenous metabolic biomarker (metabolites) taken from a biological sample at a single point in time.

This is accomplished by obtaining a biomarker panel at a single point in time from an individual, particularly an individual at risk of developing brain injury, infants having brain injury, or suspected of having brain injury, and comparing the biomarker profile from the individual to reference biomarker values or scores. The reference biomarker values may be obtained from a population of individuals (a "reference population") who are, for example, afflicted with brain injury assigned to affected brain tissues, in particular hippocampus and basal ganglia, or who are suffering from brain injury assignable to distinct brain tissues or a particular stage in the progression of brain injury. If the biomarker panel values or score from the individual contains appropriately characteristic features of the biomarker values or scores from the reference population, then the individual is diagnosed as being likely of having or developing brain injury assignable but not limited to damage of hippocampus and or basal ganglia brain tissues, as being afflicted with brain injury attributable but not limited to damage of hippocampus and/or basal ganglia brain tissues allowing also an assessment of neurological outcome.

Figure 1A:
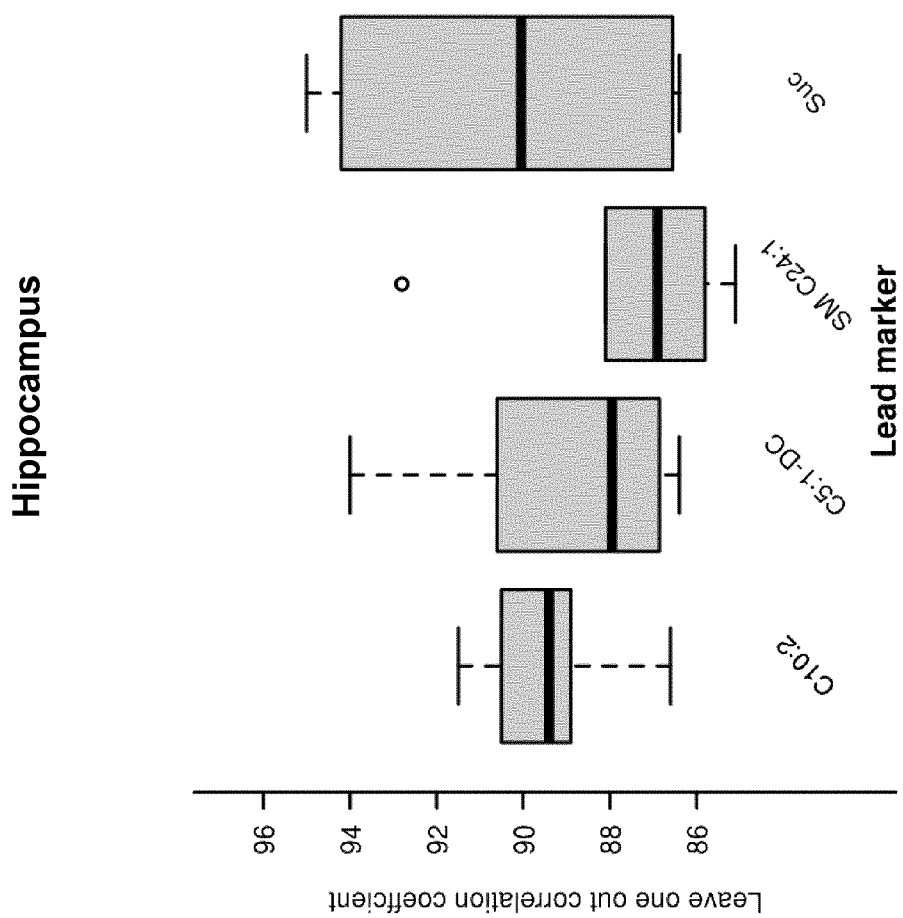
FIG. 1a illustrates the predictive abilities (i.e. accuracy) of the combination of metabolites based on a lead metabolite correlating with the extent of brain damage in the hippocampus. The box-and-whisker diagrams represent the distribution of the cross-validated correlation coefficient (y-axis) for combinations comprising a lead metabolite (x-axis) and up to 6 metabolites from the initial dataset.

DETAILED DESCRIPTION OF THE INVENTION a) Definitions

"Neonatal encephalopathy" (or NE) in the context of the present invention is defined as disturbed neurological function in the earliest days of life in the newborn infant resulting in long-term adverse neurological, psychological and neurobehavioral adverse outcome. NE can result from a wide variety of conditions and often remains unexplained. Given that the underlying nature of brain injury causing neurologic impairment in a newborn is often poorly understood, NE has emerged as the preferred terminology to describe central nervous system dysfunction in the newborn period, as it does not imply a specific underlying pathophysiology.

"Brain injury" or "brain damage" in the context of the present invention is defined as the occurrence of increased cell death by apoptosis and necrosis in any brain area of any cell type and abnormal neuronal function and network compared to healthy controls. Brain injury is assessed with the aEEG for both EEG pattern and epileptic activity, with a clinical neurological score, by histology (haematoxylin and eosin staining) and for caspase-3 activity in 4 cortical areas.

Unless otherwise stated the short names of chemical compounds as used herein shall have the following meanings which can be taken from subsequent Table 1:

TABLE 1

Short names of chemical compounds (metabolites or metabolic markers) as analysed in the context of the present invention

| Short Name | Common name | Chemical class | Chemical class short | Potential CAS-Numb |
|---|---|---|---|---|
| alpha-KGA | alpha-Ketoglutaric acid | dicarboxylic acids | En.Met | 328-50-7 |
| Fum | Fumaric acid | dicarboxylic acids | En.Met | 110-17-8; 110-16-7 |
| Hex-P | Hexosephosphate (e.g. | sugars | En.Met | 56-73-5; 643-13-0; 59-56-3; 3672-15- |

TABLE 1-continued

Short names of chemical compounds (metabolites or metabolic markers)
as analysed in the context of the present invention

| Short Name | Common name | Chemical class | Chemical class short | Potential CAS-Numb |
|---|---|---|---|---|
| | Glucose-1-phosphate + Glucose-6-phosphate + Fructose-6-phosphate) | | | 9; 2255-14-3; 27251-84-9; 55607-88-0; 15978-08-2; 53798-20-2; 19046-69-6; 2255-14-3 |
| Lac | Lactate | sugars | En.Met | 79-33-4; 10326-41-7; 503-66-2; 50-21-5 |
| Pent-P | Pentosephosphate (e.g. Ribose-5-phosphate + Ribulose-5-phosphate) | sugars | En.Met | 3615-55-2; 4300-28-1; 4151-19-3; 14075-00-4; 13137-52-5 |
| OAA | Pyruvate + Oxaloacetate | carboxylic acids | En.Met | 328-42-7 |
| Suc | Succinic acid | dicarboxylic acids | En.Met | 110-15-6 |
| C0 | Carnitine (free) | acylcarnitines | Ac.Ca. | 541-14-0; 541-15-1; 406-76-8 |
| C10 | Decanoylcarnitine [Caprylcarnitine] (Fumarylcarnitine) | acylcarnitines | Ac.Ca. | 1492-27-9 |
| C10:2 | Decadienoylcarnitine | acylcarnitines | Ac.Ca. | |
| C12 | Dodecanoylcarnitine [Laurylcarnitine] | acylcarnitines | Ac.Ca. | 25518-54-1 |
| C14:1 | Tetradecenoylcarnitine [Myristoleylcarnitine] | acylcarnitines | Ac.Ca. | 835598-21-5 |
| C14:1-OH | 3-Hydroxytetradecenoylcarnitine [3-Hydroxymyristoleylcarnitine] | acylcarnitines | Ac.Ca. | |
| C14:2 | Tetradecadienoylcarnitine | acylcarnitines | Ac.Ca. | |
| C14:2-OH | 3-Hydroxytetradecadienoylcarnitine | acylcarnitines | Ac.Ca. | |
| C16 | Hexadecanoylcarnitine [Palmitoylcarnitine] | acylcarnitines | Ac.Ca. | 1935-18-8; 2364-66-1; 2364-67-2 |
| C16:2 | Hexadecadienoylcarnitine | acylcarnitines | Ac.Ca. | |
| C18 | Octadecanoylcarnitine [Stearylcarnitine] | acylcarnitines | Ac.Ca. | 1976-27-8 |
| C18:1 | Octadecenoylcarnitine [Oleylcarnitine] | acylcarnitines | Ac.Ca. | 13962-05-5 |
| C18:1-OH | 3-Hydroxyoctadecenoylcarnitine] [3-Hydroxyoleylcarnitine] | acylcarnitines | Ac.Ca. | |
| C18:2 | Octadecadienoylcarnitine [Linoleylcarnitine] | acylcarnitines | Ac.Ca. | 36816-10-1 |
| C2 | Acetylcarnitine | acylcarnitines | Ac.Ca. | 4398-79-2; 870-77-9; 14992-62-2 |
| C3 | Propionylcarnitine | acylcarnitines | Ac.Ca. | 113817-31-5; 17298-37-2 |
| C3-DC (C4-OH) | 3-Hydroxybutyrylcarnitine/ Malonylcarnitine | acylcarnitines | Ac.Ca. | |
| C5-OH (C3-DC-M) | 3-Hydroxyisovalerylcarnitine/ 3-Hydroxy-2-methylbutyryl | acylcarnitines | Ac.Ca. | |
| C4 | Butyrylcarnitine/ Isobutyrylcarnitine | acylcarnitines | Ac.Ca. | 25518-49-4; 25576-40-3 |
| C4:1 | Butenoylcarnitine | acylcarnitines | Ac.Ca. | |
| C5 | Isovalerylcarnitine/2-Methylbutyrylcarnitine/ Valerylcarnitine | acylcarnitines | Ac.Ca. | 31023-24-2; 31023-25-3 |
| C5:1 | Tiglylcarnitine/3-Methyl-crotonylcarnitine | acylcarnitines | Ac.Ca. | 64191-86-2 |
| C5:1-DC | Glutaconylcarnitine/ Mesaconylcarnitine (Undecanoylcarnitine) | acylcarnitines | Ac.Ca. | |
| C5-DC (C6-OH) | Glutarylcarnitine | acylcarnitines | Ac.Ca. | |
| C6:1 | Hexenoylcarnitine | acylcarnitines | Ac.Ca. | |
| C6 (C4:1-DC) | Hexanoylcarnitine [Caproylcarnitine] | acylcarnitines | Ac.Ca. | 6920-35-0; 14919-34-7 |
| C8:1 | Octenoylcarnitine | acylcarnitines | Ac.Ca. | |
| C9 | Nonanoylcarnitine [Pelargonylcarnitine] | acylcarnitines | Ac.Ca. | |

TABLE 1-continued

Short names of chemical compounds (metabolites or metabolic markers) as analysed in the context of the present invention

| Short Name | Common name | Chemical class | Chemical class short | Potential CAS-Numb |
|---|---|---|---|---|
| H1 | Hexoses | sugars | En.Met | 57-48-7; 59-23-4; 4205-23-6; 2152-76-3; 87-81-0; 7635-11-2; 15572-79-9; 5934-56-5; 87-79-6; 23567-25-1; 10030-80-5; 10030-80-5; 6027-89-0; 921-60-8; 7776-48-9; 1949-88-8; 19163-87-2; 3615-56-3; 551-68-8; 1990-29-0; 50-99-7; 530-26-7; 492-61-5; 87-79-6; 492-62-6; 59-23-4; 3615-56-3; 87-81-0; 7296-15-3; 7296-64-2; 3646-73-9 59-23-4; 23140-52-5; 2595-97-3; 2595-97-3; 7776-48-9; 15572-79-9; 53188-23-1; 1990-29-0; 4205-23-6; 5978-95-0; 2595-98-4; 2595-98-4; 551-68-8; 57-48-7; 6027-89-0 |
| SM C16:0 | sphingomyelin with acyl residue sum C16:0 | sphingolipids | S.L. | |
| SM C16:1 | sphingomyelin with acyl residue sum C16:1 | sphingolipids | S.L. | |
| SM C18:0 | sphingomyelin with acyl residue sum C18:0 | sphingolipids | S.L. | 58909-84-5 |
| SM C18:1 | sphingomyelin with acyl residue sum C18:1 | sphingolipids | S.L. | 108392-10-5 |
| SM C20:2 | sphingomyelin with acyl residue sum C20:2 | sphingolipids | S.L. | |
| SM C24:0 | sphingomyelin with acyl residue sum C24:0 | sphingolipids | S.L. | |
| SM C24:1 | sphingomyelin with acyl residue sum C24:1 | sphingolipids | S.L. | |
| SM C26:0 | sphingomyelin with acyl residue sum C26:0 | sphingolipids | S.L. | |
| SM C26:1 | sphingomyelin with acyl residue sum C26:1 | sphingolipids | S.L. | |
| SM (OH) C14:1 | Hydroxysphingomyelin with acyl residue sum C14:1 | sphingolipids | S.L. | |
| SM (OH) C16:1 | Hydroxysphingomyelin with acyl residue sum C16:1 | sphingolipids | S.L. | |
| SM (OH) C22:1 | Hydroxysphingomyelin with acyl residue sum C22:1 | sphingolipids | S.L. | |
| SM (OH) C22:2 | Hydroxysphingomyelin with acyl residue sum C22:2 | sphingolipids | S.L. | |
| SM (OH) C24:1 | Hydroxysphingomyelin with acyl residue sum C24:1 | sphingolipids | S.L. | |
| Ala | Alanine | aminoacids | Am.Ac. | 56-41-7; 107-95-9; 338-69-2; 302-72-7 |
| Arg | Arginine | aminoacids | Am.Ac. | 74-79-3; 157-06-2; 7200-25-1 |
| Asn | Asparagine | aminoacids | Am.Ac. | 70-47-3; 2058-58-4; 3130-87-8 |
| Asp | Aspartic acid | aminoacids | Am.Ac. | 56-84-8; 1783-96-6; 617-45-8 |
| Cit | Citrulline | aminoacids | Am.Ac. | 627-77-0; 372-75-8 |
| Gln | Glutamine | aminoacids | Am.Ac. | 56-85-9; 6899-04-3; 5959-95-5 |
| Glu | Glutamate | aminoacids | Am.Ac. | 56-86-0; 6893-26-1; 617-65-2 |
| Gly | Glycine | aminoacids | Am.Ac. | 56-40-6 |
| His | Histidine | aminoacids | Am.Ac. | 71-00-1; 4998-57-6; 351-50-8 |
| Ile | Isoleucine | aminoacids | Am.Ac. | 73-32-5; 1509-34-8; 319-78-8; 1509-35-9; 443-79-8 |
| Leu | Leucine | aminoacids | Am.Ac. | 40469-85-0; 5699-54-7; 61-90-5; 328-38-1; 75992-50-6; 328-39-2 |
| Lys | Lysine | aminoacids | Am.Ac. | 56-87-1; 923-27-3; 70-54-2 |
| Met | Methionine | aminoacids | Am.Ac. | 63-68-3; 348-67-4; 59-51-8 |
| Orn | Ornithine | aminoacids | Am.Ac. | 70-26-8; 348-66-3; 616-07-9 |
| Phe | Phenylalanine | aminoacids | Am.Ac. | 63-91-2; 150-30-1; 673-06-3 |
| Pro | Proline | aminoacids | Am.Ac. | 147-85-3; 344-25-2; 609-36-9 |
| Ser | Serine | aminoacids | Am.Ac. | 56-45-1; 302-84-1; 312-84-5 |
| Thr | Threonine | aminoacids | Am.Ac. | 80-68-2; 72-19-5; 632-20-2; 28954-12-3; 24830-94-2 |
| Trp | Tryptophane | aminoacids | Am.Ac. | 73-22-3; 153-94-6; 54-12-6 |
| Tyr | Tyrosine | aminoacids | Am.Ac. | 60-18-4; 556-03-6; 556-02-5 |
| Val | Valine | aminoacids | Am.Ac. | 72-18-4; 640-68-6; 516-06-3 |
| Ac-Orn | N-acetylornithine | biogenic amines | B.Am. | 6205-Aug-09 |
| ADMA | Asymmetric dimethylarginine | biogenic amines | B.Am. | 102783-24?-4; 30315-93-6 |
| alpha-AAA | 2-Aminoadipic acid | biogenic amines | B.Am. | 7620-28-2; 542-32-5; 1118-90-7 |
| Carnosine | Carnosine | biogenic amines | B.Am. | 7683-28-5; 305-84-0 |
| Creatinine | Creatinine | biogenic amines | B.Am. | 60-27-5 |
| Histamine | Histamine | biogenic amines | B.Am. | 51-45-6 |
| Kynurenine | Kynurenine | biogenic amines | B.Am. | 13441-51-5; 2922-83-0; 343-65-7 |
| Met-SO | Methionine-Sulfoxide | biogenic amines | B.Am. | 62697-73-8; 3226-65-1 |

TABLE 1-continued

Short names of chemical compounds (metabolites or metabolic markers) as analysed in the context of the present invention

| Short Name | Common name | Chemical class | Chemical class short | Potential CAS-Numb |
|---|---|---|---|---|
| Sarcosine | Sarcosine | biogenic amines | B.Am. | 107-97-1 |
| SDMA | Symmetric dimethylarginine | biogenic amines | B.Am. | |
| Serotonin | Serotonin | biogenic amines | B.Am. | 50-67-9 |
| Spermidine | Spermidine | biogenic amines | B.Am. | 124-20-9 |
| Taurine | Taurine | biogenic amines | B.Am. | 107-35-7 |
| total DMA | Total dimethylarginine | biogenic amines | B.Am. | 102783-24?-4; 30315-93-6 |
| 20a-OH-C | 20α-Hydroxycholesterol | oxysterols | O.St. | 516-72-3 |
| 22R-OH-C | 22-R-Hydroxycholesterol | oxysterols | O.St. | 22348-64-7 |
| 24,25-EpoxyC | 24,25-Epoxycholesterol | oxysterols | O.St. | 77058-74-3 |
| 24-DH-Lanosterol | 24-Dihydrolanosterol | oxysterols | O.St. | 79-62-9 |
| 24S-OH-C | 24-S-Hydroxycholesterol | oxysterols | O.St. | 474-73-7 |
| 25-OH-C | 25-Hydroxycholesterol | oxysterols | O.St. | 2140-46-7 |
| 27-OH-C | 27-Hydroxycholesterol | oxysterols | O.St. | 20380-11-4; 26259-77-8 |
| 5a,6a-EpoxyC | 5α,6α-Epoxycholesterol | oxysterols | O.St. | 1250-95-9 |
| Cholestenone | Cholestenone | oxysterols | O.St. | 601-57-0 |
| Desmosterol | Desmosterol | oxysterols | O.St. | 313-04-2 |
| 3b,5a,6b-THC | 3β,5α,6β-Trihydroxycholestan | oxysterols | O.St. | 1253-84-5 |
| 8-iso-PGF2a | 8-iso-Prostaglandin F2alpha | prostaglandins | P.G. | 27415-26-5 |
| AA | Arachidonic acid | prostaglandins | P.G. | 506-32-1 |
| DHA | Docosahexaenoic acid | prostaglandins | P.G. | 6217-54-5; 25167-62-8; 25377-50-8 |
| LTB4 | Leukotriene B4 | prostaglandins | P.G. | 71160-24-2; 73151-67-4; 71160-24-2 |
| TXB2 | Tromboxane B2 | prostaglandins | P.G. | 54397-85-2 |

En.Met. = Energy metabolite;
Ac.Ca. = Acyl carnitine;
S.L. = sphingolipid;
Am.Ac. = amiono acid;
B.Am. = biogenic amine;
O.St. = oxysterol;
P.G. = prostaglandin As used here, the term "metabolite" or "metabolic marker" or "low molecular weight metabolic marker" denotes endogenous organic compounds of a cell, an organism, a tissue or being present in body liquids, in particular blood, and in extracts or fractions obtained from the aforementioned sources. Typical examples of metabolites are carbohydrates, lipids, phospholipids, sphingolipids and sphingophospholipids, amino acids, cholesterol, steroid hormones and oxidized sterols and other compounds such as collected in the Human Metabolite database [Wishart D S et al., *HMDB: the Human Metabolome Database. Nucleic Acids Res.* 2007 January; 35 (Database issue):D521-6 (see http://www.hmdb.ca/)] and other databases and literature. This includes any substance produced by metabolism or by a metabolic process and any substance involved in metabolism. In particular, suitable metabolites are defined in above Table 1. More particular, they may have a molecular weight typically of up to 1500 Dalton, as for example in the range of 50 to 1500 Dalton.

More particularly the present invention also refers to "Hippocampus-specific" metabolites. They are listed in subsequent Table 2. These metabolites, individually or combinations of several of such metabolites, may be applied as markers for brain injury affecting the hippocampus of an infant.

TABLE 2

"Hippocampus-specific" metabolites

| No | Short name | Full name | Contribution |
|---|---|---|---|
| 1 | Lac | Lactate | + |
| 2 | Fum | Fumaric acid | + |
| 3 | Ac-Orn | N-acetylornithine | + |
| 4 | Carnosine | Carnosine | − |
| 5 | C5:1-DC | Glutaconylcarnitine/Mesaconylcarnitine (Undecanoylcarnitine) | + |
| 6 | C16:2 | Hexadecadienoylcarnitine | + |
| 7 | Pent-P | Pentosephosphate (e.g. Ribose-5-phosphate + Ribulose-5-phosphate) | + |
| 8 | C10:2 | Decadienoylcarnitine | − |
| 9 | Met-SO | Methionine-Sulfoxide | + |
| 10 | SM (OH) C22:2 | Hydroxysphingomyelin with acyl residue sum C22:2 | − |
| 11 | SM C24:1 | sphingomyelin with acyl residue sum C24:1 | − |
| 12 | ADMA | Asymmetric dimethylarginine | + |
| 13 | C5:1 | Tiglylcarnitine/3-Methyl-crotonylcarnitine | − |
| 14 | 3b,5a,6b-THC | 3β,5α,6β-Trihydroxycholestan | + |
| 15 | 27-OH-C | 27-Hydroxycholesterol | + |

TABLE 2-continued

"Hippocampus-specific" metabolites

| No | Short name | Full name | Contribution |
|---|---|---|---|
| 16 | Suc | Succinic acid | + |
| 17 | 8-iso-PGF2a | 8-iso-Prostaglandin F2alpha | + |
| 18 | total DMA | Total dimethylarginine | + |
| 19 | 25-OH-C | 25-Hydroxycholesterol | + |
| 20 | SM (OH) C22:1 | Hydroxysphingomyelin with acyl residue sum C22:1 | − |
| 21 | Creatinine | Creatinine | − |
| 22 | Phe | Phenylalanine | + |
| 23 | C4:1 | Butenoylcarnitine | − |
| 24 | LTB4 | Leukotriene B4 | + |
| 25 | 24S-OH-C | 24-S-Hydroxycholesterol | + |
| 26 | Orn | Ornithine | + |
| 27 | Cit | Citrulline | − |
| 28 | SM (OH) C14:1 | Hydroxysphingomyelin with acyl residue sum C14:1 | − |
| 29 | H1 | Hexoses | − |
| 30 | C8:1 | Octenoylcarnitine | − |
| 31 | 5a,6a-EpoxyC | 5α,6α-Epoxycholesterol | + |
| 32 | alpha-AAA | 2-Aminoadipic acid | + |
| 33 | Pro | Proline | + |
| 34 | Lys | Lysine | + |
| 35 | Arg | Arginine | + |
| 36 | SM C16:1 | sphingomyelin with acyl residue sum C16:1 | − |
| 37 | SDMA | Symmetric dimethylarginine | + |
| 38 | Met | Methionine | + |
| 39 | Gln | Glutamine | + |
| 40 | SM C26:1 | sphingomyelin with acyl residue sum C26:1 | − |
| 41 | SM C18:1 | sphingomyelin with acyl residue sum C18:1 | − |
| 42 | Hex-P | Hexosephosphate (e.g. Glucose-1-phosphate + Glucose-6-phosphate + Fructose-6-phosphate) | − |

Contribution:
+ = increased level/concentration versus control in case of damage of hippocampus
− = decreased level/concentration versus control in case of damage of hippocampus The present invention also refers to "Basal ganglia-specific" metabolites. They are listed in subsequent Table 3. These metabolites, individually or combinations of several of such metabolites, may be applied as markers for brain injury affecting basal ganglia of an infant.

TABLE 3

"Basal ganglia-specific" metabolites

| No | Short name | Full name | Contribution |
|---|---|---|---|
| 1 | Met | Methionine | + |
| 2 | SM (OH) C22:2 | Hydroxysphingomyelin with acyl residue sum C22:2 | − |
| 3 | SM (OH) C14:1 | Hydroxysphingomyelin with acyl residue sum C14:1 | − |
| 4 | Met-SO | Methionine-Sulfoxide | + |
| 5 | SM C16:1 | sphingomyelin with acyl residue sum C16:1 | − |
| 6 | SM (OH) C22:1 | Hydroxysphingomyelin with acyl residue sum C22:1 | − |
| 7 | Pro | Proline | + |
| 8 | Tyr | Tyrosine | + |
| 9 | Gln | Glutamine | + |
| 10 | SM C24:1 | sphingomyelin with acyl residue sum C24:1 | − |
| 11 | SM C24:0 | sphingomyelin with acyl residue sum C24:0 | − |
| 12 | SM C16:0 | sphingomyelin with acyl residue sum C16:0 | − |
| 13 | Orn | Ornithine | + |
| 14 | Ac-Orn | N-acetylornithine | + |
| 15 | Arg | Arginine | + |
| 16 | SM C18:1 | sphingomyelin with acyl residue sum C18:1 | − |
| 17 | alpha-KGA | alpha-Ketoglutaric acid | − |
| 18 | Trp | Tryptophane | + |
| 19 | SM (OH) C24:1 | Hydroxysphingomyelin with acyl residue sum C24:1 | − |
| 20 | SM (OH) C16:1 | Hydroxysphingomyelin with acyl residue sum C16:1 | − |
| 21 | Cholestenone | Cholestenone | − |
| 22 | C5:1-DC | Glutaconylcarnitine/Mesaconylcarnitine (Undecanoylcarnitine) | + |
| 23 | Lys | Lysine | + |
| 24 | Histamine | Histamine | − |
| 25 | His | Histidine | + |
| 26 | Lac | Lactate | + |
| 27 | Phe | Phenylalanine | + |
| 28 | C6:1 | Hexenoylcarnitine | + |
| 29 | SM C18:0 | sphingomyelin with acyl residue sum C18:0 | − |

TABLE 3-continued

"Basal ganglia-specific" metabolites

| No | Short name | Full name | Contribution |
|---|---|---|---|
| 30 | 20a-OH-C | 20α-Hydroxycholesterol | + |
| 31 | 24-DH-Lanosterol | 24-Dihydrolanosterol | − |
| 32 | Kynurenine | Kynurenine | + |
| 33 | Leu | Leucine | + |
| 34 | SM C20:2 | sphingomyelin with acyl residue sum C20:2 | − |
| 35 | Ala | Alanine | + |
| 36 | C14:1 | Tetradecenoylcarnitine [Myristoleylcarnitine] | − |
| 37 | LTB4 | Leukotriene B4 | + |
| 38 | Suc | Succinic acid | + |
| 39 | TXB2 | Tromboxane B2 | + |
| 40 | Fum | Fumaric acid | + |
| 41 | Gly | Glycine | + |
| 42 | 25-OH-C | 25-Hydroxycholesterol | − |
| 43 | SM C26:1 | sphingomyelin with acyl residue sum C26:1 | − |
| 44 | Ser | Serine | + |
| 45 | alpha-AAA | 2-Aminoadipic acid | + |
| 46 | 8-iso-PGF2a | 8-iso-Prostaglandin F2alpha | + |
| 47 | Val | Valine | + |
| 48 | Asn | Asparagine | + |
| 49 | Pent-P | Pentosephosphate (e.g. Ribose-5-phosphate + Ribulose-5-phosphate) | + |
| 50 | total DMA | Total dimethylarginine | + |
| 51 | Creatinine | Creatinine | |

Contribution:
+ = increased level/concentration versus control in case of damage of basal ganglia
− = decreased level/concentration versus control in case of damage of basal ganglia The present invention also refers to "Neurological behavioural score-specific" metabolites. They are listed in subsequent Table 4. These metabolites, individually or combinations of several of such metabolites, may be applied as markers for neurological behavioural deficits of an infant.

TABLE 4

"Neurological behavioural score-specific" metabolites

| No. | Short name | Full name | Contribution |
|---|---|---|---|
| 1 | 27-OH-C | 27-Hydroxycholesterol | + |
| 2 | Fum | Fumaric acid | + |
| 3 | Carnosine | Carnosine | − |
| 4 | total DMA | Total dimethylarginine | + |
| 5 | C5-DC (C6-OH) | Glutarylcarnitine | + |
| 6 | SDMA | Symmetric dimethylarginine | + |
| 7 | C5:1 | Tiglylcarnitine/3-Methyl-crotonylcarnitine | − |
| 8 | Met-SO | Methionine-Sulfoxide | + |
| 9 | C10:2 | Decadienoylcarnitine | − |
| 10 | SM (OH) C22:2 | Hydroxysphingomyelin with acyl residue sum C22:2 | − |
| 11 | C8:1 | Octenoylcarnitine | − |
| 12 | Phe | Phenylalanine | + |
| 13 | Ac-Orn | N-acetylornithine | + |
| 14 | SM (OH) C14:1 | Hydroxysphingomyelin with acyl residue sum C14:1 | − |
| 15 | 24,25-EpoxyC | 24,25-Epoxycholesterol | + |
| 16 | Tyr | Tyrosine | + |
| 17 | alpha-AAA | 2-Aminoadipic acid | + |
| 18 | C14:1 | Tetradecenoylcarnitine [Myristoleylcarnitine] | − |
| 19 | Pent-P | Pentosephosphate (e.g. Ribose-5-phosphate + Ribulose-5-phosphate) | + |
| 20 | C6 (C4:1-DC) | Hexanoylcarnitine [Caproylcarnitine] | − |
| 21 | SM C16:1 | sphingomyelin with acyl residue sum C16:1 | − |
| 22 | C14:1-OH | 3-Hydroxytetradecenoylcarnitine [3-Hydroxymyristoleylcarnitine] | − |
| 23 | SM C24:1 | sphingomyelin with acyl residue sum C24:1 | − |
| 24 | Cholestenone | Cholestenone | − |
| 25 | Lac | Lactate | + |
| 26 | 8-iso-PGF2a | 8-iso-Prostaglandin F2alpha | + |
| 27 | 3b,5a,6b-THC | 3β,5α,6β-Trihydroxycholestan | − |
| 28 | Suc | Succinic acid | + |
| 29 | C0 | Carnitine (free) | + |
| 30 | 24-DH-Lanosterol | 24-Dihydrolanosterol | − |
| 31 | Val | Valine | + |
| 32 | SM C16:0 | sphingomyelin with acyl residue sum C16:0 | − |
| 33 | C3-DC (C4-OH) | 3-Hydroxybutyrylcarnitine/Malonylcarnitine | + |

TABLE 4-continued

"Neurological behavioural score-specific" metabolites

| No. | Short name | Full name | Contribution |
|---|---|---|---|
| 34 | Lys | Lysine | + |
| 35 | Leu | Leucine | + |
| 36 | SM C26:0 | sphingomyelin with acyl residue sum C26:0 | + |
| 37 | Cit | Citrulline | + |
| 38 | LTB4 | Leukotriene B4 | + |
| 39 | 5a,6a-EpoxyC | 5α,6α-Epoxycholesterol | − |
| 40 | C4:1 | Butenoylcarnitine | − |
| 41 | Met | Methionine | + |
| 42 | C5:1-DC | Glutaconylcarnitine/Mesaconylcarnitine (Undecanoylcarnitine) | + |
| 43 | Pro | Proline | + |
| 44 | SM (OH) C16:1 | Hydroxysphingomyelin with acyl residue sum C16:1 | − |
| 45 | C14:2-OH | 3-Hydroxytetradecadienoylcarnitine | + |
| 46 | Thr | Threonine | + |
| 47 | SM (OH) C22:1 | Hydroxysphingomyelin with acyl residue sum C22:1 | − |

Contribution:
+ = increased level/concentration versus control in case of neurological behavioural deficits
− = decreased level/concentration versus control in case of neurological behavioural deficits "Metabolomics" as understood within the scope of the present invention designates the comprehensive qualitative, or in particular quantitative measurement of several metabolites as defined herein; in particular by, but not limited to, analytical methods such as mass spectrometry, coupling of liquid chromatography, gas chromatography and other separation methods, like chromatography with mass spectrometry.

The term "metabolism" refers to the chemical changes that occur within the tissues of an organism, including "anabolism" and "catabolism". Anabolism refers to biosynthesis or the buildup of molecules and catabolism refers to the breakdown of molecules.

A "biomarker" in this context is a characteristic, comprising concentration data of at least two, as for example 2, 3, 4, 5, 6, 7, 8, 9 or 10, metabolites (also designated as a "panel" of metabolites, "signature" of metabolites, "model" or "profile" using quantitative data or concentration data directly or processed by any mathematical transformation (e.g. by a classification method) and evaluated as an indicator of biologic processes, pathogenic processes, or responses to a therapeutic intervention associated with NE in infants.

A "score" in the context of the invention denotes a value, in particular a quantitative value, generated from metabolite data by means of any mathematical transformation or by subjecting to any mathematical equation and comparing these data to data or mathematically transformed or processed data of a reference population.

The "onset of NE in infants" refers to an early stage of NE in infants, i.e., prior to a stage when the clinical manifestations are sufficient to support a clinical suspicion of brain injury in infants. The exact mechanism by which a patient acquires NE in infants is not a critical aspect of the invention. The methods of the present invention can detect changes in the biomarker score independent of the origin of the brain injury in infants. Regardless of how NE in infants arises (as for example by asphyxia, hypoxia and/or ischemia), the methods of the present invention allow for determining the status of a patient having, or suspected of having, NE, as classified by previously used criteria.

"Specific" in the context of "specific metabolites" as used above may not necessarily be understood as if said metabolite is exclusively detected in or associated with a certain disease or damage. However, changes in level or concentration of said metabolite when a certain disease or damage emerges may be more significant than in another type of disease or damage.

As used herein, the term "NE in infants-specific metabolite" refers to metabolites that are differentially present or differentially concentrated in an infant suffering from NE compared to healthy infant.

A "specific metabolite" or "NE in infants-specific metabolite" is preferably differentially present at a level that is statistically significant (e.g., an adjusted p-value less than 0.05 as determined using either linear model including Analysis of Variance and Welch's t-test or its non parametric equivalent versions). Exemplary NE in infants-specific metabolites are described herein.

"NE in infants-specific" metabolites encompass the groups of "hippocampus-specific" (or "hippocampus damage-specific"), "basal-ganglia-specific" (or "basal ganglia damage-specific") or "Neurological behavioural score-specific" metabolites (see Tables 2, 3 and 4).

The term "differentially present" or "differentially concentrated" describes the situation that a metabolite is present in increased or decreased level or concentration in a sample obtained from an NE patient if compared to level or concentration of said metabolite observed for one or more otherwise healthy individuals, i.e. not suffering from NE.

A "biological sample" may contain any biological material suitable for detecting the desired biomarkers, and may comprise cellular and/or non-cellular material from a subject. The sample can be isolated from any suitable biological tissue or body fluid such as, for example, tissue, and, in particular, blood. "Blood" as used herein encompassed whole blood, blood plasma, and blood serum. The sample, like blood samples, may be analyzed without or after a pre-treatment. Examples of pre-treated blood samples are pre-treated blood, like EDTA-blood, or EDTA-plasma, citrate-plasma, heparin plasma. The originally obtained (blood) samples or fractions thereof may be further modified by methods known in the art, as for example by fractionation or dilution. Fractionation may be performed to remove constituents which might disturb the analysis. Dilution may be performed by mixing the original (blood) sample or fraction with a suitable sample liquid, like a suitable buffer, in order to adjust the concentration the constituents, as for example of the analyte. Such modified (blood) samples exemplify samples "derived from" the original body fluid sample collected or isolated from the body of the individual.

A "reference level" of a metabolite means a level of the metabolite that is indicative of a particular disease state, phenotype, or lack thereof, as well as combinations of disease states, phenotypes, or lack thereof. A "positive" reference level of a metabolite means a level that is indicative of a particular disease state or phenotype. A "negative" reference level of a metabolite means a level that is indicative of a lack of a particular disease state or phenotype. For example, a "NE in infants-positive reference level" of a metabolite means a level of a metabolite that is indicative of a positive diagnosis of NE in infants in a subject, and a "NE in infants-negative reference level" of a metabolite means a level of a metabolite that is indicative of a negative diagnosis of NE in infants in a subject. A "reference level" of a metabolite may be an absolute or relative amount or concentration of the metabolite, a presence or absence of the metabolite, a range of amount or concentration of the metabolite, a minimum and/or maximum amount or concentration of the metabolite, a mean amount or concentration of the metabolite, and/or a median amount or concentration of the metabolite; and, in addition, "reference levels" of combinations of metabolites may also be ratios of absolute or relative amounts or concentrations of two or more metabolites with respect to each other or a composed value/score obtained by a statistical model.

As used herein, the term "processor" refers to a device that performs a set of steps according to a program (e.g., a digital computer). Processors, for example, include Central Processing Units ("CPUs"), electronic devices, or systems for receiving, transmitting, storing and/or manipulating data under programmed control.

As used herein, the term "memory device," or "computer memory" refers to any data storage device that is readable by a computer, including, but not limited to, random access memory, hard disks, magnetic (floppy) disks, compact discs, DVDs, magnetic tape, flash memory, and the like.

"Mass Spectrometry" (MS) is a technique for measuring and analysing molecules that involves fragmenting a target molecule, then analysing the fragments, based on their mass/charge ratios, to produce a mass spectrum that serves as a "molecular fingerprint". Determining the mass/charge ratio of an object is done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain definitive identifications of target molecules.

The term "separation" refers to separating a complex mixture into its component proteins or metabolites. Common laboratory separation techniques include gel electrophoresis and chromatography.

The term "capillary electrophoresis" refers to an automated analytical technique that separates molecules in a solution by applying voltage across buffer-filled capillaries.

Capillary electrophoresis is generally used for separating ions, which move at different speeds when the voltage is applied, depending upon the size and charge of the ions. The solutes (ions) are seen as peaks as they pass through a detector and the area of each peak is proportional to the concentration of ions in the solute, which allows quantitative determinations of the ions.

The term "chromatography" refers to a physical method of separation in which the components to be separated are distributed between two phases, one of which is stationary (stationary phase) while the other (the mobile phase) moves in a definite direction. Chromatographic output data may be used for manipulation by the present invention.

A "mass spectrum" is a plot of data produced by a mass spectrometer, typically containing m/z values on x-axis and intensity values on y-axis.

A "peak" is a point on a mass spectrum with a relatively high y-value.

The term "m/z" refers to the dimensionless quantity formed by dividing the mass number of an ion by its charge number. It has long been called the "mass-to-charge" ratio.

As used herein, the terms "detect", "detecting", or "detection" may describe either the general act of discovering or discerning or the specific observation of a detectable compound or composition or metabolite or biomarker.

"Assessing" or "assessment" is intended to include both quantitative and qualitative determination in the sense of obtaining an absolute value for the amount or concentration of the metabolite or metabolites to be analyzed present in the sample, and also obtaining an index, ratio, percentage or other value indicative of the level of metabolite in the sample. Assessment may be direct or indirect and the chemical species actually detected need not of course be the analyte itself but may for example be a derivative thereof. The purpose of such assessment of metabolite(s) may be different. In particular, an assessment may be performed for evaluating the likelihood (or risk) of brain damage or encephalopathy to occur in a patient. Purpose of an assessment may also be the determination of the severity (severity assessment) of brain damage or encephalopathy (optionally already diagnosed) and long-term neurological outcome in a patient. Assessment also encompasses the analysis of progression or regression of brain damage or encephalopathy. Assessment in the context of the invention also encompasses identification and/or differentiation of brain areas (as, for example, hippocampus and basal ganglia) affected (optionally to a different extent) by said damage.

Unless otherwise stated, the expression "patient" refers in particular to a "neonatal" patient, in particular pre-term born, or term born baby.

As used herein, the term "clinical failure" refers to a negative outcome following NE treatment in infants.

"Accuracy" or "predictive ability" as used herein is, unless otherwise stated, as defined in the experimental section, below.

b) Particular Embodiments of the Invention

The present invention refers to the following particular embodiments:
1. An in vitro or in vivo diagnostic method for early assessing encephalopathy, in particular NE in a mammalian patient, which method comprises
   a) optionally obtaining a blood sample, as for example whole blood, serum or plasma sample, of said patient and
   b) assessing in said blood sample at least one, like 1 to 100, 1 to 50, 1 to 25, 1 to 10 or 2, 3, 4, 5 or 6 panels (models) of low molecular weight endogenous early metabolic markers indicative of and/or specific for the presence or absence, in particular presence, of encephalopathy, in particular NE, in said patient.

Said assessment may also comprise the differentiation between affected (damaged) and non-affected (non-damaged) brain areas and/or may comprise predicting the neurological behavioural outcome of the patient.

In vitro methods usually do not encompass step a) while in vivo methods of the invention may comprise said step a) and/or another method step performed to the patient.
2. The method of embodiment 1, wherein said mammalian patient is a human neonate.
3. The method of embodiment 1, wherein said human neonate is suspected to suffer from a NE.
4. The method of one of the embodiments 2 and 3, wherein said blood sample is obtained immediately, at an early as possible stage, in particular 1 minute to 6 hours, like 2 to 180 or 5 to 120 minutes after birth or after initiating resuscitation or suspicion of NE.
5. The method of one of the preceding embodiments, wherein said brain injury predominantly affects one or more specific brain areas, in particular basal ganglia and/or the hippocampus of the neonatal brain and/or causes behavioural deficits of the child.
6. The method of one of the preceding embodiments, wherein said panel of low molecular early metabolic markers indicative of the presence of NE comprises at least 2, like 2, 3, 4, 5, 6, or 7, different metabolites selected from at least one of the following classes of chemical substances:
   a) low molecular organic carboxylic acids, like saturated or non-saturated mono- or polyvalent $C_1$-$C_{20}$- or $C_2$-$C_{10}$-carboxylic acids, in particular mono- or dicarboxylic acids, optionally substituted by one or more hydroxy or keto-groups; their salts, ester or anhydrides;
   b) sugars, like pentoses and hexoses, and phosphate derivatives thereof,
   c) acylcarnitines,
   d) sphingomyelins,
   e) amino acids,
   f) biogenic amines
   g) oxysterols, and
   h) prostaglandins
7. The method of one of the preceding embodiments, wherein said panel (model) of low molecular early metabolic markers indicative of the presence of NE comprises at least 2, like 2, 3, 4, 5, 6, or 7, metabolites selected from at least one of the following functional classes of metabolites
   a) energy metabolism related metabolites indicating the occurrence of or the previous lack of oxygen
   b) metabolite markers of oxidative stress and anti-oxidative capacities
   c) metabolite with neurotoxic or neuroprotective potential,
   d) metabolite markers predominantly occurring in the brain.
8. The method of one of the preceding embodiments, wherein said panel (model) is indicative of the presence of NE with high statistic significance, as for example with an accuracy of at least 75, in particular at least about 80, as for example at least about 85, 90, 91, 92, 93, 94, 95, 96, 97, 98 or 99, as, for example, determined in a non-human animal model (for example piglet animal model).
9. The method of one of the preceding embodiments, wherein said chemical classes of metabolites comprise the following individual members:
   a) low molecular weight organic carboxylic acids, selected from dicarboxylic acids, like alpha-ketoglutaric acid, fumaric acid and succinic acid, and monocarboxylic acids, like lactic acid, pyruvic acid and oxaloacetic acid; in particular lactic acid
   b) sugars, selected from like hexoses and hexosephosphates, like glucose-1-phosphate, glucose-6-phosphate, fructose-6-phosphate and pentose phospates, like ribose-5-phosphate and ribulose-5-phosphate;
   c) acylcarnitines, like carnitine (free), decanoylcarnitine, decadienoylcarnitine, dodecanoylcarnitine, tetradecenoylcarnitine, 3-hydroxytetradecenoylcarnitine, tetradecadienoylcarnitine, 3-hydroxytetradecadienoylcarnitine, hexadecanoylcarnitine, hexadecadienoylcarnitine, octadecanoylcarnitine, octadecenoylcarnitin, 3-hydroxyoctadecenoylcarnitine, octadecadienoylcarnitine, acetylcarnitine, propionylcarnitine, 3-hydroxybutyrylcarnitine, malonylcarnitine, 3-hydroxyisovalerylcarnitine (3-hydroxy-2-methylbutyrylcarnitine), butyrylcarnitine, isobutyrylcarnitine, butenoylcarnitine, isovalerylcarnitine, 2-methylbutyrylcarnitine, valerylcarnitine, tiglylcarnitine, 3-methyl-crotonylcarnitine, glutaconylcarnitine, mesaconylcarnitine (undecanoylcarnitine), glutarylcarnitine, hexenoylcarnitine, hexanoylcarnitine, octenoylcarnitine and nonanoylcarnitine; in particular, carnitine (free), decadienoylcarnitine, tetradecenoylcarnitine, 3-hydroxytetradecenoylcarnitine, tetradecadienoylcarnitine, 3-hydroxytetradecadienoylcarnitine, hexadecadienoylcarnitine, 3-hydroxybutyrylcarnitine, 3-hydroxyisovalerylcarnitine (3-hydroxy-2-methylbutyrylcarnitine), butenoylcarnitine, tiglylcarnitine, glutaconylcarnitine, mesaconylcarnitine (undecanoylcarnitine), glutarylcarnitine, hexenoylcarnitine, hexanoylcarnitine, octenoylcarnitine
   d) sphingomyelins, like sphingomyelin with acyl residue sum C16:0, sphingomyelin with acyl residue sum C16:1, sphingomyelin with acyl residue sum C18:0, sphingomyelin with acyl residue sum C18:1, sphingomyelin with acyl residue sum C20:2, sphingomyelin with acyl residue sum C24:0, sphingomyelin with acyl residue sum C24:1, sphingomyelin with acyl residue sum C26:0 and sphingomyelin with acyl residue sum C26:1, hydroxysphingomyelin with acyl residue sum C14:1, hydroxysphingomyelin with acyl residue sum C16:1, hydroxysphingomyelin with acyl residue sum C22:1, hydroxysphingomyelin with acyl residue sum C22:2, hydroxysphingomyelin with acyl residue sum C24:1;
   e) amino acids, like alanine, arginine, asparagine, aspartic acid, citrulline, glutamine, glutamate, glycine, histidine, isoleucine, leucine, lysine, methionine, ornithine, phenylalanine, proline, serine, threonine, tryptophane, tyrosine and valine; in particular, alanine, arginine, asparagine, citrulline, glutamine, glycine, histidine, leucine, lysine, methionine, ornithine, phenylalanine, proline, serine, threonine, tryptophane, tyrosine and valine;
   f) biogenic amines, like N-acetylornithine, asymmetric dimethylarginine, 2-aminoadipic acid, carnosine, creatinine, histamine, kynurenine, methionine-sulfoxide, sarcosine, symmetric dimethylarginine, serotonin, spermidine, taurine and total dimethylarginine; in particular, N-acetylornithine, asymmetric dimethylarginine, 2-aminoadipic acid, carnosine, creatinine, histamine, kynurenine, methionine-sulfoxide, symmetric dimethylarginine and total dimethylarginine;
   g) oxysterols, like 20a-hydroxycholesterol, 22-R-hydroxycholesterol, 24,25-epoxycholesterol, 24-dihydrolanosterol, 24-S-hydroxycholesterol, 25-hydroxycholesterol, 27-hydroxycholesterol, 5α,6α-epoxycholesterol, cholestenone, desmosterol and 3β,5α,6β-trihydroxycholestan; in particular, 20α-hydroxycholesterol, 24,25-epoxycholesterol, 24-dihydrolanosterol, 24-S-hydroxycholesterol, 25-hydroxycholesterol, 27-hydroxycholesterol, 5α,6α-epoxycholesterol, cholestenone and 3β,5α,6β-trihydroxycholestan;
h) prostaglandins, like 8-iso-prostaglandin F2alpha, arachidonic acid, docosahexaenoic acid, leukotriene B4 and tromboxane B2; in particular, like 8-iso-prostaglandin F2alpha, leukotriene B4 and tromboxane B2.

10. The method of one of the preceding claims, wherein said functional classes of metabolites comprise the following individual members:
    a) energy metabolism related metabolites indicating the occurrence or previous lack of oxygen, like alanine, fumarate, succinate, alpha-ketoglutaric acid, decadienoyl carnitines and mesaconylcarnitine;
    b) metabolites of oxidative stress and anti-oxidative capacities and inflammation, like methioninsulfoxide, hydroxykynurenine and hydroxysphingomyelins and sphingomyelins; in particular, methioninsulfoxide, hydroxysphingomyelins and sphingomyelins;
    c) metabolites with neurotoxic or neuroprotective potential, like 2-aminoadipic acid, carnosine, hydroxykynurenine, kynurenine, spermidine, Serotonin, and spermin, in particular, 2-aminoadipic acid, carnosine, kynurenine; and
    d) metabolites predominantly occurring in the brain, like 25-hydroxycholesterol, 24-hydroxycholesterol, 24,25-epoxycholesterol.

11. The method of one of the preceding embodiments, wherein said at least one, like 1 to 100, 1 to 50, 1 to 25, 1 to 10 or 2, 3, 4, 5 or 6 panels indicative of the presence of brain injury, are selected within one of the following sets of models:
    a) set of hippocampus damage-related models 1 to 145 of Table 8;
    b) set of basal ganglia damage-related models 1 to 3945 of Table 9; or
    c) set of neurological behavioural abnormality-related models 1 to 717 of Table 10.

12. The method of one of the preceding embodiments, wherein said panel of metabolic markers comprises at least one first metabolic marker (lead marker or lead metabolite), like 1, 2, 3, 4, 5, 6, or 7 markers selected form:
    a) fumarate (Fum);
    b) carnosine (Car);
    c) 24,25-epoxycholesterol (24,25 EpoxyC);
    d) alpha-aminoadipic acid (alpha-AAA);
    e) hydroxysphingomyelin with acyl residue sum C22:2 (SM(OH) C22:2);
    f) methionine sulfoxide (Met-SO);
    g) hydroxysphingomyelin with acyl residue sum C14:1 (SM(OH) C14:1);
    h) alpha-ketoglutaric acid (alpha-KGA);
    i) cholestenone;
    k) sphingomyelin with acyl residue sum C16:1 (SM C16:1)
    l) decadienoyl carnitine (C10:2);
    m) sphingomyelin with acyl residue sum C24:1 (SM C24:1);
    n) mesaconylcarnitine (C5:1-DC); and
    o) succinate (Suc).
    optionally in combination with at least one, like 1, 2, 3, 4, 5, or 6, second marker different from said lead markers and selected from the markers as defined in anyone of said claims 6 to 9 or above tables 1 to 4.

13. The method of embodiment 12, wherein
    a) hippocampus damage-related panels comprise as lead marker C10:2; SM C24:1; C5:1-DC and/or Suc;
    b) basal ganglia damage-related panels comprise as lead marker Met-SO; SM(OH) C14:1; alpha-KGA, Cholestenone and/or SM C16:1; and
    c) neurological behavioural abnormality-related panels comprise as lead marker Fum; Car; 24,25-EpoxyC; alpha-AAA; and/or SM(OH) C22:2.

14. The method of embodiment 13, wherein said panels are selected from one of the following sets of panels:
    a) set of hippocampus damage-related panels 1 to 25 of Table 11;
    b) set of basal ganglia damage-related panels 1 to 181 of Table 12; or c) set of neurological behavioural abnormality-related panels 1 to 163 of Table 13.

15. The method of one of the preceding embodiments, wherein the metabolites are detected by nuclear magnetic resonance spectroscopy (NMR), mass spectroscopy, ELISA, fluorescence labeling techniques, flow cytometry, chromatography, capillary electrophoresis or chemical sensor.

16. An in vitro or in vivo diagnostic method for early differentiating types of brain damage, selected from damages of the brain compartments hippocampus and basal ganglia, in human neonates,
    which method comprises
    a) optionally obtaining a blood sample of said neonate and
    b) assessing in said body fluid sample at least one panel (model) of low molecular early metabolic markers indicative of the presence of brain injury in a brain compartment, selected from hippocampus and basal ganglia; in particular et least one panel (model) selected from panels of hippocampus damage-related panels 1 to 145 of Table 8 or 1 to 25 of Table 11; and basal ganglia damage-related panels 1 to 3945 of Table 9 or 1 to 181 of Table 12.

17. An in vitro or in vivo diagnostic method for early predicting a neurological behavioural abnormality caused by neonatal encephalopathy in human neonates,
    which method comprises
    a) optionally obtaining a body fluid (blood, serum) sample of said neonate and
    b) assessing in said body fluid sample at least one panel (model) of low molecular early metabolic markers indicative of neonatal encephalopathy-related behavioural abnormality, in particular et least one panel (model) selected from panels (models) 1 to 717 of Table 10 or panels 1 to 183 of Table 13.

18. The method of one of the preceding embodiments, wherein assessing said blood sample comprises:
    a) detecting said panel of metabolites;
    b) determining a profile of said detected metabolites; and
    c) comparing the profile of the detected metabolites to a standard metabolite profile, thereby diagnosing said disease or damage.

19. The method of one of the preceding embodiments, wherein an increase or decrease (versus standard/control/level of metabolites in healthy mammal) of at least one of said metabolites of said at least one panel is observed.

20. A method of assessing the progression or regression of neonatal encephalopathy which method comprises performing an in vitro diagnostic method of any one of the embodiments 1 to 19, repeating said method at least once, and comparing the obtained set of analytical parameter for said panel of metabolites with the previously determined set.

21. A method of treating a mammalian patient, in particular human neonate suffering from neonatal encephalopathy, which method comprising
   a) performing a diagnostic method of anyone of the embodiments 1 to 19 and
   b) treating a mammalian patient, in particular a neonate who as been positively assessed for neonatal encephalopathy in order to reduce disease symptoms.
22. The method of embodiment 21, wherein said treatment comprises hypothermia.
23. A panel of early metabolic metabolites as defined in anyone of the Tables 8, 9, 10, 11, 12 or 13 for use in diagnosis.
24. A kit for assessing the disease state of a neonatal encephalopathy in a blood sample of a mammalian patient, comprising:
   a) means for measuring a panel of low molecular early metabolic markers indicative of (specific for) the presence of neonatal encephalopathy, wherein the metabolites as defined in anyone of the embodiments 3 to 19;
   b) at least one standard or control panel of low molecular early metabolic markers indicative of non-injured brain, and/or at least one standard or control panel of low molecular early metabolic markers indicative of a certain state of progression or regression of neonatal encephalopathy; and
   c) means for identifying the disease state based on a comparison of the metabolite panel of the patient and the standard panel.
25. A diagnostic method for early assessing neonatal encephalopathy (NE) in a human neonatal patient, which method comprises
   d) obtaining a blood sample of said neonatal patient immediately, in particular 1 minute to 6 hours, or 2 to 180 or 5 to 120 minutes after birth or after initiating resuscitation or suspicion of NE and
   e) assessing in said blood sample at least one panel, like 1 to 100, 1 to 50, 1 to 25, 1 to 10 or 2, 3, 4, 5 or 6 panels, of low molecular weight early metabolic markers indicative of the presence or absence of NE in said patient;
   wherein said at least one panel indicative of the presence of NE, is selected within one of the following sets of models:
   (1) set of hippocampus damage-related models 1 to 145 of Table 8;
   (2) set of basal ganglia damage-related models 1 to 3945 of Table 9; or
   (3) set of neurological behavioural abnormality-related models 1 to 717 of Table 10
26. A diagnostic method for early assessing neonatal encephalopathy (NE) in a human neonatal patient, which method comprises
   a. obtaining a blood sample of said neonatal patient immediately, in particular 1 minute to 6 hours, or 2 to 180 or 5 to 120 minutes after birth or after initiating resuscitation or suspicion of NE and
   b. assessing in said blood sample at least one panel, like 1 to 100, 1 to 50, 1 to 25, 1 to 10 or 2, 3, 4, 5 or 6 panels, of low molecular weight early metabolic markers indicative of the presence or absence of NE in said patient;
   wherein said at least one panel, like 1 to 100, 1 to 50, 1 to 25, 1 to 10 or 2, 3, 4, 5 or 6 panels, indicative of the presence of NE, is selected within one of the following sets of models:
   (1) set of hippocampus damage-related models 1 to 25 of Tablet;
   (2) set of basal ganglia damage-related models 1 to 181 of Table 12; or
   (3) set of neurological behavioural abnormality-related models 1 to 163 of Table 13.
27. A diagnostic method for early differentiating types of brain damage, selected from damages of the brain compartments hippocampus and basal ganglia, in human neonates, which method comprises
   a) optionally obtaining a blood sample of said neonate, in particular 1 minute to 6 hours, or 2 to 180 or 5 to 120 minutes after birth or after initiating resuscitation or suspicion of NE and
   b) assessing in said body fluid sample at least one panel, like 1 to 100, 1 to 50, 1 to 25, 1 to 10 or 2, 3, 4, 5 or 6 panels, of low molecular early metabolic markers indicative of the presence of brain injury in a brain compartment, selected from hippocampus and basal ganglia, which panels of markers are as defined above, as for example in embodiment 1 to 23.
28. A diagnostic method for early predicting a neurological behavioural abnormality caused by neonatal encephalopathy in human neonates, which method comprises
   a) optionally obtaining a body fluid (blood, serum) sample of said neonate, in particular 1 minute to 6 hours, or 2 to 180 or 5 to 120 minutes after birth or after initiating resuscitation or suspicion of NE and
   b) assessing in said body fluid sample at least one panel of low molecular early metabolic markers indicative of neonatal encephalopathy-related neurological behavioural abnormality. which panels of markers are as defined above, as for example in embodiment 1 to 23.

In particular the claimed analytical methods are performed in vitro.

c) Further embodiments of the invention

Further aspects of the present invention are described below. In particular, by following the general teaching of the present invention at least the following additional embodiments are available to skilled reader.

c1) Diagnostic Applications

In some embodiments, the present invention provides methods and compositions for
   diagnosing brain injury affecting basal ganglia, hippocampus or other distinct brain tissues in infants and diagnosing adverse neurological outcome in infants,
   a. characterising the risk of brain injury in basal ganglia, hippocampus or other distinct brain tissues in infants and the risk of adverse neurological outcome in infants,
   b. diagnosing the stage of brain injury in basal ganglia, hippocampus or other distinct brain tissues in infants and severity etc. based on the presence of brain injury-specific endogenous metabolites or their chemical derivatives, precursors, metabolites, etc.

Exemplary diagnostic methods are described below.

Thus, for example, a method of diagnosing (or aiding in diagnosing) whether a subject has NE comprises detecting the presence or absence or a differential level of a plurality of metabolites being specific for brain injury in basal ganglia, hippocampus or other distinct brain tissues in infants or specific for adverse neurological outcome in infants and diagnosing brain injury in basal ganglia, hippocampus or other distinct brain tissues in infants or adverse neurological outcome in infants based on the presence, absence or differential concentration levels of these compounds. The presence, absence or concentration changes of these endogenous metabolites is used for differentiation of damaged brain regions and damaged brain tissues. Such specific metabolites are selected from Tables 2, 3 or 4.

In some embodiments, a computer-based analysis program is used to translate the raw data generated by the detection assay (e.g., the presence, absence, or amount of a NE specific metabolite) into data of predictive value for a clinician. The clinician can access the predictive data using any suitable means. Thus, in some embodiments, the present invention provides the further benefit that the clinician, who is not likely to be trained in metabolite analysis, need not understand the raw data. The data is presented directly to the clinician in its most useful form. The clinician is then able to immediately utilise the information in order to optimise the care of the subject.

The present invention contemplates any method capable of receiving, processing, and transmitting the information to and from laboratories conducting the assays, information providers, medical personal, and subjects. The profile data is then prepared in a format suitable for interpretation by a treating clinician. For example, rather than providing raw data, the prepared format may represent a diagnosis or risk assessment (e.g., likelihood of NE in infants being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analysed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

When the amounts or levels of a plurality of metabolites in the sample are determined, the amounts or levels may be compared to NE metabolite-reference levels, such as NE in infants-positive and/or NE in infants-negative reference levels to aid in diagnosing or to diagnose whether the subject has NE. Levels of the plurality of metabolites in a sample corresponding to the NE in infants-positive reference levels (e.g., levels that are the same as the reference levels, substantially the same as the reference levels, above and/or below the minimum and/or maximum of the reference levels, and/or within the range of the reference levels) are indicative of a diagnosis of NE in infants in the subject.

In addition, levels of a plurality metabolites that are differentially present (especially at a level that is statistically significant) in the sample as compared to NE in infants-negative reference levels are indicative of a diagnosis of NE in the subject. Levels of the two or more metabolites that are differentially present (especially at a level that is statistically significant) in the sample as compared to NE-positive respectively brain injury in a distinct brain tissue positive reference levels are indicative of a diagnosis of no brain injury in infants in the subject.

The level(s) of a plurality of the metabolites may be compared to NE in infants-positive respectively brain injury in a distinct brain tissue positive and/or NE-negative reference levels using various techniques, including a simple comparison (e.g., a manual comparison) of the level(s) of the one or more metabolites in the biological sample to NE-positive and/or NE-negative reference levels. The level(s) of the one or more metabolites in the biological sample may also be compared to NE in infants-positive respectively brain injury in a distinct brain tissue positive and/or brain injury in infants-negative reference levels using one or more statistical analyses (e.g., linear models, t-test, logistic regression, Wilcoxon's rank sum test, decision tree, linear discriminant analysis, k nearest neighbours etc.).

Embodiments of the present invention provide for multiplex or panel assays that simultaneously detect a plurality (at least two) of the markers of the present invention depicted in table 1, 2, 3 or 4. For example, in some embodiments, panel or combination assays are provided that detected 2 or more, 3 or more, 4 or more, 5 or more, 6 or more, 7 or more, 8 or more, 9 or more, 10 or more, 5 or more markers in a single assay. Non-limiting examples of panels are given in Tables 8, 9, 10, 11, 12 or 13. In some embodiments, assays are automated or high-throughput.

In the following non-limiting examples of particular diagnostic applications of the diagnostic principal method of the invention are given:

Thus, for example, the present invention provides a method for predicting the likelihood of NE in infants, characterised by
in vitro detecting, in particular quantitatively, in at least one biological sample of a neonate patient a plurality of, like 2, 3, 4, 5, 6, 7, 8, 9 or 10, compounds being associated with, in particular specific for NE, and having a molecular weight of less than about 1500 Dalton (like in the range of 50 to 1500), which method comprises the steps of:
 a) selecting said compounds from a group of endogenous metabolites as defined in anyone of the above tables 2 and 3;
 b) measuring at least two, like 2, 3, 4 or 5, of the parameters selected from the group consisting of: concentration, level or amount of each specific compound of said plurality of compounds in said sample, qualitative and/or quantitative molecular pattern and/or molecular signature; and storing the obtained set of values in a database;
 c) calibrating said values, as for example by comparing clinically confirmed "NE in infants-positive" by assignment of NE to distinct brain tissues and/or clinically confirmed "NE in infants-negative" reference parameters;
 d) comparing said measured values in the sample with the calibrated values, in order to assess whether the neonate patient has or is likely to develop NE or is unlikely to develop NE.

The levels of one or more of the recited metabolites may be determined in the methods of the present invention. For example, the level(s) of one metabolite, two or more metabolites, three or more metabolites, four or more metabolites, five or more metabolites, six or more metabolites, seven or more metabolites, eight or more metabolites, nine or more metabolites, ten or more metabolites, etc., including a combination of some or all of the metabolites including, but not limited to those listed in Table 2 and Table 3, may be determined and used in such methods.

The present invention also relates to a method for predicting neurological outcome due to NE in infants characterized by
in vitro detecting, in particular quantitatively, in at least one biological sample of a neonate patient a plurality of, like 2, 3, 4, 5, 6, 7, 8, 9 or 10, compounds being associated with, in particular specific for NE, and having a molecular weight of less than about 1500 Dalton (like in the range of 50 to 1500), comprising the steps of:
a) selecting said compounds from a group of endogenous metabolites as defined in above Table 4;
b) measuring at least two, like 2, 3, 4 or 5, of the parameters selected from the group consisting of: concentration, level or amount of each specific compound of said plurality of compounds in said sample, qualitative and/or quantitative molecular pattern and/or molecular signature; and storing the obtained set of values in a database;
c) calibrating said values, as for example by comparing clinically confirmed "NE in infants-positive" with neurological behavioral evaluation and/or clinically confirmed "NE in infants-negative" reference parameters;
d) comparing said measured values in the sample with the calibrated values, in order to assess brain-damage related neurological outcome of the neonate.

The levels of one or more of the recited metabolites may be determined in the methods of the present invention. For example, the level(s) of one metabolites, two or more metabolites, three or more metabolites, four or more metabolites, five or more metabolites, six or more metabolites, seven or more metabolites, eight or more metabolites, nine or more metabolites, ten or more metabolites, etc., including a combination of some or all of the metabolites including, but not limited to those listed in Table 4, may be determined and used in such methods.

Determining levels of combinations of the metabolites may allow greater sensitivity and specificity in the methods, such as diagnosing NE related to brain damage of basal ganglia and or hippocampus or for determining neurological outcome and aiding in the diagnosis of NE, and may allow better differentiation or characterisation of NE due to damage of distinct brain tissues from other disorders that may have similar or overlapping metabolites to NE due to damage of distinct brain tissues such as—but not limited to—basal ganglia and or hippocampus (as compared to a subject not having brain damage or having brain damage due to damage of other brain tissues). Determining levels of combinations of the metabolites may also allow greater sensitivity and specificity in the methods for determining neurological outcome.

Accordingly, the present invention provides, inter alia, methods of predicting the extent of brain damage and therefore the likelihood of an onset of NE together with an identification of damaged brain tissues such as—but not limited to—hippocampus tissue and or basal ganglia in an individual. The invention further provides methods for predicting the neurological outcome due to brain damage and therefore the likelihood of NE.

The methods of the invention may also comprise obtaining a biomarker score at a single point of time from the individual and comparing the individual's biomarker profile to a reference biomarker profile. Comparison of the biomarker profiles can predict the onset of NE in the individual preferably with an accuracy of at least about 75%. This method may be repeated again at any time prior to the onset of NE in infants.

Additionally, the present invention provides a method of diagnosing NE in infants related to damage of distinct brain tissues such as—but not limited to—hippocampus and or basal ganglia—in an individual having or suspected of having NE in infants. This method comprises obtaining a biomarker score (as for example selected from the scores or models as listed in the attached tables 8, 9, 11 or 12) at a single point in time from the individual and comparing the individual's biomarker score to a reference biomarker score. Comparison of the biomarker profiles can diagnose NE in infants in the individual with an accuracy of at least about 75%. This method may also be repeated on the individual at any time.

The present invention further provides a method of determining the progression (i.e., the stage) of NE involving distinct brain tissues such as, but not limited to, basal ganglia and or hippocampus in an individual. This method comprises obtaining a biomarker profile composed of concentrations of metabolites (two or more) selected from Tables 2 or 3 (or selected from the scores or models as listed in the attached tables 8, 9, 11 or 12) at a single point in time from the individual and comparing the individual's biomarker profile to a reference biomarker score. Comparison of the biomarker scores can determine the progression of NE related to damaged brain tissues in individual infants preferably with an accuracy of at least about 75%. This method may also be repeated on the individual at any time.

In yet another embodiment, the present invention provides, inter alia, a method of determining the status of NE in infants or diagnosing NE related to damage of distinct brain areas in infants. The method comprises comparing a measurable characteristic of more than one metabolite of a metabolite biomarker panel or biomarker score composed of (processed or unprocessed) values of this panel obtained from a biological sample from the individual infant and a biomarker score obtained from biological samples from a reference population. Based on this comparison, the individual is classified as belonging to or not belonging to the reference population. The comparison, therefore, determines the likelihood of NE in infants due to likely damage of distinct brain tissues or diagnoses of such NE in infants in the individual. The biomarkers, in one embodiment, are selected from the list of metabolites shown in Tables 2 or 3 or, for example, are selected from the scores or models as listed in the attached tables 8, 9, 11 or 12.

The present invention also provides methods for predicting NE related to damage of hippocampus and or basal ganglia tissue in infants. Such methods comprise the steps of: analyzing a biological sample from a subject to determine the levels of more than one metabolites for NE in infants in the sample, where the one or more metabolites are selected from Tables 2 and 3 (or are, for example, selected from the scores or models as listed in the attached tables 8, 9, 11 or 12) and comparing the levels of the metabolites, as well as a composed value/score generated by subjecting the concentrations of individual metabolite in the sample to a classification method such as affording an equation to process single concentration values—to obtain a separation between both (diseased and healthy) groups or comparing the level(s) of the one or more metabolites in the sample to NE positive or NE negative reference levels of the two or more metabolites in order to determine whether the subject is developing NE related to damage of hippocampus, basal ganglia or other distinct brain tissues.

The above methods for determining progression, status of disease or predicting disease may also be applied to the aspect of the invention related to neurological behavioural damages or deficits. For these purposes one or more metabolites as listed in Table 4 or one or more metabolite combinations listed in Table 10 or 13 may be applied accordingly.

Furthermore, in some embodiments, the present invention provides a method of diagnosing brain damage in infants and/or duration/severity of brain damage of distinct brain areas, identification of affected area(s) of NE and risk of neonatal encephalopathy and prognosis and neurological outcome due to identification of type and extent of damage of distinct brain tissues, in particular of hippocampus and/or basal ganglia comprising: detecting (the presence or absence of 2 or more, 3 or more, 5 or more, 10 or more, etc. metabolites measured together in a multiplex or panel format) brain damage in infants specific metabolites in a sample (e.g., a tissue (e.g., biopsy) sample, a blood sample, a serum sample) from a subject; and diagnosing brain damage in the aforementioned brain tissues in infants based on the presence of specific metabolites.

In a further embodiment the invention uses analytical kits, comprising i) detection agents for the determination of NE in infants by determination of concentrations of metabolites of the subject, wherein said metabolites are selected from the group consisting of hippocampus specific compounds as listed in Table 2, above, basal ganglia-specific compounds as listed in Table 3, above or neurological behavioural score-specific compounds as listed in table 4, or detecting agents for hippocampus specific, basal ganglia-specific or neurological behavioural score-specific sets of such metabolites from compounds of tables 2, 3 or 4, as for example sets of metabolites as defined in any one of the tables 8 to 13;

ii) positive and/or negative controls; and iii) regression software for correlating the results achieved with said detection agents.

c2) Further Particular Aspects for Performing the Methods of the Invention

The present invention provides a solution to the problems described above, and generally relates to the use of metabolomics data, generated by quantization of endogenous metabolites by but not limited to mass spectrometry (MS), in particular MS-technologies such as MALDI, ESI, atmospheric pressure chemical ionization (APCI), and other methods, determination of metabolite concentrations by use of MS-technologies or alternative methods coupled to separation (LC-MS, GC-MS, CE-MS), subsequent feature selection and combination of features to classifiers including molecular data of at least two molecules.

The concentrations of the individual markers, analytes, metabolites thus are measured and compared to reference values or data combined and processed to scores and compared to reference values thus indicating diseased states etc. with superior sensitivities and specificities compared to known procedures, clinical parameters and biomarkers.

Those skilled in the art will understand that for the quantitation of certain metabolites, also chemically modified metabolites may be used as one may get a better separation on the column material used prior to the MS-technologies.

Typically analysed samples are e.g., a tissue (e.g., biopsy) sample, a blood sample, a serum sample, from a subject.

In a preferred embodiment of the invention, the analytical procedure is also characterized in that a deproteination step and/or a separation step is performed before metabolite measurement, wherein said separation step is selected from the group consisting of liquid chromatography (LC), high performance liquid chromatography (H PLC), gas chromatography, liquid-liquid-extraction (LLE).

Said deproteinization step preferably is carried out by mixing said biological sample with organic solvents such as ethanol, methanol or acetonitrile.

In order to enhance sensitivity and/or volatility, e.g. for a better evaporation as used in mass spectrometry, the compounds can be derivatized. They may be converted, py applying chemical methods known in the art, to the corresponding esters, amines or amides, wherein said derivatization includes: 2-Hydrazinopyridine (HP), 2-picolylamine (PA); Girard derivatization; oximation with hydroxylamine first and then silylation with hexamethyldisilazane and trifluoroacetic acid.

It is further preferred that said calibration step is carried out by a) mathematically preprocessing said values in order to reduce technical errors being inherent to the measuring procedures used in accordance with the present invention, such as mass spectrometry.

b) selecting at least one suitable supervised algorithm from the group consisting of logistic regression, (diagonal) linear or quadratic discriminant analysis (LDA, QDA, DLDA, DQDA), perceptron, shrunken centroids regularized discriminant analysis (RDA), random forests (RF), neural networks (NN), Bayesian networks, hidden Markov models, support vector machines (SVM), generalized partial least squares (GPLS), partitioning around medoids (PAM), inductive logic programming (ILP), generalized additive models, gaussian processes, regularized least square regression, self organizing maps (SOM), recursive partitioning and regression trees, K-nearest neighbor classifiers (K-NN), and applying said selected supervisedalgorithm to said preprocessed data of step a);

c) said supervised algorithm of step b) being trained on at least one training data set containing preprocessed data from subjects being divided into classes according to their NE in infants-related pathophysiological, physiological, prognostic, or responder conditions, in order to select a classifier function to map said preprocessed data to said conditions;

d) applying said trained supervised algorithm of step c) to a pre-processed data set of a subject with unknown NE in infants-related pathophysiological, physiological, prognostic, or responder condition, and using the trained classifier algorithms to predict the class label of said data set in order to predict the likelihood of an onset of NE in infants of the subject.

The step of mathematically preprocessing can be carried out e.g. by means of a statistical method on obtained raw data, particularly raw intensity data obtained by a measuring device, wherein said statistical method is selected from the group consisting of raw data obtained by mass spectrometry or mass spectrometry coupled to liquid or gas chromatography or capillary electrophoresis or by 2D gel electrophoresis, quantitative determination with RIA or determination of concentrations/amounts by quantitation of immunoblots; smoothing, baseline correction, peak picking, optionally, additional further data transformation such as taking the logarithm in order to carry out a stabilization of the variances.

Furthermore, for reasons of better accuracy of the prognostic results, a further step of feature selection is inserted into said preprocessing step, in order to find a lower dimensional subset of features with the highest discriminatory power between classes; and/or said feature selection is carried out by a filter and/or a wrapper approach; and/or wherein said filter approach includes rankers and/or feature subset evaluation methods; and/or wherein said wrapper approach is applied, where a classifier is used to evaluate attribute subsets.

For the purpose of the present application, said pathophysiological condition corresponds to the label "diseased" and said physiological condition corresponds to the label "healthy" or said pathophysiological condition corresponds to different labels of "grades of a disease", "subtypes of a disease", different values of a "score for a defined disease"; said prognostic condition corresponds to a label "good", "medium", "poor", or "therapeutically responding" or "therapeutically non-responding" or "therapeutically poor responding".

Typically, the method of the present invention is characterised in that said measuring step is carried out by high-throughput mass spectrometry.

It is preferred, that said NE in infants specific endogenous compounds indicate neonatal encephalopathy, NE of affected brain area(s) and prognosis and neurological outcome due to determination of type and extent of damage of distinct brain tissues, in particular of hippocampus and/or basal ganglia in infants specific endogenous metabolites.

Furthermore, in the method according to the present invention, typically, said mammalian subject is a human being, and said biological sample is blood wherein raw data of metabolite concentrations are preprocessed using the log transformation; wherein linear models are used to identify metabolites which are correlated to the extend of NE present; wherein least square regression is selected as suitable supervised algorithm, and is trained with preprocessed metabolite concentrations, applying the obtained trained regression function to said pre-processed metabolite concentration data set of a subject under suspicion of having NE in infants, and using said trained regression function to diagnose or predict the extent of brain tissue-specific injury in infants.

The present invention allows prognosis of NE-related neurological outcome and neurological behavioural score by metabolites of the subject (with or without determination of type and extent of damage of distinct brain tissues, in particular of hippocampus and/or basal ganglia in infants specific endogenous metabolites) wherein linear models are used to identify metabolites which are differentially present; wherein linear least squares regression is selected as suitable algorithm to delineate a relationship between metabolite and extent of damage, and is trained with preprocessed metabolite concentrations, applying the obtained trained regression function to said preprocessed metabolite concentration data set of a subject under suspicion of having NE in infants, and using said trained regression to diagnose or predict the extent of brain tissue-specific injury in infants.

In a further embodiment, categorization of data relies on the application of (un-) supervised learning techniques. Supervised learning algorithms are typically deterministic functions that map a multi-dimensional vector of biological measurements to a binary or n-ary or continuous outcome variable that encodes the absence or existence of a clinically-relevant class, phenotype, distinct physiological state or distinct state of disease or risk of developing a disease or disease treatment adequacy. To achieve these various methods such as, but not limited to, logistic regression (LR), (diagonal) linear or quadratic discriminant analysis (LDA, QDA, DLDA, DQDA), perceptron, shrunken centroids regularized discriminant analysis (RDA), random forests (RF), neural networks (NN), support vector machine (SVM), generalised least square regression, (non-)linear mixed-effects models, generalised (non-)linear models, mixed hidden Markov models, generalised partial least square regression (GPLS), principal component regression, partial least square regression coupled with a classification algorithm (such as LDA, K—NN or LR), projection to latent structures, partitioning around medoids (PAM), naïve Bayes (NB), inductive logic programming (ILP), generalized additive models, gaussian processes, regularized least square regression, least absolute deviations, self organizing maps (SOM), recursive partitioning and regression trees, K-nearest neighbour classifiers (K-NN), fuzzy classifiers can be used as a standalone classifier or within the framework of ensemble strategy such as voting, stacking, Bayseian model averaging, bagging or boosting.

EXAMPLES

The following examples are provided in order to further illustrate certain preferred embodiments of the present invention and are not to be construed as limiting the scope thereof.

I. Material and Methods

1. Animal Model

When comparing brain growth spurts, the brain of the pig resembles most that of the term born human baby (see Dobbing J, Sands J. Comparative aspects of the brain growth spurt. Early Hum Dev 1979 March; 3(1):79-83).

In this study we chose the inhalational hypoxia model since it mimics the human pathophysiology of a global hypoxic ischemic insult and produces spontaneous clinical and subclinical seizures, but with a high survival rate (~80%). The encephalopathy is clinically, electrophysiologically, and neuropathologically similar to that in the asphyxiated term infant and is suitable for examining mechanisms of damage and evaluation of potential protective therapies after birth asphyxia (see Thoresen M, Haaland K, Loberg E M, Whitelaw A, Apricena F, Hanko E, et al. A piglet survival model of posthypoxic encephalopathy. Pediatr Res 1996 November; 40(5):738-48).

The animals were bred in a piggery in Brisbane. After ventilation and detubation piglets stayed in a small animal cage with liberate access to water. Piglets were bottlefed every 3-4 hours with Survive Pig Milk Replacer (Think Pig-Country Vet Wholesaling Pty Ltd, VIC, Australia). Animals were cared for in accordance with the institution's guidelines for experimental animals. All experiments were approved by the animal protection committee of the local authorities.

9 newborn piglets were used for this study. Piglets were anaesthetized with 1-2% isofluran via a nose mask, and placed supine on a heating table to maintain body temperature around 38.5° C. An ear vein was cannulated and an induction dose of propofol (10 mg/ml, 0.5 ml/kg Diprivan 1%, AstraZeneca Pty Ltd, NSW, Australia) was administered. Propofol (9 mg/ml) and alfentanil infusion was maintained at a rate of 10 mg/kg/hr until intubation. Pulse oximeter and ECG (Marquette Tramscope 12C, Medical Systems, WI, USA) was connected as well as the amplitude-integrated EEG (BRM2; BrainZ Instruments, Auckland, NZ). piglets were intubated with an uncuffed tube and pigs were ventilated pressure-controlled with an SLE Newborn 250 (Surrey, UK). Anesthesia was reduced to 10 mg/kg/hr until the end of HI. An additional peripheral venous line was inserted for continuous 10% dextrose infusion at a rate of 3 ml/kg/hr and antibiotics (cephalotin 20 mg/kg and gentamicine 2.5 mg/kg). An umbilical artery was inserted for continuous blood pressure monitoring and blood gas analysis. Blood gasses were collected before HI, every 10 minutes during HI until 60 min after HI.

Hypoxia (4% $O_2$) was induced in anaesthetised newborn piglets for 30 min with a final 10 min period of hypotension; piglets were recovered and survived to 48 h. Animals were monitored daily for seizures both visually and with electro-encephalogram (EEG) recordings. Clinical seizures were treated with phenobarbitone (20 mg/kg i.v., Sigma, Croydan, VIC, Australia) and midazolam (0.2 mg/kg iv, Sandoz, Pyrmont, NSW, Australia). When seizures continued, piglets were euthanized with an overdose pentobarbitone.

For metabolomic analysis, blood samples were taken at the following time points: 30 min after asphyxia and 21 hours after resuscitation.

Outcome Measures:

Brain injury was assessed with the aEEG for both EEG pattern and epileptic activity, with a clinical neurological score, by histology (haematoxylin and eosin staining) using a previously described rating system (see Lorek A, Takei Y, Cady E B, Wyatt J S, Penrice J, Edwards A D, et al. Delayed ("secondary") cerebral energy failure after acute hypoxia-ischemia in the newborn piglet: continuous 48-hour studies by phosphorus magnetic resonance spectroscopy. Pediatr Res 1994 Dec; 36(6):699-706) and for caspase-3 activity in 4 cortical areas, thalamus, basal ganglia and hippocampus. Thereby the hippocampus and basal ganglia are of outmost interest.

Caspase-3 Activity:

Caspase 3-activity (in pmole/min/mg protein) was determined at 48 h after HI in all other brain regions, including 4 cortical areas, basal ganglia and hippocampus.

Histology:

Histology was performed using the earlier described score in each brain region. Also a total histology score was calculated for each treatment group, summing all the individual histology scores.

Clinical Neurobehavioral Score:

A neurobehavioral score was assessed at least at 4 hourly time points in the first 24 h and at 48 h. This score contains 9 items of maximal 2 points, so the maximal score is 18 points. The nine neurologic items were scored as: 2, normal; 1, moderately abnormal; or 0, definitely pathologic. Neurologic items were: 1) Normal respiration, without apnea, retractions, or need for oxygen; 2) consciousness; 3) orientation. Looking at and investigating the surroundings; 4) ability to walk on all four limbs in one direction without falling; 5) ability to control the forelimbs using them to raise quickly from a lying position; 6) ability to control the hind limbs using them to raise quickly from a lying position and keeping them together in the upright position; 7) maintenance of steady and equal tone in forelimbs and hind limbs; 8) almost continuous activity when awake; 9) absence of pathologic movements were scored as 2. Sustained clonic movements or persistent tonic postures were scored as 0. Occasional cycling movements or jerks were scored as 1.

2. Metabolomic Analytics:

2.1 General

Sample preparation and metabolomic analyses were performed at Biocrates life sciences AG, Innsbruck, Austria. We used a multi-parametric, highly robust, sensitive and high-throughput targeted metabolomic platform consisting of flow injection analysis (FIA)-MS/MS and LC-MS/MS methods for the simultaneous quantification of a broad range of endogenous intermediates, namely acylcarnitines, sphingomyelins, hexoses, glycerophospholipids, amino acids, biogenic amines, oxysterols and small organic acids, in plasma. A detailed list of all analyzed metabolites is depicted in Table 1, above. All procedures (sample handling, analytics) were performed by co-workers blinded to the experimental groups.

2.2. Sample Handling 2.2.1 Plasma

Plasma samples were prepared by standard procedures and stored at (−75° C.). To enable analysis of all samples simultaneously within one batch, samples were thawed on ice (1 h) on the day of analysis and centrifuged at 18000 g at 2° C. for 5 min. All tubes were prepared with 0.001% BHT (butylated hydroxytoluene; Sigma-Aldrich, Vienna, Austria) to prevent autoxidation.

2.2.2 LC-MS/MS System

The LC-MS/MS system consisted of an API 5000™ triple quadrupole mass spectrometer (AB Sciex) equipped with a TurboV™ ESI source and an Agilent 1200 HPLC system (Agilent Technologies). Chromatographic separation was performed using an Agilent Zorbax Eclipse XDB C18 column (100×3.0 mm, 3.5 µm) with guard column (C 18, 4×2 mm in Security Guard Cartridge, Phenomenex). Analyst.™ software (version 1.4.2, Applied Biosystems) was used for data acquisition and processing. For comprehensive statistical analysis the data were exported.

2.2.3 LC-MS/MS Conditions

The ESI source was operated in negative ion mode and an ion-spray voltage of −3 kV was applied. Heater temperature was set at 400° C.

2.3. Mass Spectroscopy of Different Analytes 2.3.1 Acylcarnitines, Sphingomyelins, Hexoses, Glycerophospholipids (FIA-MS/MS)

To determine the concentration of acylcarnitines, sphingomyelins and glycerophospholipids in plasma, the AbsolutelDQ kit p150 (Biocrates Life Sciences AG, Innsbruck, Austria) was prepared as described in the manufacturer's protocol. In brief, 10 µL of plasma was added to the center of the filter on the upper 96-well kit plate and was dried using a nitrogen evaporator (VLM Laboratories, Bielefeld, Germany). Subsequently, 20 µL of a 5% solution of phenyl-isothiocyanate was added for derivatization. After incubation, the filter spots were dried again using an evaporator. The metabolites were extracted using 300 µL of a 5 mM ammonium acetate solution in methanol. The extracts were obtained by centrifugation into the lower 96-deep well plate, followed by a dilution step with 600 µL of kit MS running solvent. Mass spectrometric analysis was performed on an API4000 Qtrap® tandem mass spectrometry instrument (Applied Biosystems/MDS Analytical Technologies, Foster City, Calif.) equipped with an electro-spray ionization (ESI)-source, using the analysis acquisition method as provided in the AbsolutelDQ kit. The standard FIA-MS/MS method was applied for all measurements with two subsequent 20-µL injections (one for positive and one for negative mode analysis). Multiple reaction monitoring (MRM) detection was used for quantification, applying the spectra parsing algorithm integrated into the MetIQ software (Biocrates Life Sciences AG, Innsbruck, Austria). The concentrations for 148 metabolites (all analytes were determined with the metabolomics kit except for the amino acids, which were determined by a different method) obtained by internal calibration were exported for comprehensive statistical analysis.

2.3.2 Amino Acids, Biogenic Amines (LC-MS/MS)

Amino acids and biogenic amines were quantitatively analyzed by reversed phase LC-MS/MS to obtain the chromatographic separation of isobaric (same MRM ion pairs) metabolites for individual quantification performed by external calibration and by use of internal standards. A 10 µL sample volume is required for the analysis using the following sample preparation procedure. Samples were added on filter spots placed in a 96-solvinert well plate (internal standards were placed and dried down under nitrogen before), fixed above a 96 deep well plate (capture plate). 20 µL of 5% phenyl-isothiocyanate derivatization reagent was added. The derivative samples were extracted after incubation by aqueous methanol into the capture plate. Sample extracts were analyzed by LC-ESI-MS/MS in positive MRM detection mode with an API4000 Qtrap® tandem mass spectrometry instrument (Applied Biosystems/MDS Analytical Technologies, Foster City, Calif.). The analyzed individual metabolite concentrations (Analyst 1.4.2 software, Applied Biosystems, Foster City, Calif.) were exported for comprehensive statistical analysis.

2.3.3 Oxysterols (LC-MS/MS)

Oxysterols were quantitatively analyzed by reversed phase LC-ESI-MS/MS to realize liquid chromatographic separation and thus individual quantification of isobaric oxysterols. The most selective detection was performed in positive MRM detection mode using a 4000 Qtrap® tandem mass spectrometry instrument (Applied Biosystems/MDS Analytical Technologies, Foster City, Calif.). Data were quantified with Analyst 1.4.2 software (Applied Biosystems, Foster City, Calif.). Ratios of external to internal standards were applied for quantification by means of external 6-point calibration. A sample volume of 20 µL (plasma) was necessary for the analysis. The sample preparation included: I) protein precipitation by placing a 20 µL sample volume on the filter spot, and precipitation by 200 µL Naïve; II) hydrolysis by 100 µL of 0.35 M KOH in 95% ethanol for 2 hrs; Ill) a washing step (3×200 µL $H_2O$) to remove hydrolysis reagent; and, finally, IV) extraction by means of 100 µL aqueous methanol. The 20 µL sample extracts were analyzed by the developed LC-ESI-MS/MS method.

2.3.4 Energy Metabolism (Organic Acids) (LC-MS/MS)

For the quantitative analysis of energy metabolism intermediates (glycolysis, citrate cycle, pentose phosphate pathway, urea cycle), a hydrophilic interaction liquid chromatography (HILIC)-ESI-MS/MS method in a highly selective negative MRM detection mode was used. The MRM detection was performed using an API4000 QTrap® tandem mass spectrometry instrument (Applied Biosystems/MDS Analytical Technologies, Foster City, Calif.). A 20 µL sample volume (plasma) was protein-precipitated and simultaneously extracted with aqueous methanol in a 96-well plate format. Internal standards (ratio external to internal standard) and external calibration were used for highly accurate quantification. Data were quantified with Analyst 1.4.2 software (Applied Biosystems, Foster City, Calif.) and finally exported for statistical analysis.

2.3.5 Eicosanoids

The determination of eicosanoids (like prostaglanidins, thromboxanes) was performed according to a previously published method (Unterwurzacher I., Koal T., Bonn G. K., Weinberger K. M., Ramsay S. L., Clin Chem Lab Med 2008, 46(11), 1589). In brief, 20 µL of plasma was protein precipitated and extracted simultaneously with aqueous acetonitrile in a 96-well Solvinert filter plate. The ratio of external to internal standard and external calibration were used for highly accurate quantitation. Sample extracts were analyzed by reversed phase LC-ESI-MS/MS in negative ionization MRM detection mode with a 4000 Q Trap® tandem mass spectrometry instrument (Applied Biosystems/MDS Analytical Technologies, Darmstadt, Germany).

2.4. Statistical Analysis

All statistical calculations have been performed using the statistics software R (R: A Language and Environment for Statistical Computing, R Development Core Team, R Foundation for Statistical Computing, Vienna, Austria, 2010, ISBN 3-900051-07-0).

All analytes that were detected in at least 15% of the samples were selected for further analyses. The metabolic data is left censored due to thresholding of the mass spectrometer data resulting in non detected peak/signals. By a combination of metabolic pathway dynamism, complex sample molecular interaction and overall efficiency of the analytical protocol, replacement of missing data by means of a multivariate algorithm is preferred to a naive imputation by a pre-specified value like for instance zero. Hence, missing metabolite concentrations are replaced by the average value of the 6 closest samples to the one where the measurement is missing (Kim H., Golub G. H. and Park, H. Missing value estimation for DNA microarray gene expression data: local least squares imputation. Bioinformatics. 2005 21(2):187-198). All statistical analyses are performed on preprocessed—that is, log transformed—data. The log-transformation is used to stabilize variance and to transform to Gaussian distribution—at least approximately.

Parsimonious multi-metabolite panels can be used for predicting each outcome described in the present invention rather than individual metabolite marker. Approach to search for marker composites is done using a population-based incremental learning algorithm using all 101 metabolites. For each model, regression coefficient (i.e. marker weights in the model) are determined according to Zuber, V., & Strimmer, K. (High-Dimensional Regression and Variable Selection Using CAR Scores, Statistical Applications in Genetics and Molecular Biology. 2011 10(1), Article 34). Predictive power of the model is assessed by leave one out cross-validation. In the following, model accuracy is defined as the correlation coefficient between the original (or true) values of the predictand and their predicted values by resampling. Each model is then further subjected to backward elimination and this until no improvement to the accuracy (plus/minus 10%) is observed. All together, these conditions satisfy parsimony and predictive power of the final model, and eliminate issues related to multicollinearity between markers. While the invention described herein may comprise combinations with adequate predictive power other than those shown, combination of metabolites of the invention would exhibit accuracies greater than 80%.

II. Experimental Results

Induced asphyxia resulted in different grades of brain injury by inducing cell death in basal ganglia and hippocampus as well as by a deterioration of the neurological behavioral score. Neonatal encephalopathy was associated with major changes in the plasma metabolome. We discovered intermediates which correlated alone or in combination with the extent of brain injury in the hippocampus, basal ganglia and the neurological score.

These experimental results are explained in more detail below.

Example 1: Hypoxia-Induced Damage of Hippocampus

As mentioned above the lack oxygen resulted in increased apoptotic and/or necrotic cell death assessed in the brain of newborn piglets 48 hours after the lack of oxygen. Blood samples were taken 30 minutes after the period of lack of oxygen and the metabolite concentrations were analysed as described above. These metabolite concentrations were then correlated with the absolute quantitative amount of dying cell in the hippocampus. Table 5 summarises the result of univariate correlation statistics between metabolite concentration as determined in plasma 30 minutes after asphyxia and the amount of cell death in hippocampus at 48 hours after asphyxia. For each metabolite, Pearson correlation coefficient (Cor) and its corresponding p value are given alongside the coefficient of determination (Rsq). Prob designates the actual probability (in %) to enter a combination of metabolites.

whisker diagrams represent the distribution of the cross-validated correlation coefficient (y-axis) for combinations of 2 to 6 (x-axis) metabolites.

TABLE 5

Outcome parameter: Brain damage in hippocampus

| | Short | Full name | Cor | Pvalue | Rsq | Prob |
|---|---|---|---|---|---|---|
| 1 | Lac | Lactate | 0.870 | 0.002 | 75.69 | 61.38 |
| 2 | Fum | Fumaric acid | 0.753 | 0.019 | 56.63 | 43.45 |
| 3 | Ac-Orn | N-acetylornithine | 0.747 | 0.021 | 55.73 | 40.69 |
| 4 | Carnosine | Carnosine | −0.741 | 0.022 | 54.96 | 27.59 |
| 5 | C5:1-DC | Glutaconylcarnitine/Mesaconylcarnitine (Undecanoylcarnitine) | 0.666 | 0.050 | 44.35 | 20.00 |
| 6 | C16:2 | Hexadecadienoylcarnitine | 0.464 | 0.208 | 21.53 | 16.55 |
| 7 | Pent-P | Pentosephosphate (e.g. Ribose-5-phosphate + Ribulose-5-phosphate) | 0.651 | 0.057 | 42.40 | 13.79 |
| 8 | C10:2 | Decadienoylcarnitine | −0.485 | 0.186 | 23.51 | 13.10 |
| 9 | Met-SO | Methionine-Sulfoxide | 0.650 | 0.058 | 42.28 | 12.41 |
| 10 | SM (OH) C22:2 | Hydroxysphingomyelin with acyl residue sum C22:2 | −0.689 | 0.040 | 47.52 | 12.41 |
| 11 | SM C24:1 | sphingomyelin with acyl residue sum C24:1 | −0.586 | 0.098 | 34.29 | 11.72 |
| 12 | ADMA | Asymmetric dimethylarginine | 0.592 | 0.093 | 35.02 | 10.34 |
| 13 | C5:1 | Tiglylcarnitine/3-Methyl-crotonylcarnitine | −0.405 | 0.280 | 16.37 | 9.66 |
| 14 | 3b,5a,6b-THC | 3β,5α,6β-Trihydroxycholestan | 0.290 | 0.449 | 8.40 | 8.28 |
| 15 | 27-OH-C | 27-Hydroxycholesterol | 0.448 | 0.226 | 20.10 | 6.90 |
| 16 | Suc | Succinic acid | 0.533 | 0.139 | 28.41 | 6.90 |
| 17 | 8-iso-PGF2a | 8-iso-Prostaglandin F2alpha | 0.525 | 0.147 | 27.52 | 6.21 |
| 18 | total DMA | Total dimethylarginine | 0.502 | 0.168 | 25.24 | 6.21 |
| 19 | 25-OH-C | 25-Hydroxycholesterol | 0.229 | 0.553 | 5.25 | 5.52 |
| 20 | SM (OH) C22:1 | Hydroxysphingomyelin with acyl residue sum C22:1 | −0.495 | 0.176 | 24.46 | 4.14 |
| 21 | Creatinine | Creatinine | −0.344 | 0.364 | 11.85 | 3.45 |
| 22 | Phe | Phenylalanine | 0.648 | 0.059 | 41.95 | 3.45 |
| 23 | C4:1 | Butenoylcarnitine | −0.275 | 0.474 | 7.55 | 3.45 |
| 24 | LTB4 | Leukotriene B4 | 0.449 | 0.225 | 20.18 | 2.76 |
| 25 | 24S-OH-C | 24-S-Hydroxycholesterol | 0.239 | 0.536 | 5.72 | 2.76 |
| 26 | Orn | Ornithine | 0.468 | 0.204 | 21.90 | 2.76 |
| 27 | Cit | Citrulline | −0.354 | 0.350 | 12.51 | 2.76 |
| 28 | SM (OH) C14:1 | Hydroxysphingomyelin with acyl residue sum C14:1 | −0.515 | 0.156 | 26.53 | 2.76 |
| 29 | H1 | Hexoses | −0.582 | 0.100 | 33.88 | 2.76 |
| 30 | C8:1 | Octenoylcarnitine | −0.307 | 0.422 | 9.41 | 2.76 |
| 31 | 5a,6a-EpoxyC | 5α,6α-Epoxycholesterol | 0.222 | 0.567 | 4.91 | 2.07 |
| 32 | alpha-AAA | 2-Aminoadipic acid | 0.399 | 0.287 | 15.96 | 2.07 |
| 33 | Pro | Proline | 0.625 | 0.072 | 39.04 | 2.07 |
| 34 | Lys | Lysine | 0.466 | 0.206 | 21.76 | 2.07 |
| 35 | Arg | Arginine | 0.541 | 0.132 | 29.30 | 2.07 |
| 36 | SM C16:1 | sphingomyelin with acyl residue sum C16:1 | −0.389 | 0.301 | 15.13 | 2.07 |
| 37 | SDMA | Symmetric dimethylarginine | 0.247 | 0.521 | 6.12 | 1.38 |
| 38 | Met | Methionine | 0.513 | 0.158 | 26.35 | 1.38 |
| 39 | Gln | Glutamine | 0.213 | 0.582 | 4.55 | 1.38 |
| 40 | SM C26:1 | sphingomyelin with acyl residue sum C26:1 | −0.409 | 0.274 | 16.76 | 1.38 |
| 41 | SM C18:1 | sphingomyelin with acyl residue sum C18:1 | −0.621 | 0.074 | 38.52 | 1.38 |
| 42 | Hex-P | Hexosephosphate (e.g. Glucose-1-phosphate + Glucose-6-phosphate + Fructose-6-phosphate) | −0.526 | 0.146 | 27.69 | 1.38 |

In the attached FIG. 1a, the distribution of accuracies that can be achieved with models formed with a lead metabolite is illustrated.

FIG. 1a illustrates the predictive abilities of the combination of metabolites based on a lead metabolite correlating with the extent of brain damage in the hippocampus. The box-and-whisker diagrams represent the distribution of the cross-validated correlation coefficient (y-axis) for combinations comprising a lead metabolite (x-axis) and up to 6 metabolites from the initial dataset.

Figure 1B:
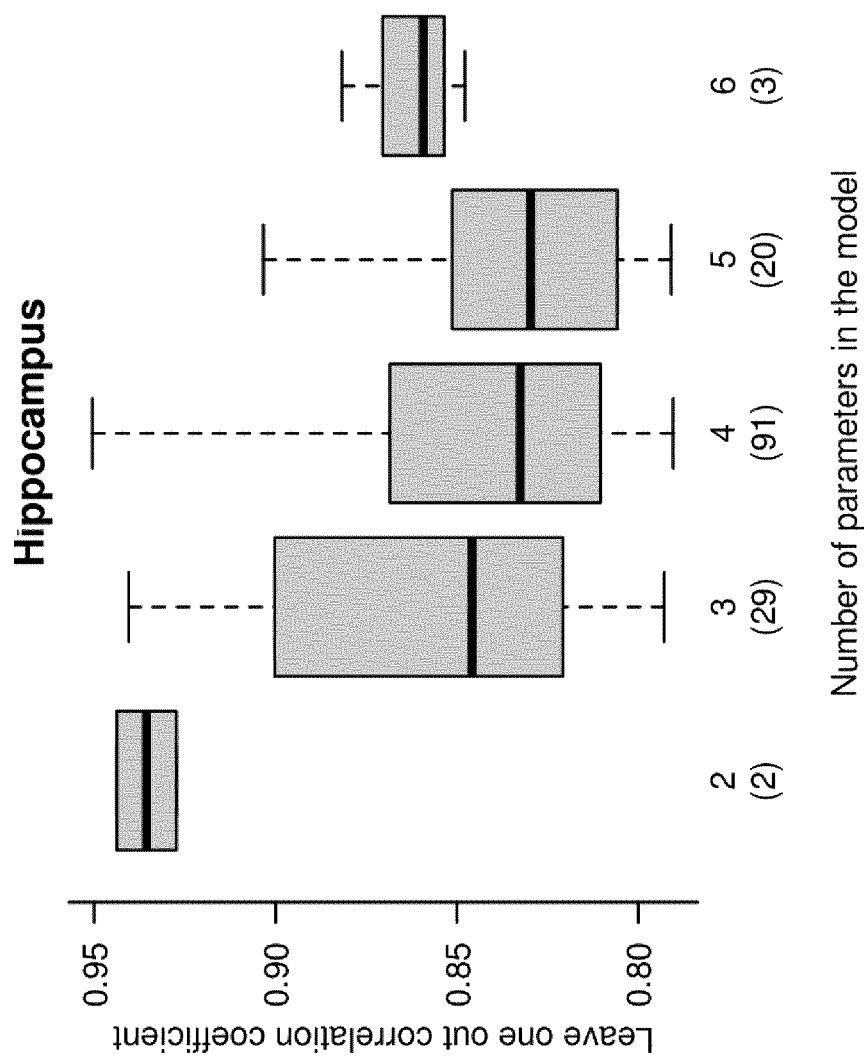
FIG. 1b illustrates the predictive abilities (i.e. accuracy) of all adequate metabolite combinations correlating with the extent of brain damage in the hippocampus. The box-and-whisker diagrams represent the distribution of the cross-validated correlation coefficient (y-axis) for combinations of 2 to 6 (x-axis) metabolites.

In the attached FIG. 1b, the distribution of the accuracies that can be achieved from models comprising up to 6 metabolites is illustrated.

FIG. 1b illustrates the predictive abilities (i.e. accuracy) of all adequate metabolite combinations correlating with the extent of brain damage in the hippocampus. The box-and- In the attached FIG. 1c the probability of a metabolite to enter a model with adequate accuracy is illustrated.

Figure 1C:
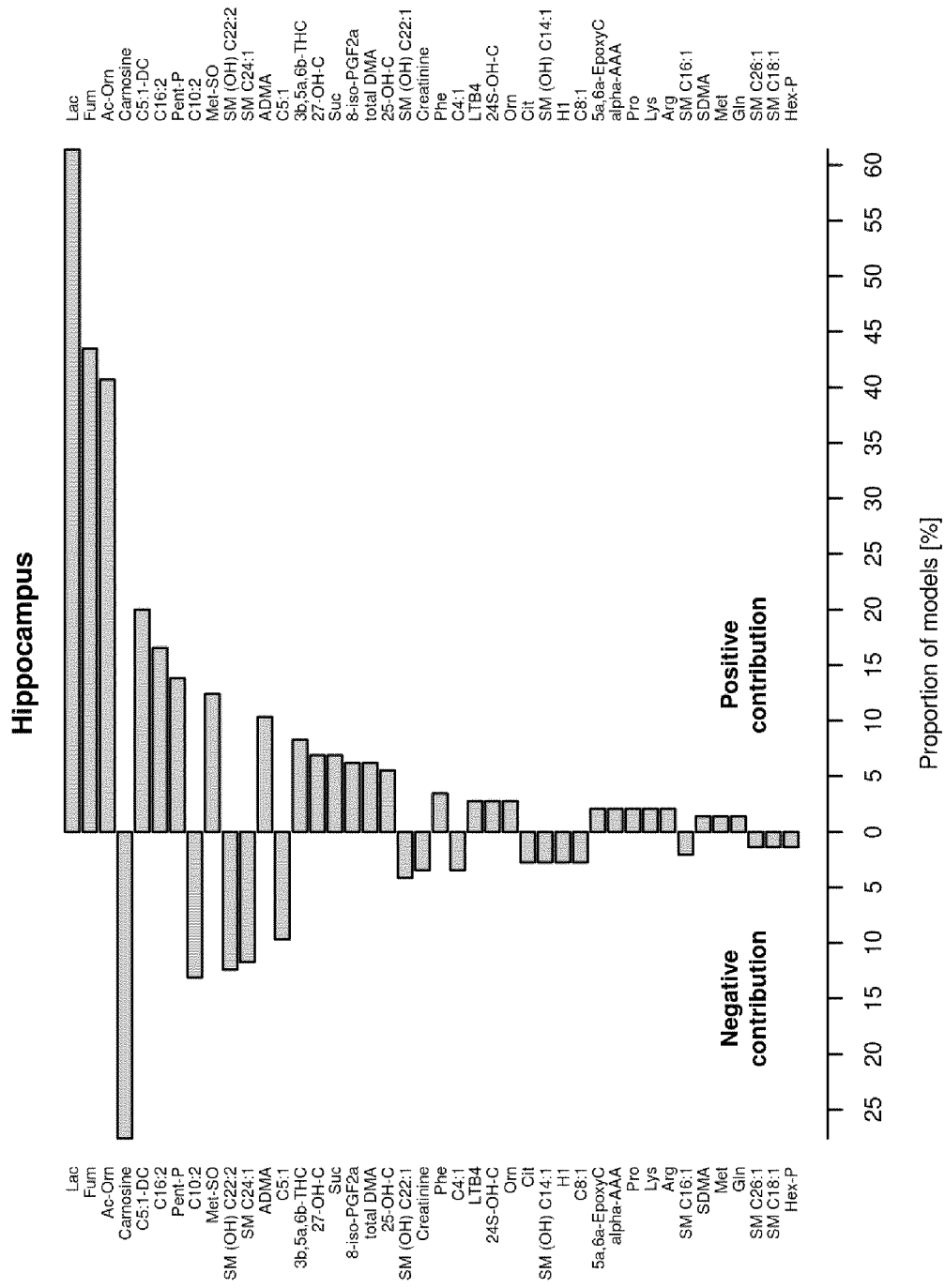
FIG. 1c illustrates the probabilities of single metabolites to enter a combination of metabolites correlating with the extent of brain injury in the hippocampus. Probabilities are calculated over all models presented in FIG. 1b. Metabolites are sorted according to their likelihood to be included in a model and graphed back-to-back depending of their respective (i.e. positive or negative) contributions to the regression models. Left: metabolites inducing less damage in the hippocampus. Right: metabolites inducing more damage in the hippocampus.

FIG. 1c illustrates the probabilities of single metabolites to enter a combination of metabolites correlating with cell death in the hippocampus. Probabilities are calculated over all models presented in FIG. 1b. Metabolites are sorted according to their likelihood to be included in a model and graphed back-to-back depending of their respective (i.e. positive or negative) contributions to the regression models. Left: metabolites inducing less damage in the hippocampus. Right: metabolites inducing more damage in the hippocampus.

Example 2: Hypoxia-Induced Damage of Basal Ganglia

As mentioned above the lack oxygen resulted in increased apoptotic and/or apoptotic cell death assessed in the brain of newborn piglets 48 hours after the lack of oxygen. Blood samples were taken 30 minutes after the period of lack of oxygen and the metabolite concentrations were analysed as described above. These metabolite concentrations were then correlated with the absolute quantitative amount of dying cell in the basal ganglia. Table 6 summarises the result of univariate correlation statistics between metabolite concentration as determined in plasma 30 minutes after asphyxia and the amount of cell death in basal ganglia at 48 hours after asphyxia. For each metabolite, Pearson correlation coefficient (Cor) and its corresponding p value are given alongside the coefficient of determination (Rsq). Prob designates the actual probability (in %) to enter a combination of metabolites.

TABLE 6

Outcome parameter: Brain damage in Basal ganglia

| | Short | Full name | Cor | Pvalue | Rsq | Prob |
|---|---|---|---|---|---|---|
| 1 | Met | Methionine | 0.821 | 0.007 | 67.41 | 20.79 |
| 2 | SM (OH) C22:2 | Hydroxysphingomyelin with acyl residue sum C22:2 | −0.840 | 0.005 | 70.54 | 19.19 |
| 3 | SM (OH) C14:1 | Hydroxysphingomyelin with acyl residue sum C14:1 | −0.770 | 0.015 | 59.36 | 19.06 |
| 4 | Met-SO | Methionine-Sulfoxide | 0.774 | 0.014 | 59.97 | 18.63 |
| 5 | SM C16:1 | sphingomyelin with acyl residue sum C16:1 | −0.772 | 0.015 | 59.52 | 17.67 |
| 6 | SM (OH) C22:1 | Hydroxysphingomyelin with acyl residue sum C22:1 | −0.768 | 0.016 | 59.00 | 16.60 |
| 7 | Pro | Proline | 0.812 | 0.008 | 66.00 | 16.58 |
| 8 | Tyr | Tyrosine | 0.803 | 0.009 | 64.48 | 15.41 |
| 9 | Gln | Glutamine | 0.744 | 0.021 | 55.37 | 15.11 |
| 10 | SM C24:1 | sphingomyelin with acyl residue sum C24:1 | −0.805 | 0.009 | 64.75 | 14.52 |
| 11 | SM C24:0 | sphingomyelin with acyl residue sum C24:0 | −0.676 | 0.045 | 45.76 | 13.46 |
| 12 | SM C16:0 | sphingomyelin with acyl residue sum C16:0 | −0.713 | 0.031 | 50.91 | 13.16 |
| 13 | Orn | Ornithine | 0.655 | 0.055 | 42.96 | 12.78 |
| 14 | Ac-Orn | N-acetylornithine | 0.699 | 0.036 | 48.86 | 11.76 |
| 15 | Arg | Arginine | 0.675 | 0.046 | 45.60 | 11.00 |
| 16 | SM C18:1 | sphingomyelin with acyl residue sum C18:1 | −0.803 | 0.009 | 64.55 | 10.32 |
| 17 | alpha-KGA | alpha-Ketoglutaric acid | −0.730 | 0.025 | 53.34 | 9.94 |
| 18 | Trp | Tryptophane | 0.562 | 0.115 | 31.62 | 9.66 |
| 19 | SM (OH) C24:1 | Hydroxysphingomyelin with acyl residue sum C24:1 | −0.707 | 0.033 | 50.03 | 9.00 |
| 20 | SM (OH) C16:1 | Hydroxysphingomyelin with acyl residue sum C16:1 | −0.778 | 0.014 | 60.46 | 8.95 |
| 21 | Cholestenone | Cholestenone | −0.644 | 0.061 | 41.48 | 8.92 |
| 22 | C5:1-DC | Glutaconylcarnitine/Mesaconylcarnitine (Undecanoylcarnitine) | 0.578 | 0.103 | 33.40 | 8.59 |
| 23 | Lys | Lysine | 0.662 | 0.052 | 43.88 | 8.49 |
| 24 | Histamine | Histamine | −0.547 | 0.127 | 29.94 | 7.45 |
| 25 | His | Histidine | 0.756 | 0.018 | 57.13 | 7.28 |
| 26 | Lac | Lactate | 0.670 | 0.048 | 44.84 | 7.22 |
| 27 | Phe | Phenylalanine | 0.681 | 0.044 | 46.35 | 6.16 |
| 28 | C6:1 | Hexenoylcarnitine | 0.546 | 0.128 | 29.85 | 5.70 |
| 29 | SM C18:0 | sphingomyelin with acyl residue sum C18:0 | −0.689 | 0.040 | 47.53 | 5.20 |
| 30 | 20a-OH-C | 20α-Hydroxycholesterol | 0.550 | 0.125 | 30.28 | 5.12 |
| 31 | 24-DH-Lanosterol | 24-Dihydrolanosterol | −0.655 | 0.055 | 42.92 | 4.18 |
| 32 | Kynurenine | Kynurenine | 0.445 | 0.230 | 19.79 | 4.13 |
| 33 | Leu | Leucine | 0.666 | 0.050 | 44.31 | 4.08 |
| 34 | SM C20:2 | sphingomyelin with acyl residue sum C20:2 | −0.490 | 0.181 | 23.98 | 4.08 |
| 35 | Ala | Alanine | 0.641 | 0.063 | 41.15 | 3.98 |
| 36 | C14:1 | Tetradecenoylcarnitine [Myristoleylcarnitine] | −0.523 | 0.148 | 27.40 | 3.68 |
| 37 | LTB4 | Leukotriene B4 | 0.389 | 0.301 | 15.12 | 3.40 |
| 38 | Suc | Succinic acid | 0.368 | 0.330 | 13.53 | 3.32 |
| 39 | TXB2 | Tromboxane B2 | 0.313 | 0.412 | 9.80 | 2.79 |
| 40 | Fum | Fumaric acid | 0.443 | 0.232 | 19.62 | 2.74 |
| 41 | Gly | Glycine | 0.461 | 0.211 | 21.30 | 2.15 |
| 42 | 25-OH-C | 25-Hydroxycholesterol | −0.343 | 0.366 | 11.78 | 2.03 |
| 43 | SM C26:1 | sphingomyelin with acyl residue sum C26:1 | −0.589 | 0.095 | 34.74 | 1.85 |
| 44 | Ser | Serine | 0.413 | 0.269 | 17.04 | 1.52 |
| 45 | alpha-AAA | 2-Aminoadipic acid | 0.394 | 0.294 | 15.52 | 1.39 |
| 46 | 8-iso-PGF2a | 8-iso-Prostaglandin F2alpha | 0.443 | 0.232 | 19.66 | 1.37 |
| 47 | Val | Valine | 0.508 | 0.163 | 25.76 | 1.19 |
| 48 | Asn | Asparagine | 0.546 | 0.128 | 29.79 | 1.14 |
| 49 | Pent-P | Pentosephosphate (e.g. Ribose-5-phosphate + Ribulose-5-phosphate) | 0.514 | 0.157 | 26.44 | 1.14 |
| 50 | total DMA | Total dimethylarginine | 0.546 | 0.128 | 29.80 | 1.12 |
| 51 | Creatinine | Creatinine | −0.199 | 0.607 | 3.97 | 1.04 |

Figure 2A:
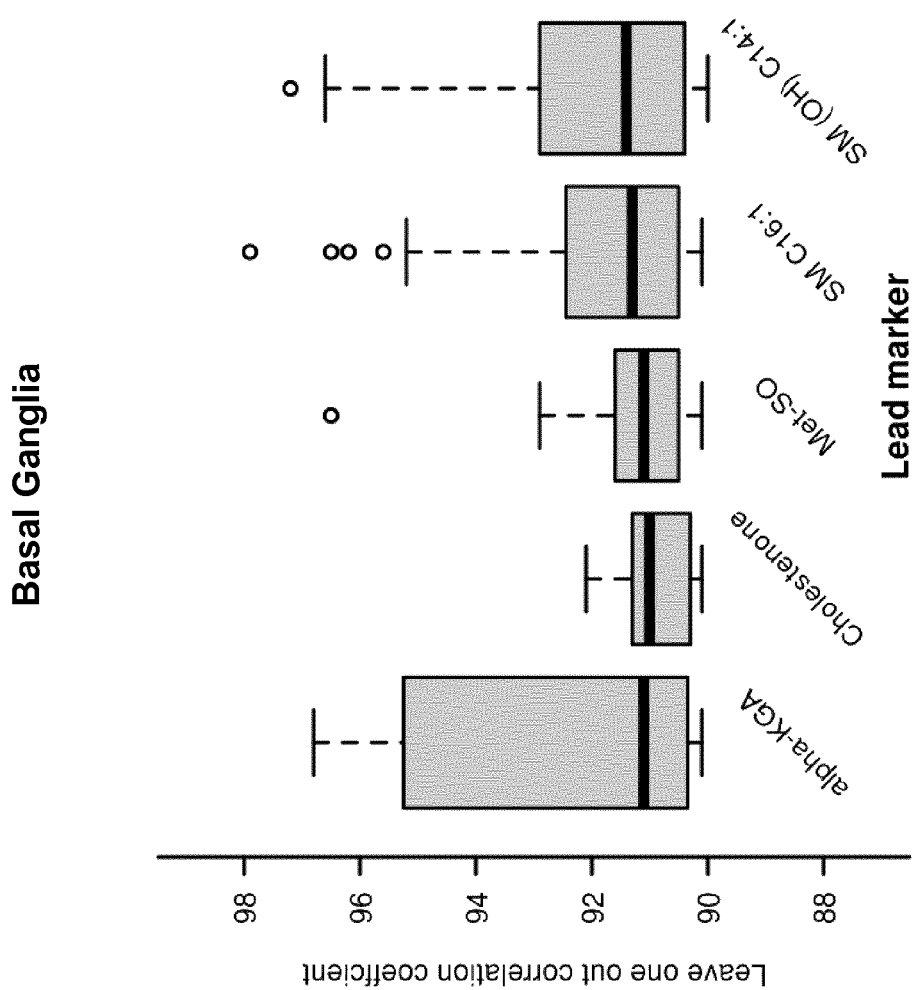
FIG. 2a illustrates the predictive abilities (i.e. accuracy) of the combination of metabolites based on a lead metabolite correlating with the extent of brain damage in the basal ganglia. The box-and-whisker diagrams represent the distribution of the cross-validated correlation coefficient (y-axis) for combinations comprising a lead metabolite (x-axis) and up to 6 metabolites from the initial dataset.

In the attached FIG. 2a, the distribution of accuracies that can be achieved in models formed with a lead metabolite is illustrated.

FIG. 2a illustrates the predictive abilities of combinations of metabolites based on a lead metabolite correlating with the extent of brain damage in the basal ganglia. The box-and-whisker diagrams represent the distribution of the cross-validated correlation coefficient (y-axis) for combinations comprising a lead metabolite (x-axis) and up to 7 metabolites from the initial dataset.

Figure 2B:
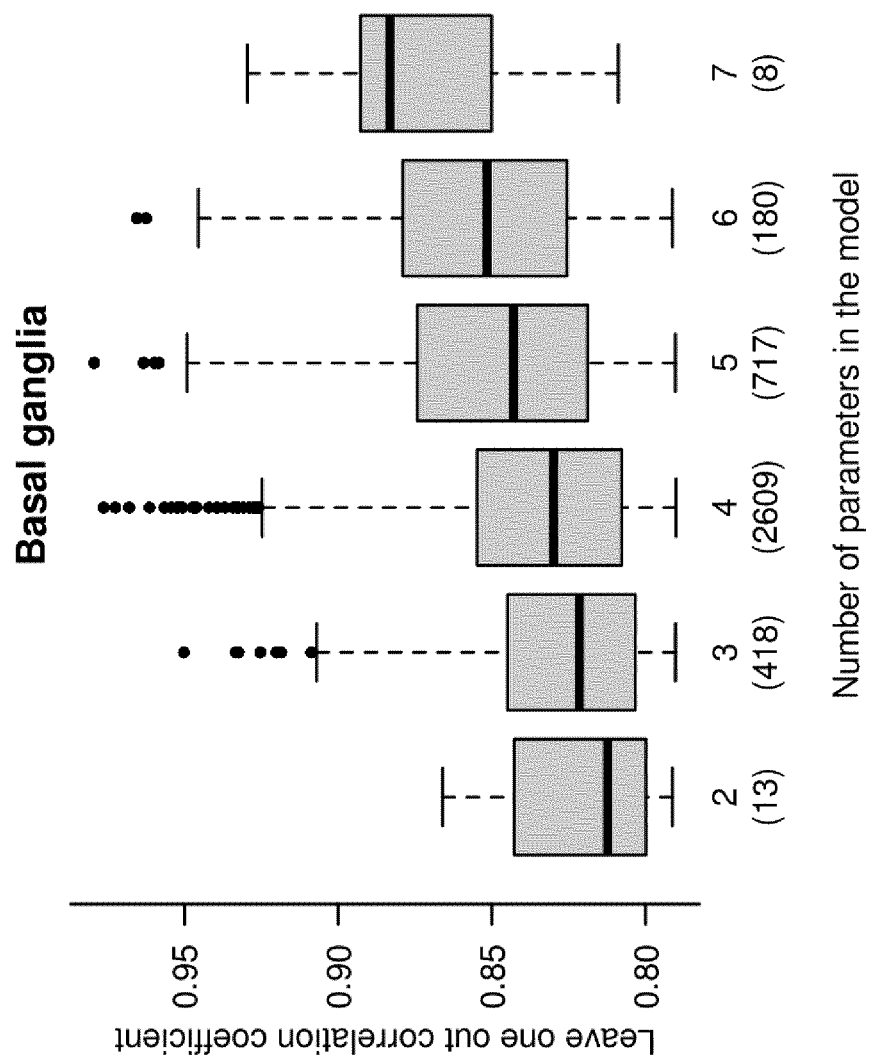
FIG. 2b illustrates the predictive abilities (i.e. accuracy) of all adequate metabolite combinations correlating with the extent of brain damage in the basal ganglia. The box-and-whisker diagrams represent the distribution of the cross-validated correlation coefficient (y-axis) for combinations of 2 to 7 (x-axis) metabolites.

In the attached FIG. 2b, the distribution of the accuracies that can be achieved in models comprising up to 7 metabolites is illustrated.

FIG. 2b illustrates the predictive abilities (i.e. accuracy) of all adequate metabolite combinations correlating with the extent of brain damage in the basal ganglia. The box-and-whisker diagrams represent the distribution of the cross-validated correlation coefficient (y-axis) for combinations of 2 to 7 (x-axis) metabolites.

Figure 2C:
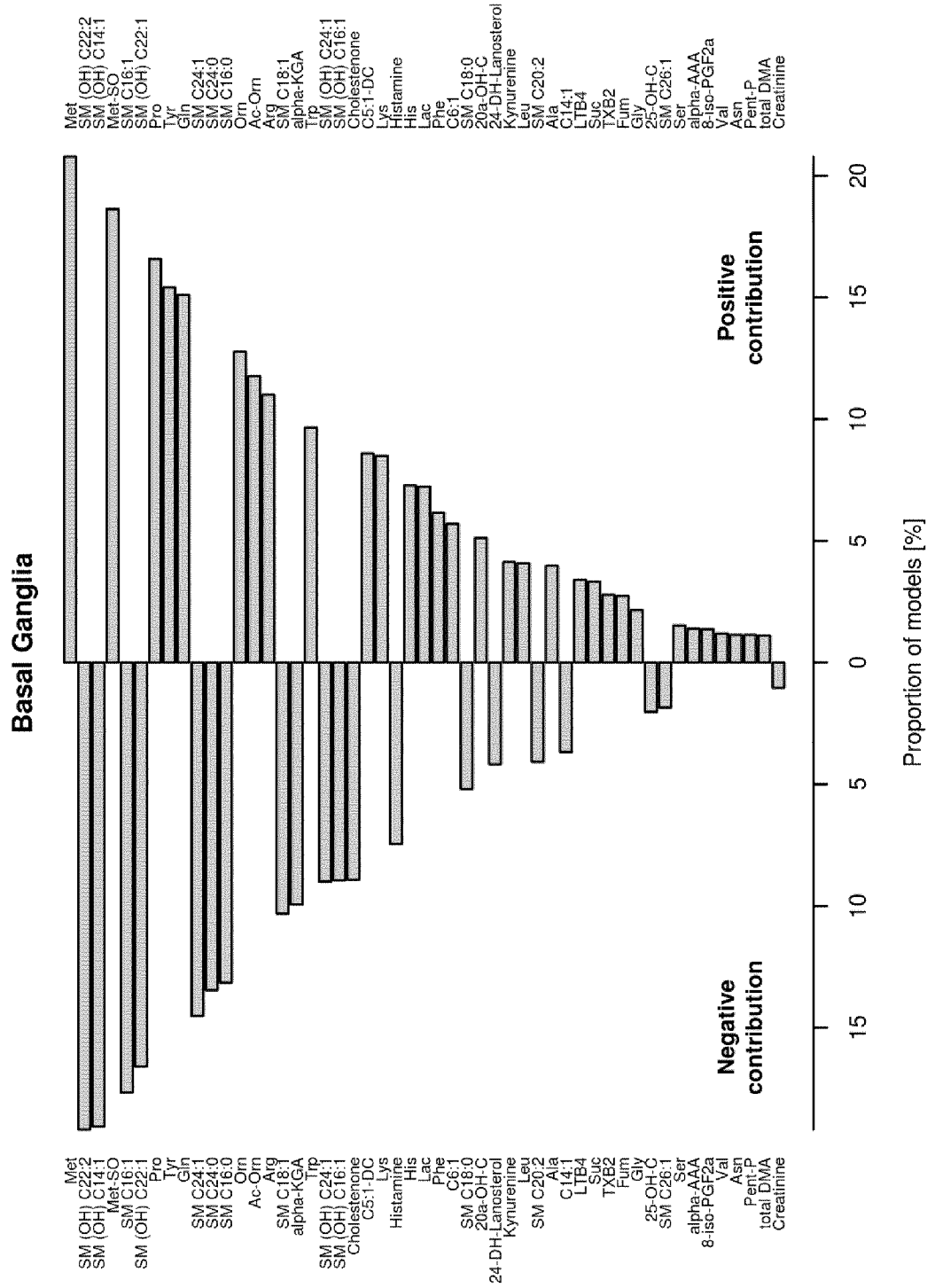
FIG. 2c illustrates the probabilities of single metabolites to enter a combination of metabolites correlating with the extent of brain injury in the basal ganglia. Probabilities are calculated over all models presented in FIG. 2b. Metabolites are sorted according to their likelihood to be included in a model and graphed back-to-back depending of their respective (i.e. positive or negative) contributions to the regression models. Left: metabolites inducing less damage in the basal ganglia. Right: metabolites inducing more damage in the basal ganglia.

In the attached FIG. 2c the probability of a metabolite to enter a model with adequate accuracy is illustrated.

FIG. 2c illustrates the probabilities of single metabolites to enter a combination of metabolites correlating with the extent of brain damage in the basal ganglia. Probabilities are calculated over all models presented in FIG. 2b. Metabolites are sorted according to their likelihood to be included in a model and graphed back-to-back depending of their respective (i.e. positive or negative) contributions to the regression models. Left: metabolites inducing less damage in the basal ganglia. Right: metabolites inducing more damage in the basal ganglia.

Example 3: Hypoxia-Induced Effect on Neurological Score

Lack oxygen resulted in alteration of the neurobehavioural score at 4 hourly time points in the first 24 hours and at 48 h. This score contains 9 items of maximal 2 points, so the maximal score is 18 points and exists of the nine neurologic items as described above. Blood samples were taken 30 minutes after the period of lack of oxygen and the metabolite concentrations were analysed as described above. These metabolite concentrations were then correlated with the neurobehavioural score. Table 7 summarizes the result of univariate correlation statistics between metabolite concentration as determined in plasma 30 minutes after asphyxia and the neurological behavioral score at 48 hours after asphyxia. For each metabolite, Pearson correlation coefficient (Cor) and its corresponding p value are given alongside the coefficient of determination (Rsq). Prob designates the actual probability (in %) to enter a combination of metabolites.

TABLE 7

| | Short | Full name | Cor | Pvalue | Rsq | Prob |
|---|---|---|---|---|---|---|
| | Outcome parameter: Brain Injury indicated by neurological behavioural score | | | | | |
| 1 | 27-OH-C | 27-Hydroxycholesterol | 0.072 | 0.853 | 0.53 | 41.14 |
| 2 | Fum | Fumaric acid | 0.443 | 0.232 | 19.62 | 36.54 |
| 3 | Carnosine | Carnosine | −0.286 | 0.456 | 8.17 | 30.13 |
| 4 | total DMA | Total dimethylarginine | 0.546 | 0.128 | 29.80 | 23.57 |
| 5 | C5-DC (C6-OH) | Glutarylcarnitine | 0.188 | 0.628 | 3.53 | 19.11 |
| 6 | SDMA | Symmetric dimethylarginine | 0.424 | 0.256 | 17.94 | 18.27 |
| 7 | C5:1 | Tiglylcarnitine/3-Methyl-crotonylcarnitine | −0.051 | 0.896 | 0.26 | 17.99 |
| 8 | Met-SO | Methionine-Sulfoxide | 0.774 | 0.014 | 59.97 | 17.15 |
| 9 | C10:2 | Decadienoylcarnitine | −0.303 | 0.428 | 9.17 | 15.76 |
| 10 | SM (OH) C22:2 | Hydroxysphingomyelin with acyl residue sum C22:2 | −0.840 | 0.005 | 70.54 | 15.06 |
| 11 | C8:1 | Octenoylcarnitine | −0.272 | 0.479 | 7.40 | 12.83 |
| 12 | Phe | Phenylalanine | 0.681 | 0.044 | 46.35 | 9.76 |
| 13 | Ac-Orn | N-acetylornithine | 0.699 | 0.036 | 48.86 | 9.07 |
| 14 | SM (OH) C14:1 | Hydroxysphingomyelin with acyl residue sum C14:1 | −0.770 | 0.015 | 59.36 | 9.07 |
| 15 | 24,25-EpoxyC | 24,25-Epoxycholesterol | 0.063 | 0.872 | 0.40 | 8.51 |
| 16 | Tyr | Tyrosine | 0.803 | 0.009 | 64.48 | 8.09 |
| 17 | alpha-AAA | 2-Aminoadipic acid | 0.394 | 0.294 | 15.52 | 6.69 |
| 18 | C14:1 | Tetradecenoylcarnitine [Myristoleylcarnitine] | −0.523 | 0.148 | 27.40 | 6.69 |
| 19 | Pent-P | Pentosephosphate (e.g. Ribose-5-phosphate + Ribulose-5-phosphate) | 0.514 | 0.157 | 26.44 | 6.28 |
| 20 | C6 (C4:1-DC) | Hexanoylcarnitine [Caproylcarnitine] | −0.245 | 0.525 | 6.00 | 5.86 |
| 21 | SM C16:1 | sphingomyelin with acyl residue sum C16:1 | −0.772 | 0.015 | 59.52 | 4.88 |
| 22 | C14:1-OH | 3-Hydroxytetradecenoylcarnitine [3-Hydroxymyristoleylcarnitine] | −0.334 | 0.379 | 11.18 | 4.32 |
| 23 | SM C24:1 | sphingomyelin with acyl residue sum C24:1 | −0.805 | 0.009 | 64.75 | 4.04 |
| 24 | Cholestenone | Cholestenone | −0.644 | 0.061 | 41.48 | 3.77 |
| 25 | Lac | Lactate | 0.670 | 0.048 | 44.84 | 3.63 |
| 26 | 8-iso-PGF2a | 8-iso-Prostaglandin F2alpha | 0.443 | 0.232 | 19.66 | 3.49 |
| 27 | 3b,5a,6b-THC | 3β,5α,6β-Trihydroxycholestan | −0.114 | 0.769 | 1.31 | 3.49 |
| 28 | Suc | Succinic acid | 0.368 | 0.330 | 13.53 | 3.21 |
| 29 | C0 | Carnitine (free) | 0.068 | 0.862 | 0.46 | 3.07 |
| 30 | 24-DH-Lanosterol | 24-Dihydrolanosterol | −0.655 | 0.055 | 42.92 | 2.65 |
| 31 | Val | Valine | 0.508 | 0.163 | 25.76 | 2.65 |
| 32 | SM C16:0 | sphingomyelin with acyl residue sum C16:0 | −0.713 | 0.031 | 50.91 | 2.65 |
| 33 | C3-DC (C4-OH) | 3-Hydroxybutyrylcarnitine/Malonylcarnitine | 0.173 | 0.657 | 2.98 | 2.65 |
| 34 | Lys | Lysine | 0.662 | 0.052 | 43.88 | 2.37 |
| 35 | Leu | Leucine | 0.666 | 0.050 | 44.31 | 2.37 |
| 36 | SM C26:0 | sphingomyelin with acyl residue sum C26:0 | 0.184 | 0.635 | 3.40 | 2.37 |
| 37 | Cit | Citrulline | 0.032 | 0.935 | 0.10 | 2.23 |
| 38 | LTB4 | Leukotriene B4 | 0.389 | 0.301 | 15.12 | 2.09 |
| 39 | 5a,6a-EpoxyC | 5α,6α-Epoxycholesterol | −0.166 | 0.669 | 2.76 | 2.09 |
| 40 | C4:1 | Butenoylcarnitine | −0.078 | 0.841 | 0.61 | 2.09 |

TABLE 7-continued

Outcome parameter: Brain Injury indicated by neurological behavioural score

| | Short | Full name | Cor | Pvalue | Rsq | Prob |
|---|---|---|---|---|---|---|
| 41 | Met | Methionine | 0.821 | 0.007 | 67.41 | 1.95 |
| 42 | C5:1-DC | Glutaconylcarnitine/Mesaconylcarnitine (Undecanoylcarnitine) | 0.578 | 0.103 | 33.40 | 1.95 |
| 43 | Pro | Proline | 0.812 | 0.008 | 66.00 | 1.81 |
| 44 | SM (OH) C16:1 | Hydroxysphingomyelin with acyl residue sum C16:1 | −0.778 | 0.014 | 60.46 | 1.81 |
| 45 | C14:2-OH | 3-Hydroxytetradecadienoylcarnitine | 0.196 | 0.614 | 3.83 | 1.81 |
| 46 | Thr | Threonine | 0.482 | 0.189 | 23.24 | 1.53 |
| 47 | SM (OH) C22:1 | Hydroxysphingomyelin with acyl residue sum C22:1 | −0.768 | 0.016 | 59.00 | 1.12 |

Figure 3A:
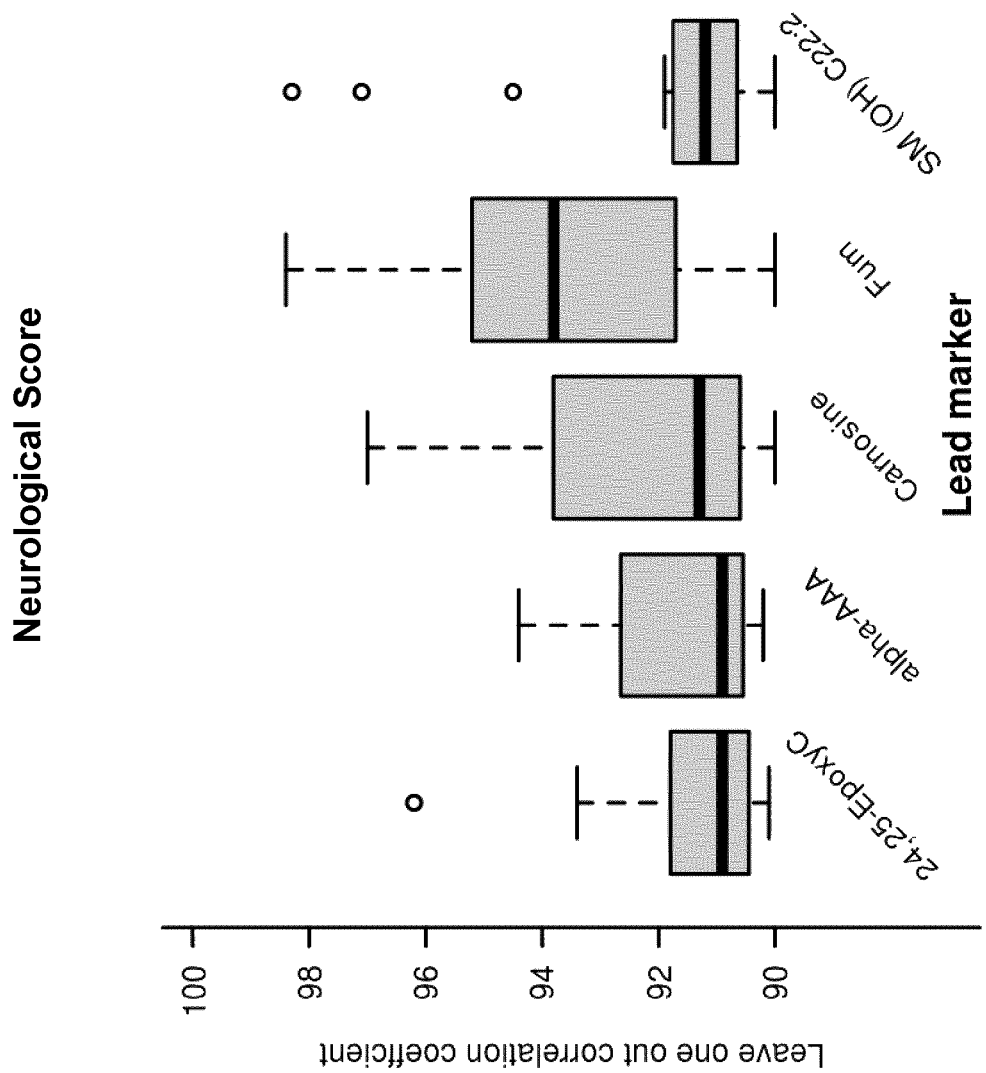
FIG. 3a illustrates the predictive abilities (i.e. accuracy) of the combination of metabolites based on a lead metabolite correlating with the extent of brain injury as described by the neurological score at 48 h. The box-and-whisker diagrams represent the distribution of the cross-validated correlation coefficient (y-axis) for combinations comprising a lead metabolite (x-axis) and up to 7 metabolites from the initial dataset.

In the attached FIG. 3a, the distribution of accuracies that can be achieved in models formed with a lead metabolite is illustrated.

FIG. 3a illustrates the predictive abilities of the combination of metabolites based on a lead metabolite correlating with the extent of brain injury as described by the neurological score at 48 h. The box-and-whisker diagrams represent the distribution of the cross-validated correlation coefficient (y-axis) for combinations comprising a lead metabolite (x-axis) and up to 6 metabolites from the initial dataset.

Figure 3B:
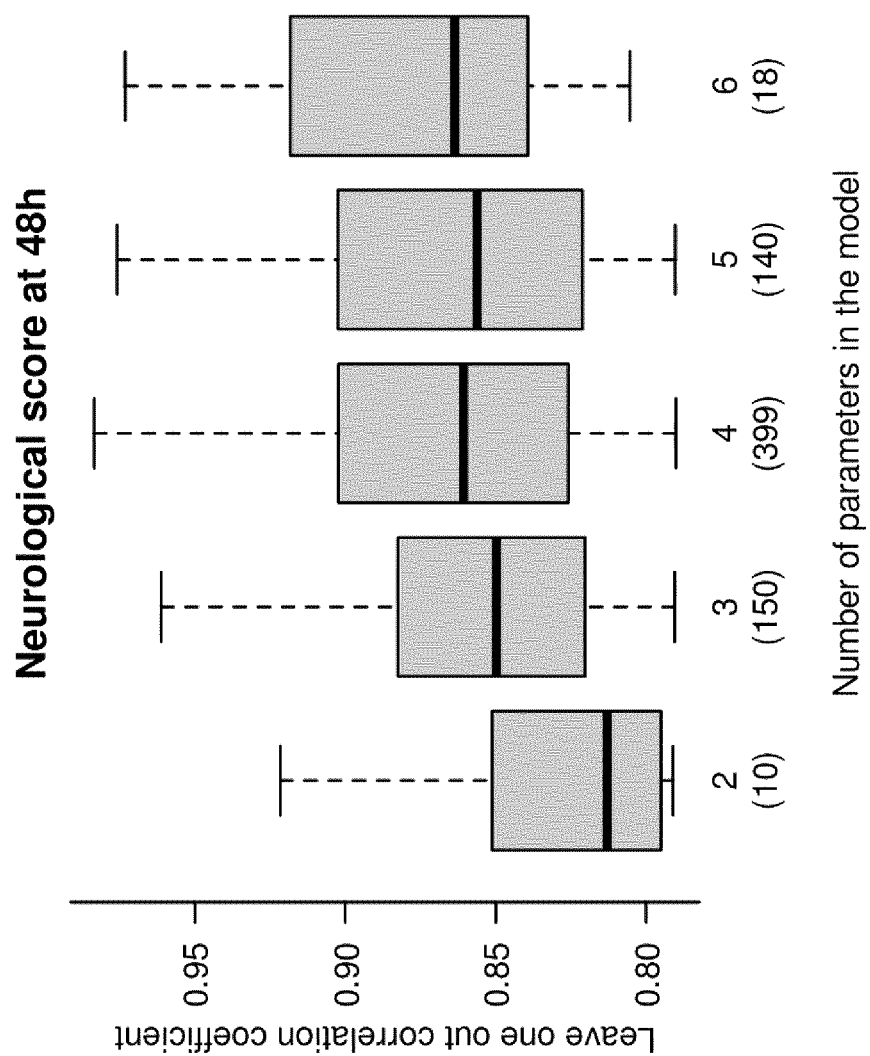
FIG. 3b illustrates the predictive abilities (i.e. accuracy) of all adequate metabolite combinations correlating with the extent of brain injury as described by the neurological score at 48 h. The box-and-whisker diagrams represent the distribution of the cross-validated correlation coefficient (y-axis) for combinations of 2 to 6 (x-axis) metabolites.

In the attached FIG. 3b, the distribution of the accuracies that can be achieved in models comprising up to 6 metabolites is illustrated.

FIG. 3b illustrates the predictive abilities (i.e. accuracy) of all adequate metabolite combinations correlating with the extent of brain injury as described by the neurological score at 48 h. The box-and-whisker diagrams represent the distribution of the cross-validated correlation coefficient (y-axis) for combinations of 2 to 6 (x-axis) metabolites.

Figure 3C:
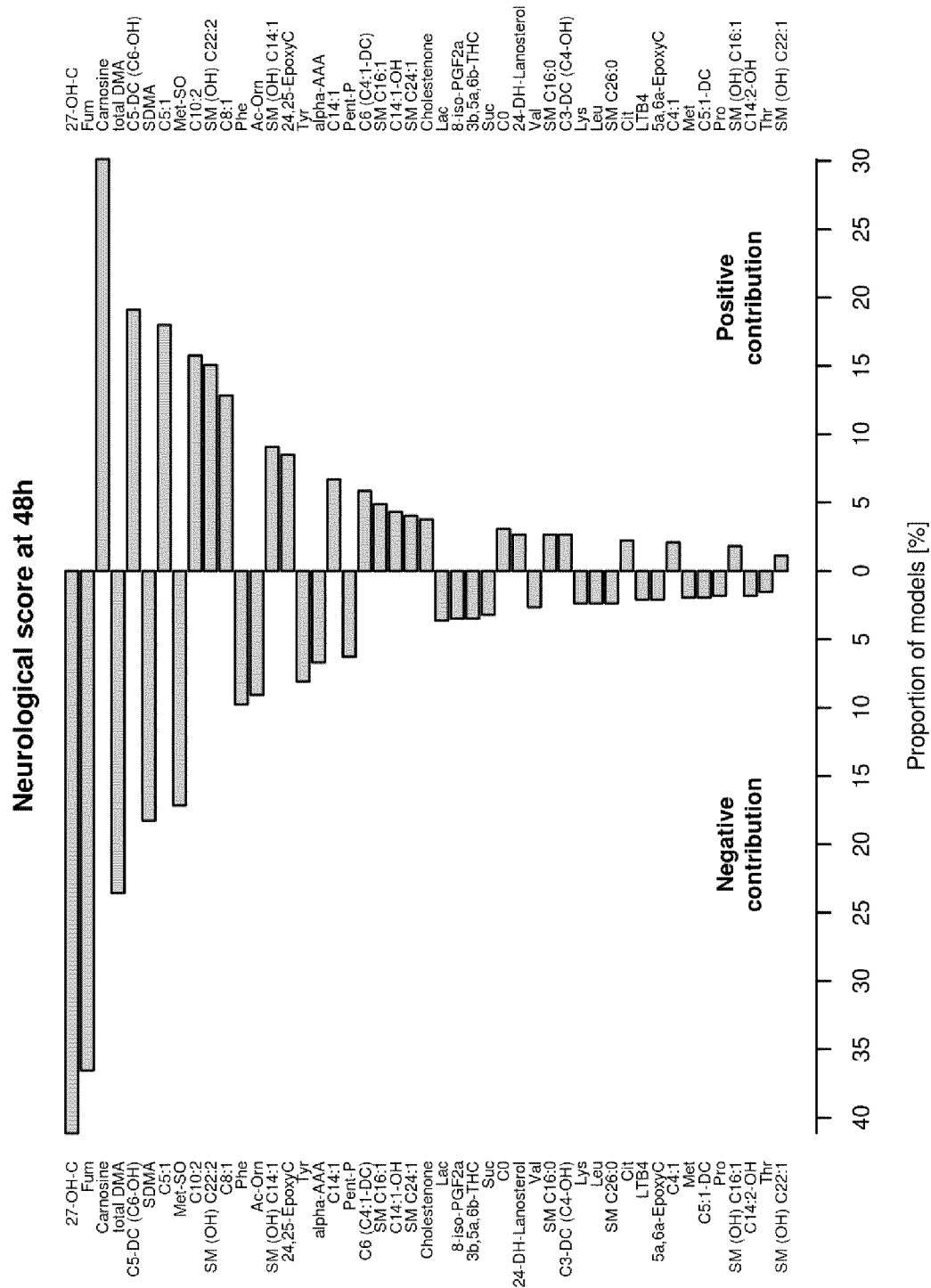
FIG. 3c illustrates the probabilities of single metabolites to enter a combination of metabolites correlating with the extent of brain injury as described by the neurological score at 48 h. Probabilities are calculated over all models presented in FIG. 3b. Metabolites are sorted according to their likelihood to be included in a model and graphed back-to-back depending of their respective (i.e. positive or negative) contributions to the regression models. Left: metabolites worsening the neurological outcome. Right: metabolites improving the neurological outcome.

In the attached FIG. 3c the probability of a metabolite to enter a model with adequate accuracy is illustrated.

FIG. 3c illustrates the probabilities of single metabolites to enter a combination of metabolites correlating with the extent of brain injury as described by the neurological score at 48 h. Probabilities are calculated over all models presented in FIG. 3b.

Metabolites are sorted according to their likelihood to be included in a model and graphed back-to-back depending of their respective (i.e. positive or negative) contributions to the regression models. Left: metabolites worsening the neurological outcome. Right: metabolites improving the neurological outcome.

Explanation on attached Tables 8 to 13:

The data were generated as described above in the Material and Methods section.

The attached Tables 8, 9 and 10 summarize the obtained metabolite combinations. Preferred combinations are listed in Tables 11, 12 and 13.

In particular these tables are related to:

Tables 8 and 11: Combination of metabolites, correlated with affection of hippocampus brain tissue Tables 9 and 12: Combination of metabolites, correlated with affection of basal ganglia brain tissue Tables 10 and 13: Combination of metabolites, correlated with neurological behavioral score The following parameters are shown in tables 8, 9 and 10:

Npar=total number of parameters (metabolites) in the model

Chemical class=metabolite chemical classes represented in the model

Accuracy=defined as the correlation coefficient (given in %) between true and predicted predictand values Model=List of metabolites in the model The following parameters are shown in tables 11, 12 and 13:

Npar=total number of metabolites in the final model

Accuracy=defined as the correlation coefficient (given in %) between true and predicted predictand values Lead metabolite=lead metabolite of the model Additional metabolites=list of metabolites accompanying the lead metabolite in the final model The disclosure of documents cited herein is incorporated by reference

TABLE 8

Metabolite combinations describing damage of hippocampus

| No | Npar | Chemical Class | Accuracy | Model |
|---|---|---|---|---|
| 1 | 3 | En.Met/Ac.Ca./S.L. | 83.2 | Lac; C5:1; SM C24:1 |
| 2 | 3 | En.Met/B.Am. | 93.4 | Lac; Suc; Carnosine |
| 3 | 2 | En.Met | 94.4 | Lac; Pent-P |
| 4 | 3 | En.Met/B.Am. | 92.4 | Fum; Lac; Ac-Orn |
| 5 | 4 | En.Met/Ac.Ca./S.L./B.Am. | 83.3 | Pent-P; C16:2; SM C24:1; Carnosine |
| 6 | 4 | En.Met/S.L./B.Am./O.St. | 79.2 | Lac; SM (OH) C22:1; Carnosine; 25-OH-C |
| 7 | 4 | En.Met/Ac.Ca. | 86.4 | Fum; Lac; Pent-P; C5:1-DC |
| 8 | 2 | En.Met/B.Am. | 92.7 | Fum; Ac-Orn |
| 9 | 3 | En.Met/Ac.Ca./B.Am. | 90 | Fum; C16:2; Ac-Orn |
| 10 | 3 | En.Met/B.Am. | 91.7 | Fum; Ac-Orn; Carnosine |
| 11 | 4 | En.Met/B.Am. | 79.4 | Fum; ADMA; Carnosine; Met-SO |
| 12 | 5 | En.Met/Ac.Ca./B.Am./P.G. | 79.3 | Fum; Lac; C10:2; Met-SO; 8-iso-PGF2a |
| 13 | 4 | Ac.Ca./S.L./Am.Ac./B.Am. | 81.9 | C16:2; SM C24:1; Gln; Met-SO |
| 14 | 3 | En.Met/Am.Ac./B.Am. | 90.9 | Fum; Cit; Ac-Orn |
| 15 | 4 | En.Met/Ac.Ca./B.Am. | 88.7 | Lac; C10:2; C5:1-DC; Carnosine |
| 16 | 3 | En.Met/Ac.Ca./B.Am. | 80.3 | Fum; C16:2; Met-SO |
| 17 | 3 | En.Met/S.L./B.Am. | 84.8 | Lac; SM C24:1; Carnosine |
| 18 | 4 | En.Met | 80.2 | Fum; Lac; Pent-P; H1 |
| 19 | 4 | En.Met/Ac.Ca./S.L./B.Am. | 85.5 | Pent-P; C16:2; SM (OH) C22:2; Ac-Orn |

TABLE 8-continued

Metabolite combinations describing damage of hippocampus

| No | Npar | Chemical Class | Accuracy | Model |
|----|------|----------------|----------|-------|
| 20 | 3 | En.Met/Ac.Ca. | 83.6 | Fum; C4:1; C5:1-DC |
| 21 | 3 | En.Met/Ac.Ca./B.Am. | 81.8 | Fum; C5:1-DC; Carnosine |
| 22 | 3 | En.Met/B.Am. | 89.9 | Fum; Pent-P; Ac-Orn |
| 23 | 5 | En.Met/S.L./B.Am./O.St. | 79.1 | Fum; SM (OH) C14:1; Ac-Orn; 24-DH-Lanosterol; 3b,5a,6b-THC |
| 24 | 5 | En.Met/S.L./Am.Ac./O.St. | 81.4 | Lac; SM (OH) C22:1; SM (OH) C22:2; Lys; 25-OH-C |
| 25 | 3 | En.Met/Ac.Ca./B.Am. | 79.3 | Lac; C8:1; Carnosine |
| 26 | 3 | En.Met/B.Am. | 86.5 | Lac; Ac-Orn; Carnosine |
| 27 | 4 | En.Met/Am.Ac. | 81.6 | Fum; Lac; Suc; Phe |
| 28 | 3 | En.Met/Ac.Ca./B.Am. | 94 | Fum; C5:1-DC; Ac-Orn |
| 29 | 3 | En.Met/S.L./B.Am. | 80.7 | Lac; SM (OH) C22:2; Carnosine |
| 30 | 3 | En.Met/Ac.Ca. | 84.6 | Lac; C4:1; C5:1-DC |
| 31 | 3 | En.Met/B.Am. | 87 | Fum; Ac-Orn; ADMA |
| 32 | 4 | En.Met/B.Am. | 86.4 | Fum; Lac; Suc; Met-SO |
| 33 | 4 | En.Met/S.L./O.St./P.G. | 81.7 | Lac; SM (OH) C22:2; 3b,5a,6b-THC; 8-iso-PGF2a |
| 34 | 4 | En.Met/Ac.Ca./P.G. | 84 | Fum; Lac; C5:1-DC; 8-iso-PGF2a |
| 35 | 3 | En.Met/Ac.Ca. | 83.6 | Fum; C10:2; C5:1-DC |
| 36 | 5 | En.Met/Ac.Ca./S.L./B.Am./P.G. | 84 | Fum; C16:2; SM (OH) C22:2; Ac-Orn; LTB4 |
| 37 | 4 | En.Met/Ac.Ca./S.L./B.Am. | 86.2 | Lac; C16:2; SM C24:1; Ac-Orn |
| 38 | 3 | En.Met/Ac.Ca. | 82.2 | Lac; C10:2; C5:1-DC |
| 39 | 3 | En.Met/Ac.Ca./Am.Ac. | 86.6 | Lac; C10:2; Phe |
| 40 | 3 | En.Met/Ac.Ca./B.Am. | 91.5 | Lac; C10:2; Ac-Orn |
| 41 | 4 | En.Met/S.L./B.Am. | 81.3 | Fum; SM C24:1; SM (OH) C22:2; Ac-Orn |
| 42 | 5 | En.Met/Am.Ac./B.Am./O.St. | 83.6 | Fum; Arg; Lys; Ac-Orn; 25-OH-C |
| 43 | 5 | En.Met/S.L./B.Am. | 86 | Lac; SM C24:0; SM (OH) C22:1; Ac-Orn; Carnosine |
| 44 | 3 | Ac.Ca./S.L./B.Am. | 81.6 | C16:2; SM C24:1; Carnosine |
| 45 | 4 | En.Met/Ac.Ca./B.Am. | 83.6 | Fum; C10:2; C5:1-DC; Carnosine |
| 46 | 4 | En.Met/Ac.Ca./B.Am. | 89.1 | Lac; C10:2; Ac-Orn; Carnosine |
| 47 | 5 | En.Met/Ac.Ca./S.L./B.Am./O.St. | 87.6 | Lac; C5:1; SM C24:1; Ac-Orn; 5a,6a-EpoxyC |
| 48 | 4 | En.Met/Ac.Ca./Am.Ac./O.St. | 81 | Lac; C5:1-DC; Pro; 27-OH-C |
| 49 | 4 | En.Met/B.Am./O.St. | 87.6 | Lac; Ac-Orn; Carnosine; 5a,6a-EpoxyC |
| 50 | 3 | En.Met/Am.Ac./B.Am. | 90.6 | Lac; Cit; Ac-Orn |
| 51 | 4 | En.Met/Ac.Ca./B.Am. | 85.8 | Lac; C5:1; H1; Ac-Orn |
| 52 | 4 | En.Met/Ac.Ca./B.Am. | 88.8 | Lac; C5:1; Ac-Orn; Carnosine |
| 53 | 4 | En.Met/B.Am. | 85.4 | Lac; Ac-Orn; Carnosine; Creatinine |
| 54 | 4 | En.Met/Ac.Ca./Am.Ac./B.Am. | 84.2 | Lac; C16:2; Cit; Ac-Orn |
| 55 | 4 | En.Met/Ac.Ca./S.L. | 84.3 | Lac; Suc; C16:2; SM C24:1 |
| 56 | 4 | En.Met/Ac.Ca./S.L./B.Am. | 92.8 | Lac; C5:1; SM C24:1; Carnosine |
| 57 | 3 | En.Met/B.Am. | 82.1 | Fum; Lac; Met-SO |
| 58 | 4 | En.Met/B.Am./O.St. | 93.3 | H1; Creatinine; total DMA; 3b,5a,6b-THC |
| 59 | 4 | En.Met/Ac.Ca./S.L./B.Am. | 86 | Lac; C5:1; SM (OH) C22:2; Ac-Orn |
| 60 | 4 | En.Met/S.L./Am.Ac./O.St. | 83.6 | Lac; SM (OH) C22:2; Lys; 25-OH-C |
| 61 | 3 | Ac.Ca./S.L. | 85.1 | C16:2; C5:1; SM C24:1 |
| 62 | 4 | En.Met/Ac.Ca./S.L./B.Am. | 89 | Lac; C5-DC (C6-OH); SM C18:1; Carnosine |
| 63 | 4 | En.Met/Ac.Ca./B.Am./P.G. | 91.3 | Fum; C10:2; Ac-Orn; 8-iso-PGF2a |
| 64 | 4 | En.Met/B.Am. | 94.8 | Hex-P; Lac; Pent-P; Carnosine |
| 65 | 4 | En.Met/Ac.Ca./B.Am. | 84.9 | Lac; C4:1; C5:1-DC; Carnosine |
| 66 | 4 | En.Met/S.L./O.St. | 81.8 | Lac; SM C16:1; SM (OH) C22:2; 24S-OH-C |
| 67 | 4 | Ac.Ca./B.Am./O.St. | 82.2 | C10:2; C5:1-DC; alpha-AAA; 3b,5a,6b-THC |
| 68 | 4 | En.Met/Ac.Ca./B.Am./O.St. | 79.3 | Lac; C5:1-DC; Ac-Orn; 27-OH-C |
| 69 | 4 | En.Met/Ac.Ca./B.Am. | 86.7 | Suc; C5:1-DC; alpha-AAA; Carnosine |
| 70 | 5 | En.Met/Am.Ac./B.Am./O.St. | 85.3 | Fum; Orn; Pro; Ac-Orn; 24S-OH-C |
| 71 | 5 | En.Met/Ac.Ca./Am.Ac./B.Am. | 79.8 | Lac; C10:2; Arg; Orn; Ac-Orn |
| 72 | 3 | En.Met/B.Am./O.St. | 81.2 | Lac; total DMA; 3b,5a,6b-THC |
| 73 | 3 | En.Met/B.Am./O.St. | 83.1 | Lac; Ac-Orn; 5a,6a-EpoxyC |
| 74 | 4 | En.Met/Ac.Ca. | 84.4 | Lac; Pent-P; C4:1; C5:1-DC |
| 75 | 4 | En.Met/Ac.Ca./B.Am. | 80 | Hex-P; Lac; C8:1; Ac-Orn |
| 76 | 4 | En.Met/Ac.Ca./B.Am. | 92.7 | Fum; C16:2; Ac-Orn; Met-SO |
| 77 | 4 | En.Met/Ac.Ca./S.L./O.St. | 83.7 | Lac; C6:1; SM C16:1; 25-OH-C |
| 78 | 4 | En.Met/B.Am. | 80.7 | Fum; Carnosine; Creatinine; Met-SO |
| 79 | 3 | Ac.Ca./S.L./B.Am. | 83.3 | C16:2; SM C24:1; Ac-Orn |
| 80 | 4 | En.Met/Ac.Ca./S.L. | 82.9 | Fum; Lac; C5:1-DC; SM (OH) C22:2 |
| 81 | 4 | En.Met/Ac.Ca./S.L./B.Am. | 85.8 | Pent-P; C16:2; SM C24:1; Ac-Orn |
| 82 | 5 | En.Met/Am.Ac./B.Am./O.St. | 85 | Lac; Arg; Carnosine; Met-SO; 27-OH-C |
| 83 | 4 | En.Met/B.Am./O.St. | 82.4 | Lac; Ac-Orn; ADMA; 27-OH-C |
| 84 | 4 | En.Met/B.Am. | 91.1 | Fum; Lac; Ac-Orn; Carnosine |
| 85 | 4 | En.Met/Am.Ac./P.G. | 79.8 | Fum; Lac; Phe; 8-iso-PGF2a |
| 86 | 4 | En.Met/Ac.Ca./S.L./B.Am. | 87 | Fum; C5:1-DC; SM (OH) C22:2; Carnosine |
| 87 | 5 | Ac.Ca./S.L./B.Am. | 81 | C10:2; C16:2; SM (OH) C22:2; Ac-Orn; Carnosine |
| 88 | 4 | En.Met/B.Am. | 87.9 | Fum; Lac; Ac-Orn; ADMA |
| 89 | 5 | En.Met/B.Am. | 79.9 | Fum; Lac; ADMA; Carnosine; Met-SO |
| 90 | 4 | En.Met/Ac.Ca./B.Am. | 81.5 | Fum; Pent-P; C16:2; Met-SO |
| 91 | 5 | Ac.Ca./S.L./B.Am. | 81.1 | C16:2; SM C24:1; SM C26:1; SM (OH) C22:1; Ac-Orn |
| 92 | 4 | En.Met/Am.Ac./B.Am./O.St. | 82.9 | Lac; Phe; Ac-Orn; 27-OH-C |
| 93 | 5 | En.Met/B.Am. | 82.3 | Lac; Pent-P; ADMA; SDMA; total DMA |
| 94 | 5 | En.Met/B.Am./O.St. | 80.2 | Lac; Suc; ADMA; total DMA; 3b,5a,6b-THC |
| 95 | 3 | En.Met/B.Am. | 81.3 | Lac; Creatinine; total DMA |

TABLE 8-continued

Metabolite combinations describing damage of hippocampus

| No | Npar | Chemical Class | Accuracy | Model |
|---|---|---|---|---|
| 96 | 6 | En.Met/Ac.Ca./S.L./B.Am./O.St. | 88.2 | Lac; C16:2; SM (OH) C22:2; Ac-Orn; ADMA; 27-OH-C |
| 97 | 4 | En.Met/Ac.Ca./S.L./O.St. | 79.9 | Lac; C10:2; SM (OH) C22:2; 3b,5a,6b-THC |
| 98 | 4 | En.Met/Am.Ac./O.St./P.G. | 79 | Lac; Orn; 3b,5a,6b-THC; 8-iso-PGF2a |
| 99 | 4 | En.Met/Am.Ac./B.Am./P.G. | 79.8 | Fum; Met; Ac-Orn; DHA |
| 100 | 5 | En.Met/B.Am./O.St. | 82.2 | Lac; H1; ADMA; Met-SO; 27-OH-C |
| 101 | 4 | En.Met/B.Am. | 95 | Lac; Pent-P; Suc; Carnosine |
| 102 | 4 | En.Met/B.Am./O.St. | 87.6 | Fum; Ac-Orn; ADMA; 3b,5a,6b-THC |
| 103 | 4 | En.Met/Ac.Ca. | 83.9 | Fum; Lac; C5:1-DC; C8:1 |
| 104 | 4 | Ac.Ca./S.L./B.Am. | 81 | C16; C5:1-DC; SM (OH) C14:1; Carnosine |
| 105 | 4 | En.Met/S.L./O.St. | 80 | Lac; SM (OH) C22:1; 24S-OH-C; 25-OH-C |
| 106 | 5 | En.Met/Ac.Ca./S.L./B.Am. | 84.8 | Fum; C5:1-DC; SM C16:1; SM (OH) C14:1; Carnosine |
| 107 | 4 | En.Met/S.L./B.Am. | 81.9 | Fum; SM C16:0; SM (OH) C22:2; Ac-Orn |
| 108 | 4 | En.Met/Ac.Ca./B.Am. | 79.5 | Fum; Lac; C5:1; Met-SO |
| 109 | 4 | En.Met/Ac.Ca./B.Am. | 81.5 | Lac; C16:2; Ac-Orn; Carnosine |
| 110 | 4 | En.Met/B.Am. | 93.8 | Fum; Lac; Pent-P; Ac-Orn |
| 111 | 4 | En.Met/Ac.Ca./S.L./B.Am. | 81.6 | Lac; C5:1; SM C24:1; Ac-Orn |
| 112 | 4 | En.Met/Ac.Ca. | 80.7 | Fum; Lac; C10:2; C5:1-DC |
| 113 | 6 | En.Met/Ac.Ca./B.Am./P.G. | 84.8 | Fum; Pent-P; C18:2; Ac-Orn; Met-SO; LTB4 |
| 114 | 4 | En.Met/B.Am./O.St./P.G. | 85.7 | Lac; total DMA; 3b,5a,6b-THC; 8-iso-PGF2a |
| 115 | 4 | En.Met/Ac.Ca./B.Am. | 84.6 | Fum; Lac; C5:1-DC; SDMA |
| 116 | 4 | En.Met/Ac.Ca./B.Am. | 82.7 | Fum; C4:1; C5:1-DC; Carnosine |
| 117 | 4 | En.Met/Ac.Ca./B.Am. | 89.7 | Lac; Pent-P; C10:2; Ac-Orn |
| 118 | 4 | En.Met/Am.Ac./P.G. | 81.8 | Lac; Suc; Orn; 8-iso-PGF2a |
| 119 | 4 | Ac.Ca./S.L./B.Am. | 82.7 | C5:1; SM C24:1; ADMA; Carnosine |
| 120 | 4 | En.Met/Ac.Ca. | 82.7 | Fum; Pent-P; Suc; C5:1-DC |
| 121 | 4 | En.Met/Ac.Ca./B.Am. | 89.4 | Fum; C10:2; C16:2; Ac-Orn |
| 122 | 4 | En.Met/B.Am. | 80.2 | Fum; Lac; Pent-P; ADMA |
| 123 | 4 | En.Met/Ac.Ca./B.Am. | 80 | Lac; C10:2; Carnosine; Met-SO |
| 124 | 4 | En.Met/B.Am./O.St. | 83.2 | Fum; ADMA; Met-SO; 27-OH-C |
| 125 | 4 | En.Met/Ac.Ca./B.Am./O.St. | 79.9 | Lac; C5:1; Ac-Orn; 3b,5a,6b-THC |
| 126 | 4 | En.Met/Am.Ac./B.Am./P.G. | 80 | Lac; Phe; Carnosine; LTB4 |
| 127 | 5 | En.Met/Ac.Ca./S.L./B.Am./O.St. | 86.7 | Lac; C8:1; SM C18:1; ADMA; 27-OH-C |
| 128 | 4 | Ac.Ca./S.L./B.Am. | 88.1 | C16:2; C5:1; SM C24:1; Ac-Orn |
| 129 | 4 | En.Met/B.Am. | 83.3 | Fum; Lac; Suc; Carnosine |
| 130 | 4 | En.Met/Ac.Ca./B.Am. | 87.2 | Fum; Lac; C5:1-DC; total DMA |
| 131 | 4 | En.Met/Ac.Ca./S.L./B.Am. | 80.7 | Lac; C5:1; SM (OH) C16:1; Carnosine |
| 132 | 5 | En.Met/B.Am./O.St. | 90.3 | Fum; Ac-Orn; total DMA; Cholestenone; 3b,5a,6b-THC |
| 133 | 6 | En.Met/Ac.Ca./Am.Ac./B.Am. | 85.9 | Fum; C16:2; Met; Ac-Orn; Histamine; Met-SO |
| 134 | 4 | En.Met/Ac.Ca. | 81.6 | Fum; Lac; Pent-P; C10:2 |
| 135 | 4 | En.Met/Ac.Ca./B.Am. | 89.5 | Fum; C5:1-DC; Creatinine; total DMA |
| 136 | 4 | Ac.Ca./S.L./B.Am. | 82.2 | C16:2; C5:1; SM (OH) C22:2; Ac-Orn |
| 137 | 5 | En.Met/Am.Ac./B.Am./O.St. | 84.4 | Lac; Pent-P; Pro; ADMA; 27-OH-C |
| 138 | 4 | En.Met/Ac.Ca./S.L. | 81 | Fum; C5:1-DC; SM (OH) C14:1; SM (OH) C22:2 |
| 139 | 4 | En.Met/S.L./B.Am. | 80.8 | Fum; SM C26:1; SM (OH) C22:1; Ac-Orn |
| 140 | 4 | En.Met/Ac.Ca./B.Am./P.G. | 79.8 | Lac; C10:2; Ac-Orn; LTB4 |
| 141 | 4 | En.Met/Ac.Ca./Am.Ac./B.Am. | 91 | Fum; C16:2; Cit; Ac-Orn |
| 142 | 4 | En.Met/S.L./Am.Ac./O.St. | 81.8 | Lac; SM (OH) C22:2; Gln; 25-OH-C |
| 143 | 4 | En.Met/P.G. | 83.5 | Fum; Lac; Pent-P; 8-iso-PGF2a |
| 144 | 4 | Ac.Ca./B.Am./O.St. | 91.7 | C5:1-DC; alpha-AAA; 24S-OH-C; 25-OH-C |
| 145 | 4 | En.Met/B.Am. | 80.3 | Fum; Lac; Carnosine; Met-SO |

TABLE 9

Metabolite combinations describing damage of basal ganglia

| No. | Npar | Chemical Class | Accuracy | Model |
|---|---|---|---|---|
| 1 | 4 | En.Met/S.L./Am.Ac./B.Am. | 88.6 | OAA; SM C24:1; Gly; alpha-AAA |
| 2 | 4 | En.Met/S.L./Am.Ac. | 84.5 | Hex-P; SM C24:1; Gln; Met |
| 3 | 2 | Am.Ac. | 86.6 | Lys; Met |
| 4 | 4 | En.Met/S.L./Am.Ac. | 87.8 | Lac; SM C16:1; SM (OH) C22:1; Met |
| 5 | 3 | En.Met/S.L./B.Am. | 79.8 | alpha-KGA; SM C16:0; Ac-Orn |
| 6 | 3 | Ac.Ca./S.L./Am.Ac. | 80.8 | C6:1; SM (OH) C22:2; Trp |
| 7 | 2 | S.L./Am.Ac. | 80 | SM (OH) C22:2; Arg |
| 8 | 4 | S.L./Am.Ac./O.St. | 92.1 | SM C16:0; SM (OH) C22:2; Tyr; 20a-OH-C |
| 9 | 3 | Ac.Ca./Am.Ac. | 79.9 | C14:1; His; Pro |
| 10 | 3 | S.L./Am.Ac. | 79.3 | SM (OH) C22:2; Gln; Phe |
| 11 | 4 | En.Met/S.L./O.St. | 81.4 | alpha-KGA; SM C24:1; SM (OH) C22:2; 20a-OH-C |
| 12 | 3 | Ac.Ca./S.L. | 84.8 | C5:1-DC; SM C16:0; SM (OH) C14:1 |
| 13 | 6 | S.L./Am.Ac./O.St. | 91.5 | SM C16:1; SM (OH) C22:2; Ile; Lys; 20a-OH-C; 24-DH-Lanosterol |
| 14 | 3 | Am.Ac. | 85.6 | Lys; Met; Orn |
| 15 | 3 | S.L./Am.Ac. | 82.3 | SM (OH) C14:1; Pro; Tyr |
| 16 | 3 | S.L./Am.Ac. | 80 | SM (OH) C14:1; SM (OH) C16:1; Tyr |

TABLE 9-continued

Metabolite combinations describing damage of basal ganglia

| No. | Npar | Chemical Class | Accuracy | Model |
|---|---|---|---|---|
| 17 | 3 | Ac.Ca./S.L./Am.Ac. | 83.8 | C14:1; SM C18:0; Pro |
| 18 | 5 | S.L./Am.Ac. | 84.7 | SM C24:1; SM (OH) C14:1; SM (OH) C24:1; Ala; Orn |
| 19 | 3 | S.L./Am.Ac. | 80 | SM C20:2; SM (OH) C16:1; Tyr |
| 20 | 2 | S.L./Am.Ac. | 79.1 | SM (OH) C22:2; Trp |
| 21 | 4 | S.L./Am.Ac./B.Am. | 79.9 | SM C16:0; Orn; Tyr; Kynurenine |
| 22 | 4 | En.Met/S.L./Am.Ac./B.Am. | 79 | Suc; SM (OH) C24:1; Gln; Met-SO |
| 23 | 3 | S.L./B.Am. | 83.8 | SM (OH) C22:2; Ac-Orn; Histamine |
| 24 | 4 | S.L./Am.Ac. | 81.1 | SM (OH) C14:1; SM (OH) C22:1; SM (OH) C22:2; Met |
| 25 | 4 | En.Met/S.L./Am.Ac. | 80.7 | alpha-KGA; SM C18:0; SM (OH) C22:1; Met |
| 26 | 2 | S.L./B.Am. | 80.3 | SM (OH) C22:1; Met-SO |
| 27 | 4 | S.L./Am.Ac./O.St. | 86.7 | SM C24:0; Arg; Tyr; 24S-OH-C |
| 28 | 3 | S.L./B.Am. | 81.1 | SM C24:0; SM (OH) C14:1; Met-SO |
| 29 | 6 | Ac.Ca./S.L./Am.Ac./B.Am. | 83.8 | C18; SM C18:0; SM (OH) C24:1; Lys; Pro; Met-SO |
| 30 | 6 | Ac.Ca./S.L./Am.Ac./B.Am. | 82.9 | SM C16:0; SM C18:1; SM (OH) C14:1; Orn; Phe; Ac-Orn |
| 31 | 5 | Ac.Ca./S.L./Am.Ac. | 90.5 | C5:1-DC; SM C16:1; SM (OH) C16:1; SM (OH) C22:2; Orn |
| 32 | 4 | En.Met/S.L./Am.Ac./O.St. | 83 | alpha-KGA; SM (OH) C22:1; Tyr; 25-OH-C |
| 33 | 4 | S.L./B.Am./P.G. | 79.4 | SM C16:1; SM C18:1; Ac-Orn; LTB4 |
| 34 | 3 | S.L./Am.Ac./B.Am. | 92.5 | SM (OH) C14:1; Tyr; Kynurenine |
| 35 | 2 | S.L./Am.Ac. | 84.3 | SM C24:1; Pro |
| 36 | 4 | S.L./Am.Ac. | 80.1 | SM C18:1; SM (OH) C14:1; SM (OH) C22:2; Asn |
| 37 | 4 | Ac.Ca./S.L./Am.Ac. | 81.3 | C5:1-DC; SM C18:1; SM (OH) C22:2; Orn |
| 38 | 5 | S.L./Am.Ac./O.St. | 79.8 | SM (OH) C14:1; SM (OH) C22:1; His; Orn; 25-OH-C |
| 39 | 5 | Ac.Ca./S.L./Am.Ac./B.Am. | 85.7 | C6:1; SM C16:0; SM (OH) C22:1; Pro; Ac-Orn |
| 40 | 4 | S.L./Am.Ac. | 88.4 | SM C16:1; SM (OH) C22:1; Met; Pro |
| 41 | 4 | S.L./Am.Ac. | 84.6 | SM C16:1; SM (OH) C14:1; Phe; Pro |
| 42 | 4 | S.L./Am.Ac./P.G. | 80.1 | SM C16:1; Orn; Trp; 8-iso-PGF2a |
| 43 | 5 | En.Met/S.L./Am.Ac./B.Am./O.St. | 80.3 | alpha-KGA; SM C18:0; Orn; Ac-Orn; 24-DH-Lanosterol |
| 44 | 5 | S.L./Am.Ac./P.G. | 89.4 | SM (OH) C22:1; SM (OH) C22:2; Arg; Gln; TXB2 |
| 45 | 3 | S.L./Am.Ac. | 83 | SM C24:1; His; Orn |
| 46 | 3 | S.L./B.Am./O.St. | 82 | SM (OH) C22:1; Met-SO; 25-OH-C |
| 47 | 4 | S.L./Am.Ac./O.St. | 80.4 | SM C18:0; SM C24:1; Tyr; Cholestenone |
| 48 | 4 | Ac.Ca./S.L./B.Am. | 89.4 | C6:1; SM (OH) C22:1; Kynurenine; Met-SO |
| 49 | 4 | S.L./Am.Ac./B.Am. | 89.1 | SM (OH) C16:1; Gln; Orn; Met-SO |
| 50 | 5 | S.L./Am.Ac./B.Am. | 87 | SM C24:0; SM C24:1; SM (OH) C16:1; Orn; Met-SO |
| 51 | 4 | S.L./Am.Ac./B.Am. | 84.4 | SM (OH) C24:1; Arg; Gln; Met-SO |
| 52 | 4 | S.L./Am.Ac./B.Am. | 80.9 | SM C18:1; SM (OH) C22:2; Orn; Ac-Orn |
| 53 | 4 | Ac.Ca./S.L. | 89.5 | C5:1-DC; C6:1; SM C16:1; SM C18:1 |
| 54 | 3 | S.L./Am.Ac. | 79.4 | SM C16:0; Pro; Trp |
| 55 | 4 | En.Met/S.L./Am.Ac. | 79.4 | alpha-KGA; SM C16:0; SM C24:1; Phe |
| 56 | 2 | S.L./Am.Ac. | 81.9 | SM C24:0; Tyr |
| 57 | 3 | S.L./Am.Ac. | 79.4 | SM C24:1; SM (OH) C22:2; Orn |
| 58 | 4 | S.L./Am.Ac. | 80.6 | SM (OH) C22:1; Ala; His; Met |
| 59 | 3 | S.L./Am.Ac. | 79.2 | SM C20:2; SM C24:1; Leu |
| 60 | 5 | S.L./Am.Ac./B.Am. | 83.1 | SM C24:1; SM (OH) C16:1; Leu; Met; Kynurenine |
| 61 | 2 | S.L./Am.Ac. | 84.5 | SM (OH) C22:1; Tyr |
| 62 | 5 | En.Met/S.L./Am.Ac. | 80 | Suc; SM C18:1; SM (OH) C14:1; Gln; Orn |
| 63 | 6 | Ac.Ca./S.L./Am.Ac./B.Am. | 79.8 | C18; SM C16:0; SM C18:0; Phe; Pro; Histamine |
| 64 | 3 | S.L./Am.Ac./B.Am. | 88.7 | SM (OH) C22:1; Orn; Met-SO |
| 65 | 4 | S.L./Am.Ac./O.St. | 79.6 | SM C24:1; Met; Pro; 5a.6a-EpoxyC |
| 66 | 4 | Ac.Ca./S.L./Am.Ac./O.St. | 85.9 | C5:1-DC; SM C16:0; Arg; 24-DH-Lanosterol |
| 67 | 4 | S.L./B.Am. | 79.8 | SM C18:0; SM C24:0; SM C24:1; Met-SO |
| 68 | 4 | S.L./Am.Ac./B.Am. | 83.3 | SM C16:1; SM C20:2; Trp; Met-SO |
| 69 | 4 | S.L./B.Am. | 83 | SM (OH) C16:1; SM (OH) C22:1; SM (OH) C24:1; Met-SO |
| 70 | 4 | S.L./Am.Ac./B.Am. | 87.7 | SM C18:1; Gln; Lys; Ac-Orn |
| 71 | 3 | S.L./Am.Ac. | 81.7 | SM C16:1; His; Pro; Tyr |
| 72 | 4 | En.Met/S.L./Am.Ac./P.G. | 79.4 | alpha-KGA; SM C24:1; Orn; 8-iso-PGF2a |
| 73 | 4 | Am.Ac./B.Am. | 79.2 | Gln; Orn; Tyr; Met-SO |
| 74 | 4 | S.L./Am.Ac./B.Am. | 83.7 | SM (OH) C22:1; Met; Orn; Histamine |
| 75 | 3 | S.L./Am.Ac. | 85.5 | SM (OH) C14:1; Arg; Met |
| 76 | 6 | Am.Ac./B.Am./P.G. | 85.6 | Gln; His; Orn; Tyr; Histamine; 8-iso-PGF2a |
| 77 | 4 | S.L./Am.Ac./B.Am. | 80.4 | SM C24:1; SM (OH) C14:1; Met; Creatinine |
| 78 | 3 | Ac.Ca./S.L. | 81.7 | C5:1-DC; SM C16:0; SM (OH) C22:1 |
| 79 | 5 | S.L./Am.Ac./O.St. | 91 | SM C16:1; SM (OH) C22:1; SM (OH) C22:2; Ser; 20a-OH-C |
| 80 | 3 | S.L./Am.Ac./O.St. | 83.4 | SM (OH) C22:1; Leu; 20a-OH-C |
| 81 | 2 | Ac.Ca./S.L. | 85.5 | C5:1-DC; SM C16:1 |
| 82 | 3 | Am.Ac./O.St. | 82.5 | Gln; Pro; Cholestenone |
| 83 | 3 | S.L./Am.Ac./B.Am. | 89.2 | SM C16:1; Pro; Ac-Orn |
| 84 | 4 | S.L./Am.Ac./O.St. | 86.5 | SM C26:1; SM (OH) C22:2; Orn; 22R-OH-C |
| 85 | 5 | S.L./Am.Ac./B.Am. | 82.9 | SM C26:1; SM (OH) C16:1; Lys; Ac-Orn; Histamine |
| 86 | 3 | Am.Ac./O.St. | 80.1 | Gln; Pro; 24-DH-Lanosterol |
| 87 | 3 | Ac.Ca./S.L. | 81.1 | C5:1-DC; C6:1; SM C22:1 |
| 88 | 4 | En.Met/S.L./B.Am. | 80.3 | alpha-KGA; SM C18:0; SM (OH) C14:1; Ac-Orn |
| 89 | 4 | S.L./Am.Ac. | 79.7 | SM C18:1; SM (OH) C14:1; Leu; Met |
| 90 | 4 | Ac.Ca./S.L./Am.Ac. | 86.3 | C5:1-DC; C6:1; SM (OH) C14:1; Pro |
| 91 | 3 | Am.Ac. | 79.5 | Arg; Gln; Met |
| 92 | 4 | En.Met/S.L./O.St. | 85.8 | alpha-KGA; SM C16:1; SM (OH) C14:1; 20a-OH-C |

TABLE 9-continued

Metabolite combinations describing damage of basal ganglia

| No. | Npar | Chemical Class | Accuracy | Model |
|---|---|---|---|---|
| 93 | 4 | En.Met/S.L./Am.Ac. | 90.8 | Lac; SM (OH) C14:1; Gln; Met |
| 94 | 3 | Ac.Ca./S.L. | 93.3 | C5:1-DC; C6:1; SM C16:1 |
| 95 | 5 | En.Met/S.L./Am.Ac./B.Am. | 87.3 | alpha-KGA; SM C16:1; SM (OH) C14:1; Trp; Met-SO |
| 96 | 4 | En.Met/S.L./B.Am. | 82.4 | alpha-KGA; SM C16:1; SM (OH) C24:1; Met-SO |
| 97 | 4 | S.L./Am.Ac./B.Am. | 84.3 | SM (OH) C14:1; SM (OH) C16:1; Orn; Ac-Orn |
| 98 | 3 | S.L./Am.Ac. | 79.8 | SM (OH) C22:1; SM (OH) C22:2; Asn |
| 99 | 3 | Ac.Ca./Am.Ac. | 79.6 | C8:1; Gln; Pro |
| 100 | 4 | S.L./Am.Ac./B.Am. | 79.4 | SM C16:0; SM C24:1; Trp; Met-SO |
| 101 | 3 | S.L./Am.Ac. | 83.1 | SM C16:1; SM (OH) C22:2; Arg |
| 102 | 3 | Ac.Ca./S.L. | 82 | C5:1-DC; SM C16:0; SM (OH) C22:2 |
| 103 | 3 | S.L./Am.Ac. | 80.6 | SM C16:1; Gln; Pro |
| 104 | 4 | S.L./Am.Ac./B.Am. | 84.3 | SM C20:2; SM (OH) C22:2; Tyr; Histamine |
| 105 | 4 | S.L./Am.Ac./B.Am. | 80.7 | SM C16:0; Orn; Histamine; Met-SO |
| 106 | 4 | S.L./Am.Ac. | 80.9 | SM C16:0; SM C24:1; Gly; Lys |
| 107 | 4 | S.L./Am.Ac./B.Am. | 79.8 | SM (OH) C14:1; Gln; Met; Ac-Orn |
| 108 | 5 | S.L./Am.Ac./B.Am. | 85 | SM (OH) C14:1; SM (OH) C22:1; His; Tyr; Ac-Orn |
| 109 | 4 | S.L./Am.Ac./B.Am./O.St. | 80.4 | SM (OH) C14:1; Tyr; Ac-Orn; 24S-OH-C |
| 110 | 4 | S.L./Am.Ac./O.St. | 85.6 | SM C18:1; SM C24:1; Trp; Cholestenone |
| 111 | 2 | S.L./Am.Ac. | 81.2 | SM (OH) C14:1; Met |
| 112 | 4 | S.L./Am.Ac./B.Am. | 88 | SM C16:0; SM C26:1; Tyr; Kynurenine |
| 113 | 4 | S.L./Am.Ac./B.Am. | 83 | SM C18:1; SM (OH) C14:1; Met; Creatinine |
| 114 | 3 | S.L./Am.Ac. | 81.7 | SM C24:0; Phe; Pro |
| 115 | 4 | S.L./Am.Ac./B.Am. | 80.7 | SM C24:1; SM (OH) C14:1; Val; Kynurenine |
| 116 | 4 | S.L./Am.Ac./B.Am. | 86.2 | SM (OH) C16:1; SM (OH) C22:1; Trp; Met-SO |
| 117 | 4 | S.L./Am.Ac./B.Am./O.St. | 80.9 | SM (OH) C22:1; His; Met-SO; Cholestenone |
| 118 | 4 | Ac.Ca./S.L./Am.Ac. | 80.1 | C14:1; SM (OH) C16:1; Arg; Tyr |
| 119 | 4 | S.L./Am.Ac. | 86.8 | SM (OH) C14:1; SM (OH) C22:2; Met; Trp |
| 120 | 3 | S.L./Am.Ac. | 79.8 | SM C18:1; SM (OH) C14:1; Phe |
| 121 | 4 | S.L./Am.Ac. | 80 | SM (OH) C22:2; Ile; Met; Pro |
| 122 | 6 | S.L./Am.Ac./B.Am. | 80 | SM (OH) C16:1; SM (OH) C22:2; Gln; Ac-Orn; alpha-AAA; Kynurenine |
| 123 | 3 | S.L./Am.Ac. | 88.8 | SM C20:2; SM (OH) C22:1; Tyr |
| 124 | 3 | S.L./Am.Ac. | 81.1 | SM C24:0; His; Tyr |
| 125 | 4 | S.L./Am.Ac./B.Am. | 87 | SM (OH) C16:1; Gln; Lys; Ac-Orn |
| 126 | 4 | S.L./Am.Ac. | 85.9 | SM (OH) C14:1; SM (OH) C22:1; Met; Orn |
| 127 | 3 | Ac.Ca./S.L./Am.Ac. | 82.4 | C5:1-DC; SM C16:1; His |
| 128 | 4 | S.L./Am.Ac./B.Am. | 80.8 | SM (OH) C16:1; SM (OH) C22:1; Pro; Met-SO |
| 129 | 4 | En.Met/S.L./Am.Ac./O.St. | 86.2 | OAA; SM (OH) C14:1; Leu; 20a-OH-C |
| 130 | 4 | En.Met/S.L./Am.Ac. | 86.3 | Fum; SM (OH) C14:1; Met; Pro |
| 131 | 4 | S.L./Am.Ac./O.St. | 80.6 | SM C24:1; His; Trp; Cholestenone |
| 132 | 4 | S.L./Am.Ac. | 85.4 | SM C16:0; SM (OH) C14:1; Gly; Met |
| 133 | 4 | S.L./Am.Ac. | 85.1 | SM (OH) C14:1; His; Met; Pro |
| 134 | 5 | En.Met/S.L./B.Am. | 86 | Lac; SM C16:0; SM C24:1; Histamine; Met-SO |
| 135 | 4 | S.L./Am.Ac./O.St. | 91.2 | SM C16:1; SM (OH) C22:2; Leu; 20a-OH-C |
| 136 | 5 | Ac.Ca./S.L./Am.Ac./B.Am. | 86 | C14:1; SM C18:1; Met; Tyr; Kynurenine |
| 137 | 3 | S.L./Am.Ac. | 79.3 | SM C16:1; SM (OH) C22:2; Phe |
| 138 | 6 | S.L./Am.Ac./B.Am. | 88.7 | SM C18:1; SM C24:1; SM (OH) C14:1; Ala; Gln; Ac-Orn |
| 139 | 4 | En.Met/S.L./Am.Ac./B.Am. | 84.9 | alpha-KGA; SM (OH) C14:1; Orn; Ac-Orn |
| 140 | 4 | En.Met/S.L./Am.Ac./B.Am. | 84 | alpha-KGA; SM C16:1; Lys; Ac-Orn |
| 141 | 4 | S.L./Am.Ac./O.St. | 86 | SM (OH) C16:1; SM (OH) C22:2; Trp; Cholestenone |
| 142 | 6 | En.Met/S.L./Am.Ac./B.Am. | 85.3 | Pent-P; SM C18:1; SM C24:0; SM (OH) C14:1; Pro; Sarcosine |
| 143 | 5 | S.L./Am.Ac./B.Am./O.St. | 83.6 | SM C24:0; SM (OH) C22:1; Gln; Carnosine; 20a-OH-C |
| 144 | 4 | S.L./Am.Ac. | 80.6 | SM C18:1; SM C24:0; SM (OH) C22:2; Met |
| 145 | 3 | S.L./Am.Ac./B.Am. | 85.2 | SM (OH) C22:2; Leu; Kynurenine |
| 146 | 5 | S.L./Am.Ac./O.St. | 83.2 | SM C18:1; SM (OH) C14:1; Ala; Met; Cholestenone |
| 147 | 2 | S.L./Am.Ac. | 79.7 | SM C16:1; Pro |
| 148 | 3 | S.L./Am.Ac./B.Am. | 84.4 | SM C16:1; Lys; Met-SO |
| 149 | 3 | S.L./Am.Ac. | 81.2 | SM C16:1; SM C18:0; Tyr |
| 150 | 2 | S.L./B.Am. | 80.4 | SM (OH) C22:2; Kynurenine |
| 151 | 3 | S.L./Am.Ac./O.St. | 88.7 | SM (OH) C22:2; Trp; Cholestenone |
| 152 | 4 | S.L./Am.Ac. | 86.4 | SM C20:2; SM (OH) C14:1; SM (OH) C16:1; Tyr |
| 153 | 4 | Ac.Ca./S.L./Am.Ac. | 82.9 | C5:1-DC; SM C24:1; SM (OH) C22:2; Lys |
| 154 | 4 | S.L./Am.Ac./P.G. | 80.5 | SM C24:1; Arg; Trp; LTB4 |
| 155 | 3 | S.L./Am.Ac. | 87.1 | SM C24:0; SM C24:1; Tyr |
| 156 | 5 | S.L./Am.Ac./B.Am./O.St. | 81.7 | SM C24:0; Lys; Tyr; Histamine; 20a-OH-C |
| 157 | 4 | En.Met/S.L./B.Am. | 82.2 | Lac; SM (OH) C14:1; SM (OH) C22:2; Met-SO |
| 158 | 4 | S.L./Am.Ac./B.Am. | 83.2 | SM (OH) C14:1; SM (OH) C22:2; Pro; Met-SO |
| 159 | 4 | En.Met/S.L./Am.Ac./O.St. | 79.5 | alpha-KGA; SM (OH) C14:1; Tyr; Cholestenone |
| 160 | 3 | Ac.Ca./S.L./O.St. | 82.5 | C5:1-DC; SM C16:0; Cholestenone |
| 161 | 4 | S.L./Am.Ac./B.Am. | 81.9 | SM C26:1; SM (OH) C16:1; Orn; Met-SO |
| 162 | 4 | S.L./Am.Ac. | 80.3 | SM C18:1; SM C24:0; SM (OH) C22:2; Ala |
| 163 | 4 | Ac.Ca./S.L./Am.Ac. | 81.5 | C5:1-DC; SM C24:1; SM C24:0; His |
| 164 | 4 | Ac.Ca./S.L./B.Am. | 79.6 | C6:1; SM C16:1; SM C18:0; Ac-Orn |
| 165 | 4 | S.L./Am.Ac./P.G. | 85.5 | SM (OH) C14:1; Arg; Orn; TXB2 |
| 166 | 4 | Ac.Ca./S.L./B.Am. | 88.6 | C5:1-DC; SM C16:0; SM (OH) C22:2; Histamine |
| 167 | 3 | Am.Ac./B.Am. | 84 | Gln; Orn; Met-SO |
| 168 | 4 | En.Met/Ac.Ca./S.L./Am.Ac. | 79.7 | alpha-KGA; C6:1; SM (OH) C22:2; Met |

TABLE 9-continued

Metabolite combinations describing damage of basal ganglia

| No. | Npar | Chemical Class | Accuracy | Model |
|---|---|---|---|---|
| 169 | 3 | S.L./Am.Ac. | 82.1 | SM C16:0; SM (OH) C22:1; Met |
| 170 | 3 | S.L./Am.Ac. | 87.4 | SM C24:1; SM (OH) C22:2; Ala |
| 171 | 4 | En.Met/S.L./Am.Ac./P.G. | 81.6 | Fum; SM (OH) C14:1; Met; LTB4 |
| 172 | 4 | S.L./Am.Ac./B.Am. | 79 | SM (OH) C22:1; SM (OH) C22:2; Lys; Ac-Orn |
| 173 | 3 | S.L./Am.Ac. | 80.6 | SM C24:1; SM (OH) C14:1; Ser |
| 174 | 4 | S.L./Am.Ac. | 86.6 | SM C16:1; SM C18:0; SM C20:2; Tyr |
| 175 | 3 | S.L./Am.Ac. | 84.5 | SM C16:0; SM (OH) C22:1; Tyr |
| 176 | 4 | S.L./Am.Ac. | 79.2 | SM C16:1; SM (OH) C16:1; Ile; Pro |
| 177 | 4 | S.L./Am.Ac. | 82.6 | SM C18:1; SM (OH) C22:1; Met; Orn |
| 178 | 5 | S.L./Am.Ac./B.Am. | 79.3 | SM C24:0; SM (OH) C22:1; Ile; Pro; SDMA |
| 179 | 3 | S.L./Am.Ac./B.Am. | 81.3 | SM (OH) C24:1; Pro; Ac-Orn |
| 180 | 4 | S.L./B.Am./O.St. | 80 | SM C18:1; SM (OH) C22:1; Met-SO; 25-OH-C |
| 181 | 3 | S.L./Am.Ac. | 81.4 | SM C24:0; SM (OH) C14:1; Tyr |
| 182 | 5 | En.Met/S.L./Am.Ac./O.St. | 83 | Suc; SM (OH) C24:1; His; Orn; Cholestenone |
| 183 | 3 | S.L./Am.Ac. | 84.6 | SM C24:1; SM (OH) C22:2; Pro |
| 184 | 3 | S.L./Am.Ac. | 80.9 | SM C16:1; SM C24:1; Tyr |
| 185 | 5 | Ac.Ca./S.L./Am.Ac./B.Am. | 79.7 | C6:1; SM C16:0; SM (OH) C16:1; Lys; Met-SO |
| 186 | 5 | Ac.Ca./S.L./Am.Ac. | 80.9 | C9; SM C16:1; SM C24:1; Met; Orn |
| 187 | 4 | S.L./Am.Ac. | 82.2 | SM (OH) C14:1; Gln; Met; Phe |
| 188 | 4 | En.Met/S.L./B.Am. | 83.7 | alpha-KGA; SM C24:0; SM C24:1; Met-SO |
| 189 | 4 | En.Met/S.L./B.Am. | 86.5 | alpha-KGA; SM C24:0; SM (OH) C22:1; Met-SO |
| 190 | 4 | S.L./Am.Ac. | 84.7 | SM (OH) C14:1; SM (OH) C22:1; Arg; Tyr |
| 191 | 4 | S.L./Am.Ac./B.Am. | 81.9 | SM C24:0; Gln; Orn; Ac-Orn |
| 192 | 3 | S.L./Am.Ac. | 89.7 | SM (OH) C22:1; Lys; Met |
| 193 | 6 | En.Met/Ac.Ca./S.L./Am.Ac. | 85.2 | Lac; C18; SM C18:1; SM (OH) C22:2; Pro; Tyr |
| 194 | 3 | S.L./Am.Ac. | 80.6 | SM C16:1; SM (OH) C22:2; Tyr |
| 195 | 4 | Ac.Ca./Am.Ac./P.G. | 80.1 | C18:1; Orn; Pro; LTB4 |
| 196 | 4 | S.L./Am.Ac. | 83.5 | SM C16:1; SM (OH) C16:1; Gly; Orn |
| 197 | 4 | S.L./Am.Ac. | 89.4 | SM C16:1; SM C20:2; SM (OH) C22:1; Tyr |
| 198 | 5 | Ac.Ca./S.L./Am.Ac. | 81.9 | C5:1-DC; SM C24:0; SM C24:1; SM (OH) C14:1; Phe |
| 199 | 3 | En.Met/S.L./Am.Ac. | 81.2 | Lac; SM C24:1; Gln |
| 200 | 5 | En.Met/S.L./Am.Ac./B.Am. | 81.1 | Suc; SM C18:0; Gln; Tyr; Histamine |
| 201 | 3 | S.L./Am.Ac. | 79.8 | SM C16:0; SM (OH) C14:1; Met |
| 202 | 4 | En.Met/S.L./Am.Ac. | 79.6 | alpha-KGA; SM (OH) C22:1; SM (OH) C22:2; Asn |
| 203 | 3 | Ac.Ca./S.L. | 89.1 | C5:1-DC; SM C16:1; SM (OH) C24:1 |
| 204 | 4 | En.Met/S.L./B.Am. | 79.9 | Hex-P; SM C24:1; SM (OH) C22:2; Histamine |
| 205 | 4 | S.L./B.Am. | 82.8 | SM C16:0; SM (OH) C22:1; SM (OH) C22:2; Met-SO |
| 206 | 4 | En.Met/S.L./Am.Ac./P.G. | 81.1 | Suc; SM (OH) C16:1; Orn; LTB4 |
| 207 | 4 | S.L./Am.Ac./B.Am. | 79.3 | SM C24:0; His; Ac-Orn; Serotonin |
| 208 | 4 | En.Met/S.L./Am.Ac. | 82.7 | Lac; SM (OH) C16:1; Met; Trp |
| 209 | 3 | Am.Ac./O.St. | 86.1 | Pro; Trp; 24-DH-Lanosterol |
| 210 | 4 | Ac.Ca./S.L./Am.Ac. | 80.2 | C5:1-DC; SM (OH) C16:1; Leu; Tyr |
| 211 | 4 | S.L./Am.Ac./B.Am. | 91.8 | SM C16:1; SM C24:1; Tyr; Kynurenine |
| 212 | 3 | En.Met/S.L./Am.Ac. | 79.5 | Lac; SM C16:1; His |
| 213 | 3 | S.L./Am.Ac./B.Am. | 82.1 | SM (OH) C22:1; Pro; Ac-Orn |
| 214 | 4 | S.L./Am.Ac. | 84.5 | SM C18:0; SM C24:0; SM (OH) C16:1; Tyr |
| 215 | 4 | S.L./Am.Ac. | 81.4 | SM C24:1; SM (OH) C14:1; SM (OH) C16:1; Tyr |
| 216 | 4 | S.L./Am.Ac./B.Am. | 81.6 | SM C18:1; SM (OH) C24:1; Trp; Met-SO |
| 217 | 3 | S.L./Am.Ac./O.St. | 80.2 | SM (OH) C14:1; Met; Cholestenone |
| 218 | 4 | S.L./Am.Ac./B.Am. | 84.7 | SM (OH) C14:1; His; Phe; Kynurenine |
| 219 | 3 | S.L./Am.Ac. | 82.6 | SM C16:1; SM (OH) C22:2; Pro |
| 220 | 3 | S.L./Am.Ac. | 83.2 | SM (OH) C22:2; Gln; Pro |
| 221 | 4 | S.L./Am.Ac./B.Am./O.St. | 89.7 | SM C16:1; Pro; Ac-Orn; Cholestenone |
| 222 | 4 | S.L./Am.Ac./B.Am. | 80 | SM C26:1; SM (OH) C14:1; Tyr; Ac-Orn |
| 223 | 4 | S.L./Am.Ac./P.G. | 80.4 | SM C24:1; Leu; Orn; LTB4 |
| 224 | 4 | S.L./Am.Ac./B.Am. | 85.4 | SM C16:0; His; Orn; Met-SO |
| 225 | 2 | Ac.Ca./Am.Ac. | 79.2 | C14:1; Pro |
| 226 | 4 | Ac.Ca./S.L./Am.Ac./B.Am. | 79.8 | C14:1; SM C18:1; Met; Kynurenine |
| 227 | 3 | S.L./Am.Ac. | 82.7 | SM C16:1; Pro; Trp |
| 228 | 3 | S.L./Am.Ac./O.St. | 79.2 | SM C16:0; Leu; 20a-OH-C |
| 229 | 3 | S.L./Am.Ac. | 82.9 | SM (OH) C22:1; SM (OH) C24:1; Tyr |
| 230 | 3 | S.L./Am.Ac. | 82 | SM (OH) C14:1; SM (OH) C22:2; Ala |
| 231 | 3 | S.L./Am.Ac. | 82.9 | SM C24:0; Phe; Tyr |
| 232 | 3 | S.L./Am.Ac. | 87.2 | SM C16:0; Lys; Met |
| 233 | 4 | S.L./Am.Ac./B.Am. | 80.9 | SM (OH) C22:2; Arg; Orn; Ac-Orn |
| 234 | 4 | S.L./Am.Ac. | 82.3 | SM C18:0; SM (OH) C16:1; Gln; Tyr |
| 235 | 4 | S.L./Am.Ac./O.St. | 82.5 | SM C16:0; SM (OH) C22:2; Ala; Cholestenone |
| 236 | 4 | Ac.Ca./S.L./Am.Ac./B.Am. | 82.3 | C14:1; SM (OH) C22:2; Met; Kynurenine |
| 237 | 4 | En.Met/Ac.Ca./S.L./Am.Ac. | 79.1 | Pent-P; C9; SM C24:1; Lys |
| 238 | 4 | En.Met/S.L./B.Am. | 83.1 | alpha-KGA; SM C16:0; SM C16:1; Met-SO |
| 239 | 4 | Am.Ac./O.St. | 88 | Met; Pro; Trp; Cholestenone |
| 240 | 3 | S.L./Am.Ac. | 79.1 | SM C16:1; SM C18:1; Ala |
| 241 | 4 | S.L./Am.Ac./B.Am./P.G. | 84.3 | SM (OH) C22:2; Orn; Ac-Orn; LTB4 |
| 242 | 5 | En.Met/Ac.Ca./S.L./Am.Ac./B.Am. | 83 | Suc; C6:1; SM C24:1; Orn; Histamine |
| 243 | 3 | S.L./Am.Ac. | 80.6 | SM C16:0; SM C24:1; Tyr |
| 244 | 3 | S.L./Am.Ac. | 88.4 | SM C16:1; Lys; Met |

TABLE 9-continued

Metabolite combinations describing damage of basal ganglia

| No. | Npar | Chemical Class | Accuracy | Model |
|---|---|---|---|---|
| 245 | 4 | En.Met/S.L./Am.Ac./B.Am. | 80.4 | alpha-KGA; SM (OH) C22:1; His; Met-SO |
| 246 | 4 | S.L./Am.Ac./B.Am. | 84.7 | SM C24:0; SM (OH) C22:2; Trp; Met-SO |
| 247 | 4 | S.L./Am.Ac. | 82.8 | SM C18:0; SM (OH) C22:1; Met; Trp |
| 248 | 4 | S.L./B.Am. | 81.4 | SM C16:0; SM C24:0; SM (OH) C24:1; Met-SO |
| 249 | 3 | S.L./B.Am. | 85.3 | SM (OH) C22:1; Histamine; Met-SO |
| 250 | 5 | S.L./Am.Ac./O.St. | 83.9 | SM C16:1; SM (OH) C14:1; SM (OH) C16:1; Trp; 20a-OH-C |
| 251 | 3 | S.L./Am.Ac. | 83.2 | SM C24:1; Gln; Tyr |
| 252 | 4 | En.Met/S.L./Am.Ac./B.Am. | 80.8 | alpha-KGA; SM (OH) C22:2; Orn; Met-SO |
| 253 | 4 | En.Met/S.L./Am.Ac. | 85.2 | alpha-KGA; SM (OH) C14:1; Met; Trp |
| 254 | 3 | S.L./Am.Ac. | 87 | SM (OH) C14:1; Met; Orn |
| 255 | 4 | S.L./Am.Ac./O.St. | 86.7 | SM (OH) C16:1; Orn; Trp; 24-DH-Lanosterol |
| 256 | 3 | S.L./Am.Ac. | 83.4 | SM C16:0; Met; Trp |
| 257 | 4 | En.Met/S.L./Am.Ac. | 80.1 | alpha-KGA; SM C16:1; Asn; Met |
| 258 | 5 | S.L./Am.Ac./B.Am./O.St. | 79.8 | SM (OH) C14:1; Arg; Phe; Histamine; Cholestenone |
| 259 | 4 | Ac.Ca./S.L./Am.Ac. | 81.4 | C18; SM (OH) C22:2; Ala; Arg |
| 260 | 4 | S.L./Am.Ac. | 80.4 | SM C16:0; SM C24:1; SM (OH) C16:1; Tyr |
| 261 | 5 | S.L./Am.Ac./O.St. | 83.3 | SM C24:1; Gln; Orn; Phe; 24-DH-Lanosterol |
| 262 | 7 | Ac.Ca./S.L./Am.Ac./O.St./P.G. | 88.3 | C5:1-DC; SM (OH) C24:1; Gln; Lys; Orn; Cholestenone; LTB4 |
| 263 | 3 | Am.Ac./B.Am. | 81.8 | Lys; Ac-Orn; Histamine |
| 264 | 4 | S.L./Am.Ac. | 82.1 | SM C24:1; SM (OH) C14:1; Met; Ser |
| 265 | 4 | En.Met/Am.Ac./B.Am. | 81.7 | Pent-P; Pro; Ac-Orn; Histamine |
| 266 | 4 | S.L./Am.Ac. | 83.9 | SM C16:0; SM C20:2; SM C24:1; Tyr |
| 267 | 5 | En.Met/S.L./Am.Ac. | 84.9 | alpha-KGA; Hex-P; SM (OH) C22:2; Gln; Met |
| 268 | 4 | S.L./Am.Ac./B.Am. | 82.8 | SM C24:1; Pro; Tyr; Histamine |
| 269 | 5 | S.L./Am.Ac. | 81.5 | SM C16:0; SM (OH) C16:1; Gln; Met; Tyr |
| 270 | 4 | S.L./Am.Ac./B.Am. | 82.9 | SM C24:0; Arg; His; Met-SO |
| 271 | 5 | En.Met/S.L./Am.Ac./B.Am. | 80 | alpha-KGA; Suc; SM C18:0; Orn; Met-SO |
| 272 | 5 | En.Met/S.L./Am.Ac./B.Am. | 84.4 | alpha-KGA; SM C16:0; SM C18:1; Trp; Met-SO |
| 273 | 3 | S.L./Am.Ac. | 79 | SM C18:1; SM (OH) C22:1; Phe |
| 274 | 4 | S.L./Am.Ac. | 84.7 | SM C24:1; SM (OH) C22:2; His; Orn |
| 275 | 4 | Ac.Ca./S.L./P.G. | 83.2 | C5:1-DC; SM C16:0; SM (OH) C14:1; LTB4 |
| 276 | 4 | En.Met/Am.Ac. | 80.2 | Fum; Arg; Met; Pro |
| 277 | 4 | S.L./B.Am./O.St. | 85 | SM C16:1; Kynurenine; Met-SO; Cholestenone |
| 278 | 4 | En.Met/S.L./P.G. | 88.6 | alpha-KGA; SM (OH) C22:2; SM (OH) C24:1; TXB2 |
| 279 | 4 | En.Met/S.L./Am.Ac./O.St. | 85.2 | alpha-KGA; SM (OH) C14:1; Arg; 20a-OH-C |
| 280 | 4 | S.L./Am.Ac. | 79.5 | SM C24:1; SM (OH) C22:1; SM (OH) C22:2; Asn |
| 281 | 4 | En.Met/S.L./Am.Ac. | 80.5 | alpha-KGA; Fum; SM C24:1; Met |
| 282 | 4 | S.L./Am.Ac. | 80 | SM C16:0; SM (OH) C22:2; Ala; Gln |
| 283 | 4 | En.Met/S.L./Am.Ac. | 80 | Lac; SM (OH) C24:1; Arg; Met |
| 284 | 3 | S.L./Am.Ac. | 80.1 | SM C24:1; SM (OH) C22:1; Phe |
| 285 | 5 | S.L./Am.Ac. | 85.8 | SM C16:1; SM C20:2; SM C24:1; Lys; Met |
| 286 | 4 | S.L./Am.Ac./B.Am. | 79.3 | SM C16:1; Tyr; Ac-Orn; Histamine |
| 287 | 4 | S.L./Am.Ac./B.Am. | 79.8 | SM C18:1; SM (OH) C22:1; Lys; Met-SO |
| 288 | 4 | S.L./Am.Ac./O.St. | 87.7 | SM C18:1; Trp; Tyr; Cholestenone |
| 289 | 4 | S.L./Am.Ac./B.Am. | 81.7 | SM C16:1; SM (OH) C24:1; Tyr; Creatinine |
| 290 | 5 | En.Met/S.L./Am.Ac. | 81.1 | Lac; SM C24:0; SM (OH) C14:1; His; Phe |
| 291 | 3 | S.L./B.Am. | 85.7 | SM C24:0; SM (OH) C22:1; Met-SO |
| 292 | 4 | S.L./Am.Ac. | 86.4 | SM C16:1; SM (OH) C14:1; SM (OH) C22:2; Gly |
| 293 | 4 | S.L./Am.Ac. | 84.6 | SM C16:1; SM (OH) C22:2; Phe; Pro |
| 294 | 3 | Ac.Ca./S.L. | 83.5 | C5:1-DC; SM C16:1; SM C24:0 |
| 295 | 4 | S.L./Am.Ac./B.Am. | 80.6 | SM C24:0; Arg; Pro; total DMA |
| 296 | 4 | S.L./Am.Ac. | 84.7 | SM C24:0; SM (OH) C16:1; Arg; Tyr |
| 297 | 3 | Ac.Ca./S.L. | 81.7 | C5:1-DC; SM (OH) C14:1; SM (OH) C22:1 |
| 298 | 4 | Ac.Ca./S.L./B.Am. | 81.7 | C6:1; SM C16:1; SM (OH) C14:1; Taurine |
| 299 | 3 | S.L./Am.Ac. | 87.5 | SM C24:1; SM (OH) C22:1; Tyr |
| 300 | 4 | En.Met/S.L./Am.Ac. | 87.1 | Lac; SM C20:2; Gln; Met |
| 301 | 3 | S.L./Am.Ac. | 79.7 | SM C16:0; Pro; Tyr |
| 302 | 4 | S.L./Am.Ac. | 79.7 | SM (OH) C14:1; SM (OH) C22:2; His; Met |
| 303 | 4 | S.L./Am.Ac./P.G. | 87.5 | SM C16:0; SM C16:1; Arg; TXB2 |
| 304 | 4 | S.L./Am.Ac. | 86.9 | SM C24:1; SM (OH) C22:1; Pro; Tyr |
| 305 | 4 | S.L./Am.Ac./B.Am. | 88 | SM C16:0; His; Orn; Ac-Orn |
| 306 | 3 | S.L./Am.Ac. | 87.2 | SM C16:1; SM C24:1; Pro |
| 307 | 5 | Ac.Ca./S.L./O.St. | 83.3 | C14:1; C5:1-DC; C6:1; SM C18:1; 25-OH-C |
| 308 | 5 | S.L./Am.Ac. | 88 | SM C24:1; SM (OH) C16:1; SM (OH) C22:2; Ala; Orn |
| 309 | 3 | S.L./Am.Ac. | 84.5 | SM C16:1; SM (OH) C22:1; Tyr |
| 310 | 4 | S.L./Am.Ac./B.Am. | 82.4 | SM C18:1; SM (OH) C14:1; Pro; Ac-Orn |
| 311 | 5 | Ac.Ca./S.L./Am.Ac. | 83 | C14:1; C5:1-DC; SM C16:1; SM C18:1; Leu |
| 312 | 3 | S.L./Am.Ac./O.St. | 79.6 | SM (OH) C22:1; Trp; Cholestenone |
| 313 | 3 | S.L./Am.Ac. | 82.8 | SM (OH) C22:1; Arg; Met |
| 314 | 4 | S.L./Am.Ac./B.Am. | 82.5 | SM C18:0; SM (OH) C22:2; Gln; Met-SO |
| 315 | 5 | En.Met/S.L./Am.Ac. | 82 | Pent-P; SM (OH) C16:1; SM (OH) C22:2; Orn; Pro |
| 316 | 3 | S.L./Am.Ac. | 84 | SM C16:1; Phe; Pro |
| 317 | 4 | S.L./Am.Ac./B.Am. | 86 | SM C18:1; SM (OH) C14:1; Trp; Ac-Orn |
| 318 | 4 | Ac.Ca./S.L./O.St. | 79.7 | C5:1-DC; SM C24:1; SM (OH) C24:1; Cholestenone |
| 319 | 4 | Ac.Ca./S.L./B.Am. | 79 | C6:1; SM C16:1; SM (OH) C22:2; Met-SO |
| 320 | 2 | S.L./Am.Ac. | 82.3 | SM (OH) C22:1; Met |

TABLE 9-continued

Metabolite combinations describing damage of basal ganglia

| No. | Npar | Chemical Class | Accuracy | Model |
|---|---|---|---|---|
| 321 | 3 | S.L./Am.Ac. | 83.1 | SM C18:1; Gln; Tyr |
| 322 | 6 | En.Met/Ac.Ca./S.L./Am.Ac./P.G. | 79.3 | alpha-KGA; C5:1-DC; SM C24:0; SM (OH) C22:2; Lys; AA |
| 323 | 4 | S.L./Am.Ac./B.Am. | 81.5 | SM C16:0; Arg; His; Ac-Orn |
| 324 | 4 | En.Met/S.L./Am.Ac. | 83.7 | Lac; SM C16:0; Arg; Met |
| 325 | 4 | S.L./Am.Ac./B.Am. | 85.5 | SM (OH) C22:1; SM (OH) C24:1; Tyr; Kynurenine |
| 326 | 3 | S.L./Am.Ac. | 81.7 | SM C18:0; SM (OH) C14:1; Tyr |
| 327 | 4 | En.Met/S.L./Am.Ac. | 82.5 | Fum; SM C16:1; SM (OH) C16:1; Met |
| 328 | 4 | En.Met/S.L./Am.Ac. | 85 | Lac; SM C24:1; SM (OH) C22:2; Tyr |
| 329 | 4 | En.Met/S.L./Am.Ac. | 91.8 | Lac; SM C24:1; Gln; Tyr |
| 330 | 4 | En.Met/Ac.Ca./S.L./Am.Ac. | 79.5 | alpha-KGA; C14:1; SM C18:1; Tyr |
| 331 | 3 | S.L./Am.Ac. | 80.1 | SM C16:1; SM C24:0; Tyr |
| 332 | 3 | S.L./Am.Ac. | 83.1 | SM (OH) C22:2; His; Orn |
| 333 | 4 | Ac.Ca./S.L./B.Am. | 86.7 | C5:1-DC; SM C24:1; SM (OH) C22:2; Histamine |
| 334 | 4 | S.L./Am.Ac./O.St. | 83.4 | SM C24:1; SM (OH) C24:1; Ala; Cholestenone |
| 335 | 4 | En.Met/S.L./Am.Ac./B.Am. | 85.4 | alpha-KGA; SM C24:0; Pro; Met-SO |
| 336 | 5 | S.L./Am.Ac./P.G. | 83.5 | SM C24:1; SM (OH) C14:1; SM (OH) C22:2; Arg; LTB4 |
| 337 | 4 | S.L./B.Am. | 82.5 | SM C24:1; SM (OH) C22:2; Ac-Orn; Histamine |
| 338 | 4 | S.L./Am.Ac. | 85.5 | SM C16:1; Arg; Met; Pro |
| 339 | 4 | Ac.Ca./Am.Ac./B.Am. | 90.5 | C6:1; Gln; Lys; Ac-Orn |
| 340 | 4 | S.L./Am.Ac./B.Am. | 86.7 | SM (OH) C24:1; Gln; Orn; Met-SO |
| 341 | 4 | Am.Ac./O.St. | 82.6 | His; Orn; Trp; 24-DH-Lanosterol |
| 342 | 4 | S.L./Am.Ac. | 82.2 | SM C24:1; SM (OH) C14:1; His; Tyr |
| 343 | 5 | S.L./Am.Ac./B.Am./O.St. | 81.9 | SM C16:1; Lys; Tyr; Histamine; 20a-OH-C |
| 344 | 5 | Ac.Ca./S.L./Am.Ac./B.Am. | 83.8 | C14:1; C5:1-DC; SM (OH) C16:1; Pro; Histamine |
| 345 | 3 | S.L./Am.Ac. | 84.4 | SM (OH) C14:1; SM (OH) C22:1; Tyr |
| 346 | 3 | S.L./Am.Ac. | 79.3 | SM C16:0; SM (OH) C16:1; Gly |
| 347 | 3 | Ac.Ca./S.L./B.Am. | 79.6 | C6:1; SM C16:1; Taurine |
| 348 | 3 | S.L./Am.Ac. | 82.6 | SM (OH) C22:1; Pro; Tyr |
| 349 | 4 | S.L./B.Am. | 84.2 | SM C20:2; SM C24:0; SM (OH) C22:1; Met-SO |
| 350 | 5 | En.Met/S.L./Am.Ac./B.Am. | 84 | H1; SM C16:1; Orn; Trp; Met-SO |
| 351 | 3 | S.L./Am.Ac. | 83.3 | SM (OH) C14:1; SM (OH) C22:1; Met |
| 352 | 4 | S.L./Am.Ac./O.St. | 80.7 | SM C18:1; SM (OH) C14:1; Tyr; Cholestenone |
| 353 | 4 | S.L./Am.Ac. | 81.2 | SM (OH) C14:1; SM (OH) C22:1; Ile; Met |
| 354 | 4 | S.L./Am.Ac./B.Am. | 80.6 | SM C16:1; Lys; Histamine; Met-SO |
| 355 | 4 | S.L./Am.Ac./B.Am. | 93.4 | SM C24:1; SM (OH) C22:2; Tyr; Kynurenine |
| 356 | 3 | Ac.Ca./S.L. | 82.6 | C5:1-DC; SM (OH) C22:2; SM (OH) C24:1 |
| 357 | 3 | S.L./Am.Ac. | 80.1 | SM C20:2; SM (OH) C14:1; Phe |
| 358 | 6 | S.L./Am.Ac./P.G. | 86.1 | SM (OH) C22:1; Arg; Met; Trp; Tyr; LTB4 |
| 359 | 3 | S.L./Am.Ac. | 88.9 | SM (OH) C14:1; Lys; Met |
| 360 | 6 | S.L./Am.Ac./O.St. | 85 | SM C16:1; SM C24:0; SM (OH) C22:2; Ala; Tyr; Cholestenone |
| 361 | 4 | En.Met/S.L./B.Am. | 84.3 | alpha-KGA; SM (OH) C22:2; Ac-Orn; Histamine |
| 362 | 3 | S.L./Am.Ac. | 81.8 | SM C16:1; SM C24:1; Arg |
| 363 | 4 | S.L./Am.Ac./B.Am. | 79.3 | SM C24:1; SM (OH) C24:1; Arg; Ac-Orn |
| 364 | 4 | En.Met/S.L./Am.Ac. | 82.2 | Fum; SM C18:0; SM (OH) C22:1; Met |
| 365 | 5 | S.L./Am.Ac./B.Am. | 84 | SM C16:0; SM C24:1; SM (OH) C24:1; Lys; Met-SO |
| 366 | 4 | S.L./Am.Ac./O.St. | 80.1 | Lac; SM C16:1; Tyr; Cholestenone |
| 367 | 6 | Ac.Ca./S.L./Am.Ac./O.St. | 87.7 | C18; C5:1-DC; SM C16:1; Lys; Pro; 25-OH-C |
| 368 | 4 | S.L./Am.Ac. | 81 | SM C26:1; Met; Orn; Pro |
| 369 | 3 | S.L./Am.Ac. | 84.5 | SM C16:1; SM C24:1; Ala |
| 370 | 4 | S.L./Am.Ac./B.Am. | 85.7 | SM C24:0; Pro; Trp; Met-SO |
| 371 | 4 | En.Met/S.L./Am.Ac. | 81.8 | alpha-KGA; SM (OH) C14:1; Met; Tyr |
| 372 | 5 | S.L./Am.Ac./P.G. | 94.2 | SM C24:0; SM (OH) C14:1; SM (OH) C22:2; Arg; TXB2 |
| 373 | 5 | S.L./Am.Ac./O.St. | 87.5 | SM (OH) C14:1; Gln; His; Orn; 20a-OH-C |
| 374 | 3 | S.L./Am.Ac./B.Am. | 85.6 | SM (OH) C14:1; Pro; Ac-Orn |
| 375 | 4 | S.L./Am.Ac./O.St. | 88.4 | SM C18:1; Pro; Trp; Cholestenone |
| 376 | 4 | Ac.Ca./S.L. | 87.5 | C5:1-DC; C6:1; SM C16:1; SM (OH) C16:1 |
| 377 | 4 | S.L./Am.Ac. | 81 | SM C16:1; SM C24:1; SM (OH) C22:1; Gly |
| 378 | 4 | S.L./Am.Ac. | 83.2 | SM (OH) C16:1; SM (OH) C22:2; Met; Orn |
| 379 | 3 | S.L./Am.Ac. | 85.5 | SM C24:0; SM (OH) C22:2; Tyr |
| 380 | 4 | S.L./Am.Ac./B.Am. | 79.9 | SM (OH) C24:1; Arg; Ac-Orn; Histamine |
| 381 | 4 | Ac.Ca./S.L./Am.Ac. | 90.3 | C5:1-DC; SM C16:1; SM (OH) C14:1; Tyr |
| 382 | 4 | S.L./Am.Ac. | 79.8 | SM C16:0; SM C18:0; Met; Pro |
| 383 | 4 | S.L./Am.Ac./B.Am. | 83.1 | SM C24:1; Orn; Pro; Histamine |
| 384 | 4 | S.L./Am.Ac. | 79.4 | SM (OH) C22:2; Leu; Met; Pro |
| 385 | 5 | En.Met/Ac.Ca./S.L./Am.Ac. | 86.5 | Lac; C14:1-OH; SM C20:2; His; Pro |
| 386 | 4 | S.L./Am.Ac./B.Am. | 81.5 | SM C16:1; SM (OH) C16:1; Arg; Met-SO |
| 387 | 3 | S.L./Am.Ac. | 79.8 | SM C18:1; Gln; Ac-Orn |
| 388 | 4 | Ac.Ca./S.L./O.St. | 83.7 | C5:1-DC; SM C18:1; SM (OH) C14:1; Cholestenone |
| 389 | 4 | S.L./Am.Ac./B.Am. | 89.2 | SM (OH) C14:1; Pro; Trp; Ac-Orn |
| 390 | 5 | S.L./Am.Ac./B.Am. | 85.8 | SM (OH) C16:1; SM (OH) C22:1; Orn; Trp; Ac-Orn |
| 391 | 3 | Am.Ac./O.St. | 83.4 | Lys; Met; 25-OH-C |
| 392 | 3 | Ac.Ca./S.L. | 86.9 | C5:1-DC; SM C16:1; SM (OH) C22:2 |
| 393 | 3 | S.L./Am.Ac. | 79.8 | SM C24:0; SM (OH) C22:2; Ser |
| 394 | 5 | S.L./Am.Ac./O.St. | 79.2 | SM C16:0; SM C24:0; SM (OH) C14:1; Thr; 20a-OH-C |
| 395 | 4 | En.Met/S.L./B.Am. | 79.9 | H1; SM (OH) C22:2; Kynurenine; Met-SO |
| 396 | 4 | Ac.Ca./S.L./O.St. | 85.3 | C5:1-DC; SM (OH) C22:1; SM (OH) C24:1; Cholestenone |

TABLE 9-continued

Metabolite combinations describing damage of basal ganglia

| No. | Npar | Chemical Class | Accuracy | Model |
|---|---|---|---|---|
| 397 | 4 | Ac.Ca./S.L./Am.Ac. | 90.4 | C5:1-DC; SM (OH) C14:1; SM (OH) C22:1; Tyr |
| 398 | 4 | S.L./Am.Ac./B.Am. | 80.1 | SM (OH) C24:1; Orn; Tyr; Ac-Orn |
| 399 | 4 | Ac.Ca./S.L./Am.Ac. | 79.1 | C14:1; C5:1-DC; SM (OH) C16:1; Lys |
| 400 | 4 | En.Met/S.L./Am.Ac./O.St. | 88.7 | alpha-KGA; SM C16:1; Pro; 20a-OH-C |
| 401 | 4 | En.Met/S.L./Am.Ac./B.Am. | 84.7 | Suc; SM C16:0; Pro; Histamine |
| 402 | 3 | S.L./O.St. | 80.5 | SM (OH) C22:2; SM (OH) C24:1; 20a-OH-C |
| 403 | 4 | S.L./Am.Ac. | 81.9 | SM C16:1; Met; Phe; Trp |
| 404 | 4 | S.L./B.Am. | 79.4 | SM C18:1; SM (OH) C24:1; Kynurenine; Met-SO |
| 405 | 4 | En.Met/S.L./Am.Ac. | 83.3 | Lac; SM (OH) C22:2; Gln; Orn |
| 406 | 4 | En.Met/S.L./Am.Ac. | 80.2 | alpha-KGA; SM C24:1; SM (OH) C22:2; Ser |
| 407 | 4 | S.L./Am.Ac. | 84.6 | SM (OH) C14:1; Pro; Trp; Tyr |
| 408 | 4 | En.Met/S.L./Am.Ac. | 80.6 | alpha-KGA; SM C24:0; Leu; Met |
| 409 | 4 | S.L./Am.Ac./B.Am./O.St. | 87.9 | SM C16:1; Met; Creatinine; 24-DH-Lanosterol |
| 410 | 3 | S.L./Am.Ac. | 79.5 | SM C24:0; SM (OH) C24:1; Tyr |
| 411 | 4 | Am.Ac./B.Am./O.St. | 79.4 | Leu; Tyr; Kynurenine; Cholestenone |
| 412 | 3 | Am.Ac./B.Am. | 91.9 | Gln; Lys; Met-SO |
| 413 | 4 | S.L./Am.Ac. | 79.3 | SM (OH) C14:1; SM (OH) C22:1; SM (OH) C24:1; Met |
| 414 | 3 | S.L./Am.Ac. | 88.2 | SM C16:0; SM (OH) C22:2; Gly |
| 415 | 5 | En.Met/S.L./Am.Ac./P.G. | 95.8 | alpha-KGA; SM (OH) C22:2; His; Orn; TXB2 |
| 416 | 5 | S.L./Am.Ac./B.Am. | 87.2 | SM C16:0; SM C16:1; SM (OH) C22:2; Arg; Ac-Orn |
| 417 | 4 | S.L./Am.Ac. | 80.8 | SM (OH) C14:1; SM (OH) C22:1; Phe; Pro |
| 418 | 4 | S.L./Am.Ac. | 82.3 | SM (OH) C14:1; SM (OH) C22:2; Arg; Phe |
| 419 | 3 | S.L./Am.Ac. | 80.3 | SM C16:0; SM C24:0; Tyr |
| 420 | 4 | S.L./Am.Ac. | 79.8 | SM (OH) C16:1; SM (OH) C22:2; Ala; Gln |
| 421 | 5 | S.L./Am.Ac./P.G. | 86.7 | SM C24:0; Leu; Met; Orn; LTB4 |
| 422 | 4 | S.L./Am.Ac. | 80.1 | SM C16:1; SM C18:0; SM (OH) C16:1; Tyr |
| 423 | 3 | S.L./Am.Ac. | 79.3 | SM C16:1; Arg; His |
| 424 | 4 | S.L./Am.Ac. | 88.5 | SM (OH) C14:1; SM (OH) C16:1; SM (OH) C22:2; Gly |
| 425 | 5 | S.L./Am.Ac./B.Am. | 82.6 | SM C24:0; SM (OH) C22:2; Leu; Lys; Ac-Orn |
| 426 | 5 | S.L./Am.Ac./B.Am. | 85.8 | SM C24:1; SM C14:1; SM (OH) C22:2; Val; Kynurenine |
| 427 | 4 | S.L./Am.Ac. | 88.9 | SM C24:0; Gln; Met; Pro |
| 428 | 4 | Ac.Ca./S.L./Am.Ac. | 80.6 | C6:1; SM C24:1; SM (OH) C14:1; Tyr |
| 429 | 4 | En.Met/S.L./Am.Ac. | 81.9 | alpha-KGA; SM C20:2; SM (OH) C14:1; Met |
| 430 | 4 | Ac.Ca./S.L./Am.Ac. | 85.2 | C5:1-DC; SM (OH) C14:1; Gln; Pro |
| 431 | 5 | Ac.Ca./S.L./Am.Ac. | 87.7 | C5:1-DC; SM C16:1; SM C18:1; SM C24:1; Lys |
| 432 | 5 | S.L./Am.Ac./B.Am. | 84 | SM C16:0; SM (OH) C14:1; SM (OH) C24:1; Gly; Ac-Orn |
| 433 | 4 | S.L./Am.Ac. | 82.9 | SM C18:1; SM C24:0; Met; Phe |
| 434 | 4 | En.Met/S.L./B.Am. | 80.1 | Suc; SM C18:1; Ac-Orn; Histamine |
| 435 | 5 | S.L./Am.Ac./B.Am./O.St. | 81.8 | SM C16:0; SM (OH) C24:1; Tyr; Ac-Orn; Cholestenone |
| 436 | 3 | S.L./B.Am. | 81.2 | SM (OH) C14:1; SM (OH) C24:1; Met-SO |
| 437 | 3 | S.L./Am.Ac. | 83.1 | SM C24:1; SM (OH) C14:1; Tyr |
| 438 | 4 | Ac.Ca./S.L./Am.Ac./B.Am. | 79.9 | C6:1; SM (OH) C22:2; Lys; Ac-Orn |
| 439 | 3 | Ac.Ca./S.L./O.St. | 88 | C5:1-DC; SM C16:1; Cholestenone |
| 440 | 5 | S.L./Am.Ac./O.St. | 92.3 | SM (OH) C22:2; Gln; His; Orn; 20a-OH-C |
| 441 | 3 | S.L./Am.Ac./O.St. | 83.7 | SM C24:0; Tyr; 24S-OH-C |
| 442 | 4 | En.Met/S.L./Am.Ac. | 81.3 | Suc; SM C18:1; His; Orn |
| 443 | 4 | En.Met/Ac.Ca./Am.Ac./P.G. | 96.8 | alpha-KGA; C14:1; Pro; TXB2 |
| 444 | 4 | S.L./Am.Ac. | 84 | SM (OH) C22:1; SM (OH) C22:2; Asn; Orn |
| 445 | 3 | En.Met/S.L./Am.Ac. | 79.6 | alpha-KGA; SM (OH) C14:1; Tyr |
| 446 | 4 | S.L./Am.Ac. | 82.8 | SM C16:0; SM (OH) C22:1; Met; Phe |
| 447 | 4 | En.Met/Am.Ac. | 82.9 | alpha-KGA; Lac; Gln; Tyr |
| 448 | 4 | S.L./Am.Ac./B.Am. | 90.1 | SM C24:0; His; Orn; Met-SO |
| 449 | 4 | Ac.Ca./Am.Ac./B.Am. | 82.3 | C14:1; Met; Pro; Ac-Orn |
| 450 | 6 | En.Met/S.L./Am.Ac./B.Am. | 83.4 | Lac; Pent-P; Suc; SM C16:1; His; Ac-Orn |
| 451 | 4 | S.L./Am.Ac./B.Am./O.St. | 79.7 | SM C16:1; Leu; Histamine; 20a-OH-C |
| 452 | 4 | En.Met/S.L./Am.Ac. | 79.3 | Lac; SM C16:1; SM (OH) C24:1; Phe |
| 453 | 3 | Ac.Ca./S.L. | 80.5 | C5:1-DC; SM C16:1; SM C24:1 |
| 454 | 3 | Ac.Ca./S.L./Am.Ac. | 79.3 | C6:1; SM C24:1; Arg |
| 455 | 4 | En.Met/Am.Ac./O.St. | 82.9 | alpha-KGA; Suc; Arg; Cholestenone |
| 456 | 3 | Ac.Ca./S.L./B.Am. | 86.7 | C5:1-DC; SM C16:1; Histamine |
| 457 | 4 | S.L./Am.Ac./B.Am. | 86.3 | SM (OH) C22:1; Pro; Trp; Met-SO |
| 458 | 4 | S.L./Am.Ac./B.Am. | 81.2 | SM C16:1; SM C18:0; Met; Kynurenine |
| 459 | 3 | S.L./Am.Ac. | 83.4 | SM C16:1; SM C20:2; Pro |
| 460 | 4 | S.L./Am.Ac./P.G. | 84.5 | SM C24:1; Gln; Orn; LTB4 |
| 461 | 4 | S.L./Am.Ac. | 84.4 | SM (OH) C14:1; SM (OH) C16:1; Met; Pro |
| 462 | 4 | Ac.Ca./S.L./Am.Ac. | 83.2 | C5:1; SM C18:0; SM (OH) C24:1; Met |
| 463 | 3 | En.Met/S.L./Am.Ac. | 79.9 | alpha-KGA; SM C24:0; Met-SO |
| 464 | 6 | S.L./Am.Ac./B.Am. | 87.7 | SM C24:0; SM (OH) C16:1; SM (OH) C22:2; Ser; Kynurenine; total DMA |
| 465 | 4 | S.L./Am.Ac. | 83.8 | SM C16:0; SM C24:1; Ala; Met |
| 466 | 4 | S.L./Am.Ac./O.St. | 79.3 | SM C16:0; Lys; Tyr; 20a-OH-C |
| 467 | 4 | S.L./Am.Ac./O.St. | 84.6 | SM (OH) C22:2; SM (OH) C22:2; Ala; Cholestenone |
| 468 | 4 | Am.Ac./B.Am. | 80.1 | Gln; Tyr; Ac-Orn; Histamine |
| 469 | 4 | S.L./Am.Ac. | 86.7 | SM (OH) C22:2; Gln; Pro; Tyr |
| 470 | 4 | En.Met/Ac.Ca./S.L./B.Am. | 81.4 | alpha-KGA; C5:1-DC; SM C16:0; Histamine |
| 471 | 3 | Ac.Ca./S.L./Am.Ac. | 85.4 | C6:1; SM (OH) C22:1; Tyr |
| 472 | 5 | S.L./Am.Ac./P.G. | 92.4 | SM C24:0; SM (OH) C14:1; His; Orn; TXB2 |

TABLE 9-continued

Metabolite combinations describing damage of basal ganglia

| No. | Npar | Chemical Class | Accuracy | Model |
|---|---|---|---|---|
| 473 | 5 | S.L./Am.Ac./O.St. | 85.9 | SM C16:0; SM C16:1; His; Lys; 20a-OH-C |
| 474 | 3 | En.Met/S.L./Am.Ac. | 83.9 | Fum; SM (OH) C14:1; Met |
| 475 | 4 | S.L./B.Am. | 84.3 | SM (OH) C14:1; SM (OH) C22:1; Ac-Orn; Histamine |
| 476 | 4 | S.L./Am.Ac. | 83.9 | SM (OH) C16:1; SM (OH) C22:1; Met; Trp |
| 477 | 5 | En.Met/Am.Ac./B.Am./O.St. | 80.4 | Suc; Arg; Met; Histamine; Cholestenone |
| 478 | 6 | S.L./Am.Ac./P.G. | 90.1 | SM C16:0; SM (OH) C16:1; Gln; Orn; Tyr; TXB2 |
| 479 | 6 | S.L./Am.Ac./B.Am./O.St. | 84.2 | SM (OH) C14:1; SM (OH) C16:1; SM (OH) C22:1; Lys; Met-SO; 5a,6a-EpoxyC |
| 480 | 6 | S.L./Am.Ac./B.Am./P.G. | 88.2 | SM (OH) C14:1; SM (OH) C16:1; Pro; Trp; Ac-Orn; LTB4 |
| 481 | 4 | Am.Ac./B.Am./O.St. | 81.5 | Leu; Met; Kynurenine; Cholestenone |
| 482 | 4 | Ac.Ca./S.L./Am.Ac. | 80.6 | C5:1-DC; C6:1; SM C24:1; Gln |
| 483 | 4 | S.L./Am.Ac./B.Am. | 89.4 | SM C24:0; Gln; Pro; Ac-Orn |
| 484 | 5 | S.L./Am.Ac./B.Am. | 84.1 | SM (OH) C14:1; SM (OH) C24:1; Trp; Ac-Orn; Histamine |
| 485 | 4 | S.L./Am.Ac./B.Am. | 80.9 | SM (OH) C22:1; SM (OH) C22:2; Leu; Met-SO |
| 486 | 4 | S.L./Am.Ac./P.G. | 91.5 | SM C16:1; His; Pro; TXB2 |
| 487 | 4 | S.L./Am.Ac./B.Am. | 85.3 | SM (OH) C14:1; Orn; Pro; Met-SO |
| 488 | 5 | S.L./Am.Ac./B.Am. | 92.8 | SM C16:1; SM C24:0; Pro; Trp; Met-SO |
| 489 | 5 | En.Met/S.L./Am.Ac./B.Am. | 82.1 | Hex-P; SM C16:0; SM C24:1; Gln; Ac-Orn |
| 490 | 4 | Am.Ac./B.Am. | 79.5 | Gln; Pro; Trp; SDMA |
| 491 | 5 | Ac.Ca./S.L./Am.Ac./P.G. | 85.3 | C6:1; SM C16:0; Arg; Leu; TXB2 |
| 492 | 4 | S.L./Am.Ac./B.Am. | 86.7 | SM C24:0; SM (OH) C24:1; Pro; Ac-Orn |
| 493 | 5 | En.Met/S.L./Am.Ac. | 87.8 | Suc; SM C24:0; SM C26:1; Lys; Met |
| 494 | 3 | Ac.Ca./S.L. | 85.8 | C5:1-DC; SM C16:1; SM (OH) C16:1 |
| 495 | 5 | S.L./Am.Ac./P.G. | 94.8 | SM (OH) C16:1; SM (OH) C22:1; Orn; Tyr; TXB2 |
| 496 | 4 | Ac.Ca./S.L./Am.Ac. | 80.2 | C10; SM C24:0; SM (OH) C22:1; Met |
| 497 | 4 | S.L./Am.Ac./B.Am. | 81.7 | SM (OH) C22:2; Pro; Trp; Histamine |
| 498 | 3 | S.L./Am.Ac. | 79.5 | SM C16:0; Phe; Pro |
| 499 | 3 | Ac.Ca./S.L./Am.Ac. | 79.4 | C14:1-OH; SM C18:0; Arg |
| 500 | 4 | En.Met/S.L./Am.Ac./B.Am. | 82 | Pent-P; SM (OH) C22:2; Orn; Ac-Orn |
| 501 | 4 | S.L./Am.Ac. | 83.2 | SM (OH) C14:1; SM (OH) C24:1; Met; Trp |
| 502 | 3 | En.Met/S.L./B.Am. | 81.6 | alpha-KGA; SM (OH) C14:1; Ac-Orn |
| 503 | 3 | S.L./Am.Ac. | 79.8 | SM C16:1; SM C18:1; Trp |
| 504 | 4 | Ac.Ca./S.L./B.Am. | 81.5 | C5:1-DC; SM C24:0; SM (OH) C22:2; Serotonin |
| 505 | 4 | S.L./Am.Ac./B.Am. | 80.2 | SM (OH) C14:1; SM (OH) C22:2; Lys; Met-SO |
| 506 | 4 | Ac.Ca./S.L./Am.Ac. | 82.3 | C14:1; SM (OH) C16:1; Arg; Met |
| 507 | 4 | S.L./Am.Ac./P.G. | 87.8 | SM C24:1; SM (OH) C14:1; Lys; TXB2 |
| 508 | 4 | S.L./B.Am. | 84.1 | SM (OH) C14:1; SM (OH) C22:2; Ac-Orn; Histamine |
| 509 | 3 | S.L./Am.Ac. | 82.8 | SM C18:0; SM (OH) C22:1; Tyr |
| 510 | 4 | S.L./Am.Ac./B.Am./P.G. | 81.8 | SM (OH) C14:1; Orn; Met-SO; 8-iso-PGF2a |
| 511 | 4 | Am.Ac./B.Am. | 87.2 | Gln; Met; Pro; total DMA |
| 512 | 4 | S.L./Am.Ac./O.St. | 80.9 | SM (OH) C22:1; SM (OH) C22:2; Met; Cholestenone |
| 513 | 4 | S.L./Am.Ac. | 81.6 | SM C18:0; SM C24:1; Trp; Tyr |
| 514 | 3 | En.Met/S.L./Am.Ac. | 83 | alpha-KGA; SM (OH) C22:1; Tyr |
| 515 | 4 | S.L./Am.Ac. | 84.1 | SM C24:0; SM (OH) C22:2; Arg; Phe |
| 516 | 3 | S.L./Am.Ac. | 81.6 | SM (OH) C14:1; Arg; Phe |
| 517 | 3 | S.L./Am.Ac./O.St. | 80.9 | SM C24:0; Tyr; Cholestenone |
| 518 | 4 | S.L./Am.Ac. | 84.5 | SM (OH) C16:1; SM (OH) C22:2; Met; Trp |
| 519 | 3 | S.L./Am.Ac. | 80.5 | SM (OH) C22:1; SM (OH) C22:2; Ser |
| 520 | 3 | Ac.Ca./S.L./O.St. | 84 | C5:1-DC; SM C16:1; 24-DH-Lanosterol |
| 521 | 4 | S.L./Am.Ac./P.G. | 80.6 | SM C16:0; Arg; Met; 8-iso-PGF2a |
| 522 | 4 | Ac.Ca./S.L./Am.Ac. | 80.9 | C14:1; SM C24:0; Arg; Met |
| 523 | 4 | S.L./Am.Ac./P.G. | 90.2 | SM C16:0; SM (OH) C24:1; Pro; TXB2 |
| 524 | 4 | S.L./Am.Ac./B.Am. | 88.1 | SM C16:1; SM (OH) C14:1; Arg; Met-SO |
| 525 | 3 | S.L./Am.Ac. | 81.3 | SM (OH) C22:1; SM (OH) C22:2; Met |
| 526 | 4 | S.L./Am.Ac./O.St. | 79.3 | SM (OH) C22:1; Gln; Pro; 20a-OH-C |
| 527 | 6 | Ac.Ca./S.L./Am.Ac./O.St. | 94.5 | C6:1; SM C16:1; SM (OH) C22:2; Orn; Pro; 22R-OH-C |
| 528 | 4 | En.Met/S.L./Am.Ac. | 83.4 | Lac; SM C16:1; SM (OH) C14:1; Tyr |
| 529 | 4 | Ac.Ca./S.L./B.Am. | 87.1 | C5:1-DC; C6:1; SM (OH) C22:2; Histamine |
| 530 | 4 | S.L./Am.Ac. | 79.4 | SM C18:1; SM C24:1; SM (OH) C22:2; Thr |
| 531 | 4 | En.Met/Am.Ac./O.St. | 85 | Lac; His; Trp; 24-DH-Lanosterol |
| 532 | 3 | S.L./Am.Ac. | 86.3 | SM C18:0; SM C24:0; Tyr |
| 533 | 4 | S.L./Am.Ac. | 80.2 | SM C16:1; SM C24:1; Orn; Tyr |
| 534 | 4 | En.Met/S.L./Am.Ac./B.Am. | 80.7 | alpha-KGA; SM (OH) C22:2; Gln; Ac-Orn |
| 535 | 5 | Ac.Ca./S.L./Am.Ac. | 81 | C18; C5:1-DC; SM (OH) C22:1; Arg; Pro |
| 536 | 4 | Ac.Ca./S.L./Am.Ac. | 80 | C14:1; SM C16:0; Arg; Met |
| 537 | 5 | Ac.Ca./S.L./Am.Ac./B.Am. | 82.6 | C14:1; SM C18:1; SM (OH) C22:2; Pro; Met-SO |
| 538 | 4 | Ac.Ca./S.L./Am.Ac./O.St. | 81.4 | C5:1-DC; SM (OH) C22:1; Lys; Cholestenone |
| 539 | 4 | S.L./Am.Ac./B.Am. | 91.3 | SM (OH) C22:1; Gln; Lys; Met-SO |
| 540 | 4 | Ac.Ca./Am.Ac./B.Am. | 81.3 | C18; Arg; Pro; Met-SO |
| 541 | 4 | S.L./Am.Ac./B.Am. | 84.3 | SM C18:0; SM (OH) C14:1; Arg; Ac-Orn |
| 542 | 4 | S.L./Am.Ac./B.Am. | 80.5 | SM C16:0; SM C16:1; Ala; Met-SO |
| 543 | 4 | En.Met/S.L./O.St. | 79.7 | alpha-KGA; SM C24:0; SM (OH) C14:1; 20a-OH-C |
| 544 | 4 | En.Met/S.L./Am.Ac./B.Am. | 83.6 | Lac; SM (OH) C22:1; Pro; Met-SO |
| 545 | 3 | S.L./Am.Ac./O.St. | 86.6 | SM (OH) C16:1; Trp; 24-DH-Lanosterol |
| 546 | 3 | S.L./Am.Ac./O.St. | 81.9 | SM (OH) C22:1; Trp; 24-DH-Lanosterol |
| 547 | 4 | Ac.Ca./S.L./Am.Ac. | 83.1 | C6:1; SM C16:0; Met; Pro |
| 548 | 4 | Ac.Ca./S.L./B.Am. | 82.6 | C14:1; SM (OH) C22:2; Kynurenine; Met-SO |

TABLE 9-continued

Metabolite combinations describing damage of basal ganglia

| No. | Npar | Chemical Class | Accuracy | Model |
|---|---|---|---|---|
| 549 | 3 | Ac.Ca./Am.Ac. | 84.6 | C6:1; Lys; Met |
| 550 | 4 | S.L./Am.Ac./B.Am. | 83.8 | SM C16:1; Met; Pro; Histamine |
| 551 | 4 | S.L./Am.Ac. | 85.9 | SM C16:1; SM (OH) C14:1; Ala; Met |
| 552 | 4 | Ac.Ca./S.L./Am.Ac./O.St. | 83.8 | C6:1; SM (OH) C16:1; Trp; Cholestenone |
| 553 | 4 | S.L./Am.Ac. | 85.4 | SM C16:1; SM C20:2; SM (OH) C16:1; Tyr |
| 554 | 4 | S.L./Am.Ac. | 83.8 | SM C24:1; SM (OH) C22:2; Met; Orn |
| 555 | 4 | S.L./Am.Ac. | 80.3 | SM C16:1; SM (OH) C14:1; SM (OH) C22:1; Met |
| 556 | 4 | En.Met/S.L./Am.Ac./B.Am. | 79.7 | Lac; SM (OH) C22:2; Tyr; Histamine |
| 557 | 4 | Am.Ac./B.Am. | 83.4 | Gln; Orn; Histamine; Met-SO |
| 558 | 4 | En.Met/S.L./Am.Ac./O.St. | 82.2 | alpha-KGA; SM (OH) C22:1; Leu; 20a-OH-C |
| 559 | 5 | S.L./Am.Ac./B.Am. | 85.9 | SM C18:0; Gln; Leu; Orn; Ac-Orn |
| 560 | 4 | Ac.Ca./S.L./O.St. | 83 | C5:1-DC; SM (OH) C22:1; SM (OH) C24:1; 24-DH-Lanosterol |
| 561 | 5 | S.L./Am.Ac./O.St. | 85.6 | SM (OH) C14:1; SM (OH) C22:2; Trp; Kynurenine; 24-DH-Lanosterol |
| 562 | 4 | S.L./Am.Ac./B.Am. | 83.9 | SM (OH) C14:1; Trp; Histamine; Met-SO |
| 563 | 3 | Ac.Ca./S.L. | 82.8 | C5:1-DC; SM C18:1; SM (OH) C14:1 |
| 564 | 3 | En.Met/S.L./O.St. | 84.3 | alpha-KGA; SM (OH) C14:1; 20a-OH-C |
| 565 | 4 | En.Met/S.L./Am.Ac./O.St. | 86.1 | alpha-KGA; SM C16:1; Arg; 20a-OH-C |
| 566 | 4 | S.L./Am.Ac./O.St. | 83.2 | SM (OH) C22:1; Arg; Met; 25-OH-C |
| 567 | 4 | En.Met/S.L./Am.Ac. | 80.5 | Lac; SM C16:1; Met; Tyr |
| 568 | 3 | En.Met/Ac.Ca./S.L. | 89.4 | alpha-KGA; C5:1-DC; SM C16:1 |
| 569 | 3 | En.Met/S.L./Am.Ac. | 80.2 | Lac; SM C16:1; Phe |
| 570 | 4 | S.L./Am.Ac. | 82.1 | SM C24:1; SM (OH) C14:1; SM (OH) C22:2; Tyr |
| 571 | 4 | Ac.Ca./S.L./Am.Ac. | 80.7 | C18; SM C18:0; Phe; Pro |
| 572 | 4 | Ac.Ca./S.L./O.St. | 81.8 | C5:1-DC; C6:1; SM C24:0; 24S-OH-C |
| 573 | 4 | En.Met/Ac.Ca./S.L./Am.Ac. | 83.9 | Suc; C6:1; SM C16:0; Tyr |
| 574 | 4 | S.L./Am.Ac./O.St. | 82.7 | SM C16:1; His; Lys; 20a-OH-C |
| 575 | 4 | En.Met/Am.Ac./B.Am. | 82.6 | alpha-KGA; His; Orn; Ac-Orn |
| 576 | 4 | S.L./Am.Ac./B.Am. | 86 | SM (OH) C22:2; SM (OH) C24:1; Trp; Met-SO |
| 577 | 3 | En.Met/S.L./B.Am. | 85.3 | alpha-KGA; SM C16:1; Ac-Orn |
| 578 | 4 | S.L./Am.Ac. | 80.5 | SM C24:1; SM (OH) C24:1; Tyr |
| 579 | 4 | S.L./Am.Ac./B.Am./P.G. | 80 | SM (OH) C14:1; Trp; Met-SO; LTB4 |
| 580 | 3 | Ac.Ca./S.L./B.Am. | 79.1 | C6:1; SM (OH) C14:1; Ac-Orn |
| 581 | 4 | S.L./Am.Ac./B.Am. | 87.9 | SM (OH) C14:1; SM (OH) C22:2; Met; Kynurenine |
| 582 | 4 | S.L./Am.Ac. | 85.2 | SM (OH) C16:1; SM (OH) C22:1; Trp; Tyr |
| 583 | 4 | En.Met/S.L./Am.Ac. | 81.4 | Suc; SM C16:1; SM (OH) C16:1; Orn |
| 584 | 4 | S.L./Am.Ac./B.Am. | 80.1 | SM C16:0; SM (OH) C16:1; Ala; Ac-Orn |
| 585 | 4 | En.Met/B.Am./O.St. | 80.2 | alpha-KGA; Ac-Orn; Histamine; Cholestenone |
| 586 | 4 | S.L./Am.Ac./B.Am./O.St. | 89.2 | SM C16:1; Met; Creatinine; Cholestenone |
| 587 | 3 | S.L./Am.Ac./B.Am. | 80.8 | SM (OH) C14:1; Orn; Ac-Orn |
| 588 | 3 | S.L./B.Am. | 81.8 | SM C26:1; SM (OH) C22:1; Met-SO |
| 589 | 4 | S.L./Am.Ac. | 85.6 | SM C20:2; SM (OH) C14:1; Phe; Tyr |
| 590 | 5 | En.Met/S.L./Am.Ac./P.G. | 89.7 | alpha-KGA; SM (OH) C14:1; SM (OH) C16:1; Tyr; TXB2 |
| 591 | 4 | S.L./Am.Ac./O.St. | 86.6 | SM C16:1; Met; Pro; Cholestenone |
| 592 | 3 | Ac.Ca./S.L. | 87.5 | C5:1-DC; SM C16:0; SM C16:1 |
| 593 | 4 | Ac.Ca./S.L./Am.Ac. | 86.9 | C5:1-DC; SM C16:1; SM (OH) C22:2; Lys |
| 594 | 3 | S.L./Am.Ac./O.St. | 82.6 | SM C18:0; Trp; 24-DH-Lanosterol |
| 595 | 4 | S.L./Am.Ac./P.G. | 81.1 | SM C18:0; SM C26:1; Lys; TXB2 |
| 596 | 3 | S.L./Am.Ac. | 81 | SM C16:1; SM C18:1; Phe |
| 597 | 4 | En.Met/Am.Ac./P.G. | 79.4 | alpha-KGA; Gln; Met; LTB4 |
| 598 | 5 | En.Met/S.L./B.Am. | 81.5 | Suc; SM (OH) C14:1; SM (OH) C24:1; Histamine; Met-SO |
| 599 | 4 | S.L./Am.Ac. | 80.2 | SM C16:0; SM (OH) C22:1; Phe; Pro |
| 600 | 4 | Ac.Ca./S.L./Am.Ac. | 84.4 | C18; C5:1-DC; SM (OH) C22:2; Pro |
| 601 | 4 | S.L./Am.Ac. | 85.4 | SM C24:0; SM C24:1; SM (OH) C22:2; Tyr |
| 602 | 4 | S.L./Am.Ac./B.Am. | 79.4 | SM C16:0; His; Pro; Met-SO |
| 603 | 4 | S.L./Am.Ac./B.Am. | 81 | SM C20:2; SM C24:0; Gln; Met-SO |
| 604 | 3 | S.L./Am.Ac. | 82.5 | SM (OH) C14:1; Arg; Tyr |
| 605 | 5 | Ac.Ca./S.L./Am.Ac./O.St. | 94.9 | C10; SM C24:0; SM (OH) C22:2; Val; 20a-OH-C |
| 606 | 3 | S.L./Am.Ac. | 82.9 | SM (OH) C22:1; Gln; Tyr |
| 607 | 4 | S.L./Am.Ac./B.Am. | 79.5 | SM C16:1; SM C24:0; Val; Ac-Orn |
| 608 | 4 | S.L./Am.Ac. | 84.6 | SM C24:0; SM (OH) C22:1; Met; Phe |
| 609 | 4 | S.L./Am.Ac./B.Am. | 88.8 | SM C16:0; SM C24:0; Pro; Met-SO |
| 610 | 3 | S.L./Am.Ac./B.Am. | 85.7 | SM C24:0; Orn; Met-SO |
| 611 | 4 | S.L./Am.Ac./B.Am. | 80.7 | SM C16:0; Arg; Orn; Met-SO |
| 612 | 3 | S.L./Am.Ac. | 81.3 | SM C20:2; SM C24:1; Tyr |
| 613 | 5 | S.L./Am.Ac./B.Am./O.St. | 88.2 | SM (OH) C16:1; Gln; Pro; Ac-Orn; Cholestenone |
| 614 | 4 | S.L./Am.Ac./O.St. | 85.2 | SM C16:1; SM (OH) C24:1; Pro; 20a-OH-C |
| 615 | 6 | S.L./Am.Ac./B.Am./O.St./P.G. | 81.1 | SM (OH) C14:1; Phe; Trp; Met-SO; 24S-OH-C; LTB4 |
| 616 | 4 | S.L./Am.Ac./B.Am. | 80.1 | SM C16:1; SM C24:0; Phe; Ac-Orn |
| 617 | 4 | S.L./Am.Ac. | 84 | SM C16:1; SM (OH) C14:1; Pro; Tyr |
| 618 | 4 | S.L./Am.Ac./B.Am. | 80.3 | SM (OH) C22:2; Tyr; Ac-Orn; Histamine |
| 619 | 4 | En.Met/S.L./Am.Ac. | 86.4 | Lac; SM C24:0; Met; Trp |
| 620 | 3 | S.L./Am.Ac. | 86.3 | SM C24:1; Gln; Pro |
| 621 | 4 | Ac.Ca./S.L./Am.Ac./B.Am. | 81.9 | C6:1; SM (OH) C22:1; Phe; Met-SO |
| 622 | 5 | Ac.Ca./S.L./Am.Ac./O.St. | 82.2 | C10; SM (OH) C14:1; Gln; Orn; 20a-OH-C |
| 623 | 4 | S.L./Am.Ac./O.St. | 80.2 | SM C18:0; SM (OH) C22:1; Phe; Cholestenone |
| 624 | 4 | S.L./Am.Ac. | 81.8 | SM C16:0; SM (OH) C22:1; Met; Val |

TABLE 9-continued

Metabolite combinations describing damage of basal ganglia

| No. | Npar | Chemical Class | Accuracy | Model |
|---|---|---|---|---|
| 625 | 4 | S.L./Am.Ac./B.Am. | 83.9 | SM (OH) C22:2; SM (OH) C24:1; Orn; Met-SO |
| 626 | 3 | S.L./Am.Ac. | 80.8 | SM C16:0; Met; Orn |
| 627 | 4 | Am.Ac./O.St. | 85.7 | Gln; Pro; Tyr; Cholestenone |
| 628 | 4 | S.L./Am.Ac./B.Am. | 86 | SM (OH) C14:1; SM (OH) C22:1; Arg; Ac-Orn |
| 629 | 3 | S.L./Am.Ac. | 82.3 | SM C18:1; SM C24:0; Phe |
| 630 | 3 | S.L./Am.Ac./B.Am. | 84.4 | SM C16:0; Pro; Ac-Orn |
| 631 | 4 | En.Met/Am.Ac./O.St. | 81.8 | alpha-KGA; Pro; Tyr; 20a-OH-C |
| 632 | 4 | S.L./Am.Ac./B.Am. | 83.8 | SM C16:0; SM (OH) C22:1; Gln; Met-SO |
| 633 | 4 | S.L./Am.Ac./O.St. | 82.5 | SM C18:0; SM C24:1; Trp; Cholestenone |
| 634 | 4 | S.L./Am.Ac. | 83.3 | SM (OH) C22:1; SM (OH) C24:1; Arg; Met |
| 635 | 3 | S.L./Am.Ac. | 84.5 | SM C20:2; SM (OH) C22:2; Tyr |
| 636 | 5 | S.L./Am.Ac./B.Am. | 89.2 | SM C24:0; SM (OH) C24:1; His; Orn; Met-SO |
| 637 | 4 | En.Met/S.L./Am.Ac. | 79.4 | alpha-KGA; SM C24:1; SM (OH) C14:1; Met |
| 638 | 5 | En.Met/S.L./Am.Ac./O.St. | 82.8 | Lac; SM C24:1; Tyr; 24-DH-Lanosterol; Cholestenone |
| 639 | 4 | S.L./Am.Ac. | 79.3 | SM C16:0; SM (OH) C14:1; Gly; Orn |
| 640 | 3 | S.L./Am.Ac. | 80.9 | SM C18:1; SM (OH) C14:1; Tyr |
| 641 | 4 | En.Met/S.L./Am.Ac. | 87.5 | Lac; SM (OH) C14:1; SM (OH) C22:1; Met |
| 642 | 3 | S.L./Am.Ac. | 81.7 | SM (OH) C14:1; SM (OH) C22:2; Tyr |
| 643 | 3 | En.Met/S.L./Am.Ac. | 80.7 | alpha-KGA; SM (OH) C22:1; Met |
| 644 | 4 | S.L./Am.Ac./B.Am. | 82.9 | SM C24:0; Phe; Ac-Orn; Histamine |
| 645 | 4 | S.L./Am.Ac./B.Am. | 79.4 | SM C24:1; Gln; Carnosine; Met-SO |
| 646 | 4 | S.L./Am.Ac./P.G. | 90.6 | SM (OH) C16:1; His; Lys; TXB2 |
| 647 | 5 | En.Met/Am.Ac./B.Am./O.St. | 85.5 | H1; Arg; Gln; Met-SO; Cholestenone |
| 648 | 3 | S.L./B.Am. | 79.7 | SM C16:0; SM C24:0; Met-SO |
| 649 | 4 | Ac.Ca./S.L./Am.Ac. | 83.7 | C5:1-DC; SM C16:1; His; Lys |
| 650 | 4 | En.Met/Ac.Ca./Am.Ac./B.Am. | 80.3 | Pent-P; C6:1; Pro; Histamine |
| 651 | 4 | En.Met/S.L./Am.Ac. | 85.3 | alpha-KGA; SM C24:1; SM (OH) C14:1; Ala |
| 652 | 3 | S.L./Am.Ac. | 81.6 | SM (OH) C16:1; Gln; Tyr |
| 653 | 3 | S.L./Am.Ac./B.Am. | 87.6 | SM (OH) C24:1; Lys; Met-SO |
| 654 | 4 | Am.Ac./B.Am. | 89.2 | Gln; Lys; Met; Ac-Orn |
| 655 | 4 | En.Met/S.L./Am.Ac./B.Am. | 85 | Pent-P; SM (OH) C14:1; Pro; Met-SO |
| 656 | 3 | S.L./Am.Ac. | 82.2 | SM C18:1; SM (OH) C22:2; Trp |
| 657 | 4 | En.Met/Am.Ac./B.Am. | 79.4 | Suc; Gln; Pro; Serotonin |
| 658 | 4 | S.L./Am.Ac./B.Am. | 83.1 | SM (OH) C16:1; SM (OH) C22:2; Asn; Orn |
| 659 | 5 | Am.Ac./O.St./P.G. | 88.1 | Gln; Orn; Tyr; 24S-OH-C; 8-iso-PGF2a |
| 660 | 4 | En.Met/S.L./Am.Ac. | 79.2 | H1; SM (OH) C14:1; Met; Phe |
| 661 | 4 | S.L./Am.Ac./B.Am. | 79.5 | SM (OH) C22:2; Met; Ac-Orn; Histamine |
| 662 | 6 | S.L./Am.Ac. | 85.9 | SM C16:1; SM C24:1; SM (OH) C14:1; Lys; Met; Kynurenine |
| 663 | 4 | En.Met/Am.Ac./P.G. | 82.9 | Lac; Arg; Gln; 8-iso-PGF2a |
| 664 | 5 | En.Met/S.L./Am.Ac./B.Am. | 90.7 | Suc; SM (OH) C22:2; Arg; Orn; Histamine |
| 665 | 4 | S.L./Am.Ac./O.St. | 79.7 | SM C16:1; SM (OH) C22:1; Gly; Cholestenone |
| 666 | 4 | S.L./Am.Ac. | 79.1 | SM C24:1; SM (OH) C16:1; SM (OH) C24:1; Tyr |
| 667 | 4 | S.L./Am.Ac. | 79.1 | SM C16:0; SM (OH) C22:1; Asn; Pro |
| 668 | 4 | S.L./Am.Ac./O.St. | 83.9 | SM (OH) C22:1; Gln; Phe; 20a-OH-C |
| 669 | 5 | En.Met/Ac.Ca./S.L./Am.Ac. | 86.4 | alpha-KGA; C5:1-DC; SM (OH) C14:1; SM (OH) C16:1; Orn |
| 670 | 4 | En.Met/S.L./Am.Ac./B.Am. | 87.6 | Lac; SM C18:0; Gln; Met-SO |
| 671 | 3 | S.L./Am.Ac. | 80 | SM (OH) C14:1; His; Tyr |
| 672 | 4 | Ac.Ca./S.L./Am.Ac. | 87.6 | C6:1; SM C24:1; SM (OH) C14:1; Ala |
| 673 | 4 | En.Met/S.L./B.Am./O.St. | 81 | alpha-KGA; SM (OH) C22:1; Ac-Orn; Cholestenone |
| 674 | 5 | Ac.Ca./S.L./Am.Ac./B.Am. | 84.5 | C18; C5:1-DC; SM (OH) C14:1; Arg; Histamine |
| 675 | 4 | En.Met/S.L./B.Am. | 79.5 | Lac; SM C18:0; SM (OH) C22:1; Met-SO |
| 676 | 5 | Ac.Ca./S.L./Am.Ac./B.Am. | 79.2 | C5:1-DC; SM C24:0; SM (OH) C16:1; Lys; Histamine |
| 677 | 4 | Ac.Ca./S.L./Am.Ac. | 86.7 | C6:1; SM C24:1; SM (OH) C14:1; Gly |
| 678 | 3 | S.L./Am.Ac. | 81.8 | SM C24:1; SM (OH) C14:1; Gly |
| 679 | 4 | S.L./Am.Ac./O.St. | 81.1 | SM C16:0; Met; Pro; 25-OH-C |
| 680 | 4 | Ac.Ca./S.L./Am.Ac./B.Am. | 82.9 | C5:1-DC; SM (OH) C14:1; Ile; Histamine |
| 681 | 4 | En.Met/S.L./Am.Ac. | 83.1 | Fum; SM C16:0; SM (OH) C24:1; Met |
| 682 | 3 | Ac.Ca./S.L./Am.Ac. | 81.2 | C6:1; SM C16:1; Pro |
| 683 | 5 | S.L./Am.Ac./O.St. | 87 | SM C16:1; SM (OH) C14:1; SM (OH) C22:1; Leu; 20a-OH-C |
| 684 | 5 | S.L./Am.Ac./P.G. | 83.8 | SM (OH) C14:1; SM (OH) C16:1; Asn; Orn; LTB4 |
| 685 | 4 | Ac.Ca./S.L./Am.Ac. | 80.1 | C18; SM (OH) C16:1; Phe; Pro |
| 686 | 3 | S.L./Am.Ac. | 82.4 | SM C24:1; SM (OH) C14:1; Arg |
| 687 | 4 | S.L./Am.Ac./B.Am. | 85.3 | SM C24:0; SM (OH) C14:1; Ala; Ac-Orn |
| 688 | 5 | S.L./Am.Ac./B.Am. | 87.3 | SM (OH) C14:1; Gln; His; Lys; Met-SO |
| 689 | 4 | En.Met/Ac.Ca./S.L./Am.Ac. | 81.3 | alpha-KGA; C6:1; SM C24:0; Tyr |
| 690 | 6 | S.L./Am.Ac./B.Am./P.G. | 89 | SM C24:0; SM C26:1; SM (OH) C14:1; Orn; Met-SO; LTB4 |
| 691 | 4 | S.L./Am.Ac./O.St. | 89.8 | SM C24:1; SM (OH) C22:1; Ala; Cholestenone |
| 692 | 5 | Ac.Ca./S.L./Am.Ac./O.St. | 88.7 | C5:1-DC; SM C16:1; Arg; Orn; 24-DH-Lanosterol |
| 693 | 4 | S.L./Am.Ac. | 85.7 | SM C16:1; SM C18:0; SM C24:0; Tyr |
| 694 | 4 | S.L./Am.Ac./B.Am. | 88.8 | SM (OH) C14:1; Pro; Trp; Met-SO |
| 695 | 4 | Ac.Ca./Am.Ac./B.Am./O.St. | 85 | C6:1; Trp; Met-SO; 24-DH-Lanosterol |
| 696 | 4 | Am.Ac./B.Am./O.St. | 82.4 | Lys; Trp; Ac-Orn; 24-DH-Lanosterol |
| 697 | 4 | S.L./B.Am. | 79.6 | SM C24:1; SM (OH) C22:2; Histamine; Met-SO |
| 698 | 3 | S.L./Am.Ac. | 81.6 | SM C18:0; Gln; Tyr |
| 699 | 4 | En.Met/Ac.Ca./Am.Ac. | 80.6 | alpha-KGA; Suc; C14:1; Pro |
| 700 | 3 | S.L./Am.Ac. | 80.1 | SM C18:1; SM (OH) C14:1; Ser |

TABLE 9-continued

Metabolite combinations describing damage of basal ganglia

| No. | Npar | Chemical Class | Accuracy | Model |
|---|---|---|---|---|
| 701 | 4 | S.L./B.Am. | 88.9 | SM C24:0; SM (OH) C22:2; Kynurenine; Met-SO |
| 702 | 3 | En.Met/Ac.Ca./S.L. | 81.3 | alpha-KGA; C5:1-DC; SM C16:0 |
| 703 | 4 | S.L./Am.Ac./B.Am. | 81.4 | SM C16:0; His; Lys; Met-SO |
| 704 | 4 | Ac.Ca./S.L./Am.Ac. | 80.2 | C10; SM C18:1; SM C24:1; Tyr |
| 705 | 4 | Ac.Ca./S.L./Am.Ac. | 85.6 | SM (OH) C14:1; Lys; Ac-Orn; Histamine |
| 706 | 5 | Ac.Ca./S.L./Am.Ac./P.G. | 79.9 | C10; SM C26:1; SM (OH) C22:1; Leu; TXB2 |
| 707 | 3 | Ac.Ca./S.L./B.Am. | 83.4 | C6:1; SM (OH) C22:1; Met-SO |
| 708 | 4 | En.Met/S.L./Am.Ac./O.St. | 79.3 | alpha-KGA; SM C16:1; Tyr; 25-OH-C |
| 709 | 5 | S.L./Am.Ac./B.Am. | 85.3 | SM C16:1; SM C18:1; SM (OH) C22:2; Arg; Ac-Orn |
| 710 | 4 | Ac.Ca./S.L. | 85.3 | C5:1-DC; C6:1; SM C18:1; SM (OH) C14:1 |
| 711 | 4 | S.L./B.Am. | 82.9 | SM C20:2; SM C24:0; SM (OH) C24:1; Met-SO |
| 712 | 5 | Ac.Ca./S.L./Am.Ac. | 79.7 | C14:1; C5:1-DC; SM C20:2; SM (OH) C16:1; Lys |
| 713 | 4 | Ac.Ca./S.L./Am.Ac. | 85.3 | C5:1-DC; C6:1; SM (OH) C14:1; Met |
| 714 | 3 | S.L./Am.Ac./B.Am. | 81 | SM (OH) C22:1; Orn; Ac-Orn |
| 715 | 3 | S.L./Am.Ac. | 80.9 | SM C16:0; SM C24:1; Arg |
| 716 | 3 | S.L./Am.Ac. | 82.8 | SM C18:1; SM (OH) C22:1; Tyr |
| 717 | 5 | Ac.Ca./S.L./Am.Ac. | 80.8 | C9; SM C16:1; SM C18:1; SM (OH) C14:1; Trp |
| 718 | 4 | S.L./Am.Ac./B.Am. | 84.6 | SM C16:1; Gln; Tyr; Ac-Orn |
| 719 | 4 | S.L./Am.Ac. | 79.4 | SM (OH) C14:1; SM (OH) C16:1; Phe; Pro |
| 720 | 4 | S.L./Am.Ac./B.Am. | 86.8 | SM (OH) C22:1; His; Tyr; Kynurenine |
| 721 | 4 | En.Met/S.L./Am.Ac./O.St. | 87.9 | Fum; SM (OH) C22:2; Leu; 20a-OH-C |
| 722 | 5 | S.L./Am.Ac./B.Am. | 79.5 | SM C16:0; SM (OH) C16:1; Gln; Phe; Ac-Orn |
| 723 | 3 | S.L./B.Am. | 79.4 | SM C16:1; SM (OH) C14:1; Met-SO |
| 724 | 4 | S.L./Am.Ac./O.St. | 82.6 | SM C24:1; SM (OH) C22:1; Gly; Cholestenone |
| 725 | 4 | Ac.Ca./S.L./Am.Ac. | 84.8 | C5:1-DC; C6:1; SM C16:0; Gln |
| 726 | 4 | S.L./Am.Ac. | 81.3 | SM C18:0; SM (OH) C14:1; SM (OH) C22:2; Tyr |
| 727 | 5 | Ac.Ca./S.L./Am.Ac./O.St. | 79.2 | C14:1; SM C24:0; Lys; Tyr; 20a-OH-C |
| 728 | 4 | S.L./Am.Ac./B.Am. | 84.9 | SM (OH) C22:1; SM (OH) C22:2; Met; Kynurenine |
| 729 | 4 | En.Met/Ac.Ca./Am.Ac. | 80.4 | Lac; C18; Arg; Tyr |
| 730 | 4 | S.L./Am.Ac. | 88.2 | SM (OH) C22:2; Met; Orn; Trp |
| 731 | 4 | Am.Ac./O.St./P.G. | 83.3 | Pro; Trp; 24-DH-Lanosterol; LTB4 |
| 732 | 4 | S.L./Am.Ac. | 83.1 | SM C24:0; SM (OH) C24:1; Arg; Met |
| 733 | 3 | S.L./Am.Ac. | 79.7 | SM (OH) C14:1; Pro; Trp |
| 734 | 4 | En.Met/S.L./B.Am./O.St. | 80.8 | alpha-KGA; SM C16:0; Met-SO; Cholestenone |
| 735 | 5 | S.L./Am.Ac./B.Am. | 82.7 | SM (OH) C16:1; SM (OH) C24:1; Gln; Tyr; Ac-Orn |
| 736 | 4 | S.L./Am.Ac. | 80.3 | SM C16:0; SM C24:1; SM (OH) C14:1; Gly |
| 737 | 5 | S.L./Am.Ac. | 85.2 | SM C16:0; SM C18:0; SM (OH) C16:1; Trp; Tyr |
| 738 | 4 | S.L./Am.Ac./B.Am. | 83.7 | SM C24:0; Leu; Tyr; Kynurenine |
| 739 | 4 | S.L./Am.Ac./B.Am./O.St. | 82 | SM (OH) C24:1; Lys; Met-SO; 24S-OH-C |
| 740 | 3 | Ac.Ca./S.L./Am.Ac. | 84.2 | C5:1-DC; SM C16:1; Ile |
| 741 | 5 | S.L./Am.Ac./B.Am. | 83 | SM C18:1; SM C24:1; Lys; Kynurenine; Met-SO |
| 742 | 4 | Ac.Ca./S.L./Am.Ac. | 85.4 | C5:1-DC; SM C16:0; SM C24:1; Lys |
| 743 | 4 | En.Met/S.L./B.Am. | 79.8 | Lac; SM C16:1; SM (OH) C22:1; Ac-Orn |
| 744 | 4 | En.Met/S.L./Am.Ac./B.Am. | 81.3 | alpha-KGA; SM C24:1; Gln; Met-SO |
| 745 | 4 | En.Met/S.L./Am.Ac./O.St. | 79.3 | alpha-KGA; SM (OH) C22:1; Trp; 24-DH-Lanosterol |
| 746 | 4 | S.L./Am.Ac./P.G. | 91.3 | SM C26:1; SM (OH) C14:1; Pro; TXB2 |
| 747 | 4 | S.L./Am.Ac./B.Am. | 80.5 | SM C18:0; SM (OH) C24:1; Trp; Met-SO |
| 748 | 4 | S.L./Am.Ac. | 80.3 | SM C20:2; SM C26:1; SM (OH) C16:1; Tyr |
| 749 | 4 | S.L./Am.Ac./O.St. | 84.8 | SM C16:1; SM (OH) C22:2; His; 20a-OH-C |
| 750 | 4 | S.L./Am.Ac. | 82.3 | SM C16:1; Met; Orn; Trp |
| 751 | 3 | Am.Ac./B.Am. | 81.7 | His; Lys; Met-SO |
| 752 | 4 | S.L./B.Am. | 83.3 | SM C24:0; SM (OH) C22:2; Ac-Orn; Histamine |
| 753 | 4 | En.Met/Ac.Ca./S.L./Am.Ac. | 86.9 | Suc; C6:1; SM (OH) C24:1; Tyr |
| 754 | 4 | S.L./Am.Ac./B.Am. | 79 | SM C20:2; SM (OH) C22:1; Leu; Histamine |
| 755 | 4 | En.Met/S.L./Am.Ac. | 84.9 | Fum; SM C16:1; SM (OH) C14:1; Met |
| 756 | 3 | En.Met/S.L./Am.Ac. | 82.8 | Lac; SM (OH) C22:2; Gln |
| 757 | 4 | S.L./Am.Ac./B.Am. | 79.5 | SM C16:1; Ile; Pro; Histamine |
| 758 | 4 | S.L./Am.Ac. | 81.5 | SM C24:0; SM C24:1; Met; Val |
| 759 | 4 | S.L./Am.Ac./B.Am. | 81.6 | SM (OH) C16:1; SM (OH) C22:2; Gln; Met-SO |
| 760 | 4 | S.L./Am.Ac./P.G. | 88.6 | SM C18:1; Orn; Trp; 8-iso-PGF2a |
| 761 | 4 | En.Met/S.L./P.G. | 85.9 | alpha-KGA; SM C24:0; SM (OH) C22:2; TXB2 |
| 762 | 4 | Am.Ac./O.St. | 82.4 | His; Met; Orn; 24-DH-Lanosterol |
| 763 | 4 | S.L./Am.Ac./O.St. | 82.7 | SM C16:0; SM (OH) C24:1; Pro; 22R-OH-C |
| 764 | 4 | S.L./Am.Ac./B.Am. | 83.4 | SM (OH) C14:1; His; Pro; Ac-Orn |
| 765 | 4 | En.Met/S.L./Am.Ac. | 79.4 | Fum; SM C16:0; SM C24:1; Met |
| 766 | 5 | En.Met/S.L./Am.Ac. | 88.1 | Suc; SM C16:0; SM (OH) C14:1; Orn; Tyr |
| 767 | 4 | S.L./Am.Ac./P.G. | 82.8 | SM (OH) C22:1; Gln; Lys; TXB2 |
| 768 | 4 | En.Met/S.L./Am.Ac. | 86.3 | Suc; SM (OH) C22:2; Orn; Pro |
| 769 | 3 | S.L./Am.Ac. | 84 | SM C24:0; SM C24:1; Ala |
| 770 | 4 | En.Met/S.L./Am.Ac./B.Am. | 79.3 | alpha-KGA; SM (OH) C24:1; Pro; Ac-Orn |
| 771 | 3 | S.L./Am.Ac. | 82 | SM C16:1; SM (OH) C22:2; Ser |
| 772 | 4 | S.L./Am.Ac./B.Am./O.St. | 85.7 | SM (OH) C22:1; Pro; Met-SO; Cholestenone |
| 773 | 4 | Ac.Ca./S.L. | 90.7 | C5:1-DC; C6:1; SM C16:0; SM (OH) C14:1 |
| 774 | 4 | Ac.Ca./S.L./Am.Ac. | 79.3 | C14:1; SM C18:0; SM (OH) C22:2; Ala |
| 775 | 4 | S.L./Am.Ac./B.Am. | 84.5 | SM C24:1; Lys; Met; Ac-Orn |
| 776 | 4 | En.Met/S.L./Am.Ac. | 84.2 | Suc; SM (OH) C22:2; Arg; Orn |

TABLE 9-continued

Metabolite combinations describing damage of basal ganglia

| No. | Npar | Chemical Class | Accuracy | Model |
|---|---|---|---|---|
| 777 | 4 | S.L./Am.Ac./O.St. | 83.3 | SM C16:1; Met; Trp; Cholestenone |
| 778 | 5 | S.L./Am.Ac./P.G. | 89.5 | SM (OH) C16:1; His; Lys; Orn; TXB2 |
| 779 | 3 | S.L./Am.Ac. | 85 | SM C24:1; SM (OH) C14:1; Pro |
| 780 | 4 | En.Met/S.L./Am.Ac. | 86 | alpha-KGA; SM (OH) C14:1; Arg; Met |
| 781 | 4 | S.L./B.Am. | 83.4 | SM C16:1; SM (OH) C22:1; SM (OH) C22:2; Met-SO |
| 782 | 4 | En.Met/S.L./Am.Ac. | 82 | alpha-KGA; SM C16:1; Met; Phe |
| 783 | 4 | Ac.Ca./S.L./Am.Ac. | 86 | C5:1-DC; SM C16:1; Arg; Orn |
| 784 | 4 | En.Met/S.L./Am.Ac. | 83.8 | Lac; SM C16:1; SM (OH) C16:1; Tyr |
| 785 | 3 | S.L./Am.Ac./B.Am. | 81.6 | SM (OH) C22:2; Lys; Met-SO |
| 786 | 4 | S.L./Am.Ac./P.G. | 80 | SM C18:1; SM C24:0; Met; LTB4 |
| 787 | 4 | S.L./Am.Ac. | 83.6 | SM C16:0; SM C20:2; SM (OH) C14:1; Ala |
| 788 | 5 | Ac.Ca./S.L./Am.Ac./O.St. | 90.2 | C5:1-DC; C6:1; SM C24:0; Orn; 24-DH-Lanosterol |
| 789 | 6 | En.Met/S.L./Am.Ac./O.St. | 96.2 | Fum; SM C16:1; SM C26:1; His; Tyr; 20a-OH-C |
| 790 | 3 | S.L./Am.Ac. | 87.6 | SM C16:1; SM (OH) C22:2; Gly |
| 791 | 6 | S.L./Am.Ac. | 81.4 | SM C16:0; His; Leu; Lys; Met; Pro |
| 792 | 3 | S.L./Am.Ac. | 81.8 | SM (OH) C22:2; Arg; Gln |
| 793 | 4 | En.Met/S.L./Am.Ac. | 80.1 | Lac; SM C24:1; Met; Pro |
| 794 | 4 | En.Met/S.L./Am.Ac. | 81.4 | Hex-P; SM C16:1; His; Met |
| 795 | 4 | S.L./Am.Ac. | 82.7 | SM C16:0; SM (OH) C14:1; Pro; Tyr |
| 796 | 3 | S.L./Am.Ac. | 79 | SM (OH) C14:1; SM (OH) C22:1; Gly |
| 797 | 4 | Ac.Ca./S.L./Am.Ac./B.Am. | 87.3 | C14:1; SM (OH) C16:1; Tyr; Kynurenine |
| 798 | 5 | S.L./Am.Ac./O.St. | 91.2 | SM (OH) C22:2; Arg; Met; Trp; 24-DH-Lanosterol |
| 799 | 4 | S.L./B.Am./O.St. | 80 | SM (OH) C16:1; SM (OH) C22:2; Histamine; 20a-OH-C |
| 800 | 4 | Am.Ac. | 80.5 | Gln; Pro; Tyr; Val |
| 801 | 3 | S.L./Am.Ac. | 87 | SM (OH) C22:2; Lys; Met |
| 802 | 4 | S.L./Am.Ac. | 84.7 | SM C24:0; SM (OH) C14:1; Met; Orn |
| 803 | 4 | En.Met/Ac.Ca./S.L./O.St. | 79.2 | alpha-KGA; C14:1; SM C18:0; 20a-OH-C |
| 804 | 4 | S.L./Am.Ac. | 82.3 | SM C20:2; SM C24:1; SM (OH) C16:1; Tyr |
| 805 | 5 | S.L./Am.Ac./B.Am./P.G. | 82.5 | SM (OH) C22:1; SM (OH) C22:2; His; Histamine; TXB2 |
| 806 | 5 | S.L./Am.Ac./O.St. | 85.3 | SM (OH) C16:1; SM (OH) C22:2; SM (OH) C24:1; Ala; 20a-OH-C |
| 807 | 4 | Ac.Ca./S.L./B.Am. | 85.4 | C5:1-DC; SM (OH) C14:1; SM (OH) C16:1; Histamine |
| 808 | 5 | S.L./Am.Ac./B.Am./O.St. | 82.2 | SM C24:1; His; Kynurenine; total DMA; Cholestenone |
| 809 | 4 | S.L./Am.Ac./P.G. | 80.4 | SM C26:1; SM (OH) C22:1; Tyr; LTB4 |
| 810 | 4 | S.L./Am.Ac. | 82.3 | SM C16:0; SM (OH) C14:1; Met; Tyr |
| 811 | 4 | S.L./Am.Ac./B.Am. | 79.4 | SM C18:0; SM C18:1; Gln; Ac-Orn |
| 812 | 4 | En.Met/S.L./Am.Ac. | 85.3 | alpha-KGA; SM C24:0; SM C24:1; Tyr |
| 813 | 3 | S.L./Am.Ac./B.Am. | 80 | SM (OH) C22:1; Arg; Ac-Orn |
| 814 | 4 | En.Met/S.L./Am.Ac. | 79.3 | Lac; SM (OH) C24:1; His; Met |
| 815 | 4 | En.Met/S.L./Am.Ac. | 86.9 | Suc; SM (OH) C14:1; Orn; Tyr |
| 816 | 6 | S.L./Am.Ac./B.Am./O.St. | 87.3 | SM (OH) C14:1; SM (OH) C24:1; Pro; Tyr; Histamine; 22R-OH-C |
| 817 | 4 | S.L./Am.Ac. | 87.5 | SM C16:0; SM C24:1; SM (OH) C22:2; Gly |
| 818 | 5 | S.L./Am.Ac. | 83.1 | SM C24:0; SM (OH) C14:1; SM (OH) C24:1; Lys; Met |
| 819 | 3 | S.L./Am.Ac. | 86.6 | SM C18:1; SM C24:0; Tyr |
| 820 | 3 | En.Met/S.L./Am.Ac. | 84.7 | Fum; SM C16:1; Met |
| 821 | 4 | S.L./Am.Ac./B.Am. | 79 | SM C18:0; SM (OH) C22:2; Trp; Met-SO |
| 822 | 4 | S.L./Am.Ac. | 82.2 | SM C16:0; SM (OH) C14:1; Phe; Pro |
| 823 | 4 | En.Met/S.L./Am.Ac. | 82.6 | alpha-KGA; Suc; SM (OH) C22:2; Orn |
| 824 | 4 | S.L./Am.Ac./B.Am. | 89 | SM (OH) C14:1; His; Orn; Met-SO |
| 825 | 4 | S.L./Am.Ac. | 84.1 | SM (OH) C22:1; Arg; Met; Orn |
| 826 | 4 | S.L./Am.Ac. | 83.6 | SM (OH) C16:1; SM (OH) C22:2; SM (OH) C24:1; Gly |
| 827 | 5 | Ac.Ca./S.L./Am.Ac./O.St. | 89 | C14:1; SM (OH) C16:1; SM (OH) C22:1; Pro; 20a-OH-C |
| 828 | 4 | S.L./Am.Ac./O.St. | 85.8 | SM (OH) C22:2; SM (OH) C24:1; Orn; 20a-OH-C |
| 829 | 5 | S.L./Am.Ac./B.Am. | 84.3 | SM C18:1; SM (OH) C14:1; SM (OH) C24:1; Ala; Ac-Orn |
| 830 | 4 | S.L./Am.Ac./B.Am. | 84.6 | SM C18:1; SM (OH) C22:1; Trp; Met-SO |
| 831 | 4 | S.L./Am.Ac. | 82.2 | SM (OH) C22:1; His; Met; Tyr |
| 832 | 5 | Ac.Ca./S.L./Am.Ac./O.St. | 80.3 | C14:1; SM C16:0; SM C18:1; Leu; 20a-OH-C |
| 833 | 4 | Ac.Ca./S.L./B.Am. | 79.1 | C5:1-DC; SM (OH) C16:1; SM (OH) C24:1; alpha-AAA |
| 834 | 4 | Ac.Ca./Am.Ac. | 81 | C14:1; Met; Pro; Tyr |
| 835 | 4 | En.Met/S.L./Am.Ac./O.St. | 82.3 | Lac; SM (OH) C14:1; Met; 24-DH-Lanosterol |
| 836 | 4 | S.L./Am.Ac./B.Am. | 81.7 | SM (OH) C22:2; Gln; Pro; Histamine |
| 837 | 4 | En.Met/S.L./Am.Ac./B.Am. | 87.6 | alpha-KGA; SM C16:1; Trp; Met-SO |
| 838 | 3 | S.L./Am.Ac./O.St. | 83.5 | SM (OH) C14:1; Leu; 20a-OH-C |
| 839 | 4 | S.L./Am.Ac./B.Am./O.St. | 80.8 | SM C24:0; Lys; Ac-Orn; Cholestenone |
| 840 | 3 | S.L./Am.Ac. | 79.8 | SM C18:0; SM C24:0; Phe |
| 841 | 4 | S.L./Am.Ac. | 83.8 | SM (OH) C14:1; Arg; Met; Tyr |
| 842 | 4 | En.Met/S.L./Am.Ac. | 87.6 | Lac; SM C18:1; Gln; Tyr |
| 843 | 6 | S.L./Am.Ac./B.Am. | 83 | SM C18:0; SM C24:1; SM (OH) C14:1; Orn; Phe; Ac-Orn |
| 844 | 5 | Ac.Ca./S.L./Am.Ac. | 83 | C14:1; SM C18:0; SM (OH) C14:1; Phe; Pro |
| 845 | 4 | En.Met/S.L./B.Am. | 80.3 | alpha-KGA; H1; SM C16:0; Met-SO |
| 846 | 4 | S.L./Am.Ac./B.Am. | 88.9 | SM (OH) C22:1; SM (OH) C24:1; Trp; Met-SO |
| 847 | 3 | S.L./Am.Ac./B.Am. | 80.7 | SM C16:1; Gln; Met-SO |
| 848 | 4 | S.L./Am.Ac./O.St. | 87.6 | SM (OH) C22:2; SM (OH) C24:1; Leu; 20a-OH-C |
| 849 | 4 | S.L./Am.Ac./P.G. | 93.2 | SM (OH) C22:2; SM (OH) C24:1; Pro; TXB2 |
| 850 | 5 | En.Met/Ac.Ca./S.L. | 79.5 | Lac; C14:1-OH; C9; SM C18:1; SM (OH) C16:1 |
| 851 | 4 | En.Met/Am.Ac. | 79.1 | alpha-KGA; Fum; His; Met |
| 852 | 4 | S.L./Am.Ac./O.St. | 87.8 | SM (OH) C14:1; SM (OH) C22:2; Gly; Cholestenone |

TABLE 9-continued

Metabolite combinations describing damage of basal ganglia

| No. | Npar | Chemical Class | Accuracy | Model |
|---|---|---|---|---|
| 853 | 4 | En.Met/S.L./Am.Ac. | 85.4 | Fum; SM C16:1; SM (OH) C22:1; Met |
| 854 | 4 | S.L./Am.Ac./B.Am. | 81.3 | SM C16:1; SM C24:0; Leu; Met-SO |
| 855 | 3 | S.L./Am.Ac. | 85.5 | SM C16:1; SM C20:2; Tyr |
| 856 | 4 | S.L./Am.Ac./B.Am. | 79.1 | SM C24:1; Lys; Val; Ac-Orn |
| 857 | 4 | Ac.Ca./S.L./B.Am. | 82.7 | C5:1-DC; SM C18:1; SM (OH) C22:2; Histamine |
| 858 | 4 | Ac.Ca./S.L./P.G. | 82 | C5:1-DC; SM (OH) C14:1; SM (OH) C22:2; LTB4 |
| 859 | 4 | S.L./B.Am./O.St. | 83 | SM (OH) C14:1; Ac-Orn; Histamine; 25-OH-C |
| 860 | 4 | S.L./Am.Ac. | 85.8 | SM C16:1; SM C18:1; SM C24:1; Gly |
| 861 | 4 | S.L./Am.Ac./B.Am. | 80.3 | SM (OH) C16:1; Gln; Histamine; Met-SO |
| 862 | 4 | S.L./Am.Ac./B.Am. | 86.5 | SM (OH) C14:1; SM (OH) C24:1; Orn; Met-SO |
| 863 | 3 | En.Met/Ac.Ca./S.L. | 82.5 | alpha-KGA; C5:1-DC; SM (OH) C14:1 |
| 864 | 4 | En.Met/S.L./B.Am./O.St. | 80.3 | Lac; SM C24:0; Met-SO; Cholestenone |
| 865 | 4 | Ac.Ca./S.L./Am.Ac. | 86.9 | C14:1; SM C18:0; Met; Pro |
| 866 | 5 | S.L./Am.Ac./B.Am./P.G. | 86.9 | SM C24:0; SM (OH) C22:1; Pro; Ac-Orn; LTB4 |
| 867 | 3 | S.L./B.Am. | 80.5 | SM C16:1; SM (OH) C24:1; Met-SO |
| 868 | 4 | S.L./Am.Ac. | 86.6 | SM C24:0; SM (OH) C22:1; Arg; Met |
| 869 | 4 | S.L./Am.Ac./B.Am. | 79.7 | SM C24:1; SM (OH) C24:1; Arg; Met-SO |
| 870 | 4 | Ac.Ca./S.L./B.Am. | 79.5 | C14:1; SM C24:0; alpha-AAA; Met-SO |
| 871 | 5 | En.Met/Ac.Ca./Am.Ac. | 84.1 | alpha-KGA; Lac; C18:2; His; Tyr |
| 872 | 4 | S.L./Am.Ac./O.St. | 86 | SM C18:1; SM (OH) C14:1; Gly; Cholestenone |
| 873 | 4 | S.L./Am.Ac./O.St. | 84.5 | SM (OH) C22:2; His; Val; 20a-OH-C |
| 874 | 4 | En.Met/Ac.Ca./S.L./Am.Ac. | 80 | alpha-KGA; C14:1; SM C20:2; Tyr |
| 875 | 5 | S.L./Am.Ac./B.Am./O.St. | 88.1 | SM C16:0; SM (OH) C16:1; Trp; Met-SO; Cholestenone |
| 876 | 5 | S.L./Am.Ac./B.Am. | 86.1 | SM C16:1; SM (OH) C22:1; Gln; Creatinine; Met-SO |
| 877 | 6 | S.L./Am.Ac./P.G. | 90.8 | SM C24:1; SM C26:1; Leu; Lys; Pro; TXB2 |
| 878 | 3 | S.L./Am.Ac. | 80.1 | SM C16:0; SM C18:1; Gly |
| 879 | 5 | En.Met/S.L./Am.Ac./P.G. | 86.1 | alpha-KGA; SM C16:0; SM (OH) C16:1; Tyr; TXB2 |
| 880 | 4 | S.L./Am.Ac. | 83.2 | SM (OH) C22:2; SM (OH) C24:1; Met; Orn |
| 881 | 4 | Ac.Ca./S.L./B.Am. | 82.6 | C5:1-DC; SM (OH) C14:1; SM (OH) C16:1; Serotonin |
| 882 | 4 | S.L./Am.Ac. | 81.4 | SM C16:0; Gln; Phe; Pro |
| 883 | 4 | S.L./Am.Ac./P.G. | 80 | SM C16:0; SM (OH) C22:2; Pro; LTB4 |
| 884 | 4 | S.L./Am.Ac./P.G. | 84.1 | SM (OH) C14:1; Lys; Met; LTB4 |
| 885 | 3 | S.L./Am.Ac./B.Am. | 85.2 | SM C24:1; Lys; Met-SO |
| 886 | 4 | En.Met/S.L./Am.Ac. | 82 | alpha-KGA; SM C24:0; SM (OH) C22:2; Met |
| 887 | 5 | S.L./Am.Ac. | 88 | SM C16:1; SM C20:2; SM (OH) C16:1; Trp; Tyr |
| 888 | 4 | Ac.Ca./S.L. | 87.7 | C5:1-DC; SM C16:1; SM C18:1; SM C20:2 |
| 889 | 5 | S.L./Am.Ac./B.Am. | 87.4 | SM (OH) C14:1; SM (OH) C22:2; His; Orn; Met-SO |
| 890 | 4 | En.Met/S.L./Am.Ac. | 85.1 | Lac; SM (OH) C22:1; SM (OH) C24:1; Met |
| 891 | 4 | S.L./Am.Ac./O.St. | 81.1 | SM C16:1; SM C18:0; Tyr; Cholestenone |
| 892 | 4 | S.L./Am.Ac./P.G. | 84.3 | SM (OH) C22:1; SM (OH) C24:1; Phe; TXB2 |
| 893 | 5 | En.Met/Ac.Ca./S.L./Am.Ac./B.Am. | 79 | alpha-KGA; C18:1; SM C18:1; Trp; Met-SO |
| 894 | 4 | S.L./Am.Ac./B.Am./O.St. | 85.5 | SM C18:1; Gln; Met-SO; Cholestenone |
| 895 | 5 | S.L./Am.Ac./P.G. | 85.1 | SM C24:1; SM (OH) C14:1; Trp; Tyr; LTB4 |
| 896 | 4 | Ac.Ca./Am.Ac./O.St. | 85.3 | C14:1; Met; Pro; 24-DH-Lanosterol |
| 897 | 4 | En.Met/S.L./Am.Ac. | 81.5 | alpha-KGA; SM C24:0; SM C24:1; Ala |
| 898 | 3 | Ac.Ca./S.L. | 88.7 | C5:1-DC; SM C16:1; SM (OH) C14:1 |
| 899 | 4 | S.L./Am.Ac. | 86.6 | SM C24:1; SM C22:1; Arg; Tyr |
| 900 | 4 | En.Met/S.L./Am.Ac. | 82.2 | alpha-KGA; Fum; SM (OH) C24:1; Met |
| 901 | 4 | S.L./Am.Ac./B.Am. | 79.8 | SM (OH) C16:1; SM (OH) C22:1; Met; Creatinine |
| 902 | 5 | Ac.Ca./S.L./Am.Ac./O.St. | 85.6 | C5:1-DC; SM C16:1; SM C24:1; Tyr; Cholestenone |
| 903 | 3 | Ac.Ca./S.L. | 90.9 | C5:1-DC; C6:1; SM (OH) C14:1 |
| 904 | 4 | Ac.Ca./S.L./Am.Ac. | 82.6 | C5:1-DC; SM C18:1; SM (OH) C22:2; Gln |
| 905 | 4 | S.L./Am.Ac. | 82 | SM (OH) C22:2; SM (OH) C24:1; Arg; Met |
| 906 | 4 | S.L./Am.Ac. | 92.2 | SM C16:1; SM C18:1; SM (OH) C22:2; Gly |
| 907 | 4 | S.L./Am.Ac./B.Am./O.St. | 87 | SM (OH) C14:1; Trp; Met-SO; 24-DH-Lanosterol |
| 908 | 6 | S.L./Am.Ac./O.St. | 90.6 | SM C24:1; SM (OH) C22:2; SM (OH) C24:1; Pro; Tyr; 20a-OH-C |
| 909 | 4 | S.L./Am.Ac. | 85.4 | SM C24:1; SM (OH) C14:1; SM (OH) C16:1; Ala |
| 910 | 4 | Am.Ac./P.G. | 87.2 | Gln; Orn; Phe; LTB4 |
| 911 | 4 | En.Met/S.L./Am.Ac. | 85 | Lac; SM (OH) C14:1; His; Met |
| 912 | 3 | Ac.Ca./S.L./Am.Ac. | 79.9 | C5:1-DC; SM C16:1; Gln |
| 913 | 4 | En.Met/S.L./Am.Ac. | 84.3 | Lac; SM (OH) C16:1; Gln; Phe |
| 914 | 4 | Ac.Ca./S.L./Am.Ac./B.Am. | 84.1 | C5:1-DC; SM (OH) C14:1; Gln; alpha-AAA |
| 915 | 4 | S.L./Am.Ac./B.Am. | 83.3 | SM (OH) C14:1; SM (OH) C22:2; Arg; Met-SO |
| 916 | 6 | En.Met/S.L./Am.Ac. | 82.8 | Lac; Suc; SM C16:1; SM (OH) C22:1; SM (OH) C22:2; Thr |
| 917 | 4 | Ac.Ca./S.L./B.Am./O.St. | 79.5 | C6:1; SM C16:1; Ac-Orn; 25-OH-C |
| 918 | 4 | En.Met/S.L./Am.Ac./B.Am. | 83.4 | alpha-KGA; SM (OH) C14:1; Arg; Met-SO |
| 919 | 4 | S.L./Am.Ac./P.G. | 81.2 | SM C24:1; Arg; Tyr; LTB4 |
| 920 | 3 | En.Met/S.L./Am.Ac. | 92 | OAA; SM (OH) C22:2; Gly |
| 921 | 4 | S.L./Am.Ac. | 83.9 | SM C16:1; SM (OH) C14:1; Met; Orn |
| 922 | 6 | S.L./Am.Ac./B.Am./O.St. | 81.6 | SM C16:0; SM C18:0; SM C18:1; Lys; Met-SO; Desmosterol |
| 923 | 4 | Ac.Ca./S.L./O.St. | 84.2 | C5:1-DC; SM (OH) C14:1; SM (OH) C22:2; 25-OH-C |
| 924 | 4 | S.L./Am.Ac./O.St. | 84.9 | SM C24:0; Arg; Met; 25-OH-C |
| 925 | 5 | En.Met/S.L./Am.Ac. | 82.4 | H1; SM C16:1; SM (OH) C14:1; Ala; Gln |
| 926 | 3 | S.L./Am.Ac./B.Am. | 82 | SM C24:0; Gln; Met-SO |
| 927 | 4 | Am.Ac./O.St. | 86.4 | Gln; Pro; 25-OH-C; Cholestenone |
| 928 | 5 | S.L./Am.Ac./B.Am. | 84.2 | SM C18:1; SM C24:0; Met; Orn; Ac-Orn |

TABLE 9-continued

Metabolite combinations describing damage of basal ganglia

| No. | Npar | Chemical Class | Accuracy | Model |
|---|---|---|---|---|
| 929 | 4 | S.L./Am.Ac./B.Am. | 81.3 | SM C18:0; SM C24:0; Arg; Met-SO |
| 930 | 4 | S.L./Am.Ac. | 88 | SM C16:1; SM C20:2; Pro; Tyr |
| 931 | 4 | S.L./B.Am. | 82.5 | SM (OH) C16:1; SM (OH) C22:1; Histamine; Met-SO |
| 932 | 4 | S.L./Am.Ac. | 82.7 | OAA; SM C26:1; SM (OH) C22:2; Gly |
| 933 | 5 | En.Met/S.L./B.Am. | 84 | Lac; SM C16:1; SM (OH) C14:1; SM (OH) C16:1; Met-SO |
| 934 | 5 | S.L./Am.Ac./B.Am. | 80.5 | SM C20:2; SM C24:0; Orn; Phe; Ac-Orn |
| 935 | 4 | S.L./Am.Ac./P.G. | 79.6 | SM (OH) C14:1; SM (OH) C22:2; Tyr; LTB4 |
| 936 | 4 | Am.Ac. | 83.3 | Gln; Leu; Met; Pro |
| 937 | 5 | S.L./Am.Ac./O.St. | 87.2 | SM C18:0; SM (OH) C16:1; Orn; Trp; 24-DH-Lanosterol |
| 938 | 4 | S.L./Am.Ac./B.Am. | 81.1 | SM (OH) C22:1; SM (OH) C24:1; Met; Creatinine |
| 939 | 4 | En.Met/S.L./Am.Ac. | 89.2 | Suc; SM (OH) C22:1; Met; Orn |
| 940 | 4 | S.L./Am.Ac./B.Am. | 84.6 | SM (OH) C14:1; SM (OH) C22:2; Orn; Ac-Orn |
| 941 | 4 | S.L./Am.Ac./O.St. | 79.2 | SM C18:1; SM (OH) C14:1; Asn; Cholestenone |
| 942 | 4 | S.L./Am.Ac./B.Am. | 85.4 | SM C20:2; SM (OH) C22:1; Gln; Met-SO |
| 943 | 5 | S.L./Am.Ac./B.Am./O.St. | 89.5 | SM (OH) C22:2; Arg; Gln; Ac-Orn; Cholestenone |
| 944 | 4 | En.Met/S.L./Am.Ac. | 82.5 | Lac; SM C24:0; SM (OH) C22:2; Phe |
| 945 | 4 | S.L./B.Am. | 81.9 | SM C24:0; SM (OH) C22:2; SM (OH) C24:1; Met-SO |
| 946 | 4 | En.Met/S.L./Am.Ac. | 80.1 | Lac; SM C16:0; Phe; Tyr |
| 947 | 4 | S.L./Am.Ac. | 82.6 | SM C20:2; SM (OH) C22:2; Orn; Tyr |
| 948 | 4 | S.L./Am.Ac. | 81.5 | SM (OH) C16:1; Arg; Gln; Tyr |
| 949 | 3 | S.L./Am.Ac. | 84.8 | SM (OH) C22:1; SM (OH) C22:2; Tyr |
| 950 | 4 | S.L./Am.Ac./B.Am./O.St. | 85.6 | SM C16:0; Tyr; Creatinine; 24-DH-Lanosterol |
| 951 | 5 | Ac.Ca./S.L./Am.Ac./O.St. | 80.7 | C14:1; SM C16:1; SM C18:0; Leu; 20a-OH-C |
| 952 | 4 | S.L./Am.Ac. | 80.2 | SM C18:0; SM C24:1; SM (OH) C22:2; Orn |
| 953 | 4 | S.L./Am.Ac./B.Am./O.St. | 83.9 | SM C24:1; Trp; Met-SO; Cholestenone |
| 954 | 3 | S.L./Am.Ac. | 79.3 | SM C18:1; Gln; Phe |
| 955 | 4 | En.Met/S.L./Am.Ac./O.St. | 81.6 | alpha-KGA; SM (OH) C14:1; Met; Cholestenone |
| 956 | 4 | S.L./Am.Ac. | 84.5 | SM (OH) C22:2; SM (OH) C24:1; Gly; Met |
| 957 | 3 | Am.Ac./O.St. | 86.4 | Pro; Trp; Cholestenone |
| 958 | 4 | S.L./Am.Ac./O.St. | 81.1 | SM C24:1; Arg; His; 24-DH-Lanosterol |
| 959 | 4 | En.Met/S.L./Am.Ac./B.Am. | 84.5 | Fum; SM C24:0; Pro; Met-SO |
| 960 | 4 | S.L./Am.Ac./B.Am. | 82.1 | SM (OH) C16:1; Arg; Gln; Met-SO |
| 961 | 6 | Ac.Ca./Am.Ac./B.Am./O.St. | 84.2 | C5:1-DC; Arg; Gln; Orn; Histamine; 24-DH-Lanosterol |
| 962 | 5 | S.L./Am.Ac. | 82.7 | SM C16:0; SM C16:1; His; Lys; Met |
| 963 | 3 | S.L./B.Am. | 83.8 | SM (OH) C14:1; SM (OH) C22:1; Met-SO |
| 964 | 3 | S.L./Am.Ac. | 81.3 | SM C24:0; Met; Tyr |
| 965 | 4 | En.Met/S.L./Am.Ac./P.G. | 95.4 | alpha-KGA; SM (OH) C22:2; Lys; TXB2 |
| 966 | 4 | S.L./Am.Ac./O.St. | 86 | SM C16:1; SM (OH) C14:1; Leu; 20a-OH-C |
| 967 | 5 | En.Met/S.L./Am.Ac./P.G. | 88.9 | Lac; SM (OH) C22:2; Gln; Tyr; LTB4 |
| 968 | 4 | Ac.Ca./S.L./Am.Ac. | 85.5 | C5:1; SM (OH) C22:1; SM (OH) C22:2; Met |
| 969 | 4 | S.L./Am.Ac. | 79.9 | SM (OH) C16:1; Met; Orn; Pro |
| 970 | 3 | S.L./Am.Ac. | 79.9 | SM C24:1; SM (OH) C24:1; Ala |
| 971 | 4 | Ac.Ca./S.L./Am.Ac. | 88.9 | C14:1; SM (OH) C22:1; Met; Pro |
| 972 | 4 | Ac.Ca./Am.Ac./B.Am. | 81.1 | C6:1; Gln; Trp; Met-SO |
| 973 | 4 | S.L./Am.Ac./P.G. | 84.1 | SM C16:1; SM (OH) C22:1; Orn; TXB2 |
| 974 | 4 | En.Met/S.L./Am.Ac./O.St. | 85.9 | Lac; SM C16:1; Met; Cholestenone |
| 975 | 6 | S.L./Am.Ac./B.Am. | 82.7 | SM C16:0; SM C24:1; Met; Histamine; Kynurenine; Met-SO |
| 976 | 5 | S.L./Am.Ac./O.St. | 82.1 | SM C16:0; SM (OH) C16:1; SM (OH) C22:2; Phe; 20a-OH-C |
| 977 | 4 | Ac.Ca./S.L./P.G. | 86.6 | C6:1; SM (OH) C22:1; SM (OH) C22:2; TXB2 |
| 978 | 4 | Ac.Ca./S.L. | 85.8 | C5:1-DC; C6:1; SM C16:1; SM C24:1 |
| 979 | 5 | En.Met/S.L./Am.Ac. | 81.3 | alpha-KGA; Suc; SM C24:1; SM (OH) C16:1; Orn |
| 980 | 4 | S.L./Am.Ac./B.Am. | 82.1 | SM C26:1; SM (OH) C14:1; Pro; Met-SO |
| 981 | 4 | S.L./Am.Ac./O.St. | 82.8 | SM C24:0; SM (OH) C22:2; Gly; Cholestenone |
| 982 | 4 | Am.Ac./B.Am. | 80.4 | Gln; Orn; Ac-Orn; Met-SO |
| 983 | 5 | S.L./Am.Ac./B.Am./P.G. | 89.4 | SM C16:0; Pro; Trp; Ac-Orn; LTB4 |
| 984 | 3 | S.L./Am.Ac./B.Am. | 80.3 | SM C24:0; Arg; Ac-Orn |
| 985 | 4 | Ac.Ca./S.L. | 82.3 | C14:1; C5:1-DC; C6:1; SM C18:1 |
| 986 | 4 | En.Met/S.L./Am.Ac. | 85 | Fum; SM (OH) C22:1; Met; Pro |
| 987 | 4 | S.L./Am.Ac. | 81.5 | SM C16:0; SM C24:1; Ala; Gln |
| 988 | 4 | En.Met/S.L./Am.Ac./B.Am. | 80.8 | Lac; SM C24:0; Met; Histamine |
| 989 | 4 | En.Met/S.L./Am.Ac. | 83.9 | Lac; SM (OH) C14:1; SM (OH) C16:1; Met |
| 990 | 4 | S.L./B.Am. | 79.1 | SM C20:2; SM C24:1; SM (OH) C22:1; Met-SO |
| 991 | 3 | En.Met/Am.Ac./B.Am. | 81.7 | Suc; Pro; Histamine |
| 992 | 4 | En.Met/S.L./Am.Ac. | 83.7 | Lac; SM C16:0; SM (OH) C24:1; Met |
| 993 | 4 | Ac.Ca./S.L./B.Am. | 87.4 | C5:1-DC; SM (OH) C22:2; Ac-Orn; Histamine |
| 994 | 4 | En.Met/Ac.Ca./S.L./Am.Ac. | 80.7 | Lac; C14:1; SM (OH) C16:1; Met |
| 995 | 4 | Ac.Ca./S.L./Am.Ac. | 82.1 | C14:1-OH; SM C18:1; Met; Pro |
| 996 | 4 | En.Met/S.L./B.Am. | 83.3 | Fum; Lac; SM (OH) C22:1; Met-SO |
| 997 | 5 | S.L./Am.Ac./O.St. | 92.3 | SM C24:0; SM (OH) C16:1; SM (OH) C24:1; Tyr; 20a-OH-C |
| 998 | 4 | En.Met/S.L./Am.Ac. | 87.9 | Lac; SM (OH) C16:1; Gln; Tyr |
| 999 | 4 | En.Met/S.L./B.Am. | 83.4 | alpha-KGA; Lac; SM (OH) C22:1; Met-SO |
| 1000 | 4 | S.L./Am.Ac. | 84.7 | SM C20:2; SM (OH) C16:1; Gln; Tyr |
| 1001 | 4 | S.L./Am.Ac. | 85.1 | SM (OH) C22:1; SM (OH) C22:2; Arg; Met |
| 1002 | 4 | S.L./B.Am. | 89.1 | SM C24:0; SM (OH) C22:1; Kynurenine; Met-SO |
| 1003 | 4 | S.L./Am.Ac./P.G. | 80.3 | SM (OH) C16:1; Trp; Tyr; LTB4 |
| 1004 | 4 | En.Met/Ac.Ca./B.Am. | 84.6 | Suc; C6:1; Ac-Orn; Histamine |

TABLE 9-continued

Metabolite combinations describing damage of basal ganglia

| No. | Npar | Chemical Class | Accuracy | Model |
|---|---|---|---|---|
| 1005 | 5 | S.L./Am.Ac./B.Am. | 89.5 | SM C24:1; SM (OH) C22:1; Ala; Orn; Ac-Orn |
| 1006 | 4 | En.Met/S.L./B.Am. | 80 | Lac; SM C18:1; SM (OH) C22:1; Met-SO |
| 1007 | 4 | S.L./Am.Ac./O.St. | 85.8 | SM (OH) C22:2; Gln; Pro; Cholestenone |
| 1008 | 5 | S.L./Am.Ac./O.St./P.G. | 81.1 | SM C24:1; SM C26:1; Lys; 20a-OH-C; LTB4 |
| 1009 | 4 | En.Met/S.L./Am.Ac./B.Am. | 80.3 | Lac; SM C16:0; Met; Histamine |
| 1010 | 4 | S.L./Am.Ac./B.Am. | 83.6 | SM (OH) C22:1; Lys; Met; Histamine |
| 1011 | 4 | S.L./Am.Ac. | 83.6 | SM C18:1; SM C24:1; SM (OH) C22:1; Ala |
| 1012 | 3 | Ac.Ca./S.L./Am.Ac. | 82.2 | C14:1; SM C18:1; Pro |
| 1013 | 4 | S.L./Am.Ac./O.St. | 90.6 | SM C16:1; SM (OH) C24:1; Tyr; 20a-OH-C |
| 1014 | 4 | S.L./Am.Ac./B.Am./O.St. | 82.4 | SM C16:0; Arg; Ac-Orn; Cholestenone |
| 1015 | 4 | S.L./Am.Ac./B.Am. | 82.6 | SM C16:1; His; Lys; Met-SO |
| 1016 | 4 | S.L./Am.Ac. | 82.2 | SM C16:0; His; Met; Orn |
| 1017 | 5 | S.L./Am.Ac./B.Am. | 86.4 | SM (OH) C14:1; SM (OH) C22:1; SM (OH) C24:1; Tyr; Ac-Orn |
| 1018 | 4 | En.Met/Ac.Ca./S.L./B.Am. | 82.1 | alpha-KGA; C6:1; SM C16:0; Ac-Orn |
| 1019 | 4 | S.L./Am.Ac./P.G. | 82.4 | SM (OH) C22:1; Gln; Orn; TXB2 |
| 1020 | 6 | S.L./Am.Ac./B.Am. | 89.8 | SM C16:1; SM C24:0; SM (OH) C22:2; Lys; Ser; Ac-Orn |
| 1021 | 4 | Ac.Ca./S.L./Am.Ac./B.Am. | 85.4 | C6:1; SM C16:0; Pro; Ac-Orn |
| 1022 | 4 | En.Met/S.L./Am.Ac./B.Am. | 82.6 | Lac; SM (OH) C24:1; Gln; Ac-Orn |
| 1023 | 4 | S.L./Am.Ac./O.St. | 85.8 | SM C24:0; Met; Pro; 25-OH-C |
| 1024 | 4 | S.L./Am.Ac. | 82 | SM C24:1; SM (OH) C16:1; Ala; Gln |
| 1025 | 4 | S.L./Am.Ac./B.Am. | 81.6 | SM C18:1; SM C20:2; SM (OH) C14:1; Phe |
| 1026 | 5 | En.Met/Ac.Ca./Am.Ac./O.St. | 81.4 | alpha-KGA; C14:1; Phe; Pro; Cholestenone |
| 1027 | 5 | Ac.Ca./S.L./Am.Ac./B.Am. | 88.1 | C5:1-DC; SM C16:1; SM C24:0; Orn; Histamine |
| 1028 | 5 | Ac.Ca./S.L./P.G. | 81.1 | C5:1-DC; SM C16:0; SM C18:1; SM C24:0; LTB4 |
| 1029 | 3 | S.L./Am.Ac. | 79.8 | SM (OH) C14:1; SM (OH) C22:2; Met |
| 1030 | 4 | S.L./Am.Ac. | 84.4 | SM C20:2; SM (OH) C22:1; Met; Pro |
| 1031 | 3 | S.L./B.Am. | 83.6 | SM (OH) C22:1; SM (OH) C24:1; Met-SO |
| 1032 | 3 | S.L./Am.Ac. | 80.7 | SM C16:1; SM C18:0; Phe |
| 1033 | 4 | S.L./Am.Ac./P.G. | 89.4 | SM (OH) C14:1; SM (OH) C16:1; Orn; TXB2 |
| 1034 | 3 | S.L./Am.Ac. | 88.5 | SM C20:2; SM (OH) C14:1; Tyr |
| 1035 | 4 | S.L./Am.Ac. | 83.8 | SM C18:1; SM C20:2; Gln; Tyr |
| 1036 | 4 | Ac.Ca./S.L. | 87.4 | C5:1-DC; SM C16:0; SM C16:1; SM (OH) C24:1 |
| 1037 | 5 | En.Met/S.L./Am.Ac. | 82.1 | alpha-KGA; Lac; SM (OH) C14:1; SM (OH) C22:2; Asn |
| 1038 | 4 | Ac.Ca./S.L./Am.Ac. | 84.6 | C14:1; SM (OH) C22:2; Arg; Met |
| 1039 | 3 | S.L./Am.Ac./O.St. | 81.3 | SM (OH) C22:2; Pro; Cholestenone |
| 1040 | 4 | Ac.Ca./S.L./Am.Ac. | 87.8 | C10:2; SM (OH) C14:1; Met; Trp |
| 1041 | 4 | Ac.Ca./S.L./B.Am. | 90.4 | C5:1-DC; SM C16:1; SM (OH) C22:2; Histamine |
| 1042 | 4 | S.L./Am.Ac./O.St. | 82.2 | SM C24:1; Gln; Tyr; Cholestenone |
| 1043 | 4 | En.Met/Ac.Ca./Am.Ac. | 83.4 | Lac; C14:1; His; Met |
| 1044 | 4 | En.Met/Ac.Ca./S.L. | 85.5 | alpha-KGA; C5:1-DC; SM C16:1; SM (OH) C16:1 |
| 1045 | 4 | En.Met/Ac.Ca./S.L./Am.Ac. | 81.8 | alpha-KGA; C14:1; SM C18:0; Tyr |
| 1046 | 3 | S.L./Am.Ac. | 87.2 | SM (OH) C16:1; SM (OH) C22:2; Gly |
| 1047 | 4 | S.L./Am.Ac./B.Am. | 82.6 | SM C24:0; Lys; Pro; Ac-Orn |
| 1048 | 4 | S.L./Am.Ac./B.Am. | 92.5 | SM (OH) C16:1; SM (OH) C22:2; Tyr; Kynurenine |
| 1049 | 4 | S.L./Am.Ac. | 79.5 | SM C16:0; SM (OH) C22:1; His; Met |
| 1050 | 4 | S.L./Am.Ac. | 82.2 | SM C24:1; SM (OH) C14:1; Orn; Tyr |
| 1051 | 5 | Ac.Ca./S.L./Am.Ac./B.Am. | 84.2 | C14:1; SM (OH) C24:1; His; Pro; Met-SO |
| 1052 | 4 | Ac.Ca./S.L./Am.Ac. | 80.5 | C9; SM C24:0; SM (OH) C14:1; Phe |
| 1053 | 5 | S.L./Am.Ac./B.Am. | 79.6 | SM C16:1; SM C20:2; SM (OH) C16:1; His; Met-SO |
| 1054 | 4 | S.L./Am.Ac./O.St. | 82.8 | SM (OH) C22:1; Met; Pro; 25-OH-C |
| 1055 | 3 | S.L./Am.Ac. | 80.4 | SM C26:1; Met; Orn |
| 1056 | 5 | S.L./Am.Ac./B.Am. | 86.6 | SM C16:0; Lys; Met; Orn; Met-SO |
| 1057 | 4 | S.L./Am.Ac./O.St. | 85.1 | SM C16:0; SM (OH) C14:1; Leu; 20a-OH-C |
| 1058 | 6 | En.Met/Ac.Ca./S.L./Am.Ac./B.Am. | 86.9 | alpha-KGA; C14:1-OH; SM C18:0; SM C20:2; Arg; Ac-Orn |
| 1059 | 5 | En.Met/Am.Ac./B.Am. | 80.7 | H1; Arg; Gln; His; Met-SO |
| 1060 | 4 | S.L./Am.Ac./B.Am. | 84.9 | SM (OH) C22:1; SM (OH) C22:2; Gln; Met-SO |
| 1061 | 4 | En.Met/Ac.Ca./Am.Ac. | 81.1 | Lac; C18:2; Leu; Pro |
| 1062 | 4 | En.Met/S.L./Am.Ac. | 82.6 | Fum; SM (OH) C16:1; SM (OH) C22:1; Met |
| 1063 | 4 | S.L./Am.Ac./B.Am./O.St. | 82.5 | SM (OH) C24:1; Lys; Met-SO; Cholestenone |
| 1064 | 5 | Ac.Ca./S.L./Am.Ac./B.Am. | 82.9 | C5:1-DC; SM (OH) C14:1; Tyr; Creatinine; SDMA |
| 1065 | 4 | En.Met/Ac.Ca./S.L./Am.Ac. | 80.8 | Lac; C6:1; SM C24:1; Gln |
| 1066 | 4 | En.Met/S.L./Am.Ac. | 87.9 | Fum; SM (OH) C22:2; Gln; Met |
| 1067 | 4 | S.L./Am.Ac. | 84 | SM C24:0; Arg; Met; Tyr |
| 1068 | 3 | S.L./Am.Ac. | 81.8 | SM (OH) C14:1; Phe; Pro |
| 1069 | 4 | S.L./Am.Ac./B.Am. | 92.8 | SM (OH) C22:2; Gln; Tyr; Kynurenine |
| 1070 | 4 | En.Met/S.L./Am.Ac. | 85.6 | Suc; SM C16:1; SM C18:1; Tyr |
| 1071 | 4 | S.L./Am.Ac. | 84.8 | alpha-KGA; SM C18:1; SM C24:0; Tyr |
| 1072 | 5 | En.Met/S.L./Am.Ac./B.Am. | 80.5 | Pent-P; Suc; SM (OH) C14:1; Lys; Met-SO |
| 1073 | 4 | Ac.Ca./S.L. | 85.8 | C5:1-DC; SM C16:1; SM C18:0; SM C18:1 |
| 1074 | 4 | S.L./Am.Ac./O.St. | 79.5 | SM C24:0; SM C24:1; Phe; Cholestenone |
| 1075 | 4 | S.L./Am.Ac. | 85.8 | SM C24:0; SM (OH) C24:1; Met; Pro |
| 1076 | 4 | Ac.Ca./S.L. | 81.1 | C5:1-DC; SM (OH) C22:1; SM (OH) C22:2; SM (OH) C24:1 |
| 1077 | 4 | S.L./Am.Ac./B.Am. | 81.4 | SM (OH) C16:1; SM (OH) C24:1; Orn; Met-SO |
| 1078 | 3 | S.L./Am.Ac./B.Am. | 80.8 | SM (OH) C16:1; Lys; Met-SO |
| 1079 | 4 | S.L./Am.Ac. | 83.1 | SM C16:1; SM C18:1; SM (OH) C22:2; Ala |
| 1080 | 4 | S.L./Am.Ac. | 86.9 | SM C18:1; SM C24:1; SM (OH) C14:1; Ala |

TABLE 9-continued

Metabolite combinations describing damage of basal ganglia

| No. | Npar | Chemical Class | Accuracy | Model |
|---|---|---|---|---|
| 1081 | 4 | S.L./Am.Ac./B.Am. | 83.6 | SM (OH) C16:1; Pro; Trp; total DMA |
| 1082 | 6 | En.Met/Ac.Ca./S.L./Am.Ac./B.Am. | 89.9 | Suc; C6:1; SM C24:1; SM (OH) C22:2; Thr; Kynurenine |
| 1083 | 4 | En.Met/Ac.Ca./S.L./Am.Ac. | 84.9 | Suc; C6:1; SM (OH) C14:1; Arg |
| 1084 | 5 | Ac.Ca./S.L./Am.Ac. | 89 | Suc; SM C16:1; SM (OH) C22:2; Met; Orn |
| 1085 | 4 | En.Met/S.L./Am.Ac./O.St. | 85 | Fum; SM C16:1; Met; Cholestenone |
| 1086 | 5 | En.Met/S.L./B.Am./O.St./P.G. | 83.4 | alpha-KGA; SM (OH) C22:1; Met-SO; 24-DH-Lanosterol; LTB4 |
| 1087 | 5 | Ac.Ca./S.L./Am.Ac. | 82.1 | C5:1-DC; SM (OH) C14:1; SM (OH) C16:1; SM (OH) C22:1; Asn |
| 1088 | 4 | S.L./Am.Ac. | 82.7 | SM C24:0; SM (OH) C14:1; Asn; Pro |
| 1089 | 5 | En.Met/S.L./Am.Ac./P.G. | 83.8 | Lac; SM (OH) C22:2; Orn; Tyr; AA |
| 1090 | 4 | S.L./Am.Ac./B.Am. | 89.8 | SM C24:0; Lys; Met; Met-SO |
| 1091 | 3 | S.L./Am.Ac. | 83.4 | SM (OH) C22:2; Pro; Trp |
| 1092 | 4 | En.Met/S.L./B.Am./O.St. | 84.1 | alpha-KGA; SM C16:1; Met-SO; Cholestenone |
| 1093 | 4 | S.L./Am.Ac./B.Am. | 83.2 | SM C16:0; SM (OH) C14:1; Met; Kynurenine |
| 1094 | 3 | S.L./Am.Ac. | 79.8 | SM (OH) C16:1; Trp; Tyr |
| 1095 | 5 | Ac.Ca./S.L./Am.Ac./B.Am. | 84.5 | C18; SM (OH) C22:2; Met; Pro; Histamine |
| 1096 | 5 | S.L./Am.Ac./B.Am. | 86.2 | SM C18:0; SM C18:1; Pro; Trp; SDMA |
| 1097 | 4 | Ac.Ca./S.L./Am.Ac. | 80.6 | C5:1-DC; SM C24:0; SM C24:1; Lys |
| 1098 | 4 | S.L./Am.Ac./B.Am. | 82.7 | SM (OH) C22:1; Met; Histamine; Met-SO |
| 1099 | 6 | En.Met/S.L./Am.Ac./B.Am. | 84.4 | Pent-P; SM C24:1; SM C26:1; Lys; Trp; Met-SO |
| 1100 | 4 | En.Met/S.L./B.Am./O.St. | 79.3 | alpha-KGA; SM C24:0; Ac-Orn; 25-OH-C |
| 1101 | 4 | En.Met/S.L./Am.Ac. | 80.2 | alpha-KGA; SM C24:1; SM (OH) C14:1; Gly |
| 1102 | 4 | Ac.Ca./S.L./Am.Ac. | 85.5 | C5:1-DC; SM C24:0; SM (OH) C14:1; Met |
| 1103 | 4 | Ac.Ca./S.L./O.St. | 86.8 | C5:1-DC; C6:1; SM (OH) C22:1; 24-DH-Lanosterol |
| 1104 | 3 | En.Met/S.L./Am.Ac. | 82.1 | Fum; SM C16:0; Met |
| 1105 | 4 | S.L./Am.Ac./O.St. | 94.6 | SM C16:1; SM (OH) C22:2; Pro; 20a-OH-C |
| 1106 | 4 | S.L./Am.Ac./B.Am. | 80.2 | SM C18:0; SM C24:1; Trp; SDMA |
| 1107 | 4 | S.L./Am.Ac. | 80.7 | SM (OH) C22:2; His; Met; Trp |
| 1108 | 4 | S.L./Am.Ac./B.Am. | 83.4 | SM C16:1; SM (OH) C22:2; Lys; Ac-Orn |
| 1109 | 5 | En.Met/Ac.Ca./S.L./B.Am. | 81.9 | alpha-KGA; C5:1-DC; SM C24:0; SM (OH) C22:2; total DMA |
| 1110 | 6 | Ac.Ca./S.L./Am.Ac. | 83.3 | C14:1; SM C18:0; SM (OH) C22:1; SM (OH) C22:2; Met; Tyr |
| 1111 | 5 | En.Met/Ac.Ca./S.L./B.Am. | 80.8 | Fum; C18; SM C18:1; Histamine; Met-SO |
| 1112 | 4 | S.L./Am.Ac. | 80.8 | SM C16:1; SM C24:1; SM (OH) C16:1; Ser |
| 1113 | 5 | S.L./Am.Ac./B.Am. | 85.3 | SM C24:0; SM (OH) C14:1; Orn; Phe; Ac-Orn |
| 1114 | 5 | En.Met/S.L./Am.Ac./O.St. | 81.6 | alpha-KGA; SM C24:1; Gln; Leu; 20a-OH-C |
| 1115 | 6 | S.L./Am.Ac./O.St. | 84.9 | SM C16:0; SM (OH) C24:1; His; Lys; Tyr; 22R-OH-C |
| 1116 | 5 | S.L./Am.Ac./B.Am./P.G. | 90 | SM (OH) C14:1; SM (OH) C22:2; Phe; Kynurenine; LTB4 |
| 1117 | 3 | Ac.Ca./S.L. | 88.1 | C5:1-DC; SM C16:1; SM C18:1 |
| 1118 | 4 | S.L./Am.Ac. | 88.2 | SM C26:0; Gln; His; Met |
| 1119 | 4 | Ac.Ca./S.L./Am.Ac. | 89.8 | C14:1; C5:1-DC; SM (OH) C14:1; Pro |
| 1120 | 4 | S.L./Am.Ac. | 87.5 | SM C16:1; SM C18:1; Met; Trp |
| 1121 | 4 | S.L./Am.Ac./B.Am. | 83.7 | SM C18:0; Arg; Gln; total DMA |
| 1122 | 4 | S.L./Am.Ac./B.Am. | 90.8 | SM C16:0; SM (OH) C22:1; Tyr; Kynurenine |
| 1123 | 4 | S.L./B.Am./O.St. | 85.1 | SM (OH) C22:2; Kynurenine; Met-SO; Cholestenone |
| 1124 | 4 | S.L./Am.Ac. | 86.1 | SM (OH) C14:1; Met; Orn; Pro |
| 1125 | 5 | S.L./Am.Ac./O.St. | 91.9 | SM C16:0; SM (OH) C22:2; Gln; Pro; 20a-OH-C |
| 1126 | 4 | S.L./Am.Ac. | 79.5 | SM C18:0; SM (OH) C16:1; Trp; Tyr |
| 1127 | 6 | S.L./Am.Ac./B.Am./O.St. | 82.5 | SM C18:0; SM C24:1; SM (OH) C22:2; Lys; Met-SO; Cholestenone |
| 1128 | 5 | En.Met/S.L./Am.Ac./O.St. | 82.5 | alpha-KGA; SM C24:1; SM (OH) C14:1; Trp; 20a-OH-C |
| 1129 | 3 | S.L./Am.Ac./O.St. | 89.2 | SM C18:1; Trp; Cholestenone |
| 1130 | 4 | S.L./Am.Ac./O.St. | 88.4 | SM C24:0; Tyr; Creatinine; Cholestenone |
| 1131 | 4 | S.L./Am.Ac./O.St. | 79.6 | SM C24:1; SM (OH) C24:1; Leu; 20a-OH-C |
| 1132 | 3 | S.L./Am.Ac. | 80.8 | SM (OH) C14:1; SM (OH) C22:2; Arg |
| 1133 | 5 | S.L./Am.Ac./P.G. | 88.8 | SM (OH) C14:1; Gln; Leu; Orn; TXB2 |
| 1134 | 4 | S.L./Am.Ac./O.St. | 83.7 | SM C16:1; SM C18:1; Trp; Cholestenone |
| 1135 | 6 | Ac.Ca./Am.Ac./B.Am./O.St. | 85.5 | C14:1; C5:1-DC; Met; Pro; Histamine; Cholestenone |
| 1136 | 5 | S.L./Am.Ac./O.St. | 83.5 | SM C16:0; SM C16:1; Ile; Pro; Cholestenone |
| 1137 | 3 | Ac.Ca./Am.Ac. | 79.7 | C14:1; C6:1; Pro |
| 1138 | 4 | S.L./B.Am./O.St. | 81.5 | SM C24:0; SM (OH) C14:1; Met-SO; 24S-OH-C |
| 1139 | 4 | S.L./Am.Ac. | 84.9 | SM C16:1; SM (OH) C24:1; Met; Pro |
| 1140 | 4 | Ac.Ca./S.L./B.Am. | 84 | C5:1-DC; SM C16:1; SM C24:1; Histamine |
| 1141 | 5 | En.Met/S.L./Am.Ac./B.Am. | 80.4 | alpha-KGA; SM (OH) C24:1; Lys; Ac-Orn |
| 1142 | 3 | Ac.Ca./S.L./Am.Ac. | 79.8 | C14:1-OH; SM C18:1; Arg |
| 1143 | 5 | S.L./Am.Ac./B.Am. | 88.4 | SM (OH) C22:1; SM (OH) C22:2; Orn; Histamine; Met-SO |
| 1144 | 5 | S.L./Am.Ac./B.Am./O.St. | 85.1 | SM C18:1; Trp; Histamine; 24-DH-Lanosterol |
| 1145 | 4 | S.L./Am.Ac./O.St. | 81.1 | SM (OH) C22:1; Gln; Phe; 24-DH-Lanosterol |
| 1146 | 4 | S.L./Am.Ac. | 81.6 | SM C16:0; SM C24:1; SM (OH) C22:2; Tyr |
| 1147 | 4 | S.L./Am.Ac./O.St. | 80.2 | SM C16:1; SM C18:1; Tyr; Cholestenone |
| 1148 | 4 | En.Met/S.L./Am.Ac. | 81.4 | Lac; SM C16:0; Met; Orn |
| 1149 | 5 | Ac.Ca./S.L./Am.Ac. | 83.3 | C5:1-DC; SM C16:0; SM C24:0; SM (OH) C24:1; Phe |
| 1150 | 3 | S.L./Am.Ac. | 80.8 | SM C24:1; SM (OH) C22:2; Tyr |
| 1151 | 4 | S.L./Am.Ac./B.Am./O.St. | 81.2 | SM C16:0; Arg; Met-SO; Cholestenone |
| 1152 | 3 | S.L./Am.Ac. | 81.1 | SM C16:0; SM (OH) C22:2; Ala |
| 1153 | 5 | S.L./Am.Ac./B.Am. | 82.5 | SM C16:0; SM (OH) C14:1; SM (OH) C24:1; Tyr; Creatinine |
| 1154 | 3 | S.L./Am.Ac. | 81.8 | SM C16:1; Met; Orn |
| 1155 | 5 | S.L./Am.Ac./B.Am./O.St. | 81.7 | SM C16:0; SM (OH) C16:1; Gly; Ac-Orn; Cholestenone |
| 1156 | 4 | S.L./Am.Ac./B.Am. | 86.8 | SM (OH) C14:1; SM (OH) C22:1; Pro; Met-SO |

TABLE 9-continued

Metabolite combinations describing damage of basal ganglia

| No. | Npar | Chemical Class | Accuracy | Model |
|---|---|---|---|---|
| 1157 | 4 | S.L./Am.Ac./O.St. | 81.1 | SM C18:1; SM (OH) C22:1; Tyr; 25-OH-C |
| 1158 | 4 | S.L./Am.Ac./B.Am. | 81 | SM C18:0; SM (OH) C24:1; Gln; Met-SO |
| 1159 | 3 | Am.Ac./B.Am. | 81 | Gln; Met; alpha-AAA |
| 1160 | 4 | S.L./Am.Ac. | 79.4 | SM C18:1; SM C24:1; Ala; Lys |
| 1161 | 3 | S.L./Am.Ac. | 87 | SM (OH) C22:1; SM (OH) C22:2; Gly |
| 1162 | 4 | S.L./Am.Ac. | 87.3 | SM (OH) C22:2; Lys; Met; Trp |
| 1163 | 6 | En.Met/S.L./Am.Ac./B.Am. | 87.8 | alpha-KGA; SM C24:0; SM C24:1; Met; Tyr; Kynurenine |
| 1164 | 4 | En.Met/S.L./B.Am. | 79.5 | H1; SM (OH) C22:2; SM (OH) C24:1; Met-SO |
| 1165 | 4 | Ac.Ca./S.L./B.Am. | 90.2 | C5:1-DC; SM C16:0; SM (OH) C14:1; Histamine |
| 1166 | 3 | S.L./Am.Ac. | 80.1 | SM (OH) C22:2; Gln; Orn |
| 1167 | 4 | En.Met/S.L./Am.Ac. | 84 | Lac; SM C24:1; Gln; Leu |
| 1168 | 3 | S.L./Am.Ac./O.St. | 86.6 | SM C24:1; Pro; Cholestenone |
| 1169 | 4 | En.Met/S.L./Am.Ac. | 88.1 | Lac; SM C18:1; Gln; Met |
| 1170 | 4 | En.Met/Am.Ac./O.St. | 85.4 | Lac; Gln; Tyr; Cholestenone |
| 1171 | 4 | S.L./B.Am. | 80.2 | SM C16:1; Kynurenine; Met-SO; total DMA |
| 1172 | 4 | Ac.Ca./S.L./B.Am. | 84.8 | C6:1; SM C24:0; SM (OH) C24:1; Met-SO |
| 1173 | 4 | Ac.Ca./Am.Ac./B.Am./O.St. | 82.4 | C6:1; Gln; Ac-Orn; 24S-OH-C |
| 1174 | 5 | S.L./Am.Ac./O.St. | 84.2 | SM (OH) C16:1; Gln; Phe; Pro; 24-DH-Lanosterol |
| 1175 | 5 | En.Met/S.L./Am.Ac./B.Am. | 81.5 | Lac; SM C24:1; His; Histamine |
| 1176 | 4 | Ac.Ca./S.L./Am.Ac./B.Am. | 87.4 | C6:1; SM C16:1; Tyr; Kynurenine |
| 1177 | 4 | S.L./Am.Ac./B.Am. | 84.1 | SM C24:1; Leu; Met; Kynurenine |
| 1178 | 4 | S.L./Am.Ac./B.Am. | 82.5 | SM C24:0; SM C24:1; Arg; Ac-Orn |
| 1179 | 5 | S.L./Am.Ac./B.Am. | 83.9 | SM (OH) C22:2; Gln; Phe; Pro; Histamine |
| 1180 | 4 | Ac.Ca./S.L./Am.Ac. | 84.3 | C14:1; SM (OH) C22:1; Arg; Met |
| 1181 | 4 | En.Met/S.L./Am.Ac. | 81.9 | Lac; SM C16:0; SM C16:1; Tyr |
| 1182 | 4 | S.L./Am.Ac. | 81.7 | SM C16:0; SM C24:1; SM (OH) C24:1; Ala |
| 1183 | 4 | S.L./B.Am. | 84.3 | SM C24:1; SM (OH) C14:1; Kynurenine; Met-SO |
| 1184 | 5 | Ac.Ca./S.L./Am.Ac./B.Am./O.St. | 86.9 | C5:1-DC; SM C16:0; Orn; Histamine; 24-DH-Lanosterol |
| 1185 | 4 | En.Met/S.L./Am.Ac. | 82.1 | Suc; SM C16:0; SM (OH) C24:1; Tyr |
| 1186 | 5 | En.Met/Ac.Ca./Am.Ac. | 90.2 | alpha-KGA; C10:2; Arg; Gln; Met |
| 1187 | 4 | S.L./Am.Ac. | 85.3 | SM C16:0; SM C16:1; SM (OH) C22:2; Gly |
| 1188 | 3 | S.L./Am.Ac./B.Am. | 89 | SM (OH) C22:1; Lys; Met-SO |
| 1189 | 5 | En.Met/S.L./B.Am./O.St. | 88.3 | alpha-KGA; SM C16:1; SM (OH) C22:2; Histamine; 20a-OH-C |
| 1190 | 5 | Ac.Ca./S.L./Am.Ac. | 80.2 | C14:1; C5:1-DC; C6:1; SM (OH) C22:1; Lys |
| 1191 | 4 | En.Met/S.L./Am.Ac./O.St. | 82.8 | Lac; SM C24:1; His; Cholestenone |
| 1192 | 5 | Ac.Ca./S.L./Am.Ac./B.Am. | 80.4 | C6:1; SM C16:1; SM C24:1; Leu; Ac-Orn |
| 1193 | 4 | S.L./Am.Ac./O.St. | 79.5 | SM (OH) C24:1; Pro; Trp; Cholestenone |
| 1194 | 4 | Ac.Ca./S.L./B.Am. | 88.5 | C5:1-DC; SM (OH) C22:1; SM (OH) C22:2; Histamine |
| 1195 | 3 | S.L./Am.Ac. | 88.4 | SM (OH) C14:1; Met; Trp |
| 1196 | 4 | S.L./Am.Ac. | 79.3 | SM C20:2; SM (OH) C14:1; SM (OH) C22:2; Phe |
| 1197 | 4 | S.L./Am.Ac./O.St. | 83.3 | SM C24:0; SM C24:1; Leu; 20a-OH-C |
| 1198 | 5 | En.Met/Ac.Ca./Am.Ac./B.Am. | 83 | Suc; C6:1; His; Lys; Ac-Orn |
| 1199 | 4 | Ac.Ca./Am.Ac./O.St. | 79.2 | C6:1; Gln; Pro; 24-DH-Lanosterol |
| 1200 | 4 | En.Met/Ac.Ca./Am.Ac./O.St. | 79.2 | Fum; C6:1; Met; Cholestenone |
| 1201 | 4 | En.Met/S.L./Am.Ac. | 80.6 | alpha-KGA; Suc; SM C24:1; Orn |
| 1202 | 5 | En.Met/Ac.Ca./S.L./Am.Ac. | 86.7 | Lac; C18:1; SM C18:0; Pro; Tyr |
| 1203 | 4 | En.Met/S.L./Am.Ac. | 85.5 | Lac; SM C16:0; SM C24:1; Tyr |
| 1204 | 4 | S.L./Am.Ac. | 83.8 | SM C24:0; Arg; His; Met |
| 1205 | 3 | Ac.Ca./S.L./Am.Ac. | 79.1 | C6:1; SM (OH) C22:1; Phe |
| 1206 | 5 | S.L./Am.Ac./B.Am. | 80.9 | SM C16:1; SM C24:1; Trp; Histamine; Met-SO |
| 1207 | 4 | S.L./Am.Ac. | 79.5 | SM C16:1; SM C18:0; SM (OH) C22:2; Trp |
| 1208 | 4 | S.L./Am.Ac. | 81.6 | SM C18:1; SM C24:0; SM C24:1; Phe |
| 1209 | 4 | S.L./Am.Ac./B.Am. | 90.5 | SM C16:1; SM (OH) C22:1; Tyr; Kynurenine |
| 1210 | 4 | S.L./Am.Ac./B.Am. | 83.4 | SM C16:0; SM C16:1; Lys; Ac-Orn |
| 1211 | 5 | Ac.Ca./S.L./Am.Ac./B.Am. | 85.3 | C5:1-DC; SM (OH) C22:1; Orn; Tyr; Histamine |
| 1212 | 3 | S.L./Am.Ac. | 80.9 | SM C24:1; SM (OH) C16:1; Ala |
| 1213 | 6 | S.L./Am.Ac./P.G. | 96.6 | SM C18:1; SM (OH) C14:1; SM (OH) C22:1; Lys; Tyr; TXB2 |
| 1214 | 4 | S.L./Am.Ac./P.G. | 83.9 | SM C24:0; SM C24:1; Pro; LTB4 |
| 1215 | 4 | S.L./Am.Ac. | 80.4 | SM C16:1; SM C20:2; His; Met |
| 1216 | 4 | Ac.Ca./S.L. | 87.9 | C5:1-DC; SM C16:1; SM C18:1; SM (OH) C14:1 |
| 1217 | 4 | S.L./Am.Ac./B.Am. | 84.5 | SM C16:1; Lys; Trp; Met-SO |
| 1218 | 4 | S.L./Am.Ac./B.Am. | 80.8 | SM (OH) C14:1; Lys; Tyr; Met-SO |
| 1219 | 4 | S.L./Am.Ac./O.St. | 80.2 | SM (OH) C16:1; SM (OH) C22:1; Phe; Cholestenone |
| 1220 | 5 | S.L./Am.Ac./B.Am. | 91.4 | SM C24:0; Gln; Pro; Ac-Orn; Histamine |
| 1221 | 3 | En.Met/Ac.Ca./Am.Ac. | 79.8 | Lac; C18:2; Pro |
| 1222 | 4 | S.L./Am.Ac./B.Am. | 87.4 | SM C16:0; SM C24:0; Lys; Met-SO |
| 1223 | 3 | S.L./Am.Ac. | 82.1 | SM (OH) C22:2; Gln; Met |
| 1224 | 5 | En.Met/S.L./Am.Ac./P.G. | 84.1 | Lac; SM C24:1; Orn; Tyr; AA |
| 1225 | 4 | Ac.Ca./S.L./Am.Ac./B.Am. | 80.6 | C5:1-DC; SM C16:0; Tyr; Histamine |
| 1226 | 3 | Am.Ac. | 79.8 | Gln; Pro; Tyr |
| 1227 | 4 | Ac.Ca./S.L./Am.Ac./O.St. | 81.8 | C5:1-DC; SM (OH) C14:1; Lys; 24-DH-Lanosterol |
| 1228 | 4 | En.Met/S.L./Am.Ac./P.G. | 83 | alpha-KGA; SM C16:0; Val; TXB2 |
| 1229 | 4 | S.L./Am.Ac./O.St. | 86.6 | SM C24:0; Phe; Pro; Cholestenone |
| 1230 | 4 | Ac.Ca./S.L./Am.Ac./B.Am. | 81.1 | C10; SM C16:0; Gln; Met-SO |
| 1231 | 4 | S.L./Am.Ac./O.St. | 79.7 | SM (OH) C16:1; Gln; Orn; 25-OH-C |
| 1232 | 4 | S.L./Am.Ac. | 79.4 | SM (OH) C16:1; SM (OH) C22:1; SM (OH) C22:2; Ser |

TABLE 9-continued

Metabolite combinations describing damage of basal ganglia

| No. | Npar | Chemical Class | Accuracy | Model |
|---|---|---|---|---|
| 1233 | 5 | S.L./Am.Ac. | 88.5 | SM C18:1; SM C20:2; SM (OH) C14:1; Gln; Tyr |
| 1234 | 3 | S.L./Am.Ac./B.Am. | 84.2 | SM C26:1; Orn; Met-SO |
| 1235 | 5 | S.L./Am.Ac./B.Am. | 89.3 | SM (OH) C14:1; SM (OH) C22:1; His; Orn; Ac-Orn |
| 1236 | 3 | S.L./Am.Ac./B.Am. | 79.1 | SM C18:1; Gln; total DMA |
| 1237 | 6 | Ac.Ca./S.L./Am.Ac./B.Am./O.St. | 85.3 | C14:1; SM C18:1; Leu; Tyr; Histamine; 20a-OH-C |
| 1238 | 6 | En.Met/S.L./Am.Ac. | 89.9 | Suc; SM (OH) C16:1; Gln; Orn; Pro; Tyr |
| 1239 | 4 | S.L./B.Am. | 82.1 | SM C16:0; SM C18:1; SM C24:0; Met-SO |
| 1240 | 3 | Am.Ac./B.Am. | 83.8 | Gln; Pro; Ac-Orn |
| 1241 | 4 | Ac.Ca./S.L./Am.Ac./O.St. | 80.2 | C10; SM (OH) C14:1; His; 20a-OH-C |
| 1242 | 4 | S.L./Am.Ac./O.St. | 83.1 | SM C16:0; Met; Pro; Cholestenone |
| 1243 | 4 | S.L./B.Am. | 84 | SM (OH) C14:1; SM (OH) C22:1; SM (OH) C24:1; Met-SO |
| 1244 | 3 | S.L./Am.Ac. | 80.1 | SM (OH) C22:1; His; Met |
| 1245 | 5 | S.L./Am.Ac. | 85.5 | SM C18:1; SM C20:2; SM C24:1; SM (OH) C14:1; Tyr |
| 1246 | 5 | En.Met/S.L./Am.Ac. | 80 | Hex-P; SM C16:0; SM C24:1; SM (OH) C14:1; Trp |
| 1247 | 5 | En.Met/S.L./Am.Ac./B.Am. | 82.1 | alpha-KGA; SM (OH) C22:1; Arg; Met-SO |
| 1248 | 4 | En.Met/Ac.Ca./Am.Ac. | 84.2 | Lac; C14:1; Arg; Met |
| 1249 | 4 | S.L./Am.Ac./B.Am. | 81.8 | SM C16:0; SM C16:1; Phe; Kynurenine |
| 1250 | 4 | S.L./Am.Ac. | 83.2 | SM C24:1; SM (OH) C16:1; Pro; Trp |
| 1251 | 4 | En.Met/S.L./Am.Ac. | 82.9 | Suc; SM (OH) C16:1; Orn; Pro |
| 1252 | 5 | En.Met/Ac.Ca./S.L./Am.Ac. | 83.3 | Lac; C6:1; SM C18:1; SM (OH) C14:1; Met |
| 1253 | 4 | En.Met/S.L./Am.Ac. | 83.7 | alpha-KGA; SM C24:0; Met; Tyr |
| 1254 | 4 | S.L./Am.Ac. | 80.3 | SM C18:1; Gln; Met; Trp |
| 1255 | 3 | S.L./Am.Ac. | 83.3 | SM C16:1; SM (OH) C16:1; Gly |
| 1256 | 4 | S.L./Am.Ac./B.Am. | 86.1 | SM C18:0; Gln; Pro; total DMA |
| 1257 | 4 | Ac.Ca./S.L./Am.Ac. | 83.4 | C5:1-DC; SM C16:0; SM (OH) C14:1; Lys |
| 1258 | 5 | S.L./Am.Ac./B.Am. | 92.6 | SM (OH) C14:1; SM (OH) C16:1; SM (OH) C22:1; Tyr; Kynurenine |
| 1259 | 5 | En.Met/S.L./Am.Ac. | 89.1 | Lac; SM C16:1; His; Met; Trp |
| 1260 | 4 | S.L./Am.Ac. | 83.1 | SM C24:0; SM (OH) C14:1; Met; Phe |
| 1261 | 5 | S.L./Am.Ac./B.Am. | 87.4 | SM C16:0; SM (OH) C14:1; SM (OH) C22:1; Arg; Met-SO |
| 1262 | 4 | Ac.Ca./S.L./Am.Ac. | 80.2 | C14:1; SM C18:1; Met; Trp |
| 1263 | 4 | S.L./Am.Ac./B.Am. | 80.7 | SM C24:1; Orn; Histamine; Met-SO |
| 1264 | 4 | En.Met/Ac.Ca./S.L./Am.Ac. | 80.3 | OAA; C5:1-DC; SM C16:1; Lys |
| 1265 | 3 | S.L./Am.Ac./O.St. | 84.8 | SM (OH) C22:1; Tyr; 24S-OH-C |
| 1266 | 4 | En.Met/S.L./Am.Ac./O.St. | 80.2 | alpha-KGA; SM C24:0; Met; Cholestenone |
| 1267 | 4 | S.L./Am.Ac./O.St. | 81.4 | SM (OH) C24:1; Gln; Tyr; 24S-OH-C |
| 1268 | 4 | S.L./Am.Ac./B.Am. | 79.4 | SM C16:0; SM (OH) C16:1; Trp; Ac-Orn |
| 1269 | 4 | En.Met/S.L./Am.Ac./O.St. | 79.1 | Pent-P; SM (OH) C16:1; Pro; Cholestenone |
| 1270 | 4 | Am.Ac./B.Am. | 81.4 | Lys; Pro; Ac-Orn; Histamine |
| 1271 | 3 | S.L./Am.Ac. | 83.2 | SM C24:1; SM (OH) C22:2; Arg |
| 1272 | 4 | En.Met/S.L./Am.Ac./B.Am. | 82.6 | alpha-KGA; SM C16:0; Orn; Ac-Orn |
| 1273 | 4 | S.L./Am.Ac./B.Am. | 85.6 | SM C20:2; SM (OH) C22:1; Arg; Met-SO |
| 1274 | 5 | S.L./Am.Ac./B.Am./O.St. | 90.4 | SM C16:1; SM (OH) C14:1; Pro; Ac-Orn; Cholestenone |
| 1275 | 3 | Ac.Ca./S.L. | 88.2 | C5:1-DC; SM C16:1; SM (OH) C22:1 |
| 1276 | 4 | En.Met/S.L./Am.Ac./B.Am. | 81.2 | Hex-P; SM C24:1; Gln; Ac-Orn |
| 1277 | 4 | En.Met/S.L./Am.Ac. | 79.5 | Suc; SM C16:0; Arg; Pro |
| 1278 | 4 | S.L./Am.Ac./B.Am. | 84.7 | SM (OH) C22:1; SM (OH) C22:2; Orn; Ac-Orn |
| 1279 | 4 | En.Met/Ac.Ca./S.L./Am.Ac. | 81.9 | alpha-KGA; C10:2; SM C16:1; Met |
| 1280 | 4 | En.Met/S.L./B.Am. | 79.7 | alpha-KGA; SM (OH) C22:2; SM (OH) C24:1; Met-SO |
| 1281 | 6 | S.L./Am.Ac./P.G. | 86.2 | SM C16:0; SM (OH) C14:1; Arg; Gln; Tyr; 8-iso-PGF2a |
| 1282 | 4 | S.L./Am.Ac. | 79.6 | SM C24:0; SM C24:1; Leu; Met |
| 1283 | 4 | Am.Ac./B.Am. | 85.1 | Gln; Lys; Orn; Ac-Orn |
| 1284 | 4 | S.L./Am.Ac./B.Am. | 79.6 | SM C24:0; SM (OH) C16:1; Ala; Ac-Orn |
| 1285 | 5 | S.L./Am.Ac./B.Am./P.G. | 81 | SM C16:1; SM C18:1; Orn; Met-SO; LTB4 |
| 1286 | 4 | En.Met/S.L./Am.Ac./O.St. | 81.3 | alpha-KGA; SM C18:0; Trp; 24-DH-Lanosterol |
| 1287 | 4 | S.L./B.Am. | 81 | SM C18:0; SM C18:1; SM C24:0; Met-SO |
| 1288 | 5 | S.L./Am.Ac./O.St. | 92.8 | SM (OH) C16:1; SM (OH) C22:2; His; Orn; 20a-OH-C |
| 1289 | 4 | En.Met/Am.Ac./O.St. | 82 | alpha-KGA; His; Tyr; 20a-OH-C |
| 1290 | 4 | S.L./Am.Ac./B.Am. | 86.2 | SM C16:0; Met; Pro; Kynurenine |
| 1291 | 4 | S.L./Am.Ac. | 81.7 | SM (OH) C14:1; Arg; Pro; Tyr |
| 1292 | 5 | S.L./Am.Ac./B.Am./P.G. | 94.2 | SM (OH) C14:1; SM (OH) C16:1; Tyr; Kynurenine; LTB4 |
| 1293 | 4 | S.L./Am.Ac./B.Am. | 87.6 | SM (OH) C14:1; Arg; Ac-Orn; Histamine |
| 1294 | 4 | S.L./Am.Ac./P.G. | 79.5 | SM C16:1; Arg; Orn; Tyr; LTB4 |
| 1295 | 5 | S.L./Am.Ac./B.Am. | 89.7 | SM C16:1; SM (OH) C22:2; Pro; Trp; Met-SO |
| 1296 | 5 | En.Met/S.L./Am.Ac./B.Am. | 79.9 | Pent-P; SM C18:1; Pro; Histamine |
| 1297 | 4 | Ac.Ca./Am.Ac./B.Am. | 82.4 | C14:1; Lys; Pro; Ac-Orn |
| 1298 | 3 | S.L./Am.Ac./B.Am. | 84.2 | SM C16:0; Lys; Met-SO |
| 1299 | 4 | S.L./Am.Ac./O.St. | 85.8 | SM C24:1; Trp; Tyr; Cholestenone |
| 1300 | 4 | En.Met/S.L./Am.Ac. | 80.2 | alpha-KGA; SM (OH) C14:1; Arg; Phe |
| 1301 | 4 | S.L./B.Am. | 81.6 | SM C16:1; SM C18:1; SM C20:2; Met-SO |
| 1302 | 4 | S.L./Am.Ac. | 83.5 | SM C16:1; SM C18:1; SM (OH) C14:1; Ser |
| 1303 | 4 | S.L./Am.Ac./O.St. | 79.2 | SM C16:0; Met; Orn; 24S-OH-C |
| 1304 | 4 | S.L./Am.Ac./P.G. | 82 | SM (OH) C22:2; Orn; Tyr; AA |
| 1305 | 4 | S.L./Am.Ac./B.Am. | 82.1 | SM C16:1; Leu; Lys; Ac-Orn |
| 1306 | 5 | S.L./Am.Ac./B.Am. | 80.7 | SM (OH) C16:1; Lys; Met; Histamine; Kynurenine |
| 1307 | 5 | S.L./Am.Ac./O.St. | 82.2 | SM C24:1; SM (OH) C22:2; Asn; Lys; Cholestenone |
| 1308 | 4 | Ac.Ca./S.L./Am.Ac. | 82.9 | C5:1-DC; SM (OH) C14:1; SM (OH) C22:1; Pro |

TABLE 9-continued

Metabolite combinations describing damage of basal ganglia

| No. | Npar | Chemical Class | Accuracy | Model |
|---|---|---|---|---|
| 1309 | 4 | Ac.Ca./S.L. | 80 | C5:1-DC; SM C18:1; SM (OH) C22:2; SM (OH) C24:1 |
| 1310 | 4 | S.L./Am.Ac./B.Am. | 84.9 | SM C24:1; SM (OH) C14:1; Arg; Met-SO |
| 1311 | 4 | S.L./Am.Ac. | 79.5 | SM C16:0; SM C18:1; Arg; Met |
| 1312 | 4 | Ac.Ca./S.L./Am.Ac. | 86.1 | C14:1; SM C24:1; Pro; Tyr |
| 1313 | 4 | S.L./Am.Ac. | 84 | SM (OH) C22:2; SM (OH) C24:1; Met; Trp |
| 1314 | 3 | S.L./Am.Ac./B.Am. | 80.1 | SM C16:0; Gln; Met-SO |
| 1315 | 4 | S.L./Am.Ac. | 84.3 | SM C20:2; SM (OH) C22:2; Pro; Tyr |
| 1316 | 4 | En.Met/Ac.Ca./Am.Ac./O.St. | 84.1 | Pent-P; C6:1; Pro; Cholestenone |
| 1317 | 4 | S.L./Am.Ac./B.Am./P.G. | 79.8 | SM (OH) C22:2; Pro; Ac-Orn; LTB4 |
| 1318 | 4 | Ac.Ca./S.L. | 83.1 | C5:1-DC; C6:1; SM C16:0; SM (OH) C16:1 |
| 1319 | 4 | S.L./Am.Ac./O.St. | 80 | SM (OH) C14:1; SM (OH) C22:2; Lys; 20a-OH-C |
| 1320 | 4 | S.L./Am.Ac. | 81.7 | SM C18:1; SM (OH) C22:2; Gln; Met |
| 1321 | 4 | S.L./Am.Ac./B.Am. | 79.8 | SM C18:1; SM C24:0; Phe; Met-SO |
| 1322 | 4 | S.L./Am.Ac./O.St. | 90.2 | SM (OH) C22:2; Met; Trp; 24-DH-Lanosterol |
| 1323 | 3 | S.L./Am.Ac. | 85.6 | SM (OH) C24:1; Lys; Met |
| 1324 | 5 | S.L./Am.Ac./O.St. | 83.7 | SM C24:1; Arg; His; Trp; Cholestenone |
| 1325 | 3 | Ac.Ca./S.L./Am.Ac. | 80.1 | C14:1-OH; SM C18:1; Pro |
| 1326 | 4 | S.L./Am.Ac./B.Am. | 83.7 | SM C24:1; SM (OH) C22:1; Pro; Ac-Orn |
| 1327 | 4 | Ac.Ca./S.L./Am.Ac. | 82.9 | C9; SM (OH) C14:1; SM (OH) C22:2; Orn |
| 1328 | 5 | En.Met/S.L./B.Am. | 82.1 | Hex-P; SM C16:1; SM C20:2; SM C24:1; Ac-Orn |
| 1329 | 4 | S.L./Am.Ac./P.G. | 82.1 | SM C24:0; Arg; Met; LTB4 |
| 1330 | 5 | En.Met/S.L./Am.Ac./O.St. | 84.8 | Suc; SM C18:1; Arg; Gln; Cholestenone |
| 1331 | 4 | S.L./Am.Ac./B.Am. | 79.6 | SM C26:1; Orn; Ac-Orn; Histamine |
| 1332 | 3 | Ac.Ca./S.L. | 80.5 | C5:1-DC; SM C16:0; SM C18:1 |
| 1333 | 4 | Ac.Ca./S.L./Am.Ac./B.Am. | 90.1 | C5:1-DC; SM C16:1; Pro; Histamine |
| 1334 | 3 | Ac.Ca./S.L. | 85.4 | C5:1-DC; SM (OH) C14:1; SM (OH) C24:1 |
| 1335 | 4 | En.Met/Ac.Ca./S.L./B.Am. | 79.9 | alpha-KGA; C6:1; SM C24:1; Ac-Orn |
| 1336 | 4 | En.Met/S.L./Am.Ac. | 80.7 | alpha-KGA; SM (OH) C14:1; SM (OH) C16:1; Met |
| 1337 | 4 | S.L./B.Am./O.St. | 81.5 | SM (OH) C16:1; SM (OH) C22:1; Met-SO; Cholestenone |
| 1338 | 4 | Ac.Ca./S.L./O.St. | 83.5 | C5:1-DC; SM C24:0; SM (OH) C22:1; Cholestenone |
| 1339 | 4 | S.L./Am.Ac. | 85.1 | SM (OH) C14:1; Gln; Met; Orn |
| 1340 | 4 | S.L./Am.Ac./B.Am. | 87.8 | SM (OH) C14:1; SM (OH) C22:1; Arg; Met-SO |
| 1341 | 5 | S.L./Am.Ac./O.St. | 81.4 | SM (OH) C16:1; SM (OH) C22:2; Arg; His; 20a-OH-C |
| 1342 | 4 | S.L./Am.Ac. | 87.3 | SM C16:0; SM C24:1; SM (OH) C22:2; Ala |
| 1343 | 4 | S.L./Am.Ac./B.Am. | 88.3 | SM C18:0; SM C18:1; Trp; SDMA |
| 1344 | 6 | En.Met/Ac.Ca./Am.Ac./O.St. | 79.6 | alpha-KGA; C6:1; Gln; Orn; Tyr; 24-DH-Lanosterol |
| 1345 | 4 | Ac.Ca./S.L./Am.Ac. | 84.4 | C5:1-DC; SM (OH) C14:1; Gln; Met |
| 1346 | 4 | S.L./Am.Ac./B.Am. | 84.9 | SM C16:1; SM C24:1; Lys; Ac-Orn |
| 1347 | 5 | Ac.Ca./S.L./Am.Ac./O.St. | 88 | C5:1-DC; SM (OH) C22:1; Gln; Phe; Cholestenone |
| 1348 | 3 | S.L./Am.Ac./O.St. | 81.7 | SM (OH) C22:1; Phe; Cholestenone |
| 1349 | 4 | S.L./Am.Ac./B.Am. | 81.5 | SM C18:1; SM C24:0; Lys; Ac-Orn |
| 1350 | 5 | S.L./Am.Ac./P.G. | 92.5 | SM (OH) C14:1; SM (OH) C22:1; SM (OH) C22:2; Lys; TXB2 |
| 1351 | 3 | S.L./Am.Ac. | 80.7 | SM C16:0; SM (OH) C22:2; Ser |
| 1352 | 3 | S.L./Am.Ac. | 87.3 | SM C24:1; SM (OH) C14:1; Ala |
| 1353 | 4 | S.L./Am.Ac./P.G. | 82.2 | SM C24:0; Leu; Orn; TXB2 |
| 1354 | 4 | S.L./Am.Ac. | 79.3 | SM C18:1; SM C20:2; SM (OH) C14:1; Met |
| 1355 | 3 | S.L./Am.Ac. | 84.3 | SM C16:0; SM C24:1; Pro |
| 1356 | 4 | S.L./Am.Ac./B.Am. | 86.8 | SM C18:1; Gln; Orn; Ac-Orn |
| 1357 | 6 | S.L./Am.Ac./O.St. | 88.7 | SM C24:1; SM (OH) C14:1; SM (OH) C22:1; His; Lys; 20a-OH-C |
| 1358 | 5 | S.L./Am.Ac./O.St. | 85.4 | SM (OH) C14:1; SM (OH) C22:2; Arg; Ile; Cholestenone |
| 1359 | 4 | S.L./Am.Ac./O.St. | 81.6 | SM (OH) C22:1; Gln; Leu; 20a-OH-C |
| 1360 | 4 | En.Met/S.L./Am.Ac. | 84.4 | Lac; SM C16:1; Met; Phe |
| 1361 | 4 | S.L./Am.Ac./B.Am./O.St. | 79.9 | SM C24:1; Met; Creatinine; Cholestenone |
| 1362 | 4 | En.Met/Ac.Ca./Am.Ac. | 83.7 | Lac; C18; Phe; Pro |
| 1363 | 4 | S.L./Am.Ac. | 86.2 | SM (OH) C14:1; SM (OH) C22:2; Met; Orn |
| 1364 | 5 | En.Met/S.L./B.Am./O.St. | 79.9 | Hex-P; SM C16:1; SM C24:1; Ac-Orn; Cholestenone |
| 1365 | 3 | S.L./Am.Ac./B.Am. | 89 | SM C24:0; Lys; Met-SO |
| 1366 | 6 | Ac.Ca./S.L./B.Am. | 83.9 | C14:1; SM C16:0; SM (OH) C14:1; alpha-AAA; Kynurenine; Met-SO |
| 1367 | 3 | S.L./O.St. | 79.9 | SM (OH) C22:1; SM (OH) C22:2; 20a-OH-C |
| 1368 | 4 | S.L./Am.Ac./B.Am. | 91.8 | SM (OH) C22:2; Gln; Orn; Met-SO |
| 1369 | 4 | S.L./Am.Ac. | 85.3 | SM (OH) C14:1; Arg; Leu; Met |
| 1370 | 5 | S.L./Am.Ac. | 86.8 | SM C16:0; SM C20:2; SM (OH) C16:1; Trp; Tyr |
| 1371 | 5 | Ac.Ca./S.L./Am.Ac./P.G. | 79.4 | C6:1; SM C16:0; Phe; Trp; LTB4 |
| 1372 | 3 | S.L./B.Am. | 79.5 | SM C16:0; SM C24:0; SM (OH) C16:1; Met-SO |
| 1373 | 4 | S.L./Am.Ac. | 86.9 | SM C16:0; SM (OH) C14:1; Arg; Met |
| 1374 | 4 | En.Met/S.L./Am.Ac. | 81 | alpha-KGA; SM C16:0; Met; Trp |
| 1375 | 5 | Ac.Ca./S.L./Am.Ac./B.Am. | 83.9 | C14:1; SM (OH) C22:2; Arg; His; Ac-Orn |
| 1376 | 4 | En.Met/S.L./Am.Ac. | 81.6 | alpha-KGA; SM (OH) C22:2; Gln; Tyr |
| 1377 | 4 | S.L./Am.Ac. | 83.3 | SM (OH) C22:2; Arg; Met; Trp |
| 1378 | 4 | S.L./Am.Ac. | 81.3 | SM C16:1; SM C18:0; SM (OH) C14:1; Ser |
| 1379 | 5 | S.L./Am.Ac./B.Am. | 80.5 | SM C18:0; SM C18:1; His; Kynurenine; total DMA |
| 1380 | 4 | S.L./Am.Ac./P.G. | 82.8 | SM C16:0; SM C24:0; Arg; TXB2 |
| 1381 | 4 | S.L./Am.Ac. | 80.3 | SM (OH) C16:1; SM (OH) C22:2; Lys; Met |
| 1382 | 4 | S.L./Am.Ac./B.Am. | 84.6 | SM C18:0; SM C24:0; Gln; Met-SO |
| 1383 | 3 | S.L./Am.Ac./O.St. | 86.5 | SM (OH) C22:2; Gly; Cholestenone |
| 1384 | 4 | S.L./Am.Ac. | 91.5 | SM (OH) C14:1; Met; Pro; Trp |

TABLE 9-continued

Metabolite combinations describing damage of basal ganglia

| No. | Npar | Chemical Class | Accuracy | Model |
|---|---|---|---|---|
| 1385 | 5 | Ac.Ca./S.L./Am.Ac. | 84.6 | C5:1-DC; C6:1; SM (OH) C22:1; Gln; Met |
| 1386 | 4 | S.L./Am.Ac./B.Am. | 84.3 | SM C18:1; Gln; Pro; Ac-Orn |
| 1387 | 6 | En.Met/S.L./Am.Ac. | 83.2 | Suc; SM C18:1; SM C24:0; SM (OH) C22:1; Orn; Thr |
| 1388 | 5 | S.L./Am.Ac./B.Am. | 87.7 | SM C24:0; SM (OH) C22:2; Arg; Orn; Met-SO |
| 1389 | 4 | En.Met/S.L./Am.Ac./B.Am. | 85.6 | alpha-KGA; SM (OH) C14:1; Arg; Ac-Orn |
| 1390 | 5 | S.L./Am.Ac./B.Am./O.St. | 88.6 | SM C24:1; SM (OH) C22:1; Trp; Met-SO; Cholestenone |
| 1391 | 3 | Ac.Ca./S.L. | 83.6 | C5:1-DC; SM C16:0; SM (OH) C24:1 |
| 1392 | 4 | S.L./Am.Ac. | 86 | SM C24:1; SM (OH) C22:2; Gln; Pro |
| 1393 | 4 | S.L./Am.Ac./O.St. | 84.4 | SM C24:0; Ala; Met; Cholestenone |
| 1394 | 4 | S.L./Am.Ac. | 80.6 | SM C24:0; SM (OH) C16:1; Met; Trp |
| 1395 | 5 | S.L./B.Am. | 87.5 | SM C16:0; SM C16:1; SM (OH) C22:1; Creatinine; Met-SO |
| 1396 | 4 | En.Met/S.L./Am.Ac. | 82.6 | Lac; SM C24:0; Met; Tyr |
| 1397 | 3 | S.L./Am.Ac. | 84.4 | SM (OH) C16:1; Tyr |
| 1398 | 4 | S.L./Am.Ac. | 79.8 | SM C18:1; SM (OH) C14:1; Asn; Met |
| 1399 | 4 | En.Met/S.L./B.Am. | 79.6 | alpha-KGA; SM C16:0; SM C24:1; Met-SO |
| 1400 | 4 | S.L./Am.Ac./B.Am. | 81.5 | SM C24:1; SM (OH) C22:1; Phe; Histamine |
| 1401 | 6 | En.Met/S.L./Am.Ac./P.G. | 84.4 | Lac; SM C18:0; SM C24:0; SM C24:1; Met; LTB4 |
| 1402 | 4 | En.Met/Ac.Ca./Am.Ac. | 80.5 | Suc; C6:1; Gln; Orn |
| 1403 | 3 | S.L./Am.Ac. | 79.5 | SM C16:1; Arg; Tyr |
| 1404 | 4 | S.L./Am.Ac./B.Am./O.St. | 85.5 | SM C24:0; Pro; Met-SO; 25-OH-C |
| 1405 | 4 | Am.Ac./P.G. | 80.5 | Arg; Gln; Pro; 8-iso-PGF2a |
| 1406 | 6 | En.Met/S.L./Am.Ac. | 88.6 | Hex-P; SM C16:1; SM C24:1; SM (OH) C16:1; Trp; Tyr |
| 1407 | 4 | En.Met/S.L./Am.Ac./O.St. | 81.9 | alpha-KGA; SM (OH) C14:1; Gln; 20a-OH-C |
| 1408 | 4 | S.L./Am.Ac. | 84.7 | SM C18:0; SM C24:0; Arg; Tyr |
| 1409 | 3 | S.L./Am.Ac. | 80.6 | SM C16:0; Met; Pro |
| 1410 | 4 | En.Met/Ac.Ca./S.L./O.St. | 81.5 | alpha-KGA; C5:1-DC; SM C24:1; Cholestenone |
| 1411 | 3 | S.L./Am.Ac. | 83.1 | SM C16:1; SM (OH) C22:2; Ala |
| 1412 | 4 | S.L./Am.Ac./B.Am. | 82.1 | SM (OH) C22:1; SM (OH) C24:1; Orn; Ac-Orn |
| 1413 | 4 | En.Met/S.L./Am.Ac. | 90.3 | Lac; SM (OH) C22:2; Gln; Tyr |
| 1414 | 5 | S.L./Am.Ac./B.Am. | 83.2 | SM C18:1; SM C24:1; SM (OH) C14:1; Orn; Ac-Orn |
| 1415 | 3 | S.L./Am.Ac./P.G. | 90.7 | SM (OH) C16:1; Lys; TXB2 |
| 1416 | 6 | Ac.Ca./S.L./Am.Ac./O.St. | 85.7 | C14:1; SM (OH) C22:1; Lys; Tyr; 20a-OH-C; Cholestenone |
| 1417 | 4 | S.L./Am.Ac. | 81.7 | SM C16:0; SM (OH) C22:2; Arg; Phe |
| 1418 | 6 | S.L./Am.Ac./O.St. | 86.1 | SM C16:0; SM C24:0; SM (OH) C16:1; Pro; Thr; 20a-OH-C |
| 1419 | 5 | Am.Ac./O.St. | 87.3 | Gln; Lys; Met; Pro; 25-OH-C |
| 1420 | 3 | S.L./Am.Ac. | 82.1 | SM (OH) C14:1; SM (OH) C22:2; Ser |
| 1421 | 4 | S.L./Am.Ac./O.St. | 80.8 | SM (OH) C14:1; His; Tyr; Cholestenone |
| 1422 | 4 | En.Met/Ac.Ca./Am.Ac. | 80.3 | Suc; C18:1; Arg; Pro |
| 1423 | 4 | S.L./Am.Ac./B.Am. | 83.2 | SM (OH) C14:1; SM (OH) C16:1; Pro; Ac-Orn |
| 1424 | 4 | S.L./Am.Ac./B.Am. | 82.3 | SM (OH) C14:1; Lys; Met; Histamine |
| 1425 | 4 | S.L./Am.Ac. | 82.4 | SM (OH) C16:1; SM (OH) C22:1; Arg; Met |
| 1426 | 6 | S.L./Am.Ac./B.Am./P.G. | 79.4 | SM (OH) C22:1; Gln; Val; Ac-Orn; 8-iso-PGF2a; LTB4 |
| 1427 | 4 | S.L./Am.Ac. | 83.9 | SM C24:0; SM (OH) C16:1; Arg; Met |
| 1428 | 4 | S.L./Am.Ac./O.St. | 84.3 | SM (OH) C14:1; SM (OH) C22:1; Arg; 20a-OH-C |
| 1429 | 3 | Ac.Ca./S.L./Am.Ac. | 80.1 | C6:1; SM C16:1; Arg |
| 1430 | 5 | En.Met/S.L./Am.Ac./O.St. | 85 | OAA; SM C18:1; SM (OH) C22:2; Val; 20a-OH-C |
| 1431 | 5 | En.Met/Ac.Ca./S.L./Am.Ac. | 81.4 | Hex-P; C14:1; SM C18:1; SM (OH) C22:2; Met |
| 1432 | 4 | S.L./Am.Ac. | 80.6 | SM (OH) C22:1; SM (OH) C24:1; Met; Val |
| 1433 | 4 | En.Met/S.L./B.Am. | 84.3 | alpha-KGA; H1; SM C24:0; Met-SO |
| 1434 | 3 | S.L./B.Am. | 83.5 | SM (OH) C22:1; Ac-Orn; Histamine |
| 1435 | 3 | S.L./Am.Ac. | 80.3 | SM C16:1; SM C18:1; Tyr |
| 1436 | 4 | S.L./Am.Ac./O.St. | 79.5 | SM (OH) C22:1; His; Met; 5a,6a-EpoxyC |
| 1437 | 4 | S.L./Am.Ac./B.Am. | 84.5 | SM C24:0; SM (OH) C22:2; Ala; Ac-Orn |
| 1438 | 4 | En.Met/S.L./B.Am. | 83.7 | alpha-KGA; H1; SM C16:1; Met-SO |
| 1439 | 4 | S.L./Am.Ac./O.St. | 86.8 | SM (OH) C22:2; Arg; Gln; 24-DH-Lanosterol |
| 1440 | 5 | En.Met/S.L./Am.Ac. | 81.1 | Lac; SM C18:1; SM C24:1; SM (OH) C14:1; Trp |
| 1441 | 4 | Ac.Ca./S.L./Am.Ac./O.St. | 80 | C5:1-DC; SM C16:0; His; Cholestenone |
| 1442 | 5 | S.L./Am.Ac./O.St. | 90.3 | SM C16:0; SM (OH) C22:2; Gly; Pro; Cholestenone |
| 1443 | 4 | En.Met/S.L./Am.Ac. | 81 | alpha-KGA; SM C16:1; Met; Val |
| 1444 | 4 | S.L./Am.Ac. | 79.7 | SM C16:0; Met; Orn; Tyr |
| 1445 | 4 | S.L./Am.Ac. | 79.2 | SM C18:0; SM C24:1; SM (OH) C22:2; Thr |
| 1446 | 5 | S.L./Am.Ac./B.Am. | 90.1 | SM (OH) C22:2; Gln; His; Orn; Met-SO |
| 1447 | 5 | En.Met/S.L./Am.Ac. | 81 | Lac; SM C16:0; SM C24:0; SM C24:1; Phe |
| 1448 | 5 | S.L./Am.Ac./B.Am./P.G. | 84.4 | SM C16:1; SM C18:1; Orn; Ac-Orn; LTB4 |
| 1449 | 4 | S.L./Am.Ac. | 81.4 | SM C16:0; SM C24:1; SM (OH) C22:1; Ser |
| 1450 | 4 | En.Met/S.L./Am.Ac./B.Am. | 79.5 | alpha-KGA; SM (OH) C22:2; Met; Creatinine |
| 1451 | 3 | En.Met/Am.Ac. | 80.3 | Fum; Met; Pro |
| 1452 | 4 | S.L./Am.Ac. | 87.3 | SM (OH) C14:1; SM (OH) C22:1; Met; Ser |
| 1453 | 4 | S.L./Am.Ac. | 82 | SM (OH) C22:1; SM (OH) C22:2; Asn; Met |
| 1454 | 4 | En.Met/S.L./Am.Ac./O.St. | 79.6 | alpha-KGA; SM C24:1; Trp; Cholestenone |
| 1455 | 4 | S.L./Am.Ac. | 82.6 | SM C16:1; SM C24:1; Ala; Lys |
| 1456 | 4 | S.L./Am.Ac./B.Am. | 83.7 | SM C16:1; SM (OH) C22:1; Leu; Met-SO |
| 1457 | 5 | S.L./Am.Ac./P.G. | 90.2 | SM (OH) C14:1; Gln; Met; Orn; 8-iso-PGF2a |
| 1458 | 5 | S.L./Am.Ac./P.G. | 81.1 | SM C18:1; Gln; Pro; Trp; 8-iso-PGF2a |
| 1459 | 4 | Ac.Ca./S.L./O.St. | 84.2 | C5:1-DC; SM (OH) C14:1; SM (OH) C22:1; 24-DH-Lanosterol |
| 1460 | 3 | S.L./Am.Ac. | 80.5 | SM C24:0; SM (OH) C22:2; Ala |

TABLE 9-continued

Metabolite combinations describing damage of basal ganglia

| No. | Npar | Chemical Class | Accuracy | Model |
|---|---|---|---|---|
| 1461 | 5 | En.Met/S.L./Am.Ac./B.Am. | 82.9 | alpha-KGA; SM C24:1; Orn; Ac-Orn; Histamine |
| 1462 | 4 | S.L./Am.Ac. | 87.6 | SM C24:0; SM (OH) C14:1; Ala; Met |
| 1463 | 3 | En.Met/Am.Ac. | 79.8 | alpha-KGA; Fum; Met |
| 1464 | 4 | S.L./Am.Ac./P.G. | 92.1 | SM C16:0; His; Lys; TXB2 |
| 1465 | 4 | En.Met/Am.Ac. | 85.1 | Fum; Gln; Met; Tyr |
| 1466 | 4 | S.L./Am.Ac./B.Am. | 84.7 | SM C16:0; SM (OH) C14:1; Tyr; Creatinine |
| 1467 | 5 | S.L./Am.Ac. | 85 | SM C16:0; SM (OH) C22:2; Gln; Orn; Ser |
| 1468 | 4 | S.L./Am.Ac. | 79.7 | SM (OH) C22:2; Arg; Met; Pro |
| 1469 | 3 | S.L./Am.Ac. | 80.9 | SM C24:0; SM (OH) C22:2; Met |
| 1470 | 4 | S.L./Am.Ac./B.Am. | 84.7 | SM C24:1; SM (OH) C24:1; Tyr; Kynurenine |
| 1471 | 5 | Ac.Ca./S.L./Am.Ac./O.St. | 85.1 | C5:1-DC; SM C16:1; His; Tyr; Cholestenone |
| 1472 | 4 | En.Met/S.L./Am.Ac. | 82.5 | alpha-KGA; Suc; SM (OH) C14:1; Tyr |
| 1473 | 4 | S.L./Am.Ac. | 86.8 | SM C16:1; SM C18:0; Trp; Tyr |
| 1474 | 4 | S.L./Am.Ac./P.G. | 80.1 | SM (OH) C22:1; Orn; Phe; LTB4 |
| 1475 | 4 | En.Met/S.L./Am.Ac. | 79.5 | Lac; SM C24:1; SM (OH) C16:1; Trp |
| 1476 | 5 | S.L./Am.Ac./B.Am./O.St. | 87.4 | SM (OH) C14:1; SM (OH) C22:1; Pro; Ac-Orn; Cholestenone |
| 1477 | 4 | Ac.Ca./S.L./Am.Ac. | 88 | C10:2; SM (OH) C14:1; Arg; Met |
| 1478 | 4 | En.Met/S.L./Am.Ac./B.Am. | 86.5 | H1; SM (OH) C22:1; Gln; Met-SO |
| 1479 | 4 | En.Met/S.L./Am.Ac./O.St. | 95.1 | alpha-KGA; SM C16:1; Tyr; 20a-OH-C |
| 1480 | 4 | Ac.Ca./S.L. | 86.4 | C5:1-DC; C6:1; SM C16:0; SM (OH) C22:2 |
| 1481 | 4 | S.L./Am.Ac. | 80.9 | SM C24:1; Leu; Met; Orn |
| 1482 | 4 | En.Met/S.L./Am.Ac. | 87.7 | Lac; SM C24:0; Gln; Tyr |
| 1483 | 4 | S.L./Am.Ac./B.Am. | 80.7 | SM C24:1; SM (OH) C22:1; Gly; alpha-AAA |
| 1484 | 5 | S.L./Am.Ac./B.Am. | 80.4 | SM C16:0; SM C18:0; SM (OH) C24:1; Tyr; Ac-Orn |
| 1485 | 4 | S.L./Am.Ac./B.Am. | 87.6 | SM (OH) C22:1; His; Orn; Ac-Orn |
| 1486 | 4 | S.L./Am.Ac./P.G. | 85.3 | SM C26:1; Gln; Lys; TXB2 |
| 1487 | 3 | En.Met/S.L./Am.Ac. | 79.9 | alpha-KGA; SM C24:1; Tyr |
| 1488 | 4 | S.L./Am.Ac./P.G. | 80.2 | SM C16:0; SM C16:1; Lys; TXB2 |
| 1489 | 3 | Ac.Ca./Am.Ac. | 84.4 | C14:1; Met; Pro |
| 1490 | 4 | S.L./Am.Ac./B.Am. | 89.7 | SM C24:1; SM (OH) C16:1; Tyr; Kynurenine |
| 1491 | 4 | Ac.Ca./S.L./Am.Ac. | 80.6 | C9; SM (OH) C22:1; SM (OH) C22:2; Orn |
| 1492 | 4 | S.L./Am.Ac./B.Am. | 87.3 | SM C16:0; SM (OH) C14:1; Arg; Ac-Orn |
| 1493 | 6 | Ac.Ca./S.L./Am.Ac./O.St. | 79.5 | C10; SM (OH) C14:1; SM (OH) C22:1; Gln; Phe; 24-DH-Lanosterol |
| 1494 | 4 | S.L./Am.Ac./P.G. | 86.2 | SM C26:1; Lys; Pro; TXB2 |
| 1495 | 4 | En.Met/S.L./Am.Ac. | 81.9 | Fum; SM C26:1; SM (OH) C24:1; Met |
| 1496 | 4 | S.L./Am.Ac./B.Am. | 83.6 | SM C18:0; Gln; Trp; total DMA |
| 1497 | 4 | Ac.Ca./S.L./Am.Ac. | 79.6 | C6:1; SM C18:1; Met; Trp |
| 1498 | 4 | S.L./Am.Ac./O.St. | 81.4 | SM (OH) C14:1; SM (OH) C22:2; His; 20a-OH-C |
| 1499 | 4 | S.L./Am.Ac. | 79.1 | SM C24:1; SM C26:1; Met; Pro |
| 1500 | 4 | En.Met/S.L./Am.Ac. | 81.4 | H1; SM (OH) C24:1; Gln; Tyr |
| 1501 | 4 | S.L./Am.Ac./B.Am. | 81.8 | SM (OH) C24:1; Orn; Pro; Ac-Orn |
| 1502 | 3 | Am.Ac./O.St. | 79.9 | Met; Trp; Cholestenone |
| 1503 | 4 | Ac.Ca./S.L./O.St. | 81.6 | C5:1-DC; SM C24:0; 25-OH-C; Cholestenone |
| 1504 | 4 | S.L./Am.Ac./O.St. | 85 | SM (OH) C16:1; SM (OH) C22:2; Pro; 20a-OH-C |
| 1505 | 4 | S.L./Am.Ac. | 86.9 | SM C24:0; Arg; Met; Pro |
| 1506 | 4 | En.Met/Ac.Ca./S.L. | 84.1 | alpha-KGA; C5:1-DC; SM (OH) C14:1; SM (OH) C24:1 |
| 1507 | 3 | S.L./Am.Ac. | 80.8 | SM C24:0; SM (OH) C22:2; Gly |
| 1508 | 4 | Ac.Ca./S.L./Am.Ac./B.Am. | 79.8 | C14:1; SM C18:1; Arg; Met-SO |
| 1509 | 3 | S.L./Am.Ac. | 84.9 | SM C16:0; SM C24:1; Ala |
| 1510 | 4 | S.L./Am.Ac./B.Am./O.St. | 84.2 | SM C16:1; Lys; Ac-Orn; Cholestenone |
| 1511 | 4 | S.L./Am.Ac./O.St. | 82 | SM C20:2; SM C24:1; Tyr; Cholestenone |
| 1512 | 5 | En.Met/S.L./Am.Ac./O.St. | 84.7 | Lac; SM C24:1; SM (OH) C22:2; Tyr; 25-OH-C |
| 1513 | 3 | S.L./Am.Ac. | 83.9 | SM C16:1; Met; Pro |
| 1514 | 5 | S.L./Am.Ac./O.St. | 82.1 | SM C18:0; His; Met; Trp; 24-DH-Lanosterol |
| 1515 | 3 | S.L./Am.Ac./B.Am. | 80 | SM (OH) C22:1; Met; Histamine |
| 1516 | 5 | Ac.Ca./S.L./Am.Ac./B.Am. | 87.1 | C5:1-DC; SM (OH) C14:1; Gln; Ac-Orn; Histamine |
| 1517 | 4 | S.L./Am.Ac./B.Am. | 79.4 | SM C18:0; SM (OH) C22:2; Orn; Met-SO |
| 1518 | 4 | En.Met/S.L./Am.Ac. | 84.2 | Pent-P; SM C16:1; SM C18:1; Pro |
| 1519 | 6 | En.Met/Ac.Ca./S.L./Am.Ac. | 81.8 | Lac; C14:1-OH; SM C16:1; SM C18:1; Arg; His |
| 1520 | 3 | S.L./Am.Ac. | 83.2 | SM (OH) C16:1; SM (OH) C22:1; Tyr |
| 1521 | 4 | Ac.Ca./S.L./Am.Ac. | 82 | C14:1; SM C18:0; SM C18:1; Ala |
| 1522 | 5 | S.L./Am.Ac./B.Am. | 90.4 | SM (OH) C14:1; SM (OH) C22:2; Gln; Pro; Ac-Orn |
| 1523 | 4 | S.L./B.Am. | 82.7 | SM C16:1; SM (OH) C24:1; Kynurenine; Met-SO |
| 1524 | 3 | S.L./Am.Ac./B.Am. | 95 | SM (OH) C22:2; Tyr; Kynurenine |
| 1525 | 3 | S.L./O.St. | 79.1 | SM C16:1; SM (OH) C22:2; 20a-OH-C |
| 1526 | 4 | Ac.Ca./S.L./Am.Ac. | 81.3 | C5:1-DC; SM C24:0; SM (OH) C24:1; Met |
| 1527 | 4 | S.L./Am.Ac. | 79.8 | SM C24:1; Arg; Gln; Phe |
| 1528 | 4 | En.Met/S.L./Am.Ac./O.St. | 81.7 | alpha-KGA; SM (OH) C16:1; Trp; 24-DH-Lanosterol |
| 1529 | 4 | S.L./Am.Ac./B.Am. | 83.4 | SM C18:1; SM (OH) C22:2; Gln; Met-SO |
| 1530 | 5 | Ac.Ca./S.L./Am.Ac. | 82.6 | C6:1; SM C24:1; SM (OH) C22:1; Gly; Orn |
| 1531 | 4 | S.L./Am.Ac. | 79.2 | SM (OH) C14:1; SM (OH) C22:2; Ile; Met |
| 1532 | 4 | S.L./Am.Ac./B.Am. | 83 | SM (OH) C14:1; Arg; His; Met-SO |
| 1533 | 4 | En.Met/Am.Ac. | 80.6 | alpha-KGA; Fum; Arg; Met |
| 1534 | 4 | S.L./Am.Ac./P.G. | 80.4 | SM (OH) C14:1; His; Met; LTB4 |
| 1535 | 4 | En.Met/S.L./Am.Ac./O.St. | 79.2 | alpha-KGA; SM (OH) C22:2; Phe; Cholestenone |
| 1536 | 4 | S.L./Am.Ac./O.St. | 80.3 | SM C16:1; SM (OH) C22:1; Ala; Cholestenone |

TABLE 9-continued

Metabolite combinations describing damage of basal ganglia

| No. | Npar | Chemical Class | Accuracy | Model |
|---|---|---|---|---|
| 1537 | 4 | S.L./Am.Ac. | 80.8 | SM (OH) C22:1; SM (OH) C22:2; Ala; Orn |
| 1538 | 4 | S.L./Am.Ac. | 80.1 | SM C18:1; SM C24:1; SM (OH) C22:1; Ser |
| 1539 | 4 | S.L./Am.Ac./B.Am. | 85.6 | SM C16:0; Phe; Kynurenine; Met-SO |
| 1540 | 5 | Ac.Ca./S.L./Am.Ac./B.Am. | 84.2 | C18; SM C18:1; SM (OH) C24:1; Lys; Met-SO |
| 1541 | 5 | Am.Ac./B.Am. | 84.4 | Gln; Leu; Orn; Val; Ac-Orn |
| 1542 | 5 | S.L./Am.Ac. | 84.6 | SM C16:1; SM C18:1; SM C24:1; SM (OH) C14:1; Ser |
| 1543 | 4 | Ac.Ca./Am.Ac./P.G. | 83.7 | C18:1; Arg; Pro; LTB4 |
| 1544 | 4 | S.L./Am.Ac. | 84 | SM (OH) C14:1; SM (OH) C22:2; Trp; Tyr |
| 1545 | 3 | S.L./Am.Ac. | 79.9 | SM (OH) C22:1; SM (OH) C22:2; Ala |
| 1546 | 6 | S.L./Am.Ac./B.Am./O.St./P.G. | 93.4 | SM (OH) C14:1; SM (OH) C22:2; Arg; Histamine; 25-OH-C; TXB2 |
| 1547 | 4 | En.Met/S.L./O.St. | 82.6 | alpha-KGA; SM C16:0; SM (OH) C14:1; 20a-OH-C |
| 1548 | 4 | S.L./Am.Ac. | 81.2 | SM C24:1; SM (OH) C14:1; Leu; Tyr |
| 1549 | 4 | En.Met/S.L./P.G. | 90.2 | alpha-KGA; SM (OH) C14:1; SM (OH) C22:2; TXB2 |
| 1550 | 4 | En.Met/S.L./Am.Ac./B.Am. | 80.6 | alpha-KGA; SM (OH) C16:1; Orn; Ac-Orn |
| 1551 | 3 | En.Met/S.L./Am.Ac. | 81.8 | Lac; SM C16:1; Met |
| 1552 | 3 | Am.Ac. | 79.1 | His; Met; Orn |
| 1553 | 4 | En.Met/S.L./Am.Ac. | 82.3 | alpha-KGA; SM C16:1; SM C24:1; Tyr |
| 1554 | 4 | En.Met/S.L./Am.Ac. | 85.6 | Lac; SM (OH) C14:1; SM (OH) C22:2; Met |
| 1555 | 4 | S.L./Am.Ac. | 84.3 | SM (OH) C16:1; SM (OH) C22:2; Trp; Tyr |
| 1556 | 3 | Am.Ac./B.Am. | 83 | Gln; Lys; Ac-Orn |
| 1557 | 4 | En.Met/S.L./Am.Ac. | 86.8 | Hex-P; SM (OH) C22:2; Gln; Met |
| 1558 | 4 | Ac.Ca./S.L./Am.Ac. | 82.3 | C10; SM C24:1; SM (OH) C22:1; Ser |
| 1559 | 5 | Ac.Ca./S.L./Am.Ac./B.Am. | 86.3 | C5:1-DC; SM C16:1; SM (OH) C24:1; Gln; Met-SO |
| 1560 | 5 | S.L./B.Am. | 88.4 | SM (OH) C14:1; SM (OH) C24:1; Histamine; Kynurenine; Met-SO |
| 1561 | 6 | S.L./Am.Ac./O.St. | 87.7 | SM C24:1; SM (OH) C22:1; Leu; Lys; Pro; 20a-OH-C |
| 1562 | 4 | Ac.Ca./S.L./Am.Ac. | 82.4 | C5:1-DC; SM C24:1; SM (OH) C14:1; Lys |
| 1563 | 4 | S.L./Am.Ac./B.Am. | 85.7 | SM C16:1; SM (OH) C24:1; Pro; Met-SO |
| 1564 | 4 | S.L./B.Am. | 83 | SM (OH) C22:2; alpha-AAA; Kynurenine; Met-SO |
| 1565 | 5 | S.L./Am.Ac./O.St. | 80.4 | SM C24:1; SM (OH) C22:1; Arg; His; Cholestenone |
| 1566 | 3 | S.L./Am.Ac. | 87.6 | SM C20:2; SM C24:0; Tyr |
| 1567 | 4 | S.L./Am.Ac. | 81.1 | SM C16:1; SM (OH) C22:1; Arg; Asn |
| 1568 | 4 | Ac.Ca./S.L./Am.Ac. | 87.9 | C5:1-DC; SM C16:1; SM (OH) C22:1; Met |
| 1569 | 4 | En.Met/S.L./Am.Ac./B.Am. | 79.2 | Lac; SM C16:0; Orn; Met-SO |
| 1570 | 4 | S.L./Am.Ac./B.Am. | 80.6 | SM (OH) C22:2; Gln; Leu; Ac-Orn |
| 1571 | 4 | S.L./Am.Ac./B.Am. | 81.2 | SM C24:1; Leu; Lys; Ac-Orn |
| 1572 | 4 | S.L./Am.Ac./O.St. | 86.4 | SM (OH) C22:2; Ile; Orn; 24-DH-Lanosterol |
| 1573 | 3 | S.L./Am.Ac. | 84.4 | SM (OH) C14:1; Met; Pro |
| 1574 | 4 | S.L./Am.Ac./B.Am. | 81.6 | Lac; SM (OH) C16:1; SM (OH) C22:1; Met-SO |
| 1575 | 3 | En.Met/S.L./Am.Ac. | 82.7 | alpha-KGA; SM C24:0; Tyr |
| 1576 | 5 | Ac.Ca./S.L./Am.Ac./B.Am. | 86.7 | C14:1; SM (OH) C16:1; SM (OH) C22:1; Pro; Met-SO |
| 1577 | 4 | S.L./Am.Ac. | 83.9 | SM C16:0; SM C24:0; Arg; Tyr |
| 1578 | 3 | S.L./Am.Ac. | 80.6 | SM C16:0; SM (OH) C22:2; Arg |
| 1579 | 4 | S.L./Am.Ac. | 83.5 | SM C16:1; SM (OH) C22:2; Ala; Orn |
| 1580 | 4 | S.L./Am.Ac. | 82.7 | SM C24:0; SM C24:1; SM (OH) C22:2; Ser |
| 1581 | 4 | En.Met/Am.Ac./B.Am. | 81 | H1; Gln; Histamine; Met-SO |
| 1582 | 6 | En.Met/S.L./Am.Ac./B.Am. | 81.9 | Suc; SM C24:1; His; Leu; Lys; Met-SO |
| 1583 | 4 | S.L./B.Am. | 81.7 | SM C24:0; SM (OH) C16:1; Histamine; Met-SO |
| 1584 | 4 | En.Met/Am.Ac./B.Am./O.St. | 84.4 | alpha-KGA; Gln; Ac-Orn; Cholestenone |
| 1585 | 3 | Ac.Ca./S.L./Am.Ac. | 81.8 | C14:1; SM C20:2; Pro |
| 1586 | 4 | S.L./Am.Ac./B.Am. | 80.7 | SM (OH) C22:2; SM (OH) C24:1; Lys; Met-SO |
| 1587 | 4 | En.Met/S.L./Am.Ac./O.St. | 83.5 | alpha-KGA; SM C16:0; Arg; 22R-OH-C |
| 1588 | 6 | En.Met/Ac.Ca./S.L./Am.Ac. | 82.9 | Lac; C14:1-OH; C9; SM C18:1; Orn; Pro |
| 1589 | 5 | En.Met/Ac.Ca./S.L./Am.Ac. | 87.3 | alpha-KGA; Suc; C6:1; SM C24:0; Tyr |
| 1590 | 4 | S.L./Am.Ac. | 81.1 | SM C16:0; His; Met; Pro |
| 1591 | 4 | Ac.Ca./S.L./Am.Ac. | 79.9 | C18:1; SM C18:0; Pro; Tyr |
| 1592 | 4 | S.L./Am.Ac./B.Am. | 81.3 | SM C18:0; SM C18:1; Gln; Met-SO |
| 1593 | 5 | En.Met/Ac.Ca./S.L./B.Am. | 79.8 | alpha-KGA; Lac; C14:1; SM (OH) C22:1; Sarcosine |
| 1594 | 5 | Ac.Ca./S.L./Am.Ac./B.Am./O.St. | 87.1 | C5:1-DC; SM C16:0; Lys; Histamine; 24-DH-Lanosterol |
| 1595 | 4 | S.L./B.Am. | 79.6 | SM C18:1; SM (OH) C14:1; SM (OH) C24:1; Met-SO |
| 1596 | 4 | Ac.Ca./S.L./O.St. | 84.9 | C5:1-DC; SM C18:1; SM C24:0; Cholestenone |
| 1597 | 3 | Am.Ac./O.St. | 83.1 | Arg; Trp; 24-DH-Lanosterol |
| 1598 | 4 | En.Met/S.L./O.St. | 84.3 | alpha-KGA; SM (OH) C22:2; SM (OH) C24:1; 20a-OH-C |
| 1599 | 4 | S.L./Am.Ac./B.Am. | 79.5 | SM C16:1; SM (OH) C24:1; His; Met-SO |
| 1600 | 5 | En.Met/S.L./Am.Ac./B.Am. | 85.3 | alpha-KGA; SM C16:1; SM (OH) C22:1; Orn; Ac-Orn |
| 1601 | 5 | En.Met/S.L./Am.Ac. | 81.2 | Lac; SM C24:1; SM (OH) C22:1; SM (OH) C24:1; Asn |
| 1602 | 4 | Ac.Ca./S.L./Am.Ac. | 83.6 | C6:1; SM (OH) C14:1; Arg; Tyr |
| 1603 | 5 | S.L./Am.Ac./O.St. | 82.8 | SM C16:1; Ile; Orn; Pro; 24-DH-Lanosterol |
| 1604 | 3 | S.L./B.Am. | 83.9 | SM C24:0; SM C24:1; Met-SO |
| 1605 | 4 | S.L./Am.Ac. | 88 | SM C24:1; SM (OH) C22:1; SM (OH) C22:2; Gly |
| 1606 | 4 | Ac.Ca./En.Met/S.L./Am.Ac. | 85.3 | C5:1; H1; SM (OH) C24:1; Met |
| 1607 | 4 | En.Met/S.L./Am.Ac./B.Am. | 88 | Suc; SM (OH) C22:2; Arg; Histamine |
| 1608 | 5 | S.L./Am.Ac./O.St. | 97.9 | SM C16:1; SM (OH) C22:2; Pro; Trp; 20a-OH-C |
| 1609 | 4 | S.L./Am.Ac./B.Am. | 86 | SM (OH) C24:1; Gln; Pro; Ac-Orn |
| 1610 | 5 | S.L./Am.Ac./O.St. | 91.4 | SM C24:0; SM (OH) C24:1; Leu; Tyr; 20a-OH-C |
| 1611 | 4 | S.L./Am.Ac. | 87.8 | SM (OH) C14:1; Arg; Gln; Met |
| 1612 | 4 | S.L./Am.Ac./B.Am. | 81.6 | SM (OH) C22:1; Arg; Gln; Ac-Orn |

TABLE 9-continued

Metabolite combinations describing damage of basal ganglia

| No. | Npar | Chemical Class | Accuracy | Model |
|---|---|---|---|---|
| 1613 | 6 | En.Met/S.L./Am.Ac./O.St. | 83 | Pent-P; SM C18:1; SM (OH) C22:1; Leu; Lys; 20a-OH-C |
| 1614 | 4 | En.Met/S.L./Am.Ac./O.St. | 80.9 | Suc; SM (OH) C24:1; Arg; Cholestenone |
| 1615 | 4 | Ac.Ca./S.L./Am.Ac. | 88.1 | C14:1; SM C16:1; Met; Pro |
| 1616 | 4 | En.Met/S.L./Am.Ac./B.Am. | 85.6 | alpha-KGA; SM C16:1; Met; Creatinine |
| 1617 | 4 | S.L./Am.Ac. | 83.5 | SM (OH) C14:1; SM (OH) C24:1; Ala; Met |
| 1618 | 4 | S.L./Am.Ac./B.Am. | 83.3 | SM C16:0; Pro; Creatinine; Met-SO |
| 1619 | 4 | S.L./Am.Ac. | 83.6 | SM (OH) C22:1; Gln; Met; Orn |
| 1620 | 6 | En.Met/S.L./Am.Ac./B.Am. | 81.8 | Lac; SM (OH) C24:1; Pro; Trp; Histamine; Met-SO |
| 1621 | 5 | Ac.Ca./S.L./Am.Ac./P.G. | 86.3 | C6:1; SM (OH) C22:2; Arg; His; TXB2 |
| 1622 | 4 | S.L./Am.Ac. | 84.9 | SM C16:0; SM C24:0; Ala; Met |
| 1623 | 4 | En.Met/S.L./Am.Ac. | 84.3 | Suc; SM (OH) C24:1; Pro; Tyr |
| 1624 | 4 | S.L./Am.Ac./O.St. | 86.7 | SM C16:0; Pro; Trp; Cholestenone |
| 1625 | 3 | En.Met/Am.Ac. | 83.7 | Lac; Gln; Met |
| 1626 | 4 | S.L./Am.Ac./O.St. | 82.3 | SM C16:0; Lys; Met; Cholestenone |
| 1627 | 6 | En.Met/S.L./Am.Ac./B.Am. | 80.1 | Hex-P; SM C18:1; SM (OH) C22:1; Met; Kynurenine; Met-SO |
| 1628 | 5 | S.L./Am.Ac./P.G. | 90.7 | SM C18:1; SM C24:1; SM (OH) C22:2; Lys; TXB2 |
| 1629 | 4 | S.L./Am.Ac. | 90 | SM C24:1; SM (OH) C22:2; Ala; Orn |
| 1630 | 4 | En.Met/S.L./Am.Ac./B.Am. | 89.9 | Lac; SM (OH) C22:2; Gln; Met-SO |
| 1631 | 4 | S.L./Am.Ac./B.Am. | 84 | SM C24:1; SM (OH) C14:1; Pro; Histamine |
| 1632 | 3 | S.L./Am.Ac./B.Am. | 81.2 | SM (OH) C24:1; Orn; Met-SO |
| 1633 | 4 | En.Met/S.L./Am.Ac./B.Am. | 89.5 | Lac; SM (OH) C14:1; Gln; Met-SO |
| 1634 | 4 | Ac.Ca./S.L./Am.Ac. | 83.7 | C6:1; SM C24:0; SM C24:1; Tyr |
| 1635 | 4 | Ac.Ca./S.L./Am.Ac. | 81.9 | C5:1-DC; SM (OH) C14:1; Arg; Pro |
| 1636 | 4 | S.L./Am.Ac. | 87.3 | SM C16:1; SM C18:1; SM C24:1; Ala |
| 1637 | 4 | S.L./B.Am./O.St. | 80.1 | SM C24:0; SM C16:1; Met-SO; 24S-OH-C |
| 1638 | 4 | S.L./Am.Ac. | 82.6 | SM C18:1; SM (OH) C22:2; Ala; Gln |
| 1639 | 3 | Ac.Ca./S.L./Am.Ac. | 82.2 | C14:1; SM (OH) C22:2; Pro |
| 1640 | 4 | S.L./Am.Ac./B.Am. | 92.1 | SM (OH) C14:1; Leu; Met; Kynurenine |
| 1641 | 4 | S.L./B.Am. | 82.9 | SM C24:1; SM (OH) C22:1; SM (OH) C24:1; Met-SO |
| 1642 | 4 | S.L./Am.Ac./O.St. | 89.1 | SM (OH) C22:2; Orn; Trp; 24-DH-Lanosterol |
| 1643 | 4 | En.Met/S.L./Am.Ac. | 81.5 | Pent-P; SM (OH) C14:1; Arg; Pro |
| 1644 | 5 | S.L./Am.Ac./B.Am. | 90.9 | SM C18:1; SM (OH) C14:1; SM (OH) C16:1; Tyr; Kynurenine |
| 1645 | 4 | S.L./Am.Ac. | 82.7 | SM C16:0; SM (OH) C14:1; Lys; Met |
| 1646 | 4 | S.L./Am.Ac./B.Am. | 82.9 | SM C24:1; SM (OH) C22:2; Arg; Histamine |
| 1647 | 6 | Ac.Ca./S.L./Am.Ac./B.Am./O.St. | 91 | C5:1-DC; SM (OH) C14:1; SM (OH) C22:1; Orn; Histamine; Cholestenone |
| 1648 | 3 | S.L./Am.Ac./B.Am. | 88.5 | SM C16:1; Tyr; Kynurenine |
| 1649 | 4 | Ac.Ca./S.L./Am.Ac./O.St. | 82 | C6:1; SM C16:0; Pro; 20a-OH-C |
| 1650 | 4 | S.L./Am.Ac./B.Am. | 83.6 | SM C26:1; His; Orn; Met-SO |
| 1651 | 4 | Ac.Ca./S.L./Am.Ac. | 92.3 | C5:1-DC; SM C16:1; SM C14:1; Pro |
| 1652 | 5 | S.L./Am.Ac./O.St. | 88.9 | SM (OH) C22:2; His; Orn; Trp; 24-DH-Lanosterol |
| 1653 | 3 | S.L./Am.Ac./P.G. | 80 | SM (OH) C14:1; Lys; TXB2 |
| 1654 | 4 | S.L./Am.Ac. | 82.2 | SM (OH) C14:1; Ala; His; Met |
| 1655 | 4 | S.L./Am.Ac. | 81.4 | SM C16:0; SM (OH) C22:1; SM (OH) C22:2; Met |
| 1656 | 4 | En.Met/Am.Ac. | 81.1 | Suc; Orn; Pro; Tyr |
| 1657 | 4 | En.Met/S.L./B.Am. | 79.7 | alpha-KGA; SM C16:0; SM (OH) C22:2; Ac-Orn |
| 1658 | 3 | S.L./Am.Ac./B.Am. | 79.6 | SM (OH) C22:1; Arg; Met-SO |
| 1659 | 3 | En.Met/S.L./Am.Ac. | 79.1 | Lac; SM C24:0; Met |
| 1660 | 5 | S.L./Am.Ac./B.Am. | 91.4 | SM C16:1; Gln; Orn; Pro; Met-SO |
| 1661 | 4 | En.Met/S.L./B.Am. | 85.3 | alpha-KGA; SM C24:0; Histamine; Met-SO |
| 1662 | 3 | Am.Ac. | 85.8 | His; Lys; Met |
| 1663 | 4 | S.L./Am.Ac. | 90 | SM C20:2; SM (OH) C14:1; SM (OH) C22:1; Tyr |
| 1664 | 6 | Ac.Ca./En.Met/S.L./Am.Ac./B.Am. | 85.2 | C14:1; H1; SM (OH) C14:1; Pro; Tyr; alpha-AAA |
| 1665 | 4 | S.L./Am.Ac. | 79.9 | SM C24:1; SM (OH) C16:1; Met; Orn |
| 1666 | 3 | S.L./Am.Ac. | 88.8 | SM C24:1; SM (OH) C22:2; Gly |
| 1667 | 3 | S.L./Am.Ac./B.Am. | 82.7 | SM (OH) C24:1; Gln; Met-SO |
| 1668 | 4 | En.Met/S.L./Am.Ac. | 81.6 | alpha-KGA; SM C16:1; SM C24:1; Ser |
| 1669 | 5 | En.Met/S.L./Am.Ac. | 87.4 | Lac; SM C16:1; SM (OH) C14:1; His; Met |
| 1670 | 4 | S.L./Am.Ac. | 79.7 | SM C16:0; SM C18:1; SM (OH) C22:1; Met |
| 1671 | 5 | S.L./Am.Ac./O.St. | 93 | SM C16:1; SM (OH) C14:1; Arg; Leu; 20a-OH-C |
| 1672 | 4 | En.Met/S.L./Am.Ac. | 79.9 | Pent-P; SM C18:1; SM (OH) C14:1; Arg |
| 1673 | 4 | Am.Ac./B.Am. | 87.5 | Gln; His; Lys; Ac-Orn |
| 1674 | 4 | S.L./Am.Ac./B.Am. | 80.7 | SM C20:2; SM (OH) C14:1; His; Met-SO |
| 1675 | 5 | S.L./Am.Ac./O.St. | 89.1 | SM C24:1; SM (OH) C22:1; SM (OH) C22:2; Gly; Cholestenone |
| 1676 | 4 | S.L./B.Am. | 82.9 | SM C24:0; Ac-Orn; Histamine; Met-SO |
| 1677 | 4 | S.L./Am.Ac. | 82.2 | SM (OH) C22:1; SM (OH) C22:2; Arg; Asn |
| 1678 | 4 | S.L./Am.Ac. | 86.6 | SM (OH) C14:1; SM (OH) C22:2; Arg; Met |
| 1679 | 4 | En.Met/S.L./Am.Ac. | 85.9 | Fum; SM C16:1; Arg; Met |
| 1680 | 4 | S.L./Am.Ac./P.G. | 93.1 | SM (OH) C14:1; Gln; Pro; TXB2 |
| 1681 | 4 | En.Met/S.L./Am.Ac. | 82.9 | Fum; SM (OH) C14:1; Met; Orn |
| 1682 | 5 | En.Met/S.L./Am.Ac. | 81.9 | Lac; SM C18:0; SM (OH) C14:1; Asn; Gln |
| 1683 | 4 | S.L./Am.Ac./B.Am. | 83 | SM C24:0; Orn; Phe; Met-SO |
| 1684 | 4 | En.Met/S.L./B.Am. | 80 | alpha-KGA; SM C16:0; SM (OH) C14:1; Ac-Orn |
| 1685 | 6 | Ac.Ca./S.L./Am.Ac./P.G. | 85.5 | C6:1; SM C20:2; SM C24:0; Gln; Phe; 8-iso-PGF2a |
| 1686 | 4 | Ac.Ca./S.L./Am.Ac. | 80.4 | C6:1; SM C16:0; SM (OH) C22:1; Met |
| 1687 | 5 | S.L./Am.Ac./B.Am./O.St. | 80.3 | SM C16:0; SM C18:0; Orn; Met-SO; 25-OH-C |
| 1688 | 6 | En.Met/S.L./Am.Ac./B.Am. | 79.1 | OAA; Suc; SM C24:1; Orn; alpha-AAA; Met-SO |

TABLE 9-continued

Metabolite combinations describing damage of basal ganglia

| No. | Npar | Chemical Class | Accuracy | Model |
|---|---|---|---|---|
| 1689 | 4 | S.L./B.Am. | 81.9 | SM C18:1; SM (OH) C22:2; Kynurenine; Met-SO |
| 1690 | 6 | S.L./Am.Ac./B.Am./O.St. | 80.7 | SM C24:1; SM (OH) C14:1; SM (OH) C16:1; Arg; Histamine; 20a-OH-C |
| 1691 | 4 | En.Met/S.L./B.Am./O.St. | 79.3 | alpha-KGA; SM (OH) C22:1; Ac-Orn; 25-OH-C |
| 1692 | 5 | En.Met/S.L./Am.Ac./B.Am./O.St. | 86.5 | Suc; SM C24:1; Lys; Ac-Orn; 25-OH-C |
| 1693 | 4 | S.L./Am.Ac./Am.Ac./O.St. | 85.2 | SM C24:0; Arg; Met-SO; Cholestenone |
| 1694 | 4 | S.L./Am.Ac. | 80.8 | SM C16:0; SM (OH) C16:1; Gly; Met |
| 1695 | 4 | En.Met/S.L./Am.Ac. | 79.1 | Fum; SM (OH) C22:2; His; Met |
| 1696 | 4 | S.L./Am.Ac. | 81.3 | SM C18:1; SM (OH) C14:1; SM (OH) C22:2; Ser |
| 1697 | 4 | S.L./Am.Ac./B.Am./O.St. | 79.4 | SM C24:0; His; Met-SO; Cholestenone |
| 1698 | 4 | En.Met/S.L./Am.Ac. | 83.2 | alpha-KGA; SM (OH) C22:1; Met; Pro |
| 1699 | 4 | S.L./Am.Ac. | 83.1 | SM (OH) C16:1; Gln; Met; Orn |
| 1700 | 4 | S.L./Am.Ac. | 86.4 | SM (OH) C22:1; SM (OH) C22:2; Met; Trp |
| 1701 | 3 | S.L./Am.Ac. | 86.1 | SM C24:0; SM (OH) C22:1; Tyr |
| 1702 | 4 | S.L./Am.Ac. | 87.7 | SM C24:0; SM (OH) C22:2; Met; Pro |
| 1703 | 5 | En.Met/S.L./Am.Ac./O.St. | 96 | alpha-KGA; SM (OH) C22:2; Gln; Tyr; 20a-OH-C |
| 1704 | 4 | Ac.Ca./S.L./Am.Ac. | 91.4 | C5:1-DC; C6:1; SM C16:1; Pro |
| 1705 | 3 | Ac.Ca./S.L. | 80.6 | C5:1-DC; C6:1; SM (OH) C22:2 |
| 1706 | 4 | S.L./B.Am. | 89.6 | SM C16:0; SM (OH) C22:1; Kynurenine; Met-SO |
| 1707 | 4 | S.L./Am.Ac./B.Am. | 83.6 | SM C24:1; SM (OH) C24:1; Lys; Ac-Orn |
| 1708 | 4 | Ac.Ca./S.L./Am.Ac. | 85.9 | C10:2; SM (OH) C14:1; Met; Pro |
| 1709 | 4 | S.L./Am.Ac./B.Am. | 85.3 | SM C16:0; Lys; Ac-Orn; Histamine |
| 1710 | 4 | Ac.Ca./S.L./Am.Ac./B.Am. | 82 | C6:1; SM C16:0; Arg; Met-SO |
| 1711 | 4 | S.L./Am.Ac./B.Am. | 86.6 | SM C16:0; SM (OH) C14:1; Arg; Met-SO |
| 1712 | 5 | Ac.Ca./Am.Ac./O.St. | 84.3 | C14:1; Arg; Phe; Pro; 24-DH-Lanosterol |
| 1713 | 4 | S.L./Am.Ac./P.G. | 85.3 | SM C24:0; Lys; Met; LTB4 |
| 1714 | 4 | Ac.Ca./Am.Ac./B.Am. | 85.6 | C14:1; Leu; Met; Kynurenine |
| 1715 | 4 | Ac.Ca./S.L./Am.Ac. | 82 | C6:1; SM C16:1; Arg; Tyr |
| 1716 | 4 | S.L./Am.Ac. | 86.6 | SM C24:1; SM (OH) C14:1; Pro; Trp |
| 1717 | 4 | En.Met/S.L./Am.Ac./P.G. | 81.4 | alpha-KGA; SM C24:0; Met; 8-iso-PGF2a |
| 1718 | 5 | S.L./Am.Ac./B.Am. | 89.1 | SM (OH) C14:1; SM (OH) C24:1; Gln; Pro; Met-SO |
| 1719 | 4 | S.L./Am.Ac./B.Am. | 79.4 | SM C16:0; SM C24:0; Met; Met-SO |
| 1720 | 3 | S.L./Am.Ac. | 80.7 | SM C16:1; SM C20:2; Phe |
| 1721 | 4 | S.L./Am.Ac./B.Am. | 81.6 | SM (OH) C14:1; Gln; Ac-Orn; Histamine |
| 1722 | 4 | S.L./Am.Ac. | 83.6 | SM C16:1; SM C18:0; Met; Pro |
| 1723 | 5 | S.L./Am.Ac./B.Am. | 86.5 | SM C24:1; SM (OH) C14:1; Met; Pro; Histamine |
| 1724 | 4 | S.L./Am.Ac. | 84.8 | SM C24:0; SM (OH) C22:1; Met; Ser |
| 1725 | 4 | S.L./Am.Ac. | 79.6 | SM (OH) C14:1; Met; Tyr; Val |
| 1726 | 4 | S.L./Am.Ac./B.Am. | 81.7 | SM (OH) C14:1; His; Pro; Met-SO |
| 1727 | 5 | En.Met/S.L./Am.Ac. | 89 | Suc; SM C16:1; SM (OH) C14:1; Pro; Tyr |
| 1728 | 4 | S.L./Am.Ac./P.G. | 91.2 | SM (OH) C14:1; SM (OH) C16:1; Lys; TXB2 |
| 1729 | 5 | Am.Ac./B.Am. | 82.1 | Gln; Pro; Tyr; alpha-AAA; Met-SO |
| 1730 | 5 | En.Met/S.L./Am.Ac./O.St. | 81.5 | Pent-P; SM (OH) C22:1; Orn; Pro; 24-DH-Lanosterol |
| 1731 | 5 | Ac.Ca./S.L./Am.Ac./B.Am./O.St. | 83.5 | C5:1-DC; SM (OH) C24:1; Tyr; alpha-AAA; 24-DH-Lanosterol |
| 1732 | 4 | S.L./Am.Ac./B.Am./O.St. | 81.3 | SM C16:0; Lys; Ac-Orn; Cholestenone |
| 1733 | 4 | S.L./Am.Ac./B.Am. | 84.6 | SM C16:1; SM (OH) C22:2; Orn; Ac-Orn |
| 1734 | 4 | S.L./Am.Ac./P.G. | 82.9 | SM (OH) C22:1; Orn; Tyr; LTB4 |
| 1735 | 6 | S.L./Am.Ac./B.Am. | 88.2 | SM C24:0; SM C24:1; SM (OH) C16:1; Orn; Pro; Ac-Orn |
| 1736 | 4 | Ac.Ca./S.L./Am.Ac. | 79.7 | C6:1; SM C16:1; SM C20:2; Phe |
| 1737 | 5 | Ac.Ca./S.L./Am.Ac./O.St. | 82.3 | C14:1; SM (OH) C24:1; Arg; Leu; 20a-OH-C |
| 1738 | 4 | S.L./Am.Ac./B.Am. | 81.4 | SM C20:2; SM C24:0; Phe; Met-SO |
| 1739 | 4 | S.L./Am.Ac./B.Am. | 84.2 | SM C16:1; SM (OH) C22:1; Phe; Met-SO |
| 1740 | 4 | S.L./B.Am./O.St. | 80.7 | SM C18:0; SM C24:0; Met-SO; Cholestenone |
| 1741 | 5 | En.Met/S.L./Am.Ac. | 83.2 | Lac; SM C24:1; SM (OH) C14:1; SM (OH) C16:1; Asn |
| 1742 | 4 | En.Met/S.L./Am.Ac. | 84 | Lac; SM (OH) C22:1; Met; Pro |
| 1743 | 4 | Ac.Ca./S.L./Am.Ac. | 84.9 | C10; SM (OH) C22:1; Met; Orn |
| 1744 | 4 | Am.Ac. | 83.2 | Gln; Met; Pro; Trp |
| 1745 | 4 | En.Met/S.L./Am.Ac. | 86.9 | H1; SM C18:1; Gln; Tyr |
| 1746 | 4 | S.L./Am.Ac./B.Am. | 83.4 | SM (OH) C14:1; SM (OH) C22:1; Phe; Met-SO |
| 1747 | 5 | Ac.Ca./S.L./Am.Ac./B.Am. | 83 | C6:1; SM C18:1; Arg; Gln; total DMA |
| 1748 | 4 | Am.Ac./O.St. | 82.1 | Arg; Gln; Tyr; 24-DH-Lanosterol |
| 1749 | 4 | S.L./Am.Ac. | 84.1 | SM (OH) C22:1; His; Lys; Met |
| 1750 | 6 | En.Met/S.L./Am.Ac./P.G. | 83.7 | Fum; SM (OH) C14:1; Arg; Met; Tyr; AA |
| 1751 | 5 | Am.Ac./O.St. | 84.5 | Arg; Gln; Met; 24-DH-Lanosterol; Cholestenone |
| 1752 | 4 | Ac.Ca./S.L./Am.Ac. | 84.1 | C6:1; SM C16:1; Phe; Pro |
| 1753 | 5 | En.Met/S.L./Am.Ac./B.Am. | 85.2 | Fum; SM C24:1; Met; Histamine |
| 1754 | 4 | En.Met/S.L./Am.Ac. | 83 | alpha-KGA; SM C16:0; SM C24:1; Ala |
| 1755 | 6 | Ac.Ca./Am.Ac./P.G. | 83.9 | C6:1; Lys; Met; Trp; Val; 8-iso-PGF2a |
| 1756 | 4 | En.Met/S.L./B.Am. | 87.7 | Lac; SM C16:1; SM (OH) C22:1; Met-SO |
| 1757 | 4 | En.Met/S.L./Am.Ac./O.St. | 79.8 | alpha-KGA; SM (OH) C22:2; Tyr; Cholestenone |
| 1758 | 4 | S.L./Am.Ac./B.Am. | 80 | SM C16:0; Arg; Histamine; Met-SO |
| 1759 | 4 | S.L./Am.Ac./P.G. | 82.5 | SM (OH) C14:1; SM (OH) C22:2; Leu; TXB2 |
| 1760 | 4 | En.Met/S.L./B.Am./O.St. | 82.2 | Fum; (OH) C22:1; Met-SO; Cholestenone |
| 1761 | 5 | Ac.Ca./S.L./Am.Ac./O.St. | 88.2 | C5:1-DC; SM C24:0; SM (OH) C22:1; Arg; 24-DH-Lanosterol |
| 1762 | 6 | S.L./Am.Ac. | 84.3 | SM C24:0; SM (OH) C14:1; SM (OH) C22:1; His; Lys; Met |
| 1763 | 4 | Ac.Ca./S.L./Am.Ac. | 81 | C5:1-DC; SM C16:0; SM C18:1; Gln |
| 1764 | 3 | S.L./Am.Ac. | 82.9 | SM (OH) C22:1; Arg; Tyr |

TABLE 9-continued

Metabolite combinations describing damage of basal ganglia

| No. | Npar | Chemical Class | Accuracy | Model |
|---|---|---|---|---|
| 1765 | 4 | S.L./Am.Ac. | 79.9 | SM C16:0; SM (OH) C16:1; Met; Orn |
| 1766 | 5 | S.L./Am.Ac./B.Am./O.St. | 88.1 | SM C16:1; SM (OH) C22:2; Trp; Histamine; 20a-OH-C |
| 1767 | 3 | Ac.Ca./S.L./B.Am. | 80.6 | C6:1; SM (OH) C22:1; Ac-Orn |
| 1768 | 4 | S.L./Am.Ac./P.G. | 82.1 | SM C18:1; Arg; Gln; 8-iso-PGF2a |
| 1769 | 4 | En.Met/S.L./Am.Ac. | 80.2 | alpha-KGA; SM C16:1; SM C24:1; Phe |
| 1770 | 5 | S.L./Am.Ac./B.Am. | 83.8 | SM (OH) C22:2; SM (OH) C24:1; Lys; Met; Met-SO |
| 1771 | 4 | Ac.Ca./S.L./Am.Ac. | 79.8 | C6:1; SM (OH) C14:1; Leu; Met |
| 1772 | 4 | S.L./Am.Ac./B.Am. | 80.8 | SM (OH) C16:1; Met; Trp; Kynurenine |
| 1773 | 4 | S.L./Am.Ac. | 82.4 | SM C16:1; SM (OH) C16:1; SM (OH) C22:1; Tyr |
| 1774 | 3 | S.L./Am.Ac. | 80.6 | SM (OH) C22:1; SM (OH) C24:1; Met |
| 1775 | 4 | S.L./Am.Ac. | 80.9 | SM C16:1; SM C24:1; Gly; Lys |
| 1776 | 4 | S.L./Am.Ac./O.St. | 80.2 | SM C18:1; SM C24:0; Ser; Cholestenone |
| 1777 | 5 | S.L./Am.Ac. | 88.3 | SM C24:0; SM (OH) C22:2; Lys; Met; Trp |
| 1778 | 4 | En.Met/S.L./Am.Ac./B.Am. | 80.6 | Lac; SM C24:1; Arg; Histamine |
| 1779 | 4 | Ac.Ca./S.L./Am.Ac./P.G. | 85.2 | C5:1-DC; SM (OH) C14:1; Orn; LTB4 |
| 1780 | 4 | S.L./Am.Ac. | 82.9 | SM C16:0; SM C24:1; SM (OH) C22:2; Arg |
| 1781 | 4 | En.Met/S.L./Am.Ac./O.St. | 86.4 | alpha-KGA; SM (OH) C22:2; Gln; 20a-OH-C |
| 1782 | 4 | En.Met/S.L./Am.Ac./B.Am. | 83.1 | alpha-KGA; SM (OH) C14:1; Tyr; Ac-Orn |
| 1783 | 4 | S.L./Am.Ac. | 89.3 | SM (OH) C14:1; SM (OH) C22:2; Gly; Orn |
| 1784 | 4 | Ac.Ca./Am.Ac. | 79 | C18; Met; Phe; Pro |
| 1785 | 4 | En.Met/S.L./Am.Ac./O.St. | 80.8 | alpha-KGA; SM C18:1; SM (OH) C14:1; Ac-Orn |
| 1786 | 4 | S.L./Am.Ac./B.Am. | 83.6 | SM C24:0; His; Lys; Ac-Orn |
| 1787 | 3 | Ac.Ca./S.L. | 79.3 | C5:1-DC; SM C16:0; SM (OH) C16:1 |
| 1788 | 4 | En.Met/S.L./B.Am. | 84.1 | Lac; SM C24:0; SM C24:1; Met-SO |
| 1789 | 4 | En.Met/Ac.Ca./Am.Ac./B.Am. | 79.5 | alpha-KGA; C14:1; Met; Creatinine |
| 1790 | 4 | Ac.Ca./S.L./Am.Ac. | 79.1 | C5:1-DC; SM C16:0; SM C18:1; Pro |
| 1791 | 5 | Ac.Ca./S.L./Am.Ac./O.St. | 80.1 | C14:1; SM C24:1; Lys; Val; 20a-OH-C |
| 1792 | 3 | S.L./Am.Ac. | 80.3 | SM C16:0; SM (OH) C22:2; Tyr |
| 1793 | 4 | S.L./Am.Ac. | 79 | SM C18:1; SM C24:1; SM (OH) C22:2; Ser |
| 1794 | 3 | S.L./Am.Ac./B.Am. | 89 | SM C16:0; Tyr; Kynurenine |
| 1795 | 6 | Ac.Ca./S.L./Am.Ac./B.Am. | 85 | C18:2; SM C16:1; SM C18:0; Lys; Pro; Met-SO |
| 1796 | 4 | S.L./Am.Ac. | 84.2 | SM C16:0; SM (OH) C16:1; Trp; Tyr |
| 1797 | 4 | S.L./Am.Ac. | 85.1 | SM C24:1; SM (OH) C16:1; SM (OH) C22:1; Tyr |
| 1798 | 4 | S.L./Am.Ac. | 84.5 | SM C24:0; SM (OH) C16:1; Pro; Tyr |
| 1799 | 5 | S.L./Am.Ac./B.Am./O.St. | 79 | SM C24:1; SM (OH) C14:1; Thr; Kynurenine; 24-DH-Lanosterol |
| 1800 | 4 | S.L./Am.Ac. | 86.4 | SM C16:1; SM (OH) C22:2; Met; Pro |
| 1801 | 5 | Ac.Ca./S.L./Am.Ac. | 83.4 | C14:1; SM (OH) C16:1; SM (OH) C22:1; Met; Tyr |
| 1802 | 5 | S.L./Am.Ac./B.Am. | 83.3 | SM (OH) C16:1; Pro; Trp; Ac-Orn; Histamine |
| 1803 | 4 | S.L./Am.Ac./B.Am. | 81.8 | SM (OH) C22:1; SM (OH) C22:2; Met; Histamine |
| 1804 | 4 | S.L./Am.Ac./P.G. | 83.4 | SM (OH) C16:1; SM (OH) C22:2; Pro; TXB2 |
| 1805 | 4 | En.Met/S.L./B.Am. | 87.4 | Lac; SM (OH) C22:1; SM (OH) C24:1; Met-SO |
| 1806 | 4 | S.L./Am.Ac./B.Am. | 85.1 | SM (OH) C14:1; SM (OH) C22:2; Trp; Met-SO |
| 1807 | 4 | S.L./Am.Ac./B.Am. | 87.4 | SM C16:0; SM (OH) C22:2; Phe; Kynurenine |
| 1808 | 4 | S.L./Am.Ac. | 82.3 | SM C24:1; SM (OH) C22:2; Ala; Met |
| 1809 | 5 | En.Met/Ac.Ca./S.L./Am.Ac. | 82.9 | Lac; C5:1-DC; SM C16:0; SM (OH) C24:1; Gln |
| 1810 | 4 | S.L./Am.Ac./B.Am. | 82.4 | Pent-P; SM (OH) C22:2; Met; Kynurenine |
| 1811 | 4 | Ac.Ca./S.L. | 86.9 | C5:1-DC; SM C16:1; SM (OH) C14:1; SM (OH) C22:2 |
| 1812 | 5 | En.Met/S.L./Am.Ac./B.Am. | 85.2 | Fum; SM C24:1; His; Ac-Orn; Histamine |
| 1813 | 5 | En.Met/Am.Ac./B.Am./O.St. | 81.8 | alpha-KGA; His; Leu; total DMA; 20a-OH-C |
| 1814 | 5 | S.L./Am.Ac./B.Am. | 89.5 | SM C16:0; SM (OH) C22:2; Gln; Pro; Ac-Orn |
| 1815 | 4 | S.L./Am.Ac./B.Am. | 79.5 | SM (OH) C16:1; SM (OH) C22:1; Met; Kynurenine |
| 1816 | 4 | S.L./Am.Ac./O.St. | 87.6 | SM (OH) C16:1; Met; Trp; Cholestenone |
| 1817 | 4 | S.L./Am.Ac./O.St. | 93.3 | SM C24:1; Arg; Trp; 24-DH-Lanosterol |
| 1818 | 4 | S.L./Am.Ac./B.Am. | 87.5 | SM C24:0; SM C24:1; Lys; Met-SO |
| 1819 | 4 | S.L./B.Am. | 85.8 | SM (OH) C22:1; SM (OH) C22:2; Ac-Orn; Histamine |
| 1820 | 4 | S.L./Am.Ac./O.St. | 84.7 | SM (OH) C22:1; His; Orn; 22R-OH-C |
| 1821 | 4 | S.L./Am.Ac./P.G. | 89.6 | SM C24:1; Orn; Trp; LTB4 |
| 1822 | 4 | En.Met/S.L./Am.Ac. | 81.3 | Suc; SM C24:1; SM (OH) C16:1; Orn |
| 1823 | 5 | S.L./Am.Ac./B.Am. | 81.4 | SM (OH) C14:1; SM (OH) C22:2; His; Ac-Orn; Serotonin |
| 1824 | 4 | S.L./Am.Ac./O.St. | 81.2 | SM (OH) C14:1; SM (OH) C22:2; Tyr; Cholestenone |
| 1825 | 4 | S.L./B.Am. | 86.1 | SM (OH) C14:1; SM (OH) C22:1; Histamine; Met-SO |
| 1826 | 4 | Ac.Ca./S.L./Am.Ac. | 82.1 | C5:1-DC; SM (OH) C16:1; SM (OH) C22:1; Orn |
| 1827 | 5 | S.L./Am.Ac. | 80.1 | SM C16:0; SM C20:2; Gln; Leu; Ac-Orn |
| 1828 | 5 | S.L./Am.Ac./O.St. | 87.4 | SM (OH) C14:1; SM (OH) C22:1; SM (OH) C22:2; Orn; 22R-OH-C |
| 1829 | 4 | S.L./Am.Ac./B.Am. | 83 | SM C20:2; SM (OH) C14:1; Gln; Met-SO |
| 1830 | 5 | En.Met/S.L./Am.Ac. | 81.1 | alpha-KGA; Lac; SM C24:0; SM (OH) C22:2; Phe |
| 1831 | 4 | Ac.Ca./S.L./B.Am. | 79.5 | C6:1; SM (OH) C14:1; SM (OH) C22:2; Ac-Orn |
| 1832 | 4 | Ac.Ca./S.L./Am.Ac. | 79.7 | C6:1; SM C18:1; SM (OH) C14:1; Asn |
| 1833 | 3 | S.L./Am.Ac./O.St. | 79.8 | SM C24:1; Arg; Cholestenone |
| 1834 | 4 | S.L./Am.Ac. | 79.5 | SM C24:0; SM (OH) C24:1; Met; Phe |
| 1835 | 5 | S.L./Am.Ac. | 84.8 | SM C16:0; SM C16:1; SM C24:0; Ala; Met |
| 1836 | 4 | En.Met/S.L./Am.Ac. | 85.6 | Fum; SM (OH) C22:1; Arg; Met |
| 1837 | 4 | S.L./Am.Ac./B.Am. | 85.7 | SM C16:1; SM C24:1; Gly; alpha-AAA |
| 1838 | 6 | S.L./Am.Ac./O.St. | 90.9 | SM C16:1; SM C18:1; SM (OH) C16:1; Gln; Tyr; 20a-OH-C |
| 1839 | 5 | S.L./Am.Ac. | 83 | SM C16:1; SM (OH) C14:1; Arg; His; Tyr |
| 1840 | 5 | En.Met/S.L./B.Am. | 80.5 | alpha-KGA; Fum; SM C24:0; SM C24:1; Sarcosine |

TABLE 9-continued

Metabolite combinations describing damage of basal ganglia

| No. | Npar | Chemical Class | Accuracy | Model |
|---|---|---|---|---|
| 1841 | 5 | S.L./Am.Ac./B.Am. | 79.1 | SM C18:0; SM (OH) C22:2; His; Trp; total DMA |
| 1842 | 6 | S.L./Am.Ac./B.Am./P.G. | 82.8 | SM C16:1; Gln; Orn; Pro; Histamine; 8-iso-PGF2a |
| 1843 | 5 | S.L./Am.Ac./P.G. | 96.3 | SM (OH) C16:1; SM (OH) C22:2; SM (OH) C24:1; Lys; TXB2 |
| 1844 | 4 | S.L./Am.Ac. | 81.5 | SM C16:1; SM C18:0; SM C18:1; Tyr |
| 1845 | 4 | S.L./Am.Ac. | 79.8 | SM C16:0; SM C18:1; SM (OH) C22:2; Tyr |
| 1846 | 4 | En.Met/S.L./Am.Ac. | 84.2 | Lac; SM C16:1; SM (OH) C16:1; Met |
| 1847 | 4 | S.L./Am.Ac. | 85.6 | SM C16:0; SM C20:2; SM C24:0; Tyr |
| 1848 | 4 | S.L./Am.Ac./B.Am. | 85.3 | SM C20:2; SM (OH) C22:1; Lys; Met-SO |
| 1849 | 5 | S.L./Am.Ac./O.St. | 82.6 | SM (OH) C16:1; Gln; Orn; Phe; 24-DH-Lanosterol |
| 1850 | 4 | S.L./Am.Ac. | 81.8 | SM C18:1; SM C20:2; SM (OH) C22:2; Tyr |
| 1851 | 3 | En.Met/Am.Ac. | 88 | Fum; Gln; Met |
| 1852 | 5 | S.L./Am.Ac./B.Am. | 81.8 | SM C16:1; SM C24:1; Arg; Phe; Histamine |
| 1853 | 5 | S.L./Am.Ac./B.Am. | 88.2 | SM C24:0; SM (OH) C22:1; SM (OH) C24:1; Pro; Met-SO |
| 1854 | 5 | S.L./Am.Ac. | 83.4 | SM C18:0; SM (OH) C14:1; Gln; Met; Phe |
| 1855 | 4 | Ac.Ca./S.L./Am.Ac./B.Am. | 90.5 | C6:1; SM (OH) C22:1; Trp; Met-SO |
| 1856 | 4 | Am.Ac./B.Am. | 79.8 | Gln; Met; Trp; total DMA |
| 1857 | 4 | S.L./Am.Ac./B.Am./P.G. | 85.6 | SM (OH) C22:1; Gln; Met-SO; LTB4 |
| 1858 | 4 | Ac.Ca./S.L./Am.Ac. | 80.3 | C6:1; SM C16:0; Arg; Tyr |
| 1859 | 4 | S.L./Am.Ac./B.Am./O.St. | 84.6 | SM C16:0; Trp; Met-SO; Cholestenone |
| 1860 | 4 | S.L./Am.Ac. | 81.1 | SM C18:1; SM C24:1; SM (OH) C22:1; Thr |
| 1861 | 4 | S.L./Am.Ac./O.St. | 87.7 | SM C18:1; SM (OH) C14:1; Trp; 24-DH-Lanosterol |
| 1862 | 4 | S.L./Am.Ac./B.Am. | 80.9 | SM C18:1; SM (OH) C22:2; Trp; Histamine |
| 1863 | 4 | En.Met/S.L./Am.Ac./B.Am. | 83.5 | Lac; SM C16:0; Met; Kynurenine |
| 1864 | 5 | S.L./Am.Ac./B.Am./O.St. | 88.1 | SM C16:0; Met; Tyr; Kynurenine; Cholestenone |
| 1865 | 3 | S.L./Am.Ac. | 79.6 | SM C16:1; SM C20:2; Leu |
| 1866 | 5 | En.Met/S.L./Am.Ac. | 83.4 | Suc; SM (OH) C16:1; Arg; Met; Orn |
| 1867 | 5 | En.Met/Ac.Ca./S.L./Am.Ac. | 79.3 | alpha-KGA; C14:1; SM (OH) C22:2; Met |
| 1868 | 6 | Ac.Ca./S.L./Am.Ac./B.Am. | 88.9 | C14:1-OH; SM C18:0; SM (OH) C22:2; Lys; Kynurenine; Met-SO |
| 1869 | 4 | S.L./Am.Ac. | 87.2 | SM C24:0; SM C24:1; Phe; Pro |
| 1870 | 4 | En.Met/S.L./Am.Ac./O.St. | 80.2 | Lac; SM C16:1; Trp; Cholestenone |
| 1871 | 6 | En.Met/S.L./Am.Ac./B.Am. | 84.8 | Suc; SM C16:0; SM C18:0; Orn; Val; Ac-Orn |
| 1872 | 4 | S.L./Am.Ac./B.Am. | 80.6 | SM C24:1; His; Lys; Met-SO |
| 1873 | 4 | S.L./Am.Ac./B.Am. | 83.1 | SM C16:0; SM C24:1; Lys; Ac-Orn |
| 1874 | 4 | S.L./Am.Ac. | 86 | SM C16:1; SM C24:0; Ala; Met |
| 1875 | 6 | S.L./Am.Ac./B.Am. | 90.5 | SM C16:1; SM (OH) C22:2; His; Met; Phe; Kynurenine |
| 1876 | 4 | Ac.Ca./S.L./P.G. | 82.7 | C5:1-DC; SM C18:1; SM (OH) C14:1; LTB4 |
| 1877 | 4 | S.L./Am.Ac. | 85.5 | SM C18:1; SM C24:0; SM (OH) C22:2; Tyr |
| 1878 | 5 | Ac.Ca./Am.Ac./B.Am. | 82.5 | C6:1; Gln; Tyr; Ac-Orn; Histamine |
| 1879 | 5 | S.L./Am.Ac. | 83.5 | SM (OH) C14:1; SM (OH) C16:1; Gln; Met; Tyr |
| 1880 | 4 | Ac.Ca./S.L./Am.Ac. | 79.9 | C14:1; SM C20:2; SM (OH) C22:2; Tyr |
| 1881 | 5 | En.Met/Ac.Ca./S.L./Am.Ac. | 79.7 | Pent-P; C6:1; SM C18:1; SM (OH) C22:1; Ala |
| 1882 | 5 | S.L./Am.Ac. | 90.2 | SM C16:0; SM C24:1; SM (OH) C14:1; Gly; Pro |
| 1883 | 4 | Ac.Ca./S.L./Am.Ac./B.Am. | 80.2 | C6:1; SM C16:1; Gln; Ac-Orn |
| 1884 | 6 | En.Met/S.L./Am.Ac./B.Am. | 88.3 | Pent-P; SM C16:1; SM C20:2; Gln; Lys; Met-SO |
| 1885 | 4 | S.L./Am.Ac. | 82.8 | SM C24:0; His; Pro; Tyr |
| 1886 | 4 | S.L./Am.Ac./B.Am. | 82.7 | SM C16:1; SM (OH) C16:1; Orn; Met-SO |
| 1887 | 5 | En.Met/S.L./B.Am. | 83.1 | Hex-P; SM C16:1; SM C24:1; SM (OH) C22:2; Met-SO |
| 1888 | 4 | S.L./Am.Ac./O.St. | 79.3 | SM C16:1; SM (OH) C14:1; Ala; Cholestenone |
| 1889 | 6 | En.Met/S.L./B.Am./P.G. | 84 | Lac; SM C18:0; SM (OH) C14:1; SM (OH) C22:1; Met-SO; LTB4 |
| 1890 | 5 | S.L./Am.Ac./P.G. | 85.2 | SM (OH) C14:1; SM (OH) C22:1; SM (OH) C24:1; Thr; TXB2 |
| 1891 | 3 | S.L./Am.Ac. | 80.1 | SM C24:0; Gln; Tyr |
| 1892 | 4 | Ac.Ca./Am.Ac./O.St. | 79.4 | C18; Phe; Pro; Cholestenone |
| 1893 | 4 | Ac.Ca./Am.Ac. | 85.3 | C14:1; Leu; Met; Pro |
| 1894 | 4 | S.L./Am.Ac./P.G. | 80.5 | SM (OH) C14:1; Leu; Lys; TXB2 |
| 1895 | 4 | Ac.Ca./S.L./Am.Ac./B.Am. | 85.1 | C6:1; SM (OH) C22:2; Gln; Ac-Orn |
| 1896 | 5 | Ac.Ca./S.L./Am.Ac./O.St./P.G. | 86.3 | C5:1-DC; SM C16:1; Trp; 24-DH-Lanosterol; LTB4 |
| 1897 | 6 | En.Met/S.L./Am.Ac./B.Am./O.St. | 81.8 | alpha-KGA; Fum; SM C18:0; Gln; SDMA; 20a-OH-C |
| 1898 | 4 | S.L./Am.Ac. | 79.1 | SM C18:1; SM (OH) C14:1; Ile; Met |
| 1899 | 4 | S.L./Am.Ac./B.Am./S.L. | 85.2 | SM C18:0; Trp; Met-SO; Cholestenone |
| 1900 | 4 | S.L./Am.Ac./P.G. | 85.9 | SM (OH) C14:1; Lys; Tyr; TXB2 |
| 1901 | 4 | Am.Ac./B.Am. | 87.4 | Gln; Lys; Met; Met-SO |
| 1902 | 4 | S.L./Am.Ac./O.St. | 88.1 | SM (OH) C14:1; Pro; Trp; 24-DH-Lanosterol |
| 1903 | 4 | S.L./Am.Ac./B.Am. | 86.7 | SM C24:1; His; Tyr; Kynurenine |
| 1904 | 5 | En.Met/S.L./Am.Ac./O.St. | 92.1 | Suc; SM C16:1; Arg; Pro; Cholestenone |
| 1905 | 4 | Ac.Ca./S.L. | 81.6 | C10; C5:1-DC; SM C24:0; SM (OH) C22:2 |
| 1906 | 4 | S.L./Am.Ac./O.St. | 92.3 | SM (OH) C14:1; SM (OH) C22:2; Arg; 20a-OH-C |
| 1907 | 4 | S.L./Am.Ac. | 79.4 | SM C16:1; SM C24:0; His; Tyr |
| 1908 | 5 | En.Met/S.L./Am.Ac./B.Am. | 80.2 | Suc; SM (OH) C22:1; Gln; Orn; Histamine |
| 1909 | 3 | En.Met/Am.Ac. | 82.4 | Lac; Gln; Tyr |
| 1910 | 4 | Ac.Ca./S.L./Am.Ac. | 80.8 | C6:1; SM C24:0; Phe; Pro |
| 1911 | 3 | S.L./Am.Ac. | 85.6 | SM C24:1; SM (OH) C22:1; Ala |
| 1912 | 5 | S.L./Am.Ac./B.Am. | 88.5 | SM C24:0; SM C24:1; SM (OH) C14:1; Pro; Ac-Orn |
| 1913 | 4 | S.L./Am.Ac./B.Am. | 90.5 | SM (OH) C14:1; Gln; Pro; Met-SO |
| 1914 | 6 | S.L./Am.Ac./B.Am./O.St. | 85.6 | SM C18:0; SM C24:0; His; Phe; alpha-AAA; 20a-OH-C |
| 1915 | 4 | S.L./Am.Ac./P.G. | 81 | SM (OH) C16:1; SM (OH) C24:1; Orn; TXB2 |
| 1916 | 5 | S.L./Am.Ac./B.Am. | 88.6 | SM (OH) C14:1; SM (OH) C16:1; Gln; Kynurenine; Met-SO |

TABLE 9-continued

Metabolite combinations describing damage of basal ganglia

| No. | Npar | Chemical Class | Accuracy | Model |
|---|---|---|---|---|
| 1917 | 4 | S.L./Am.Ac./O.St. | 88.4 | SM C24:0; Met; Pro; Cholestenone |
| 1918 | 5 | S.L./Am.Ac./P.G. | 86.1 | SM C24:0; SM (OH) C22:1; Pro; Tyr; LTB4 |
| 1919 | 5 | Ac.Ca./S.L./Am.Ac./B.Am. | 82.8 | C14:1; SM C18:0; SM (OH) C24:1; Arg; Met-SO |
| 1920 | 4 | Ac.Ca./Am.Ac./B.Am. | 85 | C18; Orn; Pro; Met-SO |
| 1921 | 3 | S.L./Am.Ac./O.St. | 85.8 | SM C24:1; Trp; 24-DH-Lanosterol |
| 1922 | 4 | Ac.Ca./S.L./B.Am. | 79.7 | C5:1-DC; SM C16:0; Histamine; Met-SO |
| 1923 | 3 | S.L./Am.Ac. | 82 | SM (OH) C22:2; Orn; Trp |
| 1924 | 4 | Ac.Ca./S.L./Am.Ac./B.Am. | 83.3 | C6:1; SM (OH) C14:1; Gln; Met-SO |
| 1925 | 4 | S.L./B.Am. | 79.7 | SM C16:0; SM C20:2; SM (OH) C24:1; Met-SO |
| 1926 | 4 | En.Met/Ac.Ca./Am.Ac./B.Am. | 82.8 | alpha-KGA; C14:1; Arg; Met-SO |
| 1927 | 3 | S.L./Am.Ac./O.St. | 85.3 | SM (OH) C22:1; Tyr; Cholestenone |
| 1928 | 4 | Am.Ac./B.Am. | 87.7 | Gln; Lys; Pro; Ac-Orn |
| 1929 | 4 | S.L./Am.Ac. | 85.5 | SM C18:1; SM C24:0; Phe; Tyr |
| 1930 | 3 | Ac.Ca./S.L./Am.Ac. | 80.7 | C14:1-OH; SM C20:2; Pro |
| 1931 | 4 | S.L./Am.Ac. | 79.7 | SM C18:1; SM C24:1; Met; Trp |
| 1932 | 4 | S.L./Am.Ac./B.Am. | 80.6 | SM (OH) C16:1; SM (OH) C24:1; Lys; Ac-Orn |
| 1933 | 6 | Ac.Ca./S.L./Am.Ac./B.Am. | 82.4 | C14:1; SM C24:0; SM C24:1; Lys; Phe; Met-SO |
| 1934 | 3 | En.Met/S.L./Am.Ac. | 84.3 | Fum; SM C24:0; Met |
| 1935 | 4 | S.L./Am.Ac./O.St. | 84.5 | SM C16:1; SM C20:2; Tyr; 25-OH-C |
| 1936 | 5 | En.Met/S.L./Am.Ac./O.St. | 80.3 | Lac; SM C16:0; SM (OH) C22:2; Phe; Cholestenone |
| 1937 | 4 | S.L./B.Am. | 85.8 | SM C16:0; SM C24:0; Kynurenine; Met-SO |
| 1938 | 4 | En.Met/S.L./Am.Ac. | 85.1 | Fum; SM C16:0; SM C24:0; Met |
| 1939 | 4 | En.Met/S.L./Am.Ac. | 80.8 | H1; SM C24:0; Met; Phe |
| 1940 | 3 | S.L./Am.Ac. | 80 | SM (OH) C22:2; Ala; Gln |
| 1941 | 4 | S.L./B.Am. | 79.9 | SM C16:1; SM C18:1; SM (OH) C14:1; Met-SO |
| 1942 | 4 | S.L./Am.Ac./B.Am. | 87.7 | SM (OH) C24:1; Gln; Lys; Ac-Orn |
| 1943 | 5 | S.L./Am.Ac./B.Am. | 85.9 | SM C16:0; SM C24:0; Lys; Histamine; Met-SO |
| 1944 | 5 | En.Met/Ac.Ca./Am.Ac. | 82.9 | Suc; C6:1; Arg; Gln; Met |
| 1945 | 4 | S.L./Am.Ac./B.Am. | 87.7 | SM C16:0; SM C24:0; Tyr; Kynurenine |
| 1946 | 4 | En.Met/S.L./Am.Ac./B.Am. | 85.2 | Lac; SM (OH) C16:1; Gln; Ac-Orn |
| 1947 | 4 | S.L./Am.Ac. | 79.4 | SM C16:0; SM C18:1; Met; Pro |
| 1948 | 4 | En.Met/S.L./Am.Ac. | 88.8 | Suc; SM C16:1; Arg; Pro |
| 1949 | 3 | S.L./Am.Ac. | 82.3 | SM (OH) C22:1; Met; Pro |
| 1950 | 6 | S.L./Am.Ac./O.St. | 90 | SM C24:0; SM (OH) C14:1; Ala; Met; Orn; 25-OH-C |
| 1951 | 4 | En.Met/S.L./Am.Ac. | 87.5 | alpha-KGA; Lac; SM C24:0; Met |
| 1952 | 4 | S.L./Am.Ac./O.St. | 79.1 | SM C16:0; Ala; Met; Cholestenone |
| 1953 | 4 | S.L./Am.Ac./O.St./P.G. | 80.9 | SM C24:1; Trp; 24-DH-Lanosterol; LTB4 |
| 1954 | 4 | S.L./Am.Ac./B.Am. | 88.2 | SM C24:1; Lys; Ac-Orn; Histamine |
| 1955 | 4 | S.L./Am.Ac./P.G. | 80.6 | SM C18:1; Gln; Lys; TXB2 |
| 1956 | 4 | S.L./B.Am. | 79.1 | SM C24:1; SM (OH) C14:1; Histamine; Met-SO |
| 1957 | 4 | S.L./Am.Ac./P.G. | 94.7 | SM C16:0; SM (OH) C14:1; Pro; TXB2 |
| 1958 | 4 | Ac.Ca./S.L./B.Am. | 86.7 | C5:1-DC; SM C16:1; Ac-Orn; Histamine |
| 1959 | 4 | En.Met/S.L./Am.Ac. | 83.6 | Lac; SM C18:1; SM (OH) C14:1; Met |
| 1960 | 4 | S.L./Am.Ac./B.Am. | 95.2 | SM C16:0; SM (OH) C22:2; Tyr; Kynurenine |
| 1961 | 4 | S.L./Am.Ac./P.G. | 79.8 | SM C16:1; Arg; Gln; LTB4 |
| 1962 | 5 | S.L./Am.Ac./B.Am. | 84.9 | SM C16:1; SM C24:0; Gln; Tyr; Met-SO |
| 1963 | 5 | Ac.Ca./S.L./Am.Ac./O.St. | 80.5 | C5:1-DC; SM C24:0; SM (OH) C24:1; Gln; 24-DH-Lanosterol |
| 1964 | 4 | S.L./Am.Ac./B.Am. | 86.3 | SM C24:0; Lys; Ac-Orn; Histamine |
| 1965 | 4 | S.L./Am.Ac. | 82 | SM (OH) C22:1; SM (OH) C24:1; Met; Trp |
| 1966 | 4 | S.L./Am.Ac. | 84.3 | SM C18:1; SM (OH) C22:1; Met; Trp |
| 1967 | 4 | En.Met/S.L./B.Am. | 84.1 | alpha-KGA; SM C24:0; Ac-Orn; Histamine |
| 1968 | 3 | S.L./B.Am. | 83.4 | SM C16:0; SM (OH) C22:1; Met-SO |
| 1969 | 4 | En.Met/S.L./Am.Ac./P.G. | 87.7 | alpha-KGA; SM C16:1; Orn; TXB2 |
| 1970 | 5 | S.L./Am.Ac./O.St. | 90.2 | SM C16:0; SM C24:1; Pro; Trp; 24-DH-Lanosterol |
| 1971 | 5 | En.Met/S.L./Am.Ac. | 88.5 | Lac; H1; SM C18:1; Gln; Tyr |
| 1972 | 4 | Ac.Ca./S.L. | 87 | C5:1-DC; SM C16:1; SM (OH) C22:2; SM (OH) C24:1 |
| 1973 | 4 | S.L./Am.Ac. | 82.1 | SM (OH) C14:1; SM (OH) C22:2; Phe; Pro |
| 1974 | 6 | S.L./Am.Ac./B.Am. | 80.8 | SM C18:0; SM C24:0; Leu; Lys; Phe; Met-SO |
| 1975 | 4 | Ac.Ca./S.L./B.Am. | 84.7 | C6:1; SM C20:2; SM (OH) C22:1; Met-SO |
| 1976 | 4 | S.L./Am.Ac./B.Am. | 81.4 | SM C18:1; His; Orn; Ac-Orn |
| 1977 | 4 | En.Met/Am.Ac./B.Am. | 80.4 | Suc; Arg; Ac-Orn; Histamine |
| 1978 | 5 | Am.Ac./B.Am./O.St. | 84.7 | Trp; Ac-Orn; Histamine; 24-DH-Lanosterol; Cholestenone |
| 1979 | 4 | En.Met/S.L./Am.Ac. | 83.6 | alpha-KGA; SM C24:0; Met; Phe |
| 1980 | 4 | S.L./Am.Ac. | 80.8 | SM C16:0; Arg; His; Met |
| 1981 | 3 | En.Met/S.L./Am.Ac. | 80.6 | alpha-KGA; SM C24:0; Met |
| 1982 | 4 | S.L./Am.Ac. | 80.4 | SM C16:1; SM C18:0; SM (OH) C22:2; Phe |
| 1983 | 4 | S.L./Am.Ac. | 79.2 | SM C18:1; SM (OH) C22:1; SM (OH) C22:2; Phe |
| 1984 | 5 | En.Met/S.L./Am.Ac./O.St./P.G. | 81 | Lac; SM C18:0; Trp; 24-DH-Lanosterol; AA |
| 1985 | 4 | S.L./Am.Ac./B.Am. | 84.8 | SM C24:1; Lys; Histamine; Met-SO |
| 1986 | 4 | S.L./Am.Ac. | 81.2 | SM C16:0; Leu; Met; Pro |
| 1987 | 4 | S.L./Am.Ac./B.Am. | 79.9 | SM (OH) C24:1; Gln; Phe; Met-SO |
| 1988 | 4 | S.L./Am.Ac./B.Am. | 83.5 | SM (OH) C14:1; Arg; Pro; Met-SO |
| 1989 | 4 | S.L./Am.Ac. | 84.1 | SM C18:1; SM C24:0; Arg; Met |
| 1990 | 4 | S.L./Am.Ac./B.Am. | 81.3 | SM C16:0; Arg; Orn; Ac-Orn |
| 1991 | 4 | En.Met/S.L./Am.Ac./B.Am. | 83 | H1; SM C16:1; Arg; Met-SO |
| 1992 | 5 | En.Met/S.L./Am.Ac. | 80.2 | Hex-P; SM C16:0; SM C24:0; SM (OH) C14:1; Phe |

TABLE 9-continued

Metabolite combinations describing damage of basal ganglia

| No. | Npar | Chemical Class | Accuracy | Model |
|---|---|---|---|---|
| 1993 | 5 | En.Met/Ac.Ca./S.L./Am.Ac./O.St. | 83.8 | alpha-KGA; C14:1; SM (OH) C24:1; Leu; 20a-OH-C |
| 1994 | 4 | S.L./B.Am. | 79.2 | SM C16:1; SM (OH) C14:1; SM (OH) C24:1; Met-SO |
| 1995 | 5 | S.L./Am.Ac./B.Am./O.St. | 84 | SM C16:0; SM (OH) C24:1; Gln; Carnosine; 20a-OH-C |
| 1996 | 4 | S.L./Am.Ac./B.Am. | 79.8 | SM C18:1; SM (OH) C24:1; Lys; Ac-Orn |
| 1997 | 5 | En.Met/Am.Ac./O.St. | 81.2 | alpha-KGA; Arg; Gln; 24S-OH-C; Cholestenone |
| 1998 | 3 | Ac.Ca./S.L. | 85.6 | C5:1-DC; SM C16:1; SM C18:0 |
| 1999 | 5 | S.L./Am.Ac./B.Am. | 84 | SM C16:1; SM C24:1; SM (OH) C24:1; Tyr; ADMA |
| 2000 | 3 | S.L./Am.Ac. | 83.3 | SM C24:0; Arg; Tyr |
| 2001 | 4 | S.L./Am.Ac. | 81.3 | SM C16:0; SM C24:1; Trp; Tyr |
| 2002 | 5 | En.Met/Am.Ac./B.Am./O.St. | 81.9 | Suc; Pro; Tyr; Histamine; 25-OH-C |
| 2003 | 4 | En.Met/S.L./Am.Ac./B.Am. | 85.5 | Lac; SM (OH) C14:1; Arg; Met-SO |
| 2004 | 4 | S.L./Am.Ac./P.G. | 86.2 | SM (OH) C22:2; Orn; Trp; AA |
| 2005 | 4 | S.L./Am.Ac./O.St. | 88.7 | SM (OH) C14:1; Pro; Trp; Cholestenone |
| 2006 | 4 | En.Met/S.L./Am.Ac./B.Am. | 79.6 | alpha-KGA; SM (OH) C24:1; Orn; Met-SO |
| 2007 | 4 | S.L./Am.Ac./B.Am. | 86.4 | SM C16:1; His; Orn; Met-SO |
| 2008 | 5 | En.Met/S.L./Am.Ac./B.Am./O.St. | 82.1 | alpha-KGA; SM C16:0; Orn; Met-SO; 25-OH-C |
| 2009 | 6 | S.L./Am.Ac./B.Am./O.St. | 83.2 | SM C16:1; SM (OH) C16:1; Gln; Gly; alpha-AAA; 20a-OH-C |
| 2010 | 3 | Ac.Ca./S.L./O.St. | 85.7 | C5:1-DC; SM (OH) C14:1; Cholestenone |
| 2011 | 4 | En.Met/S.L./Am.Ac. | 80.2 | Fum; SM C16:0; Leu; Met |
| 2012 | 5 | S.L./Am.Ac./B.Am. | 79.2 | SM C16:0; SM C18:1; Arg; His; Ac-Orn |
| 2013 | 5 | Ac.Ca./S.L./Am.Ac./B.Am. | 86 | C6:1; SM C16:1; SM (OH) C22:2; Tyr; Creatinine |
| 2014 | 4 | S.L./Am.Ac. | 79.7 | SM C24:1; SM (OH) C16:1; Leu; Orn |
| 2015 | 4 | En.Met/Am.Ac./O.St. | 79.7 | Suc; Pro; Val; Cholestenone |
| 2016 | 4 | En.Met/S.L./P.G. | 82.9 | Lac; SM (OH) C14:1; SM (OH) C24:1; TXB2 |
| 2017 | 5 | S.L./Am.Ac./O.St. | 82.5 | SM C20:2; Gln; Tyr; 24-DH-Lanosterol; Cholestenone |
| 2018 | 4 | Ac.Ca./S.L./Am.Ac. | 80.4 | C5:1-DC; SM (OH) C14:1; His; Pro |
| 2019 | 4 | Ac.Ca./S.L./Am.Ac./B.Am. | 80 | C18; SM C24:1; Pro; Met-SO |
| 2020 | 4 | En.Met/Ac.Ca./S.L./Am.Ac. | 79.6 | alpha-KGA; C5:1-DC; SM (OH) C22:2; Gln |
| 2021 | 4 | S.L./Am.Ac./B.Am. | 82.6 | SM C16:0; Gln; Met; Carnosine |
| 2022 | 4 | En.Met/S.L./B.Am. | 81.1 | Lac; SM (OH) C14:1; SM (OH) C16:1; Met-SO |
| 2023 | 4 | Am.Ac./B.Am./O.St. | 88.4 | Gln; Lys; Ac-Orn; Cholestenone |
| 2024 | 4 | S.L./Am.Ac. | 83.7 | SM C16:0; SM C18:1; SM C20:2; Tyr |
| 2025 | 3 | S.L./Am.Ac./P.G. | 84.7 | SM (OH) C22:1; Lys; TXB2 |
| 2026 | 3 | S.L./Am.Ac. | 85.1 | SM C16:1; Met; Trp |
| 2027 | 4 | S.L./Am.Ac./B.Am. | 82 | SM C24:0; SM (OH) C22:1; Val; Ac-Orn |
| 2028 | 4 | En.Met/S.L./Am.Ac./B.Am. | 85.6 | Pent-P; SM (OH) C14:1; Arg; Met-SO |
| 2029 | 5 | En.Met/S.L./Am.Ac./B.Am. | 85.4 | alpha-KGA; SM C24:1; His; Kynurenine; total DMA |
| 2030 | 4 | S.L./Am.Ac./B.Am. | 79.4 | SM (OH) C22:2; Asn; Gln; Met-SO |
| 2031 | 4 | En.Met/S.L./Am.Ac. | 83.3 | Suc; SM (OH) C22:2; Leu; Orn |
| 2032 | 4 | S.L./Am.Ac./B.Am. | 85 | SM C16:0; SM (OH) C24:1; Pro; Ac-Orn |
| 2033 | 4 | S.L./Am.Ac. | 80.5 | SM (OH) C14:1; SM (OH) C22:2; Leu; Met |
| 2034 | 5 | S.L./Am.Ac./B.Am. | 81.3 | SM C24:0; Arg; His; Pro; total DMA |
| 2035 | 5 | En.Met/S.L./Am.Ac./P.G. | 81.3 | Lac; SM C16:1; SM (OH) C14:1; Tyr; LTB4 |
| 2036 | 4 | S.L./Am.Ac./B.Am. | 87.8 | SM (OH) C22:2; Arg; Tyr; Kynurenine |
| 2037 | 4 | En.Met/S.L./Am.Ac./B.Am. | 79.5 | alpha-KGA; SM C24:1; Orn; Ac-Orn |
| 2038 | 4 | Ac.Ca./S.L./Am.Ac. | 83.6 | C10; SM (OH) C22:2; Gln; Met |
| 2039 | 4 | En.Met/S.L./Am.Ac. | 80.2 | Lac; SM C16:1; SM (OH) C22:2; His |
| 2040 | 4 | S.L./Am.Ac./B.Am. | 84 | SM C16:1; SM (OH) C14:1; Met; Kynurenine |
| 2041 | 4 | S.L./Am.Ac./B.Am. | 82 | SM (OH) C22:1; Gln; Pro; total DMA |
| 2042 | 3 | Ac.Ca./Am.Ac./B.Am. | 81.7 | C6:1; Gln; Ac-Orn |
| 2043 | 5 | En.Met/S.L./Am.Ac. | 82.8 | alpha-KGA; SM C16:0; SM C18:1; SM C20:2; Tyr |
| 2044 | 4 | En.Met/Am.Ac. | 82.7 | alpha-KGA; Hex-P; Gln; Met; Orn |
| 2045 | 3 | S.L./Am.Ac./O.St. | 89.3 | SM (OH) C22:2; Trp; 24-DH-Lanosterol |
| 2046 | 4 | S.L./Am.Ac. | 81.6 | SM (OH) C16:1; Met; Pro; Trp |
| 2047 | 4 | S.L./Am.Ac. | 85.8 | SM C18:0; SM C20:2; SM (OH) C22:1; Tyr |
| 2048 | 4 | En.Met/S.L./Am.Ac./P.G. | 85.3 | alpha-KGA; SM C16:1; His; TXB2 |
| 2049 | 4 | S.L./Am.Ac. | 80.1 | SM C24:0; SM C24:1; Met; Ser |
| 2050 | 4 | S.L./Am.Ac./P.G. | 86 | SM (OH) C14:1; SM (OH) C22:2; Gly; LTB4 |
| 2051 | 4 | S.L./Am.Ac./B.Am. | 81.4 | SM C24:1; SM (OH) C24:1; Trp; Met-SO |
| 2052 | 4 | S.L./Am.Ac./B.Am. | 81 | SM C24:0; Tyr; Histamine; Met-SO |
| 2053 | 4 | En.Met/Am.Ac./P.G. | 81.3 | alpha-KGA; Gln; Orn; 8-iso-PGF2a |
| 2054 | 4 | En.Met/S.L./Am.Ac. | 89 | Suc; SM (OH) C24:1; Orn; Tyr |
| 2055 | 3 | En.Met/S.L./Am.Ac. | 81.9 | alpha-KGA; SM (OH) C14:1; Met |
| 2056 | 4 | Ac.Ca./S.L./Am.Ac. | 81.1 | C5:1-DC; SM C16:0; SM (OH) C16:1; Lys |
| 2057 | 5 | S.L./Am.Ac./O.St. | 85.9 | SM (OH) C22:1; SM (OH) C24:1; Phe; Pro; 20a-OH-C |
| 2058 | 4 | En.Met/S.L./Am.Ac. | 80.5 | Fum; SM C18:1; SM (OH) C24:1; Met |
| 2059 | 4 | S.L./Am.Ac. | 81.8 | SM C16:1; SM C18:0; SM (OH) C22:1; Phe |
| 2060 | 4 | En.Met/S.L./Am.Ac. | 85.4 | alpha-KGA; SM C18:0; SM C24:0; Tyr |
| 2061 | 5 | S.L./Am.Ac./B.Am./O.St. | 83 | SM (OH) C14:1; Pro; Met-SO; 24-DH-Lanosterol |
| 2062 | 4 | En.Met/S.L./Am.Ac. | 86.1 | Lac; SM C24:0; Phe; Tyr |
| 2063 | 4 | S.L./Am.Ac./O.St. | 85.1 | SM C18:1; Gln; Phe; Cholestenone |
| 2064 | 4 | Ac.Ca./S.L./Am.Ac./B.Am. | 86.7 | C5:1-DC; SM C16:1; His; alpha-AAA |
| 2065 | 5 | S.L./Am.Ac./B.Am. | 87 | SM C18:1; Gln; His; Orn; Ac-Orn |
| 2066 | 5 | S.L./Am.Ac./P.G. | 82.6 | SM C18:0; SM C24:0; SM (OH) C14:1; Val; TXB2 |
| 2067 | 4 | Am.Ac./O.St. | 83.6 | His; Trp; 24-DH-Lanosterol; Cholestenone |
| 2068 | 4 | S.L./Am.Ac./B.Am. | 92.2 | SM (OH) C14:1; Gln; Orn; Met-SO |

TABLE 9-continued

Metabolite combinations describing damage of basal ganglia

| No. | Npar | Chemical Class | Accuracy | Model |
|---|---|---|---|---|
| 2069 | 4 | En.Met/S.L./Am.Ac. | 86.1 | Suc; SM (OH) C22:2; Orn; Tyr |
| 2070 | 5 | Ac.Ca./S.L./Am.Ac./B.Am. | 86.2 | C10; SM C16:1; SM C24:0; Tyr; Met-SO |
| 2071 | 4 | En.Met/Am.Ac./B.Am. | 81.5 | Lac; Gln; Phe; Met-SO |
| 2072 | 4 | S.L./Am.Ac./O.St. | 86.7 | SM C20:2; SM (OH) C14:1; Tyr; Cholestenone |
| 2073 | 4 | En.Met/S.L./Am.Ac. | 89.1 | Suc; SM (OH) C22:1; Orn; Tyr |
| 2074 | 4 | S.L./B.Am./O.St. | 81.7 | SM C24:0; SM (OH) C24:1; Met-SO; Cholestenone |
| 2075 | 4 | S.L./Am.Ac./O.St. | 85.3 | SM C24:0; Arg; Phe; 24-DH-Lanosterol |
| 2076 | 4 | Am.Ac. | 79.6 | Met; Orn; Pro; Trp |
| 2077 | 4 | En.Met/Am.Ac./B.Am. | 83 | Lac; Gln; His; Met-SO |
| 2078 | 4 | S.L./Am.Ac./B.Am. | 87 | SM C24:0; SM (OH) C22:2; Pro; Ac-Orn |
| 2079 | 4 | S.L./Am.Ac./B.Am./P.G. | 81.8 | SM C16:1; Orn; Met-SO; LTB4 |
| 2080 | 4 | En.Met/S.L./Am.Ac. | 84.3 | Lac; SM (OH) C14:1; Leu; Met |
| 2081 | 4 | S.L./Am.Ac./O.St. | 79.7 | SM C16:0; SM (OH) C22:2; His; 20a-OH-C |
| 2082 | 4 | S.L./Am.Ac. | 87.4 | SM C16:1; SM C24:1; SM (OH) C14:1; Ala |
| 2083 | 4 | S.L./Am.Ac. | 84.3 | SM C24:0; SM C24:1; Arg; Met |
| 2084 | 5 | En.Met/S.L./Am.Ac./B.Am./O.St. | 79.9 | OAA; SM C24:0; Ser; Ac-Orn; Cholestenone |
| 2085 | 4 | S.L./Am.Ac./O.St. | 90.1 | SM C16:1; SM (OH) C14:1; Pro; 20a-OH-C |
| 2086 | 4 | S.L./Am.Ac. | 81.3 | SM C16:0; SM C16:1; SM C18:0; Tyr |
| 2087 | 4 | S.L./Am.Ac./B.Am. | 88.5 | SM (OH) C16:1; Gln; Orn; Ac-Orn |
| 2088 | 3 | S.L./B.Am./O.St. | 80.1 | SM C24:0; Met-SO; 24S-OH-C |
| 2089 | 5 | S.L./Am.Ac./B.Am. | 90.6 | SM C16:1; SM C24:1; Pro; Trp; Met-SO |
| 2090 | 6 | S.L./Am.Ac./B.Am./O.St. | 90.5 | SM C24:0; SM (OH) C22:1; Gln; Lys; Met-SO; Cholestenone |
| 2091 | 4 | En.Met/S.L./Am.Ac./B.Am. | 83.5 | H1; SM C24:0; Orn; Met-SO |
| 2092 | 5 | S.L./Am.Ac./B.Am./O.St. | 87.4 | SM C16:0; SM (OH) C22:2; Gly; alpha-AAA; Cholestenone |
| 2093 | 4 | S.L./Am.Ac. | 80.5 | SM C16:0; SM C24:1; SM (OH) C14:1; Ser |
| 2094 | 3 | S.L./Am.Ac. | 88 | SM (OH) C14:1; SM (OH) C22:2; Gly |
| 2095 | 3 | S.L./Am.Ac./B.Am. | 79.3 | SM (OH) C22:1; Pro; Met-SO |
| 2096 | 4 | En.Met/Ac.Ca./S.L. | 87.9 | alpha-KGA; C5:1-DC; SM C16:1; SM C18:1 |
| 2097 | 4 | En.Met/S.L./Am.Ac./B.Am. | 84.4 | Fum; SM (OH) C16:1; Gln; Met-SO |
| 2098 | 4 | Ac.Ca./S.L./B.Am. | 79.2 | C5:1-DC; SM C24:1; SM (OH) C24:1; Histamine |
| 2099 | 3 | S.L./Am.Ac./O.St. | 82.5 | SM C16:1; Leu; 20a-OH-C |
| 2100 | 4 | S.L./Am.Ac./B.Am. | 83.8 | SM C16:0; SM C24:1; Lys; Met-SO |
| 2101 | 4 | En.Met/S.L./Am.Ac. | 89.9 | Lac; SM C16:0; Gln; Met |
| 2102 | 3 | S.L./Am.Ac. | 80.8 | SM C16:1; SM (OH) C14:1; Met |
| 2103 | 4 | En.Met/S.L./B.Am. | 84.1 | Lac; SM C16:1; SM C18:0; Met-SO |
| 2104 | 4 | S.L./Am.Ac. | 82.8 | SM (OH) C22:1; SM (OH) C22:2; Met; Val |
| 2105 | 3 | S.L./Am.Ac. | 79.3 | SM C16:1; His; Tyr |
| 2106 | 6 | S.L./Am.Ac./P.G. | 82.3 | SM C18:1; SM C24:0; SM C24:1; Gln; Lys; TXB2 |
| 2107 | 4 | S.L./Am.Ac./B.Am. | 83.7 | SM C24:1; SM (OH) C22:1; Pro; Met-SO |
| 2108 | 4 | S.L./Am.Ac./B.Am. | 89.3 | SM C24:0; SM (OH) C22:1; Pro; Met-SO |
| 2109 | 3 | S.L./Am.Ac./B.Am. | 80.1 | SM (OH) C22:2; Gln; Met-SO |
| 2110 | 4 | En.Met/Am.Ac./B.Am. | 83.6 | alpha-KGA; Gln; Pro; total DMA |
| 2111 | 4 | S.L./Am.Ac./B.Am. | 88.1 | SM (OH) C22:1; Trp; alpha-AAA; Met-SO |
| 2112 | 4 | S.L./Am.Ac./O.St. | 82 | SM C24:0; SM (OH) C22:1; Leu; 20a-OH-C |
| 2113 | 4 | S.L./Am.Ac. | 87.9 | SM C24:0; SM C24:1; Arg; Tyr |
| 2114 | 4 | En.Met/S.L./B.Am. | 80 | Fum; SM (OH) C16:1; SM (OH) C24:1; Met-SO |
| 2115 | 5 | S.L./Am.Ac./P.G. | 90 | SM (OH) C16:1; Gln; Met; Orn; 8-iso-PGF2a |
| 2116 | 4 | S.L./Am.Ac./B.Am. | 83.1 | SM C16:1; SM C18:0; Orn; Ac-Orn |
| 2117 | 4 | Ac.Ca./S.L./Am.Ac./O.St. | 83.2 | C5:1-DC; SM (OH) C14:1; His; Cholestenone |
| 2118 | 4 | S.L./Am.Ac. | 82.9 | SM C16:1; SM C18:1; Arg; Met |
| 2119 | 3 | S.L./Am.Ac. | 79.8 | SM (OH) C22:1; SM (OH) C22:2; Phe |
| 2120 | 4 | S.L./Am.Ac./O.St. | 88.3 | SM C24:1; Trp; Tyr; 24-DH-Lanosterol |
| 2121 | 4 | En.Met/Am.Ac. | 79.9 | Fum; His; Met; Pro |
| 2122 | 4 | S.L./Am.Ac. | 85.8 | SM C16:1; SM C24:0; Pro; Tyr |
| 2123 | 5 | En.Met/S.L./Am.Ac./B.Am. | 80 | Suc; SM C18:1; SM C24:1; Lys; Met-SO |
| 2124 | 4 | Ac.Ca./S.L./Am.Ac. | 83 | C18:2; SM C18:1; SM (OH) C22:2; Pro |
| 2125 | 4 | S.L./Am.Ac. | 87 | SM C20:2; SM C24:0; Met; Pro |
| 2126 | 3 | S.L./Am.Ac. | 83.9 | SM (OH) C22:2; Gln; Tyr |
| 2127 | 5 | S.L./Am.Ac. | 85.4 | SM C24:0; SM C24:1; SM (OH) C14:1; Met; Tyr |
| 2128 | 4 | S.L./Am.Ac./O.St. | 90.3 | SM C16:0; SM (OH) C22:2; Pro; 20a-OH-C |
| 2129 | 6 | S.L./Am.Ac./B.Am./P.G. | 86.3 | SM C16:0; Arg; Gln; His; Met-SO; LTB4 |
| 2130 | 5 | En.Met/S.L./Am.Ac./P.G. | 82.8 | Lac; SM C16:1; SM (OH) C14:1; Trp; AA |
| 2131 | 4 | Ac.Ca./S.L./B.Am. | 89.7 | C6:1; SM (OH) C22:2; Kynurenine; Met-SO |
| 2132 | 4 | En.Met/S.L./B.Am. | 84.1 | alpha-KGA; SM C16:1; SM C18:1; Ac-Orn |
| 2133 | 4 | S.L./Am.Ac./B.Am. | 80.2 | SM C18:1; Pro; Trp; total DMA |
| 2134 | 6 | En.Met/Ac.Ca./S.L./Am.Ac. | 85.6 | Lac; C18:2; SM C24:1; Lys; Phe; Pro |
| 2135 | 4 | S.L./Am.Ac. | 83.7 | SM C16:0; SM (OH) C22:2; Met; Pro |
| 2136 | 4 | En.Met/S.L./Am.Ac. | 79.5 | Suc; SM (OH) C24:1; Lys; Tyr |
| 2137 | 3 | S.L./B.Am. | 80.5 | SM C16:1; SM C18:1; Ac-Orn |
| 2138 | 4 | S.L./Am.Ac. | 86.2 | SM C24:0; SM C24:1; Ala; Orn |
| 2139 | 4 | Ac.Ca./S.L./Am.Ac./B.Am. | 80.6 | C18; SM C20:2; Pro; Ac-Orn |
| 2140 | 4 | En.Met/Ac.Ca./S.L. | 80 | Lac; C14:1; C9; SM C18:1 |
| 2141 | 4 | Ac.Ca./S.L./Am.Ac. | 83.7 | C10:2; SM (OH) C24:1; Arg; Met |
| 2142 | 5 | S.L./Am.Ac./B.Am. | 83.2 | SM C18:0; SM C20:2; SM (OH) C22:1; Lys; Met-SO |
| 2143 | 4 | En.Met/S.L./B.Am. | 81.4 | alpha-KGA; SM C24:1; Ac-Orn; Histamine |
| 2144 | 5 | Ac.Ca./S.L./Am.Ac./O.St. | 90.2 | C5:1-DC; SM C24:0; SM (OH) C22:2; Orn; Cholestenone |

TABLE 9-continued

Metabolite combinations describing damage of basal ganglia

| No. | Npar | Chemical Class | Accuracy | Model |
|---|---|---|---|---|
| 2145 | 4 | En.Met/Am.Ac./O.St. | 80.9 | alpha-KGA; Fum; Met; Cholestenone |
| 2146 | 4 | En.Met/S.L./B.Am. | 79.2 | Fum; Lac; SM (OH) C14:1; Met-SO |
| 2147 | 5 | S.L./Am.Ac./B.Am. | 86.4 | SM C16:0; Gln; Met; Tyr; Creatinine |
| 2148 | 5 | C6:1; SM (OH) C16:1; Gln; Trp; Ac-Orn |
| 2149 | 4 | Ac.Ca./S.L./Am.Ac. | 81.3 | C6:1; SM C16:1; SM (OH) C22:2; Ser |
| 2150 | 4 | S.L./Am.Ac. | 89.4 | SM (OH) C22:1; SM (OH) C22:2; Gly; Met |
| 2151 | 4 | S.L./Am.Ac./B.Am. | 81.4 | SM C24:1; SM (OH) C24:1; Pro; Met-SO |
| 2152 | 4 | S.L./Am.Ac. | 84.6 | SM C16:0; SM C18:0; SM C24:0; Tyr |
| 2153 | 4 | S.L./Am.Ac./P.G. | 87.4 | SM C18:1; SM (OH) C14:1; Orn; TXB2 |
| 2154 | 5 | Ac.Ca./S.L./Am.Ac. | 82.1 | C6:1; SM C16:1; SM C18:1; Arg; Phe |
| 2155 | 4 | Am.Ac./B.Am./O.St. | 86.5 | Trp; Tyr; Creatinine; Cholestenone |
| 2156 | 4 | S.L./Am.Ac./O.St. | 83.7 | SM C16:1; SM (OH) C22:1; Tyr; 25-OH-C |
| 2157 | 4 | S.L./Am.Ac. | 85 | SM C16:1; SM C18:0; Gln; Tyr |
| 2158 | 4 | En.Met/S.L./Am.Ac. | 82 | Hex-P; SM C18:1; Gln; Met |
| 2159 | 4 | S.L./Am.Ac./B.Am. | 86.5 | SM (OH) C22:1; SM (OH) C24:1; Tyr; Ac-Orn |
| 2160 | 5 | S.L./Am.Ac./B.Am. | 80.3 | SM (OH) C14:1; SM (OH) C24:1; His; Kynurenine; total DMA |
| 2161 | 4 | S.L./B.Am. | 91.4 | SM (OH) C14:1; SM (OH) C22:1; Kynurenine; Met-SO |
| 2162 | 4 | Am.Ac./B.Am./O.St. | 91.1 | Trp; Creatinine; Met-SO; Cholestenone |
| 2163 | 4 | S.L./Am.Ac. | 81.3 | SM C16:1; SM C24:1; Orn; Ser |
| 2164 | 5 | Ac.Ca./S.L./Am.Ac./B.Am. | 86.8 | C6:1; SM (OH) C14:1; SM (OH) C24:1; Orn; Met-SO |
| 2165 | 4 | En.Met/Am.Ac./B.Am. | 85.5 | Lac; SM C18:0; Gln; Met-SO |
| 2166 | 4 | En.Met/S.L./Am.Ac. | 84 | Fum; SM C16:0; SM (OH) C14:1; Met |
| 2167 | 4 | S.L./Am.Ac./B.Am. | 80.7 | SM (OH) C22:2; Gln; Met; total DMA |
| 2168 | 5 | S.L./Am.Ac./B.Am./O.St. | 81.2 | SM C20:2; SM (OH) C22:2; Phe; Histamine; Cholestenone |
| 2169 | 4 | Ac.Ca./S.L./Am.Ac./O.St. | 88.2 | C5:1-DC; SM C16:0; Trp; Cholestenone |
| 2170 | 4 | S.L./Am.Ac./B.Am. | 89.4 | SM C16:0; Phe; Tyr; Kynurenine |
| 2171 | 4 | S.L./Am.Ac. | 82.5 | SM C18:0; SM C20:2; SM (OH) C22:2; Tyr |
| 2172 | 4 | S.L./Am.Ac. | 82.1 | SM C18:1; SM (OH) C22:1; Arg; Met |
| 2173 | 4 | Ac.Ca./S.L./Am.Ac./B.Am. | 79.1 | C6:1; SM (OH) C24:1; Gln; Ac-Orn |
| 2174 | 5 | Ac.Ca./S.L./Am.Ac./B.Am./O.St. | 79.8 | C14:1; SM (OH) C22:1; Phe; Histamine; 20a-OH-C |
| 2175 | 4 | En.Met/S.L./Am.Ac. | 83.7 | Suc; SM C24:1; Orn; Val |
| 2176 | 6 | S.L./Am.Ac./P.G. | 85.1 | SM (OH) C22:2; Gln; His; Lys; Met; 8-iso-PGF2a |
| 2177 | 4 | S.L./Am.Ac./B.Am. | 85.7 | SM C16:0; SM (OH) C22:1; Ala; Ac-Orn |
| 2178 | 4 | S.L./Am.Ac./B.Am./O.St. | 85 | SM C24:1; Pro; Histamine; Cholestenone |
| 2179 | 4 | S.L./Am.Ac./O.St. | 81.4 | SM C24:0; SM (OH) C22:2; Arg; 24-DH-Lanosterol |
| 2180 | 4 | S.L./B.Am./O.St. | 83.7 | SM C24:0; SM (OH) C24:1; Met-SO; 25-OH-C |
| 2181 | 4 | S.L./Am.Ac. | 81.1 | SM C24:1; SM (OH) C24:1; Met; Pro |
| 2182 | 4 | S.L./Am.Ac./B.Am./O.St. | 82.4 | SM C24:0; Lys; Ac-Orn; 25-OH-C |
| 2183 | 4 | S.L./Am.Ac./O.St. | 81.7 | SM C24:1; Met; Pro; 24-DH-Lanosterol |
| 2184 | 4 | En.Met/S.L./Am.Ac. | 83.5 | alpha-KGA; SM C24:1; SM (OH) C22:1; Ala |
| 2185 | 4 | S.L./Am.Ac./B.Am. | 83.4 | SM C16:0; SM (OH) C22:2; Orn; Met-SO |
| 2186 | 5 | En.Met/Ac.Ca./Am.Ac. | 83.7 | Lac; C18:1; His; Pro; Tyr |
| 2187 | 4 | En.Met/S.L./Am.Ac./B.Am. | 83 | alpha-KGA; SM (OH) C22:2; Orn; Ac-Orn |
| 2188 | 4 | S.L./Am.Ac./P.G. | 84.1 | SM C24:0; Arg; Met; 8-iso-PGF2a |
| 2189 | 4 | Ac.Ca./S.L./B.Am. | 81.6 | C5:1-DC; SM C24:0; SM (OH) C22:1; Histamine |
| 2190 | 4 | Ac.Ca./S.L./Am.Ac./B.Am. | 85.3 | C18; SM (OH) C22:1; Pro; Met-SO |
| 2191 | 4 | En.Met/S.L./Am.Ac. | 85.5 | Lac; SM C16:1; SM C18:1; Met |
| 2192 | 3 | Ac.Ca./Am.Ac. | 79.2 | C14:1; Arg; Pro |
| 2193 | 5 | En.Met/Am.Ac./O.St. | 83.7 | alpha-KGA; Lac; Gln; Trp; 24-DH-Lanosterol |
| 2194 | 5 | S.L./Am.Ac./B.Am. | 82.2 | SM C20:2; SM C24:1; SM (OH) C14:1; Phe; Histamine |
| 2195 | 3 | S.L./Am.Ac./O.St. | 84.9 | SM C18:0; Trp; Cholestenone |
| 2196 | 4 | S.L./Am.Ac. | 79 | SM C16:1; SM C20:2; SM C24:1; Leu |
| 2197 | 5 | S.L./Am.Ac./B.Am./O.St. | 81.6 | SM (OH) C14:1; Lys; Ac-Orn; 25-OH-C; Cholestenone |
| 2198 | 5 | En.Met/S.L./B.Am./P.G. | 80 | Hex-P; SM C16:1; SM (OH) C16:1; Met-SO; LTB4 |
| 2199 | 4 | S.L./Am.Ac. | 83.1 | SM C16:0; SM C18:1; SM (OH) C22:1; Tyr |
| 2200 | 4 | En.Met/Am.Ac./B.Am. | 84.7 | Lac; Arg; Gln; Met-SO |
| 2201 | 4 | Ac.Ca./S.L./Am.Ac. | 80.9 | C5:1-DC; SM (OH) C14:1; His; Met |
| 2202 | 4 | S.L./Am.Ac./B.Am. | 85 | SM C24:1; SM (OH) C22:1; Lys; Met-SO |
| 2203 | 4 | En.Met/S.L./Am.Ac./O.St. | 88.2 | alpha-KGA; SM (OH) C22:2; Pro; 20a-OH-C |
| 2204 | 5 | Ac.Ca./S.L./O.St./P.G. | 81.9 | C5:1-DC; SM (OH) C22:1; 24-DH-Lanosterol; 8-iso-PGF2a; LTB4 |
| 2205 | 4 | En.Met/S.L./Am.Ac. | 80.3 | Lac; SM C16:0; SM C18:0; Met |
| 2206 | 4 | S.L./Am.Ac. | 80.8 | SM C16:0; SM C16:1; Ile; Pro |
| 2207 | 4 | S.L./Am.Ac./O.St. | 86.4 | SM C20:2; SM C24:0; Tyr; 25-OH-C |
| 2208 | 4 | Ac.Ca./S.L./B.Am. | 87.1 | C10; SM C16:1; SM (OH) C22:1; Met-SO |
| 2209 | 4 | S.L./Am.Ac./O.St. | 81.2 | SM C16:1; SM (OH) C22:1; Trp; 20a-OH-C |
| 2210 | 4 | S.L./Am.Ac. | 85.9 | SM C24:0; Met; Pro; Val |
| 2211 | 4 | S.L./Am.Ac./O.St. | 86.1 | Lac; SM C24:1; Trp; Cholestenone |
| 2212 | 4 | S.L./Am.Ac. | 85.7 | SM (OH) C14:1; Arg; His; Met |
| 2213 | 5 | S.L./Am.Ac./P.G. | 81 | SM C24:0; SM (OH) C24:1; His; Orn; TXB2 |
| 2214 | 4 | S.L./Am.Ac./B.Am. | 82 | SM C16:1; Arg; Met; Histamine |
| 2215 | 4 | S.L./Am.Ac./B.Am. | 81.4 | SM (OH) C14:1; His; Lys; Met-SO |
| 2216 | 6 | Ac.Ca./S.L./Am.Ac./O.St. | 79.7 | C6:1; SM C16:0; SM (OH) C14:1; Gln; Lys; 20a-OH-C |
| 2217 | 4 | En.Met/S.L./B.Am./O.St. | 81.5 | Lac; SM C16:1; Met-SO; 25-OH-C |
| 2218 | 4 | En.Met/Am.Ac./O.St. | 79.5 | alpha-KGA; Gln; Met; 24-DH-Lanosterol |
| 2219 | 5 | En.Met/S.L./Am.Ac./O.St. | 92.1 | Lac; SM C24:1; His; Trp; 24-DH-Lanosterol |
| 2220 | 5 | En.Met/S.L./Am.Ac./O.St. | 90.2 | alpha-KGA; SM C24:1; Pro; Trp; 24-DH-Lanosterol |

TABLE 9-continued

Metabolite combinations describing damage of basal ganglia

| No. | Npar | Chemical Class | Accuracy | Model |
|---|---|---|---|---|
| 2221 | 4 | Ac.Ca./S.L./Am.Ac. | 91.8 | C5:1-DC; SM C16:0; SM C16:1; Pro |
| 2222 | 3 | S.L./Am.Ac./O.St. | 86.9 | SM (OH) C16:1; Trp; Cholestenone |
| 2223 | 5 | En.Met/S.L./B.Am. | 83.9 | Lac; SM C24:0; SM (OH) C22:2; SM (OH) C24:1; Sarcosine |
| 2224 | 4 | S.L./Am.Ac. | 83.1 | Suc; SM C16:1; SM (OH) C14:1; Pro |
| 2225 | 3 | Ac.Ca./S.L./O.St. | 83.6 | C5:1-DC; SM (OH) C22:1; Cholestenone |
| 2226 | 5 | S.L./Am.Ac./B.Am./P.G. | 81.6 | SM C16:1; SM (OH) C14:1; Lys; Met-SO; LTB4 |
| 2227 | 4 | S.L./B.Am./O.St. | 85.1 | SM (OH) C22:1; Histamine; Met-SO; Cholestenone |
| 2228 | 5 | S.L./Am.Ac./O.St. | 85.3 | SM (OH) C16:1; Lys; Tyr; 20a-OH-C; 25-OH-C |
| 2229 | 6 | S.L./Am.Ac./B.Am. | 85.3 | SM C18:1; Gln; Pro; Tyr; Ac-Orn; alpha-AAA |
| 2230 | 4 | Ac.Ca./S.L./Am.Ac./O.St. | 80.3 | C5:1-DC; SM (OH) C24:1; Gln; Cholestenone |
| 2231 | 4 | S.L./Am.Ac./B.Am. | 81.4 | SM (OH) C22:2; Lys; Histamine; Met-SO |
| 2232 | 3 | S.L./Am.Ac./O.St. | 93.2 | SM C18:1; Trp; 24-DH-Lanosterol |
| 2233 | 3 | Ac.Ca./S.L./Am.Ac. | 82.8 | C6:1; SM C24:0; Tyr |
| 2234 | 4 | En.Met/S.L./Am.Ac./B.Am. | 86.9 | Suc; SM (OH) C24:1; Orn; Met-SO |
| 2235 | 4 | En.Met/S.L./Am.Ac. | 82.9 | Lac; SM C18:1; SM C24:0; Phe |
| 2236 | 4 | En.Met/Am.Ac./O.St./P.G. | 83.9 | Lac; Trp; Cholestenone; AA |
| 2237 | 4 | En.Met/S.L./Am.Ac. | 85.6 | OAA; SM C24:1; SM (OH) C14:1; Gly |
| 2238 | 4 | En.Met/S.L./Am.Ac. | 83.8 | Lac; SM C16:1; SM C24:0; Tyr |
| 2239 | 4 | S.L./Am.Ac./O.St. | 84.4 | SM C16:1; SM (OH) C22:1; Arg; 20a-OH-C |
| 2240 | 5 | S.L./Am.Ac./B.Am. | 81.5 | SM C16:1; SM C20:2; SM (OH) C14:1; Gln; Met-SO |
| 2241 | 4 | S.L./B.Am. | 84.6 | SM (OH) C16:1; SM (OH) C22:2; Kynurenine; Met-SO |
| 2242 | 4 | S.L./Am.Ac./B.Am. | 79.1 | SM C24:1; SM (OH) C14:1; Phe; Histamine |
| 2243 | 4 | S.L./Am.Ac. | 80.1 | SM C16:1; SM C18:0; Met; Orn |
| 2244 | 5 | En.Met/Ac.Ca./S.L./Am.Ac./P.G. | 79.7 | alpha-KGA; C6:1; SM C26:1; Orn; TXB2 |
| 2245 | 4 | S.L./Am.Ac./O.St. | 81.5 | SM C16:1; SM (OH) C22:2; Lys; 22R-OH-C |
| 2246 | 4 | S.L./Am.Ac. | 82 | SM (OH) C22:1; SM (OH) C24:1; Ala; Met |
| 2247 | 4 | Am.Ac./B.Am. | 83.1 | Arg; Gln; Pro; Ac-Orn |
| 2248 | 4 | S.L./B.Am. | 82.1 | SM C18:1; SM (OH) C22:2; Ac-Orn; Histamine |
| 2249 | 5 | S.L./Am.Ac./O.St. | 88.1 | SM C16:0; SM (OH) C14:1; SM (OH) C22:2; Leu; 20a-OH-C |
| 2250 | 4 | S.L./Am.Ac. | 83 | SM C24:1; SM (OH) C22:2; Ala; Lys |
| 2251 | 4 | En.Met/Ac.Ca./S.L./B.Am. | 80.3 | alpha-KGA; C6:1; SM (OH) C24:1; Ac-Orn |
| 2252 | 4 | En.Met/S.L./Am.Ac./O.St. | 80.5 | Suc; SM (OH) C24:1; Pro; Cholestenone |
| 2253 | 6 | Ac.Ca./S.L./Am.Ac./B.Am./P.G. | 81.1 | C18; SM C16:0; SM C18:1; Arg; Met-SO; LTB4 |
| 2254 | 4 | Ac.Ca./S.L./Am.Ac./P.G. | 79.3 | C18:1; SM C18:1; Pro; 8-iso-PGF2a |
| 2255 | 4 | S.L./Am.Ac. | 85 | SM C16:1; SM C20:2; Arg; Met |
| 2256 | 4 | S.L./Am.Ac./O.St. | 85.4 | SM C24:1; SM (OH) C22:1; Ser; Cholestenone |
| 2257 | 5 | En.Met/Am.Ac./O.St. | 87.5 | Pent-P; Arg; Gln; Pro; Cholestenone |
| 2258 | 4 | S.L./Am.Ac./B.Am. | 87.4 | SM C16:1; SM (OH) C16:1; Trp; Met-SO |
| 2259 | 4 | S.L./Am.Ac. | 83.8 | SM (OH) C22:1; SM (OH) C24:1; Lys; Met |
| 2260 | 4 | En.Met/S.L./Am.Ac./O.St. | 87.7 | alpha-KGA; SM (OH) C14:1; Orn; 22R-OH-C |
| 2261 | 4 | S.L./Am.Ac. | 88.9 | SM C20:2; SM (OH) C14:1; Pro; Tyr |
| 2262 | 4 | S.L./B.Am. | 82.4 | SM (OH) C22:2; SM (OH) C24:1; Ac-Orn; Histamine |
| 2263 | 4 | En.Met/S.L./Am.Ac. | 81.3 | Pent-P; SM C16:1; Orn; Pro |
| 2264 | 5 | En.Met/Ac.Ca./S.L./Am.Ac. | 81.6 | Lac; C18:1; SM C18:0; SM C18:1; Pro |
| 2265 | 4 | En.Met/S.L./Am.Ac. | 85.8 | Lac; SM C16:1; SM C24:1; Tyr |
| 2266 | 4 | S.L./Am.Ac./O.St. | 87.5 | SM C16:1; SM (OH) C22:1; Leu; 20a-OH-C |
| 2267 | 5 | S.L./Am.Ac. | 84.7 | SM C16:1; SM C20:2; SM C24:0; SM (OH) C22:2; Ser |
| 2268 | 4 | S.L./Am.Ac./B.Am. | 82.1 | SM C24:1; Met; Pro; total DMA |
| 2269 | 5 | En.Met/S.L./Am.Ac. | 81.4 | Fum; SM C16:1; SM C18:1; SM C24:1; Asn |
| 2270 | 4 | S.L./Am.Ac./B.Am. | 82.4 | SM (OH) C22:2; SM (OH) C24:1; Met; Kynurenine |
| 2271 | 4 | S.L./Am.Ac./B.Am. | 82.7 | SM C24:0; SM (OH) C14:1; Trp; Met-SO |
| 2272 | 4 | S.L./Am.Ac./O.St. | 82.8 | SM (OH) C22:1; Phe; Pro; Cholestenone |
| 2273 | 4 | En.Met/S.L./O.St. | 79.3 | alpha-KGA; SM (OH) C14:1; SM (OH) C16:1; 20a-OH-C |
| 2274 | 4 | En.Met/S.L./O.St. | 85.8 | alpha-KGA; SM C16:0; SM (OH) C22:2; 20a-OH-C |
| 2275 | 4 | S.L./Am.Ac. | 80.1 | SM C16:1; SM C18:1; SM C24:0; Ser |
| 2276 | 4 | En.Met/S.L./Am.Ac. | 80.9 | alpha-KGA; SM C16:0; SM (OH) C22:1; Met |
| 2277 | 4 | Ac.Ca./S.L./Am.Ac. | 80.2 | C14:1; SM C18:0; Gln; Tyr |
| 2278 | 4 | S.L./Am.Ac. | 80.9 | SM C20:2; SM C24:0; SM (OH) C22:2; Phe |
| 2279 | 4 | S.L./B.Am. | 84.4 | SM C24:0; SM (OH) C24:1; Creatinine; Met-SO |
| 2280 | 5 | S.L./Am.Ac./B.Am. | 83.9 | SM (OH) C14:1; SM (OH) C16:1; Orn; Pro; Met-SO |
| 2281 | 4 | S.L./Am.Ac. | 83.3 | SM C18:1; SM (OH) C22:2; Orn; Trp |
| 2282 | 4 | S.L./Am.Ac./B.Am. | 91.1 | SM C16:1; Gln; Pro; Met-SO |
| 2283 | 4 | S.L./Am.Ac./B.Am. | 81.4 | SM (OH) C22:2; Orn; Pro; Met-SO |
| 2284 | 4 | S.L./Am.Ac. | 91 | SM C16:1; Met; Pro; Trp |
| 2285 | 4 | S.L./Am.Ac. | 86.5 | SM C16:1; SM C18:1; SM C20:2; Tyr |
| 2286 | 3 | S.L./Am.Ac. | 82.3 | SM (OH) C22:1; His; Tyr |
| 2287 | 4 | Ac.Ca./S.L./Am.Ac. | 80.8 | C10; SM C24:1; Met; Pro |
| 2288 | 4 | S.L./B.Am. | 79.7 | SM C24:1; SM (OH) C14:1; Ac-Orn; Histamine |
| 2289 | 5 | S.L./Am.Ac./B.Am. | 82.7 | SM (OH) C16:1; SM (OH) C24:1; Pro; Trp; Ac-Orn |
| 2290 | 3 | Ac.Ca./S.L./Am.Ac. | 81.6 | C5:1-DC; SM (OH) C14:1; Orn |
| 2291 | 4 | S.L./Am.Ac./B.Am. | 82.4 | SM C18:1; Gln; Met; total DMA |
| 2292 | 4 | S.L./Am.Ac. | 81.7 | SM (OH) C14:1; SM (OH) C24:1; Met; Tyr |
| 2293 | 4 | S.L./Am.Ac. | 79.2 | SM C16:1; SM C18:0; SM C24:1; Gly |
| 2294 | 4 | S.L./Am.Ac./O.St. | 87.9 | SM (OH) C22:1; SM (OH) C22:2; Orn; 20a-OH-C |
| 2295 | 4 | S.L./Am.Ac./B.Am. | 80.1 | SM C18:1; SM (OH) C14:1; Arg; Met-SO |
| 2296 | 4 | S.L./Am.Ac./O.St. | 79.1 | SM (OH) C22:2; SM (OH) C24:1; His; 20a-OH-C |

TABLE 9-continued

Metabolite combinations describing damage of basal ganglia

| No. | Npar | Chemical Class | Accuracy | Model |
|---|---|---|---|---|
| 2297 | 4 | Ac.Ca./S.L./Am.Ac. | 88.4 | C14:1; SM C24:0; Met; Pro |
| 2298 | 5 | Ac.Ca./S.L./Am.Ac./B.Am./O.St. | 80.1 | C5:1-DC; SM C24:1; Gln; Histamine; 24-DH-Lanosterol |
| 2299 | 5 | S.L./Am.Ac./B.Am. | 85.7 | SM C16:0; SM C24:1; SM (OH) C22:1; Lys; Met-SO |
| 2300 | 4 | En.Met/Ac.Ca./S.L./O.St. | 83.3 | alpha-KGA; C5:1-DC; SM (OH) C22:2; Cholestenone |
| 2301 | 4 | S.L./Am.Ac. | 87 | SM C16:1; SM (OH) C22:1; SM (OH) C22:2; Gly |
| 2302 | 4 | S.L./Am.Ac. | 80.8 | SM (OH) C14:1; SM (OH) C22:1; Arg; Phe |
| 2303 | 4 | Am.Ac./B.Am. | 85.4 | Gln; Lys; Tyr; Ac-Orn |
| 2304 | 4 | En.Met/S.L./B.Am. | 84.9 | alpha-KGA; SM (OH) C22:1; Ac-Orn; Histamine |
| 2305 | 4 | S.L./Am.Ac. | 79.3 | SM C16:0; SM C18:1; SM C20:2; Phe |
| 2306 | 4 | En.Met/S.L./Am.Ac./O.St. | 83.5 | Lac; SM C16:1; Met; 24-DH-Lanosterol |
| 2307 | 4 | S.L./Am.Ac. | 79.4 | SM C18:1; SM (OH) C22:1; Asn; Met |
| 2308 | 4 | S.L./B.Am./O.St. | 81.4 | SM C16:1; Kynurenine; Met-SO; 24-DH-Lanosterol |
| 2309 | 4 | Ac.Ca./S.L./B.Am. | 81.9 | C5:1-DC; SM C16:1; Ac-Orn; alpha-AAA |
| 2310 | 4 | S.L./Am.Ac./B.Am. | 88.8 | SM C16:1; SM (OH) C22:1; Ala; Ac-Orn |
| 2311 | 5 | S.L./Am.Ac. | 80.6 | SM C24:0; SM C24:1; SM (OH) C16:1; Arg; Thr |
| 2312 | 5 | En.Met/S.L./Am.Ac./P.G. | 81.1 | alpha-KGA; SM C18:1; SM C24:0; Leu; TXB2 |
| 2313 | 4 | S.L./Am.Ac. | 80.1 | Lac; SM C24:1; SM (OH) C22:2; Trp |
| 2314 | 4 | En.Met/S.L./Am.Ac./P.G. | 89.6 | Fum; SM (OH) C14:1; Pro; TXB2 |
| 2315 | 4 | Ac.Ca./S.L./Am.Ac. | 90.3 | C5:1-DC; SM C16:1; SM (OH) C16:1; Orn |
| 2316 | 4 | S.L./Am.Ac./B.Am. | 79.2 | SM (OH) C14:1; SM (OH) C22:2; Leu; Ac-Orn |
| 2317 | 4 | S.L./Am.Ac. | 80.8 | SM (OH) C14:1; His; Met; Tyr |
| 2318 | 5 | Am.Ac./B.Am./O.St. | 83.6 | Gln; Orn; Tyr; Ac-Orn; 25-OH-C |
| 2319 | 5 | S.L./Am.Ac./B.Am. | 84.9 | SM (OH) C22:2; Lys; Met; Orn; Met-SO |
| 2320 | 4 | S.L./Am.Ac./B.Am. | 85.4 | SM C16:0; Orn; Trp; Met-SO |
| 2321 | 5 | S.L./Am.Ac./P.G. | 80 | SM C16:1; SM (OH) C24:1; Arg; Tyr; LTB4 |
| 2322 | 4 | S.L./Am.Ac./B.Am. | 79.3 | SM (OH) C14:1; Arg; Phe; Histamine |
| 2323 | 5 | S.L./Am.Ac./O.St. | 85.9 | SM (OH) C14:1; Gln; Phe; Pro; 24-DH-Lanosterol |
| 2324 | 5 | Ac.Ca./S.L./Am.Ac. | 85 | C14:1; SM C18:0; SM (OH) C14:1; Pro; Tyr |
| 2325 | 4 | S.L./Am.Ac./B.Am. | 89 | SM (OH) C14:1; Gln; Lys; Met-SO |
| 2326 | 6 | S.L./B.Am./O.St. | 86.1 | SM (OH) C14:1; alpha-AAA; Met-SO; 20a-OH-C; 22R-OH-C; 24S-OH-C |
| 2327 | 4 | S.L./Am.Ac. | 86.6 | SM C18:1; SM C20:2; SM (OH) C14:1; Tyr |
| 2328 | 4 | S.L./Am.Ac. | 83.5 | SM C24:1; SM (OH) C24:1; Lys; Met |
| 2329 | 4 | S.L./B.Am. | 84.2 | SM C16:1; SM (OH) C14:1; SM (OH) C22:1; Met-SO |
| 2330 | 4 | En.Met/S.L./Am.Ac./O.St. | 80.2 | alpha-KGA; SM C18:0; Trp; Cholestenone |
| 2331 | 3 | S.L./Am.Ac. | 79.2 | SM C16:1; SM (OH) C22:2; Met |
| 2332 | 4 | S.L./Am.Ac./B.Am. | 81.3 | SM C16:1; Gln; Phe; Met-SO |
| 2333 | 4 | S.L./Am.Ac. | 85.8 | SM C24:0; Leu; Met; Pro |
| 2334 | 4 | S.L./Am.Ac./O.St. | 84.6 | SM (OH) C22:2; His; Leu; 20a-OH-C |
| 2335 | 4 | S.L./Am.Ac./O.St. | 85.3 | SM (OH) C16:1; SM (OH) C22:2; Val; 20a-OH-C |
| 2336 | 5 | S.L./Am.Ac./O.St. | 82 | SM C20:2; SM (OH) C14:1; Gln; Pro; 24-DH-Lanosterol |
| 2337 | 4 | S.L./Am.Ac. | 80.3 | SM (OH) C14:1; SM (OH) C22:1; Asn; Orn |
| 2338 | 4 | Ac.Ca./S.L. | 80.5 | C5:1-DC; SM C16:0; SM C18:1; SM (OH) C22:2 |
| 2339 | 4 | S.L./Am.Ac./B.Am./O.St. | 83.8 | SM (OH) C22:1; Gln; Met-SO; 24-DH-Lanosterol |
| 2340 | 3 | S.L./Am.Ac. | 85.1 | SM (OH) C22:2; SM (OH) C24:1; Gly |
| 2341 | 6 | En.Met/Ac.Ca./S.L./Am.Ac. | 81.6 | Lac; C6:1; SM C16:1; SM (OH) C16:1; Asn; Orn |
| 2342 | 4 | Ac.Ca./S.L./Am.Ac. | 88.7 | C5:1-DC; SM C16:1; SM C24:1; Lys |
| 2343 | 4 | S.L./Am.Ac. | 79.1 | SM C16:0; SM C16:1; SM C18:1; Tyr |
| 2344 | 4 | En.Met/S.L./Am.Ac. | 81.5 | alpha-KGA; SM (OH) C14:1; Arg; Tyr |
| 2345 | 4 | S.L./Am.Ac. | 83.4 | SM (OH) C16:1; Gln; Met; Pro |
| 2346 | 5 | S.L./Am.Ac./O.St. | 88.6 | SM (OH) C22:2; SM (OH) C24:1; Pro; Trp; 22R-OH-C |
| 2347 | 4 | S.L./Am.Ac. | 83.3 | SM C20:2; SM (OH) C22:2; Met; Trp |
| 2348 | 4 | S.L./Am.Ac./B.Am. | 80.2 | SM C16:1; SM (OH) C22:2; His; Kynurenine |
| 2349 | 5 | S.L./Am.Ac./P.G. | 82 | SM C16:0; SM (OH) C22:1; Met; 8-iso-PGF2a; LTB4 |
| 2350 | 4 | S.L./Am.Ac. | 85.7 | Lac; SM C16:1; SM C24:1; Met |
| 2351 | 6 | En.Met/S.L./Am.Ac. | 89.4 | Lac; SM (OH) C14:1; SM (OH) C16:1; Gln; Met; Orn |
| 2352 | 5 | Ac.Ca./S.L./Am.Ac./B.Am. | 86.2 | C6:1; SM C16:0; SM (OH) C14:1; Arg; Met-SO |
| 2353 | 5 | En.Met/S.L./Am.Ac./B.Am. | 83.7 | Suc; SM (OH) C22:1; Lys; Ac-Orn; Met-SO |
| 2354 | 4 | Ac.Ca./S.L./Am.Ac. | 84.8 | C10:2; SM C18:1; Gln; Met |
| 2355 | 4 | S.L./Am.Ac./B.Am./O.St. | 86.4 | SM C16:0; Trp; Met-SO; 24-DH-Lanosterol |
| 2356 | 4 | S.L./Am.Ac./O.St. | 90.1 | SM C24:1; SM (OH) C22:2; Ala; Cholestenone |
| 2357 | 5 | En.Met/Ac.Ca./S.L./Am.Ac. | 84.7 | alpha-KGA; C6:1; SM C24:0; Met; Tyr |
| 2358 | 5 | En.Met/S.L./Am.Ac. | 80.6 | alpha-KGA; H1; SM C16:0; Trp; Tyr |
| 2359 | 4 | En.Met/S.L./Am.Ac./P.G. | 87 | alpha-KGA; SM C16:0; Orn; TXB2 |
| 2360 | 4 | Ac.Ca./S.L./B.Am. | 86.2 | C6:1; SM C16:1; SM (OH) C22:1; Met-SO |
| 2361 | 5 | En.Met/Ac.Ca./S.L./B.Am. | 84.1 | alpha-KGA; C6:1; SM (OH) C14:1; Ac-Orn |
| 2362 | 4 | S.L./Am.Ac./B.Am. | 90.6 | SM C16:1; SM (OH) C14:1; Tyr; Kynurenine |
| 2363 | 4 | S.L./Am.Ac./B.Am. | 85.3 | SM C24:1; SM (OH) C22:2; Pro; Histamine |
| 2364 | 4 | S.L./Am.Ac./P.G. | 83.4 | SM C16:1; SM (OH) C16:1; Orn; TXB2 |
| 2365 | 4 | En.Met/S.L./Am.Ac./P.G. | 80.1 | Suc; SM C24:1; Orn; 8-iso-PGF2a |
| 2366 | 4 | S.L./Am.Ac./O.St. | 86.8 | SM C18:1; Orn; Trp; 24-DH-Lanosterol |
| 2367 | 6 | Ac.Ca./S.L./Am.Ac./O.St. | 86.1 | C6:1; SM C16:0; SM C24:1; SM (OH) C22:1; Val; 20a-OH-C |
| 2368 | 5 | S.L./Am.Ac. | 81.6 | SM C20:2; SM C24:0; SM C24:1; Leu; Phe |
| 2369 | 4 | En.Met/S.L./Am.Ac./B.Am. | 84.7 | Pent-P; SM (OH) C22:2; Pro; Histamine |
| 2370 | 3 | S.L./Am.Ac./O.St. | 83 | SM C24:0; Tyr; 25-OH-C |
| 2371 | 6 | S.L./Am.Ac./B.Am. | 80.6 | SM C24:1; SM (OH) C22:1; Gln; Val; Kynurenine; total DMA |
| 2372 | 6 | Ac.Ca./S.L./Am.Ac./B.Am. | 82.6 | C12; SM C16:1; SM C18:1; Arg; Pro; Met-SO |

TABLE 9-continued

Metabolite combinations describing damage of basal ganglia

| No. | Npar | Chemical Class | Accuracy | Model |
|---|---|---|---|---|
| 2373 | 4 | En.Met/S.L./Am.Ac. | 83.2 | Fum; SM (OH) C22:2; Arg; Met |
| 2374 | 4 | En.Met/S.L./B.Am. | 84.8 | alpha-KGA; SM C24:0; SM (OH) C24:1; Met-SO |
| 2375 | 5 | Ac.Ca./S.L./Am.Ac./O.St. | 92.1 | C5:1-DC; SM C16:1; Gln; Lys; Cholestenone |
| 2376 | 4 | Ac.Ca./Am.Ac. | 79.5 | C18; His; Met; Pro |
| 2377 | 4 | En.Met/S.L./Am.Ac. | 84.8 | Lac; SM C20:2; SM (OH) C14:1; Met |
| 2378 | 5 | S.L./Am.Ac./B.Am. | 82 | SM C16:0; SM C16:1; SM (OH) C24:1; Gly; Ac-Orn |
| 2379 | 4 | Am.Ac. | 86.1 | Gln; Met; Orn; Pro |
| 2380 | 4 | Am.Ac./B.Am./O.St. | 79.1 | Lys; Ac-Orn; 24-DH-Lanosterol; Cholestenone |
| 2381 | 5 | S.L./Am.Ac./B.Am. | 90 | SM C24:1; SM (OH) C14:1; Pro; Trp; Ac-Orn |
| 2382 | 4 | En.Met/Ac.Ca./S.L./B.Am. | 84.2 | alpha-KGA; C6:1; SM C16:1; Met-SO |
| 2383 | 4 | S.L./Am.Ac./P.G. | 81.6 | SM C16:0; Arg; Gln; 8-iso-PGF2a |
| 2384 | 5 | S.L./Am.Ac./B.Am. | 87.5 | SM C16:1; SM (OH) C22:2; Orn; Trp; Ac-Orn |
| 2385 | 4 | S.L./Am.Ac. | 83.1 | SM (OH) C16:1; SM (OH) C22:1; SM (OH) C22:2; Tyr |
| 2386 | 4 | Ac.Ca./S.L./B.Am. | 79.3 | C5:1-DC; SM (OH) C24:1; Ac-Orn; alpha-AAA |
| 2387 | 4 | S.L./Am.Ac. | 79.5 | SM C18:1; SM (OH) C22:1; Met; Phe |
| 2388 | 4 | En.Met/Ac.Ca./Am.Ac./B.Am. | 87.2 | Suc; C6:1; Arg; Histamine |
| 2389 | 4 | S.L./Am.Ac./P.G. | 80.7 | SM C16:1; Met; Orn; 8-iso-PGF2a |
| 2390 | 4 | Ac.Ca./S.L./B.Am./O.St. | 86.1 | C6:1; SM (OH) C22:1; Met-SO; 24S-OH-C |
| 2391 | 4 | S.L./Am.Ac. | 80.1 | SM C16:1; SM C24:1; Gly; Met |
| 2392 | 4 | En.Met/Ac.Ca./S.L./Am.Ac. | 80.4 | alpha-KGA; C14:1-OH; SM C18:1; Met |
| 2393 | 4 | S.L./Am.Ac./P.G. | 96.1 | SM (OH) C16:1; SM (OH) C22:2; Lys; TXB2 |
| 2394 | 4 | S.L./Am.Ac./B.Am. | 79.6 | SM C20:2; SM C16:1; Orn; Met-SO |
| 2395 | 4 | S.L./Am.Ac./B.Am. | 79.8 | SM (OH) C14:1; SM (OH) C16:1; Lys; Met-SO |
| 2396 | 4 | S.L./Am.Ac./B.Am. | 88.4 | SM C16:0; SM C18:1; Tyr; Kynurenine |
| 2397 | 5 | S.L./Am.Ac./B.Am./O.St. | 90.1 | SM C18:0; SM (OH) C22:1; Trp; Met-SO; Cholestenone |
| 2398 | 4 | En.Met/S.L./Am.Ac. | 81.8 | Lac; SM C18:1; SM (OH) C14:1; Asn |
| 2399 | 4 | En.Met/Ac.Ca./Am.Ac./B.Am. | 79.5 | alpha-KGA; C14:1; His; Met-SO |
| 2400 | 6 | S.L./Am.Ac./B.Am./O.St. | 96.5 | SM C16:1; Arg; Trp; Creatinine; Met-SO; 24-DH-Lanosterol |
| 2401 | 4 | S.L./Am.Ac./B.Am. | 82.5 | SM C24:1; SM C16:1; Lys; Ac-Orn |
| 2402 | 4 | En.Met/Ac.Ca./S.L./Am.Ac. | 84.7 | Fum; C6:1; SM (OH) C22:1; Met |
| 2403 | 4 | S.L./Am.Ac./B.Am. | 81.5 | SM C24:0; SM (OH) C22:2; Leu; Met-SO |
| 2404 | 4 | En.Met/Ac.Ca./Am.Ac. | 85.1 | alpha-KGA; Lac; C14:1; Met |
| 2405 | 6 | S.L./Am.Ac./B.Am. | 87.5 | SM C24:0; SM (OH) C22:1; Arg; His; Tyr; Ac-Orn |
| 2406 | 4 | Ac.Ca./S.L./O.St. | 88.1 | C5:1-DC; SM (OH) C14:1; SM (OH) C24:1; Cholestenone |
| 2407 | 5 | En.Met/Ac.Ca./S.L./B.Am./O.St. | 81.6 | alpha-KGA; C6:1; SM (OH) C22:2; Ac-Orn; 25-OH-C |
| 2408 | 5 | En.Met/Ac.Ca./S.L./Am.Ac. | 79.8 | alpha-KGA; C9; SM C24:1; Lys; Tyr |
| 2409 | 6 | S.L./Am.Ac./B.Am./O.St. | 87.6 | SM C18:1; SM C24:0; Leu; Trp; Ac-Orn; Cholestenone |
| 2410 | 4 | En.Met/S.L./Am.Ac. | 88.8 | Lac; SM C16:0; Met; Trp |
| 2411 | 4 | S.L./Am.Ac./B.Am. | 84.7 | SM (OH) C14:1; Met; Pro; Histamine |
| 2412 | 5 | S.L./Am.Ac./B.Am. | 79.3 | SM C24:0; SM (OH) C24:1; Ile; Pro; total DMA |
| 2413 | 4 | S.L./Am.Ac./B.Am. | 80.2 | SM (OH) C22:1; SM (OH) C22:2; His; Met-SO |
| 2414 | 6 | Ac.Ca./S.L./Am.Ac./B.Am. | 87 | C5:1-DC; SM C24:1; Gln; His; Lys; Met-SO |
| 2415 | 4 | En.Met/S.L./Am.Ac. | 82.6 | Lac; SM C16:1; SM C24:1; Phe |
| 2416 | 4 | S.L./Am.Ac. | 87.7 | SM (OH) C14:1; SM (OH) C22:1; Met; Pro |
| 2417 | 4 | S.L./Am.Ac./B.Am. | 89.1 | SM C24:0; Arg; Gln; Met-SO |
| 2418 | 4 | S.L./B.Am./O.St. | 85.4 | SM (OH) C22:1; SM (OH) C24:1; Met-SO; 25-OH-C |
| 2419 | 4 | S.L./Am.Ac./B.Am. | 88.7 | SM (OH) C14:1; Pro; Ac-Orn; Histamine |
| 2420 | 4 | S.L./Am.Ac. | 87.5 | SM C16:1; SM C24:1; SM (OH) C22:1; Ala |
| 2421 | 4 | S.L./B.Am. | 86.9 | SM C16:1; SM C24:0; Kynurenine; Met-SO |
| 2422 | 4 | S.L./Am.Ac./B.Am. | 80.3 | SM (OH) C14:1; SM (OH) C24:1; Phe; Ac-Orn |
| 2423 | 4 | En.Met/S.L./Am.Ac. | 83 | Suc; SM C24:1; SM (OH) C24:1; Tyr |
| 2424 | 4 | En.Met/S.L./Am.Ac./P.G. | 80.6 | alpha-KGA; SM (OH) C22:2; His; TXB2 |
| 2425 | 5 | S.L./Am.Ac./P.G. | 87.5 | SM C24:0; Gln; Orn; Tyr; LTB4 |
| 2426 | 4 | S.L./Am.Ac./B.Am. | 81.8 | SM C16:0; SM (OH) C22:1; His; Met-SO |
| 2427 | 5 | Ac.Ca./S.L./Am.Ac. | 83.4 | C5:1-DC; SM C16:0; SM C24:1; SM (OH) C22:2; Tyr |
| 2428 | 4 | S.L./Am.Ac./B.Am./O.St. | 80.3 | SM C16:0; Pro; Histamine; 20a-OH-C |
| 2429 | 6 | En.Met/S.L./Am.Ac. | 83.5 | Lac; SM C24:1; SM (OH) C22:1; Asp; Gln; Orn |
| 2430 | 4 | Ac.Ca./S.L./Am.Ac. | 81.9 | C5:1-DC; SM C16:1; SM C26:1; His |
| 2431 | 3 | S.L./Am.Ac./B.Am. | 80.2 | SM C16:1; Orn; Met-SO |
| 2432 | 4 | S.L./Am.Ac. | 82 | SM C24:0; SM C24:1; SM C26:1; Ala |
| 2433 | 4 | En.Met/S.L./Am.Ac. | 84.4 | Fum; SM C16:0; SM C16:1; Met |
| 2434 | 4 | Ac.Ca./S.L./Am.Ac. | 79.4 | C14:1; SM C24:1; Arg; Met |
| 2435 | 4 | S.L./B.Am. | 79.5 | SM C16:0; SM (OH) C22:2; SM (OH) C24:1; Met-SO |
| 2436 | 5 | S.L./Am.Ac./B.Am./O.St. | 89.8 | SM C16:1; SM (OH) C22:2; Ala; Ac-Orn; Cholestenone |
| 2437 | 5 | S.L./Am.Ac./B.Am./O.St. | 82.6 | SM C16:1; SM (OH) C24:1; Orn; Ac-Orn; 25-OH-C |
| 2438 | 4 | S.L./Am.Ac. | 81.3 | SM C18:1; SM C20:2; SM C24:1; Tyr |
| 2439 | 4 | En.Met/S.L./Am.Ac. | 91.3 | Lac; SM C16:1; Gln; Met |
| 2440 | 4 | S.L./Am.Ac. | 84.6 | SM C24:0; SM C24:1; Ala; Arg |
| 2441 | 4 | Ac.Ca./S.L./Am.Ac. | 83.2 | C5:1-DC; SM (OH) C14:1; SM (OH) C16:1; Tyr |
| 2442 | 4 | En.Met/Ac.Ca./S.L. | 87.9 | alpha-KGA; C5:1-DC; SM C16:1; SM (OH) C24:1 |
| 2443 | 3 | S.L./Am.Ac. | 84 | SM C16:0; SM C20:2; Tyr |
| 2444 | 4 | S.L./Am.Ac./O.St. | 83 | SM C24:1; Met; Trp; Cholestenone |
| 2445 | 4 | S.L./Am.Ac. | 83.9 | SM (OH) C16:1; SM (OH) C22:1; Met; Orn |
| 2446 | 4 | S.L./Am.Ac./B.Am./O.St. | 80.5 | SM (OH) C14:1; Gln; Met-SO; 25-OH-C |
| 2447 | 4 | En.Met/S.L./Am.Ac./O.St. | 85.5 | Lac; SM C24:0; Met; Cholestenone |
| 2448 | 6 | S.L./Am.Ac./B.Am./P.G. | 90.4 | SM (OH) C22:1; Pro; Trp; Met-SO; Serotonin; 8-iso-PGF2a |

TABLE 9-continued

Metabolite combinations describing damage of basal ganglia

| No. | Npar | Chemical Class | Accuracy | Model |
|---|---|---|---|---|
| 2449 | 4 | En.Met/Am.Ac. | 79.7 | alpha-KGA; H1; Gln; Met |
| 2450 | 5 | En.Met/S.L./Am.Ac. | 82.5 | Pent-P; SM C16:0; SM (OH) C22:2; Orn; Pro |
| 2451 | 4 | Am.Ac./B.Am. | 82.2 | Gln; Pro; Trp; Met-SO |
| 2452 | 4 | En.Met/S.L./Am.Ac. | 87.1 | Lac; SM (OH) C22:2; Gln; Phe |
| 2453 | 5 | Ac.Ca./S.L./Am.Ac./P.G. | 79.2 | C14:1; SM (OH) C24:1; Arg; Leu; TXB2 |
| 2454 | 4 | S.L./B.Am. | 83.8 | SM C18:1; SM C24:0; SM (OH) C22:1; Met-SO |
| 2455 | 5 | S.L./Am.Ac./P.G. | 81.7 | SM (OH) C22:1; SM (OH) C22:2; Asn; Pro; LTB4 |
| 2456 | 4 | S.L./B.Am. | 81 | SM (OH) C14:1; SM (OH) C24:1; Ac-Orn; Histamine |
| 2457 | 4 | S.L./Am.Ac./O.St. | 84.5 | SM (OH) C14:1; SM (OH) C22:2; Ala; Cholestenone |
| 2458 | 4 | S.L./Am.Ac./B.Am./O.St. | 85.5 | SM (OH) C22:1; Gln; Met-SO; Cholestenone |
| 2459 | 5 | S.L./Am.Ac./B.Am. | 80.6 | SM C16:1; SM C20:2; SM (OH) C22:2; His; Met-SO |
| 2460 | 5 | S.L./Am.Ac. | 83.4 | SM C16:1; SM C24:0; SM (OH) C14:1; Arg; Ser |
| 2461 | 5 | S.L./Am.Ac./P.G. | 84 | SM C18:1; SM C24:1; Arg; Gln; 8-iso-PGF2a |
| 2462 | 4 | En.Met/Am.Ac./O.St. | 84 | Lac; Arg; Gln; 24-DH-Lanosterol |
| 2463 | 4 | S.L./Am.Ac./O.St. | 90.3 | SM (OH) C22:2; Met; Trp; Cholestenone |
| 2464 | 4 | Ac.Ca./S.L./Am.Ac./B.Am. | 87.3 | C14:1; SM (OH) C22:1; Arg; Met-SO |
| 2465 | 4 | S.L./Am.Ac./B.Am. | 80.8 | SM (OH) C24:1; Orn; Ac-Orn; Histamine |
| 2466 | 4 | Ac.Ca./S.L./Am.Ac. | 82 | C5:1-DC; SM (OH) C22:1; SM (OH) C22:2; Met |
| 2467 | 5 | S.L./Am.Ac./B.Am. | 93 | SM C16:1; SM (OH) C22:2; Leu; Met; Kynurenine |
| 2468 | 4 | Ac.Ca./S.L./Am.Ac. | 83.7 | C5:1-DC; SM (OH) C14:1; SM (OH) C22:2; Pro |
| 2469 | 4 | S.L./Am.Ac./P.G. | 95.2 | SM C16:1; SM (OH) C14:1; Pro; TXB2 |
| 2470 | 4 | S.L./Am.Ac./B.Am. | 82.9 | SM (OH) C24:1; Pro; Trp; Met-SO |
| 2471 | 4 | S.L./Am.Ac. | 81 | SM C24:0; SM C24:1; SM (OH) C24:1; Ala |
| 2472 | 4 | S.L./Am.Ac./B.Am. | 80.2 | SM (OH) C22:2; Arg; Histamine; Met-SO |
| 2473 | 4 | S.L./Am.Ac./B.Am. | 85.9 | SM (OH) C22:1; Orn; Tyr; Ac-Orn |
| 2474 | 4 | S.L./Am.Ac./P.G. | 80.5 | SM (OH) C14:1; SM (OH) C22:2; Pro; LTB4 |
| 2475 | 4 | Ac.Ca./S.L./Am.Ac./O.St. | 88.2 | C5:1-DC; SM (OH) C14:1; Pro; Cholestenone |
| 2476 | 4 | S.L./Am.Ac./B.Am. | 80.6 | SM C16:1; Phe; Pro; Histamine |
| 2477 | 5 | En.Met/Ac.Ca./S.L./Am.Ac. | 84.8 | Suc; C6:1; SM C16:0; Arg; Met |
| 2478 | 4 | S.L./Am.Ac./P.G. | 80.3 | SM C16:0; Arg; Trp; LTB4 |
| 2479 | 4 | En.Met/S.L./Am.Ac. | 80.3 | Suc; SM (OH) C16:1; Arg; Orn |
| 2480 | 3 | Ac.Ca./S.L./B.Am. | 85.9 | C5:1-DC; SM (OH) C14:1; Histamine |
| 2481 | 6 | Ac.Ca./S.L./Am.Ac. | 84.6 | C10:2; SM C16:0; SM C24:0; Met; Orn; Phe |
| 2482 | 5 | S.L./Am.Ac./B.Am. | 83.8 | SM C24:0; Arg; Orn; Val; Ac-Orn |
| 2483 | 4 | S.L./Am.Ac./B.Am. | 79.1 | SM C26:1; Leu; Met; Kynurenine |
| 2484 | 3 | S.L./B.Am./O.St. | 82.5 | SM (OH) C22:1; Met-SO; Cholestenone |
| 2485 | 3 | Am.Ac./P.G. | 80.4 | Gln; Orn; 8-iso-PGF2a |
| 2486 | 4 | En.Met/Am.Ac./B.Am. | 79.7 | Lac; Gln; Leu; Met-SO |
| 2487 | 4 | S.L./Am.Ac./B.Am. | 86.4 | SM C18:0; SM (OH) C14:1; Trp; Met-SO |
| 2488 | 4 | En.Met/Ac.Ca./Am.Ac. | 80.6 | alpha-KGA; Lac; C18:2; Pro |
| 2489 | 4 | S.L./Am.Ac./B.Am. | 88.3 | SM C16:0; SM (OH) C22:1; Trp; Met-SO |
| 2490 | 5 | En.Met/Am.Ac./O.St. | 83.6 | Suc; Orn; Trp; 24-DH-Lanosterol; Cholestenone |
| 2491 | 4 | S.L./Am.Ac./B.Am. | 79.8 | SM (OH) C14:1; Gln; Leu; Met-SO |
| 2492 | 4 | S.L./Am.Ac. | 84.5 | SM C20:2; SM C24:1; SM (OH) C22:2; Tyr |
| 2493 | 4 | S.L./Am.Ac./B.Am./O.St. | 85.3 | SM C24:1; Leu; Kynurenine; Cholestenone |
| 2494 | 4 | S.L./Am.Ac./B.Am. | 79 | SM C16:0; SM (OH) C16:1; Arg; Met-SO |
| 2495 | 4 | S.L./B.Am. | 85.5 | SM C24:0; SM (OH) C22:1; SM (OH) C24:1; Met-SO |
| 2496 | 4 | S.L./Am.Ac. | 83.6 | SM C20:2; SM (OH) C22:1; Arg; Met |
| 2497 | 4 | S.L./Am.Ac. | 83.8 | SM C24:0; SM (OH) C16:1; SM (OH) C22:2; Tyr |
| 2498 | 4 | S.L./Am.Ac./O.St. | 85.6 | SM C24:0; Tyr; 24S-OH-C; 25-OH-C |
| 2499 | 4 | S.L./Am.Ac./P.G. | 92.6 | SM (OH) C22:2; Gln; Lys; TXB2 |
| 2500 | 4 | En.Met/S.L./B.Am. | 83.6 | alpha-KGA; SM C16:0; SM (OH) C22:1; Met-SO |
| 2501 | 4 | En.Met/S.L./Am.Ac. | 80.9 | Lac; SM C18:0; Gln; Phe |
| 2502 | 4 | En.Met/S.L./Am.Ac./B.Am. | 79.4 | Fum; SM (OH) C22:1; Phe; Met-SO |
| 2503 | 4 | Ac.Ca./S.L./Am.Ac./B.Am. | 79.9 | C5:1-DC; SM C16:0; Gln; Histamine |
| 2504 | 4 | S.L./Am.Ac. | 83.1 | SM C16:1; SM C18:0; Arg; Met |
| 2505 | 4 | Ac.Ca./S.L./Am.Ac. | 88.3 | C6:1; SM C20:2; SM (OH) C14:1; Tyr |
| 2506 | 4 | S.L./Am.Ac. | 80 | SM C20:2; SM (OH) C22:2; Leu; Orn |
| 2507 | 6 | S.L./Am.Ac./O.St. | 92.7 | SM C24:0; SM (OH) C14:1; SM (OH) C16:1; His; Tyr; 20a-OH-C |
| 2508 | 5 | Ac.Ca./S.L./Am.Ac./O.St. | 84.6 | C5:1-DC; SM (OH) C16:1; His; Orn; 24-DH-Lanosterol |
| 2509 | 6 | En.Met/Ac.Ca./S.L./Am.Ac./O.St. | 89.3 | Suc; C5:1-DC; SM (OH) C24:1; Lys; Tyr; Cholestenone |
| 2510 | 4 | S.L./Am.Ac. | 83.4 | SM C16:1; SM (OH) C14:1; SM (OH) C22:2; Ala |
| 2511 | 4 | Ac.Ca./S.L./Am.Ac./B.Am. | 81.9 | C14:1; SM C18:1; Gln; Met-SO |
| 2512 | 4 | En.Met/S.L./Am.Ac. | 83.1 | Lac; SM C24:1; SM (OH) C22:1; Met |
| 2513 | 5 | S.L./Am.Ac./B.Am. | 83.1 | SM (OH) C14:1; SM (OH) C22:2; Gln; Ser; Ac-Orn |
| 2514 | 4 | S.L./Am.Ac./B.Am. | 81.6 | SM C24:0; Arg; Met; Histamine |
| 2515 | 4 | En.Met/Ac.Ca./S.L./B.Am. | 80 | alpha-KGA; C14:1; SM (OH) C16:1; Met-SO |
| 2516 | 4 | S.L./Am.Ac. | 83 | SM C18:1; SM C24:1; Trp; Tyr |
| 2517 | 4 | Am.Ac./B.Am. | 82.2 | Gln; Phe; Ac-Orn; alpha-AAA |
| 2518 | 4 | Ac.Ca./S.L./Am.Ac. | 84.4 | C6:1; SM C20:2; SM (OH) C22:2; Tyr |
| 2519 | 4 | Am.Ac./B.Am./O.St. | 82.4 | Gln; alpha-AAA; Met-SO; Cholestenone |
| 2520 | 4 | S.L./Am.Ac. | 84.8 | SM C16:1; SM C24:1; SM (OH) C22:1; Tyr |
| 2521 | 4 | En.Met/S.L./B.Am. | 81.7 | Lac; H1; SM (OH) C22:1; Met-SO |
| 2522 | 5 | Ac.Ca./S.L./Am.Ac./B.Am. | 84.7 | C6:1; SM (OH) C16:1; Lys; Kynurenine; Met-SO |
| 2523 | 5 | S.L./Am.Ac./O.St. | 93.7 | SM (OH) C22:1; Gln; Pro; Tyr; 20a-OH-C |
| 2524 | 4 | S.L./Am.Ac./B.Am./O.St. | 82.9 | SM C24:1; Gln; ADMA; Cholestenone |

TABLE 9-continued

Metabolite combinations describing damage of basal ganglia

| No. | Npar | Chemical Class | Accuracy | Model |
|---|---|---|---|---|
| 2525 | 4 | En.Met/S.L./Am.Ac. | 83.1 | Lac; SM C16:1; SM (OH) C22:2; Phe |
| 2526 | 4 | S.L./B.Am. | 80.1 | SM C16:0; SM C24:0; SM (OH) C22:2; Met-SO |
| 2527 | 4 | S.L./B.Am. | 79.2 | SM C20:2; SM (OH) C16:1; SM (OH) C22:1; Met-SO |
| 2528 | 4 | Ac.Ca./S.L./B.Am./O.St. | 86.9 | C5:1-DC; SM (OH) C22:1; Histamine; Cholestenone |
| 2529 | 4 | S.L./Am.Ac./O.St. | 81.2 | SM (OH) C14:1; SM (OH) C22:1; Ser; Cholestenone |
| 2530 | 4 | S.L./Am.Ac. | 87.1 | SM (OH) C22:1; Met; Pro; Trp |
| 2531 | 5 | S.L./Am.Ac./B.Am. | 89.9 | SM (OH) C14:1; SM (OH) C22:1; Gln; Lys; Met-SO |
| 2532 | 5 | Am.Ac./B.Am./O.St. | 86.5 | Lys; Met; Trp; Histamine; 24-DH-Lanosterol |
| 2533 | 4 | S.L./Am.Ac./B.Am. | 92 | SM (OH) C14:1; Leu; Tyr; Kynurenine |
| 2534 | 4 | S.L./Am.Ac./O.St. | 82.9 | SM (OH) C24:1; Lys; Met; 24S-OH-C |
| 2535 | 4 | S.L./Am.Ac./O.St. | 80.9 | SM C16:0; SM C26:1; Leu; 20a-OH-C |
| 2536 | 6 | S.L./Am.Ac./O.St. | 83.6 | SM C18:1; SM (OH) C22:1; Gln; Orn; Phe; 22R-OH-C |
| 2537 | 4 | En.Met/S.L./Am.Ac. | 81.4 | Lac; SM (OH) C14:1; Gln; Phe |
| 2538 | 5 | S.L./Am.Ac./B.Am. | 82.7 | SM C24:0; SM (OH) C22:1; Gln; Val; Ac-Orn |
| 2539 | 4 | Ac.Ca./S.L./Am.Ac. | 82.2 | C9; SM C16:1; Met; Trp |
| 2540 | 4 | Ac.Ca./S.L./B.Am./O.St. | 89.6 | C5:1-DC; SM C16:1; Creatinine; 24-DH-Lanosterol |
| 2541 | 4 | S.L./Am.Ac./B.Am. | 85.1 | SM C24:0; SM (OH) C22:1; Leu; Met-SO |
| 2542 | 4 | En.Met/S.L./Am.Ac./B.Am. | 82.2 | H1; SM C24:0; Arg; Met-SO |
| 2543 | 4 | Ac.Ca./S.L./Am.Ac./B.Am. | 87.6 | C6:1; SM C16:1; Arg; Ac-Orn |
| 2544 | 4 | S.L./Am.Ac./B.Am./O.St. | 79.1 | SM C18:1; Met; Histamine; 27-OH-C |
| 2545 | 4 | S.L./Am.Ac./B.Am./O.St. | 82.3 | SM (OH) C22:2; Gln; Met-SO; 25-OH-C |
| 2546 | 6 | S.L./Am.Ac./B.Am./O.St. | 89.1 | SM (OH) C14:1; SM (OH) C24:1; Orn; Creatinine; Met-SO; Cholestenone |
| 2547 | 4 | S.L./Am.Ac. | 80 | SM C24:1; SM (OH) C22:1; SM (OH) C22:2; Phe |
| 2548 | 5 | Ac.Ca./S.L./Am.Ac./O.St. | 80.8 | C6:1; SM C24:1; Arg; Tyr; Cholestenone |
| 2549 | 5 | En.Met/Ac.Ca./Am.Ac./O.St. | 80.9 | Suc; C6:1; Gln; Pro; 25-OH-C |
| 2550 | 4 | Am.Ac./B.Am./O.St. | 79.8 | Met; Pro; Creatinine; 24-DH-Lanosterol |
| 2551 | 4 | S.L./Am.Ac. | 85.1 | SM C16:1; SM (OH) C16:1; Met; Trp |
| 2552 | 5 | S.L./Am.Ac./B.Am./O.St. | 88.1 | SM (OH) C14:1; Tyr; Kynurenine; 24-DH-Lanosterol; Cholestenone |
| 2553 | 4 | Ac.Ca./S.L./Am.Ac. | 87.5 | C5:1-DC; SM C16:1; SM C18:1; Gln |
| 2554 | 5 | En.Met/Ac.Ca./S.L./Am.Ac./B.Am. | 91.1 | Lac; C6:1; SM C16:0; Gln; Met-SO |
| 2555 | 4 | S.L./Am.Ac. | 82.5 | SM C20:2; SM (OH) C22:2; Gln; Phe |
| 2556 | 4 | S.L./Am.Ac. | 82.7 | SM C18:0; SM (OH) C22:1; Met; Pro |
| 2557 | 5 | Ac.Ca./S.L./Am.Ac./O.St. | 80.9 | C10; SM (OH) C22:2; SM (OH) C24:1; Ac-Orn; 25-OH-C |
| 2558 | 4 | En.Met/S.L./Am.Ac. | 83.1 | Suc; SM (OH) C22:2; SM (OH) C24:1; Tyr |
| 2559 | 5 | S.L./Am.Ac./B.Am./O.St. | 89.2 | SM C16:0; His; Tyr; Kynurenine; Cholestenone |
| 2560 | 4 | S.L./Am.Ac./B.Am. | 79 | SM (OH) C22:1; Arg; His; Ac-Orn |
| 2561 | 4 | S.L./Am.Ac./B.Am./O.St. | 80.7 | SM (OH) C24:1; Gln; Met-SO; Cholestenone |
| 2562 | 4 | S.L./Am.Ac./B.Am. | 81.5 | SM (OH) C24:1; Gln; Orn; Ac-Orn |
| 2563 | 5 | S.L./Am.Ac./P.G. | 79.9 | SM C24:0; SM (OH) C22:2; Arg; 8-iso-PGF2a; LTB4 |
| 2564 | 3 | Am.Ac. | 82.9 | Gln; Met; Pro |
| 2565 | 4 | S.L./Am.Ac./B.Am. | 81.7 | SM C16:0; SM C18:0; Gln; Met-SO |
| 2566 | 4 | En.Met/S.L./Am.Ac./O.St. | 84.7 | Fum; SM (OH) C22:1; Met; Cholestenone |
| 2567 | 4 | S.L./Am.Ac./B.Am. | 86.5 | SM C16:0; SM (OH) C22:1; Arg; Met-SO |
| 2568 | 4 | S.L./Am.Ac./O.St. | 86 | SM C24:1; SM (OH) C22:2; Trp; 24-DH-Lanosterol |
| 2569 | 5 | Ac.Ca./S.L./Am.Ac./O.St. | 85.3 | C14:1; SM (OH) C22:1; Arg; Leu; 22R-OH-C |
| 2570 | 4 | Ac.Ca./S.L./Am.Ac. | 80.8 | C10; SM C24:1; SM C16:1; Tyr |
| 2571 | 5 | S.L./Am.Ac./B.Am./O.St. | 88.7 | SM C16:1; Pro; Ac-Orn; Histamine; Cholestenone |
| 2572 | 4 | En.Met/S.L./Am.Ac./B.Am. | 79.4 | alpha-KGA; SM C16:0; Lys; Met-SO |
| 2573 | 3 | S.L./B.Am. | 79.3 | SM C16:0; SM (OH) C24:1; Met-SO |
| 2574 | 4 | S.L./Am.Ac./O.St. | 79.5 | SM C16:0; SM (OH) C24:1; Pro; 20a-OH-C |
| 2575 | 4 | En.Met/S.L./B.Am. | 81.3 | alpha-KGA; Hex-P; SM (OH) C22:1; Met-SO |
| 2576 | 6 | S.L./Am.Ac./B.Am. | 89.7 | SM C16:1; SM C20:2; SM (OH) C14:1; Lys; Trp; Met-SO |
| 2577 | 4 | S.L./Am.Ac./B.Am. | 82.7 | SM C24:1; SM (OH) C24:1; Pro; Ac-Orn |
| 2578 | 3 | S.L./Am.Ac. | 79.1 | SM C16:1; SM C18:1; Asn |
| 2579 | 4 | Ac.Ca./S.L./Am.Ac. | 88.4 | C10:2; SM C18:1; Met; Trp |
| 2580 | 4 | Ac.Ca./S.L./Am.Ac./B.Am. | 82.3 | C6:1; SM C18:0; Gln; Met-SO |
| 2581 | 4 | Am.Ac./P.G. | 81.7 | Gln; Met; Trp; 8-iso-PGF2a |
| 2582 | 4 | Ac.Ca./S.L./Am.Ac. | 81.4 | C6 (C4:1-DC); SM C18:0; Met; Pro |
| 2583 | 4 | S.L./Am.Ac./P.G. | 86 | SM (OH) C22:2; SM (OH) C24:1; Leu; TXB2 |
| 2584 | 5 | S.L./Am.Ac./P.G. | 81.8 | SM (OH) C16:1; SM (OH) C22:1; Asn; Orn; 8-iso-PGF2a |
| 2585 | 4 | S.L./Am.Ac. | 82 | SM C16:1; SM C18:1; Asn; Pro |
| 2586 | 5 | S.L./Am.Ac./B.Am. | 86.6 | SM (OH) C16:1; SM (OH) C22:1; His; Orn; Ac-Orn |
| 2587 | 4 | S.L./Am.Ac. | 87.5 | SM C16:0; Met; Tyr; Kynurenine |
| 2588 | 5 | En.Met/S.L./Am.Ac./B.Am. | 84.9 | alpha-KGA; SM (OH) C22:2; His; Kynurenine; SDMA |
| 2589 | 6 | S.L./Am.Ac./O.St. | 92.8 | SM C24:1; SM (OH) C16:1; SM (OH) C22:2; Lys; Trp; 20a-OH-C |
| 2590 | 4 | S.L./Am.Ac./B.Am. | 88.9 | SM (OH) C14:1; SM (OH) C24:1; Tyr; Kynurenine |
| 2591 | 4 | S.L./Am.Ac./O.St. | 87 | SM (OH) C16:1; Met; Trp; 24-DH-Lanosterol |
| 2592 | 4 | S.L./Am.Ac. | 88.7 | SM C24:0; SM (OH) C14:1; Arg; Met |
| 2593 | 4 | S.L./Am.Ac. | 85.4 | SM C18:0; SM C24:1; Gln; Tyr |
| 2594 | 4 | S.L./Am.Ac. | 82.1 | SM C20:2; SM (OH) C22:2; Arg; Met |
| 2595 | 4 | S.L./Am.Ac./B.Am. | 80.8 | SM C20:2; His; Lys; Ac-Orn |
| 2596 | 4 | En.Met/S.L./Am.Ac./B.Am. | 81.9 | alpha-KGA; SM C18:0; Trp; SDMA |
| 2597 | 4 | Ac.Ca./Am.Ac./B.Am. | 81.6 | C18; Pro; Ac-Orn; Histamine |
| 2598 | 5 | S.L./Am.Ac./P.G. | 79.8 | SM C16:1; SM (OH) C14:1; Orn; Trp; LTB4 |
| 2599 | 4 | En.Met/S.L./Am.Ac. | 87.8 | Lac; SM (OH) C14:1; Arg; Met |
| 2600 | 4 | S.L./Am.Ac. | 84.7 | SM C24:0; SM (OH) C22:2; Asn; Pro |

TABLE 9-continued

Metabolite combinations describing damage of basal ganglia

| No. | Npar | Chemical Class | Accuracy | Model |
|---|---|---|---|---|
| 2601 | 5 | Ac.Ca./S.L./Am.Ac. | 83.9 | C5:1-DC; SM C16:1; SM C24:1; SM (OH) C22:2; Leu |
| 2602 | 4 | Ac.Ca./S.L./Am.Ac./B.Am. | 80.6 | C5:1-DC; SM C24:0; Phe; Histamine |
| 2603 | 5 | En.Met/S.L./Am.Ac./B.Am. | 90.5 | alpha-KGA; SM C24:1; SM (OH) C22:2; Tyr; Kynurenine |
| 2604 | 4 | S.L./Am.Ac./O.St. | 79.3 | SM C24:1; His; Phe; Cholestenone |
| 2605 | 4 | S.L./Am.Ac. | 83.5 | SM C16:1; SM C24:1; SM (OH) C16:1; Gly |
| 2606 | 4 | En.Met/Am.Ac./O.St. | 91.7 | Fum; Met; Trp; Cholestenone |
| 2607 | 4 | S.L./Am.Ac./B.Am. | 86.6 | SM C16:1; SM (OH) C16:1; Pro; Ac-Orn |
| 2608 | 3 | S.L./Am.Ac. | 79.7 | SM C16:0; Arg; Met |
| 2609 | 4 | En.Met/S.L./Am.Ac. | 82.3 | alpha-KGA; Suc; SM (OH) C24:1; Tyr |
| 2610 | 4 | S.L./Am.Ac. | 79.2 | SM C18:1; SM C24:1; Gln; Ser |
| 2611 | 4 | S.L./Am.Ac. | 84.4 | SM C18:1; SM C24:0; SM (OH) C14:1; Tyr |
| 2612 | 4 | Ac.Ca./S.L./Am.Ac. | 82.9 | C5:1-DC; C6:1; SM C16:0; Lys |
| 2613 | 4 | En.Met/S.L./Am.Ac. | 86.4 | alpha-KGA; SM C24:0; Met; Pro |
| 2614 | 5 | S.L./Am.Ac./P.G. | 91.3 | SM C16:1; SM C18:1; SM (OH) C14:1; Ala; TXB2 |
| 2615 | 4 | Am.Ac./B.Am. | 87.4 | Gln; Lys; Trp; Met-SO |
| 2616 | 5 | S.L./Am.Ac./B.Am./O.St. | 85 | SM C24:0; SM C24:1; Arg; Ac-Orn; Cholestenone |
| 2617 | 6 | S.L./Am.Ac./O.St. | 86.4 | SM C24:0; SM C24:1; SM (OH) C16:1; Orn; Tyr; 24S-OH-C |
| 2618 | 4 | S.L./Am.Ac./B.Am. | 82 | SM C18:0; SM C24:0; Pro; Met-SO |
| 2619 | 4 | En.Met/Ac.Ca./S.L./Am.Ac. | 79.7 | alpha-KGA; C9; SM C16:1; Met |
| 2620 | 5 | S.L./Am.Ac./P.G. | 80 | SM C16:0; SM C24:0; Gln; Lys; TXB2 |
| 2621 | 4 | S.L./Am.Ac./B.Am. | 90.9 | SM C16:1; Leu; Met; Kynurenine |
| 2622 | 3 | S.L./Am.Ac. | 85 | SM C24:0; Pro; Tyr |
| 2623 | 5 | Ac.Ca./S.L./Am.Ac./B.Am. | 80.8 | C5:1-DC; SM C16:0; SM C20:2; Orn; Ac-Orn |
| 2624 | 4 | Ac.Ca./S.L./Am.Ac. | 83.9 | C5:1-DC; SM C16:0; SM C18:1; Trp |
| 2625 | 5 | S.L./Am.Ac./O.St. | 82.6 | SM C18:0; SM C24:1; His; Trp; 24-DH-Lanosterol |
| 2626 | 4 | S.L./Am.Ac./B.Am. | 82.9 | SM (OH) C22:2; Arg; Kynurenine; Met-SO |
| 2627 | 4 | S.L./B.Am. | 83 | SM C16:1; SM C18:0; SM C24:0; Met-SO |
| 2628 | 4 | Ac.Ca./S.L./Am.Ac./P.G. | 84.8 | C18; SM (OH) C22:1; Pro; TXB2 |
| 2629 | 4 | Ac.Ca./S.L./B.Am. | 89.1 | C6:1; SM C16:1; Kynurenine; Met-SO |
| 2630 | 4 | En.Met/S.L./P.G. | 85.5 | alpha-KGA; SM C16:0; SM C16:1; TXB2 |
| 2631 | 4 | S.L./Am.Ac. | 81.9 | SM C16:0; Arg; Met; Pro |
| 2632 | 4 | S.L./Am.Ac./B.Am. | 82.9 | SM C16:1; Arg; Pro; Met-SO |
| 2633 | 5 | S.L./Am.Ac./B.Am./O.St. | 85 | SM C24:1; SM (OH) C24:1; Tyr; Kynurenine; Cholestenone |
| 2634 | 4 | En.Met/S.L./Am.Ac./O.St. | 81.2 | SM C16:0; Gln; Pro; 25-OH-C |
| 2635 | 4 | En.Met/Ac.Ca./S.L./Am.Ac. | 79.2 | Lac; C14:1; SM (OH) C24:1; Met |
| 2636 | 4 | En.Met/S.L./Am.Ac. | 85.9 | Lac; SM (OH) C14:1; SM (OH) C24:1; Met |
| 2637 | 4 | S.L./Am.Ac. | 84.8 | SM C16:0; SM C24:0; Lys; Met |
| 2638 | 4 | En.Met/S.L./Am.Ac. | 83.4 | Lac; SM C16:0; SM (OH) C14:1; Tyr |
| 2639 | 4 | S.L./Am.Ac. | 81.1 | SM C16:0; SM C24:1; SM (OH) C16:1; Gly |
| 2640 | 4 | Ac.Ca./S.L. | 87.6 | C5:1-DC; SM C16:1; SM (OH) C22:1; SM (OH) C24:1 |
| 2641 | 3 | S.L./Am.Ac. | 80.3 | SM C18:1; SM (OH) C14:1; Asn |
| 2642 | 4 | S.L./Am.Ac. | 81.3 | SM C16:1; SM C24:1; SM (OH) C14:1; Gly |
| 2643 | 4 | S.L./Am.Ac./P.G. | 86.8 | SM C24:1; His; Orn; LTB4 |
| 2644 | 4 | S.L./Am.Ac. | 85.9 | SM C16:0; SM C24:1; Ala; Orn |
| 2645 | 4 | En.Met/S.L./Am.Ac. | 87.9 | Fum; SM C16:1; Gln; Met |
| 2646 | 5 | En.Met/Ac.Ca./S.L./Am.Ac./O.St. | 80.6 | alpha-KGA; C14:1; SM (OH) C24:1; Arg; 20a-OH-C |
| 2647 | 4 | S.L./B.Am./P.G. | 79.9 | SM (OH) C22:1; SM (OH) C22:2; Met-SO; 8-iso-PGF2a |
| 2648 | 6 | En.Met/Am.Ac./P.G. | 82.2 | Lac; Arg; Gln; Phe; Tyr; AA |
| 2649 | 4 | S.L./Am.Ac. | 82.9 | SM C24:0; SM C24:1; Arg; Phe |
| 2650 | 5 | Ac.Ca./S.L./Am.Ac./P.G. | 92.3 | C10; SM C16:1; His; Orn; TXB2 |
| 2651 | 4 | En.Met/S.L./B.Am./O.St. | 84.1 | alpha-KGA; SM C16:1; Ac-Orn; Cholestenone |
| 2652 | 4 | S.L./Am.Ac. | 81.2 | SM C18:1; SM C24:1; Gln; Phe |
| 2653 | 5 | En.Met/S.L./Am.Ac./O.St. | 79.1 | alpha-KGA; SM (OH) C14:1; SM (OH) C22:1; Ser; Cholestenone |
| 2654 | 4 | Ac.Ca./Am.Ac./O.St. | 80.4 | C14:1; Pro; Tyr; Cholestenone |
| 2655 | 4 | S.L./Am.Ac./P.G. | 81.5 | SM C16:1; SM C18:1; Trp; LTB4 |
| 2656 | 5 | En.Met/S.L./Am.Ac./P.G. | 84.8 | Lac; SM C18:1; Gln; Phe; LTB4 |
| 2657 | 4 | S.L./Am.Ac./P.G. | 86.1 | SM C24:1; SM (OH) C14:1; Pro; LTB4 |
| 2658 | 4 | En.Met/S.L./Am.Ac. | 81.6 | alpha-KGA; SM (OH) C22:1; SM (OH) C22:2; Met |
| 2659 | 3 | Ac.Ca./S.L./Am.Ac. | 80.5 | C5:1-DC; SM C16:0; Orn |
| 2660 | 4 | En.Met/Am.Ac./B.Am./O.St. | 86.5 | alpha-KGA; Trp; Met-SO; Cholestenone |
| 2661 | 4 | S.L./Am.Ac./B.Am. | 85.8 | SM (OH) C22:1; Orn; Ac-Orn; Histamine |
| 2662 | 5 | Ac.Ca./S.L./Am.Ac. | 80.5 | C14:1-OH; C5:1-DC; SM C18:0; SM C18:1; Lys |
| 2663 | 4 | S.L./Am.Ac. | 83.4 | SM C18:1; SM C24:1; SM (OH) C22:2; Ala |
| 2664 | 5 | En.Met/S.L./Am.Ac./B.Am./O.St. | 88.4 | alpha-KGA; SM (OH) C22:2; Trp; Met-SO; Cholestenone |
| 2665 | 5 | S.L./Am.Ac./O.St. | 89.4 | SM (OH) C14:1; SM (OH) C22:1; SM (OH) C22:2; Ser; 20a-OH-C |
| 2666 | 3 | S.L./Am.Ac./B.Am. | 86.6 | SM (OH) C22:1; Gln; Met-SO |
| 2667 | 4 | Ac.Ca./S.L./Am.Ac. | 91.6 | C5:1-DC; SM C16:0; SM C16:1; Orn |
| 2668 | 4 | S.L./Am.Ac./B.Am. | 82.7 | SM C18:1; SM (OH) C14:1; Orn; Met-SO |
| 2669 | 6 | En.Met/S.L./Am.Ac. | 88.4 | Lac; SM C16:1; Asn; Gln; Lys; Met |
| 2670 | 4 | S.L./Am.Ac. | 79.5 | SM C16:1; SM C18:1; SM C20:2; Met |
| 2671 | 4 | S.L./Am.Ac. | 82.9 | SM C18:1; SM C24:1; Ala; Gln |
| 2672 | 4 | S.L./Am.Ac./B.Am./O.St. | 91.5 | SM C16:1; Tyr; Creatinine; Cholestenone |
| 2673 | 5 | Am.Ac./B.Am./O.St./P.G. | 80.1 | Met; Orn; Ac-Orn; 25-OH-C; LTB4 |
| 2674 | 5 | S.L./Am.Ac./B.Am. | 94.7 | SM (OH) C14:1; SM (OH) C22:1; Met; Tyr; Kynurenine |
| 2675 | 4 | S.L./Am.Ac./O.St. | 86.3 | SM C18:1; SM (OH) C22:1; Trp; 24-DH-Lanosterol |
| 2676 | 4 | En.Met/S.L./Am.Ac. | 85.5 | Pent-P; SM C16:1; Arg; Pro |

TABLE 9-continued

Metabolite combinations describing damage of basal ganglia

| No. | Npar | Chemical Class | Accuracy | Model |
| --- | --- | --- | --- | --- |
| 2677 | 4 | S.L./Am.Ac. | 81.2 | SM C26:0; SM C26:1; SM (OH) C24:1; Met |
| 2678 | 5 | S.L./Am.Ac./B.Am. | 90.9 | SM C24:0; SM (OH) C22:1; SM (OH) C22:2; Orn; Met-SO |
| 2679 | 4 | Ac.Ca./S.L./O.St. | 88.7 | C5:1-DC; C6:1; SM (OH) C14:1; 24-DH-Lanosterol |
| 2680 | 4 | S.L./Am.Ac. | 85.8 | SM C24:0; His; Met; Pro |
| 2681 | 4 | En.Met/S.L./Am.Ac. | 82.7 | Lac; SM C16:1; SM (OH) C16:1; Phe |
| 2682 | 4 | S.L./Am.Ac./B.Am. | 82.9 | SM C24:1; SM (OH) C22:1; Arg; Met-SO |
| 2683 | 4 | S.L./Am.Ac. | 82.3 | SM C16:0; Met; Orn; Pro |
| 2684 | 4 | S.L./Am.Ac. | 83.6 | SM C16:1; SM C18:1; SM C20:2; Ala |
| 2685 | 4 | Ac.Ca./S.L./Am.Ac. | 82.6 | C6:1; SM C18:1; Gln; Tyr |
| 2686 | 5 | S.L./Am.Ac./O.St. | 90.2 | SM C24:1; SM (OH) C22:2; Gln; Lys; 20a-OH-C |
| 2687 | 4 | Ac.Ca./Am.Ac. | 88 | C14:1; Arg; Met; Pro |
| 2688 | 4 | En.Met/S.L./Am.Ac./B.Am. | 80.1 | Suc; SM C16:0; Lys; Ac-Orn |
| 2689 | 4 | S.L./Am.Ac./B.Am. | 84.2 | SM (OH) C16:1; Leu; Kynurenine; Met-SO |
| 2690 | 4 | S.L./Am.Ac. | 83.1 | SM C18:1; Gln; Met; Pro |
| 2691 | 4 | Ac.Ca./S.L./Am.Ac. | 81.6 | C6:1; SM C24:1; SM (OH) C22:1; Phe |
| 2692 | 4 | En.Met/S.L./B.Am. | 83.1 | OAA; SM (OH) C22:1; SM (OH) C22:2; Met-SO |
| 2693 | 4 | Ac.Ca./S.L./Am.Ac. | 83.8 | C6:1; SM C16:1; Arg; Met-SO |
| 2694 | 4 | S.L./Am.Ac./B.Am. | 82.7 | SM C24:0; SM (OH) C16:1; Arg; Ac-Orn |
| 2695 | 4 | S.L./Am.Ac./P.G. | 84.1 | SM C16:1; Met; Orn; LTB4 |
| 2696 | 4 | Ac.Ca./S.L./Am.Ac./O.St. | 79.3 | C14:1; SM (OH) C22:2; His; 20a-OH-C |
| 2697 | 4 | Ac.Ca./S.L./Am.Ac. | 87.4 | C5:1-DC; SM C16:0; SM (OH) C14:1; Pro |
| 2698 | 4 | En.Met/S.L./Am.Ac./B.Am. | 82.7 | Lac; SM C26:1; Gln; Met-SO |
| 2699 | 4 | S.L./Am.Ac. | 85.8 | SM (OH) C22:1; SM (OH) C22:2; Trp; Tyr |
| 2700 | 4 | S.L./Am.Ac. | 87.8 | SM C20:2; SM (OH) C14:1; His; Tyr |
| 2701 | 3 | En.Met/S.L./Am.Ac. | 81.1 | alpha-KGA; SM C16:1; Met |
| 2702 | 4 | En.Met/S.L./Am.Ac./O.St. | 81.8 | Pent-P; SM C18:1; Pro; Cholestenone |
| 2703 | 4 | Ac.Ca./S.L./O.St. | 80.9 | C5:1-DC; SM C16:0; SM C18:1; Cholestenone |
| 2704 | 4 | En.Met/S.L./Am.Ac. | 87 | Pent-P; SM (OH) C14:1; Met; Pro |
| 2705 | 4 | En.Met/S.L./Am.Ac./B.Am. | 85.2 | alpha-KGA; SM C16:0; Trp; Met-SO |
| 2706 | 4 | S.L./Am.Ac. | 83.6 | SM C24:0; SM (OH) C22:2; Met; Phe |
| 2707 | 5 | S.L./Am.Ac./B.Am. | 79.8 | SM C16:1; SM C18:1; Arg; Gln; total DMA |
| 2708 | 4 | Ac.Ca./S.L./Am.Ac. | 79 | C14:1; SM C18:1; SM (OH) C22:2; Arg |
| 2709 | 5 | S.L./Am.Ac./B.Am. | 90.5 | alpha-KGA; SM C16:1; His; Kynurenine; Met-SO |
| 2710 | 4 | En.Met/S.L./B.Am. | 81.1 | Fum; SM C16:0; SM C24:0; Met-SO |
| 2711 | 4 | S.L./B.Am. | 84.4 | SM C16:0; SM C24:0; SM (OH) C22:1; Met-SO |
| 2712 | 6 | En.Met/S.L./Am.Ac./O.St. | 88 | Fum; SM C16:0; SM C24:0; SM C24:1; Thr; 20a-OH-C |
| 2713 | 4 | S.L./Am.Ac./O.St. | 87.5 | SM (OH) C14:1; SM (OH) C22:1; Leu; 20a-OH-C |
| 2714 | 4 | En.Met/S.L./Am.Ac. | 86 | Lac; SM C18:0; Gln; Tyr |
| 2715 | 4 | S.L./Am.Ac./B.Am. | 79.5 | SM C24:1; SM (OH) C16:1; Trp; Met-SO |
| 2716 | 4 | S.L./Am.Ac./B.Am. | 79.9 | SM C16:1; SM (OH) C22:2; Gln; Met-SO |
| 2717 | 5 | S.L./Am.Ac./B.Am. | 80.9 | SM C18:1; SM (OH) C22:1; SM (OH) C24:1; Ala; Ac-Orn |
| 2718 | 4 | S.L./Am.Ac./B.Am. | 85 | SM (OH) C22:1; Gln; Phe; Met-SO |
| 2719 | 4 | S.L./Am.Ac./O.St. | 88.9 | SM (OH) C14:1; SM (OH) C22:1; Arg; 22R-OH-C |
| 2720 | 4 | S.L./Am.Ac./O.St. | 79 | SM C16:1; SM C18:1; Ser; Cholestenone |
| 2721 | 4 | En.Met/Am.Ac./B.Am. | 86.9 | alpha-KGA; Gln; Lys; Ac-Orn |
| 2722 | 4 | S.L./Am.Ac./B.Am. | 79.8 | SM (OH) C16:1; SM (OH) C24:1; Lys; Met-SO |
| 2723 | 4 | S.L./B.Am./O.St. | 79 | SM C24:1; Creatinine; Met-SO; Cholestenone |
| 2724 | 4 | S.L./Am.Ac./O.St. | 81.2 | SM C16:0; Met; Pro; 24-DH-Lanosterol |
| 2725 | 4 | En.Met/S.L./Am.Ac./O.St. | 81.8 | Lac; SM (OH) C22:2; Met; 25-OH-C |
| 2726 | 5 | S.L./Am.Ac./B.Am. | 81 | SM C16:0; SM C18:1; SM (OH) C24:1; Orn; Ac-Orn |
| 2727 | 6 | Ac.Ca./S.L./Am.Ac./O.St./P.G. | 85.6 | C6:1; SM C24:0; Phe; Trp; 24-DH-Lanosterol; LTB4 |
| 2728 | 4 | En.Met/S.L./Am.Ac./B.Am. | 87.3 | alpha-KGA; SM C24:0; Gln; Met-SO |
| 2729 | 4 | Ac.Ca./Am.Ac. | 84.1 | C10:2; Gln; Met; Phe |
| 2730 | 4 | S.L./Am.Ac./B.Am. | 79.8 | SM C16:1; SM (OH) C16:1; Gln; Met-SO |
| 2731 | 4 | S.L./Am.Ac./O.St. | 84 | SM C18:1; His; Trp; 24-DH-Lanosterol |
| 2732 | 4 | S.L./Am.Ac./O.St. | 80 | SM C18:1; Arg; Gln; 24-DH-Lanosterol |
| 2733 | 4 | S.L./Am.Ac./P.G. | 79.1 | SM (OH) C22:1; SM (OH) C22:2; Ser; LTB4 |
| 2734 | 6 | S.L./Am.Ac./B.Am./P.G. | 91.6 | SM C16:1; SM (OH) C22:1; SM (OH) C22:2; Gly; Met-SO; LTB4 |
| 2735 | 4 | S.L./Am.Ac. | 80.6 | SM C18:1; SM (OH) C14:1; SM (OH) C22:2; Tyr |
| 2736 | 5 | Ac.Ca./S.L./Am.Ac./O.St. | 79 | C14:1; SM C18:1; Ile; Orn; 24-DH-Lanosterol |
| 2737 | 4 | Ac.Ca./S.L./Am.Ac./B.Am. | 83.2 | C4:1; SM C24:0; Met; alpha-AAA |
| 2738 | 4 | S.L./Am.Ac. | 83.3 | SM (OH) C14:1; Pro; Tyr; Val |
| 2739 | 4 | En.Met/Ac.Ca./Am.Ac. | 81.7 | Lac; C14:1; Gln; Met |
| 2740 | 4 | S.L./Am.Ac./B.Am. | 85.4 | SM C16:0; Trp; alpha-AAA; Met-SO |
| 2741 | 4 | En.Met/S.L./B.Am. | 80.8 | Pent-P; SM C24:0; SM (OH) C22:2; Met-SO |
| 2742 | 4 | S.L./B.Am./P.G. | 80 | SM C24:1; SM (OH) C22:1; Met-SO; LTB4 |
| 2743 | 4 | S.L./Am.Ac./O.St. | 89.4 | SM C16:1; SM (OH) C14:1; Tyr; 20a-OH-C |
| 2744 | 5 | S.L./B.Am./O.St. | 88.3 | SM C16:1; SM (OH) C22:2; Creatinine; Met-SO; Cholestenone |
| 2745 | 4 | S.L./Am.Ac. | 79.2 | SM (OH) C22:1; SM (OH) C22:2; Pro; Ser |
| 2746 | 4 | Ac.Ca./S.L./Am.Ac./B.Am. | 79.7 | C6:1; SM (OH) C14:1; His; Met-SO |
| 2747 | 4 | En.Met/S.L./Am.Ac. | 80.6 | alpha-KGA; SM (OH) C22:2; Gln; Met |
| 2748 | 5 | S.L./Am.Ac./P.G. | 79.2 | SM (OH) C14:1; SM (OH) C22:1; Arg; Trp; 8-iso-PGF2a |
| 2749 | 6 | S.L./Am.Ac./B.Am. | 84.6 | SM C18:1; SM (OH) C22:1; Gln; Leu; Ac-Orn; Serotonin |
| 2750 | 5 | S.L./Am.Ac./B.Am./O.St. | 80.6 | SM C26:1; Gln; His; alpha-AAA; 20a-OH-C |
| 2751 | 4 | Ac.Ca./S.L./B.Am. | 86.9 | C5:1-DC; SM C16:0; SM (OH) C14:1; alpha-AAA |
| 2752 | 4 | En.Met/S.L./Am.Ac./B.Am. | 82.9 | Lac; SM (OH) C22:2; Gln; Histamine |

TABLE 9-continued

Metabolite combinations describing damage of basal ganglia

| No. | Npar | Chemical Class | Accuracy | Model |
|---|---|---|---|---|
| 2753 | 4 | S.L./Am.Ac./B.Am. | 84.4 | SM (OH) C22:2; SM (OH) C24:1; Orn; alpha-AAA |
| 2754 | 4 | S.L./Am.Ac. | 79.5 | SM C24:0; SM (OH) C16:1; Arg; Phe |
| 2755 | 4 | S.L./Am.Ac. | 83.1 | SM (OH) C22:1; SM (OH) C24:1; Met; Pro |
| 2756 | 4 | Ac.Ca./S.L./Am.Ac. | 83.4 | C6:1; SM C24:1; Ala; Orn |
| 2757 | 4 | S.L./Am.Ac. | 79.6 | SM (OH) C14:1; SM (OH) C16:1; SM (OH) C22:1; Met |
| 2758 | 5 | S.L./Am.Ac./B.Am./O.St. | 81.6 | SM C16:0; SM (OH) C14:1; Trp; ADMA; Cholestenone |
| 2759 | 4 | En.Met/S.L./Am.Ac./B.Am. | 82.2 | OAA; SM C18:1; Gln; Met-SO |
| 2760 | 4 | S.L./Am.Ac./B.Am. | 81.1 | SM (OH) C16:1; Arg; Gln; Ac-Orn |
| 2761 | 4 | En.Met/Ac.Ca./S.L./B.Am. | 81.1 | alpha-KGA; C9; SM C16:1; Met-SO |
| 2762 | 5 | Am.Ac./B.Am./O.St. | 80 | His; Lys; Met; Histamine; Cholestenone |
| 2763 | 4 | En.Met/S.L./Am.Ac. | 84.5 | Hex-P; SM C16:1; SM C24:1; Met |
| 2764 | 4 | En.Met/S.L./Am.Ac. | 83.8 | Lac; SM (OH) C24:1; Met; Trp |
| 2765 | 5 | En.Met/S.L./Am.Ac. | 83.6 | alpha-KGA; Suc; SM C24:0; SM (OH) C14:1; Tyr |
| 2766 | 4 | S.L./Am.Ac./B.Am. | 84.4 | SM C24:0; SM (OH) C16:1; Lys; Met-SO |
| 2767 | 4 | S.L./Am.Ac./O.St. | 97.2 | SM (OH) C14:1; SM (OH) C22:1; Tyr; 20a-OH-C |
| 2768 | 3 | Ac.Ca./S.L./B.Am. | 81.2 | C6:1; SM C24:0; Met-SO |
| 2769 | 4 | S.L./Am.Ac./B.Am. | 88.7 | SM C16:1; Arg; Gln; Met-SO |
| 2770 | 4 | Ac.Ca./S.L./Am.Ac. | 83.4 | C9; SM C16:1; SM (OH) C22:2; Orn |
| 2771 | 5 | Ac.Ca./S.L./Am.Ac./B.Am. | 79 | C14:1-OH; SM C18:1; Leu; Pro; Ac-Orn |
| 2772 | 5 | En.Met/S.L./Am.Ac./B.Am. | 83 | Lac; SM C24:1; SM C26:1; Met; Histamine |
| 2773 | 4 | S.L./Am.Ac./P.G. | 79.4 | SM (OH) C22:1; Gln; Orn; 8-iso-PGF2a |
| 2774 | 4 | En.Met/S.L./Am.Ac. | 80 | Pent-P; SM C18:1; SM (OH) C14:1; Pro |
| 2775 | 4 | S.L./Am.Ac./B.Am. | 93.7 | SM (OH) C22:1; SM (OH) C22:2; Tyr; Kynurenine |
| 2776 | 4 | S.L./Am.Ac./B.Am. | 87.4 | SM (OH) C22:2; Orn; Ac-Orn; Histamine |
| 2777 | 4 | S.L./Am.Ac. | 83.8 | SM C16:0; SM (OH) C14:1; Gly; Pro |
| 2778 | 4 | S.L./Am.Ac./B.Am. | 81.9 | SM C26:1; His; Orn; Ac-Orn |
| 2779 | 4 | En.Met/S.L./Am.Ac. | 79.7 | Hex-P; SM (OH) C22:1; His; Met |
| 2780 | 4 | S.L./Am.Ac. | 83 | SM C20:2; SM (OH) C14:1; Met; Val |
| 2781 | 4 | En.Met/S.L./B.Am./O.St. | 79.9 | alpha-KGA; SM C16:0; Ac-Orn; Cholestenone |
| 2782 | 4 | S.L./Am.Ac./B.Am. | 87.9 | SM (OH) C22:1; SM (OH) C22:2; Orn; Met-SO |
| 2783 | 4 | S.L./Am.Ac./B.Am. | 81.5 | SM C16:1; Orn; Trp; Ac-Orn |
| 2784 | 4 | En.Met/Am.Ac./B.Am. | 86.5 | Suc; Gln; Lys; Ac-Orn |
| 2785 | 4 | S.L./Am.Ac./B.Am. | 89.7 | SM (OH) C22:2; Leu; Met; Kynurenine |
| 2786 | 4 | En.Met/S.L./Am.Ac. | 81.9 | alpha-KGA; SM C16:1; SM (OH) C22:2; Met |
| 2787 | 4 | S.L./Am.Ac./O.St. | 85.3 | SM C16:0; Arg; Trp; 24-DH-Lanosterol |
| 2788 | 5 | S.L./Am.Ac./B.Am./P.G. | 87.4 | SM (OH) C22:1; Orn; Tyr; Ac-Orn; LTB4 |
| 2789 | 4 | S.L./Am.Ac./B.Am. | 82.7 | SM C24:0; Gln; Phe; Met-SO |
| 2790 | 5 | S.L./Am.Ac./O.St. | 87.9 | SM (OH) C22:2; SM (OH) C24:1; Leu; Pro; 20a-OH-C |
| 2791 | 4 | S.L./Am.Ac./B.Am. | 83.1 | SM C16:1; Pro; Histamine; Met-SO |
| 2792 | 4 | En.Met/Ac.Ca./S.L./Am.Ac. | 83.1 | Lac; C6:1; SM C16:0; Met |
| 2793 | 4 | En.Met/S.L./Am.Ac. | 86 | Suc; SM C16:1; SM C18:1; Arg |
| 2794 | 4 | En.Met/S.L./Am.Ac. | 79.5 | alpha-KGA; SM (OH) C22:2; Asn; Orn |
| 2795 | 4 | En.Met/S.L./B.Am. | 85.7 | Lac; SM C16:1; SM C24:0; Met-SO |
| 2796 | 4 | En.Met/S.L./B.Am. | 80.2 | Fum; SM C24:1; SM (OH) C24:1; Met-SO |
| 2797 | 6 | Ac.Ca./S.L./Am.Ac./B.Am./O.St. | 93 | C6:1; SM C18:1; SM (OH) C14:1; Trp; Ac-Orn; 24-DH-Lanosterol |
| 2798 | 4 | S.L./Am.Ac. | 82.9 | SM C16:1; SM C24:1; Ala; Leu |
| 2799 | 4 | En.Met/S.L./Am.Ac. | 81.4 | alpha-KGA; SM C18:1; SM (OH) C14:1; Met |
| 2800 | 4 | S.L./B.Am./O.St. | 80.3 | SM (OH) C22:2; SM (OH) C24:1; Met-SO; 24S-OH-C |
| 2801 | 4 | Am.Ac. | 79.1 | Arg; Gln; Met; Tyr |
| 2802 | 4 | S.L./Am.Ac./B.Am. | 84.5 | SM (OH) C22:1; Gln; Creatinine; Met-SO |
| 2803 | 4 | Ac.Ca./S.L./Am.Ac. | 81.2 | C14:1; SM (OH) C16:1; Arg; Pro |
| 2804 | 4 | Ac.Ca./S.L./B.Am. | 88.3 | C6:1; SM C24:0; SM (OH) C22:1; Met-SO |
| 2805 | 4 | S.L./Am.Ac./O.St. | 81.4 | SM C16:0; Met; Trp; Cholestenone |
| 2806 | 3 | S.L./Am.Ac. | 83.4 | SM C24:0; Arg; Met |
| 2807 | 4 | Ac.Ca./S.L./Am.Ac./B.Am. | 80.4 | C14:1; SM C18:1; Lys; Ac-Orn |
| 2808 | 4 | S.L./Am.Ac./B.Am. | 86 | SM (OH) C22:2; Gly; Ac-Orn; alpha-AAA |
| 2809 | 4 | En.Met/S.L./B.Am. | 82.4 | OAA; SM (OH) C14:1; SM (OH) C24:1; Met-SO |
| 2810 | 4 | En.Met/Ac.Ca./S.L./B.Am. | 87.6 | alpha-KGA; C6:1; SM C24:0; Met-SO |
| 2811 | 5 | S.L./Am.Ac./B.Am. | 87.2 | SM C16:1; His; Lys; Ac-Orn; Histamine |
| 2812 | 4 | En.Met/S.L./Am.Ac./B.Am. | 80.2 | Lac; SM (OH) C22:2; Trp; Histamine |
| 2813 | 5 | S.L./Am.Ac./B.Am. | 84.3 | SM C16:0; SM C24:0; SM C26:1; Ala; Met-SO |
| 2814 | 5 | Ac.Ca./S.L./Am.Ac./O.St. | 85.9 | C5:1-DC; SM C24:0; SM (OH) C16:1; Lys; Cholestenone |
| 2815 | 5 | S.L./Am.Ac./B.Am. | 81.6 | SM C18:1; SM C24:1; SM (OH) C22:1; Orn; Ac-Orn |
| 2816 | 5 | En.Met/S.L./Am.Ac./B.Am. | 83.5 | alpha-KGA; SM C16:0; Gln; Met-SO |
| 2817 | 4 | S.L./Am.Ac./O.St. | 84.3 | SM C16:1; Phe; Pro; Cholestenone |
| 2818 | 4 | En.Met/S.L./Am.Ac. | 81.8 | Fum; SM C16:1; SM C24:1; Met |
| 2819 | 5 | S.L./Am.Ac./B.Am. | 86.4 | Lac; SM C16:1; SM (OH) C24:1; SM (OH) C24:1; Ser |
| 2820 | 4 | S.L./Am.Ac./B.Am. | 82.1 | SM C16:0; SM (OH) C24:1; Lys; Ac-Orn |
| 2821 | 5 | S.L./Am.Ac./B.Am. | 82.5 | SM C16:0; SM C26:1; SM (OH) C16:1; Lys; Met-SO |
| 2822 | 4 | S.L./Am.Ac./O.St. | 87.9 | SM (OH) C14:1; Met; Trp; 24-DH-Lanosterol |
| 2823 | 4 | S.L./Am.Ac./B.Am. | 79.4 | SM C24:1; Arg; Tyr; Histamine |
| 2824 | 4 | S.L./Am.Ac. | 79.9 | SM C18:1; SM (OH) C14:1; His; Tyr |
| 2825 | 5 | S.L./Am.Ac. | 90 | SM C24:1; SM (OH) C14:1; SM (OH) C22:2; Orn; Ser |
| 2826 | 5 | En.Met/Am.Ac./O.St. | 88.1 | Lac; Gln; His; Phe; Cholestenone |
| 2827 | 4 | S.L./Am.Ac. | 79.2 | SM C16:0; SM C24:0; Arg; Phe |
| 2828 | 4 | En.Met/S.L./B.Am. | 83.7 | Lac; SM C24:0; SM (OH) C16:1; Met-SO |

TABLE 9-continued

Metabolite combinations describing damage of basal ganglia

| No. | Npar | Chemical Class | Accuracy | Model |
|---|---|---|---|---|
| 2829 | 4 | En.Met/Am.Ac. | 80.2 | Fum; Arg; His; Met |
| 2830 | 5 | En.Met/S.L./Am.Ac./B.Am. | 81.9 | Fum; SM C16:0; Met; Histamine; Met-SO |
| 2831 | 5 | Ac.Ca./S.L./Am.Ac. | 85.5 | C6:1; SM C24:1; SM (OH) C22:1; Ala; Orn |
| 2832 | 4 | Ac.Ca./S.L. | 90.7 | C5:1-DC; C6:1; SM C16:1; SM C24:0 |
| 2833 | 5 | S.L./Am.Ac./B.Am. | 82 | SM C26:1; SM (OH) C24:1; Lys; Histamine; Met-SO |
| 2834 | 4 | Ac.Ca./S.L./Am.Ac. | 81.7 | C5:1-DC; SM C16:1; SM C24:1; His |
| 2835 | 5 | Ac.Ca./S.L./Am.Ac./B.Am. | 81.8 | C5:1-DC; SM C24:1; SM (OH) C22:2; His; Spermidine |
| 2836 | 4 | S.L./Am.Ac./O.St. | 90.5 | SM C16:1; His; Pro; 20a-OH-C |
| 2837 | 5 | S.L./Am.Ac./B.Am./O.St. | 80.3 | SM C16:1; Trp; Histamine; Met-SO; 24S-OH-C |
| 2838 | 4 | S.L./Am.Ac./P.G. | 82.1 | SM C18:1; Orn; Trp; LTB4 |
| 2839 | 4 | S.L./Am.Ac./O.St. | 80.2 | SM C16:1; SM (OH) C22:1; Arg; 24S-OH-C |
| 2840 | 4 | S.L./Am.Ac./O.St. | 88.4 | SM (OH) C14:1; Gln; Pro; 20a-OH-C |
| 2841 | 4 | En.Met/S.L./Am.Ac./B.Am. | 89.4 | Fum; SM (OH) C24:1; Gln; Met-SO |
| 2842 | 4 | Ac.Ca./Am.Ac. | 82.8 | C18; Arg; Met; Pro |
| 2843 | 4 | S.L./Am.Ac./O.St. | 82.1 | SM C24:1; Ala; Orn; Cholestenone |
| 2844 | 4 | Ac.Ca./Am.Ac./O.St. | 82.4 | C14:1; His; Leu; 20a-OH-C |
| 2845 | 4 | Ac.Ca./S.L./O.St. | 86.8 | C5:1-DC; SM (OH) C14:1; SM (OH) C22:1; Cholestenone |
| 2846 | 4 | En.Met/S.L./Am.Ac./O.St. | 81.5 | alpha-KGA; SM C16:1; Gln; 20a-OH-C |
| 2847 | 4 | En.Met/S.L./Am.Ac./B.Am. | 81.5 | Lac; SM (OH) C24:1; Orn; Met-SO |
| 2848 | 3 | Ac.Ca./S.L. | 82.4 | C5:1-DC; C6:1; SM C24:0 |
| 2849 | 4 | alpha-KGA/Ac.Ca./S.L./B.Am. | 81.7 | alpha-KGA; C14:1; SM C18:1; Met-SO |
| 2850 | 4 | S.L./Am.Ac./B.Am. | 88.9 | SM C16:0; SM (OH) C22:1; Orn; Met-SO |
| 2851 | 5 | S.L./B.Am. | 83.8 | SM C16:1; SM C20:2; SM (OH) C14:1; Histamine; Met-SO |
| 2852 | 4 | En.Met/Am.Ac./O.St. | 80.9 | Lac; Gln; His; 24-DH-Lanosterol |
| 2853 | 4 | En.Met/S.L./Am.Ac. | 85.4 | Suc; SM (OH) C16:1; Met; Orn |
| 2854 | 4 | Am.Ac./B.Am. | 84.1 | Arg; Gln; Orn; Met-SO |
| 2855 | 4 | Ac.Ca./S.L./Am.Ac. | 81.1 | C18:1; SM C18:1; Pro; Tyr |
| 2856 | 4 | Ac.Ca./S.L./B.Am. | 84.3 | C6:1; SM C18:1; SM C24:0; Met-SO |
| 2857 | 4 | Ac.Ca./S.L./Am.Ac./O.St. | 79.5 | C10; SM C24:0; Pro; 20a-OH-C |
| 2858 | 4 | S.L./Am.Ac./B.Am. | 85.2 | SM C24:0; Arg; Pro; Met-SO |
| 2859 | 4 | Ac.Ca./S.L./Am.Ac. | 82.9 | C9; SM C16:1; Arg; Met |
| 2860 | 6 | En.Met/S.L./Am.Ac./B.Am. | 84.8 | alpha-KGA; SM C16:1; SM C18:0; SM (OH) C22:1; Lys; Met-SO |
| 2861 | 4 | S.L./Am.Ac./B.Am. | 80.3 | SM (OH) C14:1; SM (OH) C16:1; Orn; alpha-AAA |
| 2862 | 4 | En.Met/S.L./Am.Ac./B.Am. | 83.6 | Lac; SM C18:1; Trp; SDMA |
| 2863 | 4 | S.L./Am.Ac. | 87.4 | SM C24:0; Met; Orn; Pro |
| 2864 | 5 | En.Met/S.L./Am.Ac./O.St. | 82.2 | alpha-KGA; Suc; SM (OH) C14:1; Arg; 24-DH-Lanosterol |
| 2865 | 5 | S.L./Am.Ac. | 85.8 | SM C16:1; SM C18:1; SM C24:1; Trp; Tyr |
| 2866 | 3 | Ac.Ca./S.L./B.Am. | 82 | C5:1-DC; SM C16:0; Histamine |
| 2867 | 5 | En.Met/Ac.Ca./S.L./Am.Ac. | 89.6 | Fum; C10; SM (OH) C22:2; Gln; Met |
| 2868 | 4 | En.Met/S.L./Am.Ac. | 85.5 | Fum; Lac; SM (OH) C22:1; Met |
| 2869 | 4 | En.Met/Am.Ac./B.Am. | 80.3 | Lac; His; Orn; Met-SO |
| 2870 | 4 | En.Met/S.L./Am.Ac./B.Am. | 83.8 | alpha-KGA; SM (OH) C22:2; Gln; Met-SO |
| 2871 | 4 | S.L./Am.Ac./B.Am. | 82.5 | SM (OH) C24:1; Lys; Orn; Met-SO |
| 2872 | 4 | S.L./Am.Ac./B.Am. | 83.7 | SM C18:1; Gln; Ac-Orn; Histamine |
| 2873 | 5 | S.L./Am.Ac./B.Am./O.St. | 82.7 | SM C16:0; SM (OH) C22:2; Lys; Ac-Orn; Cholestenone |
| 2874 | 4 | S.L./Am.Ac./O.St. | 85.4 | SM (OH) C14:1; Met; Pro; 24-DH-Lanosterol |
| 2875 | 4 | Ac.Ca./S.L./Am.Ac. | 91 | C5:1-DC; SM C24:0; SM (OH) C22:1; Tyr |
| 2876 | 4 | Ac.Ca./S.L./Am.Ac. | 79.3 | C18; C5:1-DC; SM (OH) C14:1; Arg |
| 2877 | 4 | S.L./Am.Ac./B.Am. | 86.5 | SM (OH) C22:2; Lys; Ac-Orn; Histamine |
| 2878 | 4 | S.L./Am.Ac. | 84.1 | SM C24:1; His; Orn; Pro |
| 2879 | 4 | Ac.Ca./S.L./Am.Ac./O.St. | 79.7 | C6:1; SM (OH) C14:1; Trp; 24-DH-Lanosterol |
| 2880 | 4 | Ac.Ca./En.Met/S.L./B.Am. | 79.6 | C5:1-DC; H1; SM C16:0; alpha-AAA |
| 2881 | 5 | S.L./Am.Ac./B.Am. | 87.6 | SM (OH) C22:1; SM (OH) C22:2; His; Kynurenine; Met-SO |
| 2882 | 4 | S.L./Am.Ac. | 89.6 | SM C20:2; SM (OH) C22:2; Gln; Tyr |
| 2883 | 5 | Ac.Ca./S.L./Am.Ac./B.Am. | 82.3 | C14:1; SM (OH) C22:2; Arg; Histamine; Met-SO |
| 2884 | 4 | Am.Ac./B.Am. | 81.8 | His; Orn; Pro; Ac-Orn |
| 2885 | 4 | Ac.Ca./S.L./Am.Ac. | 85.3 | C5:1-DC; SM C24:0; SM (OH) C14:1; Pro |
| 2886 | 4 | S.L./Am.Ac. | 82.2 | SM C16:1; SM C24:1; Arg; His |
| 2887 | 4 | Ac.Ca./S.L./B.Am. | 81.4 | C6:1; SM C24:0; SM C24:1; Met-SO |
| 2888 | 5 | S.L./Am.Ac./B.Am. | 87 | SM C16:1; SM C24:1; SM (OH) C16:1; Tyr; Creatinine |
| 2889 | 4 | Ac.Ca./S.L./B.Am./O.St. | 90.9 | C5:1-DC; SM (OH) C14:1; Histamine; 25-OH-C |
| 2890 | 4 | S.L./Am.Ac./B.Am. | 81.1 | SM (OH) C24:1; Leu; Orn; Ac-Orn |
| 2891 | 5 | En.Met/S.L./Am.Ac./B.Am. | 89 | Lac; SM (OH) C14:1; Gln; Met-SO |
| 2892 | 6 | En.Met/S.L./Am.Ac. | 89.4 | Hex-P; SM C24:1; SM (OH) C14:1; SM (OH) C22:2; Met; Trp |
| 2893 | 4 | S.L./Am.Ac. | 85.6 | SM C16:1; SM (OH) C22:2; Ala; Met |
| 2894 | 4 | En.Met/Ac.Ca./S.L./O.St. | 84.5 | alpha-KGA; C14:1; SM C18:1; 20a-OH-C |
| 2895 | 5 | En.Met/S.L./Am.Ac./P.G. | 85.4 | Lac; SM C18:1; Gln; Orn; 8-iso-PGF2a |
| 2896 | 4 | S.L./Am.Ac. | 82.1 | SM C24:0; SM (OH) C24:1; Pro; Tyr |
| 2897 | 4 | S.L./Am.Ac./O.St. | 83.1 | SM C24:0; SM C24:1; Tyr; Cholestenone |
| 2898 | 4 | Ac.Ca./S.L./B.Am. | 85.3 | C6:1; SM (OH) C22:1; Histamine; Met-SO |
| 2899 | 5 | S.L./Am.Ac./B.Am./O.St. | 81.3 | SM C24:1; Arg; Met; Histamine; 27-OH-C |
| 2900 | 4 | S.L./Am.Ac. | 80.6 | SM C20:2; SM (OH) C14:1; SM (OH) C22:2; Pro |
| 2901 | 3 | Ac.Ca./S.L. | 82.2 | C5:1-DC; SM (OH) C14:1; SM (OH) C22:2 |
| 2902 | 4 | S.L./Am.Ac. | 85.2 | SM (OH) C22:2; Gln; Orn; Tyr |
| 2903 | 4 | En.Met/S.L./B.Am. | 79 | Fum; SM C16:0; SM C16:1; Met-SO |
| 2904 | 6 | En.Met/S.L./Am.Ac./B.Am. | 88.1 | Suc; SM C16:0; SM (OH) C22:1; Met; Pro; Serotonin |

TABLE 9-continued

Metabolite combinations describing damage of basal ganglia

| No. | Npar | Chemical Class | Accuracy | Model |
|---|---|---|---|---|
| 2905 | 4 | Ac.Ca./S.L./O.St. | 86.3 | C5:1-DC; SM C16:0; SM C16:1; Cholestenone |
| 2906 | 5 | En.Met/S.L./Am.Ac. | 83.1 | alpha-KGA; SM C24:0; SM (OH) C16:1; Met; Tyr |
| 2907 | 4 | S.L./Am.Ac. | 81.5 | SM C16:1; SM C24:0; Asn; Pro |
| 2908 | 4 | S.L./Am.Ac./O.St. | 84 | SM C26:1; SM (OH) C22:2; Orn; 20a-OH-C |
| 2909 | 4 | S.L./Am.Ac./B.Am. | 90.5 | SM C16:1; SM (OH) C14:1; Pro; Ac-Orn |
| 2910 | 5 | En.Met/S.L./Am.Ac./P.G. | 87.4 | Suc; SM (OH) C16:1; Orn; Tyr; LTB4 |
| 2911 | 4 | En.Met/S.L./Am.Ac. | 80.2 | Fum; SM C16:0; SM C18:0; Met |
| 2912 | 4 | Am.Ac./B.Am. | 84.3 | Gln; Leu; Lys; Met-SO |
| 2913 | 4 | S.L./Am.Ac. | 84.3 | SM C16:1; SM C20:2; SM C24:1; Tyr |
| 2914 | 4 | Ac.Ca./S.L./Am.Ac./B.Am. | 84.5 | C5:1-DC; SM C16:0; Pro; Histamine |
| 2915 | 5 | S.L./Am.Ac./B.Am. | 85.4 | SM C24:1; SM (OH) C22:1; Arg; Tyr; Histamine |
| 2916 | 4 | S.L./Am.Ac./B.Am. | 88.5 | SM C16:1; SM C18:0; Trp; Met-SO |
| 2917 | 4 | S.L./Am.Ac./B.Am. | 84.7 | SM C16:1; SM C24:0; Ala; Met-SO |
| 2918 | 4 | Ac.Ca./S.L./Am.Ac. | 86.4 | C6:1; SM C24:1; SM (OH) C22:1; Tyr |
| 2919 | 4 | En.Met/Am.Ac./B.Am./O.St. | 79.7 | alpha-KGA; Met; Creatinine; Cholestenone |
| 2920 | 4 | En.Met/S.L./Am.Ac. | 86.9 | Lac; SM C18:0; Gln; Met |
| 2921 | 4 | S.L./Am.Ac./B.Am. | 79.3 | SM (OH) C24:1; Pro; Val; Met-SO |
| 2922 | 4 | S.L./B.Am. | 79.3 | SM C16:1; SM C18:0; SM (OH) C24:1; Met-SO |
| 2923 | 4 | En.Met/S.L./Am.Ac. | 82.2 | Suc; SM C16:1; SM (OH) C22:1; Arg |
| 2924 | 4 | S.L./Am.Ac./P.G. | 79.3 | SM (OH) C22:2; Ile; Orn; AA |
| 2925 | 4 | Am.Ac./B.Am. | 81.1 | Arg; Gln; Orn; Ac-Orn |
| 2926 | 6 | En.Met/S.L./Am.Ac./B.Am./O.St. | 80 | alpha-KGA; SM (OH) C22:2; Gln; Met; Serotonin; 24S-OH-C |
| 2927 | 5 | S.L./Am.Ac./B.Am. | 89.9 | SM C16:1; SM (OH) C16:1; Gln; Pro; Ac-Orn |
| 2928 | 4 | S.L./Am.Ac. | 82.8 | SM (OH) C22:2; Arg; Met; Orn |
| 2929 | 4 | S.L./Am.Ac./B.Am./O.St. | 81.4 | SM (OH) C22:2; Arg; alpha-AAA; 22R-OH-C |
| 2930 | 4 | En.Met/S.L./Am.Ac./O.St. | 79.7 | alpha-KGA; SM (OH) C22:1; Phe; 24-DH-Lanosterol |
| 2931 | 4 | S.L./Am.Ac. | 81.3 | SM C16:0; SM (OH) C24:1; Arg; Met |
| 2932 | 4 | S.L./Am.Ac. | 84.6 | SM C24:1; SM (OH) C14:1; Met; Orn |
| 2933 | 4 | Am.Ac./B.Am. | 82.5 | Gln; Leu; Pro; Ac-Orn |
| 2934 | 4 | S.L./Am.Ac./B.Am. | 85.7 | SM C18:0; SM C24:0; Orn; Met-SO |
| 2935 | 5 | Ac.Ca./S.L./Am.Ac./B.Am./O.St. | 90.8 | C5:1-DC; SM (OH) C14:1; Orn; Histamine; 25-OH-C |
| 2936 | 4 | En.Met/S.L./Am.Ac. | 83 | Hex-P; SM C24:1; SM C14:1; Met |
| 2937 | 5 | S.L./Am.Ac./P.G. | 81.9 | SM (OH) C22:1; SM (OH) C22:2; Ala; Orn; LTB4 |
| 2938 | 4 | S.L./Am.Ac. | 87.3 | SM C24:1; SM (OH) C14:1; Met; Pro |
| 2939 | 4 | Ac.Ca./S.L./O.St. | 83 | C5:1-DC; C6:1; SM (OH) C22:2; 25-OH-C |
| 2940 | 4 | En.Met/Am.Ac./O.St. | 83.5 | Lac; Gln; Pro; 24-DH-Lanosterol |
| 2941 | 4 | Am.Ac./B.Am. | 81.5 | Gln; His; Pro; Met-SO |
| 2942 | 4 | En.Met/Am.Ac./B.Am. | 82.7 | Suc; Lys; Met; Met-SO |
| 2943 | 4 | En.Met/S.L./Am.Ac./B.Am. | 82.1 | alpha-KGA; SM (OH) C14:1; Pro; Met-SO |
| 2944 | 5 | En.Met/S.L./Am.Ac. | 79 | Lac; SM C24:1; SM C26:1; Met; Tyr |
| 2945 | 4 | Ac.Ca./S.L./Am.Ac. | 89.5 | C5:1-DC; SM C16:1; SM C24:0; Arg |
| 2946 | 5 | En.Met/S.L./Am.Ac./B.Am. | 88.1 | Suc; SM C16:1; SM (OH) C22:2; Pro; Serotonin |
| 2947 | 4 | S.L./Am.Ac./O.St. | 89.1 | SM C18:1; SM C24:1; Trp; 24-DH-Lanosterol |
| 2948 | 4 | En.Met/S.L./B.Am. | 86.3 | alpha-KGA; SM C16:1; SM C20:2; Met-SO |
| 2949 | 4 | S.L./Am.Ac. | 85.6 | SM (OH) C22:2; His; Met; Orn |
| 2950 | 4 | S.L./Am.Ac./B.Am. | 83.8 | SM C16:0; SM (OH) C24:1; Arg; Met-SO |
| 2951 | 4 | Ac.Ca./Am.Ac./B.Am. | 88.8 | C14:1; Arg; Pro; Ac-Orn |
| 2952 | 4 | En.Met/S.L./Am.Ac./B.Am. | 82.4 | Lac; SM C24:1; Phe; Histamine |
| 2953 | 4 | S.L./Am.Ac./B.Am. | 84.3 | SM C16:1; Arg; Orn; Ac-Orn |
| 2954 | 5 | S.L./Am.Ac. | 80 | SM C16:0; SM C18:1; SM C16:1; Ala; Trp |
| 2955 | 4 | En.Met/S.L./Am.Ac./B.Am. | 84.7 | alpha-KGA; SM (OH) C22:2; Met; Kynurenine |
| 2956 | 7 | Ac.Ca./S.L./Am.Ac./B.Am. | 92.9 | C6:1; SM C16:1; SM (OH) C14:1; Ala; Gln; Orn; Ac-Orn |
| 2957 | 5 | Ac.Ca./S.L./Am.Ac./B.Am. | 83.4 | C6:1; SM C16:1; SM (OH) C22:2; Arg; Met-SO |
| 2958 | 4 | S.L./Am.Ac. | 86 | SM C26:0; SM (OH) C14:1; Gln; Met |
| 2959 | 4 | En.Met/S.L./Am.Ac./O.St. | 82.3 | Pent-P; SM (OH) C22:1; Pro; Cholestenone |
| 2960 | 4 | Ac.Ca./Am.Ac./B.Am. | 83.3 | C14:1; Arg; Pro; Met-SO |
| 2961 | 4 | Am.Ac./B.Am. | 85.4 | Gln; Met; Trp; alpha-AAA |
| 2962 | 4 | S.L./Am.Ac./O.St. | 89.2 | SM C16:1; Pro; Trp; 24-DH-Lanosterol |
| 2963 | 3 | Ac.Ca./S.L. | 88 | C5:1-DC; C6:1; SM C16:0 |
| 2964 | 3 | En.Met/S.L./Am.Ac. | 84.1 | Fum; SM (OH) C22:1; Met |
| 2965 | 4 | S.L./Am.Ac. | 94.2 | SM C24:1; SM (OH) C22:2; Gly; Orn |
| 2966 | 3 | Ac.Ca./S.L./O.St. | 88.7 | C5:1-DC; SM C16:1; 24S-OH-C |
| 2967 | 4 | Ac.Ca./S.L./Am.Ac./O.St. | 80.9 | C5:1-DC; SM (OH) C16:1; Orn; 24-DH-Lanosterol |
| 2968 | 4 | S.L./Am.Ac. | 79.5 | SM C18:0; SM C24:1; SM (OH) C22:1; Phe |
| 2969 | 4 | S.L./Am.Ac./O.St. | 84.5 | SM (OH) C22:2; Arg; Gln; Cholestenone |
| 2970 | 6 | Ac.Ca./S.L./Am.Ac./P.G. | 86.6 | C10; SM C24:0; SM (OH) C16:1; Leu; Tyr; TXB2 |
| 2971 | 4 | S.L./Am.Ac./B.Am. | 83.5 | SM (OH) C22:2; Gln; Trp; Met-SO |
| 2972 | 5 | Ac.Ca./S.L./Am.Ac. | 83.5 | C5:1-DC; C6:1; SM C24:0; SM (OH) C16:1; Phe |
| 2973 | 5 | En.Met/Ac.Ca./S.L. | 82.9 | alpha-KGA; Lac; C18; C5:1-DC; SM C18:1 |
| 2974 | 6 | Ac.Ca./S.L./Am.Ac./B.Am./O.St. | 86.8 | C5:1-DC; SM (OH) C16:1; Orn; Trp; Histamine; Cholestenone |
| 2975 | 4 | S.L./Am.Ac. | 79.1 | SM (OH) C14:1; SM (OH) C16:1; Met; Phe |
| 2976 | 4 | Ac.Ca./Am.Ac./B.Am. | 80.5 | C14:1; Arg; Gln; Met-SO |
| 2977 | 4 | S.L./Am.Ac./B.Am./O.St. | 80.6 | SM (OH) C14:1; Leu; alpha-AAA; 20a-OH-C |
| 2978 | 4 | En.Met/S.L./Am.Ac./O.St. | 88.5 | OAA; SM (OH) C22:2; Gly; Cholestenone |
| 2979 | 4 | S.L./Am.Ac./B.Am. | 79.2 | SM (OH) C24:1; Gln; Pro; total DMA |
| 2980 | 5 | S.L./Am.Ac./B.Am. | 86.1 | SM (OH) C24:1; Tyr; alpha-AAA; Kynurenine; Met-SO |

TABLE 9-continued

Metabolite combinations describing damage of basal ganglia

| No. | Npar | Chemical Class | Accuracy | Model |
|---|---|---|---|---|
| 2981 | 6 | En.Met/S.L./Am.Ac./P.G. | 79.5 | alpha-KGA; SM C16:0; Gln; Phe; Tyr; LTB4 |
| 2982 | 4 | S.L./Am.Ac./O.St. | 89.5 | SM (OH) C22:1; SM (OH) C22:2; Gly; Cholestenone |
| 2983 | 4 | En.Met/S.L./B.Am. | 84.5 | alpha-KGA; SM (OH) C14:1; SM (OH) C22:1; Met-SO |
| 2984 | 6 | S.L./Am.Ac./B.Am. | 82 | SM C24:0; SM (OH) C14:1; His; Val; Ac-Orn; Histamine |
| 2985 | 4 | S.L./Am.Ac./B.Am./O.St. | 79.9 | SM (OH) C22:1; Phe; Ac-Orn; 25-OH-C |
| 2986 | 4 | Am.Ac./B.Am./O.St. | 85.8 | Pro; Trp; Creatinine; Cholestenone |
| 2987 | 4 | En.Met/S.L./Am.Ac./B.Am. | 80.1 | Lac; SM (OH) C24:1; His; Met-SO |
| 2988 | 4 | S.L./Am.Ac./B.Am. | 84.2 | SM (OH) C22:1; Pro; Trp; total DMA |
| 2989 | 4 | Ac.Ca./S.L./Am.Ac./B.Am. | 79.5 | C6:1; SM C24:0; His; Ac-Orn |
| 2990 | 5 | S.L./Am.Ac./B.Am./O.St. | 89.4 | SM C16:0; SM (OH) C14:1; Ala; Ac-Orn; Cholestenone |
| 2991 | 4 | En.Met/S.L./Am.Ac. | 79.2 | alpha-KGA; SM C16:0; SM (OH) C22:2; Tyr |
| 2992 | 5 | En.Met/S.L./Am.Ac./O.St. | 85.8 | alpha-KGA; SM C26:1; His; Tyr; 20a-OH-C |
| 2993 | 4 | C5:1-DC/S.L./O.St. | 87.2 | C5:1-DC; SM C16:1; SM (OH) C22:2; Cholestenone |
| 2994 | 4 | S.L./Am.Ac. | 84.2 | SM C18:0; SM (OH) C22:1; Gln; Tyr |
| 2995 | 3 | Am.Ac./B.Am. | 83.7 | Gln; Pro; total DMA |
| 2996 | 4 | En.Met/S.L./Am.Ac. | 82.1 | Lac; SM C18:0; SM (OH) C22:1; Met |
| 2997 | 5 | Am.Ac./B.Am. | 85.2 | Gln; His; Met; Orn; Ac-Orn |
| 2998 | 4 | Ac.Ca./Am.Ac./B.Am. | 86.6 | C14:1; His; Pro; Ac-Orn |
| 2999 | 4 | S.L./Am.Ac./B.Am./O.St. | 82.5 | SM C24:1; Lys; Met-SO; Cholestenone |
| 3000 | 5 | S.L./Am.Ac./O.St. | 88.1 | SM C24:1; SM (OH) C22:1; Ala; Pro; Cholestenone |
| 3001 | 4 | Am.Ac./P.G. | 80.4 | Orn; Trp; 8-iso-PGF2a; LTB4 |
| 3002 | 4 | S.L./B.Am. | 84 | SM C24:0; SM (OH) C14:1; SM (OH) C22:1; Met-SO |
| 3003 | 6 | En.Met/Ac.Ca./S.L./Am.Ac./B.Am. | 83.6 | alpha-KGA; C14:1-OH; SM (OH) C22:2; Arg; Lys; Ac-Orn |
| 3004 | 5 | S.L./Am.Ac./O.St. | 79.6 | SM C24:1; SM (OH) C24:1; Arg; Phe; Cholestenone |
| 3005 | 5 | S.L./Am.Ac./B.Am. | 83.8 | SM C18:1; SM C24:1; SM (OH) C16:1; Trp; total DMA |
| 3006 | 4 | Ac.Ca./S.L. | 80.6 | C14:1; C5:1-DC; SM C18:1; SM (OH) C22:1 |
| 3007 | 4 | S.L./Am.Ac./O.St. | 79.2 | SM (OH) C22:2; SM (OH) C24:1; Ser; Cholestenone |
| 3008 | 3 | S.L./Am.Ac. | 82.3 | SM (OH) C14:1; SM (OH) C16:1; Gly |
| 3009 | 4 | Ac.Ca./S.L./O.St. | 81.6 | C5:1-DC; SM C24:0; SM (OH) C14:1; 24-DH-Lanosterol |
| 3010 | 5 | S.L./Am.Ac./O.St./P.G. | 84.2 | SM (OH) C22:2; Leu; 20a-OH-C; 8-iso-PGF2a; LTB4 |
| 3011 | 4 | En.Met/S.L./B.Am./P.G. | 84.9 | alpha-KGA; SM (OH) C24:1; total DMA; TXB2 |
| 3012 | 3 | S.L./Am.Ac. | 79.1 | SM (OH) C16:1; SM (OH) C22:2; Trp |
| 3013 | 4 | S.L./Am.Ac./B.Am. | 80.4 | SM C16:0; Trp; Ac-Orn; alpha-AAA |
| 3014 | 4 | S.L./Am.Ac./B.Am. | 83.6 | SM C16:0; SM C18:1; Gln; Met-SO |
| 3015 | 4 | S.L./Am.Ac./B.Am. | 84 | SM (OH) C14:1; Met; Orn; Histamine |
| 3016 | 4 | S.L./Am.Ac./P.G. | 80.8 | SM (OH) C22:1; Lys; Pro; TXB2 |
| 3017 | 4 | Ac.Ca./S.L./B.Am./O.St. | 88.5 | C5:1-DC; SM (OH) C14:1; alpha-AAA; Cholestenone |
| 3018 | 4 | S.L./Am.Ac./B.Am./O.St. | 84.6 | SM C16:0; Pro; Ac-Orn; 24S-OH-C |
| 3019 | 4 | En.Met/Am.Ac. | 85.5 | Lac; Gln; His; Met |
| 3020 | 4 | En.Met/S.L./Am.Ac. | 80.8 | alpha-KGA; Lac; SM (OH) C22:2; Met |
| 3021 | 4 | S.L./Am.Ac./B.Am. | 79.4 | SM C18:1; SM (OH) C14:1; Pro; Met-SO |
| 3022 | 5 | S.L./Am.Ac./O.St. | 86.7 | SM C16:0; SM C16:1; SM (OH) C22:1; Val; 20a-OH-C |
| 3023 | 4 | En.Met/S.L./Am.Ac. | 87.6 | Fum; SM C18:1; Gln; Met |
| 3024 | 6 | Ac.Ca./En.Met/S.L./Am.Ac./B.Am. | 87.4 | C5:1-DC; H1; SM (OH) C14:1; SM (OH) C24:1; Lys; Met-SO |
| 3025 | 4 | S.L./Am.Ac. | 84.7 | SM (OH) C22:2; Ala; Gln; Met |
| 3026 | 4 | Am.Ac./B.Am. | 87 | Gln; Pro; Ac-Orn; Histamine |
| 3027 | 4 | S.L./Am.Ac./B.Am. | 83.3 | SM C16:1; SM C24:0; Lys; Ac-Orn |
| 3028 | 4 | S.L./Am.Ac./B.Am. | 83.2 | SM (OH) C14:1; Orn; Tyr; Ac-Orn |
| 3029 | 5 | En.Met/Ac.Ca./Am.Ac./P.G. | 79.8 | alpha-KGA; C18:2; Phe; Pro; LTB4 |
| 3030 | 6 | S.L./B.Am./P.G. | 90.4 | SM C16:0; SM (OH) C14:1; SM (OH) C22:1; Kynurenine; Met-SO; LTB4 |
| 3031 | 4 | Ac.Ca./S.L./Am.Ac. | 84.8 | C5:1-DC; SM C16:0; SM (OH) C14:1; Met |
| 3032 | 4 | Ac.Ca./S.L./Am.Ac./B.Am. | 79.3 | C6:1; SM (OH) C22:2; Pro; Met-SO |
| 3033 | 5 | S.L./Am.Ac./B.Am. | 88.9 | SM C24:1; Gln; Pro; Ac-Orn; Histamine |
| 3034 | 4 | S.L./Am.Ac. | 83 | SM C18:1; SM C24:0; Met; Val |
| 3035 | 4 | Ac.Ca./S.L./Am.Ac. | 85.8 | C5:1-DC; SM C16:1; SM (OH) C16:1; Lys |
| 3036 | 3 | Ac.Ca./S.L./O.St. | 80.6 | C5:1-DC; SM (OH) C14:1; 25-OH-C |
| 3037 | 5 | S.L./Am.Ac./B.Am./O.St. | 85.7 | SM C26:1; SM (OH) C22:2; Lys; Histamine; 20a-OH-C |
| 3038 | 4 | En.Met/S.L./Am.Ac. | 79.8 | Lac; SM C18:1; Met; Trp |
| 3039 | 4 | S.L./Am.Ac. | 83.8 | SM (OH) C14:1; SM (OH) C22:2; Pro; Trp |
| 3040 | 5 | Ac.Ca./S.L./Am.Ac. | 85.4 | C14:1; C5:1-DC; SM (OH) C22:1; SM (OH) C22:2; Arg |
| 3041 | 4 | S.L./B.Am. | 81.5 | SM C24:0; SM (OH) C14:1; SM (OH) C24:1; Met-SO |
| 3042 | 4 | S.L./Am.Ac./B.Am. | 81.5 | SM C18:1; SM C24:0; Arg; Met-SO |
| 3043 | 4 | En.Met/S.L./Am.Ac. | 84.2 | alpha-KGA; SM C16:1; Arg; Met |
| 3044 | 5 | S.L./Am.Ac./B.Am./P.G. | 81.8 | SM C24:1; Lys; Met-SO; 8-iso-PGF2a; LTB4 |
| 3045 | 4 | S.L./Am.Ac. | 87.2 | SM C24:1; SM (OH) C14:1; Pro; Tyr |
| 3046 | 5 | S.L./Am.Ac./O.St. | 82 | SM (OH) C22:1; SM (OH) C22:2; SM (OH) C24:1; Lys; 22R-OH-C |
| 3047 | 5 | Ac.Ca./S.L./Am.Ac. | 86.9 | C14:1; C5:1-DC; SM C16:0; SM C24:0; Pro |
| 3048 | 7 | En.Met/S.L./Am.Ac./O.St. | 88.3 | Lac; SM C16:0; SM C16:1; SM (OH) C14:1; SM (OH) C22:1; Ala; 22R-OH-C |
| 3049 | 4 | En.Met/S.L./O.St. | 82.4 | alpha-KGA; SM (OH) C14:1; SM (OH) C22:1; 20a-OH-C |
| 3050 | 4 | En.Met/S.L./Am.Ac./B.Am. | 83.1 | Fum; SM (OH) C16:1; Met; Kynurenine |
| 3051 | 4 | S.L./Am.Ac./O.St. | 81.1 | SM (OH) C14:1; SM (OH) C22:1; Orn; 20a-OH-C |
| 3052 | 4 | S.L./Am.Ac. | 84.5 | SM (OH) C16:1; SM (OH) C22:2; Orn; Trp |
| 3053 | 4 | S.L./Am.Ac. | 82.7 | SM C16:1; SM C18:1; Pro; Trp |
| 3054 | 5 | Ac.Ca./S.L./Am.Ac./B.Am. | 83.7 | C14:1-OH; SM C18:0; SM C18:1; Pro; Ac-Orn |
| 3055 | 4 | Ac.Ca./S.L./Am.Ac. | 84.9 | C5:1-DC; SM C16:0; Gln; Pro |
| 3056 | 4 | S.L./Am.Ac./P.G. | 81.8 | SM C16:0; Trp; Tyr; LTB4 |

TABLE 9-continued

Metabolite combinations describing damage of basal ganglia

| No. | Npar | Chemical Class | Accuracy | Model |
|---|---|---|---|---|
| 3057 | 5 | Ac.Ca./S.L./Am.Ac./O.St. | 86.9 | C5:1-DC; SM C18:1; Gln; Lys; 24-DH-Lanosterol |
| 3058 | 5 | Ac.Ca./S.L./Am.Ac./O.St. | 82.9 | C5:1-DC; SM C24:0; SM (OH) C22:1; Gln; Cholestenone |
| 3059 | 4 | S.L./B.Am. | 80.8 | SM C26:1; SM (OH) C14:1; Kynurenine; Met-SO |
| 3060 | 4 | S.L./Am.Ac./B.Am. | 87.9 | SM C24:0; SM (OH) C24:1; Pro; Met-SO |
| 3061 | 4 | S.L./Am.Ac. | 86.3 | SM (OH) C14:1; SM (OH) C22:2; Met; Pro |
| 3062 | 4 | En.Met/S.L./B.Am. | 84 | alpha-KGA; SM C16:1; SM (OH) C14:1; Met-SO |
| 3063 | 5 | S.L./Am.Ac./B.Am. | 89.3 | SM C16:1; SM (OH) C14:1; SM (OH) C22:1; Orn; Met-SO |
| 3064 | 4 | S.L./Am.Ac. | 79.5 | SM C16:1; SM C18:1; SM (OH) C22:2; Met |
| 3065 | 4 | S.L./Am.Ac./B.Am. | 86.2 | SM (OH) C22:2; Met; Orn; Kynurenine |
| 3066 | 4 | S.L./B.Am. | 86.5 | SM (OH) C22:1; Ac-Orn; Histamine; Met-SO |
| 3067 | 5 | En.Met/S.L./Am.Ac./P.G. | 80.3 | Lac; SM (OH) C22:1; SM (OH) C22:2; Phe; AA |
| 3068 | 4 | S.L./Am.Ac. | 87.7 | SM C20:2; SM (OH) C22:1; SM (OH) C22:2; Tyr |
| 3069 | 3 | S.L./Am.Ac./B.Am. | 86.2 | SM C26:1; Lys; Met-SO |
| 3070 | 4 | Ac.Ca./S.L./Am.Ac./B.Am. | 81.4 | C5:1-DC; SM C16:1; His; Histamine |
| 3071 | 4 | En.Met/S.L./Am.Ac./O.St. | 83.3 | Lac; SM C24:0; Met; 24-DH-Lanosterol |
| 3072 | 4 | Ac.Ca./S.L./Am.Ac./O.St. | 80.3 | C5:1-DC; SM (OH) C16:1; Lys; Cholestenone |
| 3073 | 5 | S.L./Am.Ac./O.St. | 90.6 | SM C16:0; Gln; Leu; Tyr; 20a-OH-C |
| 3074 | 5 | En.Met/S.L./Am.Ac./B.Am. | 82.2 | alpha-KGA; SM (OH) C22:1; SM (OH) C22:2; Ala; Ac-Orn |
| 3075 | 5 | S.L./Am.Ac./B.Am./O.St. | 92.2 | SM (OH) C22:2; Trp; Ac-Orn; Histamine; 24-DH-Lanosterol |
| 3076 | 4 | S.L./Am.Ac. | 84.7 | SM C16:1; SM C24:0; Lys; Met |
| 3077 | 4 | En.Met/S.L./Am.Ac. | 79.8 | Hex-P; SM C24:0; His; Met |
| 3078 | 4 | S.L./Am.Ac./O.St. | 85.2 | SM (OH) C22:1; Met; Orn; 25-OH-C |
| 3079 | 4 | S.L./Am.Ac./O.St. | 84.2 | SM (OH) C14:1; SM (OH) C22:2; Ser; Cholestenone |
| 3080 | 4 | S.L./Am.Ac./O.St. | 83.3 | SM C24:1; Arg; Trp; Cholestenone |
| 3081 | 4 | S.L./Am.Ac./P.G. | 81.1 | SM C24:1; Met; Orn; 8-iso-PGF2a |
| 3082 | 5 | S.L./Am.Ac. | 84.8 | SM C16:1; SM (OH) C16:1; SM (OH) C22:2; Ser; Trp |
| 3083 | 4 | S.L./Am.Ac./B.Am. | 87.5 | SM C16:1; SM C24:0; Orn; Met-SO |
| 3084 | 4 | Ac.Ca./S.L./Am.Ac./B.Am. | 85.3 | C6:1; SM C16:1; Pro; Met-SO |
| 3085 | 4 | En.Met/Ac.Ca./S.L. | 87.5 | alpha-KGA; C5:1-DC; SM C16:1; SM (OH) C22:2 |
| 3086 | 4 | S.L./Am.Ac./B.Am. | 80.1 | SM C16:0; SM C18:1; Met; Creatinine |
| 3087 | 4 | En.Met/S.L./Am.Ac./B.Am. | 87.9 | alpha-KGA; SM C16:1; Pro; Ac-Orn |
| 3088 | 4 | Ac.Ca./S.L./Am.Ac./P.G. | 91.3 | C6:1; SM C16:0; Pro; TXB2 |
| 3089 | 5 | S.L./Am.Ac./B.Am. | 85.6 | SM C24:0; Arg; Gln; Met; total DMA |
| 3090 | 5 | En.Met/S.L./Am.Ac./P.G. | 84.6 | alpha-KGA; SM C16:1; Arg; Trp; 8-iso-PGF2a |
| 3091 | 4 | Ac.Ca./Am.Ac./O.St. | 79.2 | C14:1; Arg; Met; Cholestenone |
| 3092 | 4 | S.L./Am.Ac./P.G. | 83.8 | SM (OH) C16:1; Orn; Trp; LTB4 |
| 3093 | 4 | S.L./Am.Ac./B.Am. | 85.2 | SM C18:1; Gln; Trp; total DMA |
| 3094 | 5 | Ac.Ca./S.L./B.Am./O.St. | 89.9 | C5:1-DC; SM (OH) C22:1; SM (OH) C22:2; Histamine; Cholestenone |
| 3095 | 3 | S.L./Am.Ac. | 80.3 | SM C24:1; Ala; Gln |
| 3096 | 4 | S.L./Am.Ac. | 85.4 | SM C24:0; SM (OH) C16:1; Met; Pro |
| 3097 | 4 | S.L./Am.Ac. | 87.2 | SM C20:2; SM (OH) C14:1; Arg; Met |
| 3098 | 4 | En.Met/S.L./Am.Ac./B.Am. | 79 | alpha-KGA; SM (OH) C24:1; Tyr; Ac-Orn |
| 3099 | 4 | Ac.Ca./S.L./Am.Ac. | 79.5 | C16:2; SM (OH) C22:1; His; Met |
| 3100 | 4 | S.L./Am.Ac. | 83.6 | SM C16:1; SM C24:0; Arg; Tyr |
| 3101 | 4 | S.L./Am.Ac./B.Am. | 89.5 | SM (OH) C22:1; Met; Tyr; Kynurenine |
| 3102 | 4 | Am.Ac./O.St. | 80 | Arg; Gln; Tyr; Cholestenone |
| 3103 | 4 | S.L./Am.Ac./P.G. | 95.6 | SM C16:1; SM (OH) C22:1; Pro; TXB2 |
| 3104 | 5 | S.L./Am.Ac./B.Am. | 86.2 | SM C16:0; SM C26:1; SM (OH) C22:1; Ala; Ac-Orn |
| 3105 | 4 | En.Met/S.L./Am.Ac./B.Am. | 80.5 | alpha-KGA; SM C16:0; Arg; Met-SO |
| 3106 | 4 | S.L./Am.Ac./O.St. | 82.6 | SM C16:0; SM (OH) C22:1; Pro; 20a-OH-C |
| 3107 | 4 | Ac.Ca./S.L./Am.Ac./O.St. | 87.1 | C5:1-DC; SM (OH) C22:2; Orn; 24-DH-Lanosterol |
| 3108 | 4 | Ac.Ca./S.L./O.St. | 85.5 | C5:1-DC; SM C16:0; SM (OH) C22:1; Cholestenone |
| 3109 | 4 | S.L./Am.Ac./B.Am./P.G. | 80.3 | SM C16:1; Orn; Ac-Orn; LTB4 |
| 3110 | 4 | S.L./Am.Ac./P.G. | 84.2 | SM C24:1; Lys; Met; LTB4 |
| 3111 | 4 | En.Met/S.L./Am.Ac./O.St. | 89.9 | alpha-KGA; SM C16:1; Leu; 20a-OH-C |
| 3112 | 4 | S.L./Am.Ac. | 80.7 | SM C20:2; Gln; Pro; Tyr |
| 3113 | 4 | S.L./Am.Ac. | 83.1 | SM (OH) C22:1; Arg; Leu; Met |
| 3114 | 4 | S.L./Am.Ac./O.St. | 81.7 | SM (OH) C14:1; SM (OH) C22:2; Arg; Cholestenone |
| 3115 | 5 | En.Met/S.L./Am.Ac./B.Am. | 90.1 | Lac; SM C16:1; SM (OH) C14:1; Gln; Met-SO |
| 3116 | 4 | S.L./Am.Ac. | 84 | SM C18:1; SM (OH) C22:2; Gln; Gly |
| 3117 | 4 | En.Met/S.L./P.G. | 85.3 | alpha-KGA; SM C24:0; SM (OH) C14:1; TXB2 |
| 3118 | 4 | Ac.Ca./S.L./Am.Ac./B.Am. | 79.3 | C14:1; SM (OH) C22:2; Lys; Met-SO |
| 3119 | 6 | S.L./Am.Ac./P.G. | 80.2 | SM C16:0; SM C20:2; SM C26:1; Lys; Tyr; LTB4 |
| 3120 | 4 | S.L./B.Am. | 80.4 | SM C20:2; SM C24:0; SM (OH) C14:1; Met-SO |
| 3121 | 4 | S.L./Am.Ac. | 85 | SM C24:1; SM (OH) C22:1; SM (OH) C24:1; Tyr |
| 3122 | 5 | En.Met/Ac.Ca./S.L./Am.Ac. | 80.8 | Suc; C14:1; C6:1; SM C18:1; Arg |
| 3123 | 4 | S.L./Am.Ac./B.Am. | 85.1 | SM (OH) C22:1; Arg; Trp; Met-SO |
| 3124 | 4 | S.L./Am.Ac./B.Am. | 87.8 | SM (OH) C22:2; His; Orn; Ac-Orn |
| 3125 | 4 | S.L./Am.Ac./O.St. | 89.5 | SM (OH) C22:2; Leu; Pro; 20a-OH-C |
| 3126 | 4 | S.L./Am.Ac./O.St. | 81.1 | SM C24:1; SM (OH) C14:1; Tyr; Cholestenone |
| 3127 | 4 | S.L./Ac.Ca./Am.Ac. | 81.1 | C14:1-OH; SM C18:1; Arg; Met |
| 3128 | 4 | S.L./Am.Ac. | 84 | SM C24:1; Ala; Gln; Orn |
| 3129 | 6 | S.L./Am.Ac./B.Am. | 89 | SM C16:1; SM C24:1; Gln; Pro; Histamine; Met-SO |
| 3130 | 4 | En.Met/S.L./Am.Ac. | 87.7 | Suc; SM (OH) C22:2; Met; Orn |
| 3131 | 6 | En.Met/S.L./Am.Ac./B.Am. | 80.8 | Pent-P; SM C16:1; Arg; Met; Tyr; Histamine |
| 3132 | 4 | Am.Ac./B.Am. | 80.4 | Gln; Pro; Val; Met-SO |

TABLE 9-continued

Metabolite combinations describing damage of basal ganglia

| No. | Npar | Chemical Class | Accuracy | Model |
|---|---|---|---|---|
| 3133 | 5 | Ac.Ca./S.L./Am.Ac./B.Am. | 80.2 | C18; SM C18:0; SM C18:1; Pro; Ac-Orn |
| 3134 | 4 | S.L./Am.Ac./B.Am. | 92.7 | SM (OH) C14:1; His; Tyr; Kynurenine |
| 3135 | 5 | S.L./Am.Ac./O.St. | 84 | SM C18:0; SM C18:1; Gln; Phe; Cholestenone |
| 3136 | 4 | Ac.Ca./S.L./Am.Ac./B.Am. | 79.5 | C6:1; SM C24:1; Trp; Met-SO |
| 3137 | 4 | S.L./Am.Ac. | 79.4 | SM C20:2; Gln; Met; Tyr |
| 3138 | 4 | S.L./Am.Ac./B.Am. | 83 | SM (OH) C22:1; Tyr; Histamine; Met-SO |
| 3139 | 4 | S.L./Am.Ac. | 82 | SM C16:0; SM C16:1; SM (OH) C22:2; Ala |
| 3140 | 5 | S.L./Am.Ac./B.Am. | 87.4 | SM C24:0; SM (OH) C24:1; Pro; Tyr; Ac-Orn |
| 3141 | 4 | S.L./Am.Ac. | 86.2 | SM (OH) C14:1; SM (OH) C16:1; Gly; Met |
| 3142 | 4 | En.Met/Am.Ac. | 84.3 | Suc; Arg; Lys; Met |
| 3143 | 4 | En.Met/Ac.Ca./S.L. | 81 | alpha-KGA; C5:1-DC; SM C16:0; SM (OH) C22:1 |
| 3144 | 4 | S.L./Am.Ac./B.Am. | 85.4 | SM C24:0; Lys; Orn; Met-SO |
| 3145 | 4 | Ac.Ca./S.L./Am.Ac. | 81.9 | C14:1; SM C18:0; Arg; Tyr |
| 3146 | 4 | S.L./Am.Ac. | 80.1 | SM C18:0; SM (OH) C22:1; Met; Val |
| 3147 | 4 | S.L./Am.Ac./B.Am. | 84.4 | SM (OH) C14:1; SM (OH) C22:1; Lys; Met-SO |
| 3148 | 5 | En.Met/S.L./Am.Ac. | 83.1 | Pent-P; SM C16:1; Arg; His; Pro |
| 3149 | 4 | En.Met/Ac.Ca./Am.Ac. | 82.1 | Pent-P; C6:1; Gln; Pro |
| 3150 | 4 | S.L./Am.Ac./O.St. | 80.3 | SM C18:1; SM C24:1; Tyr; Cholestenone |
| 3151 | 5 | S.L./Am.Ac./B.Am./O.St. | 90.4 | SM (OH) C14:1; Orn; Trp; Ac-Orn; 24-DH-Lanosterol |
| 3152 | 4 | S.L./Am.Ac./O.St. | 86.2 | SM C18:0; SM C24:0; Tyr; Cholestenone |
| 3153 | 4 | En.Met/S.L./Am.Ac. | 84.8 | Fum; SM (OH) C14:1; SM (OH) C22:1; Met |
| 3154 | 5 | S.L./Am.Ac./B.Am. | 84.7 | SM C16:0; SM C24:0; Met; Orn; Ac-Orn |
| 3155 | 4 | S.L./Am.Ac./P.G. | 81 | SM C24:1; Arg; Orn; 8-iso-PGF2a |
| 3156 | 4 | S.L./Am.Ac./B.Am. | 84.3 | SM C24:0; Lys; Tyr; Met-SO |
| 3157 | 4 | En.Met/S.L./Am.Ac. | 83.5 | alpha-KGA; Fum; SM (OH) C14:1; Met |
| 3158 | 4 | S.L./Am.Ac./B.Am. | 80.2 | SM (OH) C14:1; SM (OH) C24:1; His; Met-SO |
| 3159 | 4 | S.L./Am.Ac. | 84.7 | SM C24:0; SM C24:1; SM (OH) C16:1; Tyr |
| 3160 | 3 | Ac.Ca./S.L. | 80.6 | C5:1-DC; SM (OH) C14:1; SM (OH) C16:1 |
| 3161 | 5 | En.Met/S.L./O.St. | 80.3 | Fum; SM C16:1; SM (OH) C22:2; SM (OH) C24:1; 20a-OH-C |
| 3162 | 5 | Am.Ac./B.Am. | 87.5 | Gln; His; Leu; Orn; Ac-Orn |
| 3163 | 6 | S.L./Am.Ac./P.G. | 79.7 | SM C16:0; Ala; Lys; Pro; Val; TXB2 |
| 3164 | 5 | Ac.Ca./S.L./B.Am. | 89.2 | C5:1-DC; SM C16:1; SM (OH) C14:1; SM (OH) C22:1; Serotonin |
| 3165 | 5 | S.L./Am.Ac./B.Am./O.St. | 85.2 | SM C16:1; SM (OH) C24:1; Pro; Histamine; 20a-OH-C |
| 3166 | 4 | S.L./Am.Ac. | 82.2 | SM C16:1; SM C18:1; SM C24:1; Tyr |
| 3167 | 4 | En.Met/S.L./Am.Ac./B.Am. | 81.6 | Lac; SM C24:0; His; Met-SO |
| 3168 | 4 | S.L./Am.Ac./B.Am./O.St. | 80.4 | SM C24:1; Arg; Histamine; 24-DH-Lanosterol |
| 3169 | 6 | En.Met/S.L./Am.Ac./B.Am./O.St. | 83.5 | alpha-KGA; SM (OH) C22:2; Arg; Orn; Ac-Orn; 24-DH-Lanosterol |
| 3170 | 5 | En.Met/S.L./Am.Ac./O.St. | 87.3 | alpha-KGA; SM (OH) C14:1; SM (OH) C22:1; Leu; 20a-OH-C |
| 3171 | 4 | S.L./Am.Ac. | 84.3 | SM C16:1; Arg; His; Met |
| 3172 | 4 | S.L./Am.Ac./B.Am./O.St. | 87.4 | SM (OH) C22:2; Leu; alpha-AAA; 20a-OH-C |
| 3173 | 3 | S.L./Am.Ac./O.St. | 84.6 | SM (OH) C22:1; Tyr; 25-OH-C |
| 3174 | 4 | S.L./Am.Ac./B.Am. | 80.3 | SM C18:1; Gln; Phe; Ac-Orn |
| 3175 | 6 | S.L./Am.Ac./P.G. | 87.4 | SM C20:2; Gln; Leu; Lys; Met; 8-iso-PGF2a |
| 3176 | 6 | S.L./Am.Ac./B.Am. | 87.4 | SM (OH) C22:1; SM (OH) C22:2; Arg; Trp; alpha-AAA; Met-SO |
| 3177 | 4 | S.L./Am.Ac./B.Am. | 84.9 | SM C24:0; SM (OH) C16:1; Orn; Ac-Orn |
| 3178 | 5 | S.L./Am.Ac./B.Am. | 85.1 | SM C24:0; SM (OH) C16:1; Lys; Tyr; Ac-Orn |
| 3179 | 4 | Ac.Ca./S.L. | 79.2 | C5:1-DC; C6:1; SM C26:1; SM (OH) C22:2 |
| 3180 | 4 | En.Met/S.L./Am.Ac. | 84.8 | Hex-P; SM (OH) C22:1; Gln; Met |
| 3181 | 4 | Ac.Ca./S.L./Am.Ac. | 80.6 | C6:1; SM C18:1; SM (OH) C14:1; Tyr |
| 3182 | 4 | S.L./Am.Ac./P.G. | 85.4 | SM C24:1; SM (OH) C22:2; Ala; LTB4 |
| 3183 | 4 | Ac.Ca./S.L./B.Am. | 79.9 | C10; SM C16:1; SM C18:0; Met-SO |
| 3184 | 4 | En.Met/S.L./Am.Ac./B.Am. | 82.6 | Suc; SM (OH) C14:1; Arg; Met-SO |
| 3185 | 4 | En.Met/S.L./Am.Ac./B.Am. | 80.1 | Fum; SM (OH) C22:1; His; Met-SO |
| 3186 | 5 | Ac.Ca./S.L./Am.Ac./B.Am. | 83.9 | C5:1-DC; SM C16:1; SM C26:1; Tyr; Histamine |
| 3187 | 4 | S.L./Am.Ac./B.Am. | 85.5 | SM C16:1; SM (OH) C14:1; Met; ADMA |
| 3188 | 4 | En.Met/Am.Ac./O.St. | 86.9 | Lac; His; Trp; Cholestenone |
| 3189 | 4 | S.L./Am.Ac./B.Am. | 79.6 | SM C18:0; SM C20:2; Gln; Met-SO |
| 3190 | 4 | En.Met/S.L./Am.Ac. | 83.6 | Fum; SM (OH) C22:1; Met; Orn |
| 3191 | 4 | S.L./Am.Ac./O.St. | 88.8 | SM (OH) C22:1; SM (OH) C22:2; Pro; 20a-OH-C |
| 3192 | 6 | Ac.Ca./S.L./Am.Ac./O.St. | 85.8 | C18:1-OH; SM (OH) C14:1; Gln; Met; Tyr; 24S-OH-C |
| 3193 | 5 | S.L./Am.Ac./B.Am. | 83.1 | SM C18:0; SM C20:2; SM (OH) C14:1; Pro; Met-SO |
| 3194 | 4 | En.Met/S.L./Am.Ac./O.St. | 84.2 | alpha-KGA; SM C24:1; Ala; Cholestenone |
| 3195 | 5 | S.L./Am.Ac./B.Am./O.St. | 86.5 | alpha-KGA; SM C16:1; Orn; Ac-Orn; 25-OH-C |
| 3196 | 5 | En.Met/Am.Ac./O.St. | 86.1 | alpha-KGA; Lac; Gln; Phe; Cholestenone |
| 3197 | 4 | S.L./Am.Ac. | 86.4 | SM C16:0; SM C24:1; SM (OH) C14:1; Ala |
| 3198 | 4 | S.L./Am.Ac./O.St. | 83.1 | SM (OH) C14:1; Pro; Tyr; Cholestenone |
| 3199 | 5 | S.L./Am.Ac./B.Am. | 92.7 | SM C16:1; SM (OH) C22:2; Tyr; Histamine; Kynurenine |
| 3200 | 4 | S.L./Am.Ac. | 80.6 | SM C16:0; SM C18:1; SM (OH) C14:1; Tyr |
| 3201 | 5 | En.Met/S.L./Am.Ac./O.St. | 84.3 | alpha-KGA; SM C16:1; SM C18:0; Trp; 20a-OH-C |
| 3202 | 4 | Am.Ac./P.G. | 83.3 | Gln; Orn; 8-iso-PGF2a; LTB4 |
| 3203 | 4 | En.Met/S.L./Am.Ac./B.Am. | 86.2 | OAA; SM (OH) C14:1; Trp; Met-SO |
| 3204 | 4 | S.L./Am.Ac./B.Am. | 84.6 | SM C18:0; SM (OH) C16:1; Trp; SDMA |
| 3205 | 5 | S.L./Am.Ac./O.St. | 79.5 | SM C16:0; SM (OH) C24:1; Gln; Phe; 20a-OH-C |
| 3206 | 5 | S.L./Am.Ac./B.Am. | 91.9 | SM C16:1; SM (OH) C22:2; Phe; Pro; Kynurenine |
| 3207 | 4 | En.Met/S.L./Am.Ac. | 80.7 | alpha-KGA; SM C16:1; SM C18:0; Phe |
| 3208 | 4 | Ac.Ca./S.L./Am.Ac. | 84.8 | C6:1; SM (OH) C22:1; Met; Pro |

TABLE 9-continued

Metabolite combinations describing damage of basal ganglia

| No. | Npar | Chemical Class | Accuracy | Model |
|---|---|---|---|---|
| 3209 | 3 | S.L./Am.Ac./O.St. | 79.5 | SM C24:1; Trp; Cholestenone |
| 3210 | 4 | S.L./Am.Ac./P.G. | 81.1 | SM C16:0; SM (OH) C22:2; Ala; LTB4 |
| 3211 | 4 | Ac.Ca./S.L./Am.Ac. | 84.8 | C6:1; SM C16:1; SM C24:1; Ala |
| 3212 | 4 | Ac.Ca./S.L./Am.Ac. | 81.7 | C14:1-OH; SM C18:0; SM C18:1; Pro |
| 3213 | 4 | Ac.Ca./S.L./B.Am./O.St. | 80.9 | C14:1; SM (OH) C22:1; Met-SO; 24S-OH-C |
| 3214 | 4 | Ac.Ca./S.L. | 84.2 | C5:1-DC; SM C16:1; SM C18:1; SM C24:1 |
| 3215 | 5 | En.Met/S.L./B.Am. | 79.9 | Lac; SM C16:0; SM C18:0; SM (OH) C24:1; Ac-Orn |
| 3216 | 6 | S.L./Am.Ac./B.Am. | 81.1 | SM (OH) C22:1; Lys; Pro; Tyr; Ac-Orn; Serotonin |
| 3217 | 4 | En.Met/S.L./Am.Ac. | 87.7 | Lac; SM C24:0; SM (OH) C22:1; Met |
| 3218 | 4 | S.L./Am.Ac./P.G. | 87.8 | SM (OH) C22:1; Leu; Pro; TXB2 |
| 3219 | 4 | S.L./Am.Ac./B.Am. | 82.3 | SM C24:1; SM (OH) C22:2; Met; Kynurenine |
| 3220 | 5 | S.L./Am.Ac./B.Am. | 81.3 | SM C18:0; SM (OH) C22:1; Lys; Tyr; Ac-Orn |
| 3221 | 4 | S.L./Am.Ac./B.Am. | 83.5 | SM C16:0; SM (OH) C22:2; Orn; Ac-Orn |
| 3222 | 4 | S.L./Am.Ac./O.St. | 81.4 | SM C24:0; SM (OH) C22:2; Phe; Cholestenone |
| 3223 | 4 | S.L./Am.Ac./B.Am. | 95.6 | SM (OH) C14:1; SM (OH) C22:2; Tyr; Kynurenine |
| 3224 | 4 | S.L./Am.Ac./B.Am. | 79.3 | SM C16:1; SM (OH) C14:1; Phe; Ac-Orn |
| 3225 | 4 | S.L./Am.Ac. | 83.6 | SM C16:1; SM C24:1; SM (OH) C22:2; Ser |
| 3226 | 4 | S.L./Am.Ac./B.Am./O.St. | 83.1 | SM C16:1; Arg; Met-SO; Cholestenone |
| 3227 | 4 | S.L./Am.Ac. | 79.6 | SM C24:1; SM C26:1; SM (OH) C16:1; Ala |
| 3228 | 3 | S.L./Am.Ac. | 79.2 | SM C24:1; SM (OH) C16:1; Gly |
| 3229 | 4 | S.L./Am.Ac./O.St. | 82.1 | SM C24:0; Pro; Trp; Cholestenone |
| 3230 | 4 | En.Met/S.L./Am.Ac./B.Am. | 89.4 | Suc; SM (OH) C22:2; Orn; Histamine |
| 3231 | 4 | S.L./Am.Ac./B.Am. | 85.5 | SM (OH) C24:1; Lys; Ac-Orn; Histamine |
| 3232 | 4 | S.L./Am.Ac. | 80.9 | SM C16:1; SM (OH) C14:1; Met; Phe |
| 3233 | 4 | En.Met/S.L./Am.Ac. | 83.1 | Fum; SM C24:0; Leu; Met |
| 3234 | 5 | S.L./Am.Ac./B.Am. | 87.9 | SM C16:1; SM (OH) C16:1; SM (OH) C22:2; Orn; alpha-AAA |
| 3235 | 4 | Ac.Ca./Am.Ac. | 80.1 | C8:1; His; Met; Pro |
| 3236 | 4 | Ac.Ca./Am.Ac. | 82.7 | C14:1; Arg; His; Met |
| 3237 | 4 | En.Met/S.L./Am.Ac. | 86.8 | Lac; SM C24:0; SM (OH) C22:2; Met |
| 3238 | 4 | Ac.Ca./S.L./Am.Ac. | 83 | C14:1-OH; SM C18:0; SM C20:2; Tyr |
| 3239 | 4 | En.Met/Am.Ac. | 80.4 | Fum; Lac; Met; Pro |
| 3240 | 4 | Ac.Ca./S.L./Am.Ac. | 79.4 | C14:1-OH; SM C20:2; SM (OH) C22:1; Pro |
| 3241 | 4 | S.L./Am.Ac./B.Am. | 88.7 | SM C24:0; SM (OH) C24:1; Lys; Met-SO |
| 3242 | 4 | S.L./Am.Ac. | 81.1 | SM C16:0; SM C18:1; SM C24:1; Tyr |
| 3243 | 5 | Ac.Ca./S.L./Am.Ac. | 93.7 | C5:1-DC; SM C16:0; SM C16:1; SM (OH) C14:1; Ala |
| 3244 | 5 | En.Met.Ca./S.L./Am.Ac. | 89 | alpha-KGA; C5:1-DC; SM C16:1; His; Orn |
| 3245 | 4 | Ac.Ca./S.L./Am.Ac. | 89.1 | C5:1; C6:1; SM (OH) C24:1; Met |
| 3246 | 5 | En.Met/S.L./B.Am. | 79.8 | Lac; SM C16:0; SM (OH) C22:2; SM (OH) C24:1; Sarcosine |
| 3247 | 5 | Ac.Ca./S.L./Am.Ac. | 85.2 | C5:1-DC; SM C16:0; SM C24:1; SM (OH) C24:1; Lys |
| 3248 | 5 | Am.Ac./B.Am./O.St. | 86.5 | His; Pro; Trp; SDMA; Cholestenone |
| 3249 | 6 | Ac.Ca./S.L./B.Am. | 84.8 | C5:1-DC; SM C16:0; SM (OH) C14:1; SM (OH) C22:1; alpha-AAA; Met-SO |
| 3250 | 6 | S.L./Am.Ac./B.Am. | 87.2 | SM C16:0; SM C24:0; SM (OH) C22:2; Gly; Pro; total DMA |
| 3251 | 5 | S.L./Am.Ac./B.Am. | 82.7 | SM C18:1; SM (OH) C22:2; Arg; Ac-Orn; Histamine |
| 3252 | 5 | En.Met/S.L./Am.Ac./B.Am. | 85 | Lac; SM C24:0; Orn; Phe; Met-SO |
| 3253 | 4 | S.L./Am.Ac./O.St. | 86 | SM C18:0; Arg; Trp; 24-DH-Lanosterol |
| 3254 | 4 | Ac.Ca./S.L./Am.Ac./O.St. | 83.4 | C5:1-DC; SM C16:0; Orn; Cholestenone |
| 3255 | 4 | S.L./Am.Ac./B.Am. | 79.7 | SM C16:1; SM (OH) C14:1; Leu; Met-SO |
| 3256 | 4 | S.L./Am.Ac./O.St. | 81.6 | SM C18:0; SM (OH) C14:1; Tyr; Cholestenone |
| 3257 | 4 | S.L./Am.Ac. | 82.5 | SM C24:0; Arg; His; Tyr |
| 3258 | 5 | En.Met/Ac.Ca./S.L./B.Am. | 83.2 | Lac; C18; C5:1-DC; SM (OH) C22:2; Histamine |
| 3259 | 4 | S.L./Am.Ac. | 86 | SM C16:0; SM C24:1; Pro; Tyr |
| 3260 | 5 | Ac.Ca./S.L./Am.Ac./B.Am. | 86 | C14:1; SM C18:1; SM (OH) C22:1; Pro; Met-SO |
| 3261 | 5 | S.L./Am.Ac./B.Am. | 92.6 | SM C16:0; SM C16:1; Pro; Trp; Ac-Orn |
| 3262 | 4 | S.L./Am.Ac. | 84.3 | SM C24:1; SM (OH) C14:1; Trp; Tyr |
| 3263 | 4 | S.L./Am.Ac. | 79.5 | SM C24:0; SM (OH) C24:1; Ala; Met |
| 3264 | 4 | S.L./Am.Ac./B.Am. | 80 | SM C18:0; Gln; Trp; Met-SO |
| 3265 | 4 | S.L./Am.Ac./P.G. | 80 | SM C16:0; SM C18:0; Lys; TXB2 |
| 3266 | 4 | S.L./Am.Ac. | 86.7 | SM C18:0; SM (OH) C14:1; Met; Trp |
| 3267 | 4 | S.L./Am.Ac./B.Am. | 82 | SM C26:1; SM (OH) C22:2; Lys; Met-SO |
| 3268 | 4 | En.Met/S.L./Am.Ac. | 85.6 | Suc; SM C16:0; Met; Orn |
| 3269 | 5 | Ac.Ca./S.L./Am.Ac./P.G. | 81.2 | C18:2; SM (OH) C22:2; His; Pro; LTB4 |
| 3270 | 4 | En.Met/S.L./Am.Ac. | 80.5 | Suc; SM (OH) C24:1; Gln; Tyr |
| 3271 | 4 | S.L./Am.Ac./B.Am. | 82.9 | SM (OH) C22:2; Leu; Pro; Kynurenine |
| 3272 | 3 | S.L./Am.Ac. | 83 | SM C24:0; Met; Orn |
| 3273 | 4 | S.L./Am.Ac./B.Am. | 85.1 | SM C16:0; SM C18:0; Trp; Met-SO |
| 3274 | 4 | En.Met/Ac.Ca./B.Am. | 81.4 | alpha-KGA; C14:1; C6:1; Met-SO |
| 3275 | 4 | S.L./Am.Ac./B.Am. | 82 | SM C24:0; SM (OH) C14:1; Leu; Met-SO |
| 3276 | 5 | En.Met/Ac.Ca./Am.Ac./B.Am./O.St. | 82.3 | alpha-KGA; C14:1; Orn; Met-SO; 25-OH-C |
| 3277 | 4 | S.L./Am.Ac./O.St. | 83.7 | SM C18:1; SM (OH) C22:1; Tyr; Cholestenone |
| 3278 | 5 | S.L./Am.Ac./B.Am. | 91.1 | SM (OH) C22:2; Gln; Lys; Ac-Orn; Histamine |
| 3279 | 4 | S.L./Am.Ac./O.St. | 83.9 | SM C24:1; SM (OH) C16:1; Ala; Cholestenone |
| 3280 | 4 | S.L./Am.Ac./O.St. | 84.6 | SM C24:1; Ala; Gln; Cholestenone |
| 3281 | 5 | Ac.Ca./S.L./Am.Ac. | 88.9 | C6:1; SM C20:2; SM (OH) C14:1; Pro; Tyr |
| 3282 | 4 | S.L./Am.Ac./B.Am. | 84.4 | SM (OH) C14:1; SM (OH) C22:1; Met; Creatinine |
| 3283 | 4 | En.Met/Am.Ac. | 81.1 | Lac; His; Met; Orn |
| 3284 | 4 | S.L./Am.Ac./B.Am. | 86.2 | SM (OH) C14:1; His; Met; Kynurenine |

TABLE 9-continued

Metabolite combinations describing damage of basal ganglia

| No. | Npar | Chemical Class | Accuracy | Model |
|---|---|---|---|---|
| 3285 | 4 | En.Met/S.L./Am.Ac./P.G. | 80.4 | Lac; SM C24:1; Tyr; AA |
| 3286 | 4 | S.L./Am.Ac./O.St. | 91.9 | SM (OH) C22:2; Leu; 20a-OH-C; 25-OH-C |
| 3287 | 4 | S.L./Am.Ac./B.Am. | 84.5 | SM (OH) C24:1; His; Orn; Ac-Orn |
| 3288 | 4 | En.Met/S.L./Am.Ac. | 83.8 | alpha-KGA; Fum; SM C16:1; Met |
| 3289 | 4 | Ac.Ca./S.L./Am.Ac. | 88.6 | C5:1-DC; SM (OH) C14:1; SM (OH) C16:1; Orn |
| 3290 | 4 | S.L./Am.Ac./P.G. | 81 | SM C18:1; SM (OH) C22:2; Gln; TXB2 |
| 3291 | 4 | Ac.Ca./S.L./Am.Ac./B.Am. | 85.4 | C6:1; SM (OH) C14:1; Pro; Met-SO |
| 3292 | 4 | S.L./Am.Ac. | 82.4 | SM C20:2; SM C26:1; SM (OH) C22:2; Tyr |
| 3293 | 6 | S.L./Am.Ac./B.Am. | 82.4 | SM C24:0; SM (OH) C16:1; Ala; Met; Ac-Orn; Histamine |
| 3294 | 4 | S.L./B.Am./P.G. | 79.4 | SM C24:0; SM (OH) C16:1; Met-SO; LTB4 |
| 3295 | 4 | En.Met/Ac.Ca./Am.Ac. | 82.3 | Suc; C6:1; His; Orn |
| 3296 | 4 | S.L./Am.Ac. | 88 | SM C24:1; Gln; Pro; Tyr |
| 3297 | 4 | S.L./Am.Ac. | 88.4 | SM (OH) C14:1; SM (OH) C22:1; Ala; Met |
| 3298 | 4 | En.Met/S.L./Am.Ac./B.Am. | 79.6 | Suc; SM C18:1; Gln; Met-SO |
| 3299 | 4 | En.Met/S.L./Am.Ac. | 80.2 | Lac; SM C24:0; Orn; Tyr |
| 3300 | 4 | En.Met/S.L./B.Am. | 79 | Lac; SM C24:0; SM (OH) C14:1; Sarcosine |
| 3301 | 4 | Ac.Ca./S.L./Am.Ac./B.Am. | 79.9 | C5:1-DC; SM C16:0; Asn; alpha-AAA |
| 3302 | 5 | En.Met/Am.Ac./B.Am./O.St. | 85.2 | alpha-KGA; Pro; Trp; Met-SO; Cholestenone |
| 3303 | 4 | En.Met/S.L./Am.Ac. | 86.8 | alpha-KGA; SM C20:2; SM C24:0; Tyr |
| 3304 | 5 | Ac.Ca./S.L./Am.Ac./B.Am. | 87.6 | C5:1-DC; SM C16:0; SM C24:0; Pro; Histamine |
| 3305 | 5 | S.L./Am.Ac. | 83 | SM C16:0; SM C20:2; SM (OH) C22:2; Ala; His |
| 3306 | 4 | S.L./Am.Ac./B.Am./O.St. | 79.1 | SM (OH) C22:1; Lys; Ac-Orn; 25-OH-C |
| 3307 | 4 | Am.Ac./B.Am. | 79.4 | Gln; Trp; Ac-Orn; alpha-AAA |
| 3308 | 4 | S.L./Am.Ac./B.Am./O.St. | 79.2 | SM C16:1; Gln; Met-SO; 24S-OH-C |
| 3309 | 4 | S.L./Am.Ac. | 84.1 | SM C24:0; SM (OH) C16:1; Trp; Tyr |
| 3310 | 6 | Ac.Ca./S.L./Am.Ac./O.St. | 93.5 | C14:1; SM (OH) C14:1; SM (OH) C22:2; His; Pro; 20a-OH-C |
| 3311 | 4 | S.L./Am.Ac./O.St. | 83 | SM C18:1; SM (OH) C22:2; Leu; 20a-OH-C |
| 3312 | 4 | Am.Ac./B.Am./P.G. | 86.5 | Lys; Orn; Met-SO; AA |
| 3313 | 5 | En.Met/S.L./Am.Ac./P.G. | 92.6 | alpha-KGA; SM C16:0; SM (OH) C22:2; Pro; TXB2 |
| 3314 | 4 | S.L./Am.Ac./B.Am. | 83.3 | SM C26:1; SM (OH) C22:2; Orn; Met-SO |
| 3315 | 4 | S.L./Am.Ac. | 80.2 | SM C16:1; SM C18:1; SM (OH) C22:1; Met |
| 3316 | 4 | S.L./Am.Ac./P.G. | 85.5 | SM C24:1; SM (OH) C22:1; Tyr; LTB4 |
| 3317 | 4 | En.Met/S.L./Am.Ac./O.St. | 91 | alpha-KGA; SM C16:1; Pro; 22R-OH-C |
| 3318 | 5 | S.L./Am.Ac./P.G. | 85.1 | SM C24:0; SM (OH) C16:1; Trp; Tyr; LTB4 |
| 3319 | 4 | En.Met/S.L./Am.Ac. | 88.1 | Lac; SM C24:0; SM C24:1; Tyr |
| 3320 | 5 | En.Met/Ac.Ca./S.L./Am.Ac. | 81.7 | Lac; C6:1; SM C24:1; SM (OH) C22:2; Met |
| 3321 | 4 | S.L./B.Am. | 81.7 | SM C26:1; SM (OH) C22:2; Ac-Orn; Histamine |
| 3322 | 4 | En.Met/S.L./B.Am. | 80.9 | Lac; SM (OH) C16:1; SM (OH) C24:1; Met-SO |
| 3323 | 4 | En.Met/S.L./P.G. | 84 | alpha-KGA; Fum; SM (OH) C24:1; TXB2 |
| 3324 | 4 | Am.Ac./O.St. | 90.9 | Gln; Lys; Met; 24S-OH-C |
| 3325 | 5 | Ac.Ca./S.L./Am.Ac./O.St. | 83.2 | C5:1-DC; SM C16:0; SM C20:2; Leu; Cholestenone |
| 3326 | 4 | S.L./Am.Ac./B.Am. | 79.7 | SM C16:0; Leu; Pro; Met-SO |
| 3327 | 4 | En.Met/S.L./Am.Ac. | 81.5 | alpha-KGA; SM C16:0; SM C24:1; Tyr |
| 3328 | 5 | En.Met/S.L./Am.Ac. | 83.4 | Fum; SM C16:0; SM C24:1; SM (OH) C14:1; Gly |
| 3329 | 4 | S.L./Am.Ac./O.St. | 84.6 | SM C16:1; SM (OH) C22:2; Ala; Cholestenone |
| 3330 | 4 | En.Met/S.L./P.G. | 85 | alpha-KGA; SM (OH) C14:1; SM (OH) C16:1; TXB2 |
| 3331 | 4 | S.L./Am.Ac./B.Am. | 82.1 | SM (OH) C22:2; SM (OH) C24:1; Gln; Met-SO |
| 3332 | 4 | S.L./B.Am. | 85.8 | SM (OH) C16:1; SM (OH) C22:1; Kynurenine; Met-SO |
| 3333 | 4 | Am.Ac./P.G. | 79.9 | Arg; His; Orn; 8-iso-PGF2a |
| 3334 | 4 | En.Met/S.L./B.Am. | 81.4 | alpha-KGA; SM C16:1; SM C18:0; Met-SO |
| 3335 | 5 | En.Met/S.L./B.Am./O.St. | 85 | Lac; SM C16:0; SM (OH) C24:1; Met-SO; 24S-OH-C |
| 3336 | 6 | S.L./Am.Ac./B.Am. | 81.2 | SM C18:1; SM C24:1; Ala; Gly; Met; alpha-AAA |
| 3337 | 5 | En.Met/S.L./Am.Ac./O.St./P.G. | 81.8 | Fum; SM C24:1; Trp; 24-DH-Lanosterol; DHA |
| 3338 | 6 | En.Met/S.L./Am.Ac./B.Am. | 85 | alpha-KGA; SM C24:0; SM C24:1; Orn; Phe; Ac-Orn |
| 3339 | 4 | S.L./Am.Ac./B.Am. | 89.9 | SM C16:0; Gln; Pro; Ac-Orn |
| 3340 | 4 | Am.Ac./P.G. | 84.8 | Gln; Orn; Tyr; 8-iso-PGF2a |
| 3341 | 4 | Am.Ac./B.Am. | 81.7 | Lys; Orn; Ac-Orn; Histamine |
| 3342 | 5 | S.L./Am.Ac./B.Am. | 85.1 | SM C16:0; SM (OH) C14:1; Orn; Ac-Orn; Histamine |
| 3343 | 4 | S.L./Am.Ac. | 90.2 | SM C16:1; Gln; Met; Pro |
| 3344 | 4 | Ac.Ca./S.L./Am.Ac. | 83.5 | C5:1; SM (OH) C24:1; Gln; Met |
| 3345 | 5 | Ac.Ca./S.L./Am.Ac. | 84.9 | C5:1-DC; SM C16:0; SM C18:1; SM (OH) C22:2; Trp |
| 3346 | 6 | En.Met/S.L./B.Am. | 87.8 | Lac; SM C16:1; SM C24:1; SM (OH) C22:2; Histamine; Met-SO |
| 3347 | 3 | Ac.Ca./S.L./O.St. | 81.2 | C5:1-DC; SM (OH) C24:1; Cholestenone |
| 3348 | 5 | Ac.Ca./S.L./Am.Ac./B.Am. | 81.3 | C14:1; SM C18:0; Arg; Orn; Ac-Orn |
| 3349 | 4 | En.Met/S.L./B.Am. | 85.3 | alpha-KGA; SM (OH) C14:1; Ac-Orn; Histamine |
| 3350 | 4 | En.Met/Ac.Ca./Am.Ac. | 80.6 | alpha-KGA; C8:1; Met; Pro |
| 3351 | 4 | S.L./Am.Ac./O.St. | 80.7 | SM (OH) C14:1; Arg; His; Cholestenone |
| 3352 | 6 | Ac.Ca./S.L./Am.Ac./O.St. | 84.6 | C14:1; SM C16:0; SM C26:1; Gln; Pro; 20a-OH-C |
| 3353 | 4 | S.L./Am.Ac./B.Am. | 79.5 | SM C24:0; Gln; Trp; Met-SO |
| 3354 | 4 | En.Met/S.L./B.Am. | 81 | alpha-KGA; SM C16:1; SM C18:1; Met-SO |
| 3355 | 4 | S.L./Am.Ac. | 79.4 | C14:2-OH; SM C16:1; Phe; Tyr |
| 3356 | 4 | S.L./Am.Ac./O.St. | 92.4 | SM (OH) C22:2; Pro; Trp; 24-DH-Lanosterol |
| 3357 | 4 | Ac.Ca./Am.Ac. | 91 | C10:2; Gln; Met; Pro |
| 3358 | 5 | Ac.Ca./S.L./Am.Ac./B.Am. | 84.4 | C5:1-DC; SM (OH) C14:1; Met; Histamine |
| 3359 | 4 | S.L./Am.Ac./B.Am./O.St. | 85.7 | SM (OH) C22:1; Pro; Ac-Orn; Cholestenone |
| 3360 | 4 | S.L./Am.Ac./B.Am. | 89.3 | SM C16:1; Pro; Ac-Orn; Histamine |

TABLE 9-continued

Metabolite combinations describing damage of basal ganglia

| No. | Npar | Chemical Class | Accuracy | Model |
|---|---|---|---|---|
| 3361 | 4 | S.L./Am.Ac./B.Am. | 86.1 | SM C26:1; SM (OH) C24:1; Lys; Met-SO |
| 3362 | 4 | S.L./Am.Ac./B.Am. | 83.3 | SM (OH) C14:1; SM (OH) C22:1; Leu; Met-SO |
| 3363 | 4 | S.L./Am.Ac. | 81.4 | SM (OH) C16:1; His; Met; Orn |
| 3364 | 6 | En.Met/Ac.Ca./S.L./Am.Ac./B.Am./O.St. | 84.7 | Fum; C18; SM (OH) C24:1; Pro; Met-SO; 25-OH-C |
| 3365 | 4 | S.L./Am.Ac./B.Am./O.St. | 83.4 | SM (OH) C22:1; Arg; Met-SO; 24S-OH-C |
| 3366 | 4 | En.Met/Ac.Ca./S.L. | 82.4 | alpha-KGA; C5:1-DC; SM C16:0; SM (OH) C22:2 |
| 3367 | 4 | S.L./Am.Ac./O.St. | 83.9 | SM C16:1; SM C24:0; Phe; 20a-OH-C |
| 3368 | 5 | S.L./Am.Ac./O.St. | 79.3 | SM C20:2; His; Tyr; 24-DH-Lanosterol; Cholestenone |
| 3369 | 4 | Am.Ac./B.Am./O.St. | 83.7 | Gln; Pro; Met-SO; 25-OH-C |
| 3370 | 5 | En.Met/S.L./Am.Ac. | 83.8 | alpha-KGA; Lac; SM (OH) C14:1; His; Met |
| 3371 | 5 | S.L./Am.Ac./B.Am. | 85.4 | SM C26:1; SM (OH) C16:1; Leu; Tyr; Kynurenine |
| 3372 | 5 | S.L./Am.Ac./B.Am. | 79.9 | SM C24:0; SM C24:1; Arg; His; SDMA |
| 3373 | 4 | Ac.Ca./S.L./O.St. | 81.6 | C5:1-DC; SM C18:1; SM (OH) C22:1; Cholestenone |
| 3374 | 4 | S.L./Am.Ac./B.Am. | 79.7 | SM (OH) C24:1; Lys; Tyr; Met-SO |
| 3375 | 4 | S.L./Am.Ac. | 81.2 | SM C16:1; Arg; His; Tyr |
| 3376 | 4 | S.L./Am.Ac./B.Am. | 79.8 | SM C18:1; SM (OH) C22:1; Pro; Ac-Orn |
| 3377 | 4 | S.L./Am.Ac./B.Am. | 91.5 | SM C24:0; Gln; Pro; Met-SO |
| 3378 | 4 | Ac.Ca./S.L./Am.Ac. | 85.8 | C5:1-DC; SM (OH) C14:1; SM (OH) C22:1; Met |
| 3379 | 5 | S.L./Am.Ac. | 82.3 | SM C18:0; SM C18:1; SM C24:0; Lys; Met |
| 3380 | 5 | Ac.Ca./Am.Ac./O.St. | 91.1 | C5:1-DC; Gln; Lys; 24-DH-Lanosterol; Cholestenone |
| 3381 | 4 | Ac.Ca./S.L./Am.Ac. | 83.9 | C18:1; SM (OH) C22:2; Arg; Pro |
| 3382 | 5 | S.L./Am.Ac./P.G. | 84 | SM C24:0; SM C26:1; Pro; Tyr; LTB4 |
| 3383 | 4 | En.Met/Am.Ac./B.Am. | 88.7 | Pent-P; Suc; Pro; Histamine |
| 3384 | 5 | En.Met/S.L./Am.Ac./B.Am. | 81.4 | Suc; SM C18:1; Gln; Phe; Histamine |
| 3385 | 4 | S.L./Am.Ac. | 82 | SM C16:0; SM C18:1; Gln; Tyr |
| 3386 | 4 | En.Met/Ac.Ca./Am.Ac. | 80.3 | alpha-KGA; C10:2; Met; Pro |
| 3387 | 4 | S.L./Am.Ac./B.Am. | 87.8 | SM C24:0; Arg; Orn; Met-SO |
| 3388 | 5 | Am.Ac./B.Am. | 79 | Gln; Met; Orn; Tyr; Histamine |
| 3389 | 5 | S.L./Am.Ac./B.Am. | 87.8 | SM C16:1; SM C20:2; SM (OH) C22:2; Ala; His |
| 3390 | 4 | Ac.Ca./S.L./B.Am. | 79.4 | C5:1-DC; SM C24:1; SM (OH) C16:1; Histamine |
| 3391 | 6 | S.L./Am.Ac./B.Am. | 89.6 | SM C18:1; SM (OH) C22:1; Pro; Trp; Ac-Orn; SDMA |
| 3392 | 4 | Ac.Ca./S.L. | 82.2 | C5:1-DC; SM C16:0; SM (OH) C22:1; SM (OH) C24:1 |
| 3393 | 4 | S.L./Am.Ac./B.Am. | 82.6 | SM (OH) C22:1; SM (OH) C22:2; Arg; Met-SO |
| 3394 | 4 | S.L./Am.Ac./O.St. | 81.3 | SM (OH) C22:1; SM (OH) C22:2; Asn; Cholestenone |
| 3395 | 4 | Ac.Ca./S.L./Am.Ac./O.St. | 83.2 | C5:1-DC; SM (OH) C14:1; Met; Cholestenone |
| 3396 | 6 | S.L./Am.Ac./B.Am./O.St. | 87.4 | SM C16:0; SM (OH) C14:1; Lys; Trp; Met-SO; 24-DH-Lanosterol |
| 3397 | 4 | S.L./Am.Ac./O.St. | 79.9 | SM C18:1; SM (OH) C22:1; Asn; Cholestenone |
| 3398 | 4 | S.L./Am.Ac. | 81.4 | SM (OH) C14:1; SM (OH) C22:1; Asn; Pro |
| 3399 | 4 | S.L./Am.Ac./B.Am. | 79.2 | SM C18:1; SM C24:0; Leu; Met-SO |
| 3400 | 6 | Ac.Ca./S.L./Am.Ac./O.St. | 79.1 | C6:1; SM C16:0; SM (OH) C16:1; Lys; Ser; 20a-OH-C |
| 3401 | 5 | S.L./Am.Ac./B.Am./P.G. | 84.1 | SM (OH) C22:2; Met; Kynurenine; 8-iso-PGF2a; LTB4 |
| 3402 | 4 | S.L./Am.Ac./B.Am. | 87.7 | SM (OH) C22:1; Gln; Pro; Ac-Orn |
| 3403 | 4 | En.Met/S.L./B.Am. | 79.7 | alpha-KGA; SM (OH) C14:1; SM (OH) C16:1; Ac-Orn |
| 3404 | 5 | Ac.Ca./S.L./Am.Ac. | 87 | C5:1-DC; SM C16:1; SM (OH) C22:2; Arg; His |
| 3405 | 4 | S.L./Am.Ac./B.Am. | 81.6 | SM C24:0; SM (OH) C24:1; Val; Met-SO |
| 3406 | 5 | Ac.Ca./S.L./Am.Ac. | 87.3 | C5:1-DC; SM (OH) C22:1; SM (OH) C22:2; Gln; Orn |
| 3407 | 4 | S.L./Am.Ac./B.Am. | 87.2 | SM C18:1; SM C14:1; Trp; Met-SO |
| 3408 | 4 | En.Met/S.L./B.Am. | 82.7 | alpha-KGA; SM (OH) C14:1; SM (OH) C24:1; Met-SO |
| 3409 | 4 | S.L./Am.Ac./P.G. | 83.8 | SM C26:1; Met; Orn; LTB4 |
| 3410 | 3 | S.L./Am.Ac./B.Am. | 83.5 | SM (OH) C14:1; Lys; Met-SO |
| 3411 | 4 | S.L./B.Am./O.St. | 82.5 | SM C24:0; Histamine; Met-SO; 25-OH-C |
| 3412 | 5 | S.L./Am.Ac./O.St. | 85.5 | SM C24:1; Gln; Lys; Tyr; 24S-OH-C |
| 3413 | 4 | En.Met/S.L./B.Am./O.St. | 79.2 | alpha-KGA; SM C24:1; Ac-Orn; Cholestenone |
| 3414 | 4 | S.L./Am.Ac./B.Am. | 80.5 | SM C24:0; Met; Tyr; Histamine |
| 3415 | 4 | En.Met/Ac.Ca./Am.Ac. | 83 | alpha-KGA; Fum; C14:1; Met |
| 3416 | 5 | S.L./Am.Ac. | 88.6 | SM C24:1; SM (OH) C22:1; SM (OH) C22:2; Ala; Orn |
| 3417 | 5 | En.Met/S.L./Am.Ac. | 88.7 | alpha-KGA; Suc; SM (OH) C22:1; Met; Orn |
| 3418 | 4 | S.L./Am.Ac./B.Am. | 83.7 | SM (OH) C14:1; SM (OH) C16:1; Met; Kynurenine |
| 3419 | 4 | Ac.Ca./S.L./Am.Ac./B.Am. | 80.2 | C9; SM C18:1; Gln; Met-SO |
| 3420 | 4 | En.Met/S.L./Am.Ac. | 84 | alpha-KGA; SM C16:0; SM C20:2; Tyr |
| 3421 | 4 | Am.Ac./O.St. | 88.7 | Gln; Met; Pro; Cholestenone |
| 3422 | 4 | Ac.Ca./S.L./O.St. | 83.4 | C6:1; SM (OH) C22:1; SM (OH) C22:2; 20a-OH-C |
| 3423 | 5 | En.Met/Ac.Ca./S.L./Am.Ac./B.Am. | 84.5 | Suc; C6:1; SM (OH) C24:1; Pro; Serotonin |
| 3424 | 4 | S.L./Am.Ac./O.St. | 84.1 | SM C16:1; Arg; Met; Cholestenone |
| 3425 | 4 | S.L./Am.Ac./B.Am. | 83.1 | SM C18:0; SM (OH) C16:1; Trp; total DMA |
| 3426 | 4 | S.L./Am.Ac. | 86.7 | SM C24:1; SM (OH) C22:2; SM (OH) C24:1; Gly |
| 3427 | 4 | S.L./Am.Ac./B.Am. | 79.3 | SM C24:1; SM (OH) C22:1; Lys; Sarcosine |
| 3428 | 6 | S.L./Am.Ac./B.Am. | 82.5 | SM C20:2; Gln; His; Met; Tyr; alpha-AAA |
| 3429 | 4 | S.L./Am.Ac./B.Am. | 80.6 | SM C24:0; Gln; Val; Met-SO |
| 3430 | 4 | S.L./Am.Ac./O.St. | 80.3 | SM (OH) C14:1; SM (OH) C22:1; Gly; Cholestenone |
| 3431 | 4 | S.L./Am.Ac./O.St. | 80.8 | SM C18:1; Ala; Gln; Cholestenone |
| 3432 | 5 | En.Met/S.L./Am.Ac./B.Am. | 79.2 | Suc; SM (OH) C22:2; SM (OH) C24:1; Ala; Histamine |
| 3433 | 5 | S.L./Am.Ac./B.Am./O.St. | 81.9 | SM C16:1; Gln; Phe; Met-SO; Cholestenone |
| 3434 | 4 | Ac.Ca./S.L./Am.Ac./O.St. | 79.9 | C5:1-DC; SM C16:0; Gln; 24-DH-Lanosterol |
| 3435 | 5 | S.L./Am.Ac./B.Am. | 80.1 | SM C24:0; Gln; Leu; Met; Ac-Orn |
| 3436 | 5 | Ac.Ca./S.L./Am.Ac. | 91.6 | C5:1-DC; C6:1; SM C16:0; SM (OH) C14:1; Orn |

TABLE 9-continued

Metabolite combinations describing damage of basal ganglia

| No. | Npar | Chemical Class | Accuracy | Model |
|---|---|---|---|---|
| 3437 | 5 | En.Met/S.L./Am.Ac./B.Am. | 86.9 | alpha-KGA; Fum; SM (OH) C24:1; Gln; Met-SO |
| 3438 | 4 | S.L./Am.Ac. | 85.7 | SM C16:0; SM (OH) C22:1; Met; Pro |
| 3439 | 4 | S.L./Am.Ac./B.Am. | 82.2 | SM C16:1; Lys; Met; Histamine |
| 3440 | 4 | En.Met/Am.Ac./B.Am./O.St. | 84.9 | H1; Trp; Met-SO; Cholestenone |
| 3441 | 5 | S.L./Am.Ac. | 85 | SM C18:1; SM C24:0; SM C24:1; Ala; Orn |
| 3442 | 5 | S.L./Am.Ac./B.Am./O.St. | 86.2 | SM C24:1; Gln; Orn; Ac-Orn; 24-DH-Lanosterol |
| 3443 | 5 | S.L./Am.Ac./O.St./P.G. | 86.8 | SM (OH) C22:1; Arg; Trp; 24-DH-Lanosterol; LTB4 |
| 3444 | 4 | S.L./Am.Ac. | 83.4 | SM C24:0; SM (OH) C22:2; Met; Val |
| 3445 | 4 | En.Met/S.L./B.Am. | 79.8 | alpha-KGA; SM C18:1; SM C24:0; Ac-Orn |
| 3446 | 4 | Ac.Ca./S.L./B.Am. | 87.2 | C5:1-DC; SM C16:0; SM (OH) C22:1; Histamine |
| 3447 | 5 | Ac.Ca./S.L./Am.Ac./O.St. | 84.4 | C6:1; SM C18:1; SM (OH) C22:2; Gln; 20a-OH-C |
| 3448 | 5 | En.Met/S.L./Am.Ac./B.Am. | 80.7 | Suc; SM (OH) C14:1; SM (OH) C24:1; Orn; Histamine |
| 3449 | 4 | S.L./Am.Ac./B.Am. | 82.4 | SM C16:0; SM (OH) C22:2; Leu; Kynurenine |
| 3450 | 4 | En.Met/S.L./Am.Ac. | 81.4 | Suc; SM C16:1; Orn; Phe |
| 3451 | 4 | S.L./Am.Ac. | 80.3 | SM C18:0; SM (OH) C14:1; SM (OH) C16:1; Tyr |
| 3452 | 5 | Ac.Ca./S.L./Am.Ac./O.St. | 81 | C14:1; SM C18:0; SM C18:1; Ala; Cholestenone |
| 3453 | 4 | Ac.Ca./S.L./O.St. | 80.8 | C5:1-DC; SM C24:0; SM (OH) C22:2; 24-DH-Lanosterol |
| 3454 | 4 | En.Met/S.L./B.Am. | 79.8 | Lac; SM C16:0; SM C24:1; Met-SO |
| 3455 | 4 | Am.Ac./O.St. | 89.9 | Gln; Lys; Met; 25-OH-C |
| 3456 | 3 | S.L./Am.Ac. | 88.1 | SM C26:0; Gln; Met |
| 3457 | 3 | S.L./B.Am. | 85.3 | SM C16:1; SM (OH) C22:1; Met-SO |
| 3458 | 4 | En.Met/S.L./Am.Ac. | 82.1 | Lac; SM C18:1; SM (OH) C22:1; Met |
| 3459 | 4 | S.L./Am.Ac. | 86 | SM (OH) C14:1; Met; Pro; Val |
| 3460 | 4 | En.Met/S.L./B.Am. | 82.6 | alpha-KGA; SM (OH) C14:1; Histamine; Met-SO |
| 3461 | 6 | En.Met/S.L./Am.Ac./O.St./P.G. | 84.9 | Fum; Lac; SM C24:1; Trp; 5a,6a-EpoxyC; DHA |
| 3462 | 5 | En.Met/S.L./B.Am. | 82.2 | Lac; SM C16:1; SM (OH) C16:1; SM (OH) C22:2; Met-SO |
| 3463 | 4 | En.Met/Am.Ac./B.Am. | 80.3 | alpha-KGA; Orn; Ac-Orn; Histamine |
| 3464 | 4 | S.L./Am.Ac. | 87.3 | SM C24:1; SM (OH) C14:1; Ala; Met |
| 3465 | 5 | S.L./Am.Ac./P.G. | 89.9 | SM C16:0; SM (OH) C16:1; SM (OH) C22:2; Orn; TXB2 |
| 3466 | 4 | En.Met/S.L./Am.Ac. | 80.3 | alpha-KGA; SM (OH) C22:1; SM (OH) C24:1; Met |
| 3467 | 5 | S.L./B.Am. | 82.4 | SM C16:1; SM C18:1; SM (OH) C22:2; Ac-Orn; Histamine |
| 3468 | 4 | S.L./Am.Ac./P.G. | 88 | SM (OH) C22:1; His; Lys; TXB2 |
| 3469 | 4 | S.L./Am.Ac. | 80.8 | SM (OH) C22:2; Gln; Leu; Met |
| 3470 | 4 | En.Met/Ac.Ca./S.L./Am.Ac. | 81.7 | alpha-KGA; C5:1-DC; SM (OH) C14:1; Pro |
| 3471 | 4 | S.L./Am.Ac. | 84.1 | SM C16:1; SM (OH) C22:1; Met; Trp |
| 3472 | 6 | En.Met/Ac.Ca./S.L./Am.Ac./B.Am./O.St. | 83.9 | Hex-P; C18:1; SM C18:1; Pro; Met-SO; Cholestenone |
| 3473 | 4 | S.L./Am.Ac./B.Am. | 82.3 | SM C24:1; SM (OH) C22:1; Gln; Met-SO |
| 3474 | 5 | En.Met/S.L./Am.Ac./B.Am. | 80.9 | Hex-P; SM C24:1; SM (OH) C22:2; Gln; Histamine |
| 3475 | 4 | S.L./Am.Ac./O.St. | 87 | SM C16:0; SM (OH) C22:2; Gly; Cholestenone |
| 3476 | 5 | S.L./Am.Ac./B.Am. | 82 | SM C16:1; Arg; Met; Orn; Histamine |
| 3477 | 5 | S.L./Am.Ac./B.Am. | 81.2 | SM C18:1; SM C24:1; SM (OH) C22:2; Trp; Histamine |
| 3478 | 4 | Ac.Ca./S.L./Am.Ac./B.Am. | 79.2 | C5:1-DC; SM C16:0; Met; Histamine |
| 3479 | 4 | Ac.Ca./S.L./Am.Ac./P.G. | 81.7 | C10:2; SM C24:1; Pro; LTB4 |
| 3480 | 4 | S.L./Am.Ac./P.G. | 80.8 | SM (OH) C16:1; SM (OH) C22:1; Arg; TXB2 |
| 3481 | 4 | Ac.Ca./S.L./Am.Ac. | 80.3 | C14:1; SM (OH) C16:1; Pro; Trp |
| 3482 | 4 | En.Met/Ac.Ca./Am.Ac./B.Am. | 83.4 | Suc; C14:1; Pro; Ac-Orn |
| 3483 | 5 | S.L./Am.Ac./B.Am./P.G. | 80.9 | SM (OH) C24:1; Gln; Phe; Ac-Orn; LTB4 |
| 3484 | 7 | S.L./Am.Ac./O.St. | 88 | SM C16:0; SM C24:0; SM (OH) C16:1; Ala; Gln; Phe; 20a-OH-C |
| 3485 | 4 | Am.Ac./B.Am. | 85.4 | Arg; Gln; Lys; Ac-Orn |
| 3486 | 4 | S.L./Am.Ac. | 84.4 | SM C16:1; SM C18:1; SM C24:1; Ser |
| 3487 | 3 | Am.Ac./B.Am. | 79.3 | Gln; Orn; Ac-Orn |
| 3488 | 4 | S.L./Am.Ac. | 80.1 | SM C16:1; SM C24:0; Arg; Phe |
| 3489 | 4 | S.L./Am.Ac./B.Am./P.G. | 79.3 | SM C24:0; Gln; Met-SO; LTB4 |
| 3490 | 5 | S.L./Am.Ac. | 82.8 | SM C18:1; SM (OH) C22:1; Gln; Met; Phe |
| 3491 | 4 | S.L./Am.Ac. | 82 | SM C16:0; SM (OH) C24:1; Met; Pro |
| 3492 | 6 | Ac.Ca./S.L./Am.Ac./B.Am. | 86 | C14:1; C5:1-DC; SM (OH) C14:1; Trp; Met-SO; Spermidine |
| 3493 | 5 | En.Met/S.L./Am.Ac./B.Am. | 84.3 | Suc; SM C24:1; Leu; Orn; Ac-Orn |
| 3494 | 5 | En.Met/Ac.Ca./S.L./Am.Ac. | 89.8 | alpha-KGA; C5:1-DC; SM C16:1; SM (OH) C22:1; Tyr |
| 3495 | 4 | S.L./Am.Ac./B.Am. | 83.1 | SM (OH) C22:1; His; Trp; Met-SO |
| 3496 | 5 | En.Met/S.L./Am.Ac./O.St. | 79.3 | alpha-KGA; SM C24:1; Arg; Cholestenone |
| 3497 | 4 | Ac.Ca./S.L./Am.Ac. | 85.1 | C14:1; SM C24:1; Arg; Pro |
| 3498 | 4 | S.L./Am.Ac. | 83.7 | SM (OH) C22:1; Ala; Gln; Met |
| 3499 | 4 | S.L./Am.Ac./O.St. | 86.5 | SM C16:1; His; Leu; 20a-OH-C |
| 3500 | 4 | En.Met/S.L./P.G. | 89.6 | alpha-KGA; Fum; SM C16:0; TXB2 |
| 3501 | 5 | Ac.Ca./S.L./Am.Ac. | 89.8 | C5:1-DC; SM C16:0; SM (OH) C22:1; Gln; Tyr |
| 3502 | 4 | En.Met/S.L./Am.Ac. | 82.4 | Fum; SM C16:0; SM C24:1; Gly |
| 3503 | 4 | En.Met/S.L./Am.Ac./P.G. | 80.3 | OAA; SM (OH) C14:1; Leu; TXB2 |
| 3504 | 4 | Ac.Ca./S.L./Am.Ac. | 85 | C6:1; SM C24:0; Pro; Tyr |
| 3505 | 4 | S.L./Am.Ac./B.Am. | 84.3 | SM C16:1; SM (OH) C22:2; Pro; Met-SO |
| 3506 | 5 | S.L./Am.Ac./B.Am. | 85.3 | SM C16:1; SM (OH) C16:1; SM (OH) C22:2; Tyr; Creatinine |
| 3507 | 4 | Ac.Ca./S.L./Am.Ac. | 80.4 | C5:1-DC; SM C16:0; Arg; Pro |
| 3508 | 4 | S.L./Am.Ac./O.St. | 86.4 | SM C24:1; Met; Trp; 24-DH-Lanosterol |
| 3509 | 5 | S.L./Am.Ac./B.Am. | 81.1 | SM C18:0; SM C24:0; SM C24:1; Thr; Ac-Orn |
| 3510 | 6 | En.Met/Ac.Ca./Am.Ac. | 83.1 | Lac; C14:1; Arg; Lys; Met; Trp |
| 3511 | 4 | S.L./Am.Ac. | 86.5 | SM C24:1; SM (OH) C14:1; Arg; Tyr |
| 3512 | 4 | S.L./Am.Ac./O.St. | 79 | SM C18:0; SM C26:1; Trp; 24-DH-Lanosterol |

TABLE 9-continued

Metabolite combinations describing damage of basal ganglia

| No. | Npar | Chemical Class | Accuracy | Model |
|---|---|---|---|---|
| 3513 | 5 | Ac.Ca./S.L./Am.Ac. | 81.5 | C5:1-DC; SM C16:1; SM C24:1; Gln; Leu |
| 3514 | 4 | S.L./Am.Ac./B.Am. | 80.3 | SM (OH) C22:2; Leu; Ac-Orn; Histamine |
| 3515 | 5 | S.L./Am.Ac./O.St. | 81.3 | SM (OH) C24:1; Pro; Trp; Tyr; 24-DH-Lanosterol |
| 3516 | 4 | S.L./Am.Ac./B.Am. | 80.8 | SM C18:0; SM C24:1; Gln; Met-SO |
| 3517 | 4 | S.L./Am.Ac. | 79.1 | SM C16:1; SM C18:1; SM C26:1; Ala |
| 3518 | 4 | S.L./Am.Ac./B.Am. | 81.2 | SM (OH) C22:2; Met; Pro; Histamine |
| 3519 | 4 | En.Met/S.L./B.Am./O.St. | 86.6 | alpha-KGA; SM C24:0; Met-SO; 25-OH-C |
| 3520 | 5 | En.Met/S.L./Am.Ac./O.St. | 81.5 | Suc; SM C18:1; Arg; Tyr; 24-DH-Lanosterol |
| 3521 | 4 | En.Met/S.L./Am.Ac./B.Am. | 86.1 | alpha-KGA; SM C24:0; Trp; Met-SO |
| 3522 | 4 | S.L./Am.Ac./B.Am. | 86.2 | SM (OH) C22:1; Gln; Orn; Ac-Orn |
| 3523 | 4 | S.L./Am.Ac./O.St. | 79.9 | SM (OH) C22:1; SM (OH) C22:2; Arg; Cholestenone |
| 3524 | 4 | En.Met/Am.Ac./B.Am. | 84.4 | Suc; Orn; Tyr; Histamine |
| 3525 | 6 | S.L./Am.Ac./P.G. | 86.5 | SM C16:0; SM (OH) C22:1; Met; Orn; Tyr; LTB4 |
| 3526 | 6 | En.Met/S.L./Am.Ac./B.Am. | 84.9 | Fum; SM C18:0; Gln; Met; Kynurenine; Met-SO |
| 3527 | 4 | En.Met/S.L./O.St. | 82.8 | Fum; SM (OH) C22:2; SM (OH) C24:1; 20a-OH-C |
| 3528 | 4 | S.L./Am.Ac./B.Am. | 83.2 | SM C24:0; Leu; Pro; Ac-Orn |
| 3529 | 4 | En.Met/Am.Ac./B.Am. | 79.9 | Suc; Lys; Tyr; Histamine |
| 3530 | 4 | En.Met/Ac.Ca./Am.Ac. | 79.4 | Lac; C18:1; His; Pro |
| 3531 | 4 | En.Met/S.L./Am.Ac./B.Am. | 85.7 | Lac; SM C18:0; Gln; total DMA |
| 3532 | 5 | S.L./Am.Ac. | 84.9 | SM C24:0; SM C24:1; SM (OH) C22:2; Gly; Met |
| 3533 | 4 | Ac.Ca./S.L./Am.Ac. | 80.4 | C5:1; SM (OH) C24:1; His; Met |
| 3534 | 4 | En.Met/S.L./Am.Ac. | 80.2 | alpha-KGA; SM C24:1; SM (OH) C24:1; Tyr |
| 3535 | 4 | En.Met/S.L./Am.Ac./P.G. | 87.8 | alpha-KGA; SM (OH) C22:1; Orn; TXB2 |
| 3536 | 4 | En.Met/S.L./Am.Ac./B.Am. | 92.9 | Lac; SM C24:0; Gln; Met-SO |
| 3537 | 6 | En.Met/Am.Ac./B.Am./O.St./P.G. | 91.1 | alpha-KGA; Arg; Trp; Ac-Orn; Cholestenone; LTB4 |
| 3538 | 5 | En.Met/S.L./B.Am. | 87.2 | alpha-KGA; SM C16:0; SM (OH) C24:1; Kynurenine; Met-SO |
| 3539 | 5 | En.Met/S.L./Am.Ac./B.Am. | 86.5 | Lac; SM C16:1; SM (OH) C22:1; His; Met-SO |
| 3540 | 4 | En.Met/Ac.Ca./S.L./Am.Ac. | 81 | Suc; C6:1; SM C16:1; Orn |
| 3541 | 4 | Am.Ac./B.Am./O.St. | 85.8 | Gln; Orn; Met-SO; 25-OH-C |
| 3542 | 5 | S.L./Am.Ac. | 89.3 | SM C16:0; SM (OH) C22:1; Met; Pro; Trp |
| 3543 | 4 | S.L./B.Am. | 79.7 | SM C16:1; SM C24:0; SM (OH) C22:2; Met-SO |
| 3544 | 6 | En.Met/S.L./Am.Ac./O.St. | 92.5 | alpha-KGA; SM C16:0; SM C24:0; His; Tyr; 20a-OH-C |
| 3545 | 4 | S.L./Am.Ac./B.Am. | 81.5 | SM C16:1; SM (OH) C22:1; Met; Kynurenine |
| 3546 | 5 | En.Met/Ac.Ca./Am.Ac./O.St. | 82.4 | alpha-KGA; C6:1; Gln; Met; 27-OH-C |
| 3547 | 5 | S.L./Am.Ac./B.Am. | 89 | SM (OH) C14:1; SM (OH) C22:2; Phe; Pro; Kynurenine |
| 3548 | 4 | S.L./B.Am. | 82.3 | SM C18:1; SM C24:0; SM C24:1; Met-SO |
| 3549 | 6 | En.Met/S.L./Am.Ac./B.Am. | 82.5 | alpha-KGA; SM C18:1; SM (OH) C22:1; Gln; Ser; total DMA |
| 3550 | 5 | En.Met/S.L./Am.Ac./O.St. | 86.2 | SM C16:1; SM C24:0; Tyr; Ac-Orn; Cholestenone |
| 3551 | 4 | Ac.Ca./S.L./Am.Ac. | 84.5 | C5:1; SM (OH) C24:1; Met; Pro |
| 3552 | 4 | En.Met/S.L./Am.Ac. | 82.1 | alpha-KGA; SM (OH) C14:1; Met; Phe |
| 3553 | 5 | S.L./Am.Ac./B.Am./O.St. | 84.4 | SM (OH) C14:1; SM (OH) C24:1; Gly; Ac-Orn; Cholestenone |
| 3554 | 4 | En.Met/S.L./Am.Ac./O.St. | 80.7 | alpha-KGA; SM C24:1; Arg; 24-DH-Lanosterol |
| 3555 | 4 | En.Met/Ac.Ca./S.L./Am.Ac. | 82.9 | alpha-KGA; C14:1-OH; SM C20:2; Pro |
| 3556 | 5 | S.L./Am.Ac./P.G. | 85.8 | SM C16:1; SM (OH) C14:1; SM (OH) C22:1; Orn; TXB2 |
| 3557 | 5 | Ac.Ca./S.L./Am.Ac. | 80.5 | C6:1; SM C16:0; SM (OH) C16:1; Met; Orn |
| 3558 | 4 | S.L./Am.Ac. | 80.8 | SM C16:1; SM C20:2; Met; Val |
| 3559 | 4 | En.Met/S.L./Am.Ac. | 91.3 | Lac; SM C24:0; Gln; Met |
| 3560 | 4 | S.L./Am.Ac./B.Am. | 83.6 | SM (OH) C22:1; SM (OH) C24:1; Pro; Ac-Orn |
| 3561 | 4 | S.L./Am.Ac./O.St. | 88.1 | SM (OH) C16:1; SM (OH) C22:2; Orn; 20a-OH-C |
| 3562 | 4 | S.L./Am.Ac./B.Am. | 85.1 | SM C24:1; Gln; Pro; Histamine |
| 3563 | 4 | S.L./Am.Ac. | 87.3 | SM C18:1; SM C24:1; SM (OH) C14:1; Gly |
| 3564 | 4 | En.Met/S.L./Am.Ac. | 83.4 | Lac; SM (OH) C22:2; SM (OH) C24:1; Met |
| 3565 | 5 | En.Met/S.L./Am.Ac./B.Am. | 90.1 | Lac; SM C24:1; Gln; Ac-Orn; Histamine |
| 3566 | 4 | S.L./Am.Ac./B.Am. | 80 | SM (OH) C16:1; Gln; Carnosine; Met-SO |
| 3567 | 5 | Ac.Ca./S.L./Am.Ac. | 83.4 | C5:1-DC; SM C16:0; His; Orn; Pro |
| 3568 | 4 | En.Met/S.L./O.St. | 84.7 | alpha-KGA; SM C16:1; 20a-OH-C; 25-OH-C |
| 3569 | 4 | En.Met/S.L./Am.Ac. | 79.9 | Fum; SM (OH) C22:2; Leu; Met |
| 3570 | 4 | Ac.Ca./S.L./B.Am. | 80 | C5:1-DC; SM C16:0; SM C26:1; Histamine |
| 3571 | 4 | S.L./Am.Ac. | 80.8 | SM C16:0; SM (OH) C14:1; Pro; Trp |
| 3572 | 4 | Ac.Ca./S.L./Am.Ac. | 79.3 | C9; SM C24:0; SM (OH) C22:1; Phe |
| 3573 | 6 | S.L./Am.Ac./B.Am./O.St. | 81.6 | SM C18:1; SM (OH) C22:1; SM (OH) C22:2; Arg; Met-SO; 20a-OH-C |
| 3574 | 4 | S.L./Am.Ac. | 83.5 | SM C24:1; SM (OH) C16:1; SM (OH) C22:2; Ala |
| 3575 | 4 | S.L./Am.Ac./O.St. | 97.6 | SM (OH) C22:1; SM (OH) C22:2; Tyr; 20a-OH-C |
| 3576 | 4 | S.L./B.Am. | 82.5 | SM C18:1; SM C24:0; Ac-Orn; Histamine |
| 3577 | 4 | S.L./Am.Ac./B.Am. | 82.8 | SM (OH) C14:1; SM (OH) C24:1; Lys; Met-SO |
| 3578 | 4 | Ac.Ca./S.L./Am.Ac. | 85.2 | C6:1; SM C16:0; SM C24:1; Ala |
| 3579 | 4 | En.Met/Ac.Ca./S.L./B.Am. | 89.3 | OAA; C6:1; SM C24:0; Met-SO |
| 3580 | 5 | En.Met/S.L./Am.Ac./B.Am. | 82.1 | Lac; SM C16:0; SM (OH) C14:1; Gln; Ac-Orn |
| 3581 | 4 | S.L./O.St. | 79.3 | SM (OH) C14:1; SM (OH) C22:2; 20a-OH-C; 25-OH-C |
| 3582 | 4 | Ac.Ca./S.L./B.Am. | 80 | C6:1; SM (OH) C22:2; SM (OH) C24:1; Ac-Orn |
| 3583 | 4 | S.L./Am.Ac./P.G. | 81.7 | SM (OH) C24:1; Orn; Trp; 8-iso-PGF2a |
| 3584 | 4 | S.L./Am.Ac. | 82.1 | SM C18:0; SM (OH) C22:2; Met; Orn |
| 3585 | 4 | Am.Ac./O.St. | 79.3 | Gln; His; Tyr; Cholestenone |
| 3586 | 4 | En.Met/S.L./Am.Ac. | 86.3 | Lac; SM (OH) C14:1; Met; Pro |
| 3587 | 4 | En.Met/S.L./B.Am. | 85.9 | Lac; SM C16:0; SM (OH) C22:1; Met-SO |
| 3588 | 4 | En.Met/S.L./B.Am. | 80 | Pent-P; SM (OH) C14:1; Ac-Orn; Histamine |

TABLE 9-continued

Metabolite combinations describing damage of basal ganglia

| No. | Npar | Chemical Class | Accuracy | Model |
|---|---|---|---|---|
| 3589 | 4 | S.L./Am.Ac./B.Am. | 86.3 | SM (OH) C14:1; Arg; Trp; Ac-Orn |
| 3590 | 5 | Ac.Ca./S.L./Am.Ac. | 86.9 | C14:1; SM C16:1; SM C18:0; Met; Pro |
| 3591 | 4 | Ac.Ca./S.L./Am.Ac./B.Am. | 87.2 | C6:1; SM (OH) C14:1; Pro; Ac-Orn |
| 3592 | 5 | Ac.Ca./S.L./Am.Ac. | 81.8 | C14:1; C5:1-DC; SM (OH) C14:1; Leu; Orn |
| 3593 | 4 | S.L./Am.Ac. | 84.3 | SM C24:0; SM (OH) C22:2; Arg; Asn |
| 3594 | 4 | En.Met/S.L./Am.Ac. | 87.1 | Fum; SM C24:0; Arg; Met |
| 3595 | 4 | Ac.Ca./S.L./Am.Ac./B.Am. | 82.8 | C6:1; SM (OH) C24:1; Lys; Met-SO |
| 3596 | 4 | S.L./Am.Ac. | 83 | SM C18:0; SM (OH) C22:2; Met; Trp |
| 3597 | 4 | S.L./Am.Ac./O.St. | 93.9 | SM (OH) C14:1; SM (OH) C22:2; Tyr; 20a-OH-C |
| 3598 | 5 | S.L./Am.Ac./B.Am./P.G. | 87.9 | SM C18:1; SM C24:1; Tyr; Kynurenine; LTB4 |
| 3599 | 4 | S.L./Am.Ac./B.Am. | 80.8 | SM C26:1; Lys; Tyr; Met-SO |
| 3600 | 4 | En.Met/S.L./Am.Ac./O.St. | 84.6 | alpha-KGA; SM (OH) C22:2; His; 20a-OH-C |
| 3601 | 4 | S.L./Am.Ac./B.Am. | 79.1 | SM (OH) C16:1; Orn; Histamine; Met-SO |
| 3602 | 4 | S.L./Am.Ac. | 79.5 | SM C20:2; SM C24:0; Met; Orn |
| 3603 | 7 | Ac.Ca./S.L./Am.Ac./B.Am./P.G. | 82.1 | C5:1-DC; SM C18:1; SM (OH) C22:1; SM (OH) C22:2; Gln; Sarcosine; LTB4 |
| 3604 | 5 | En.Met/Ac.Ca./S.L./Am.Ac. | 81.6 | alpha-KGA; Lac; C14:1; SM (OH) C22:2; Tyr |
| 3605 | 7 | En.Met/Ac.Ca./S.L./Am.Ac./B.Am./O.St. | 88.7 | Lac; C6:1; SM C16:0; SM (OH) C22:2; Gln; Ac-Orn; Cholestenone |
| 3606 | 4 | S.L./B.Am. | 89.6 | SM C16:1; SM (OH) C14:1; Kynurenine; Met-SO |
| 3607 | 4 | S.L./Am.Ac./B.Am. | 80.1 | SM C16:1; SM C18:1; Leu; Ac-Orn |
| 3608 | 5 | En.Met/S.L./Am.Ac./B.Am. | 86.9 | Fum; SM (OH) C14:1; Met; Ac-Orn; Histamine |
| 3609 | 5 | S.L./Am.Ac./O.St. | 83.2 | SM (OH) C22:1; SM (OH) C24:1; His; Phe; 20a-OH-C |
| 3610 | 4 | S.L./Am.Ac./B.Am. | 88.1 | SM C16:1; Pro; Tyr; Kynurenine |
| 3611 | 4 | S.L./Am.Ac./B.Am. | 91.2 | SM C16:1; SM (OH) C22:2; Phe; Kynurenine |
| 3612 | 4 | S.L./Am.Ac./B.Am. | 79 | SM C18:1; Gln; Phe; Met-SO |
| 3613 | 4 | En.Met/S.L./Am.Ac. | 89.6 | Fum; SM (OH) C14:1; Met; Trp |
| 3614 | 4 | S.L./Am.Ac. | 84 | SM C16:0; SM (OH) C22:2; Ala; Met |
| 3615 | 4 | S.L./Am.Ac./O.St. | 80.3 | SM C16:1; Arg; Phe; Cholestenone |
| 3616 | 4 | Ac.Ca./S.L./B.Am. | 86.1 | C6:1; SM (OH) C22:1; SM (OH) C24:1; Met-SO |
| 3617 | 6 | S.L./Am.Ac./B.Am./O.St. | 85.4 | SM C16:1; SM (OH) C16:1; SM (OH) C22:2; Orn; Histamine; 20a-OH-C |
| 3618 | 4 | En.Met/S.L./Am.Ac./B.Am. | 83.2 | H1; SM (OH) C16:1; Gln; Met-SO |
| 3619 | 5 | En.Met/Ac.Ca./B.Am./O.St. | 80.2 | alpha-KGA; C5:1-DC; alpha-AAA; 24-DH-Lanosterol; Cholestenone |
| 3620 | 5 | En.Met/Ac.Ca./S.L./Am.Ac. | 82.5 | Lac; C18; C5:1-DC; SM (OH) C24:1; Pro |
| 3621 | 5 | S.L./Am.Ac./O.St. | 87.8 | SM (OH) C14:1; SM (OH) C16:1; SM (OH) C22:1; Phe; 20a-OH-C |
| 3622 | 4 | Ac.Ca./S.L./Am.Ac. | 84.7 | C6:1; SM C16:1; Lys; Met |
| 3623 | 4 | En.Met/Am.Ac./B.Am./O.St. | 82.9 | Lac; Trp; Met-SO; Cholestenone |
| 3624 | 5 | Ac.Ca./S.L./Am.Ac./O.St. | 82.6 | C5:1-DC; SM C24:0; SM (OH) C22:1; Gln; 24-DH-Lanosterol |
| 3625 | 4 | S.L./Am.Ac. | 82.2 | SM C24:1; SM (OH) C14:1; SM (OH) C24:1; Ala |
| 3626 | 4 | S.L./Am.Ac. | 89.4 | SM (OH) C14:1; Met; Orn; Trp |
| 3627 | 4 | En.Met/S.L./Am.Ac. | 84.4 | Lac; SM C24:1; SM (OH) C14:1; Met |
| 3628 | 4 | Ac.Ca./S.L./Am.Ac. | 83.2 | C6:1; SM C16:1; SM (OH) C22:2; Arg |
| 3629 | 4 | S.L./Am.Ac./B.Am. | 83.8 | SM (OH) C22:1; Met; Phe; Kynurenine |
| 3630 | 4 | Ac.Ca./S.L. | 86.6 | C5:1-DC; SM C16:1; SM C18:1; SM (OH) C24:1 |
| 3631 | 5 | Ac.Ca./S.L./Am.Ac./B.Am. | 80.7 | C6:1; SM C24:0; SM (OH) C14:1; Met; Ac-Orn |
| 3632 | 4 | S.L./Am.Ac. | 87.3 | SM C20:2; SM C24:0; Pro; Tyr |
| 3633 | 4 | S.L./Am.Ac./B.Am. | 81.2 | SM C20:2; SM (OH) C22:2; Pro; Histamine |
| 3634 | 4 | Ac.Ca./S.L./Am.Ac. | 81.8 | C5:1; SM C16:1; SM C24:1; Met |
| 3635 | 4 | S.L./Am.Ac./B.Am. | 85.2 | SM C24:0; SM C24:1; Ala; Ac-Orn |
| 3636 | 5 | S.L./Am.Ac./B.Am./O.St. | 88.6 | SM C24:0; SM (OH) C22:1; Pro; Ac-Orn; Cholestenone |
| 3637 | 4 | En.Met/S.L./Am.Ac. | 86.4 | Fum; SM (OH) C16:1; Gln; Met |
| 3638 | 5 | S.L./Am.Ac./B.Am. | 90.6 | SM (OH) C22:1; Gln; Orn; Pro; Ac-Orn |
| 3639 | 4 | S.L./Am.Ac. | 86.1 | SM C24:0; SM (OH) C14:1; Pro; Tyr |
| 3640 | 5 | S.L./B.Am. | 82.2 | SM C16:0; alpha-AAA; Creatinine; Histamine; Met-SO |
| 3641 | 4 | En.Met/S.L./Am.Ac. | 86 | OAA; SM (OH) C22:2; Gly; Met |
| 3642 | 5 | S.L./Am.Ac./B.Am. | 89.6 | SM C24:1; Gln; Lys; Ac-Orn; Histamine |
| 3643 | 4 | Am.Ac./B.Am. | 83.2 | Arg; Gln; Met; total DMA |
| 3644 | 4 | En.Met/Ac.Ca./Am.Ac. | 79.2 | alpha-KGA; C10:2; C6:1; Met |
| 3645 | 4 | En.Met/S.L./Am.Ac./O.St. | 82.6 | Fum; SM (OH) C14:1; His; 20a-OH-C |
| 3646 | 5 | Ac.Ca./S.L./Am.Ac./B.Am. | 88.9 | C5:1-DC; C6:1; SM C24:0; Tyr; alpha-AAA |
| 3647 | 4 | S.L./Am.Ac./B.Am. | 82.2 | SM (OH) C22:2; Lys; Met; Histamine |
| 3648 | 6 | S.L./Am.Ac./B.Am./O.St. | 79.3 | SM (OH) C22:1; Ile; Kynurenine; SDMA; total DMA; Cholestenone |
| 3649 | 4 | S.L./Am.Ac. | 88.2 | SM C16:0; SM C24:0; Met; Pro |
| 3650 | 4 | Ac.Ca./S.L./Am.Ac. | 88.9 | C5:1-DC; SM C24:0; SM (OH) C24:1; Tyr |
| 3651 | 5 | S.L./Am.Ac./B.Am./O.St. | 89.3 | SM C24:0; SM C24:1; Tyr; Creatinine; 24-DH-Lanosterol |
| 3652 | 4 | S.L./Am.Ac. | 80.5 | SM C16:1; SM C18:0; SM C24:1; Phe |
| 3653 | 4 | En.Met/Ac.Ca./S.L./Am.Ac. | 84.6 | Lac; C6:1; SM (OH) C22:1; Met |
| 3654 | 3 | S.L./Am.Ac. | 85.6 | SM C18:1; SM (OH) C14:1; Gly |
| 3655 | 4 | S.L./Am.Ac. | 83 | SM C16:0; SM C16:1; Phe; Pro |
| 3656 | 4 | Ac.Ca./S.L./Am.Ac. | 80.8 | C6:1; SM C16:1; Ala; Met |
| 3657 | 4 | S.L./Am.Ac. | 81 | SM C16:1; SM (OH) C16:1; Phe; Pro |
| 3658 | 4 | S.L./Am.Ac./B.Am. | 79.4 | SM C18:0; SM (OH) C22:1; Arg; Met-SO |
| 3659 | 4 | Am.Ac./P.G. | 91.7 | Gln; Met; Orn; 8-iso-PGF2a |
| 3660 | 4 | En.Met/Am.Ac. | 80.8 | H1; Arg; Gln; Tyr |
| 3661 | 4 | S.L./Am.Ac./B.Am. | 85.7 | SM (OH) C14:1; SM (OH) C22:2; Orn; Met-SO |
| 3662 | 3 | S.L./Am.Ac. | 82.8 | SM (OH) C22:2; Met; Orn |
| 3663 | 4 | Ac.Ca./S.L./Am.Ac./O.St. | 86.4 | C5:1-DC; SM C18:1; Gln; Cholestenone |
| 3664 | 5 | Ac.Ca./Am.Ac./P.G. | 86.2 | C18:2; Orn; Phe; Pro; LTB4 |

TABLE 9-continued

Metabolite combinations describing damage of basal ganglia

| No. | Npar | Chemical Class | Accuracy | Model |
|---|---|---|---|---|
| 3665 | 5 | S.L./Am.Ac./P.G. | 85.1 | SM C18:1; Arg; Gln; Tyr; LTB4 |
| 3666 | 4 | Am.Ac./B.Am. | 81.6 | Lys; Met; Ac-Orn; Histamine |
| 3667 | 4 | S.L./Am.Ac./B.Am. | 84 | SM C18:0; Gln; Lys; Met-SO |
| 3668 | 5 | En.Met/S.L./Am.Ac./B.Am./O.St. | 80.4 | alpha-KGA; SM C16:1; Orn; Histamine; 22R-OH-C |
| 3669 | 4 | S.L./Am.Ac./O.St. | 88.3 | SM (OH) C16:1; Arg; Trp; 24-DH-Lanosterol |
| 3670 | 4 | S.L./Am.Ac. | 81.1 | SM (OH) C22:2; SM (OH) C24:1; Ala; Met |
| 3671 | 4 | En.Met/Am.Ac./O.St. | 79.2 | Pent-P; Pro; 24-DH-Lanosterol; Cholestenone |
| 3672 | 5 | S.L./Am.Ac./B.Am. | 90.1 | SM C16:1; SM C24:0; SM (OH) C22:2; Pro; Ac-Orn |
| 3673 | 4 | S.L./Am.Ac./B.Am. | 83.2 | SM C16:1; SM C18:1; Lys; Ac-Orn |
| 3674 | 5 | Ac.Ca./S.L./Am.Ac. | 84 | C9; SM (OH) C22:1; SM (OH) C22:2; Orn; Trp |
| 3675 | 4 | S.L./Am.Ac. | 80.3 | SM C16:0; SM (OH) C16:1; Arg; Met |
| 3676 | 4 | En.Met/S.L./Am.Ac./O.St. | 85.6 | alpha-KGA; SM (OH) C14:1; Pro; 22R-OH-C |
| 3677 | 4 | S.L./Am.Ac./B.Am. | 82.7 | SM C16:1; SM (OH) C14:1; Orn; Ac-Orn |
| 3678 | 4 | S.L./Am.Ac./B.Am. | 79.9 | SM C16:0; SM C16:1; Met; Kynurenine |
| 3679 | 6 | S.L./Am.Ac./B.Am. | 80.8 | SM C18:0; SM C20:2; Gln; His; Phe; SDMA |
| 3680 | 5 | S.L./Am.Ac./B.Am. | 86.3 | SM C24:1; Gln; Leu; Orn; Met-SO |
| 3681 | 4 | S.L./Am.Ac./O.St. | 83.5 | SM (OH) C16:1; SM (OH) C22:1; Tyr; Cholestenone |
| 3682 | 4 | En.Met/S.L./Am.Ac. | 83.3 | alpha-KGA; SM C24:0; Pro; Tyr |
| 3683 | 4 | S.L./B.Am. | 83.6 | SM C26:1; SM (OH) C22:1; SM (OH) C24:1; Met-SO |
| 3684 | 4 | S.L./Am.Ac. | 83.2 | SM C16:1; SM C18:1; Met; Pro |
| 3685 | 4 | S.L./Am.Ac. | 87.3 | SM (OH) C22:1; Gln; Met; Pro |
| 3686 | 4 | En.Met/S.L./Am.Ac./P.G. | 85.9 | alpha-KGA; SM (OH) C22:2; Leu; TXB2 |
| 3687 | 3 | S.L./Am.Ac. | 86.4 | SM (OH) C22:1; Met; Orn |
| 3688 | 5 | S.L./Am.Ac./B.Am. | 79.4 | SM (OH) C16:1; SM (OH) C22:1; SM (OH) C24:1; Phe; Ac-Orn |
| 3689 | 4 | S.L./Am.Ac./B.Am. | 82.2 | SM (OH) C16:1; SM (OH) C22:2; Trp; Met-SO |
| 3690 | 5 | S.L./Am.Ac./B.Am./O.St. | 86.5 | SM C16:1; SM C20:2; Lys; Met-SO; Cholestenone |
| 3691 | 4 | S.L./Am.Ac./B.Am. | 87.7 | SM C24:1; SM (OH) C22:1; Orn; Met-SO |
| 3692 | 5 | En.Met/S.L./Am.Ac./P.G. | 88.3 | Lac; SM C18:1; Gln; Tyr; LTB4 |
| 3693 | 4 | S.L./B.Am. | 82.7 | SM C16:1; SM C20:2; Creatinine; Met-SO |
| 3694 | 4 | S.L./Am.Ac. | 79.8 | SM C16:1; SM C24:1; Lys; Ser |
| 3695 | 4 | Am.Ac./O.St. | 81.4 | Arg; Met; Trp; Cholestenone |
| 3696 | 4 | S.L./Am.Ac./B.Am./O.St. | 80.3 | SM C26:1; Pro; Met-SO; Cholestenone |
| 3697 | 4 | Ac.Ca./S.L./Am.Ac. | 86.6 | C5:1-DC; SM C16:1; SM (OH) C14:1; His |
| 3698 | 4 | S.L./Am.Ac./B.Am. | 81.4 | SM C16:1; SM C18:0; Orn; Met-SO |
| 3699 | 4 | S.L./Am.Ac./B.Am. | 88 | SM C16:1; SM C18:1; Trp; Ac-Orn |
| 3700 | 4 | S.L./Am.Ac./B.Am. | 91.1 | SM C16:0; SM C24:1; Tyr; Kynurenine |
| 3701 | 5 | S.L./Am.Ac. | 83.5 | SM C16:0; SM (OH) C22:2; Gln; Met; Tyr |
| 3702 | 4 | Ac.Ca./S.L./Am.Ac./O.St. | 87.1 | C5:1-DC; SM (OH) C14:1; Orn; Cholestenone |
| 3703 | 5 | S.L./Am.Ac./B.Am. | 87.4 | SM C16:1; SM (OH) C22:2; Gln; Lys; Ac-Orn |
| 3704 | 4 | En.Met/Am.Ac./O.St. | 85.4 | H1; Met; Trp; Cholestenone |
| 3705 | 4 | S.L./Am.Ac./B.Am. | 81.8 | SM (OH) C16:1; Met; Tyr; Kynurenine |
| 3706 | 5 | S.L./Am.Ac./P.G. | 81.7 | SM C16:1; SM (OH) C16:1; Orn; Ser; LTB4 |
| 3707 | 4 | Ac.Ca./S.L./Am.Ac. | 82 | C5:1-DC; SM C16:0; Met; Trp |
| 3708 | 5 | S.L./B.Am. | 88.5 | SM C24:0; SM (OH) C22:1; Ac-Orn; Histamine; Met-SO |
| 3709 | 4 | S.L./Am.Ac./B.Am. | 79.2 | SM (OH) C16:1; SM (OH) C22:1; His; Met-SO |
| 3710 | 4 | En.Met/S.L./Am.Ac. | 89 | Suc; SM C16:1; Arg; Tyr |
| 3711 | 4 | En.Met/S.L./B.Am. | 84.1 | Fum; SM C16:1; SM (OH) C22:1; Met-SO |
| 3712 | 5 | S.L./Am.Ac./B.Am. | 83.6 | SM C16:0; SM C24:0; Arg; Lys; Ac-Orn |
| 3713 | 4 | S.L./Am.Ac./B.Am. | 79.9 | SM (OH) C16:1; SM (OH) C22:1; Arg; Ac-Orn |
| 3714 | 4 | S.L./Am.Ac./O.St. | 81.9 | SM (OH) C14:1; SM (OH) C16:1; Orn; 20a-OH-C |
| 3715 | 4 | S.L./Am.Ac./B.Am. | 80.1 | SM C24:0; SM (OH) C22:2; His; Met-SO |
| 3716 | 4 | S.L./Am.Ac./O.St. | 81.9 | SM C18:0; SM (OH) C22:1; Trp; 24-DH-Lanosterol |
| 3717 | 4 | En.Met/S.L./Am.Ac. | 84.6 | alpha-KGA; SM C16:1; Met; Pro |
| 3718 | 4 | S.L./Am.Ac./B.Am. | 86.7 | SM C24:0; SM (OH) C22:1; Pro; Ac-Orn |
| 3719 | 4 | S.L./Am.Ac./B.Am. | 79.4 | SM C16:0; Lys; Tyr; Met-SO |
| 3720 | 4 | Ac.Ca./S.L./Am.Ac. | 80.8 | C5:1-DC; SM (OH) C22:2; Gln; Lys |
| 3721 | 4 | S.L./Am.Ac./B.Am. | 85.8 | SM C16:1; SM (OH) C24:1; Arg; Met-SO |
| 3722 | 4 | S.L./Am.Ac./B.Am. | 80.3 | SM C16:0; Trp; Histamine; Met-SO |
| 3723 | 4 | S.L./Am.Ac./O.St. | 85.5 | SM C24:0; Arg; Tyr; 25-OH-C |
| 3724 | 4 | Ac.Ca./S.L./B.Am. | 82.2 | C6:1; SM C18:1; SM C24:0; Ac-Orn |
| 3725 | 4 | En.Met/S.L./Am.Ac. | 82 | Lac; SM (OH) C24:1; Gln; Tyr |
| 3726 | 4 | S.L./Am.Ac. | 84.6 | SM C16:0; SM C18:1; Trp; Tyr |
| 3727 | 4 | En.Met/Ac.Ca./S.L. | 81.7 | alpha-KGA; C5:1-DC; SM C16:0; SM (OH) C24:1 |
| 3728 | 4 | En.Met/S.L./Am.Ac./P.G. | 79.1 | Lac; SM (OH) C22:2; Orn; AA |
| 3729 | 5 | S.L./Am.Ac./B.Am. | 85.1 | SM C16:1; SM (OH) C22:1; Gln; Orn; Ac-Orn |
| 3730 | 5 | En.Met/S.L./Am.Ac./B.Am. | 89.4 | Suc; SM (OH) C16:1; Orn; Ac-Orn; Histamine |
| 3731 | 4 | Ac.Ca./S.L./Am.Ac./O.St. | 86.6 | C5:1-DC; SM C16:1; Orn; 25-OH-C |
| 3732 | 4 | S.L./Am.Ac./B.Am. | 85.9 | SM C24:1; SM C26:1; Tyr; Kynurenine |
| 3733 | 4 | S.L./Am.Ac./B.Am. | 79.5 | SM C16:1; SM C18:1; Orn; Met-SO |
| 3734 | 4 | S.L./Am.Ac./P.G. | 88.4 | SM C16:1; SM C18:1; Arg; Leu; TXB2 |
| 3735 | 4 | S.L./Am.Ac./B.Am. | 86.9 | SM C22:2; Gln; Pro; Met-SO |
| 3736 | 4 | S.L./Am.Ac./O.St. | 80.5 | SM (OH) C22:1; His; Phe; Cholestenone |
| 3737 | 4 | S.L./Am.Ac./B.Am. | 89.7 | SM C24:0; SM (OH) C14:1; Pro; Met-SO |
| 3738 | 5 | S.L./Am.Ac. | 84.8 | SM C24:0; SM C24:1; SM (OH) C16:1; Ala; Met |
| 3739 | 4 | En.Met/S.L./B.Am. | 83 | Lac; SM (OH) C22:1; SM (OH) C22:2; Met-SO |
| 3740 | 5 | En.Met/S.L./Am.Ac. | 83.5 | alpha-KGA; Suc; SM C16:1; SM (OH) C22:2; Tyr |

TABLE 9-continued

Metabolite combinations describing damage of basal ganglia

| No. | Npar | Chemical Class | Accuracy | Model |
|---|---|---|---|---|
| 3741 | 5 | S.L./Am.Ac./B.Am./P.G. | 82.9 | SM (OH) C24:1; Arg; Orn; Ac-Orn; LTB4 |
| 3742 | 4 | S.L./Am.Ac./P.G. | 79.1 | SM C18:1; SM (OH) C24:1; Trp; 8-iso-PGF2a |
| 3743 | 5 | Ac.Ca./S.L./Am.Ac./B.Am. | 81.9 | C14:1; SM C18:1; SM (OH) C24:1; Tyr; Kynurenine |
| 3744 | 6 | En.Met/S.L./Am.Ac./B.Am./P.G. | 83.8 | Hex-P; Pent-P; SM C24:0; SM C24:1; Met-SO; LTB4 |
| 3745 | 4 | S.L./Am.Ac./B.Am. | 80.9 | SM C16:0; SM (OH) C14:1; Orn; Taurine |
| 3746 | 4 | Ac.Ca./S.L./Am.Ac. | 79.7 | C9; SM (OH) C22:2; Met; Pro |
| 3747 | 4 | En.Met/S.L./O.St. | 90.1 | alpha-KGA; SM C16:1; SM (OH) C22:2; 20a-OH-C |
| 3748 | 4 | S.L./Am.Ac. | 80.4 | SM C18:1; SM (OH) C14:1; Pro; Tyr |
| 3749 | 4 | S.L./Am.Ac./B.Am. | 88.4 | SM C16:1; Met; Tyr; Kynurenine |
| 3750 | 5 | En.Met/S.L./Am.Ac. | 86 | Pent-P; Suc; SM C24:0; Arg; Tyr |
| 3751 | 4 | Ac.Ca./S.L./Am.Ac./B.Am. | 80.6 | C6:1; SM C24:1; Leu; Kynurenine |
| 3752 | 4 | En.Met/S.L./Am.Ac. | 79.6 | alpha-KGA; SM (OH) C22:2; Arg; Met |
| 3753 | 4 | S.L./Am.Ac./O.St. | 88.3 | SM (OH) C16:1; Pro; Trp; Cholestenone |
| 3754 | 5 | En.Met/S.L./B.Am. | 86.6 | Fum; SM C24:0; SM C26:1; Histamine; Met-SO |
| 3755 | 5 | S.L./Am.Ac./B.Am./O.St. | 79.2 | SM (OH) C22:2; Arg; Histamine; Cholestenone |
| 3756 | 4 | Am.Ac./B.Am. | 79.1 | Gln; His; Pro; SDMA |
| 3757 | 4 | En.Met/S.L./Am.Ac. | 80.1 | alpha-KGA; SM C18:1; SM (OH) C14:1; Tyr |
| 3758 | 5 | Ac.Ca./Am.Ac. | 82.1 | C14:1; C5:1-DC; Gln; Ile; Pro |
| 3759 | 4 | S.L./Am.Ac./B.Am./O.St. | 79.7 | SM C16:1; Orn; Met-SO; 24S-OH-C |
| 3760 | 5 | S.L./Am.Ac./B.Am. | 83.6 | SM C16:0; SM (OH) C16:1; Met; Val; Kynurenine |
| 3761 | 4 | Am.Ac./O.St. | 82.3 | His; Met; Trp; Cholestenone |
| 3762 | 4 | S.L./Am.Ac. | 80 | SM C16:1; SM (OH) C22:2; Met; Val |
| 3763 | 4 | S.L./Am.Ac./B.Am. | 79.2 | SM C24:0; Met; Ac-Orn; Histamine |
| 3764 | 6 | En.Met/Am.Ac./B.Am./O.St./P.G. | 83.9 | Fum; Gln; Orn; Ac-Orn; Cholestenone; AA |
| 3765 | 4 | En.Met/S.L./Am.Ac./O.St. | 84.2 | Suc; SM (OH) C22:2; Orn; 25-OH-C |
| 3766 | 3 | S.L./B.Am. | 81.1 | SM (OH) C14:1; Ac-Orn; Histamine |
| 3767 | 4 | S.L./Am.Ac. | 87.3 | SM C16:1; SM C20:2; SM (OH) C14:1; Ala |
| 3768 | 5 | Ac.Ca./S.L./Am.Ac./B.Am. | 82.6 | C6 (C4:1-DC); SM C18:0; Arg; Orn; Ac-Orn |
| 3769 | 4 | En.Met/S.L./Am.Ac. | 80.6 | alpha-KGA; SM C24:1; SM (OH) C22:1; Met-SO |
| 3770 | 7 | S.L./Am.Ac./B.Am./O.St. | 80.9 | SM C16:0; SM C24:0; Asn; Lys; Pro; Histamine; 20a-OH-C |
| 3771 | 4 | Ac.Ca./S.L./B.Am. | 87.8 | C5:1-DC; C6:1; SM C16:0; Histamine |
| 3772 | 4 | Ac.Ca./S.L./B.Am. | 83.8 | C5:1-DC; SM C16:0; SM (OH) C22:1; alpha-AAA |
| 3773 | 4 | S.L./Am.Ac./B.Am. | 80.1 | SM (OH) C14:1; Gln; His; Met-SO |
| 3774 | 4 | Ac.Ca./S.L./Am.Ac. | 81.8 | C6:1; SM (OH) C22:1; SM (OH) C22:2; Met |
| 3775 | 5 | Ac.Ca./S.L./Am.Ac. | 82.7 | C6:1; SM C24:0; SM (OH) C22:2; Ala; Orn |
| 3776 | 4 | S.L./Am.Ac. | 84.8 | SM C16:1; SM C18:0; SM (OH) C22:1; Tyr |
| 3777 | 4 | En.Met/S.L./B.Am. | 82.1 | alpha-KGA; SM C16:1; SM (OH) C22:2; Met-SO |
| 3778 | 4 | S.L./Am.Ac./B.Am. | 82.8 | SM C16:1; SM (OH) C22:1; Phe; Ac-Orn |
| 3779 | 4 | S.L./Am.Ac./B.Am. | 79.7 | SM C24:0; Ile; Pro; SDMA |
| 3780 | 4 | S.L./Am.Ac./P.G. | 83.5 | SM C24:1; SM (OH) C22:1; Pro; LTB4 |
| 3781 | 5 | En.Met/S.L./Am.Ac. | 80.4 | alpha-KGA; Lac; SM C16:1; SM (OH) C14:1; Phe |
| 3782 | 4 | En.Met/Am.Ac. | 80.8 | alpha-KGA; Fum; Lac; Met |
| 3783 | 4 | Ac.Ca./S.L./Am.Ac./B.Am. | 88.1 | C6:1; SM (OH) C22:1; Orn; Met-SO |
| 3784 | 5 | En.Met/S.L./Am.Ac. | 81.4 | alpha-KGA; SM (OH) C22:1; SM (OH) C22:2; Arg; Asn |
| 3785 | 6 | Ac.Ca./S.L./Am.Ac./B.Am. | 80.6 | C5:1-DC; SM C18:1; SM (OH) C14:1; Pro; alpha-AAA; Met-SO |
| 3786 | 4 | S.L./Am.Ac. | 86.7 | SM (OH) C14:1; Arg; Met; Pro |
| 3787 | 4 | S.L./Am.Ac./B.Am. | 79.9 | SM C16:0; SM (OH) C22:1; Lys; Ac-Orn |
| 3788 | 4 | S.L./Am.Ac. | 83.9 | SM (OH) C14:1; SM (OH) C16:1; Met; Orn |
| 3789 | 4 | S.L./Am.Ac./O.St. | 84.4 | SM (OH) C14:1; SM (OH) C24:1; Pro; 20a-OH-C |
| 3790 | 4 | S.L./Am.Ac. | 79.6 | SM C16:1; SM C18:0; His; Tyr |
| 3791 | 5 | Ac.Ca./S.L./Am.Ac./B.Am./O.St. | 86.3 | C6:1; SM C18:0; Trp; SDMA; 24-DH-Lanosterol |
| 3792 | 5 | S.L./Am.Ac./O.St. | 88 | SM C16:0; SM C24:1; SM (OH) C22:1; Ala; Cholestenone |
| 3793 | 4 | S.L./Am.Ac./B.Am. | 80.4 | SM C16:0; SM C20:2; Trp; Met-SO |
| 3794 | 4 | S.L./Am.Ac. | 82.7 | SM C16:1; SM C20:2; SM (OH) C22:1; Ala |
| 3795 | 4 | Ac.Ca./S.L./Am.Ac. | 86.9 | C5:1-DC; SM C16:1; SM (OH) C16:1; Pro |
| 3796 | 4 | Ac.Ca./S.L./Am.Ac./O.St. | 81.3 | C5:1-DC; SM (OH) C24:1; Pro; Cholestenone |
| 3797 | 4 | Ac.Ca./S.L./Am.Ac. | 82 | C6:1; SM C24:1; SM (OH) C24:1; Ala |
| 3798 | 5 | S.L./Am.Ac./B.Am. | 81.9 | SM C26:1; SM (OH) C16:1; Orn; Ac-Orn; Histamine |
| 3799 | 4 | S.L./Am.Ac./B.Am. | 81.3 | SM C24:0; SM C24:1; Phe; Met-SO |
| 3800 | 4 | S.L./Am.Ac./P.G. | 89.7 | SM (OH) C14:1; His; Pro; TXB2 |
| 3801 | 3 | S.L./B.Am./O.St. | 80.2 | SM C24:0; Met-SO; 25-OH-C |
| 3802 | 4 | Ac.Ca./S.L./Am.Ac./B.Am. | 84.6 | C6:1; SM (OH) C22:1; Pro; Ac-Orn |
| 3803 | 4 | Ac.Ca./Am.Ac./B.Am./O.St. | 79.8 | C6:1; Gln; Met-SO; 24-DH-Lanosterol |
| 3804 | 4 | S.L./Am.Ac. | 79.5 | SM (OH) C22:1; His; Leu; Met |
| 3805 | 4 | En.Met/S.L./Am.Ac./B.Am. | 82.9 | Pent-P; SM (OH) C22:1; Arg; Met-SO |
| 3806 | 5 | Ac.Ca./S.L./Am.Ac. | 80.3 | C5:1-DC; SM C24:0; SM C24:1; Gln; Lys |
| 3807 | 6 | S.L./Am.Ac./B.Am./O.St. | 81.3 | SM (OH) C22:1; Gln; Met; Met-SO; 25-OH-C; 5a.6a-EpoxyC |
| 3808 | 4 | S.L./Am.Ac./B.Am. | 81.9 | SM C16:1; Arg; Met; Ac-Orn |
| 3809 | 5 | S.L./Am.Ac./O.St. | 82.5 | SM C24:1; SM (OH) C22:1; Gln; Lys; 20a-OH-C |
| 3810 | 4 | En.Met/Ac.Ca./S.L./Am.Ac. | 79.6 | Lac; C6:1; SM C24:1; Met |
| 3811 | 4 | En.Met/Am.Ac./O.St. | 79.4 | Pent-P; Arg; Pro; Cholestenone |
| 3812 | 4 | Ac.Ca./Am.Ac./B.Am. | 80.7 | C14:1; Gln; Lys; Ac-Orn |
| 3813 | 4 | En.Met/S.L./B.Am. | 82.3 | alpha-KGA; SM C16:1; SM (OH) C22:1; Ac-Orn |
| 3814 | 4 | S.L./Am.Ac./B.Am. | 91 | SM C16:1; SM C18:1; Tyr; Kynurenine |
| 3815 | 5 | S.L./Am.Ac./B.Am. | 90.6 | SM C16:1; SM C24:0; SM (OH) C22:1; Pro; Ac-Orn |
| 3816 | 5 | S.L./Am.Ac./O.St./P.G. | 83.9 | SM (OH) C22:2; Ile; Orn; Cholestenone; LTB4 |

TABLE 9-continued

Metabolite combinations describing damage of basal ganglia

| No. | Npar | Chemical Class | Accuracy | Model |
|---|---|---|---|---|
| 3817 | 4 | S.L./Am.Ac./B.Am. | 85.3 | SM C24:0; SM (OH) C22:2; Arg; Met-SO |
| 3818 | 5 | S.L./Am.Ac./O.St. | 90 | SM C16:0; SM (OH) C22:2; Leu; Pro; 20a-OH-C |
| 3819 | 4 | Ac.Ca./S.L./Am.Ac. | 83.6 | C5:1; SM C16:1; His; Met |
| 3820 | 5 | Ac.Ca./S.L./B.Am. | 84 | C5:1-DC; SM (OH) C16:1; SM (OH) C22:1; SM (OH) C22:2; Serotonin |
| 3821 | 6 | Ac.Ca./S.L./Am.Ac./P.G. | 87.4 | C5:1-DC; SM C24:0; SM C24:1; SM (OH) C14:1; Tyr; LTB4 |
| 3822 | 5 | S.L./Am.Ac./O.St. | 88.2 | SM C16:1; SM C26:1; His; Orn; 20a-OH-C |
| 3823 | 4 | S.L./Am.Ac. | 83.8 | SM C16:1; SM (OH) C22:1; Phe; Pro |
| 3824 | 4 | Ac.Ca./S.L./Am.Ac. | 80.9 | C6:1; SM C16:1; SM C18:1; Tyr |
| 3825 | 7 | En.Met/S.L./Am.Ac./B.Am./O.St. | 89.9 | alpha-KGA; SM C16:1; SM (OH) C24:1; Gln; Met; Carnosine; 20a-OH-C |
| 3826 | 4 | S.L./Am.Ac. | 83.6 | SM (OH) C22:2; Orn; Pro; Trp |
| 3827 | 4 | S.L./Am.Ac. | 79.1 | SM C18:0; SM (OH) C14:1; Met; Phe |
| 3828 | 5 | En.Met/S.L./Am.Ac./P.G. | 80.3 | Pent-P; SM C24:0; SM (OH) C22:2; Pro; LTB4 |
| 3829 | 4 | En.Met/S.L./Am.Ac./B.Am. | 84.5 | Fum; SM C16:0; Gln; Met-SO |
| 3830 | 5 | En.Met/S.L./B.Am. | 86.6 | Lac; SM C24:0; SM C24:1; SM (OH) C24:1; Met-SO |
| 3831 | 6 | En.Met/Ac.Ca./S.L./Am.Ac. | 82.2 | alpha-KGA; Lac; C14:1-OH; SM C18:0; His; Orn |
| 3832 | 4 | Ac.Ca./S.L./Am.Ac./B.Am. | 83.8 | C5:1-DC; SM C24:0; Tyr; alpha-AAA |
| 3833 | 4 | S.L./B.Am. | 82.1 | SM C16:1; SM (OH) C22:2; Ac-Orn; Histamine |
| 3834 | 6 | En.Met/S.L./Am.Ac./P.G. | 86.8 | Lac; SM C16:1; Arg; Phe; Trp; AA |
| 3835 | 4 | S.L./Am.Ac./O.St. | 87.1 | SM (OH) C14:1; SM (OH) C22:2; Trp; 20a-OH-C |
| 3836 | 4 | En.Met/S.L./Am.Ac./P.G. | 79.6 | alpha-KGA; SM (OH) C24:1; Lys; TXB2 |
| 3837 | 4 | S.L./Am.Ac./B.Am. | 79.2 | SM C24:1; Gln; Val; Ac-Orn |
| 3838 | 4 | S.L./B.Am. | 82.7 | SM C16:1; SM C18:1; SM (OH) C22:1; Met-SO |
| 3839 | 4 | S.L./Am.Ac./B.Am./O.St. | 88.6 | SM C16:1; Pro; Ac-Orn; 25-OH-C |
| 3840 | 4 | S.L./Am.Ac./B.Am. | 86.3 | SM C16:0; SM C24:0; Arg; Ac-Orn |
| 3841 | 5 | Ac.Ca./S.L./O.St. | 79.6 | C5:1-DC; SM C18:1; SM C24:0; SM C24:1; 24-DH-Lanosterol |
| 3842 | 4 | S.L./Am.Ac. | 81.8 | SM C16:0; SM (OH) C22:2; Arg; Met-SO |
| 3843 | 6 | S.L./Am.Ac./P.G. | 82.5 | SM C18:1; SM C20:2; SM (OH) C22:2; Orn; Tyr; LTB4 |
| 3844 | 4 | En.Met/Ac.Ca./S.L./Am.Ac. | 82.4 | Lac; C14:1; SM (OH) C22:1; Met |
| 3845 | 4 | S.L./Am.Ac. | 83.5 | SM C18:0; SM C24:0; Arg; Met |
| 3846 | 4 | S.L./Am.Ac. | 79.5 | SM C16:1; Ala; Met; Phe |
| 3847 | 4 | S.L./Am.Ac./B.Am. | 80.6 | SM C20:2; His; Lys; Met-SO |
| 3848 | 5 | Ac.Ca./S.L./Am.Ac./B.Am. | 90.2 | C10; SM C16:1; SM C26:1; Tyr; Kynurenine |
| 3849 | 4 | En.Met/S.L./Am.Ac. | 80.1 | Lac; SM C16:0; SM (OH) C24:1; Tyr |
| 3850 | 4 | S.L./Am.Ac. | 84.2 | SM C24:0; Arg; Leu; Met |
| 3851 | 6 | S.L./Am.Ac./B.Am./O.St. | 86 | SM (OH) C14:1; Tyr; Kynurenine; SDMA; total DMA; 24-DH-Lanosterol |
| 3852 | 4 | En.Met/S.L./Am.Ac. | 83.5 | alpha-KGA; SM C20:2; SM C24:1; Tyr |
| 3853 | 5 | S.L./Am.Ac./O.St. | 86.2 | SM C24:0; SM (OH) C22:1; Phe; Pro; Cholestenone |
| 3854 | 4 | En.Met/S.L./Am.Ac. | 85 | alpha-KGA; SM (OH) C14:1; Met; Pro |
| 3855 | 4 | S.L./Am.Ac. | 84.9 | SM C16:1; SM C24:1; Arg; Met |
| 3856 | 4 | S.L./Am.Ac. | 85.4 | SM C20:2; SM (OH) C22:2; SM (OH) C24:1; Tyr |
| 3857 | 4 | Ac.Ca./S.L./Am.Ac./B.Am. | 85.1 | C6:1; SM (OH) C22:1; Pro; Met-SO |
| 3858 | 4 | S.L./Am.Ac./B.Am. | 80.1 | SM C16:1; SM C24:0; Leu; Ac-Orn |
| 3859 | 4 | Am.Ac./B.Am. | 87.6 | Gln; Lys; Histamine; Met-SO |
| 3860 | 4 | En.Met/Am.Ac. | 88.1 | alpha-KGA; Lac; Gln; Met |
| 3861 | 4 | Ac.Ca./S.L./B.Am./O.St. | 87.4 | C5:1-DC; SM (OH) C22:1; alpha-AAA; Cholestenone |
| 3862 | 5 | S.L./Am.Ac./B.Am. | 82.8 | SM (OH) C16:1; SM (OH) C22:1; Arg; Trp; total DMA |
| 3863 | 4 | En.Met/S.L./Am.Ac. | 83.5 | Fum; Lac; SM (OH) C24:1; Met |
| 3864 | 4 | En.Met/S.L./P.G. | 88.4 | alpha-KGA; SM C16:0; SM (OH) C22:2; TXB2 |
| 3865 | 4 | Am.Ac./B.Am./O.St. | 79.1 | His; Lys; Ac-Orn; 24-DH-Lanosterol |
| 3866 | 5 | En.Met/S.L./Am.Ac. | 85.9 | alpha-KGA; Suc; SM (OH) C24:1; Lys; Met |
| 3867 | 4 | S.L./Am.Ac./B.Am./O.St. | 79.9 | SM C16:0; Lys; Ac-Orn; 24-DH-Lanosterol |
| 3868 | 5 | S.L./Am.Ac. | 88.9 | SM C24:1; SM (OH) C22:1; SM (OH) C22:2; Orn; Ser |
| 3869 | 4 | En.Met/S.L./Am.Ac. | 81 | Lac; SM C18:1; SM C24:1; Gln |
| 3870 | 4 | S.L./Am.Ac./O.St. | 83.9 | SM (OH) C22:2; Gln; Phe; Cholestenone |
| 3871 | 4 | En.Met/S.L./Am.Ac./B.Am. | 85.7 | Fum; SM C18:1; Gln; Met-SO |
| 3872 | 4 | Ac.Ca./S.L./Am.Ac. | 81.3 | C5:1-DC; SM C16:1; SM C24:1; Met |
| 3873 | 5 | Ac.Ca./S.L./Am.Ac./O.St. | 91.5 | C6:1; SM (OH) C14:1; Gln; Tyr; 20a-OH-C |
| 3874 | 4 | S.L./Am.Ac./O.St. | 83.7 | SM (OH) C16:1; SM (OH) C22:2; Lys; 20a-OH-C |
| 3875 | 4 | S.L./Am.Ac. | 85.9 | SM C18:0; Gln; Lys; Met |
| 3876 | 4 | S.L./Am.Ac. | 83.8 | SM (OH) C22:1; Met; Orn; Phe |
| 3877 | 4 | En.Met/S.L./B.Am. | 80.5 | alpha-KGA; SM C16:1; SM (OH) C16:1; Met-SO |
| 3878 | 4 | En.Met/Ac.Ca./Am.Ac. | 80.6 | Hex-P; Lac; C18:1; Phe |
| 3879 | 4 | S.L./Am.Ac./B.Am. | 86.5 | SM (OH) C14:1; SM (OH) C22:2; Ala; Ac-Orn |
| 3880 | 4 | En.Met/Am.Ac./B.Am. | 82.1 | alpha-KGA; Gln; Met; total DMA |
| 3881 | 4 | S.L./Am.Ac./B.Am. | 87.5 | SM C16:1; SM C24:0; Lys; Met-SO |
| 3882 | 5 | S.L./Am.Ac./O.St. | 87 | SM C16:1; SM C24:1; Arg; Trp; 24-DH-Lanosterol |
| 3883 | 5 | En.Met/Ac.Ca./S.L./B.Am. | 79.7 | Lac; Suc; C6:1; SM (OH) C24:1; Histamine |
| 3884 | 4 | En.Met/S.L./B.Am./O.St. | 82.9 | alpha-KGA; SM C16:1; Histamine; 20a-OH-C |
| 3885 | 4 | S.L./Am.Ac./P.G. | 79.2 | SM (OH) C14:1; Orn; Trp; 8-iso-PGF2a |
| 3886 | 4 | S.L./Am.Ac. | 86.6 | SM (OH) C14:1; SM (OH) C22:1; Met; Tyr |
| 3887 | 5 | S.L./Am.Ac./B.Am./P.G. | 79.4 | SM C18:1; SM (OH) C22:1; Arg; Ac-Orn; LTB4 |
| 3888 | 3 | En.Met/S.L./Am.Ac. | 82.7 | Fum; SM (OH) C24:1; Met |
| 3889 | 4 | S.L./Am.Ac./B.Am. | 81.6 | SM C24:0; Pro; Tyr; Histamine |
| 3890 | 4 | En.Met/S.L./B.Am. | 81.5 | alpha-KGA; Lac; SM (OH) C24:1; Met-SO |
| 3891 | 4 | En.Met/S.L./Am.Ac. | 82 | Lac; SM C24:1; Trp; Tyr |
| 3892 | 4 | S.L./Am.Ac./B.Am. | 81.4 | SM C18:0; SM (OH) C14:1; Arg; Met-SO |

TABLE 9-continued

Metabolite combinations describing damage of basal ganglia

| No. | Npar | Chemical Class | Accuracy | Model |
|---|---|---|---|---|
| 3893 | 5 | En.Met/S.L./Am.Ac./O.St./P.G. | 82.9 | Suc; SM C24:1; Orn; 24S-OH-C; 8-iso-PGF2a |
| 3894 | 5 | Ac.Ca./S.L./Am.Ac. | 83.5 | C5:1-DC; SM C24:0; SM (OH) C14:1; SM (OH) C16:1; Ser |
| 3895 | 5 | S.L./Am.Ac./B.Am. | 87.1 | SM (OH) C14:1; SM (OH) C22:2; Lys; Ac-Orn; Histamine |
| 3896 | 4 | En.Met/Ac.Ca./S.L./B.Am. | 80.9 | alpha-KGA; C6:1; SM (OH) C22:2; Ac-Orn |
| 3897 | 4 | S.L./Am.Ac. | 83.4 | SM C16:1; SM (OH) C14:1; Arg; Tyr |
| 3898 | 4 | En.Met/Am.Ac./O.St. | 82.8 | Lac; Gln; Tyr; 25-OH-C |
| 3899 | 4 | En.Met/S.L./Am.Ac. | 81.5 | Hex-P; SM C24:1; Gln; Orn |
| 3900 | 4 | S.L./Am.Ac./B.Am. | 83.7 | SM C18:1; SM (OH) C14:1; Arg; Ac-Orn |
| 3901 | 4 | S.L./Am.Ac. | 80.2 | SM (OH) C22:1; SM (OH) C22:2; Phe; Pro |
| 3902 | 4 | Ac.Ca./S.L./Am.Ac. | 87.5 | C5:1-DC; SM (OH) C14:1; SM (OH) C22:1; Orn |
| 3903 | 6 | S.L./Am.Ac./B.Am./O.St. | 82.9 | SM C16:1; SM C18:1; SM (OH) C14:1; Lys; Met-SO; Cholestenone |
| 3904 | 4 | S.L./Am.Ac. | 83.7 | SM C16:0; SM C18:0; SM (OH) C22:1; Tyr |
| 3905 | 4 | Ac.Ca./S.L./Am.Ac. | 87.1 | C10; SM C16:1; Met; Pro |
| 3906 | 4 | S.L./Am.Ac. | 80.6 | SM (OH) C22:1; SM (OH) C22:2; Arg; Phe |
| 3907 | 4 | S.L./Am.Ac. | 85.7 | SM C18:0; SM C24:0; SM (OH) C14:1; Tyr |
| 3908 | 4 | Ac.Ca./S.L./Am.Ac. | 87.8 | C14:1; SM (OH) C22:2; Met; Pro |
| 3909 | 4 | S.L./Am.Ac./B.Am. | 79.6 | SM C16:1; SM C18:1; Pro; Met-SO |
| 3910 | 4 | S.L./Am.Ac. | 86.9 | SM C16:1; SM C20:2; SM C24:1; Ala |
| 3911 | 3 | Ac.Ca./S.L. | 83.3 | C5:1-DC; SM C16:1; SM C20:2 |
| 3912 | 4 | S.L./Am.Ac./B.Am./P.G. | 86.6 | SM (OH) C22:2; His; alpha-AAA; TXB2 |
| 3913 | 4 | S.L./Am.Ac./O.St. | 79.3 | SM C16:0; Met; Trp; 25-OH-C |
| 3914 | 4 | En.Met/S.L./Am.Ac. | 81.1 | Lac; SM C16:0; Met; Phe |
| 3915 | 4 | S.L./Am.Ac./O.St. | 84.9 | SM C18:0; SM (OH) C14:1; Trp; 24-DH-Lanosterol |
| 3916 | 5 | S.L./Am.Ac./B.Am./P.G. | 89.5 | SM (OH) C14:1; Arg; Gln; Met-SO; LTB4 |
| 3917 | 4 | S.L./Am.Ac. | 81.3 | SM C16:0; SM (OH) C22:2; Met; Ser |
| 3918 | 4 | S.L./Am.Ac./O.St. | 82.9 | SM C24:0; Met; Tyr; 24-DH-Lanosterol |
| 3919 | 4 | En.Met/S.L./B.Am./O.St. | 83.1 | alpha-KGA; SM (OH) C22:1; Met-SO; 24S-OH-C |
| 3920 | 4 | Ac.Ca./S.L./O.St. | 85.9 | C10; SM (OH) C22:2; 20a-OH-C; 25-OH-C |
| 3921 | 4 | Ac.Ca./S.L./Am.Ac./B.Am. | 79.1 | C6:1; SM C18:1; Trp; Met-SO |
| 3922 | 4 | S.L./Am.Ac./B.Am. | 85.8 | SM C16:0; SM (OH) C14:1; Pro; Met-SO |
| 3923 | 5 | En.Met/Ac.Ca./S.L./Am.Ac. | 87.7 | alpha-KGA; C5:1; SM C16:0; SM C16:1; Met |
| 3924 | 4 | En.Met/S.L./Am.Ac. | 86.7 | alpha-KGA; Lac; SM C16:1; Met |
| 3925 | 6 | En.Met/Am.Ac./O.St. | 87.3 | Lac; Pent-P; Gln; Orn; Pro; Cholestenone |
| 3926 | 5 | Ac.Ca./S.L./Am.Ac./O.St. | 87.1 | C5:1-DC; SM (OH) C16:1; SM (OH) C22:2; Orn; 24-DH-Lanosterol |
| 3927 | 4 | En.Met/S.L./Am.Ac. | 79.1 | H1; SM (OH) C22:2; Asn; Gln |
| 3928 | 4 | S.L./Am.Ac./O.St. | 85.9 | SM C16:0; Gln; Pro; 20a-OH-C |
| 3929 | 3 | S.L./Am.Ac. | 79.7 | SM (OH) C14:1; His; Met |
| 3930 | 4 | S.L./Am.Ac./P.G. | 82.8 | SM C24:0; SM (OH) C22:2; Tyr; LTB4 |
| 3931 | 4 | S.L./Am.Ac./O.St. | 83.6 | SM C24:1; SM (OH) C14:1; Ser; Cholestenone |
| 3932 | 4 | En.Met/S.L./Am.Ac./B.Am. | 84.1 | alpha-KGA; SM (OH) C16:1; Tyr; Kynurenine |
| 3933 | 4 | En.Met/S.L./Am.Ac./B.Am. | 86.9 | Pent-P; SM C16:1; Arg; Ac-Orn |
| 3934 | 4 | Am.Ac./B.Am. | 82.3 | Gln; Met; Pro; Histamine |
| 3935 | 4 | S.L./Am.Ac./B.Am. | 79.5 | SM C16:0; SM C16:1; Gly; Ac-Orn |
| 3936 | 6 | En.Met/Am.Ac./B.Am. | 81.3 | alpha-KGA; Suc; Gln; Phe; Met-SO; Serotonin |
| 3937 | 4 | Ac.Ca./S.L./Am.Ac. | 81.3 | C18:1; SM C18:0; Phe; Pro |
| 3938 | 5 | Ac.Ca./S.L./Am.Ac./O.St. | 88.9 | C5:1-DC; SM C16:1; SM C20:2; Leu; Cholestenone |
| 3939 | 4 | Am.Ac./O.St. | 87.7 | Gln; Met; Pro; 24-DH-Lanosterol |
| 3940 | 4 | En.Met/Am.Ac. | 86.7 | Lac; Gln; Met; Trp |
| 3941 | 6 | En.Met/Ac.Ca./S.L./Am.Ac. | 88.3 | Suc; C14:1; SM C18:0; SM C18:1; Orn; Tyr |
| 3942 | 5 | En.Met/S.L./B.Am. | 84.5 | Fum; SM C18:0; SM C24:1; Histamine; Met-SO |
| 3943 | 5 | Ac.Ca./S.L./Am.Ac./P.G. | 84.8 | C14:1; SM C26:1; SM (OH) C24:1; Pro; TXB2 |
| 3944 | 4 | Ac.Ca./S.L./Am.Ac./B.Am. | 82.2 | C14:1; SM (OH) C22:2; Arg; Met-SO |
| 3945 | 4 | En.Met/Am.Ac./O.St. | 84.6 | Suc; Arg; Pro; Cholestenone |

TABLE 10

Metabolite combinations correlating with neurological behavioural score

| No. | Npar | Chemical Class | Accuracy | Model |
|---|---|---|---|---|
| 1 | 2 | Am.Ac./O.St. | 92.2 | Tyr; 27-OH-C |
| 2 | 2 | En.Met/B.Am. | 83.3 | Fum; total DMA |
| 3 | 4 | En.Met/B.Am./O.St. | 95.3 | Fum; Met-SO; 24-DH-Lanosterol; 27-OH-C |
| 4 | 3 | En.Met/Ac.Ca./B.Am. | 79.8 | Fum; C8:1; SDMA |
| 5 | 4 | En.Met/Ac.Ca./O.St. | 81.1 | Pent-P; C10:2; C14:2-OH; 27-OH-C |
| 6 | 3 | Ac.Ca./S.L./B.Am. | 79.5 | C5:1; SM (OH) C14:1; SDMA |
| 7 | 2 | Ac.Ca./B.Am. | 79.5 | C14:1-OH; Carnosine |
| 8 | 5 | Ac.Ca./Am.Ac./B.Am. | 88.9 | C5-DC (C6-OH); Pro; Creatinine; SDMA; total DMA |
| 9 | 3 | En.Met/Ac.Ca./B.Am. | 91.4 | Fum; C5:1; total DMA |
| 10 | 4 | S.L./Am.Ac./O.St. | 84.7 | SM (OH) C16:1; SM (OH) C22:1; Phe; 27-OH-C |
| 11 | 3 | B.Am./O.St. | 89 | Met-SO; 24,25-EpoxyC; 27-OH-C |
| 12 | 3 | Ac.Ca./B.Am. | 83.3 | C14:1-OH; C6 (C4:1-DC); Carnosine |
| 13 | 3 | Ac.Ca./B.Am./O.St. | 90.1 | C5:1; total DMA; 27-OH-C |

TABLE 10-continued

Metabolite combinations correlating with neurological behavioural score

| No. | Npar | Chemical Class | Accuracy | Model |
|---|---|---|---|---|
| 14 | 2 | Ac.Ca./B.Am. | 85.8 | C6 (C4:1-DC); Carnosine |
| 15 | 3 | Ac.Ca./B.Am. | 79.6 | C5-DC (C6-OH); alpha-AAA; total DMA |
| 16 | 3 | Am.Ac./B.Am./O.St. | 96.1 | Tyr; total DMA; 27-OH-C |
| 17 | 4 | Ac.Ca./Am.Ac./B.Am./O.St. | 84 | C8:1; Leu; SDMA; 27-OH-C |
| 18 | 3 | Am.Ac./B.Am./O.St. | 88.7 | Phe; SDMA; 27-OH-C |
| 19 | 3 | S.L./B.Am./O.St. | 88.1 | SM (OH) C22:2; Met-SO; 27-OH-C |
| 20 | 2 | B.Am./O.St. | 85.1 | total DMA; 27-OH-C |
| 21 | 4 | Ac.Ca./S.L./Am.Ac./B.Am. | 87.8 | C5-DC (C6-OH); SM (OH) C16:1; Pro; total DMA |
| 22 | 3 | Ac.Ca./B.Am. | 83.7 | C14:1; C5:1; total DMA |
| 23 | 4 | En.Met/Ac.Ca./B.Am. | 89.6 | Fum; C14:1-OH; Carnosine; total DMA |
| 24 | 4 | En.Met/B.Am. | 90.4 | Fum; Suc; Carnosine; SDMA |
| 25 | 3 | En.Met/Am.Ac./B.Am. | 79.7 | Fum; Phe; SDMA |
| 26 | 3 | Ac.Ca./S.L./B.Am. | 90.1 | C5:1; SM (OH) C22:2; total DMA |
| 27 | 4 | En.Met/Ac.Ca./B.Am./O.St. | 83.8 | Suc; C14:1; Carnosine; 27-OH-C |
| 28 | 3 | S.L./B.Am./O.St. | 88.6 | SM C16:1; Carnosine; 27-OH-C |
| 29 | 5 | En.Met/Ac.Ca./S.L./Am.Ac./O.St. | 89 | Fum; C10; SM (OH) C22:2; Phe; 27-OH-C |
| 30 | 4 | En.Met/Ac.Ca./B.Am./O.St. | 80.9 | Pent-P; C5:1; Met-SO; 24,25-EpoxyC |
| 31 | 4 | Ac.Ca./B.Am./O.St. | 85.4 | C14:1; Ac-Orn; Carnosine; 27-OH-C |
| 32 | 3 | En.Met/Ac.Ca./Am.Ac. | 82.4 | Fum; C8:1; Phe |
| 33 | 4 | En.Met/O.St. | 80.9 | Fum; 24-DH-Lanosterol; 27-OH-C; 3b,5a,6b-THC |
| 34 | 3 | En.Met/Ac.Ca./Am.Ac. | 84.6 | Fum; C5-DC (C6-OH); Met |
| 35 | 4 | Ac.Ca./Am.Ac./O.St. | 84.6 | C5:1-DC; Phe; 24,25-EpoxyC; 27-OH-C |
| 36 | 3 | En.Met/Ac.Ca./B.Am. | 86.8 | Lac; C14:1-OH; Carnosine |
| 37 | 2 | B.Am./O.St. | 81.5 | Met-SO; 27-OH-C |
| 38 | 2 | En.Met/B.Am. | 79.1 | Fum; SDMA |
| 39 | 3 | Ac.Ca./B.Am./O.St. | 84.3 | C10:2; Met-SO; 27-OH-C |
| 40 | 3 | Ac.Ca./Am.Ac./O.St. | 95.9 | C10:2; Phe; 27-OH-C |
| 41 | 3 | Am.Ac./B.Am./O.St. | 94.6 | Phe; total DMA; 27-OH-C |
| 42 | 3 | S.L./B.Am./O.St. | 88.3 | SM (OH) C14:1; Met-SO; 27-OH-C |
| 43 | 6 | Ac.Ca./S.L./B.Am./O.St. | 86.5 | C10:2; C5:1; SM C16:1; Met-SO; total DMA; 24,25-EpoxyC |
| 44 | 3 | Ac.Ca./S.L./B.Am. | 88.5 | C5:1; SM (OH) C22:2; SDMA |
| 45 | 2 | Am.Ac./O.St. | 81.1 | Phe; 27-OH-C |
| 46 | 3 | S.L./Am.Ac./O.St. | 90.6 | SM (OH) C22:2; Phe; 27-OH-C |
| 47 | 3 | En.Met/Ac.Ca./B.Am. | 86.5 | Fum; C8:1; total DMA |
| 48 | 3 | En.Met/Ac.Ca./B.Am. | 88.3 | Fum; C14:1-OH; Carnosine |
| 49 | 3 | S.L./B.Am./O.St. | 87.3 | SM C16:0; Carnosine; 27-OH-C |
| 50 | 3 | B.Am./O.St./P.G. | 88.8 | Carnosine; 27-OH-C; DHA |
| 51 | 3 | Ac.Ca./B.Am. | 88 | C10:2; C14:1; Carnosine |
| 52 | 4 | Ac.Ca./S.L./B.Am./O.St. | 83.6 | C0; SM (OH) C22:2; total DMA; 5a,6a-EpoxyC |
| 53 | 4 | En.Met/Ac.Ca./B.Am. | 84.4 | Lac; C5; C8:1; Carnosine |
| 54 | 3 | B.Am./O.St. | 89.5 | Met-SO; total DMA; 27-OH-C |
| 55 | 4 | Ac.Ca./S.L./B.Am./O.St. | 87 | C5:1; SM (OH) C16:1; SDMA; 27-OH-C |
| 56 | 3 | En.Met/Ac.Ca./P.G. | 80.6 | Fum; C14:1; 8-iso-PGF2a |
| 57 | 4 | En.Met/B.Am./O.St. | 82.3 | Fum; Suc; Met-SO; 24,25-EpoxyC |
| 58 | 4 | En.Met/Ac.Ca./B.Am. | 83.2 | Fum; C12; C8:1; Carnosine |
| 59 | 4 | Ac.Ca./S.L./B.Am./O.St. | 90.6 | C5:1; SM (OH) C22:2; SDMA; 3b,5a,6b-THC |
| 60 | 3 | En.Met/Ac.Ca./B.Am. | 87.5 | Fum; C0; total DMA |
| 61 | 3 | B.Am./O.St. | 79.8 | Ac-Orn; 24,25-EpoxyC; 27-OH-C |
| 62 | 5 | B.Am./O.St. | 88.7 | Ac-Orn; Carnosine; SDMA; total DMA; 27-OH-C |
| 63 | 4 | S.L./B.Am./O.St. | 80.5 | SM (OH) C14:1; SDMA; 27-OH-C; 3b,5a,6b-THC |
| 64 | 3 | B.Am./O.St. | 90.2 | alpha-AAA; Met-SO; 27-OH-C |
| 65 | 4 | En.Met/Ac.Ca./B.Am. | 87.8 | Fum; C12; Ac-Orn; Carnosine |
| 66 | 3 | Ac.Ca./S.L./B.Am. | 81.1 | C6 (C4:1-DC); SM (OH) C22:2; Carnosine |
| 67 | 4 | Ac.Ca./B.Am./O.St. | 80.6 | C4:1; C5:1; Ac-Orn; 24,25-EpoxyC |
| 68 | 3 | Am.Ac./B.Am./O.St. | 87.7 | Cit; Met-SO; 27-OH-C |
| 69 | 3 | Am.Ac./B.Am./O.St. | 85 | Met; Carnosine; 27-OH-C |
| 70 | 4 | S.L./B.Am./O.St. | 87.1 | SM (OH) C16:1; total DMA; 27-OH-C; Cholestenone |
| 71 | 3 | Ac.Ca./B.Am. | 84.4 | C10:2; C6 (C4:1-DC); Carnosine |
| 72 | 3 | En.Met/Ac.Ca./B.Am. | 85.5 | Fum; C14:1; Ac-Orn |
| 73 | 5 | En.Met/Ac.Ca./S.L./B.Am. | 89.2 | Fum; OAA; C5-DC (C6-OH); SM (OH) C22:2; SDMA |
| 74 | 3 | En.Met/Ac.Ca./B.Am. | 81.5 | Fum; C6 (C4:1-DC); Carnosine |
| 75 | 3 | En.Met/Ac.Ca./B.Am. | 80.3 | Fum; C10:2; Ac-Orn |
| 76 | 4 | En.Met/Ac.Ca./B.Am./P.G. | 88.5 | Fum; C14:1; Carnosine; 8-iso-PGF2a |
| 77 | 5 | En.Met/Ac.Ca./B.Am./O.St. | 82 | Fum; C5; Ac-Orn; Met-SO; Cholestenone |
| 78 | 4 | Ac.Ca./B.Am./P.G. | 85.1 | C10:2; C8:1; Carnosine; LTB4 |
| 79 | 3 | Ac.Ca./B.Am./O.St. | 80.5 | C14:1; Carnosine; 27-OH-C |
| 80 | 4 | Ac.Ca./Am.Ac./B.Am./O.St. | 88.2 | C8:1; Pro; Carnosine; 27-OH-C |
| 81 | 4 | En.Met/Am.Ac./O.St. | 93.3 | Fum; Lac; Tyr; 27-OH-C |
| 82 | 4 | En.Met/Ac.Ca./Am.Ac. | 90.5 | Fum; C10:2; C8:1; Phe |
| 83 | 4 | En.Met/Ac.Ca./B.Am. | 82.3 | Fum; C4:1; C5:1; Met-SO |
| 84 | 3 | S.L./B.Am./O.St. | 90 | SM C26:0; Met-SO; 27-OH-C |
| 85 | 4 | S.L./B.Am./O.St. | 90.8 | SM (OH) C22:2; Carnosine; SDMA; 27-OH-C |
| 86 | 3 | Ac.Ca./Am.Ac. | 82.2 | C10:2; C6 (C4:1-DC); Phe |
| 87 | 3 | En.Met/Ac.Ca./B.Am. | 87.7 | Fum; C14:1-OH; total DMA |
| 88 | 4 | Ac.Ca./B.Am./O.St. | 90.5 | C4:1; Met-SO; 24,25-EpoxyC; 27-OH-C |
| 89 | 2 | Ac.Ca./B.Am. | 80.6 | C5:1; total DMA |

TABLE 10-continued

Metabolite combinations correlating with neurological behavioural score

| No. | Npar | Chemical Class | Accuracy | Model |
|---|---|---|---|---|
| 90 | 3 | En.Met/B.Am. | 81.9 | Fum; Met-SO; SDMA |
| 91 | 3 | B.Am./O.St. | 89.9 | Carnosine; total DMA; 27-OH-C |
| 92 | 3 | En.Met/B.Am. | 84.3 | Fum; Pent-P; SDMA |
| 93 | 3 | Ac.Ca./S.L./B.Am. | 79.5 | C6 (C4:1-DC); SM (OH) C14:1; Carnosine |
| 94 | 3 | En.Met/Ac.Ca./Am.Ac. | 80.3 | Fum; C10:2; Phe |
| 95 | 4 | Ac.Ca./S.L./B.Am. | 88.7 | C5:1; SM C24:1; SM (OH) C22:2; SDMA |
| 96 | 3 | Ac.Ca./B.Am. | 83.3 | C5:1; C8:1; total DMA |
| 97 | 3 | En.Met/B.Am./O.St. | 92.2 | Fum; total DMA; 27-OH-C |
| 98 | 4 | Ac.Ca./B.Am./O.St. | 82.9 | C10:2; C8:1; Met-SO; 5a,6a-EpoxyC |
| 99 | 3 | Ac.Ca./S.L./B.Am. | 86.4 | C5-DC (C6-OH); SM (OH) C22:2; Carnosine |
| 100 | 4 | En.Met/Ac.Ca./B.Am. | 86.4 | Fum; C10:2; C8:1; Met-SO |
| 101 | 3 | En.Met/Ac.Ca./B.Am. | 95.2 | Fum; C5-DC (C6-OH); total DMA |
| 102 | 3 | Ac.Ca./Am.Ac./B.Am. | 86.3 | C5-DC (C6-OH); Tyr; total DMA |
| 103 | 5 | En.Met/Ac.Ca./S.L./B.Am. | 82.6 | Pent-P; C3-DC (C4-OH); SM C24:1; alpha-AAA; Carnosine |
| 104 | 4 | Ac.Ca./S.L./O.St. | 79.8 | C5:1; C8:1; SM (OH) C14:1; Cholestenone |
| 105 | 4 | En.Met/Ac.Ca./B.Am. | 80.2 | Fum; C10:2; C5:1-DC; SDMA |
| 106 | 4 | Ac.Ca./S.L./B.Am. | 82.9 | C5:1; SM C24:1; SM (OH) C14:1; SDMA |
| 107 | 4 | Ac.Ca./S.L./B.Am. | 86.8 | C5-DC (C6-OH); SM (OH) C14:1; alpha-AAA; Carnosine |
| 108 | 3 | Ac.Ca./Am.Ac. | 79.1 | C10:2; C5-DC (C6-OH); Phe |
| 109 | 4 | En.Met/Ac.Ca./B.Am. | 82.1 | Lac; C0; Carnosine; total DMA |
| 110 | 3 | Ac.Ca./B.Am. | 81.9 | C5:1; SDMA; total DMA |
| 111 | 3 | En.Met/Ac.Ca. | 82.9 | Fum; Lac; C14:1-OH |
| 112 | 4 | En.Met/Ac.Ca./S.L./O.St. | 81.9 | Fum; C14:2-OH; SM (OH) C22:2; 27-OH-C |
| 113 | 3 | Ac.Ca./B.Am./O.St. | 79.1 | C14:1-OH; Carnosine; 27-OH-C |
| 114 | 3 | En.Met/B.Am. | 87.5 | Fum; Suc; SDMA |
| 115 | 4 | En.Met/Ac.Ca./S.L./B.Am. | 88 | Fum; C5-OH (C3-DC-M); SM (OH) C22:2; total DMA |
| 116 | 4 | Ac.Ca./Am.Ac./O.St. | 81.8 | C10:2; C6 (C4:1-DC); Phe; 24,25-EpoxyC |
| 117 | 3 | En.Met/B.Am. | 86 | Fum; Pent-P; total DMA |
| 118 | 4 | En.Met/Ac.Ca./B.Am./O.St. | 90.1 | Pent-P; C5:1; total DMA; 24,25-EpoxyC |
| 119 | 4 | Am.Ac./B.Am./O.St. | 91.6 | Cit; Met-SO; SDMA; 27-OH-C |
| 120 | 3 | En.Met/Ac.Ca./B.Am. | 85.8 | Fum; C14:1; Met-SO |
| 121 | 4 | En.Met/Ac.Ca./B.Am. | 90.4 | Fum; C5:1; Met-SO; SDMA |
| 122 | 4 | S.L./B.Am./O.St. | 88.7 | SM C16:1; Met-SO; 27-OH-C; Cholestenone |
| 123 | 5 | S.L./B.Am./O.St./P.G. | 87.8 | SM (OH) C22:2; Met-SO; 24-DH-Lanosterol; 27-OH-C; DHA |
| 124 | 3 | En.Met/Am.Ac./O.St. | 89.4 | Fum; Met; 27-OH-C |
| 125 | 3 | En.Met/Ac.Ca./B.Am. | 80.3 | Fum; C0; Met-SO |
| 126 | 3 | En.Met/Ac.Ca./B.Am. | 82.6 | Fum; C14:1-OH; Met-SO |
| 127 | 3 | En.Met/Ac.Ca./B.Am. | 95.7 | Lac; C6 (C4:1-DC); Carnosine |
| 128 | 4 | En.Met/Ac.Ca./B.Am. | 88 | Fum; C10:2; C6 (C4:1-DC); Met-SO |
| 129 | 3 | S.L./B.Am./O.St. | 91.2 | SM (OH) C22:2; Carnosine; 27-OH-C |
| 130 | 3 | B.Am./O.St. | 81.6 | Carnosine; SDMA; 27-OH-C |
| 131 | 4 | En.Met/Ac.Ca./S.L./B.Am. | 91.1 | Pent-P; C5-DC (C6-OH); SM (OH) C14:1; Carnosine |
| 132 | 4 | En.Met/Am.Ac./B.Am./O.St. | 92.6 | Suc; Lys; SDMA; 27-OH-C |
| 133 | 4 | Ac.Ca./S.L./B.Am. | 85.9 | C5-DC (C6-OH); C8:1; SM (OH) C14:1; Carnosine |
| 134 | 4 | En.Met/Ac.Ca./Am.Ac. | 80.1 | Pent-P; C10:2; C8:1; Tyr |
| 135 | 3 | Ac.Ca./Am.Ac./O.St. | 94.7 | C10:2; Tyr; 27-OH-C |
| 136 | 3 | S.L./B.Am./O.St. | 91.4 | SM (OH) C22:2; total DMA; 27-OH-C |
| 137 | 4 | En.Met/Ac.Ca./B.Am. | 87.1 | Fum; C10:2; C14:1; Ac-Orn |
| 138 | 4 | En.Met/B.Am./O.St. | 95.3 | Fum; Met-SO; total DMA; 27-OH-C |
| 139 | 4 | Ac.Ca./S.L./B.Am. | 90.4 | C5:1; C8:1; SM C16:1; Carnosine |
| 140 | 5 | Ac.Ca./S.L./B.Am. | 79.7 | C10:2; C5:1; SM C24:1; SM (OH) C22:2; Carnosine |
| 141 | 4 | En.Met/B.Am./O.St. | 93.9 | Fum; Pent-P; total DMA; 27-OH-C |
| 142 | 4 | En.Met/Ac.Ca./B.Am. | 89.7 | Lac; C6 (C4:1-DC); Carnosine; total DMA |
| 143 | 3 | S.L./Am.Ac./O.St. | 82.6 | SM (OH) C22:2; Val; 27-OH-C |
| 144 | 3 | En.Met/Ac.Ca./B.Am. | 90.9 | Lac; C12; Carnosine |
| 145 | 4 | En.Met/Ac.Ca./S.L./Am.Ac. | 82.3 | Fum; C3-DC (C4-OH); SM (OH) C22:2; Tyr |
| 146 | 4 | Ac.Ca./B.Am. | 81.7 | C0; C14:2-OH; Carnosine; total DMA |
| 147 | 5 | En.Met/Ac.Ca./B.Am./O.St. | 97.2 | Fum; C14:1-OH; Met-SO; total DMA; 27-OH-C |
| 148 | 4 | Ac.Ca./S.L./B.Am. | 83.8 | C3-DC (C4-OH); SM C24:1; SM (OH) C22:2; Carnosine |
| 149 | 4 | Ac.Ca./S.L./B.Am./O.St. | 81 | C5-DC (C6-OH); SM (OH) C22:2; Met-SO; 24,25-EpoxyC |
| 150 | 5 | Am.Ac./B.Am./O.St. | 80.9 | Phe; Thr; Val; alpha-AAA; 27-OH-C |
| 151 | 3 | En.Met/Ac.Ca./B.Am. | 84.7 | Fum; C6 (C4:1-DC); Met-SO |
| 152 | 4 | Ac.Ca./Am.Ac./B.Am. | 85.5 | C14:2-OH; C5-DC (C6-OH); Tyr; total DMA |
| 153 | 3 | Ac.Ca./S.L./B.Am. | 86.6 | C5:1; SM (OH) C14:1; total DMA |
| 154 | 5 | Ac.Ca./S.L./B.Am./O.St. | 96 | C5:1; SM (OH) C14:1; Met-SO; total DMA; 27-OH-C |
| 155 | 4 | Ac.Ca./S.L./Am.Ac./B.Am. | 91.4 | C5-DC (C6-OH); SM (OH) C14:1; Phe; Carnosine |
| 156 | 4 | Ac.Ca./S.L. | 83.5 | C10:2; C5:1; C8:1; SM (OH) C22:2 |
| 157 | 3 | En.Met/Ac.Ca./B.Am. | 86.3 | Fum; C6 (C4:1-DC); total DMA |
| 158 | 4 | En.Met/Ac.Ca./O.St. | 79.2 | Fum; C10:2; C5:1-DC; 24,25-EpoxyC |
| 159 | 3 | En.Met/Am.Ac./O.St. | 93.5 | Fum; Tyr; 27-OH-C |
| 160 | 5 | Ac.Ca./S.L./B.Am. | 84.9 | C5-DC (C6-OH); SM C18:1; SM (OH) C16:1; alpha-AAA; Met-SO |
| 161 | 4 | Ac.Ca./Am.Ac./B.Am./O.St. | 86.4 | C8:1; Met; Carnosine; 27-OH-C |
| 162 | 3 | Am.Ac./B.Am./O.St. | 90.4 | Lys; total DMA; 27-OH-C |
| 163 | 4 | Ac.Ca./S.L./B.Am. | 81 | C10:2; C14:1-OH; SM (OH) C14:1; Carnosine |
| 164 | 4 | Ac.Ca./S.L./B.Am./O.St. | 91.9 | C5:1; SM (OH) C22:2; SDMA; 27-OH-C |
| 165 | 4 | En.Met/Am.Ac./B.Am./O.St. | 85.7 | Fum; Leu; SDMA; 27-OH-C |

TABLE 10-continued

Metabolite combinations correlating with neurological behavioural score

| No. | Npar | Chemical Class | Accuracy | Model |
|---|---|---|---|---|
| 166 | 3 | Ac.Ca./Am.Ac./O.St. | 82.1 | C8:1; Pro; 27-OH-C |
| 167 | 4 | B.Am./O.St. | 89.2 | Ac-Orn; total DMA; 27-OH-C; 5a,6a-EpoxyC |
| 168 | 3 | En.Met/Ac.Ca./Am.Ac. | 89.8 | Fum; C5-DC (C6-OH); Tyr |
| 169 | 3 | Ac.Ca./B.Am. | 82.3 | C5-DC (C6-OH); Carnosine; total DMA |
| 170 | 4 | En.Met/Am.Ac./O.St. | 94 | Fum; Pent-P; Tyr; 27-OH-C |
| 171 | 3 | Am.Ac./B.Am./O.St. | 83.9 | Pro; SDMA; 27-OH-C |
| 172 | 5 | Ac.Ca./S.L./B.Am./P.G. | 84.4 | C6 (C4:1-DC); SM (OH) C22:2; Carnosine; 8-iso-PGF2a; LTB4 |
| 173 | 4 | S.L./Am.Ac./B.Am./O.St. | 97.1 | SM (OH) C22:2; Tyr; total DMA; 27-OH-C |
| 174 | 4 | B.Am./O.St. | 80.2 | C14:1; C5:1-DC; total DMA; 27-OH-C |
| 175 | 5 | Ac.Ca./Am.Ac./B.Am./O.St. | 91.3 | C10:2; C8:1; His; Carnosine; 27-OH-C |
| 176 | 4 | En.Met/Ac.Ca./B.Am. | 95.6 | Fum; C5:1; C8:1; total DMA |
| 177 | 4 | En.Met/Ac.Ca./B.Am. | 88.5 | Lac; C10:2; C6 (C4:1-DC); Carnosine |
| 178 | 4 | Ac.Ca./S.L./Am.Ac. | 81.2 | C10:2; C5-DC (C6-OH); SM (OH) C22:2; Phe |
| 179 | 5 | En.Met/Ac.Ca./S.L./B.Am./P.G. | 82.7 | OAA; C5:1; SM (OH) C16:1; total DMA; 8-iso-PGF2a |
| 180 | 3 | En.Met/Ac.Ca./Am.Ac. | 80.3 | Fum; C14:1; Phe |
| 181 | 3 | Ac.Ca./S.L. | 85.7 | C5:1; C8:1; SM (OH) C22:2 |
| 182 | 4 | En.Met/Ac.Ca./S.L./B.Am. | 89.1 | Fum; C5-DC (C6-OH); SM (OH) C14:1; Met-SO |
| 183 | 4 | Ac.Ca./S.L./B.Am. | 81.1 | C3-DC (C4-OH); SM C16:0; SM (OH) C22:2; Carnosine |
| 184 | 3 | En.Met/Ac.Ca./B.Am. | 88.9 | Fum; C5:1; SDMA |
| 185 | 4 | En.Met/Ac.Ca./B.Am./O.St. | 80.2 | Fum; C14:1-OH; Ac-Orn; 27-OH-C |
| 186 | 5 | S.L./Am.Ac./O.St./P.G. | 94.5 | SM C24:1; SM (OH) C16:1; Tyr; 27-OH-C; 8-iso-PGF2a |
| 187 | 4 | En.Met/Ac.Ca./S.L./O.St. | 79.1 | Fum; C5:1; SM C24:1; 24,25-EpoxyC |
| 188 | 4 | Ac.Ca./Am.Ac./O.St. | 79.2 | C10:2; C5:1; Met; 27-OH-C |
| 189 | 5 | En.Met/Ac.Ca./B.Am. | 87.5 | Pent-P; C10:2; C5:1; C8:1; total DMA |
| 190 | 3 | En.Met/Ac.Ca./B.Am. | 83.1 | Fum; C14:1; Carnosine |
| 191 | 3 | Ac.Ca./S.L./B.Am. | 79.9 | C5:1; SM C16:1; Carnosine |
| 192 | 3 | Ac.Ca./S.L./O.St. | 80.8 | C5:1; SM (OH) C22:2; 27-OH-C |
| 193 | 4 | En.Met/Ac.Ca./B.Am./O.St. | 87.7 | Lac; C5-DC (C6-OH); total DMA; 27-OH-C |
| 194 | 3 | S.L./Am.Ac./O.St. | 80.4 | SM (OH) C14:1; Thr; 27-OH-C |
| 195 | 4 | S.L./B.Am./O.St. | 94.5 | SM (OH) C22:2; Carnosine; total DMA; 27-OH-C |
| 196 | 3 | Ac.Ca./S.L./B.Am. | 90.8 | C5-DC (C6-OH); SM (OH) C22:2; total DMA |
| 197 | 4 | En.Met/Ac.Ca./B.Am./O.St. | 90.1 | Fum; C0; Met-SO; 24,25-EpoxyC |
| 198 | 4 | En.Met/S.L./B.Am./O.St. | 79.4 | Fum; SM (OH) C22:1; Ac-Orn; 27-OH-C |
| 199 | 4 | En.Met/Ac.Ca./B.Am. | 86 | Pent-P; C5:1; alpha-AAA; SDMA |
| 200 | 4 | En.Met/Am.Ac./B.Am./O.St. | 94.3 | Fum; Tyr; SDMA; 27-OH-C |
| 201 | 2 | Ac.Ca./B.Am. | 79.3 | C12; Carnosine |
| 202 | 4 | Am.Ac./B.Am./O.St. | 92.8 | Cit; Tyr; Met-SO; 27-OH-C |
| 203 | 3 | S.L./B.Am./O.St. | 80.5 | SM (OH) C22:2; SDMA; 27-OH-C |
| 204 | 3 | En.Met/Ac.Ca./P.G. | 83 | Fum; C8:1; 8-iso-PGF2a |
| 205 | 4 | En.Met/Ac.Ca./Am.Ac. | 89.5 | Fum; C10:2; C8:1; Tyr |
| 206 | 4 | Ac.Ca./S.L./B.Am. | 85.4 | C5:1; SM C24:1; SDMA; total DMA |
| 207 | 3 | En.Met/Ac.Ca./B.Am. | 85.5 | Fum; C5-DC (C6-OH); SDMA |
| 208 | 4 | Ac.Ca./Am.Ac. | 84.9 | C10:2; C5-DC (C6-OH); Lys; Tyr |
| 209 | 4 | En.Met/Am.Ac./O.St. | 79.3 | Fum; Pent-P; Phe; 24,25-EpoxyC |
| 210 | 5 | En.Met/B.Am./O.St. | 91 | Fum; Pent-P; Carnosine; SDMA; 27-OH-C |
| 211 | 4 | En.Met/B.Am./O.St./P.G. | 81.4 | Fum; SDMA; 24,25-EpoxyC; TXB2 |
| 212 | 3 | En.Met/Am.Ac./O.St. | 83.7 | Fum; Phe; 27-OH-C |
| 213 | 3 | B.Am./O.St. | 82.8 | Carnosine; Met-SO; 27-OH-C |
| 214 | 4 | Ac.Ca./S.L./B.Am. | 83 | C0; SM (OH) C22:2; Carnosine; total DMA |
| 215 | 3 | En.Met/B.Am./O.St. | 84.9 | Fum; SDMA; 27-OH-C |
| 216 | 4 | En.Met/Ac.Ca./B.Am. | 80.3 | Fum; C5-OH (C3-DC-M); Carnosine; SDMA |
| 217 | 3 | En.Met/B.Am./O.St. | 85.1 | Fum; Ac-Orn; 24,25-EpoxyC |
| 218 | 4 | Ac.Ca./S.L./Am.Ac./B.Am. | 92.1 | C5-DC (C6-OH); SM (OH) C14:1; Phe; total DMA |
| 219 | 5 | En.Met/Am.Ac./B.Am./O.St. | 91.7 | Suc; Lys; Met-SO; 24,25-EpoxyC; 27-OH-C |
| 220 | 5 | En.Met/Ac.Ca./B.Am. | 90.9 | Fum; C0; Met-SO; SDMA; total DMA |
| 221 | 3 | Am.Ac./O.St. | 82.5 | Leu; Val; 27-OH-C |
| 222 | 4 | Ac.Ca./S.L./B.Am. | 89 | C5-DC (C6-OH); SM (OH) C16:1; SM (OH) C22:2; Carnosine |
| 223 | 4 | Ac.Ca./S.L./Am.Ac./B.Am. | 85 | C5-DC (C6-OH); SM (OH) C22:2; Phe; alpha-AAA |
| 224 | 5 | En.Met/Ac.Ca./B.Am. | 94.6 | Fum; C14:1-OH; C5-DC (C6-OH); Carnosine; Met-SO |
| 225 | 5 | Ac.Ca./S.L./B.Am./O.St. | 79.6 | C10:2; C5:1; SM C24:1; Carnosine; Cholestenone |
| 226 | 3 | En.Met/B.Am. | 84.2 | Fum; Ac-Orn; SDMA |
| 227 | 4 | En.Met/Ac.Ca./Am.Ac./O.St. | 82.5 | Fum; C8:1; Thr; 27-OH-C |
| 228 | 3 | En.Met/Ac.Ca./Am.Ac. | 79.7 | Fum; C14:1; Tyr |
| 229 | 3 | B.Am./O.St. | 86.7 | Ac-Orn; Carnosine; 27-OH-C |
| 230 | 4 | Ac.Ca./S.L./B.Am. | 89.4 | C14:1; C5:1; SM (OH) C22:2; total DMA |
| 231 | 5 | En.Met/Ac.Ca./Am.Ac./B.Am. | 80.5 | Lac; C5-DC (C6-OH); Phe; Carnosine; SDMA |
| 232 | 3 | Am.Ac./B.Am./O.St. | 86.2 | Phe; Carnosine; 27-OH-C |
| 233 | 3 | Ac.Ca./B.Am. | 91.5 | C10:2; C14:1-OH; Carnosine |
| 234 | 5 | Ac.Ca./B.Am./O.St./P.G. | 80.2 | C5:1; C8:1; alpha-AAA; 3b,5a,6b-THC; 8-iso-PGF2a |
| 235 | 4 | Ac.Ca./Am.Ac./B.Am./O.St. | 89.6 | C8:1; Leu; Met-SO; 27-OH-C |
| 236 | 5 | Ac.Ca./S.L./B.Am. | 84.1 | Fum; C3-DC (C4-OH); C8:1; SM (OH) C14:1; Carnosine |
| 237 | 3 | En.Met/Ac.Ca./B.Am. | 83.3 | Fum; C8:1; Met-SO |
| 238 | 4 | En.Met/Ac.Ca./Am.Ac./O.St. | 82.2 | Fum; C8:1; Ala; 27-OH-C |
| 239 | 4 | Ac.Ca./Am.Ac./B.Am. | 82.6 | C5-DC (C6-OH); C8:1; Leu; Carnosine |
| 240 | 5 | Ac.Ca./S.L./B.Am. | 91.7 | C5-DC (C6-OH); SM C16:1; SM C24:1; SM (OH) C22:2; Carnosine |
| 241 | 4 | Ac.Ca./S.L./Am.Ac./O.St. | 86 | C5-DC (C6-OH); SM (OH) C22:2; Tyr; 24,25-EpoxyC |

TABLE 10-continued

Metabolite combinations correlating with neurological behavioural score

| No. | Npar | Chemical Class | Accuracy | Model |
|---|---|---|---|---|
| 242 | 5 | En.Met/S.L./B.Am./O.St. | 89.1 | Pent-P; SM C16:0; Ac-Orn; Carnosine; 27-OH-C |
| 243 | 4 | Ac.Ca./Am.Ac./B.Am. | 83.7 | C5-DC (C6-OH); Tyr; Carnosine; SDMA |
| 244 | 4 | Ac.Ca./B.Am./O.St./P.G. | 87.4 | C8:1; Carnosine; 27-OH-C; LTB4 |
| 245 | 4 | Ac.Ca./B.Am./O.St. | 86.7 | C5-DC (C6-OH); alpha-AAA; total DMA; 3b,5a,6b-THC |
| 246 | 4 | Ac.Ca./S.L./B.Am./O.St. | 95.5 | C5-DC (C6-OH); SM C26:0; Met-SO; 27-OH-C |
| 247 | 4 | Ac.Ca./B.Am./O.St. | 86 | C10:2; C14:1; Carnosine; 27-OH-C |
| 248 | 5 | Ac.Ca./S.L./B.Am. | 86.8 | C5:1; C8:1; SM C16:1; alpha-AAA; Met-SO |
| 249 | 4 | Ac.Ca./S.L./B.Am. | 91.7 | C5-DC (C6-OH); SM C16:0; Carnosine; total DMA |
| 250 | 3 | S.L./B.Am./O.St. | 86.9 | SM (OH) C14:1; Carnosine; 27-OH-C |
| 251 | 3 | Ac.Ca./B.Am. | 83.4 | C10:2; C8:1; Carnosine |
| 252 | 4 | Ac.Ca./S.L./B.Am. | 87.2 | C5-DC (C6-OH); SM C18:1; SM (OH) C16:1; total DMA |
| 253 | 4 | Ac.Ca./B.Am. | 79.3 | C6 (C4:1-DC); alpha-AAA; Carnosine; total DMA |
| 254 | 3 | Am.Ac./B.Am./O.St. | 88.1 | Leu; Carnosine; 27-OH-C |
| 255 | 4 | En.Met/Am.Ac./B.Am./O.St. | 93.2 | Fum; Pro; total DMA; 27-OH-C |
| 256 | 3 | En.Met/Ac.Ca./B.Am. | 85.5 | Fum; C14:1; total DMA |
| 257 | 4 | En.Met/Ac.Ca./B.Am./O.St. | 89.2 | Fum; C14:2-OH; Ac-Orn; 27-OH-C |
| 258 | 4 | En.Met/Ac.Ca./S.L./B.Am. | 81.6 | Fum; C3-DC (C4-OH); SM (OH) C14:1; Carnosine |
| 259 | 4 | Ac.Ca./Am.Ac./O.St. | 82.9 | C5-DC (C6-OH); Phe; Tyr; 24,25-EpoxyC |
| 260 | 4 | En.Met/Am.Ac./B.Am./O.St. | 93.4 | Fum; Trp; total DMA; 27-OH-C |
| 261 | 3 | Ac.Ca./Am.Ac./B.Am. | 83.5 | C5-DC (C6-OH); Tyr; alpha-AAA |
| 262 | 4 | En.Met/Ac.Ca./B.Am. | 88.8 | Fum; C5-DC (C6-OH); Carnosine; SDMA |
| 263 | 5 | En.Met/Ac.Ca./Am.Ac./B.Am./O.St. | 87.6 | Pent-P; C10:2; Lys; Ac-Orn; 27-OH-C |
| 264 | 5 | En.Met/Ac.Ca./Am.Ac./B.Am./O.St. | 87 | Lac; C6 (C4:1-DC); Phe; Carnosine; 24,25-EpoxyC |
| 265 | 3 | Ac.Ca./S.L./B.Am. | 86.4 | C5:1; SM C16:0; total DMA |
| 266 | 4 | Fum/B.Am./O.St. | 88.7 | Fum; Pent-P; SDMA; 27-OH-C |
| 267 | 4 | Ac.Ca./Am.Ac. | 87.8 | C10:2; C5-DC (C6-OH); Lys; Phe |
| 268 | 5 | Ac.Ca./S.L./B.Am./P.G. | 79.5 | C10:2; C14:1; SM (OH) C14:1; Met-SO; DHA |
| 269 | 4 | Ac.Ca./Am.Ac./B.Am. | 91.3 | C10:2; C5-DC (C6-OH); Tyr; total DMA |
| 270 | 4 | Ac.Ca./S.L./B.Am./O.St. | 82.3 | C10:2; SM (OH) C22:1; Carnosine; 27-OH-C |
| 271 | 3 | Ac.Ca./Am.Ac./O.St. | 80.7 | C8:1; Ala; 27-OH-C |
| 272 | 4 | En.Met/Ac.Ca./B.Am./P.G. | 83.9 | Fum; C8:1; Carnosine; LTB4 |
| 273 | 5 | En.Met/Ac.Ca./S.L. | 82.3 | Fum; Pent-P; C14:1-OH; SM C26:1; SM (OH) C22:2 |
| 274 | 5 | En.Met/Ac.Ca./Am.Ac. | 84.4 | Pent-P; Suc; C10:2; C5-DC (C6-OH); Tyr |
| 275 | 3 | Am.Ac./B.Am./O.St. | 82 | Leu; SDMA; 27-OH-C |
| 276 | 6 | Ac.Ca./S.L./Am.Ac./P.G. | 86.2 | C10:2; C5-DC (C6-OH); SM (OH) C14:1; SM (OH) C22:2; Tyr; DHA |
| 277 | 4 | En.Met/Ac.Ca./Am.Ac./O.St. | 95.1 | Fum; C10:2; Tyr; 27-OH-C |
| 278 | 5 | En.Met/Ac.Ca./O.St. | 82.8 | Fum; C8:1; 24-DH-Lanosterol; Cholestenone; 3b,5a,6b-THC |
| 279 | 4 | En.Met/Ac.Ca. | 80.8 | Fum; C14:1; C5:1; C8:1 |
| 280 | 4 | Ac.Ca./S.L./B.Am. | 93.8 | C5-DC (C6-OH); SM (OH) C14:1; Carnosine; total DMA |
| 281 | 3 | Ac.Ca./B.Am./O.St. | 87.9 | C4:1; Met-SO; 27-OH-C |
| 282 | 4 | En.Met/Ac.Ca./Am.Ac. | 84.3 | Fum; Pent-P; C10:2; Tyr |
| 283 | 3 | En.Met/Ac.Ca./B.Am. | 80.4 | Fum; C14:1-OH; SDMA |
| 284 | 4 | Ac.Ca./S.L./B.Am. | 91 | C5:1; SM (OH) C14:1; Carnosine; SDMA |
| 285 | 4 | En.Met/Ac.Ca./Am.Ac./O.St. | 94.1 | Fum; C8:1; Tyr; 27-OH-C |
| 286 | 4 | En.Met/B.Am./O.St. | 82.2 | Fum; Lac; Met-SO; 24,25-EpoxyC |
| 287 | 4 | En.Met/Am.Ac./B.Am. | 83.7 | Fum; Suc; Ile; Met-SO |
| 288 | 5 | Ac.Ca./B.Am./O.St. | 85.1 | C5:1; Ac-Orn; SDMA; 24,25-EpoxyC; Cholestenone |
| 289 | 4 | En.Met/Ac.Ca./Am.Ac./O.St. | 79.2 | Fum; C14:1; Ala; 27-OH-C |
| 290 | 5 | Ac.Ca./S.L./O.St. | 79.1 | C5:1; C8:1; SM (OH) C22:2; 24-DH-Lanosterol; 5a,6a-EpoxyC |
| 291 | 4 | En.Met/Ac.Ca./B.Am./O.St. | 86.5 | Fum; Leu; Ac-Orn; 27-OH-C |
| 292 | 4 | En.Met/Ac.Ca./B.Am. | 84.6 | Fum; C14:1-OH; Met-SO; SDMA |
| 293 | 4 | En.Met/Ac.Ca./Am.Ac./B.Am. | 98.4 | Fum; C5-DC (C6-OH); Tyr; total DMA |
| 294 | 5 | En.Met/Ac.Ca./Am.Ac./O.St./P.G. | 81.2 | Fum; C5-DC (C6-OH); Thr; 27-OH-C; LTB4 |
| 295 | 3 | Am./O.St. | 86.1 | Cit; Met; 27-OH-C |
| 296 | 3 | En.Met/Ac.Ca./B.Am. | 83.6 | Fum; C6 (C4:1-DC); Ac-Orn |
| 297 | 4 | Ac.Ca./B.Am. | 80.1 | C14:1; C5:1; alpha-AAA; Carnosine |
| 298 | 4 | Ac.Ca./Am.Ac. | 85.8 | C10:2; C5-DC (C6-OH); Tyr; Val |
| 299 | 5 | En.Met/Ac.Ca./B.Am. | 90.1 | Fum; C10:2; C14:1; C14:1-OH; Carnosine |
| 300 | 4 | Ac.Ca./S.L./B.Am. | 84.1 | C5:1; SM C24:1; alpha-AAA; total DMA |
| 301 | 4 | En.Met/Ac.Ca./B.Am./O.St. | 83.2 | Fum; C8:1; SDMA; 27-OH-C |
| 302 | 5 | En.Met/B.Am./O.St. | 82.5 | Suc; alpha-AAA; Carnosine; SDMA; 3b,5a,6b-THC |
| 303 | 3 | B.Am./O.St. | 82.2 | Ac-Orn; alpha-AAA; 27-OH-C |
| 304 | 5 | En.Met/Ac.Ca./B.Am./O.St. | 88.5 | Fum; C14:1-OH; Carnosine; SDMA; 3b,5a,6b-THC |
| 305 | 3 | Ac.Ca./Am.Ac./O.St. | 82 | C10:2; Val; 27-OH-C |
| 306 | 3 | B.Am./O.St./P.G. | 79.3 | Carnosine; 27-OH-C; 8-iso-PGF2a |
| 307 | 4 | Ac.Ca./B.Am./P.G. | 88.7 | C10:2; C14:1-OH; Carnosine; 8-iso-PGF2a |
| 308 | 4 | En.Met/Ac.Ca./B.Am. | 84.7 | Fum; C18:1; Carnosine; total DMA |
| 309 | 4 | Ac.Ca./S.L./B.Am. | 90.2 | C14:1; C5:1; SM C16:0; Carnosine |
| 310 | 4 | Ac.Ca./B.Am./O.St. | 90.6 | C14:1; Carnosine; Met-SO; 27-OH-C |
| 311 | 4 | En.Met/B.Am./O.St. | 85 | Fum; SDMA; 25-OH-C; 27-OH-C |
| 312 | 3 | En.Met/Ac.Ca./Am.Ac. | 82.8 | Fum; C8:1; Tyr |
| 313 | 4 | Am.Ac./B.Am./O.St. | 91.7 | Phe; SDMA; total DMA; 27-OH-C |
| 314 | 4 | Ac.Ca./S.L./B.Am. | 79.6 | C6 (C4:1-DC); SM (OH) C14:1; SM (OH) C22:2; Carnosine |
| 315 | 4 | Ac.Ca./S.L./B.Am. | 82 | C5:1; SM C16:0; alpha-AAA; total DMA |
| 316 | 3 | B.Am./O.St. | 87.7 | Met-SO; 27-OH-C; 5a,6a-EpoxyC |
| 317 | 5 | En.Met/Ac.Ca./Am.Ac./P.G. | 81.4 | Fum; C0; C10:2; Tyr; 8-iso-PGF2a |

TABLE 10-continued

Metabolite combinations correlating with neurological behavioural score

| No. | Npar | Chemical Class | Accuracy | Model |
|---|---|---|---|---|
| 318 | 4 | En.Met/B.Am./O.St. | 89.8 | Fum; SDMA; 27-OH-C; 3b,5a,6b-THC |
| 319 | 4 | En.Met/Ac.Ca./B.Am. | 86.5 | Pent-P; C10:2; C8:1; Carnosine |
| 320 | 4 | En.Met/Ac.Ca./B.Am. | 88 | Fum; C3-DC (C4-OH); Carnosine; total DMA |
| 321 | 3 | Ac.Ca./Am.Ac./O.St. | 79.9 | C10:2; Thr; 27-OH-C |
| 322 | 4 | En.Met/Ac.Ca./B.Am./O.St. | 90.2 | Fum; C5:1; SDMA; 27-OH-C |
| 323 | 4 | En.Met/Am.Ac./O.St. | 84.1 | Fum; Pent-P; Phe; 27-OH-C |
| 324 | 5 | En.Met/Ac.Ca./B.Am. | 92.9 | Fum; C14:1-OH; C5:1; Carnosine; total DMA |
| 325 | 4 | Ac.Ca./Am.Ac./B.Am. | 93.5 | C10:2; C6 (C4:1-DC); Phe; Carnosine |
| 326 | 4 | Ac.Ca./B.Am. | 88.8 | C5:1; C8:1; alpha-AAA; total DMA |
| 327 | 5 | Ac.Ca./S.L./B.Am. | 90 | C5:1; SM C16:0; SM (OH) C22:2; Carnosine; SDMA |
| 328 | 3 | Ac.Ca./S.L./B.Am. | 84.3 | C5:1; SM C16:1; total DMA |
| 329 | 3 | B.Am./O.St. | 85.1 | Met-SO; SDMA; 27-OH-C |
| 330 | 4 | En.Met/Ac.Ca./B.Am./O.St. | 81.1 | Fum; C5:1; Met-SO; Cholestenone |
| 331 | 4 | En.Met/Ac.Ca./Am.Ac. | 93.1 | Fum; C10:2; C5-DC (C6-OH); Tyr |
| 332 | 5 | Ac.Ca./B.Am./O.St. | 87 | C5:1; C8:1; Ac-Orn; total DMA; 24,25-EpoxyC |
| 333 | 4 | Ac.Ca./S.L./B.Am. | 89.1 | C10:2; C5:1; SM C24:1; total DMA |
| 334 | 5 | Ac.Ca./S.L./B.Am. | 83.9 | C5-DC (C6-OH); C6:1; SM C26:0; SM (OH) C14:1; Met-SO |
| 335 | 4 | Ac.Ca./S.L./B.Am./O.St. | 91.2 | C5:1; SM C24:1; total DMA; 24,25-EpoxyC |
| 336 | 4 | En.Met/Ac.Ca./Am.Ac./O.St. | 86.5 | Fum; C14:1; Tyr; 25-OH-C |
| 337 | 4 | Ac.Ca./B.Am. | 82.1 | C5-DC (C6-OH); Carnosine; SDMA; total DMA |
| 338 | 5 | Ac.Ca./S.L./B.Am. | 82.3 | C10:2; C2; SM (OH) C14:1; Carnosine; total DMA |
| 339 | 4 | Ac.Ca./B.Am./P.G. | 81.7 | C10:2; C5:1; total DMA; 8-iso-PGF2a |
| 340 | 4 | Ac.Ca./S.L./B.Am./O.St. | 94.1 | C8:1; SM C26:0; Met-SO; 27-OH-C |
| 341 | 4 | En.Met/B.Am./O.St. | 92.7 | Fum; Ac-Orn; SDMA; 27-OH-C |
| 342 | 4 | S.L./B.Am./O.St. | 85.8 | SM (OH) C22:2; Ac-Orn; SDMA; 27-OH-C |
| 343 | 4 | En.Met/B.Am./O.St. | 94.4 | Fum; Met-SO; 27-OH-C; 5a,6a-EpoxyC |
| 344 | 4 | En.Met/Ac.Ca./B.Am. | 87.1 | Fum; C10:2; C14:1-OH; Ac-Orn |
| 345 | 4 | En.Met/Am.Ac./B.Am./O.St. | 95.2 | Fum; Asp; Carnosine; 27-OH-C |
| 346 | 4 | En.Met/Am.Ac./O.St. | 84.9 | Fum; Asn; Phe; 27-OH-C |
| 347 | 3 | Am.Ac./B.Am./O.St. | 92.2 | Val; total DMA; 27-OH-C |
| 348 | 5 | S.L./B.Am./O.St. | 84.6 | SM C26:1; SM (OH) C22:2; Ac-Orn; 24,25-EpoxyC; 27-OH-C |
| 349 | 4 | Ac.Ca./S.L./Am.Ac./B.Am. | 84.7 | C5-DC (C6-OH); SM (OH) C14:1; Phe; SDMA |
| 350 | 5 | Ac.Ca./S.L./B.Am./O.St. | 89.9 | C5:1-DC; SM (OH) C14:1; SDMA; total DMA; 27-OH-C |
| 351 | 4 | En.Met/Ac.Ca./S.L./B.Am. | 90.8 | Fum; C5:1; SM (OH) C22:2; SDMA |
| 352 | 4 | Ac.Ca./S.L./Am.Ac./B.Am. | 83.4 | C5-DC (C6-OH); SM (OH) C22:2; Lys; SDMA |
| 353 | 4 | En.Met/B.Am./O.St. | 90 | Fum; Suc; SDMA; 27-OH-C |
| 354 | 4 | En.Met/Ac.Ca./B.Am./O.St. | 95.6 | Fum; C5:1-DC; total DMA; 27-OH-C |
| 355 | 4 | Ac.Ca./Am.Ac./B.Am./O.St. | 85.3 | C14:1; Phe; Carnosine; 27-OH-C |
| 356 | 5 | Ac.Ca./S.L./B.Am. | 81.3 | C10:2; C5:1; SM C24:1; SM (OH) C14:1; Carnosine |
| 357 | 3 | B.Am./O.St. | 85.7 | Carnosine; 24-DH-Lanosterol; 27-OH-C |
| 358 | 4 | Ac.Ca./S.L./B.Am./O.St. | 94.8 | C5:1; SM C16:0; total DMA; 27-OH-C |
| 359 | 4 | S.L./Am.Ac./B.Am./O.St. | 82.6 | SM (OH) C22:2; Pro; SDMA; 27-OH-C |
| 360 | 4 | En.Met/B.Am./O.St. | 96.3 | Fum; Met-SO; SDMA; 27-OH-C |
| 361 | 4 | S.L./B.Am./O.St. | 89.7 | SM (OH) C22:2; Met-SO; 27-OH-C; 5a,6a-EpoxyC |
| 362 | 4 | En.Met/Ac.Ca./S.L. | 85.4 | Fum; C5:1; C8:1; SM (OH) C22:2 |
| 363 | 3 | En.Met/B.Am./O.St. | 94 | Fum; Met-SO; 27-OH-C |
| 364 | 4 | B.Am./O.St. | 79.1 | Ac-Orn; SDMA; 27-OH-C; 3b,5a,6b-THC |
| 365 | 5 | En.Met/Ac.Ca./Am.Ac./B.Am. | 84.8 | Fum; C3-DC (C4-OH); Phe; Carnosine; SDMA |
| 366 | 4 | Ac.Ca./S.L./Am.Ac./B.Am. | 88.6 | C5-DC (C6-OH); SM (OH) C22:2; Lys; Carnosine |
| 367 | 4 | Ac.Ca./S.L. | 81 | Fum; C14:1; C5:1; SM (OH) C22:2 |
| 368 | 4 | En.Met/Ac.Ca./B.Am./O.St. | 82.8 | Lac; C14:1; Carnosine; 27-OH-C |
| 369 | 4 | Ac.Ca./S.L./B.Am. | 83.5 | C3-DC (C4-OH); SM C16:1; SM (OH) C22:2; Carnosine |
| 370 | 4 | B.Am./O.St. | 87.5 | Ac-Orn; Carnosine; SDMA; 27-OH-C |
| 371 | 4 | Ac.Ca./Am.Ac./B.Am. | 82.1 | C5-DC (C6-OH); Lys; alpha-AAA; total DMA |
| 372 | 4 | Ac.Ca./S.L./B.Am./O.St. | 79.8 | C10:2; SM (OH) C14:1; total DMA; 3b,5a,6b-THC |
| 373 | 5 | Ac.Ca./S.L./Am.Ac./B.Am. | 85.1 | C5-DC (C6-OH); SM C26:0; SM (OH) C14:1; Phe; total DMA |
| 374 | 5 | En.Met/Ac.Ca./Am.Ac./O.St. | 80.2 | Pent-P; C10:2; C8:1; Phe; 24,25-EpoxyC |
| 375 | 3 | En.Met/B.Am./O.St. | 87.2 | Fum; SDMA; 3b,5a,6b-THC |
| 376 | 4 | S.L./B.Am./O.St. | 88.5 | SM C26:0; Ac-Orn; 24,25-EpoxyC; 27-OH-C |
| 377 | 3 | S.L./Am.Ac./O.St. | 88.4 | SM (OH) C14:1; Phe; 27-OH-C |
| 378 | 4 | Ac.Ca./Am.Ac./B.Am./O.St. | 79.4 | C5-DC (C6-OH); Val; Met-SO; 27-OH-C |
| 379 | 5 | Ac.Ca./S.L./B.Am. | 85.1 | C5; C5:1; C6 (C4:1-DC); SM (OH) C22:2; Carnosine |
| 380 | 4 | Ac.Ca./B.Am./O.St./P.G. | 85.7 | C8:1; Carnosine; 27-OH-C; 8-iso-PGF2a |
| 381 | 4 | Ac.Ca./B.Am. | 84.4 | C10:2; C14:1-OH; alpha-AAA; Carnosine |
| 382 | 4 | Ac.Ca./B.Am./O.St. | 81.4 | C5:1-DC; Ac-Orn; 24,25-EpoxyC; 27-OH-C |
| 383 | 4 | Ac.Ca./S.L./B.Am./O.St. | 79.8 | C8:1; SM C26:0; Ac-Orn; 27-OH-C |
| 384 | 4 | Ac.Ca./B.Am. | 82.4 | C4:1; C5:1; alpha-AAA; total DMA |
| 385 | 4 | En.Met/Am.Ac./O.St. | 86.1 | Fum; Leu; Phe; 27-OH-C |
| 386 | 5 | Ac.Ca./S.L./Am.Ac./B.Am. | 90.1 | C5-DC (C6-OH); SM C16:1; SM (OH) C22:2; Tyr; Carnosine |
| 387 | 3 | En.Met/Ac.Ca./B.Am. | 82.6 | Fum; C5-DC (C6-OH); Met-SO |
| 388 | 4 | Ac.Ca./S.L./B.Am. | 84.3 | C5-DC (C6-OH); SM C16:0; SM (OH) C22:1; Carnosine |
| 389 | 4 | Ac.Ca./S.L./Am.Ac. | 81.2 | C5-DC (C6-OH); SM C24:1; SM (OH) C14:1; Tyr |
| 390 | 4 | Ac.Ca./S.L./B.Am./P.G. | 85.9 | C2; SM (OH) C22:2; Carnosine; 8-iso-PGF2a |
| 391 | 4 | En.Met/Am.Ac./B.Am./O.St. | 82 | Pent-P; Leu; Ac-Orn; 27-OH-C |
| 392 | 4 | En.Met/Ac.Ca./S.L./O.St. | 80.1 | Fum; C10; SM (OH) C22:2; 27-OH-C |
| 393 | 4 | En.Met/Ac.Ca./B.Am. | 84.2 | Fum; C5; SDMA; total DMA |

TABLE 10-continued

Metabolite combinations correlating with neurological behavioural score

| No. | Npar | Chemical Class | Accuracy | Model |
|---|---|---|---|---|
| 394 | 4 | Ac.Ca./S.L./B.Am./O.St. | 81.1 | C5:1; SM C16:1; SDMA; 3b,5a,6b-THC |
| 395 | 4 | En.Met/Ac.Ca./B.Am. | 88.8 | Fum; C5:1; C8:1; Met-SO |
| 396 | 5 | Ac.Ca./B.Am./P.G. | 82 | C10:2; C8:1; Carnosine; 8-iso-PGF2a; LTB4 |
| 397 | 4 | Ac.Ca./S.L./B.Am./O.St. | 86.7 | C5:1-DC; SM (OH) C14:1; SDMA; 27-OH-C |
| 398 | 4 | En.Met/Ac.Ca./S.L./B.Am. | 88.6 | Fum; C2; SM (OH) C22:2; total DMA |
| 399 | 6 | Ac.Ca./Am.Ac./B.Am./O.St./P.G. | 81.2 | C10:2; C14:1; Phe; total DMA; 5a,6a-EpoxyC; 8-iso-PGF2a |
| 400 | 4 | En.Met/Ac.Ca./B.Am. | 94.8 | Fum; C14:1; C5:1; total DMA |
| 401 | 5 | En.Met/Ac.Ca./B.Am. | 92.3 | Fum; C0; C10:2; Met-SO; total DMA |
| 402 | 5 | En.Met/Ac.Ca./S.L./O.St. | 83.5 | Pent-P; C5:1; SM C16:1; 24,25-EpoxyC; 3b,5a,6b-THC |
| 403 | 5 | Ac.Ca./B.Am./O.St. | 81 | C14:1; C5:1; alpha-AAA; Met-SO; Cholestenone |
| 404 | 4 | Ac.Ca./B.Am. | 88.1 | C0; C5-DC (C6-OH); alpha-AAA; Met-SO |
| 405 | 4 | S.L./Am.Ac./O.St. | 83 | SM C26:1; SM (OH) C22:2; Leu; 27-OH-C |
| 406 | 4 | En.Met/Am.Ac./B.Am./O.St. | 93.6 | Fum; Val; total DMA; 27-OH-C |
| 407 | 4 | Ac.Ca./S.L./B.Am. | 89.3 | C5-DC (C6-OH); SM (OH) C22:2; alpha-AAA; Carnosine |
| 408 | 4 | En.Met/Ac.Ca./O.St. | 79.3 | Fum; C14:2-OH; 24-DH-Lanosterol; 27-OH-C |
| 409 | 4 | En.Met/Am.Ac./B.Am./O.St. | 93.5 | Fum; Phe; SDMA; 27-OH-C |
| 410 | 4 | En.Met/Am.Ac./B.Am. | 80.7 | Fum; Tyr; Val; total DMA |
| 411 | 5 | Ac.Ca./Am.Ac./O.St./P.G. | 88.4 | C6 (C4:1-DC); Phe; 27-OH-C; 8-iso-PGF2a; LTB4 |
| 412 | 4 | Ac.Ca./S.L./B.Am. | 88.6 | C5-DC (C6-OH); C8:1; SM (OH) C22:2; Carnosine |
| 413 | 5 | En.Met/Ac.Ca./S.L./B.Am. | 95.3 | Suc; C14:2-OH; C5-DC (C6-OH); SM C26:0; total DMA |
| 414 | 4 | Ac.Ca./B.Am. | 85.8 | C5-OH (C3-DC-M); C5-DC (C6-OH); alpha-AAA; Met-SO |
| 415 | 3 | Ac.Ca./B.Am./O.St. | 81.8 | C5:1; total DMA; Cholestenone |
| 416 | 4 | En.Met/B.Am./O.St. | 95.1 | Fum; Lac; Met-SO; 27-OH-C |
| 417 | 5 | Ac.Ca./Am.Ac./B.Am./O.St. | 92.5 | C10:2; C8:1; Met; Carnosine; 27-OH-C |
| 418 | 3 | Ac.Ca./B.Am./O.St. | 85.8 | Fum; total DMA; 3b,5a,6b-THC |
| 419 | 3 | Ac.Ca./S.L./B.Am. | 79.1 | C3-DC (C4-OH); SM (OH) C22:2; Carnosine |
| 420 | 4 | En.Met/B.Am./O.St. | 89.1 | Fum; SDMA; total DMA; 3b,5a,6b-THC |
| 421 | 5 | En.Met/Ac.Ca./S.L./B.Am. | 81.2 | Fum; C3-DC (C4-OH); SM (OH) C14:1; Carnosine; Met-SO |
| 422 | 4 | En.Met/Am.Ac./O.St. | 94 | Fum; Tyr; 27-OH-C; 5a,6a-EpoxyC |
| 423 | 5 | Ac.Ca./S.L./B.Am. | 85.2 | C5:1; C5-DC (C6-OH); SM (OH) C22:2; alpha-AAA; SDMA |
| 424 | 5 | En.Met/Ac.Ca./B.Am. | 91.2 | Fum; Pent-P; C10:2; C14:1; Carnosine |
| 425 | 4 | Ac.Ca./Am.Ac./B.Am./O.St. | 83.7 | C10:2; Met; total DMA; 27-OH-C |
| 426 | 5 | Ac.Ca./B.Am. | 82.1 | C14:1; C14:2-OH; C5-DC (C6-OH); Carnosine; total DMA |
| 427 | 4 | S.L./B.Am./O.St. | 91.6 | SM C26:0; Met-SO; SDMA; 27-OH-C |
| 428 | 4 | En.Met/B.Am./O.St. | 95.2 | Fum; total DMA; 27-OH-C; 3b,5a,6b-THC |
| 429 | 3 | Ac.Ca./Am.Ac./O.St. | 82.3 | C8:1; Val; 27-OH-C |
| 430 | 4 | Ac.Ca./S.L./Am.Ac./B.Am. | 80.2 | C5-DC (C6-OH); SM (OH) C14:1; Phe; alpha-AAA |
| 431 | 4 | Ac.Ca./Am.Ac./O.St. | 83.9 | C10:2; Met; 27-OH-C; 5a,6a-EpoxyC |
| 432 | 5 | En.Met/Ac.Ca./S.L./B.Am./O.St. | 93.8 | Fum; C5-DC (C6-OH); SM C16:1; Met-SO; Cholestenone |
| 433 | 4 | En.Met/Ac.Ca./O.St. | 81.1 | Fum; C14:1; 24S-OH-C; 27-OH-C |
| 434 | 4 | En.Met/Am.Ac./O.St. | 93.6 | Fum; Tyr; 27-OH-C; Cholestenone |
| 435 | 6 | Ac.Ca./B.Am. | 85.9 | C0; C14:1; C5-DC (C6-OH); Cit; Met-SO; total DMA |
| 436 | 4 | Ac.Ca./Am.Ac./B.Am./O.St. | 92.3 | C6:1; Lys; total DMA; 27-OH-C |
| 437 | 4 | En.Met/Am.Ac./O.St./P.G. | 92.9 | Fum; Phe; 27-OH-C; 8-iso-PGF2a |
| 438 | 5 | Ac.Ca./Am.Ac./B.Am./O.St. | 85.7 | C5-DC (C6-OH); Arg; SDMA; total DMA; 27-OH-C |
| 439 | 3 | Ac.Ca./S.L./B.Am. | 80.5 | C0; SM (OH) C22:2; total DMA |
| 440 | 5 | Ac.Ca./S.L./B.Am./O.St. | 86.4 | C10:2; C8:1; SM C14:1; Carnosine; 27-OH-C |
| 441 | 5 | Ac.Ca./B.Am./O.St. | 80.6 | C16:2; C5-DC (C6-OH); C8:1; Met-SO; 27-OH-C |
| 442 | 4 | S.L./Am.Ac./B.Am./O.St. | 79.6 | SM (OH) C22:2; Cit; Ac-Orn; 27-OH-C |
| 443 | 3 | Am.Ac./B.Am./O.St. | 82 | Pro; Carnosine; 27-OH-C |
| 444 | 5 | Ac.Ca./S.L./B.Am./O.St. | 81.2 | C5:1; SM C24:1; SM (OH) C22:1; Carnosine; 24,25-EpoxyC |
| 445 | 5 | Ac.Ca./S.L./B.Am. | 82.5 | C5-DC (C6-OH); SM C16:1; SM C24:0; SM (OH) C22:1; Carnosine |
| 446 | 4 | En.Met/Ac.Ca./Am.Ac./B.Am. | 95.9 | Fum; C5-DC (C6-OH); Tyr; SDMA |
| 447 | 5 | En.Met/Ac.Ca./S.L./B.Am. | 87.4 | Lac; Pent-P; C3-DC (C4-OH); SM C16:1; Carnosine |
| 448 | 4 | Ac.Ca./S.L./B.Am. | 81.8 | C14:2-OH; C5-DC (C6-OH); SM (OH) C14:1; total DMA |
| 449 | 5 | Ac.Ca./S.L./Am.Ac./B.Am. | 80.4 | C5:1; SM C16:1; Cit; Met-SO; total DMA |
| 450 | 4 | Ac.Ca./S.L./B.Am./O.St. | 95 | C5:1; SM (OH) C14:1; total DMA; 27-OH-C |
| 451 | 4 | Ac.Ca./Am.Ac./B.Am./O.St. | 89.7 | C0; Cit; Met-SO; 27-OH-C |
| 452 | 4 | Ac.Ca./B.Am./O.St./P.G. | 87.8 | C14:1; Carnosine; 27-OH-C; 8-iso-PGF2a |
| 453 | 3 | S.L./B.Am./O.St. | 82.6 | SM (OH) C22:1; Carnosine; 27-OH-C |
| 454 | 4 | En.Met/Am.Ac./B.Am./O.St. | 93.8 | Fum; Tyr; Carnosine; 27-OH-C |
| 455 | 4 | Ac.Ca./Am.Ac./B.Am./O.St. | 82.9 | C10:2; Pro; Carnosine; 27-OH-C |
| 456 | 6 | Ac.Ca./S.L./Am.Ac./B.Am./O.St. | 91.8 | C14:2-OH; C5-DC (C6-OH); SM (OH) C22:2; Phe; SDMA; 27-OH-C |
| 457 | 5 | En.Met/Ac.Ca./S.L./B.Am. | 87 | Fum; C3-DC (C4-OH); C4:1; SM (OH) C22:2; Met-SO |
| 458 | 4 | En.Met/Ac.Ca./B.Am./O.St. | 94.6 | Fum; C5:1-DC; SDMA; 27-OH-C |
| 459 | 4 | En.Met/B.Am./O.St. | 81.3 | Pent-P; alpha-AAA; Carnosine; 27-OH-C |
| 460 | 4 | Ac.Ca./S.L./B.Am. | 86.2 | C5:1; SM C16:1; Carnosine; SDMA |
| 461 | 4 | En.Met/Ac.Ca./B.Am. | 90.3 | Fum; C2; Carnosine; total DMA |
| 462 | 5 | En.Met/Ac.Ca./S.L./B.Am. | 88.4 | Pent-P; C10:2; C6 (C4:1-DC); SM (OH) C22:2; Carnosine |
| 463 | 4 | En.Met/Ac.Ca./B.Am./P.G. | 80.1 | Lac; C8:1; Carnosine; LTB4 |
| 464 | 4 | S.L./B.Am./O.St. | 89.7 | SM (OH) C22:2; Met-SO; SDMA; 27-OH-C |
| 465 | 4 | En.Met/Ac.Ca./B.Am. | 82.5 | Lac; C10:2; C8:1; Carnosine |
| 466 | 4 | Ac.Ca./B.Am./P.G. | 82.2 | C10:2; C6 (C4:1-DC); Carnosine; LTB4 |
| 467 | 4 | Ac.Ca./S.L./B.Am./O.St. | 91.2 | C10:2; SM C26:0; Met-SO; 27-OH-C |
| 468 | 4 | Ac.Ca./S.L./Am.Ac./B.Am. | 84.6 | C5-DC (C6-OH); SM C16:1; Lys; total DMA |
| 469 | 5 | Ac.Ca./S.L./B.Am./O.St. | 90.4 | C5:1; SM C24:1; Carnosine; 24,25-EpoxyC; Cholestenone |

TABLE 10-continued

Metabolite combinations correlating with neurological behavioural score

| No. | Npar | Chemical Class | Accuracy | Model |
|---|---|---|---|---|
| 470 | 4 | En.Met/Ac.Ca./B.Am. | 87.4 | Fum; C10:2; C14:1; Carnosine |
| 471 | 6 | Ac.Ca./B.Am./O.St./P.G. | 92 | C5:1; C8:1; SDMA; total DMA; 5a,6a-EpoxyC; LTB4 |
| 472 | 4 | En.Met/Ac.Ca./B.Am./O.St. | 94.5 | Fum; C8:1; Met-SO; 27-OH-C |
| 473 | 4 | En.Met/Ac.Ca./Am.Ac. | 87.7 | Lac; Pent-P; C8:1; Cit |
| 474 | 4 | En.Met/Am.Ac./O.St./P.G. | 80.7 | Fum; Val; 27-OH-C; 8-iso-PGF2a |
| 475 | 4 | En.Met/Ac.Ca./B.Am./O.St. | 94.6 | Fum; C4:1; Met-SO; 27-OH-C |
| 476 | 4 | En.Met/Ac.Ca./B.Am. | 81.4 | Fum; C18:1; Carnosine; SDMA |
| 477 | 4 | En.Met/S.L./Am.Ac./O.St. | 87.5 | Fum; SM (OH) C22:2; Phe; 27-OH-C |
| 478 | 5 | Ac.Ca./S.L./B.Am. | 83.4 | C5-DC (C6-OH); C6:1; SM C16:0; Carnosine; SDMA |
| 479 | 6 | En.Met/Ac.Ca./S.L./B.Am./O.St./P.G. | 81.2 | Fum; C5:1; SM C16:1; Met-SO; 24-DH-Lanosterol; DHA |
| 480 | 5 | En.Met/Ac.Ca./S.L./O.St. | 79.6 | Pent-P; C10:2; C5:1; SM (OH) C14:1; 24,25-EpoxyC |
| 481 | 4 | En.Met/Ac.Ca./S.L./Am.Ac. | 83.2 | Fum; C5-DC (C6-OH); SM (OH) C22:2; Phe |
| 482 | 5 | En.Met/Ac.Ca./S.L./B.Am. | 87.3 | Fum; C5-DC (C6-OH); SM (OH) C14:1; Ac-Orn; SDMA |
| 483 | 5 | Ac.Ca./S.L./Am.Ac./B.Am. | 80.3 | C0; SM C24:1; SM (OH) C22:2; Cit; total DMA |
| 484 | 4 | Ac.Ca./S.L./Am.Ac./B.Am. | 79.7 | C5-DC (C6-OH); SM C16:1; Phe; alpha-AAA |
| 485 | 4 | B.Am./O.St. | 90.5 | Ac-Orn; Carnosine; 24,25-EpoxyC; 27-OH-C |
| 486 | 4 | Ac.Ca./Am.Ac./O.St. | 89.8 | C5-DC (C6-OH); Cit; Tyr; 27-OH-C |
| 487 | 4 | En.Met/Am.Ac./O.St. | 83.6 | Fum; Lac; Phe; 27-OH-C |
| 488 | 4 | Ac.Ca./S.L./B.Am. | 85.3 | C5-DC (C6-OH); SM C16:0; alpha-AAA; Met-SO |
| 489 | 5 | Ac.Ca./B.Am. | 80.9 | C10:2; C14:1; C4:1; C5:1; Met-SO |
| 490 | 3 | S.L./B.Am./O.St. | 86.3 | SM C24:1; Carnosine; 27-OH-C |
| 491 | 4 | En.Met/Ac.Ca./S.L. | 82.8 | Pent-P; C5:1; C8:1; SM (OH) C22:2 |
| 492 | 5 | En.Met/Ac.Ca./S.L./B.Am. | 90.4 | Fum; C5-DC (C6-OH); SM C16:1; Ac-Orn; SDMA |
| 493 | 4 | En.Met/Ac.Ca. | 79.9 | Fum; Pent-P; Suc; C14:1 |
| 494 | 4 | S.L./B.Am./O.St. | 84.9 | SM (OH) C22:2; Ac-Orn; alpha-AAA; 27-OH-C |
| 495 | 5 | Ac.Ca./S.L./Am.Ac./B.Am./O.St. | 85 | C5-DC (C6-OH); SM (OH) C22:2; Ala; SDMA; 27-OH-C |
| 496 | 3 | Ac.Ca./S.L./B.Am. | 79 | C5:1; SM C24:1; SDMA |
| 497 | 4 | En.Met/B.Am./O.St. | 90.2 | Lac; Carnosine; 24-DH-Lanosterol; 27-OH-C |
| 498 | 4 | En.Met/Ac.Ca./S.L./B.Am. | 81 | Lac; C2; SM (OH) C22:2; Carnosine |
| 499 | 4 | En.Met/B.Am./O.St./P.G. | 81.5 | Fum; Ac-Orn; 27-OH-C; DHA |
| 500 | 4 | Ac.Ca./B.Am./O.St. | 81.8 | C10:2; Carnosine; 24-DH-Lanosterol; 27-OH-C |
| 501 | 4 | En.Met/Ac.Ca./B.Am. | 84 | Fum; Suc; C14:1; SDMA |
| 502 | 4 | En.Met/Ac.Ca./B.Am. | 90.7 | Fum; Suc; C14:1; Carnosine |
| 503 | 4 | En.Met/Am.Ac./B.Am./O.St. | 95.2 | Fum; Tyr; Met-SO; 27-OH-C |
| 504 | 4 | Ac.Ca./S.L./O.St. | 84 | C5:1-DC; SM (OH) C22:2; 24,25-EpoxyC; 27-OH-C |
| 505 | 4 | En.Met/Am.Ac./O.St. | 91.7 | Fum; Phe; 24-DH-Lanosterol; 27-OH-C |
| 506 | 4 | En.Met/Ac.Ca./B.Am. | 81.9 | Fum; C0; C5:1; Met-SO |
| 507 | 4 | Ac.Ca./Am.Ac./O.St. | 93.9 | C8:1; Ala; total DMA; 27-OH-C |
| 508 | 4 | En.Met/B.Am./O.St. | 81.3 | Fum; Ac-Orn; 27-OH-C; 5a,6a-EpoxyC |
| 509 | 4 | Ac.Ca./B.Am. | 83.9 | C5:1; Creatinine; SDMA; total DMA |
| 510 | 5 | Ac.Ca./S.L./B.Am./O.St. | 80.6 | C4:1; SM C24:1; Carnosine; 24,25-EpoxyC; 27-OH-C |
| 511 | 3 | Ac.Ca./Am.Ac./O.St. | 82.9 | C8:1; Leu; 27-OH-C |
| 512 | 6 | En.Met/Ac.Ca./Am.Ac./B.Am. | 97.3 | Fum; C5:1; C5-DC (C6-OH); Phe; SDMA; total DMA |
| 513 | 3 | En.Met/Ac.Ca./B.Am. | 80.4 | Fum; C12; Carnosine |
| 514 | 4 | Ac.Ca./Am.Ac. | 88.4 | C10:2; C5-DC (C6-OH); C8:1; Phe |
| 515 | 4 | B.Am./O.St. | 83.8 | Met-SO; 24-DH-Lanosterol; 27-OH-C; Cholestenone |
| 516 | 4 | Ac.Ca./S.L./B.Am. | 81.3 | C0; C5-DC (C6-OH); SM C26:0; Met-SO |
| 517 | 5 | Ac.Ca./S.L./Am.Ac./B.Am. | 82.1 | C5-DC (C6-OH); SM (OH) C22:2; Pro; Val; SDMA |
| 518 | 4 | Ac.Ca./B.Am./O.St. | 82.9 | C4:1; C5:1; total DMA; 24,25-EpoxyC |
| 519 | 4 | Ac.Ca./B.Am./O.St. | 87.4 | Ac-Orn; total DMA; 24,25-EpoxyC; 27-OH-C |
| 520 | 4 | Ac.Ca./B.Am./P.G. | 87.5 | C10:2; C14:1-OH; Carnosine; LTB4 |
| 521 | 5 | S.L./B.Am./O.St. | 88.4 | SM C24:1; SM C26:1; SM (OH) C22:1; total DMA; 27-OH-C |
| 522 | 4 | En.Met/Ac.Ca./S.L./B.Am. | 81.2 | Suc; C8:1; SM C26:0; total DMA |
| 523 | 4 | En.Met/Am.Ac./O.St. | 93.5 | Fum; Tyr; Val; 27-OH-C |
| 524 | 5 | S.L./B.Am./O.St. | 91.2 | SM C16:1; Ac-Orn; Carnosine; SDMA; 27-OH-C |
| 525 | 4 | En.Met/Ac.Ca./S.L./B.Am. | 84.1 | Fum; C5-DC (C6-OH); SM (OH) C14:1; Carnosine |
| 526 | 5 | Ac.Ca./S.L./B.Am./O.St. | 81.4 | C10:2; C5:1; SM (OH) C14:1; Carnosine; 24,25-EpoxyC |
| 527 | 4 | Ac.Ca./S.L./B.Am. | 83.1 | C3-DC (C4-OH); SM C26:1; SM (OH) C14:1; Carnosine |
| 528 | 4 | Ac.Ca./Am.Ac./B.Am./O.St. | 87.6 | C10:2; Thr; total DMA; 27-OH-C |
| 529 | 4 | Ac.Ca./B.Am./O.St. | 95.2 | C6 (C4:1-DC); Carnosine; Met-SO; 27-OH-C |
| 530 | 4 | S.L./Am.Ac./B.Am./O.St. | 95.1 | SM (OH) C14:1; Tyr; Carnosine; 27-OH-C |
| 531 | 4 | En.Met/S.L./B.Am./O.St. | 91.9 | Fum; SM C24:1; total DMA; 27-OH-C |
| 532 | 5 | En.Met/Ac.Ca./Am.Ac./O.St. | 84.5 | Fum; C5:1; Met; 24,25-EpoxyC; Cholestenone |
| 533 | 3 | Am.Ac./B.Am./O.St. | 84.3 | Asn; Met-SO; 27-OH-C |
| 534 | 4 | Ac.Ca./S.L./B.Am. | 85.6 | C5-DC (C6-OH); SM (OH) C22:2; alpha-AAA; Met-SO |
| 535 | 4 | En.Met/S.L./Am.Ac./O.St. | 86.5 | Fum; SM (OH) C22:2; Thr; 27-OH-C |
| 536 | 5 | Ac.Ca./S.L./B.Am./O.St. | 89.7 | C5-DC (C6-OH); SM C16:1; Carnosine; total DMA; 24-DH-Lanosterol |
| 537 | 4 | Ac.Ca./Am.Ac./B.Am. | 89.8 | C5-DC (C6-OH); Leu; Val; total DMA |
| 538 | 5 | S.L./Am.Ac./B.Am./O.St. | 94.4 | SM C16:1; Phe; Carnosine; total DMA; 27-OH-C |
| 539 | 4 | Am.Ac./O.St. | 79 | Met; 24,25-EpoxyC; 27-OH-C; 5a,6a-EpoxyC |
| 540 | 5 | En.Met/Ac.Ca./B.Am./O.St. | 97.6 | Fum; C5:1; Met-SO; total DMA; 27-OH-C |
| 541 | 4 | Ac.Ca./B.Am./O.St. | 81.3 | C10:2; Ac-Orn; alpha-AAA; 27-OH-C |
| 542 | 4 | Ac.Ca./Am.Ac./O.St./P.G. | 87.8 | C0; Phe; 27-OH-C; 8-iso-PGF2a |
| 543 | 4 | Am.Ac./O.St. | 90.7 | Phe; 24-DH-Lanosterol; 27-OH-C; Cholestenone |
| 544 | 4 | En.Met/Ac.Ca./B.Am. | 84.4 | Fum; C2; SDMA; total DMA |
| 545 | 5 | En.Met/Ac.Ca./B.Am. | 84.9 | Fum; C10:2; C5-DC (C6-OH); Ac-Orn; Carnosine |

TABLE 10-continued

Metabolite combinations correlating with neurological behavioural score

| No. | Npar | Chemical Class | Accuracy | Model |
|---|---|---|---|---|
| 546 | 4 | Ac.Ca./S.L./B.Am./O.St. | 86.5 | C8:1; SM (OH) C16:1; Carnosine; 27-OH-C |
| 547 | 4 | Ac.Ca./S.L./B.Am. | 84 | C14:1; C5-DC (C6-OH); SM (OH) C22:2; Carnosine |
| 548 | 3 | Ac.Ca./Am.Ac. | 85 | C10:2; C5-DC (C6-OH); Tyr |
| 549 | 5 | En.Met/Ac.Ca./Am.Ac./O.St. | 85.5 | Lac; C5:1-DC; C6 (C4:1-DC); Phe; 24,25-EpoxyC |
| 550 | 6 | En.Met/Ac.Ca./Am.Ac./B.Am. | 91.4 | Pent-P; C5:1; C8:1; Cit; Phe; SDMA |
| 551 | 4 | En.Met/Ac.Ca./S.L./B.Am. | 82.4 | Fum; C3-DC (C4-OH); SM (OH) C22:2; SDMA |
| 552 | 4 | Ac.Ca./B.Am./O.St. | 83.2 | C5-DC (C6-OH); Carnosine; total DMA; 24-DH-Lanosterol |
| 553 | 3 | Ac.Ca./Am.Ac./B.Am. | 89.7 | C5-DC (C6-OH); Lys; total DMA |
| 554 | 4 | Ac.Ca./S.L./B.Am. | 89.1 | C5:1; SM (OH) C22:2; SDMA; total DMA |
| 555 | 5 | Ac.Ca./S.L./B.Am. | 80.8 | C10:2; C5:1; C8:1; SM (OH) C14:1; Met-SO |
| 556 | 4 | Ac.Ca./S.L./B.Am./O.St. | 88.8 | C10:2; SM C24:1; Carnosine; 27-OH-C |
| 557 | 4 | Ac.Ca./S.L./B.Am. | 84.9 | C10:2; C5:1; SM C16:1; total DMA |
| 558 | 4 | En.Met/Am.Ac./B.Am./O.St. | 94.7 | Fum; Ala; total DMA; 27-OH-C |
| 559 | 4 | En.Met/S.L./B.Am./O.St. | 91.4 | Pent-P; SM C26:0; Met-SO; 27-OH-C |
| 560 | 4 | En.Met/Ac.Ca./S.L./B.Am. | 83.4 | Fum; C6 (C4:1-DC); SM (OH) C22:2; Carnosine |
| 561 | 4 | Ac.Ca./S.L./B.Am./O.St. | 98.3 | C5:1; SM (OH) C22:2; total DMA; 27-OH-C |
| 562 | 4 | En.Met/Ac.Ca./B.Am. | 93.5 | Lac; C10:2; C14:1-OH; Carnosine |
| 563 | 4 | En.Met/Ac.Ca./O.St. | 84 | Fum; C14:1-OH; C5:1-DC; 24,25-EpoxyC |
| 564 | 4 | En.Met/Ac.Ca./B.Am./P.G. | 85.2 | Fum; C8:1; Carnosine; 8-iso-PGF2a |
| 565 | 4 | Ac.Ca./S.L./Am.Ac./O.St. | 81.9 | C5-DC (C6-OH); SM (OH) C14:1; Tyr; Cholestenone |
| 566 | 5 | En.Met/Ac.Ca./B.Am./O.St. | 87 | Fum; C14:1; Carnosine; 24S-OH-C; 27-OH-C |
| 567 | 4 | En.Met/Ac.Ca./Am.Ac./O.St. | 80.1 | Fum; C8:1; Leu; 27-OH-C |
| 568 | 4 | Ac.Ca./S.L./B.Am. | 89.4 | C5-DC (C6-OH); SM (OH) C14:1; SM (OH) C22:2; Carnosine |
| 569 | 4 | En.Met/S.L./B.Am. | 82.3 | Pent-P; Suc; SM C26:0; SDMA |
| 570 | 5 | En.Met/Ac.Ca./Am.Ac./B.Am. | 81.2 | Fum; C10:2; C6 (C4:1-DC); Tyr; SDMA |
| 571 | 6 | Ac.Ca./B.Am./O.St. | 90.9 | C5:1; C5-DC (C6-OH); Ac-Orn; alpha-AAA; total DMA; 24,25-EpoxyC |
| 572 | 5 | Ac.Ca./Am.Ac./B.Am. | 80.6 | C4:1; C5-DC (C6-OH); C8:1; Ala; total DMA |
| 573 | 5 | En.Met/Ac.Ca./O.St. | 80.5 | Fum; C14:1; C5:1; 24-DH-Lanosterol; 3b,5a,6b-THC |
| 574 | 4 | En.Met/Ac.Ca./B.Am./O.St. | 87.2 | Fum; C5:1; Met-SO; 24,25-EpoxyC |
| 575 | 5 | Ac.Ca./Am.Ac./B.Am./O.St. | 84.6 | C5:1; Glu; SDMA; 24-DH-Lanosterol; Cholestenone |
| 576 | 4 | En.Met/Ac.Ca./S.L./B.Am. | 86.1 | Pent-P; C3-DC (C4-OH); SM (OH) C22:2; Carnosine |
| 577 | 4 | Ac.Ca./Am.Ac./B.Am./O.St. | 90 | C10:2; Pro; total DMA; 27-OH-C |
| 578 | 4 | En.Met/Ac.Ca./S.L./B.Am. | 85.5 | Suc; C5-DC (C6-OH); SM C26:0; total DMA |
| 579 | 5 | En.Met/Ac.Ca./B.Am. | 91.3 | Fum; Pent-P; C6 (C4:1-DC); Ac-Orn; total DMA |
| 580 | 4 | En.Met/S.L./B.Am./O.St. | 84.9 | Fum; SM C16:1; Ac-Orn; 27-OH-C |
| 581 | 4 | En.Met/Ac.Ca./Am.Ac./O.St. | 80.2 | Fum; C5-DC (C6-OH); Phe; 24,25-EpoxyC |
| 582 | 4 | Ac.Ca./S.L./B.Am. | 88 | C5-DC (C6-OH); SM C16:0; SM (OH) C16:1; Carnosine |
| 583 | 4 | En.Met/Ac.Ca./B.Am./O.St. | 88.1 | Lac; C14:1-OH; Carnosine; 27-OH-C |
| 584 | 4 | Ac.Ca./S.L./B.Am./O.St. | 84.7 | C5:1; SM (OH) C14:1; SDMA; 27-OH-C |
| 585 | 4 | Ac.Ca./S.L./B.Am. | 91.4 | C5-DC (C6-OH); SM (OH) C22:2; Carnosine; SDMA |
| 586 | 6 | Ac.Ca./S.L./Am.Ac./O.St. | 96.2 | C10:2; C5:1; C8:1; SM C24:1; Phe; 24,25-EpoxyC |
| 587 | 4 | Ac.Ca./S.L./B.Am./O.St. | 79.8 | C5:1; SM C16:0; Carnosine; Cholestenone |
| 588 | 4 | En.Met/Ac.Ca./B.Am. | 86.4 | Fum; C14:1; Ac-Orn; Carnosine |
| 589 | 4 | Ac.Ca./S.L./Am.Ac./B.Am. | 82.6 | C5-DC (C6-OH); SM (OH) C14:1; Tyr; alpha-AAA |
| 590 | 5 | Ac.Ca./B.Am./O.St. | 95.3 | C10:2; C14:1; Carnosine; Met-SO; 27-OH-C |
| 591 | 4 | Ac.Ca./B.Am./O.St. | 80.8 | C5:1; Met-SO; total DMA; 24,25-EpoxyC |
| 592 | 4 | Ac.Ca./Am.Ac./O.St. | 91.2 | C10:2; C8:1; Val; 27-OH-C |
| 593 | 5 | Ac.Ca./S.L./Am.Ac. | 90.5 | C10:2; C5:1; C8:1; SM C16:0; Phe |
| 594 | 5 | Ac.Ca./S.L./O.St. | 80 | C5:1; SM C16:1; SM C24:1; 27-OH-C; Cholestenone |
| 595 | 5 | Ac.Ca./B.Am./O.St. | 84.8 | C5:1-DC; Ac-Orn; alpha-AAA; SDMA; 27-OH-C |
| 596 | 4 | En.Met/Ac.Ca./B.Am. | 90.6 | Fum; C5-OH (C3-DC-M); Carnosine; total DMA |
| 597 | 4 | En.Met/B.Am./O.St. | 87.1 | Fum; Carnosine; SDMA; 27-OH-C |
| 598 | 5 | En.Met/Ac.Ca./S.L./B.Am. | 87.2 | Fum; C5:1; C8:1; SM (OH) C14:1; Carnosine |
| 599 | 4 | S.L./B.Am./O.St. | 94.3 | SM (OH) C14:1; Ac-Orn; Carnosine; 27-OH-C |
| 600 | 5 | S.L./Am.Ac./B.Am./O.St. | 90.7 | SM (OH) C14:1; SM (OH) C22:2; Thr; total DMA; 27-OH-C |
| 601 | 4 | Ac.Ca./Am.Ac./B.Am. | 79.1 | C5-DC (C6-OH); Tyr; Val; SDMA |
| 602 | 4 | En.Met/B.Am./O.St./P.G. | 80.6 | Fum; Carnosine; 27-OH-C; 8-iso-PGF2a |
| 603 | 4 | En.Met/B.Am. | 85.8 | Fum; Pent-P; SDMA; total DMA |
| 604 | 5 | Ac.Ca./S.L./B.Am./O.St. | 79 | C10:2; C5:1; SM C16:0; Carnosine; 24,25-EpoxyC |
| 605 | 5 | Ac.Ca./S.L./B.Am. | 82.3 | C0; SM (OH) C14:1; SM (OH) C22:2; Carnosine; total DMA |
| 606 | 4 | En.Met/Ac.Ca. | 82.7 | Fum; Pent-P; Suc; C14:1-OH |
| 607 | 4 | En.Met/B.Am./O.St. | 86.3 | Fum; Ac-Orn; 27-OH-C; Cholestenone |
| 608 | 5 | B.Am./O.St. | 85 | Carnosine; SDMA; 24-DH-Lanosterol; 27-OH-C; Cholestenone |
| 609 | 4 | En.Met/S.L./B.Am./O.St. | 80.9 | Fum; SM C16:0; Carnosine; 27-OH-C |
| 610 | 4 | Ac.Ca./S.L./Am.Ac. | 84.8 | C5-DC (C6-OH); SM (OH) C22:2; Lys; Tyr |
| 611 | 5 | Ac.Ca./Am.Ac./B.Am./O.St. | 91.9 | C5:1; Met; total DMA; 24,25-EpoxyC; 27-OH-C |
| 612 | 4 | Ac.Ca./Am.Ac./O.St. | 83.2 | C5-DC (C6-OH); C8:1; Tyr; 24,25-EpoxyC |
| 613 | 5 | En.Met/Ac.Ca./S.L./B.Am. | 89.5 | Pent-P; C5:1; SM (OH) C14:1; alpha-AAA; SDMA |
| 614 | 4 | En.Met/Ac.Ca./Am.Ac./O.St. | 85.6 | Fum; C8:1; Phe; 27-OH-C |
| 615 | 4 | En.Met/Ac.Ca./B.Am. | 89.9 | Fum; C5-DC (C6-OH); alpha-AAA; Met-SO |
| 616 | 6 | En.Met/S.L./Am.Ac./B.Am./O.St. | 84.8 | Pent-P; SM (OH) C14:1; Cit; Phe; Ac-Orn; 27-OH-C |
| 617 | 4 | Ac.Ca./S.L./B.Am./O.St. | 82.8 | C5:1; SM C16:1; SDMA; 27-OH-C |
| 618 | 4 | Ac.Ca./S.L./B.Am. | 81.1 | C10:2; C8:1; SM (OH) C14:1; Carnosine |
| 619 | 4 | S.L./B.Am./O.St. | 83.9 | SM C16:0; alpha-AAA; Carnosine; 27-OH-C |
| 620 | 4 | En.Met/B.Am./O.St. | 93.1 | Fum; OAA; total DMA; 27-OH-C |
| 621 | 4 | En.Met/Ac.Ca./B.Am. | 90.2 | Fum; C4:1; C5-DC (C6-OH); Met-SO |

TABLE 10-continued

Metabolite combinations correlating with neurological behavioural score

| No. | Npar | Chemical Class | Accuracy | Model |
|---|---|---|---|---|
| 622 | 4 | En.Met/S.L./B.Am./O.St. | 95.5 | Fum; SM C16:1; Met-SO; 27-OH-C |
| 623 | 5 | Ac.Ca./S.L./B.Am./O.St. | 85.6 | C8:1; SM C26:0; Ac-Orn; Carnosine; 27-OH-C |
| 624 | 5 | Ac.Ca./Am.Ac./B.Am./O.St. | 84.5 | C8:1; Cit; Ac-Orn; Carnosine; 27-OH-C |
| 625 | 5 | En.Met/Ac.Ca./B.Am. | 80.6 | Fum; Pent-P; Suc; C6 (C4:1-DC); Ac-Orn |
| 626 | 4 | Ac.Ca./B.Am./O.St. | 94.4 | C5-DC (C6-OH); alpha-AAA; Met-SO; 27-OH-C |
| 627 | 4 | Ac.Ca./Am.Ac./B.Am. | 93.3 | C5-DC (C6-OH); C8:1; Pro; total DMA |
| 628 | 4 | Ac.Ca./S.L./B.Am./O.St. | 82.4 | C0; SM (OH) C22:2; total DMA; 3b,5a,6b-THC |
| 629 | 4 | En.Met/Ac.Ca./B.Am./O.St. | 95.5 | Fum; C14:1-OH; Met-SO; 27-OH-C |
| 630 | 5 | En.Met/Ac.Ca./Am.Ac./B.Am. | 94.7 | Hex-P; C5-DC (C6-OH); Leu; Pro; total DMA |
| 631 | 4 | En.Met/Ac.Ca./O.St. | 82 | Fum; Suc; C14:2-OH; 27-OH-C |
| 632 | 4 | Ac.Ca./S.L./Am.Ac./B.Am. | 83.4 | C5-DC (C6-OH); SM C16:1; Tyr; alpha-AAA |
| 633 | 4 | Ac.Ca./S.L./Am.Ac. | 82.3 | C10:2; C5-DC (C6-OH); SM (OH) C22:2; Thr |
| 634 | 4 | Ac.Ca./B.Am. | 88.1 | C10:2; C6 (C4:1-DC); C8:1; Carnosine |
| 635 | 5 | Ac.Ca./S.L./B.Am./O.St. | 91 | C10:2; SM (OH) C14:1; Met-SO; 27-OH-C; 5a,6a-EpoxyC |
| 636 | 5 | En.Met/Ac.Ca./B.Am./O.St. | 88.9 | Fum; C14:1-OH; C5:1; Ac-Orn; 3b,5a,6b-THC |
| 637 | 4 | En.Met/Am.Ac./B.Am./O.St. | 94.3 | Fum; Phe; Met-SO; 27-OH-C |
| 638 | 3 | En.Met/B.Am./O.St. | 83.6 | Fum; Met-SO; 24,25-EpoxyC |
| 639 | 4 | En.Met/Am.Ac./B.Am./O.St. | 95.6 | Fum; Val; Met-SO; 27-OH-C |
| 640 | 3 | S.L./B.Am./O.St. | 90.4 | SM C16:1; Met-SO; 27-OH-C |
| 641 | 5 | En.Met/Ac.Ca./S.L./B.Am./O.St. | 83.6 | Fum; C5:1-DC; SM (OH) C14:1; Carnosine; 27-OH-C |
| 642 | 4 | Ac.Ca./Am.Ac./O.St./P.G. | 84.6 | C14:1; Phe; 27-OH-C; 8-iso-PGF2a |
| 643 | 4 | Am.Ac./O.St./P.G. | 85.9 | Thr; 27-OH-C; 8-iso-PGF2a; LTB4 |
| 644 | 4 | En.Met/Ac.Ca./S.L./B.Am. | 86.8 | Fum; C5-DC (C6-OH); SM (OH) C22:2; Met-SO |
| 645 | 4 | Ac.Ca./B.Am./O.St. | 84.5 | C5:1; Ac-Orn; total DMA; 24,25-EpoxyC |
| 646 | 4 | En.Met/Ac.Ca./B.Am./O.St. | 94.3 | Fum; Met; total DMA; 27-OH-C |
| 647 | 5 | En.Met/Ac.Ca./B.Am. | 82.4 | Suc; C5-DC (C6-OH); alpha-AAA; Met-SO; Spermidine |
| 648 | 4 | Am.Ac./O.St. | 94 | Tyr; 24-DH-Lanosterol; 27-OH-C; Cholestenone |
| 649 | 5 | En.Met/Ac.Ca./B.Am. | 87.9 | Fum; C5; Met-SO; SDMA; total DMA |
| 650 | 6 | En.Met/Ac.Ca./B.Am./P.G. | 80.9 | Lac; C10:2; C5-DC (C6-OH); C8:1; total DMA; LTB4 |
| 651 | 3 | En.Met/Am.Ac./O.St. | 90.1 | Fum; Asp; 27-OH-C |
| 652 | 6 | Ac.Ca./S.L./B.Am./O.St. | 85.7 | C5-DC (C6-OH); C8:1; SM (OH) C22:2; Ac-Orn; Carnosine; 24,25-EpoxyC |
| 653 | 4 | En.Met/Ac.Ca./B.Am./O.St. | 95.4 | Fum; C5:1; total DMA; 27-OH-C |
| 654 | 5 | En.Met/Ac.Ca./S.L./B.Am. | 86.6 | Pent-P; C4; SM C24:1; SM (OH) C22:2; Carnosine |
| 655 | 5 | Ac.Ca./Am.Ac./B.Am. | 97 | C10:2; C5-DC (C6-OH); C6 (C4:1-DC); Tyr; Carnosine |
| 656 | 5 | En.Met/B.Am./O.St. | 85.3 | Fum; Suc; Met-SO; SDMA; 24,25-EpoxyC |
| 657 | 4 | En.Met/Ac.Ca./S.L./B.Am. | 87.5 | Fum; C3-DC (C4-OH); SM (OH) C22:2; Carnosine |
| 658 | 4 | S.L./B.Am./O.St. | 89 | SM (OH) C14:1; Carnosine; Met-SO; 27-OH-C |
| 659 | 5 | En.Met/Ac.Ca./B.Am./O.St. | 89.3 | Fum; C4:1; C5:1; Met-SO; 24,25-EpoxyC |
| 660 | 3 | S.L./B.Am./O.St. | 85 | SM (OH) C16:1; Carnosine; 27-OH-C |
| 661 | 6 | Ac.Ca./B.Am./O.St. | 83.9 | C0; C10:2; C14:2-OH; Carnosine; Met-SO; 24,25-EpoxyC |
| 662 | 6 | En.Met/Ac.Ca./Am.Ac./B.Am./O.St. | 96.4 | Fum; C5:1; His; SDMA; total DMA; 27-OH-C |
| 663 | 5 | En.Met/Am.Ac./B.Am./O.St./P.G. | 90.1 | Fum; Phe; Carnosine; 27-OH-C; DHA |
| 664 | 4 | En.Met/Ac.Ca./B.Am./O.St. | 95.5 | Fum; C3-DC (C4-OH); Met-SO; 27-OH-C |
| 665 | 6 | En.Met/Ac.Ca./Am.Ac./B.Am./O.St. | 87.7 | Suc; C5-DC (C6-OH); Tyr; Ac-Orn; alpha-AAA; 24,25-EpoxyC |
| 666 | 4 | Ac.Ca./B.Am./O.St. | 86.6 | C14:1; C5:1; total DMA; 3b,5a,6b-THC |
| 667 | 5 | Ac.Ca./S.L./B.Am. | 81.1 | C10:2; C5:1; SM C16:0; SM C16:1; Carnosine |
| 668 | 4 | Ac.Ca./Am.Ac./B.Am. | 83.5 | C5-DC (C6-OH); Tyr; SDMA; total DMA |
| 669 | 4 | Ac.Ca./Am.Ac./B.Am. | 79.9 | C5-DC (C6-OH); Leu; Lys; SDMA |
| 670 | 4 | En.Met/Ac.Ca./B.Am./O.St. | 94.3 | Fum; C6 (C4:1-DC); Met-SO; 27-OH-C |
| 671 | 5 | En.Met/Ac.Ca./Am.Ac./B.Am. | 94.7 | Fum; C10:2; C5-DC (C6-OH); Phe; SDMA |
| 672 | 3 | Ac.Ca./S.L./Am.Ac. | 87 | C5-DC (C6-OH); SM (OH) C22:2; Tyr |
| 673 | 4 | Ac.Ca./S.L./B.Am. | 79.1 | C6 (C4:1-DC); SM (OH) C22:2; Carnosine; total DMA |
| 674 | 4 | En.Met/Ac.Ca./B.Am. | 89.5 | Fum; C14:1-OH; C6 (C4:1-DC); Met-SO |
| 675 | 4 | Ac.Ca./S.L./Am.Ac./O.St. | 91.3 | C10:2; SM (OH) C22:2; Thr; 27-OH-C |
| 676 | 4 | S.L./B.Am./O.St. | 86.1 | SM C16:1; Carnosine; SDMA; 27-OH-C |
| 677 | 5 | En.Met/Ac.Ca./B.Am. | 92.7 | Fum; C10:2; C6 (C4:1-DC); Ac-Orn; Carnosine |
| 678 | 5 | Ac.Ca./S.L./B.Am. | 80.5 | C3-DC (C4-OH); SM C16:1; SM (OH) C14:1; Carnosine; total DMA |
| 679 | 4 | En.Met/B.Am./O.St. | 96.3 | Fum; Met-SO; 27-OH-C; Cholestenone |
| 680 | 4 | Ac.Ca./Am.Ac./B.Am./O.St. | 87 | C10:2; Lys; Ac-Orn; 27-OH-C |
| 681 | 4 | En.Met/Ac.Ca./B.Am. | 89.6 | Fum; C6 (C4:1-DC); Carnosine; total DMA |
| 682 | 5 | Ac.Ca./S.L./Am.Ac./B.Am./O.St. | 94.1 | C5:1; SM (OH) C14:1; Phe; SDMA; 27-OH-C |
| 683 | 4 | Ac.Ca./B.Am./O.St. | 82.7 | C5:1; total DMA; Cholestenone; 3b,5a,6b-THC |
| 684 | 4 | En.Met/Ac.Ca./B.Am. | 86.1 | Fum; SDMA; Spermidine; 27-OH-C |
| 685 | 5 | En.Met/B.Am./O.St. | 96.6 | Fum; Met-SO; SDMA; 27-OH-C; Cholestenone |
| 686 | 3 | En.Met/Am.Ac./O.St. | 80.6 | Fum; Asn; 27-OH-C |
| 687 | 5 | Ac.Ca./S.L./Am.Ac. | 79.1 | C10:2; C5-DC (C6-OH); C8:1; SM (OH) C22:2; Val |
| 688 | 5 | En.Met/Ac.Ca./B.Am. | 92.4 | Fum; C4:1; C5:1; Met-SO; SDMA |
| 689 | 5 | Ac.Ca./S.L./B.Am. | 80.4 | C0; C8:1; SM (OH) C14:1; Carnosine; total DMA |
| 690 | 4 | En.Met/Ac.Ca./B.Am. | 94.7 | Fum; C5-DC (C6-OH); Met-SO; SDMA |
| 691 | 3 | Ac.Ca./B.Am./O.St. | 83.1 | C5:1; total DMA; 3b,5a,6b-THC |
| 692 | 4 | En.Met/Ac.Ca./Am.Ac. | 87.4 | Fum; C10:2; C6 (C4:1-DC); Phe |
| 693 | 4 | Ac.Ca./S.L./B.Am. | 83.8 | C14:2-OH; C5-DC (C6-OH); SM C26:0; total DMA |
| 694 | 4 | En.Met/Ac.Ca./B.Am./O.St. | 80 | Fum; C10; Ac-Orn; 27-OH-C |
| 695 | 4 | Ac.Ca./B.Am./O.St. | 83.3 | C6 (C4:1-DC); Ac-Orn; Carnosine; 24,25-EpoxyC |
| 696 | 4 | S.L./Am.Ac./O.St. | 90.3 | SM C16:1; Phe; 27-OH-C; Cholestenone |
| 697 | 4 | En.Met/Ac.Ca./S.L./B.Am. | 82.5 | Fum; C2; SM (OH) C22:2; Carnosine |

TABLE 10-continued

Metabolite combinations correlating with neurological behavioural score

| No. | Npar | Chemical Class | Accuracy | Model |
|---|---|---|---|---|
| 698 | 5 | Ac.Ca./S.L./B.Am./O.St. | 89.6 | C5-DC (C6-OH); SM (OH) C22:2; SDMA; total DMA; 3b,5a,6b-THC |
| 699 | 3 | S.L./O.St. | 80.1 | SM C26:1; SM (OH) C22:2; 27-OH-C |
| 700 | 4 | En.Met/Ac.Ca./B.Am./O.St. | 86.1 | Fum; C16:2; SDMA; 27-OH-C |
| 701 | 5 | Ac.Ca./Am.Ac./B.Am./O.St. | 83.5 | C5:1; Cit; Ac-Orn; SDMA; 3b,5a,6b-THC |
| 702 | 5 | En.Met/Ac.Ca./Am.Ac./O.St. | 93.4 | Fum; C5:1; Met; 24,25-EpoxyC; 27-OH-C |
| 703 | 4 | Ac.Ca./S.L./B.Am. | 80 | C5-DC (C6-OH); SM C24:1; Ac-Orn; alpha-AAA |
| 704 | 4 | Ac.Ca./B.Am./P.G. | 87.5 | C6 (C4:1-DC); Carnosine; 8-iso-PGF2a; LTB4 |
| 705 | 4 | Ac.Ca./S.L./Am.Ac./B.Am. | 86.4 | C5-DC (C6-OH); SM (OH) C14:1; Lys; total DMA |
| 706 | 4 | Ac.Ca./S.L./B.Am. | 88.3 | C5-DC (C6-OH); SM C16:1; alpha-AAA; Met-SO |
| 707 | 5 | Ac.Ca./B.Am./P.G. | 85.8 | C10:2; C5:1; C8:1; total DMA; LTB4 |
| 708 | 4 | En.Met/Ac.Ca./S.L./B.Am. | 83.6 | Pent-P; C6 (C4:1-DC); SM (OH) C22:2; Carnosine |
| 709 | 4 | En.Met/Ac.Ca./B.Am. | 86 | Fum; C6 (C4:1-DC); C8:1; Carnosine |
| 710 | 4 | Ac.Ca./B.Am./O.St. | 81.4 | C5:1; Met-SO; SDMA; 24,25-EpoxyC |
| 711 | 4 | En.Met/Am.Ac./B.Am./O.St. | 82.9 | Fum; Leu; Carnosine; 27-OH-C |
| 712 | 4 | Ac.Ca./B.Am. | 87.6 | C10:2; C5-DC (C6-OH); alpha-AAA; Met-SO |
| 713 | 4 | S.L./Am.Ac./O.St. | 81.9 | SM (OH) C22:2; Lys; Val; 27-OH-C |
| 714 | 4 | En.Met/Ac.Ca./B.Am. | 90.3 | Fum; C5-DC (C6-OH); C8:1; Met-SO |
| 715 | 6 | Ac.Ca./S.L./Am.Ac./B.Am. | 80.5 | C10:2; C4:1; C5:1; SM (OH) C14:1; Phe; alpha-AAA |
| 716 | 5 | Ac.Ca./S.L./Am.Ac./B.Am./O.St. | 90.7 | C5:1; SM C24:1; Cit; SDMA; 5a,6a-EpoxyC |
| 717 | 4 | En.Met/S.L./Am.Ac./B.Am. | 79.3 | Fum; SM (OH) C22:2; Arg; total DMA |

TABLE 11

Combinations formed with a lead metabolite that correlate with damage of hippocampus

| No. | Npar | Accuracy | Lead metabolite | Additional metabolites |
|---|---|---|---|---|
| 1 | 3 | 91.5 | C10:2 | Ac-Orn; Fum |
| 2 | 3 | 86.6 | C10:2 | Lac; Phe |
| 3 | 4 | 91.3 | C10:2 | 8-iso-PGF2a; Ac-Orn; Fum |
| 4 | 4 | 89.7 | C10:2 | Ac-Orn; Lac; Pent-P |
| 5 | 4 | 89.4 | C10:2 | Ac-Orn; C16:2; Fum |
| 6 | 4 | 89.1 | C10:2 | Ac-Orn; Carnosine; Lac |
| 7 | 4 | 88.7 | C10:2 | C5:1-DC; Carnosine; Lac |
| 8 | 3 | 85.1 | SM C24:1 | C16:2; C5:1 |
| 9 | 4 | 92.8 | SM C24:1 | C5:1; Carnosine; Lac |
| 10 | 4 | 88.1 | SM C24:1 | Ac-Orn; C16:2; C5:1 |
| 11 | 4 | 86.2 | SM C24:1 | Ac-Orn; C16:2; Lac |
| 12 | 4 | 85.8 | SM C24:1 | Ac-Orn; C16:2; Pent-P |
| 13 | 5 | 87.6 | SM C24:1 | 5a,6a-EpoxyC; Ac-Orn; C5:1; Lac |
| 14 | 3 | 94 | C5:1-DC | Ac-Orn; Fum |
| 15 | 4 | 91.7 | C5:1-DC | 24S-OH-C; 25-OH-C; alpha-AAA |
| 16 | 4 | 89.5 | C5:1-DC | Creatinine; Fum; total DMA |
| 17 | 4 | 88.7 | C5:1-DC | C10:2; Carnosine; Lac |
| 18 | 4 | 87.2 | C5:1-DC | Fum; Lac; total DMA |
| 19 | 4 | 87 | C5:1-DC | Carnosine; Fum; SM (OH) C22:2 |
| 20 | 4 | 86.7 | C5:1-DC | alpha-AAA; Carnosine; Suc |
| 21 | 4 | 86.4 | C5:1-DC | Fum; Lac; Pent-P |
| 22 | 3 | 93.4 | Suc | Carnosine; Lac |
| 23 | 4 | 95 | Suc | Carnosine; Lac; Pent-P |
| 24 | 4 | 86.7 | Suc | alpha-AAA; C5:1-DC; Carnosine |
| 25 | 4 | 86.4 | Suc | Fum; Lac; Met-SO |

TABLE 12

Combinations formed with a lead metabolite that correlate with damage of basal ganglia

| No. | Npar | Accuracy | Lead metabolite | Additional metabolites |
|---|---|---|---|---|
| 1 | 3 | 91.9 | Met-SO | Gln; Lys |
| 2 | 4 | 92.9 | Met-SO | Gln; Lac; SM C24:0 |
| 3 | 4 | 92.2 | Met-SO | Gln; Orn; SM (OH) C14:1 |
| 4 | 4 | 91.8 | Met-SO | Gln; Orn; SM (OH) C22:2 |
| 5 | 4 | 91.5 | Met-SO | Gln; Pro; SM C24:0 |
| 6 | 4 | 91.4 | Met-SO | Kynurenine; SM (OH) C14:1; SM (OH) C22:1 |
| 7 | 4 | 91.3 | Met-SO | Gln; Lys; SM (OH) C22:1 |
| 8 | 4 | 91.1 | Met-SO | Cholestenone; Creatinine; Trp |
| 9 | 4 | 91.1 | Met-SO | Gln; Pro; SM C16:1 |
| 10 | 4 | 90.5 | Met-SO | C6:1; SM (OH) C22:1; Trp |
| 11 | 4 | 90.5 | Met-SO | Gln; Pro; SM (OH) C14:1 |
| 12 | 4 | 90.1 | Met-SO | His; Orn; SM C24:0 |
| 13 | 5 | 92.8 | Met-SO | Pro; SM C16:1; SM C24:0; Trp |
| 14 | 5 | 91.4 | Met-SO | Gln; Orn; Pro; SM C16:1 |
| 15 | 5 | 91.1 | Met-SO | C6:1; Gln; Lac; SM C16:0 |
| 16 | 5 | 90.9 | Met-SO | Orn; SM C24:0; SM (OH) C22:1; SM (OH) C22:2 |
| 17 | 5 | 90.6 | Met-SO | Pro; SM C16:1; SM C24:1; Trp |
| 18 | 5 | 90.5 | Met-SO | alpha-KGA; His; Kynurenine; SM C16:1 |
| 19 | 5 | 90.1 | Met-SO | Gln; His; Orn; SM (OH) C22:2 |
| 20 | 5 | 90.1 | Met-SO | Cholestenone; SM C18:0; SM (OH) C22:1; Trp |
| 21 | 5 | 90.1 | Met-SO | Gln; Lac; SM C16:1; SM (OH) C14:1 |
| 22 | 6 | 96.5 | Met-SO | 24-DH-Lanosterol; Arg; Creatinine; SM C16:1; Trp |
| 23 | 6 | 91.6 | Met-SO | Gly; LTB4; SM C16:1; SM (OH) C22:1; SM (OH) C22:2 |

TABLE 12-continued

Combinations formed with a lead metabolite that correlate with damage of basal ganglia

| No. | Npar | Accuracy | Lead metabolite | Additional metabolites |
|---|---|---|---|---|
| 24 | 6 | 90.5 | Met-SO | Cholestenone; Gln; Lys; SM C24:0; SM (OH) C22:1 |
| 25 | 6 | 90.4 | Met-SO | 8-iso-PGF2a; Pro; Serotonin; SM (OH) C22:1; Trp |
| 26 | 6 | 90.4 | Met-SO | Kynurenine; LTB4; SM C16:0; SM (OH) C14:1; SM (OH) C22:1 |
| 27 | 3 | 92.5 | SM (OH) C14:1 | Kynurenine; Tyr |
| 28 | 3 | 90.9 | SM (OH) C14:1 | C5:1-DC; C6:1 |
| 29 | 4 | 97.2 | SM (OH) C14:1 | 20a-OH-C; SM (OH) C22:1; Tyr |
| 30 | 4 | 95.6 | SM (OH) C14:1 | Kynurenine; SM (OH) C22:2; Tyr |
| 31 | 4 | 95.2 | SM (OH) C14:1 | Pro; SM C16:1; TXB2 |
| 32 | 4 | 94.7 | SM (OH) C14:1 | Pro; SM C16:0; TXB2 |
| 33 | 4 | 93.9 | SM (OH) C14:1 | 20a-OH-C; SM (OH) C22:2; Tyr |
| 34 | 4 | 93.1 | SM (OH) C14:1 | Gln; Pro; TXB2 |
| 35 | 4 | 92.7 | SM (OH) C14:1 | His; Kynurenine; Tyr |
| 36 | 4 | 92.3 | SM (OH) C14:1 | C5:1-DC; Pro; SM C16:1 |
| 37 | 4 | 92.3 | SM (OH) C14:1 | 20a-OH-C; Arg; SM (OH) C22:2 |
| 38 | 4 | 92.2 | SM (OH) C14:1 | Gln; Met-SO; Orn |
| 39 | 4 | 92.1 | SM (OH) C14:1 | Kynurenine; Leu; Met |
| 40 | 4 | 92 | SM (OH) C14:1 | Kynurenine; Leu; Tyr |
| 41 | 4 | 91.5 | SM (OH) C14:1 | Met; Pro; Trp |
| 42 | 4 | 91.4 | SM (OH) C14:1 | Kynurenine; Met-SO; SM (OH) C22:1 |
| 43 | 4 | 91.3 | SM (OH) C14:1 | Pro; SM C26:1; TXB2 |
| 44 | 4 | 91.2 | SM (OH) C14:1 | Lys; SM (OH) C16:1; TXB2 |
| 45 | 4 | 90.9 | SM (OH) C14:1 | 25-OH-C; C5:1-DC; Histamine |
| 46 | 4 | 90.8 | SM (OH) C14:1 | Gln; Lac; Met |
| 47 | 4 | 90.7 | SM (OH) C14:1 | C5:1-DC; C6:1; SM C16:0 |
| 48 | 4 | 90.6 | SM (OH) C14:1 | Kynurenine; SM C16:1; Tyr |
| 49 | 4 | 90.5 | SM (OH) C14:1 | Gln; Met-SO; Pro |
| 50 | 4 | 90.5 | SM (OH) C14:1 | Ac-Orn; Pro; SM C16:1 |
| 51 | 4 | 90.4 | SM (OH) C14:1 | C5:1-DC; SM (OH) C22:1; Tyr |
| 52 | 4 | 90.3 | SM (OH) C14:1 | C5:1-DC; SM C16:1; Tyr |
| 53 | 4 | 90.2 | SM (OH) C14:1 | C5:1-DC; Histamine; SM C16:0 |
| 54 | 4 | 90.2 | SM (OH) C14:1 | alpha-KGA; SM (OH) C22:2; TXB2 |
| 55 | 4 | 90.1 | SM (OH) C14:1 | 20a-OH-C; Pro; SM C16:1 |
| 56 | 4 | 90 | SM (OH) C14:1 | SM C20:2; SM (OH) C22:1; Tyr |
| 57 | 5 | 94.7 | SM (OH) C14:1 | Kynurenine; Met; SM (OH) C22:1; Tyr |
| 58 | 5 | 94.2 | SM (OH) C14:1 | Arg; SM C24:0; SM (OH) C22:2; TXB2 |
| 59 | 5 | 94.2 | SM (OH) C14:1 | Kynurenine; LTB4; SM (OH) C16:1; Tyr |
| 60 | 5 | 93.7 | SM (OH) C14:1 | Ala; C5:1-DC; SM C16:0; SM C16:1 |
| 61 | 5 | 93 | SM (OH) C14:1 | 20a-OH-C; Arg; Leu; SM C16:1 |
| 62 | 5 | 92.6 | SM (OH) C14:1 | Kynurenine; SM (OH) C16:1; SM (OH) C22:1; Tyr |
| 63 | 5 | 92.5 | SM (OH) C14:1 | Lys; SM (OH) C22:1; SM (OH) C22:2; TXB2 |
| 64 | 5 | 92.4 | SM (OH) C14:1 | His; Orn; SM C24:0; TXB2 |
| 65 | 5 | 91.6 | SM (OH) C14:1 | C5:1-DC; C6:1; Orn; SM C16:0 |
| 66 | 5 | 91.5 | SM (OH) C14:1 | 20a-OH-C; C6:1; Gln; Tyr |
| 67 | 5 | 91.3 | SM (OH) C14:1 | Ala; SM C16:1; SM C18:1; TXB2 |
| 68 | 5 | 90.9 | SM (OH) C14:1 | Kynurenine; SM C18:1; SM (OH) C16:1; Tyr |
| 69 | 5 | 90.8 | SM (OH) C14:1 | 25-OH-C; C5:1-DC; Histamine; Orn |
| 70 | 5 | 90.4 | SM (OH) C14:1 | Ac-Orn; Cholestenone; Pro; SM C16:1 |
| 71 | 5 | 90.4 | SM (OH) C14:1 | Ac-Orn; Gln; Pro; SM (OH) C22:2 |
| 72 | 5 | 90.4 | SM (OH) C14:1 | 24-DH-Lanosterol; Ac-Orn; Orn; Trp |
| 73 | 5 | 90.2 | SM (OH) C14:1 | 8-iso-PGF2a; Gln; Met; Orn |
| 74 | 5 | 90.2 | SM (OH) C14:1 | Gly; Pro; SM C16:0; SM C24:1 |
| 75 | 5 | 90.1 | SM (OH) C14:1 | Gln; Lac; Met-SO; SM C16:1 |
| 76 | 5 | 90 | SM (OH) C14:1 | Kynurenine; LTB4; Phe; SM (OH) C22:2 |
| 77 | 5 | 90 | SM (OH) C14:1 | Ac-Orn; Pro; SM C24:1; Trp |
| 78 | 5 | 90 | SM (OH) C14:1 | Orn; Ser; SM C24:1; SM (OH) C22:2 |
| 79 | 6 | 96.6 | SM (OH) C14:1 | Lys; SM C18:1; SM (OH) C22:1; TXB2; Tyr |
| 80 | 6 | 93.5 | SM (OH) C14:1 | 20a-OH-C; C14:1; His; Pro; SM (OH) C22:2 |
| 81 | 6 | 93.4 | SM (OH) C14:1 | 25-OH-C; Arg; Histamine; SM (OH) C22:2; TXB2 |
| 82 | 6 | 93 | SM (OH) C14:1 | 24-DH-Lanosterol; Ac-Orn; C6:1; SM C18:1; Trp |
| 83 | 6 | 92.7 | SM (OH) C14:1 | 20a-OH-C; His; SM C24:0; SM (OH) C16:1; Tyr |
| 84 | 6 | 91 | SM (OH) C14:1 | C5:1-DC; Cholestenone; Histamine; Orn; SM (OH) C22:1 |
| 85 | 6 | 90.4 | SM (OH) C14:1 | Kynurenine; LTB4; Met-SO; SM C16:0; SM (OH) C22:1 |
| 86 | 6 | 90 | SM (OH) C14:1 | 25-OH-C; Ala; Met; Orn; SM C24:0 |
| 87 | 7 | 92.9 | SM (OH) C14:1 | Ac-Orn; Ala; C6:1; Gln; Orn; SM C16:1 |
| 88 | 4 | 96.8 | alpha-KGA | C14:1; Pro; TXB2 |
| 89 | 4 | 95.4 | alpha-KGA | Lys; SM (OH) C22:2; TXB2 |
| 90 | 4 | 95.1 | alpha-KGA | 20a-OH-C; SM C16:1; Tyr |
| 91 | 4 | 91 | alpha-KGA | 22R-OH-C; Pro; SM C16:1 |
| 92 | 4 | 90.2 | alpha-KGA | SM (OH) C14:1; SM (OH) C22:2; TXB2 |
| 93 | 4 | 90.1 | alpha-KGA | 20a-OH-C; SM C16:1; SM (OH) C22:2 |
| 94 | 5 | 96 | alpha-KGA | 20a-OH-C; Gln; SM (OH) C22:2; Tyr |
| 95 | 5 | 95.8 | alpha-KGA | His; Orn; SM (OH) C22:2; TXB2 |
| 96 | 5 | 92.6 | alpha-KGA | Pro; SM C16:0; SM (OH) C22:2; TXB2 |
| 97 | 5 | 90.5 | alpha-KGA | Kynurenine; SM C24:1; SM (OH) C22:2; Tyr |
| 98 | 5 | 90.5 | alpha-KGA | His; Kynurenine; Met-SO; SM C16:1 |
| 99 | 5 | 90.2 | alpha-KGA | Arg; C10:2; Gln; Met |

TABLE 12-continued

Combinations formed with a lead metabolite that correlate with damage of basal ganglia

| No. | Npar | Accuracy | Lead metabolite | Additional metabolites |
|---|---|---|---|---|
| 100 | 5 | 90.2 | alpha-KGA | 24-DH-Lanosterol; Pro; SM C24:1; Trp |
| 101 | 6 | 92.5 | alpha-KGA | 20a-OH-C; His; SM C16:0; SM C24:0; Tyr |
| 102 | 6 | 91.1 | alpha-KGA | Ac-Orn; Arg; Cholestenone; LTB4; Trp |
| 103 | 4 | 91.7 | Cholestenone | Fum; Met; Trp |
| 104 | 4 | 91.5 | Cholestenone | Creatinine; SM C16:1; Tyr |
| 105 | 4 | 91.1 | Cholestenone | Creatinine; Met-SO; Trp |
| 106 | 4 | 90.3 | Cholestenone | Met; SM (OH) C22:2; Trp |
| 107 | 4 | 90.1 | Cholestenone | Ala; SM C24:1; SM (OH) C22:2 |
| 108 | 5 | 92.1 | Cholestenone | Arg; Pro; SM C16:1; Suc |
| 109 | 5 | 92.1 | Cholestenone | C5:1-DC; Gln; Lys; SM C16:1 |
| 110 | 5 | 91.1 | Cholestenone | 24-DH-Lanosterol; C5:1-DC; Gln; Lys |
| 111 | 5 | 90.4 | Cholestenone | Ac-Orn; Pro; SM C16:1; SM (OH) C14:1 |
| 112 | 5 | 90.3 | Cholestenone | Gly; Pro; SM C16:0; SM (OH) C22:2 |
| 113 | 5 | 90.2 | Cholestenone | C5:1-DC; Orn; SM C24:0; SM (OH) C22:2 |
| 114 | 5 | 90.1 | Cholestenone | Met-SO; SM C18:0; SM (OH) C22:1; Trp |
| 115 | 6 | 91.1 | Cholestenone | Ac-Orn; alpha-KGA; Arg; LTB4; Trp |
| 116 | 6 | 91 | Cholestenone | C5:1-DC; Histamine; Orn; SM (OH) C14:1; SM (OH) C22:1 |
| 117 | 6 | 90.5 | Cholestenone | Gln; Lys; Met-SO; SM C24:0; SM (OH) C22:1 |
| 118 | 3 | 93.3 | SM C16:1 | C5:1-DC; C6:1 |
| 119 | 4 | 95.6 | SM C16:1 | Pro; SM (OH) C22:1; TXB2 |
| 120 | 4 | 95.2 | SM C16:1 | Pro; SM (OH) C14:1; TXB2 |
| 121 | 4 | 95.1 | SM C16:1 | 20a-OH-C; alpha-KGA; Tyr |
| 122 | 4 | 94.6 | SM C16:1 | 20a-OH-C; Pro; SM (OH) C22:2 |
| 123 | 4 | 92.3 | SM C16:1 | C5:1-DC; Pro; SM (OH) C14:1 |
| 124 | 4 | 92.2 | SM C16:1 | Gly; SM C18:1; SM (OH) C22:2 |
| 125 | 4 | 91.8 | SM C16:1 | Kynurenine; SM C24:1; Tyr |
| 126 | 4 | 91.8 | SM C16:1 | C5:1-DC; Pro; SM C16:0 |
| 127 | 4 | 91.6 | SM C16:1 | C5:1-DC; Orn; SM C16:0 |
| 128 | 4 | 91.5 | SM C16:1 | His; Pro; TXB2 |
| 129 | 4 | 91.5 | SM C16:1 | Cholestenone; Creatinine; Tyr |
| 130 | 4 | 91.4 | SM C16:1 | C5:1-DC; C6:1; Pro |
| 131 | 4 | 91.3 | SM C16:1 | Gln; Lac; Met |
| 132 | 4 | 91.2 | SM C16:1 | 20a-OH-C; Leu; SM (OH) C22:2 |
| 133 | 4 | 91.2 | SM C16:1 | Kynurenine; Phe; SM (OH) C22:2 |
| 134 | 4 | 91.1 | SM C16:1 | Gln; Met-SO; Pro |
| 135 | 4 | 91 | SM C16:1 | Met; Pro; Trp |
| 136 | 4 | 91 | SM C16:1 | 22R-OH-C; alpha-KGA; Pro |
| 137 | 4 | 91 | SM C16:1 | Kynurenine; SM C18:1; Tyr |
| 138 | 4 | 90.9 | SM C16:1 | Kynurenine; Leu; Met |
| 139 | 4 | 90.7 | SM C16:1 | C5:1-DC; C6:1; SM C24:0 |
| 140 | 4 | 90.6 | SM C16:1 | 20a-OH-C; SM (OH) C24:1; Tyr |
| 141 | 4 | 90.6 | SM C16:1 | Kynurenine; SM (OH) C14:1; Tyr |
| 142 | 4 | 90.5 | SM C16:1 | Kynurenine; SM (OH) C22:1; Tyr |
| 143 | 4 | 90.5 | SM C16:1 | 20a-OH-C; His; Pro |
| 144 | 4 | 90.5 | SM C16:1 | Ac-Orn; Pro; SM (OH) C14:1 |
| 145 | 4 | 90.4 | SM C16:1 | C5:1-DC; Histamine; SM (OH) C22:2 |
| 146 | 4 | 90.3 | SM C16:1 | C5:1-DC; SM (OH) C14:1; Tyr |
| 147 | 4 | 90.3 | SM C16:1 | C5:1-DC; Orn; SM (OH) C16:1 |
| 148 | 4 | 90.2 | SM C16:1 | Gln; Met; Pro |
| 149 | 4 | 90.1 | SM C16:1 | C5:1-DC; Histamine; Pro |
| 150 | 4 | 90.1 | SM C16:1 | 20a-OH-C; Pro; SM (OH) C14:1 |
| 151 | 4 | 90.1 | SM C16:1 | 20a-OH-C; alpha-KGA; SM (OH) C22:2 |
| 152 | 5 | 97.9 | SM C16:1 | 20a-OH-C; Pro; SM (OH) C22:2; Trp |
| 153 | 5 | 93.7 | SM C16:1 | Ala; C5:1-DC; SM C16:0; SM (OH) C14:1 |
| 154 | 5 | 93 | SM C16:1 | 20a-OH-C; Arg; Leu; SM (OH) C14:1 |
| 155 | 5 | 93 | SM C16:1 | Kynurenine; Leu; Met; SM (OH) C22:2 |
| 156 | 5 | 92.8 | SM C16:1 | Met-SO; Pro; SM C24:0; Trp |
| 157 | 5 | 92.7 | SM C16:1 | Histamine; Kynurenine; SM (OH) C22:2; Tyr |
| 158 | 5 | 92.6 | SM C16:1 | Ac-Orn; Pro; SM C16:0; Trp |
| 159 | 5 | 92.3 | SM C16:1 | C10; His; Orn; TXB2 |
| 160 | 5 | 92.1 | SM C16:1 | Arg; Cholestenone; Pro; Suc |
| 161 | 5 | 92.1 | SM C16:1 | C5:1-DC; Cholestenone; Gln; Lys |
| 162 | 5 | 91.9 | SM C16:1 | Kynurenine; Phe; Pro; SM (OH) C22:2 |
| 163 | 5 | 91.4 | SM C16:1 | Gln; Met-SO; Orn; Pro |
| 164 | 5 | 91.3 | SM C16:1 | Ala; SM C18:1; SM (OH) C14:1; TXB2 |
| 165 | 5 | 91 | SM C16:1 | 20a-OH-C; Ser; SM (OH) C22:1; SM (OH) C22:2 |
| 166 | 5 | 90.6 | SM C16:1 | Met-SO; Pro; SM C24:1; Trp |
| 167 | 5 | 90.6 | SM C16:1 | Ac-Orn; Pro; SM C24:0; SM (OH) C22:1 |
| 168 | 5 | 90.5 | SM C16:1 | C5:1-DC; Orn; SM (OH) C16:1; SM (OH) C22:2 |
| 169 | 5 | 90.5 | SM C16:1 | alpha-KGA; His; Kynurenine; Met-SO |
| 170 | 5 | 90.4 | SM C16:1 | Ac-Orn; Cholestenone; Pro; SM (OH) C14:1 |
| 171 | 5 | 90.2 | SM C16:1 | C10; Kynurenine; SM C26:1; Tyr |
| 172 | 5 | 90.1 | SM C16:1 | Gln; Lac; Met-SO; SM (OH) C14:1 |
| 173 | 5 | 90.1 | SM C16:1 | Ac-Orn; Pro; SM C24:0; SM (OH) C22:2 |
| 174 | 6 | 96.5 | SM C16:1 | 24-DH-Lanosterol; Arg; Creatinine; Met-SO; Trp |
| 175 | 6 | 96.2 | SM C16:1 | 20a-OH-C; Fum; His; SM C26:1; Tyr |

TABLE 12-continued

Combinations formed with a lead metabolite that correlate with damage of basal ganglia

| No. | Npar | Accuracy | Lead metabolite | Additional metabolites |
|---|---|---|---|---|
| 176 | 6 | 94.5 | SM C16:1 | 22R-OH-C; C6:1; Orn; Pro; SM (OH) C22:2 |
| 177 | 6 | 91.6 | SM C16:1 | Gly; LTB4; Met-SO; SM (OH) C22:1; SM (OH) C22:2 |
| 178 | 6 | 91.5 | SM C16:1 | 20a-OH-C; 24-DH-Lanosterol; Ile; Lys; SM (OH) C22:2 |
| 179 | 6 | 90.9 | SM C16:1 | 20a-OH-C; Gln; SM C18:1; SM (OH) C16:1; Tyr |
| 180 | 6 | 90.5 | SM C16:1 | His; Kynurenine; Met; Phe; SM (OH) C22:2 |
| 181 | 7 | 92.9 | SM C16:1 | Ac-Orn; Ala; C6:1; Gln; Orn; SM (OH) C14:1 |

TABLE 13

Combinations formed with a lead metabolite that correlate with the neurological behavioural score

| No. | Npar | Accuracy | Lead metabolite | Additional metabolites |
|---|---|---|---|---|
| 1 | 3 | 95.2 | Fum | C5-DC (C6-OH); total DMA |
| 2 | 3 | 94 | Fum | 27-OH-C; Met-SO |
| 3 | 3 | 93.5 | Fum | 27-OH-C; Tyr |
| 4 | 3 | 92.2 | Fum | 27-OH-C; total DMA |
| 5 | 3 | 91.4 | Fum | C5:1; total DMA |
| 6 | 3 | 90.1 | Fum | 27-OH-C; Asp |
| 7 | 4 | 98.4 | Fum | C5-DC (C6-OH); total DMA; Tyr |
| 8 | 4 | 96.3 | Fum | 27-OH-C; Met-SO; SDMA |
| 9 | 4 | 96.3 | Fum | 27-OH-C; Cholestenone; Met-SO |
| 10 | 4 | 95.9 | Fum | C5-DC (C6-OH); SDMA; Tyr |
| 11 | 4 | 95.6 | Fum | C5:1; C8:1; total DMA |
| 12 | 4 | 95.6 | Fum | 27-OH-C; C5:1-DC; total DMA |
| 13 | 4 | 95.6 | Fum | 27-OH-C; Met-SO; Val |
| 14 | 4 | 95.5 | Fum | 27-OH-C; Met-SO; SM C16:1 |
| 15 | 4 | 95.5 | Fum | 27-OH-C; C14:1-OH; Met-SO |
| 16 | 4 | 95.5 | Fum | 27-OH-C; C3-DC (C4-OH); Met-SO |
| 17 | 4 | 95.4 | Fum | 27-OH-C; C5:1; total DMA |
| 18 | 4 | 95.3 | Fum | 24-DH-Lanosterol; 27-OH-C; Met-SO |
| 19 | 4 | 95.3 | Fum | 27-OH-C; Met-SO; total DMA |
| 20 | 4 | 95.2 | Fum | 27-OH-C; Asp; Carnosine |
| 21 | 4 | 95.2 | Fum | 27-OH-C; 3b,5a,6b-THC; total DMA |
| 22 | 4 | 95.2 | Fum | 27-OH-C; Met-SO; Tyr |
| 23 | 4 | 95.1 | Fum | 27-OH-C; C10:2; Tyr |
| 24 | 4 | 95.1 | Fum | 27-OH-C; Lac; Met-SO |
| 25 | 4 | 94.8 | Fum | C14:1; C5:1; total DMA |
| 26 | 4 | 94.7 | Fum | 27-OH-C; Ala; total DMA |
| 27 | 4 | 94.7 | Fum | C5-DC (C6-OH); Met-SO; SDMA |
| 28 | 4 | 94.6 | Fum | 27-OH-C; C5:1-DC; SDMA |
| 29 | 4 | 94.6 | Fum | 27-OH-C; C4:1; Met-SO |
| 30 | 4 | 94.5 | Fum | 27-OH-C; C8:1; Met-SO |
| 31 | 4 | 94.4 | Fum | 27-OH-C; 5a,6a-EpoxyC; Met-SO |
| 32 | 4 | 94.3 | Fum | 27-OH-C; SDMA; Tyr |
| 33 | 4 | 94.3 | Fum | 27-OH-C; Met-SO; Phe |
| 34 | 4 | 94.3 | Fum | 27-OH-C; Met; total DMA |
| 35 | 4 | 94.3 | Fum | 27-OH-C; C6 (C4:1-DC); Met-SO |
| 36 | 4 | 94.1 | Fum | 27-OH-C; C8:1; Tyr |
| 37 | 4 | 94 | Fum | 27-OH-C; Pent-P; Tyr |
| 38 | 4 | 94 | Fum | 27-OH-C; 5a,6a-EpoxyC; Tyr |
| 39 | 4 | 93.9 | Fum | 27-OH-C; Pent-P; total DMA |
| 40 | 4 | 93.8 | Fum | 27-OH-C; Carnosine; Tyr |
| 41 | 4 | 93.6 | Fum | 27-OH-C; total DMA; Val |
| 42 | 4 | 93.6 | Fum | 27-OH-C; Cholestenone; Tyr |
| 43 | 4 | 93.5 | Fum | 27-OH-C; Phe; SDMA |
| 44 | 4 | 93.5 | Fum | 27-OH-C; Tyr; Val |
| 45 | 4 | 93.4 | Fum | 27-OH-C; total DMA; Trp |
| 46 | 4 | 93.3 | Fum | 27-OH-C; Lac; Tyr |
| 47 | 4 | 93.2 | Fum | 27-OH-C; Pro; total DMA |
| 48 | 4 | 93.1 | Fum | C10:2; C5-DC (C6-OH); Tyr |
| 49 | 4 | 93.1 | Fum | 27-OH-C; OAA; total DMA |
| 50 | 4 | 92.9 | Fum | 27-OH-C; 8-iso-PGF2a; Phe |
| 51 | 4 | 92.7 | Fum | 27-OH-C; Ac-Orn; SDMA |
| 52 | 4 | 91.9 | Fum | 27-OH-C; SM C24:1; total DMA |
| 53 | 4 | 91.7 | Fum | 24-DH-Lanosterol; 27-OH-C; Phe |
| 54 | 4 | 90.8 | Fum | C5:1; SDMA; SM (OH) C22:2 |
| 55 | 4 | 90.7 | Fum | C14:1; Carnosine; Suc |
| 56 | 4 | 90.6 | Fum | C5-OH (C3-DC-M); Carnosine; total DMA |
| 57 | 4 | 90.5 | Fum | C10:2; C8:1; Phe |
| 58 | 4 | 90.4 | Fum | Carnosine; SDMA; Suc |
| 59 | 4 | 90.4 | Fum | C5:1; Met-SO; SDMA |
| 60 | 4 | 90.3 | Fum | C2; Carnosine; total DMA |

TABLE 13-continued

Combinations formed with a lead metabolite that correlate with the neurological behavioural score

| No. | Npar | Accuracy | Lead metabolite | Additional metabolites |
|---|---|---|---|---|
| 61 | 4 | 90.3 | Fum | C5-DC (C6-OH); C8:1; Met-SO |
| 62 | 4 | 90.2 | Fum | 27-OH-C; C5:1; SDMA |
| 63 | 4 | 90.2 | Fum | C4:1; C5-DC (C6-OH); Met-SO |
| 64 | 4 | 90.1 | Fum | 24,25-EpoxyC; C0; Met-SO |
| 65 | 4 | 90 | Fum | 27-OH-C; SDMA; Suc |
| 66 | 5 | 97.6 | Fum | 27-OH-C; C5:1; Met-SO; total DMA |
| 67 | 5 | 97.2 | Fum | 27-OH-C; C14:1-OH; Met-SO; total DMA |
| 68 | 5 | 96.6 | Fum | 27-OH-C; Cholestenone; Met-SO; SDMA |
| 69 | 5 | 94.7 | Fum | C10:2; C5-DC (C6-OH); Phe; SDMA |
| 70 | 5 | 94.6 | Fum | C14:1-OH; C5-DC (C6-OH); Carnosine; Met-SO |
| 71 | 5 | 93.8 | Fum | C5-DC (C6-OH); Cholestenone; Met-SO; SM C16:1 |
| 72 | 5 | 93.4 | Fum | 24,25-EpoxyC; 27-OH-C; C5:1; Met |
| 73 | 5 | 92.9 | Fum | C14:1-OH; C5:1; Carnosine; total DMA |
| 74 | 5 | 92.7 | Fum | Ac-Orn; C10:2; C6 (C4:1-DC); Carnosine |
| 75 | 5 | 92.4 | Fum | C4:1; C5:1; Met-SO; SDMA |
| 76 | 5 | 92.3 | Fum | C0; C10:2; Met-SO; total DMA |
| 77 | 5 | 91.3 | Fum | Ac-Orn; C6 (C4:1-DC); Pent-P; total DMA |
| 78 | 5 | 91.2 | Fum | C10:2; C14:1; Carnosine; Pent-P |
| 79 | 5 | 91 | Fum | 27-OH-C; Carnosine; Pent-P; SDMA |
| 80 | 5 | 90.9 | Fum | C0; Met-SO; SDMA; total DMA |
| 81 | 5 | 90.4 | Fum | Ac-Orn; C5-DC (C6-OH); SDMA; SM C16:1 |
| 82 | 5 | 90.1 | Fum | C10:2; C14:1; C14:1-OH; Carnosine |
| 83 | 5 | 90.1 | Fum | 27-OH-C; Carnosine; DHA; Phe |
| 84 | 6 | 97.3 | Fum | C5:1; C5-DC (C6-OH); Phe; SDMA; total DMA |
| 85 | 6 | 96.4 | Fum | 27-OH-C; C5:1; His; SDMA; total DMA |
| 86 | 3 | 95.7 | Carnosine | C6 (C4:1-DC); Lac |
| 87 | 3 | 91.5 | Carnosine | C10:2; C14:1-OH |
| 88 | 3 | 91.2 | Carnosine | 27-OH-C; SM (OH) C22:2 |
| 89 | 3 | 90.9 | Carnosine | C12; Lac |
| 90 | 4 | 95.2 | Carnosine | 27-OH-C; Asp; Fum |
| 91 | 4 | 95.2 | Carnosine | 27-OH-C; C6 (C4:1-DC); Met-SO |
| 92 | 4 | 95.1 | Carnosine | 27-OH-C; SM (OH) C14:1; Tyr |
| 93 | 4 | 94.5 | Carnosine | 27-OH-C; SM (OH) C22:2; total DMA |
| 94 | 4 | 94.3 | Carnosine | 27-OH-C; Ac-Orn; SM (OH) C14:1 |
| 95 | 4 | 93.8 | Carnosine | C5-DC (C6-OH); SM (OH) C14:1; total DMA |
| 96 | 4 | 93.8 | Carnosine | 27-OH-C; Fum; Tyr |
| 97 | 4 | 93.5 | Carnosine | C10:2; C6 (C4:1-DC); Phe |
| 98 | 4 | 93.5 | Carnosine | C10:2; C14:1-OH; Lac |
| 99 | 4 | 91.7 | Carnosine | C5-DC (C6-OH); SM C16:0; total DMA |
| 100 | 4 | 91.4 | Carnosine | C5-DC (C6-OH); Phe; SM (OH) C14:1 |
| 101 | 4 | 91.4 | Carnosine | C5-DC (C6-OH); SDMA; SM (OH) C22:2 |
| 102 | 4 | 91.1 | Carnosine | C5-DC (C6-OH); Pent-P; SM (OH) C14:1 |
| 103 | 4 | 91 | Carnosine | C5:1; SDMA; SM (OH) C14:1 |
| 104 | 4 | 90.8 | Carnosine | 27-OH-C; SDMA; SM (OH) C22:2 |
| 105 | 4 | 90.7 | Carnosine | C14:1; Fum; Suc |
| 106 | 4 | 90.6 | Carnosine | 27-OH-C; C14:1; Met-SO |
| 107 | 4 | 90.6 | Carnosine | C5-OH (C3-DC-M); Fum; total DMA |
| 108 | 4 | 90.5 | Carnosine | 24,25-EpoxyC; 27-OH-C; Ac-Orn |
| 109 | 4 | 90.4 | Carnosine | Fum; SDMA; Suc |
| 110 | 4 | 90.4 | Carnosine | C5:1; C8:1; SM C16:1 |
| 111 | 4 | 90.3 | Carnosine | C2; Fum; total DMA |
| 112 | 4 | 90.2 | Carnosine | C14:1; C5:1; SM C16:0 |
| 113 | 4 | 90.2 | Carnosine | 24-DH-Lanosterol; 27-OH-C; Lac |
| 114 | 5 | 97 | Carnosine | C10:2; C5-DC (C6-OH); C6 (C4:1-DC); Tyr |
| 115 | 5 | 95.3 | Carnosine | 27-OH-C; C10:2; C14:1; Met-SO |
| 116 | 5 | 94.6 | Carnosine | C14:1-OH; C5-DC (C6-OH); Fum; Met-SO |
| 117 | 5 | 94.4 | Carnosine | 27-OH-C; Phe; SM C16:1; total DMA |
| 118 | 5 | 92.9 | Carnosine | C14:1-OH; C5:1; Fum; total DMA |
| 119 | 5 | 92.7 | Carnosine | Ac-Orn; C10:2; C6 (C4:1-DC); Fum |
| 120 | 5 | 92.5 | Carnosine | 27-OH-C; C10:2; C8:1; Met |
| 121 | 5 | 91.7 | Carnosine | C5-DC (C6-OH); SM C16:1; SM C24:1; SM (OH) C22:2 |
| 122 | 5 | 91.3 | Carnosine | 27-OH-C; C10:2; C8:1; His |
| 123 | 5 | 91.2 | Carnosine | C10:2; C14:1; Fum; Pent-P |
| 124 | 5 | 91.2 | Carnosine | 27-OH-C; Ac-Orn; SDMA; SM C16:1 |
| 125 | 5 | 91 | Carnosine | 27-OH-C; Fum; Pent-P; SDMA |
| 126 | 5 | 90.4 | Carnosine | 24,25-EpoxyC; C5:1; Cholestenone; SM C24:1 |
| 127 | 5 | 90.1 | Carnosine | C10:2; C14:1; C14:1-OH; Fum |
| 128 | 5 | 90.1 | Carnosine | C5-DC (C6-OH); SM (OH) C16:1; SM (OH) C22:2; Tyr |
| 129 | 5 | 90.1 | Carnosine | 27-OH-C; DHA; Fum; Phe |
| 130 | 5 | 90 | Carnosine | C5:1; SDMA; SM C16:0; SM (OH) C22:2 |
| 131 | 4 | 91.2 | 24,25-EpoxyC | C5:1; SM C24:1; total DMA |
| 132 | 4 | 90.5 | 24,25-EpoxyC | 27-OH-C; C4:1; Met-SO |
| 133 | 4 | 90.5 | 24,25-EpoxyC | 27-OH-C; Ac-Orn; Carnosine |
| 134 | 4 | 90.1 | 24,25-EpoxyC | C5:1; Pent-P; total DMA |
| 135 | 4 | 90.1 | 24,25-EpoxyC | C0; Fum; Met-SO |
| 136 | 5 | 93.4 | 24,25-EpoxyC | 27-OH-C; C5:1; Fum; Met |

TABLE 13-continued

Combinations formed with a lead metabolite that correlate with the neurological behavioural score

| No. | Npar | Accuracy | Lead metabolite | Additional metabolites |
|---|---|---|---|---|
| 137 | 5 | 91.9 | 24,25-EpoxyC | 27-OH-C; C5:1; Met; total DMA |
| 138 | 5 | 91.7 | 24,25-EpoxyC | 27-OH-C; Lys; Met-SO; Suc |
| 139 | 5 | 90.4 | 24,25-EpoxyC | C5:1; Carnosine; Cholestenone; SM C24:1 |
| 140 | 6 | 96.2 | 24,25-EpoxyC | C10:2; C5:1; C8:1; Phe; SM C24:1 |
| 141 | 6 | 90.9 | 24,25-EpoxyC | Ac-Orn; alpha-AAA; C5:1; C5-DC (C6-OH); total DMA |
| 142 | 3 | 90.2 | alpha-AAA | 27-OH-C; Met-SO |
| 143 | 4 | 94.4 | alpha-AAA | 27-OH-C; C5-DC (C6-OH); Met-SO |
| 144 | 6 | 90.9 | alpha-AAA | 24,25-EpoxyC; Ac-Orn; C5:1; C5-DC (C6-OH); total DMA |
| 145 | 3 | 91.4 | SM (OH) C22:2 | 27-OH-C; total DMA |
| 146 | 3 | 91.2 | SM (OH) C22:2 | 27-OH-C; Carnosine |
| 147 | 3 | 90.8 | SM (OH) C22:2 | C5-DC (C6-OH); total DMA |
| 148 | 3 | 90.6 | SM (OH) C22:2 | 27-OH-C; Phe |
| 149 | 3 | 90.1 | SM (OH) C22:2 | C5:1; total DMA |
| 150 | 4 | 98.3 | SM (OH) C22:2 | 27-OH-C; C5:1; total DMA |
| 151 | 4 | 97.1 | SM (OH) C22:2 | 27-OH-C; total DMA; Tyr |
| 152 | 4 | 94.5 | SM (OH) C22:2 | 27-OH-C; Carnosine; total DMA |
| 153 | 4 | 91.9 | SM (OH) C22:2 | 27-OH-C; C5:1; SDMA |
| 154 | 4 | 91.4 | SM (OH) C22:2 | C5-DC (C6-OH); Carnosine; SDMA |
| 155 | 4 | 91.3 | SM (OH) C22:2 | 27-OH-C; C10:2; Thr |
| 156 | 4 | 90.8 | SM (OH) C22:2 | 27-OH-C; Carnosine; SDMA |
| 157 | 4 | 90.8 | SM (OH) C22:2 | C5:1; Fum; SDMA |
| 158 | 4 | 90.6 | SM (OH) C22:2 | 3b,5a,6b-THC; C5:1; SDMA |
| 159 | 5 | 91.7 | SM (OH) C22:2 | C5-DC (C6-OH); Carnosine; SM C16:1; SM C24:1 |
| 160 | 5 | 90.7 | SM (OH) C22:2 | 27-OH-C; SM (OH) C14:1; Thr; total DMA |
| 161 | 5 | 90.1 | SM (OH) C22:2 | C5-DC (C6-OH); Carnosine; SM (OH) C16:1; Tyr |
| 162 | 5 | 90 | SM (OH) C22:2 | C5:1; Carnosine; SDMA; SM C16:0 |
| 163 | 6 | 91.8 | SM (OH) C22:2 | 27-OH-C; C14:2-OH; C5-DC (C6-OH); Phe; SDMA |

The invention claimed is:

1. A method for early assessing and treating neonatal encephalopathy (NE) in a human neonate, which method comprises:
   A. obtaining a blood sample of said neonate,
   B. assessing in said blood sample at least one panel of metabolites indicative of the presence or absence of NE,
      wherein said at least one panel is selected from one of the following sets of models:
      i. set of hippocampus damage-related models 1 to 145 of Table 8;
      ii. set of basal ganglia damage-related models 1 to 3945 of Table 9; or
      iii. set of neurological behavioural abnormality-related models 1 to 717 of Table 10, and
      wherein said assessing in said blood sample comprises:
      a) detecting said at least one panel;
      b) determining a profile of detected metabolites;
      c) comparing the profile of the detected metabolites to a standard metabolite profile from a reference population afflicted with hippocampus damage, basal ganglia damage, or a neurological behavioural abnormality, and
      d) identifying severity of damage to the basal ganglia or hippocampus tissues or identifying neurological behavioural abnormality, thereby diagnosing neurological outcome and onset of NE,
      wherein said at least one panel is indicative of the presence of neonatal encephalopathy with an accuracy of at least 75% as determined in a non-human animal model, and
   C. treating a diagnosed neonate by administering a hypothermia therapy.

2. The method of claim 1, wherein said blood sample is obtained immediately after birth or after resuscitation.

3. The method claim 1, wherein said at least one panel comprises metabolites selected from the group consisting of:
   a) alpha-ketoglutaric acid, fumaric acid, succinic acid or lactic acid;
   b) glucose-1-phosphate, glucose-6-phosphate, fructose-6-phosphate, or ribulose-5-phosphate;
   c) decadienoylcarnitine, tetradecenoylcarnitine, 3-hydroxytetradecenoylcarnitine, tetradecadienoylcarnitine, 3-hydroxytetradecadienoylcarnitine, hexadecadienoylcarnitine, 3-hydroxybutyrylcarnitine, 3-hydroxyisovalerylcarnitine/3-hydroxy-2-methylbutyrylcarnitine, butenoylcarnitine, tiglylcarnitine, glutaconylcarnitine, mesaconylcarnitine (undecanoylcarnitine), glutarylcarnitine, hexenoylcarnitine, hexanoylcarnitine, or octenoylcarnitine;
   d) sphingomyelin with acyl residue sum C16:0, sphingomyelin with acyl residue sum C16:1, sphingomyelin with acyl residue sum C18:0, sphingomyelin with acyl residue sum C18:1, sphingomyelin with acyl residue sum C20:2, sphingomyelin with acyl residue sum C24:0, sphingomyelin with acyl residue sum C24:1, sphingomyelin with acyl residue sum C26:0 and sphingomyelin with acyl residue sum C26:1, hydroxysphingomyelin with acyl residue sum C14:1, hydroxysphingomyelin with acyl residue sum C16:1, hydroxysphingomyelin with acyl residue sum C22:1, hydroxysphingomyelin with acyl residue sum C22:2, or hydroxysphingomyelin with acyl residue sum C24:1;
   e) alanine, arginine, asparagine, citrulline, glutamine, glycine, histidine, leucine, lysine, methionine, ornithine, phenylalanine, proline, serine, threonine, tryptophane, tyrosine or valine;
   f) N-acetylornithine, asymmetric dimethylarginine, 2-aminoadipic acid, carnosine, creatinine, histamine, kynurenine, methionine-sulfoxide, symmetric dimethylarginine or total dimethylarginine;
   g) 20α-hydroxycholesterol, 24,25-epoxycholesterol, 24-dihydrolanosterol, 24-S-hydroxycholesterol, 25-hydroxycholesterol, 27-hydroxycholesterol, 5α,6α-epoxycholesterol, cholestenone, or 3β,5α,6β-trihydroxycholestan; and h) 8-iso-prostaglandin F2alpha, leukotriene B4 or tromboxane B2.

4. The method of claim 1, wherein said at least one panel comprises metabolites selected from the group consisting of:
  a) alanine, fumarate, succinate, alpha-ketoglutaric acid, decadienoyl carnitines or mesaconylcarnitine;
  b) methionine-sulfoxide, hydroxysphingomyelins or spingomyelins;
  c) 2-aminoadipic acid, carnosine, or kynurenine; and
  d) 25-hydroxycholesterol, 24-hydroxycholesterol, or 24,25-epoxycholesterol.

5. The method of claim 1, wherein said at least one panel comprises at least one first lead metabolite marker selected from the group consisting of:
  a) fumarate (Fum); fg
  b) carnosine (Car);
  c) 24,25-epoxycholesterol (24,25 EpoxyC);
  d) alpha-aminoadipic acid (alpha-AAA);
  e) hydroxysphingomyelin with acyl residue sum C22:2 (SM(OH) C22:2);
  f) methionine-sulfoxide (Met-SO);
  g) hydroxysphingomyelin with acyl residue sum C14:1 (SM(OH) C14:1);
  h) alpha-ketoglutaric acid(alpha-KGA);
  i) cholestenone;
  k) sphingomyelin with acyl residue sum C16:1 (SM C16:1);
  l) decadienoyl carnitine (C10:2);
  m) sphingomyelin with acyl residue sum C24:1 (SM C24:1); and
  n) mesaconylcarnitine (C5:1-DC),
optionally in combination with at least one second metabolite marker different from said at least one first lead metabolite marker.

6. The method of claim 5, wherein
  a) hippocampus damage-related panels comprise as lead marker C10:2; SM C24:1; and/or C5:1-DC;
  b) basal ganglia damage-related panels comprise as lead marker Met-SO; SM(OH) C14:1; alpha-KGA, Cholestenone and/or SM C16:1; and
  c) neurological behavioural abnormality-related panels comprise as lead marker Fum; Car; 24,25-EpoxyC; alpha-AAA; and/or SM(OH) C22:2.

7. The method of claim 6, wherein said panels are selected from one of the following sets of panels:
  a) set of hippocampus damage-related panels 1 to 21 of Table 11;
  b) set of basal ganglia damage-related panels 1 to 181 of Table 12; or
  c) set of neurological behavioural abnormality-related panels 1 to 163 of Table 13.

8. The method of claim 5, wherein at least one basal ganglia damage panel comprises at least one first lead metabolite marker selected from the group consisting of:
  methionine-sulfoxide (Met-SO);
  hydroxysphingomyelin with acyl residue sum C14:1 (SM (OH) C14:1);
  alpha-ketoglutaric acid(alpha-KGA);
  cholestenone; and
  sphingomyelin with acyl residue sum C16:1 (SM C16:1);
in combination with at least one second metabolite marker different from said at least one first lead metabolite marker.

9. The method of claim 1, wherein the at least one panel of metabolites are detected by nuclear magnetic resonance spectroscopy (NMR), mass spectroscopy, ELISA, fluorescence labeling techniques, flow cytometry, chromatography, capillary electrophoresis or chemical sensor or combinations thereof.

10. The method of claim 1, wherein said identifying severity of damage to the basal ganglia or hippocampus tissues is within the first 6 hours after birth of the neonate.

11. The method of claim 1, wherein said identifying neurological behavioural abnormality includes-predicting a neurological behavioural abnormality caused by neonatal encephalopathy within the first 6 hours after birth of the neonate.

12. The method of claim 1, wherein said detecting comprises:
  measuring at least two parameters selected from the group consisting of concentration, level, or amount of each specific compound of said at least one panel in said blood sample, qualitative and/or quantitative molecular pattern and/or molecular signature, thereby obtaining measured values; and
  storing said measured values in a database;
  wherein said determining comprises:
  calibrating said measured values, wherein said calibrating comprises:
  i) mathematically preprocessing said measured values to reduce technical errors inherent to a measuring procedure;
  ii) selecting at least one suitable supervised algorithm that is a deterministic function that maps a multi-dimensional vector of biological measurements to a binary or n-ary or continuous outcome variable and
  iii) applying said selected at least one suitable supervised algorithm to said mathematically preprocessed values of step i);
  said at least one suitable supervised algorithm of step ii) being trained on at least one training data set containing preprocessed data from subjects being divided into classes according to their NE in infants-related pathophysiological, physiological, prognostic, or responder conditions, in order to select a classifier function to map said preprocessed data to said conditions; and
  wherein said comparing comprises:
  applying said trained at least one suitable supervised algorithm of step iii) to a preprocessed data set of a subject with unknown NE in infants-related pathophysiological, physiological, prognostic, or responder condition, and using said trained at least one suitable supervised algorithm to predict a class label of said preprocessed data set to predict a likelihood of an onset of NE in infants of the subject.

13. The method according to claim 12, wherein the at least one suitable supervised algorithm is selected from the group consisting of logistic regression, linear or quadratic discriminant analysis, perceptron, shrunken centroids regularized discriminant analysis, random forests, neural networks, Bayesian networks, hidden Markov models, support vector machines, generalized partial least squares, partitioning around medoids, inductive logic programming, generalized additive models, gaussian processes, regularized least square regression, self-organizing maps, recursive partitioning and regression trees, and K-nearest neighbor classifiers.

14. The method of claim 1, wherein said obtaining a blood sample is within the first 6 hours after birth of the neonate.

15. The method of claim 1, wherein said obtaining a blood sample is within 1 minute to 180 minutes after birth of the neonate.

16. The method according to claim 1, wherein said at least one panel is indicative of the presence of neonatal encephalopathy with an accuracy of at least 85% as determined in a non-human animal model.

17. The method of claim 1, wherein said identifying severity of damage to the basal ganglia or hippocampus tissues comprises detecting lesions.

18. The method of claim 1, wherein said obtaining a blood sample is within 1 minute to 5 minutes after birth of the neonate.

19. The method of claim 1, wherein said at least one panel is selected from basal ganglia damage-related models 1 to 3945 of Table 9.

20. A method for early assessing and treating of neonatal encephalopathy, comprising:
   obtaining a blood sample from a human neonate;
   measuring at least one panel comprising a combination of metabolites in the blood sample, wherein said at least one panel is selected from a set of hippocampus damage-related models 1 to 145 of Table 8 and a set of basal ganglia damage-related models 1 to 3945 of Table 9;
   mathematically transforming data from said measured at least one panel into a score;
   comparing the score to a score from a reference population afflicted with hippocampus damage or basal ganglia damage;
   diagnosing of neonatal encephalopathy and differentiating between hippocampus damage and basal ganglia damage within the first 6 hours after birth of the neonate; and
   treating a diagnosed neonate by administering a hypothermia therapy,
   wherein said comparing predicts onset of neonatal encephalopathy with an accuracy of at least 75% as determined in a non-human animal model.

21. A method according to claim 20, wherein said obtaining a blood sample is within the first 6 hours after birth of the neonate.

22. The method according to claim 20, wherein said comparing predicts onset of neonatal encephalopathy with an accuracy of at least 90% as determined in a non-human animal model.

23. The method according to claim 20, wherein the at least one panel comprises 3 to 7 metabolites.

\* \* \* \* \*